(12) United States Patent
Adhikari et al.

(10) Patent No.: US 10,865,208 B2
(45) Date of Patent: Dec. 15, 2020

(54) ATG7 INHIBITORS AND THE USES THEREOF

(71) Applicant: Millennium Pharmaceuticals, Inc., Cambridge, MA (US)

(72) Inventors: Sharmila Adhikari, Natick, MA (US); Emily Frances Calderwood, Framingham, MA (US); Dylan Bradley England, Milford, MA (US); Alexandra E. Gould, Cambridge, MA (US); Sean J. Harrison, Belmont, MA (US); Shih-Chung Huang, Lexington, MA (US); Liting Ma, Needham, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/348,940

(22) PCT Filed: Nov. 10, 2017

(86) PCT No.: PCT/US2017/061094
§ 371 (c)(1),
(2) Date: May 10, 2019

(87) PCT Pub. No.: WO2018/089786
PCT Pub. Date: May 17, 2018

(65) Prior Publication Data
US 2019/0382406 A1    Dec. 19, 2019

Related U.S. Application Data

(60) Provisional application No. 62/420,630, filed on Nov. 11, 2016.

(51) Int. Cl.
| | |
|---|---|
| C07D 487/04 | (2006.01) |
| C07D 231/12 | (2006.01) |
| C07D 237/08 | (2006.01) |
| C07D 333/54 | (2006.01) |
| A61K 31/519 | (2006.01) |
| A61P 35/04 | (2006.01) |

(52) U.S. Cl.
CPC .......... *C07D 487/04* (2013.01); *A61K 31/519* (2013.01); *A61P 35/04* (2018.01); *C07D 231/12* (2013.01); *C07D 237/08* (2013.01); *C07D 333/54* (2013.01)

(58) Field of Classification Search
CPC .................................................. C07D 487/04
See application file for complete search history.

(56) References Cited

U.S. PATENT DOCUMENTS
| | | |
|---|---|---|
| 9,963,456 B2 | 5/2018 | Mizutani et al. |
| 2008/0293666 A1 | 11/2008 | Aldrich et al. |

FOREIGN PATENT DOCUMENTS
| | | |
|---|---|---|
| WO | WO 2005/021568 A2 | 3/2005 |
| WO | WO 2015/199136 A1 | 12/2015 |

OTHER PUBLICATIONS

International Search Report and Written Opinion of International Patent Application No. PCT/US2017/061094, dated Jan. 30, 2018.
Bhat, G.A., et al., "Pyrazolopyrimidine Nucleosides. 12. Synthesis and Biological Activity of Certain Pyrazolo[3,4-d]pyrimidine Nucleosides Related to Adenosine," Journal of Medicinal Chemistry, vol. 24, No. 10 (1981); pp. 1165-1172. American Chemical Society, United States.
Cottam, H.B., et al., "Synthesis and Biological Activity of Certain 3,4-Disubstituted Pyrazolo[3,4-d]pyrimidine Nucleosides," Journal of Medicinal Chemistry, vol. 27, No. 9 (1984); pp. 1119-1127; American Chemical Society, United States.
Schulman, B.A., et al., "Ubiquitin-like protein activation by E1 enzymes: the apex for downstream signalling pathways," Nature Reviews. Molecular Cell Biology, vol. 10, No. 5 (May 2009); pp. 319-331; Springer Nature Limited, United Kingdom.
Bacik, J., et al., "Crystal Structure of the Human Ubiquitin-activating Enzyme 5 (UBA5) Bound to ATP," Journal of Biological Chemistry, vol. 285, No. 26 (Jun. 25, 2010); pp. 20273-20280; American Society for Biochemistry and Molecular Biology, United States.
Soucy, T.A., et al., "An inhibitor of NEDD8-activating enzyme as a new approach to treat cancer," Nature, vol. 458 (2009); pp. 732-736; Macmillan Publishers Limited; United Kingdom.
Brownell, J.E., et al., "Substrate-assisted inhibition of ubiquitin-like protein-activating enzymes: the NEDD8 E1 inhibitor MLN4924 forms a NEDD8-AMP mimetic in situ," Molecular Cell, vol. 37, No. 1 (Jan. 15, 2010); pp. 102-111; Elsevier Inc.; United States.

(Continued)

*Primary Examiner* — Susanna Moore
(74) *Attorney, Agent, or Firm* — Sterne, Kessler, Goldstein & Fox P.L.L.C.

(57) ABSTRACT

Disclosed are chemical entities which are compounds of formula (I): or a pharmaceutically acceptable salt thereof, wherein $R^1$, $R^2$, and $R^a$ have the values described herein. Chemical entities according to the disclosure can be useful as inhibitors of ATG7. Further provided are pharmaceutical compositions comprising a chemical entity of the disclosure and methods of using the compositions in the treatment of cancer.

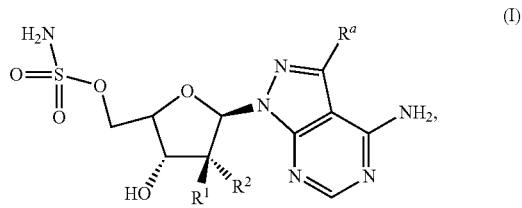

19 Claims, No Drawings

(56) References Cited

OTHER PUBLICATIONS

Chen, J.J., et al., "Mechanistic Studies of Substrate-assisted Inhibition of Ubiquitin-activating Enzyme by Adenosine Sulfamate Analogues," Journal of Biological Chemistry, vol. 286, No. 47 (Nov. 25, 2011); pp. 40867-40877; American Society for Biochemistry and Molecular Biology, United States.

He, C., et al., "Regulation Mechanisms and Signaling Pathways of Autophagy," Annual Review of Genetics, vol. 43 (2009); pp. 67-93; Annual Reviews; United States.

Singh, R., et al., "Autophagy in the Cellular Energetic Balance," Cell Metabolism, vol. 13, No. 5 (May 4, 2011); pp. 495-504; Cell Press; United States.

Amaravadi, R.K., et al., "Principles and Current Strategies for Targeting Autophagy for Cancer Treatment," Clinical Cancer Research, vol. 17, No. 4 (Feb. 2011); pp. 654-666; The American Association for Cancer Research; United States.

Degenhardt, K., et al., "Autophagy promotes tumor cell survival and restricts necrosis, inflammation, and tumorigenesis," Cancer Cell, vol. 10, No. 1 (Jul. 2006); pp. 51-64; Cell Press; United States.

Karantza-Wadsworth, V., et al., "Autophagy mitigates metabolic stress and genome damage in mammary tumorigenesis," Genes & Development, vol. 21, No. 13 (Jul. 1, 2007); pp. 1621-1635; Cold Spring Harbor Laboratory Press; United States.

Lum, J.J., et al., "Growth factor regulation of autophagy and cell survival in the absence of apoptosis," Cell, vol. 120, No. 2 (Jan. 28, 2005); pp. 237-248; Elsevier Inc; United States.

Mathew, R., et al., "Autophagy suppresses tumor progression by limiting chromosomal instability," Genes & Development, vol. 21, No. 13 (Jul. 1, 2007); pp. 1367-1381; Cold Spring Harbor Laboratory Press; United States.

Kroemer, G., et al., "Autophagy and the integrated stress response," Molecular Cell, vol. 40, No. 2 (Oct. 22, 2010); pp. 280-293; Elsevier Inc.; United States.

Ohsumi, Y., "Molecular dissection of autophagy: two ubiquitin-like systems," Nature Reviews. Molecular Cell Biology, vol. 2, No. 3 (Mar. 2001); pp. 211-216; Macmillan Magazines Ltd; United Kingdom.

ATG7 INHIBITORS AND THE USES THEREOF

BACKGROUND

The post-translational modification of proteins by ubiquitin-like proteins (Ubls) is an important regulatory process within cells, playing a key role in controlling many biological processes including cell division, cell signaling and the immune response. Ubls are small proteins that can be covalently attached to target proteins via an isopeptide linkage between a C-terminal glycine of the Ubl and a target protein lysine residue. The ubiquitin-like protein alters the molecular surface of the target protein and can affect such properties as protein-protein interactions, enzymatic activity, stability and cellular localization of the target.

Ubl conjugation requires the activity of a Ubl-specific activating or E1 enzyme (E1), an E2 conjugating enzyme (E2), and sometimes an E3 ligase (E3). There are eight E1s in humans that can be broadly classified into two groups based on domain structure (Schulman et al., Nat Rev Mol Cell Biol. 10(5):319 (2009)). The first group comprises the five 'canonical' E1s which consist of either a single polypeptide (UAE, Uba6, and Uba7) or two subunits (NAE and SAE). ATG7 along with Uba5 and Uba4 are classified as 'non-canonical' E1s. While all E1s possess adenylation domains reminiscent of MoeB and ThiF, non-canonical E1s stand apart in that they form homodimers, have significantly smaller catalytic cysteine domains, and lack the C-terminal UFD found in canonical E1s (Schulman et al., Nat Rev Mol Cell Biol. 10(5):319 (2009); Bacik et al., *J Biol Chem.* 285(26):20273 (2010)).

The catalytic mechanism for Ubl activation was first determined for UAE and subsequently for NAE and involves three discrete steps. In the first step, ATP and a Ubl bind the E1 and form a Ubl-acyl adenylate intermediate while releasing inorganic pyrophosphate (PPi). Ubl-AMP then reacts with the E1 active-site cysteine to form an E1~Ubl thioester (~ denotes a high energy bond). A second ATP and Ubl then bind the enzyme as in the first step to form a ternary complex that contains two Ubls. This 'doubly loaded' form of the E1 is competent for transfer of the thioester-bound Ubl to a pathway specific E2. It was recently reported that NAE and UAE can be inhibited by certain analogs of adenosine sulfamate by a mechanism called substrate-assisted inhibition whereby the enzyme catalyzes the formation of a covalent Ubl-inhibitor adduct which resembles Ubl-AMP (Soucy et al. *Nature.* 458(7239):732 (2009); Brownell et al. *Mol Cell.* 37(1): 102 (2010); Chen et al. *J Biol Chem.* 286(47):40867 (2011)). Inhibition by this mechanism requires the inhibitor to bind the Ubl thioester form of E1 and attack the thioester bond to form the Ubl-inhibitor adduct. Examination of a panel of the five canonical E1s and ATG7 showed that all formed cognate Ubl-inhibitor adducts demonstrating the commonality of the overall E1 mechanism and substrate-assisted inhibition (Brownell et al. *Mol Cell.* 37(1):102 (2010)).

(Macro)autophagy is a catabolic process that requires the coordinated activities of a large number of conserved ATG proteins (He and Klionsky. *Annu Rev Genet.* 43:67 (2009)). It is a process whereby cells target proteins, protein aggregates, and organelles for bulk degradation in order to maintain energy homeostasis, provide metabolites for macromolecular synthesis, and prevent toxic accumulation of damaged proteins and organelles (Singh and Cuervo. *Cell Metab.* 13(5):495 (2011)). Autophagy is induced by starvation and other forms of stress and leads to the formation of characteristic double-membrane vesicles called autophagosomes which encapsulate targeted substrates. These vesicles appear to form throughout the cytoplasm and traffic toward lysosomes. Autophagosome fusion with lysosomes results in autolysosome formation and exposes the contents to lysosomal hydrolases resulting in degradation.

The roles of autophagy in physiology and disease are still emerging. Autophagy is thought to be the primary mechanism for degrading large cytoplasmic structures such as organelles or protein aggregates. Basal autophagy serves a housekeeping function in the absence of stress which may be important for the viability of non-proliferating, terminally differentiated cells. Under starvation conditions, autophagy recycles cellular contents to provide a nutrient source and promote survival. A broad range of other stresses also induce autophagy suggesting a detoxification role for sequestering and degrading damaged cellular components, as well as, at least in some instances, intracellular pathogens.

Recent studies support the central role of autophagy for cancer cell survival (Amaravadi et al. *Clin Cancer Res.* 17(4):654 (2011)). In cancer cells, autophagy is required to survive periods of metabolic and/or hypoxic stress. Genetic inactivation of autophagy, either indirectly by constitutive activation of the phosphatidylinositol 3-kinase (PI3K) pathway or directly by allelic loss of Beclin or deficiency in Atg5, or by RNAi, prevents survival in response to metabolic deprivation even when apoptosis is inactivated (Degenhardt et al., *Cancer Cell,* 10(1):51 (2006); Karantza-Wadsworth et al., *Genes Dev.,* 21(13):1621 (2007); Lum et al., *Cell,* 120(2):237 (2005); Mathew et al., *Genes Dev.* 21(11):1367 (2007)). The catabolic capacity of autophagy can sustain viability under nutrient limiting conditions, but the role of autophagy in cellular damage control in response to stress may also be important. Amino-acid starvation, glucose and oxygen deprivation, growth-factor withdrawal and cytotoxic cellular damage are among the stimuli that potently induce autophagy. In the example of nutrient starvation, autophagy serves as a back-up energy reserve, whereas the autophagic response to cellular damage facilitates the removal of damaged proteins and organelles Autophagy induction and the formation of autophagosomes requires multiple signaling components including the ULK1/2 complexes and the Beclin1/Vps34 complex, as well as two ubiquitin-like protein pathways (Ubl) that require the function of the Ubl activating enzyme (E1) ATG7 (Kreomer et al., *Mol Cell.,* 40(2):280 (2010)).

ATG7 is the E1 enzyme that is required for activation of two Ubl conjugation pathways involved in autophagosome formation (Ohsumi. *Nat Rev Mol Cell Biol.* 2(3):211 (2001)). ATG12 is a Ubl that forms a conjugate with a protein called ATG5 in a manner dependent on the E2 conjugating enzyme ATG10. The ATG5-ATG12 conjugate stimulates a second Ubl pathway in which orthologues of yeast ATG8 form conjugates with the lipid phosphatidylethanolamine (PE) instead of target proteins in a manner dependent on the E2 ATG3; there are at least eight ATG8 orthologues in humans, including LC3A, LC3B, LC3C, GATE16, GABARAP, and GABARAPL1. Accumulation of lipidated ATG8 orthologues is considered a hallmark of active autophagy and is commonly used as a marker of autophagy in cells and tissues.

Targeting E1 activating enzymes such as ATG7 provides a unique opportunity to interfere with pathways important for authophagy induction. E1 activating enzymes function at the first step of Ubl conjugation pathways; thus, inhibition of an E1 activating enzyme will specifically modulate the downstream biological consequences of the Ubl modification. As such, inhibition of these activating enzymes, and the resultant inhibition of downstream effects of Ubl conjugation, represents a method of interfering with the integrity of several aspects of cellular physiology which are important for disease mechanisms. Thus, E1 enzymes such as ATG7, as regulators of diverse cellular functions, are potentially important therapeutic targets for the identification of novel approaches to treatment of diseases and disorders. Clearly, it would be beneficial to provide novel ATG7 inhibitors that possess good therapeutic properties, especially for the treatment of proliferative disorders.

DETAILED DESCRIPTION

In one aspect, the disclosure relates to chemical entities, each of which is a compound of Formula (I):

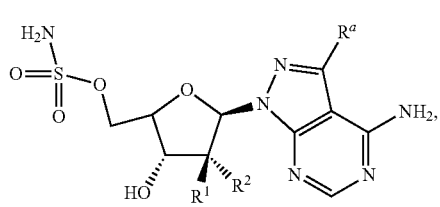

or a pharmaceutically acceptable salt thereof, wherein $R^1$, $R^2$, and $R^a$ are defined below.

In one aspect, the disclosure relates to compositions comprising one or more of the chemical entities and one or more pharmaceutically acceptable carriers.

In one aspect, the disclosure relates to methods of treating cancer comprising administering to a patient in need of such treatment one or more of the chemical entities.

In one aspect, the disclosure relates to uses of the chemical entities for the manufacture of a medicament for use in the treatment of cancer.

In one aspect, the disclosure relates to the chemical entities for use in the treatment of cancer.

Chemical entities of the present disclosure include those described generally for formula (I), above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, chemical entities of the present disclosure may be optionally substituted with one or more substituents, such as are disclosed generally above, or as exemplified by particular classes, subclasses, and species disclosed herein. It will be appreciated that the phrase "optionally substituted" is used interchangeably with the phrase "substituted or unsubstituted." In general, the term "substituted," whether preceded by the term "optionally" or not, means that a hydrogen radical of the designated moiety is replaced with the radical of a specified substituent, provided that the substitution results in a stable or chemically feasible chemical entity. The term "substitutable," when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this disclosure are, for instance, those that result in the formation of stable or chemically feasible chemical entities.

A stable chemical entity or chemically feasible chemical entity is one in which the chemical structure is not substantially altered when kept at a temperature from about −80° C. to about +40° C., in the absence of moisture or other chemically reactive conditions, for at least a week, or a chemical entity which maintains its integrity long enough to be useful for therapeutic or prophylactic administration to a patient.

The phrase "one or more substituents," as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single chemical entity.

As used herein, the term "aromatic" includes aryl and heteroaryl groups as described generally below and herein.

The term "aliphatic" or "aliphatic group," as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle," "cycloaliphatic," "cycloalkyl," or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-5, 1-4, 1-3, or 1-2 carbon atoms.

The term "alkyl," used alone or as part of a larger moiety, refers to an optionally substituted straight or branched chain saturated hydrocarbon group having 1-12, 1-10, 1-8, 1-6, 1-5, 1-4, 1-3, or 1-2 carbon atoms.

The term "alkenyl," used alone or as part of a larger moiety, refers to an optionally substituted straight or branched chain hydrocarbon group having at least one double bond and having 2-12, 2-10, 2-8, 2-6, 2-5, 2-4, or 2-3 carbon atoms.

The term "alkynyl," used alone or as part of a larger moiety, refers to an optionally substituted straight or branched chain hydrocarbon group having at least one triple bond and having 2-12, 2-10, 2-8, 2-6, 2-5, 2-4, or 2-3 carbon atoms.

The terms "cycloaliphatic," "carbocycle," "carbocyclyl," "carbocyclo," or "carbocyclic," used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8, 3-7, or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic," "carbocycle," "carbocyclyl," "carbocyclo," or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

The terms "haloaliphatic," "haloalkyl," "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon); the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-," used alone or as part of a larger moiety, e.g., "aralkyl," "aralkoxy," or "aryloxyalkyl," refer to an optionally substituted $C_{6-14}$ aromatic hydrocarbon moiety comprising one to three aromatic rings. In at least one embodiment, the aryl group is a $C_{6-10}$ aryl group. Aryl groups include, without limitation, optionally substituted phenyl, naphthyl, or anthracenyl. The terms "aryl" and "ar-," as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group," "aryl ring," and "aromatic ring."

An "aralkyl" or "arylalkyl" group comprises an aryl group covalently attached to an alkyl group, either of which independently is optionally substituted. In at least one embodiment, the aralkyl group is $C_{6-10}$ aryl $C_{1-6}$ alkyl, including, without limitation, benzyl, phenethyl, and naphthylmethyl.

The terms "heteroaryl" and "heteroar-," used alone or as part of a larger moiety, e.g., "heteroaralkyl," or "heteroaralkoxy," refer to groups having 5 to 14 ring atoms, such as 5, 6, 9, or 10 ring atoms; having 6, 10, or 14 pi electrons shared in a cyclic array; and having, in addition to carbon atoms, from one to five heteroatoms. A heteroaryl group may be mono-, bi-, tri-, or polycyclic, for instance mono-, bi-, or tricyclic, such as mono- or bicyclic. In the context of "heteroar" entities, the term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-," as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 4-10 membered heterocyclic moiety, such as a 3- to 8-membered monocyclic, a 7-10-membered bicyclic, or a 5 or 6 membered heterocyclic moiety that is either saturated or partially unsaturated, and having, in addition to carbon atoms, one or more, for instance one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, for instance mono-, bi-, or tricyclic, and such as mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, such as from 1 to 6, from 1 to 5, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein, and include double and/or triple bonds between carbons in the alkylene chain.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted." In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR°, —S(O)R°, —SO$_2$R°, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R°, —NR$^+$CO$_2$R$^+$, —NR$^+$SO$_2$R°, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R°, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R°)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl. Each R° is, independently, an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted." Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide chemical entity. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

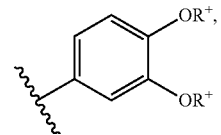

these two occurrences of R$^+$ are taken together with the oxygen atoms to which they are bound to form a fused 6-membered oxygen containing ring:

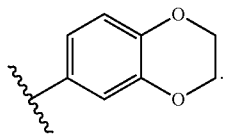

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present chemical entities are within the scope of the present disclosure. Unless otherwise stated, all tautomeric forms of the chemical entities disclosed herein are within the scope of the present disclosure. Additionally, unless otherwise stated, structures depicted herein are also meant to include chemical entities that differ only in the presence of one or more isotopically enriched atoms. For example, chemical entities having the present structures where there is a replacement of hydrogen by deuterium or tritium, or a replacement of a carbon by a $^{13}$C- or $^{14}$C-enriched carbon are within the scope of this disclosure. Such chemical entities are useful, as a nonlimiting example, as analytical tools or probes in biological assays.

It is to be understood that, when a disclosed chemical entity has at least one chiral center, the present disclosure encompasses one enantiomer of inhibitor free from the corresponding optical isomer, a racemic mixture of the inhibitor, and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95%, 99%, or 99.5%.

The enantiomers of the present disclosure may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed chemical entity has at least two chiral centers, the present disclosure encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the chemical entity, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of chemical entities disclosed herein are provided the examples herein.

For the avoidance of doubt, for chemical entities described herein, where the chemical entity is a single diastereomer and the absolute configuration of the chiral centers is known the name of the chemical entity reflects the assigned configuration at each stereochemical center; for example chemical entity I-1: [(2R,3S,4R,5R)-5-(4-amino-3-methoxy-1H-pyrazolo[3,4-d]pyrimidin-1-yl)-3,4-dihydroxytetrahydrofuran-2-yl]methyl sulfamate. Where the chemical entity is a single diastereomer and the absolute configuration is known at some of the chiral centers but is unknown at one chiral center, the name reflects the two possibilities separated by an "or"; for example chemical entity I-55a: [(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate or [(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl sulfamate. Where the chemical entity is a mixture of two or more diastereomers the name reflects the two or more possibilities by using "and" between the names of the individual diastereomers that make up the mixture; for example chemical entity I-47: [(2R,3S,4R,5R)-5-(4-amino-3-{[(1R,2R)-2-hydroxycyclohexyl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(1S,2S)-2-hydroxycyclohexyl]sulfanyl}-1H-pyrazolo[3,4-d]pyrimidin-1-yl)-3,4-dihydroxytetrahydrofuran-2-yl]methyl sulfamate.

The present disclosure is a chemical entity which is a compound or pharmaceutically acceptable salt of formula (I):

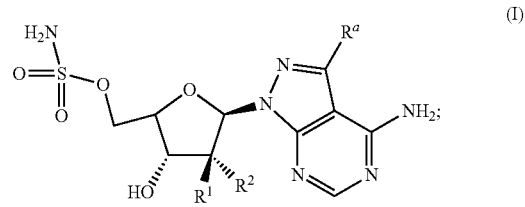

wherein:

$R^1$ is H and $R^2$ is H; or $R^1$ is H and $R^2$ is —OH; or $R^1$ is F and $R^2$ is H;

$R^a$ is H, I, —CN, —CO$_2$CH$_3$, —C(O)CH$_3$, —C(S)NH$_2$, —C(O)NH$_2$, —S(O)CH$_3$, C$_{1-3}$ fluoroaliphatic, —O—C$_{1-3}$ fluoroaliphatic, —S—C$_{1-3}$ fluoroaliphatic, -T$_1$-R$^b$, R$^{bb}$, —O-T$_1$-R$^b$, —O—R$^{dd}$, —S-T$_1$-R$^c$, or —S—R$^{ee}$;

T$_1$ is absent or C$_1$-C$_3$ alkylene optionally substituted with 1 or 2 independent occurrences of —CH$_3$;

R$^b$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each R$^b$ is substituted with 0-5 R$^d$;

R$^c$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each R$^c$ is substituted with 0-5 R$^f$;

each occurrence of R$^d$ is independently halo, —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of R$^d$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of R$^g$;

each occurrence of $R^f$ is independently halo, —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;

$R^{bb}$ is C$_{1-3}$ aliphatic substituted with 0-5 $R^{bx}$;
$R^{dd}$ is C$_{1-3}$ aliphatic substituted with 0-5 $R^{dx}$;
$R^{ee}$ is C$_{1-3}$ aliphatic substituted with 0-5 $R^{fx}$;

each occurrence of $R^{bx}$ is independently —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of $R^{bx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;

each occurrence of $R^{dx}$ is independently Cl, —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of $R^{dx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;

each occurrence of $R^{fx}$ is independently —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of $R^{fx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;

$R^g$ is C$_{1-3}$ aliphatic; and
$R^e$ is hydrogen or C$_{1-3}$ aliphatic.

In some embodiments, the chemical entity of formula (I) is represented by formula (II-a), (II-b) or (II-c):

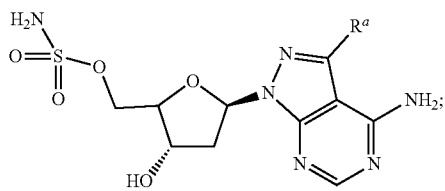

(II-a)

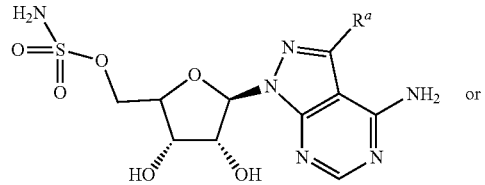

(II-b)

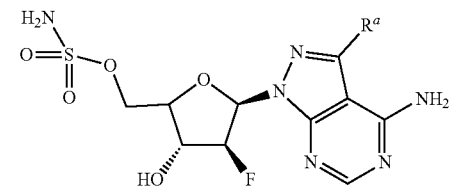

(II-c)

wherein $R^a$ has the values described herein. In some embodiments, the chemical entity of formula (I) is represented by formula (II-a), wherein $R^a$ has the values described herein. In some embodiments, the chemical entity of formula (I) is represented by formula (II-b), wherein $R^a$ has the values described herein. In some embodiments, the chemical entity of formula (I) is represented by formula (II-c), wherein $R^a$ has the values described herein.

In some embodiments, the chemical entity of formula (I) is represented by formula (III-a), (III-aa), (III-b) or (III-c):

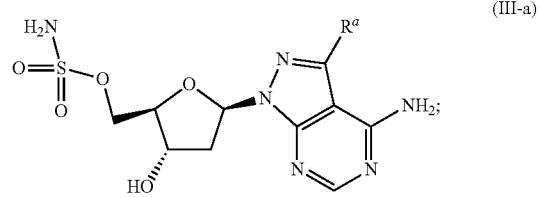

(III-a)

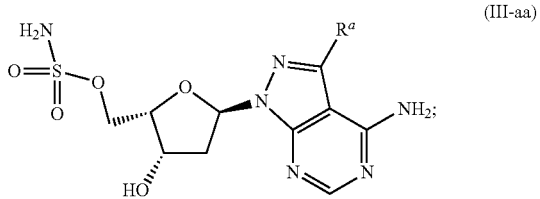

(III-aa)

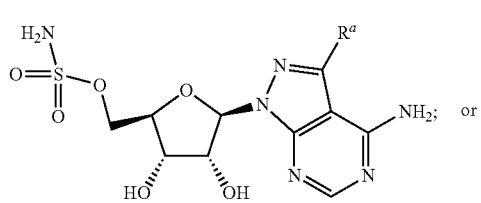

(III-b)

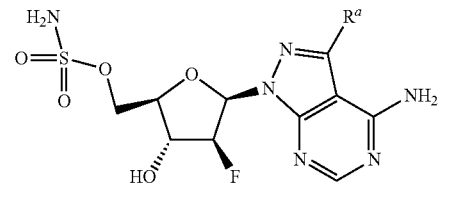

(III-c)

wherein $R^a$ has the values described herein. In some embodiments, the chemical entity of formula (II-a) is represented by formulae (III-a), or (III-aa), wherein $R^a$ has the values described herein. In some embodiments, the chemical entity of formula (II-b) is represented by formula (III-b), wherein $R^a$ has the values described herein. In some embodiments, the chemical entity of formula (II-c) is represented by formulae (III-c), wherein $R^a$ has the values described herein.

The following values are described for any of formulas (I), (II-a), (II-b), (II-c), (III-a), (III-aa), (III-b), or (III-c).

In some embodiments, $R^1$ is H and $R^2$ is H; or $R^1$ is H and $R^2$ is —OH; or $R^1$ is F and $R^2$ is H. In some embodiments, $R^1$ is H and $R^2$ is H. In some embodiments, $R^1$ is H and $R^2$ is —OH. In some embodiments, $R^1$ is F and $R^2$ is H.

In some embodiments, $R^a$ is H, I, —CN, —CO$_2$CH$_3$, —C(O)CH$_3$, —C(S)NH$_2$, —C(O)NH$_2$, —S(O)CH$_3$, C$_{1-3}$ fluoroaliphatic, —O—C$_{1-3}$ fluoroaliphatic, —S—C$_{1-3}$ fluoroaliphatic, -T$_1$-R$^b$, R$^{bb}$, —O-T$_1$-R$^b$, —O—R$^{dd}$, —S-T$_1$-R$^c$, or —S—R$^{ee}$, wherein T$_1$, R$^b$, R$^{bb}$, R$^{dd}$, R$^c$, and R$^{ee}$ have the values described herein.

In some embodiments, $R^a$ is I, C$_{1-3}$ fluoroaliphatic, —O—C$_{1-3}$ fluoroaliphatic, —S—C$_{1-3}$ fluoroaliphatic, -T$_1$-R$^b$, R$^{bb}$, —O-T$_1$-R$^b$, —O—R$^{dd}$, —S-T$_1$-R$^c$, or —S—R$^{ee}$, wherein T$_1$, R$^b$, R$^{bb}$, R$^{dd}$, R$^c$, and R$^{ee}$ have the values described herein. In some embodiments, $R^a$ is —O—C$_{1-3}$ fluoroaliphatic, or —O—R$^{dd}$, wherein R$^{dd}$ has the values described herein. In some embodiments, $R^a$ is —S—C$_{1-3}$ fluoroaliphatic, —S-T$_1$-R$^c$, or —S—R$^{ee}$, wherein T$_1$, R$^c$ and R$^{ee}$ have the values described herein.

In some embodiments, $R^a$ is I, —CN, C$_{1-3}$ fluoroaliphatic, —O—C$_{1-3}$ fluoroaliphatic, —S—C$_{1-3}$ fluoroaliphatic, -T$_1$-R$^b$, R$^{bb}$, —O-T$_1$-R$^b$, —O—R$^{dd}$, —S-T$_1$-R$^c$, or —S—R$^{ee}$ wherein T$_1$, R$^b$, R$^{bb}$, R$^{dd}$, R$^c$, and R$^{ee}$ have the values described herein. In some embodiments, $R^a$ is I, —CN, C$_{1-3}$ fluoroaliphatic, —O—C$_{1-3}$ fluoroaliphatic, R$^{bb}$, or O—R$^{dd}$, wherein R$^{bb}$ and R$^{dd}$ have the values described herein. In some embodiments, $R^a$ is I, —CN, —CH$_3$, —CH$_2$CH$_3$, —CH(CH$_3$)$_2$, —CH=CH$_2$, —C≡CH, —CH≡CCH$_2$NH$_2$, —CH≡CCH$_2$OH, —CF$_3$, —CHF$_2$, —OCH$_3$, —OCH$_2$CH$_3$, —OCHF$_2$ or cyclopropyl. In some embodiments, $R^a$ is —CN, —CH$_3$, —CH=CH$_2$, —C≡CH, —CF$_3$, —CHF$_2$, —OCH$_3$, —OCHF$_2$ or cyclopropyl.

In some embodiments, $R^a$ is —S—C$_{1-3}$ fluoroaliphatic or —S—R$^{ee}$, wherein R$^{ee}$ has the values described herein. In some embodiments, $R^a$ is —S—CH$_3$, —S—CH$_2$CH$_3$, —S—CH(CH$_3$)$_2$, —S—CH$_2$C≡CH, —S—C(CH$_3$)$_3$, —S—CH(CH$_3$)CH$_2$CH$_3$, —S—CH(CH$_2$CH$_3$)$_2$, —S—CH(CH$_3$)CH(CH$_3$)$_2$, —S—CH$_2$CH(CH$_3$)$_2$, —S—CF$_3$, —S—CHF$_2$, —S—CH$_2$CF$_3$, —S—CH$_2$CHF$_2$, —S—CH(CH$_3$)CF$_3$, —S—CH$_2$CH$_2$OH, —S—CH$_2$CH$_2$OCH$_3$, —S—CH(CH$_3$)CH$_2$OH, —S—CH$_2$CN, —S—CH(CH$_3$)CN, —S—CH$_2$—C(O)NH$_2$, —S—CH$_2$C(O)N(CH$_3$)$_2$, or —S—CH$_2$CH$_2$N(CH$_2$CH$_3$)$_2$. In some embodiments, $R^a$ is —S—CH$_3$, —S—CH$_2$CH$_3$, —S—CH(CH$_3$)$_2$, —S—CH$_2$C≡CH, —S—C(CH$_3$)$_3$, —S—CH(CH$_3$)CH$_2$CH$_3$, —S—CH$_2$CH(CH$_3$)$_2$, —S—CHF$_2$, —S—CH$_2$CF$_3$, —S—CH$_2$CHF$_2$, —S—CH$_2$CH$_2$OH, —S—CH(CH$_3$)CH$_2$OH, —S—CH$_2$CN, or —S—CH(CH$_3$)CN.

In some embodiments, $R^a$ is -T$_1$-R$^b$, —O-T$_1$-R$^b$, or —S-T$_1$-R$^c$, wherein R$^b$ and R$^c$ have the values described herein. In some embodiments, $R^a$ is -T$_1$-R$^b$, —O-T$_1$-R$^b$, wherein R$^b$ has the value described herein. In some embodiments, $R^a$ is —S-T$_1$-R$^c$, wherein T$_1$ and R$^c$ have the values described herein.

In some embodiments, T$_1$ is absent or C$_1$-C$_3$ alkylene optionally substituted with 1 or 2 independent occurrences of —CH$_3$. In some embodiments, T$_1$ is absent, —CH$_2$—, —C(CH$_3$)H—, —CH$_2$CH$_2$, or —CH(CH$_3$)CH(CH$_3$)—. In some embodiments, T$_1$ is absent, —CH$_2$— or —CH$_2$CH$_2$—. In some embodiments, T$_1$ is absent or —CH$_2$—.

In some embodiments, R$^b$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each R$^b$ is substituted with 0-5 R$^d$. In some embodiments, R$^b$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each R$^b$ is substituted with 0-2 R$^d$. In some embodiments, R$^b$ is phenyl, cyclopropyl, thiazolyl, oxazolyl, or pyrazolyl, wherein each R$^b$ is substituted with 0-2 R$^d$. In some embodiments, R$^b$ is cyclopropyl, phenyl or oxirane, each of which is unsubstituted.

In some embodiments, each occurrence of R$^d$ is independently halo, —OH, —CN, —NO$_2$, C$_{1-4}$ aliphatic, —O—C$_{1-3}$ aliphatic, C$_{1-3}$ fluoroaliphatic, —O—C$_{1-3}$ fluoroaliphatic, —S—C$_{1-3}$ aliphatic, —S—C$_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, C$_{1-3}$ aliphatic, or —O—C$_{1-3}$ aliphatic; or two occurrences of R$^d$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of R$^g$, wherein R$^g$ has the values described herein. In some embodiments, each occurrence of R$^d$ is independently halo, —OH, —CN, C$_{1-4}$ aliphatic, —O—C$_{1-3}$ aliphatic, —O—C$_{1-3}$ fluoroaliphatic, —N(R$^e$)$_2$, or —C(O)—N(R$^e$)$_2$; or two occurrences of R$^d$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of R$^g$. In some embodiments, each occurrence of R$^d$ is independently —CH$_3$, —OCH$_3$, —F, —Cl, —CN, —CF$_3$, —NO$_2$, —OCF$_3$, —CH(CH$_3$)$_2$, or —C(CH$_3$)$_3$. In some embodiments, each occurrence of R$^d$ is independently —CH$_3$, —OCH$_3$, or —F.

In some embodiments, R$^c$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each R$^c$ is substituted with 0-5 R$^f$.

In some embodiments, R$^c$ is 3-7 membered cycloaliphatic; 4-10-membered heterocyclyl having 1-4 heteroatoms independently selected from nitrogen, oxygen, and sulfur, wherein each R$^c$ is substituted with 0-2 R$^f$. In some embodiments, R$^c$ is tetrahydrofuranyl, tetrahydropyranyl, tetrahydrothienyl, pyrrolidinyl, pyrrolidonyl, piperidinyl, pyrrolinyl, oxazolidinyl, piperazinyl, dioxanyl, diazepinyl, oxazepinyl, thiazepinyl, morpholinyl, thiomorpholinyl, azetidinyl, cyclopropyl, cyclobutyl, cyclopentyl, cyclohexyl, cycloheptyl, cyclopentenyl, cyclohexenyl, or cycloheptenyl, each substituted with 0-2 R$^f$. In some embodiments, R$^c$ is tetrahydrofuranyl, azetidinyl, cyclopropyl, cyclobutyl, cyclopentyl, cyclohexyl, cyclohexenyl, each substituted with 0-2 R$^f$.

In some embodiments, R$^c$ is 6-10-membered aryl; or 5-10-membered heteroaryl having 1-5 heteroatoms independently selected from nitrogen, oxygen, and sulfur; wherein each $R^c$ is substituted with 0-2 $R^f$. In some embodiments, $R^c$ is azaindazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyranyl, pyridyl, pyridazinyl, pyrimidinyl, pyrazinyl, triazinyl, indolizinyl, imidazopyridyl, indolyl, isoquinolinyl, indazolyl, benzimidazolyl, benzthiazolyl, benzothienyl, benzofuranyl, benzoxazolyl, benzthiadiazolyl, pyrazolopyrimidinyl, purinyl, quinolyl, isoquinolyl, cinnolinyl, phthalazinyl, quinazolinyl, quinoxalinyl, naphthyridinyl, naphthyl, or pteridinyl, each substituted with 0-2 $R^f$. In some embodiments, $R^c$ is phenyl, pyrazolyl, pyridyl, naphthalyl, furanyl, imidazolyl, pyrimidyl, azaindazolyl, thiazolyl, indolyl, isoquinolinyl, or benzothiaphenyl, each substituted with 0-3 $R^f$. In some embodiments, $R^c$ is imidazolyl, thiazolyl, phenyl, pyridyl, furanyl, or pyrazolyl, each substituted with 0-3 $R^f$.

In some embodiments, $R^c$ is azaindazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyranyl, pyridyl, pyridazinyl, pyrimidinyl, pyrazinyl, triazinyl, indolizinyl, imidazopyridyl, indolyl, isoquinolinyl, indazolyl, benzimidazolyl, benzthiazolyl, benzothienyl, benzofuranyl, benzoxazolyl, benzthiadiazolyl, pyrazolopyrimidinyl, purinyl, quinolyl, isoquinolyl, cinnolinyl, phthalazinyl, quinazolinyl, quinoxalinyl, naphthyridinyl, naphthyl, or pteridinyl, each $R^c$ is optionally substituted by one occurrence of —$CH_3$, —$OCH_3$, or —F, and optionally substituted by one occurrence of —$CH_3$, —$OCH_3$, —F, —Cl, —CN, —$CF_3$, —$NO_2$, —$OCF_3$, —$OCH(CH_3)_2$, or —$C(CH_3)_3$. In some embodiments, $R^c$ is imidazolyl, thiazolyl, phenyl, pyridyl, furanyl, or pyrazolyl, each $R^c$ is optionally substituted by one occurrence of —$CH_3$, —$OCH_3$, or —F, and optionally substituted by one occurrence of —$CH_3$, —$OCH_3$, —F, —Cl, —$CF_3$, or —$OCF_3$.

In some embodiments, each occurrence of $R^f$ is independently halo, —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —$SO_2CH_3$, —$S(O)CH_3$, or —O—$CH_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^f$ is independently halo, —OH, —CN, $C_{1-4}$ aliphatic, —O—$C_{1-3}$ aliphatic, —O—$C_{1-3}$ fluoroaliphatic, or two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^f$ is independently —F, —Cl, —CN, —$NO_2$, —$CH_3$, —$OCF_3$, —$CF_3$, —OH, —$OCH(CH_3)_2$, —$OC(CH_3)_3$, —$OCH_3$, or two occurrences of $R^f$ are taken together to form

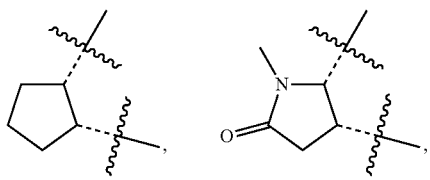

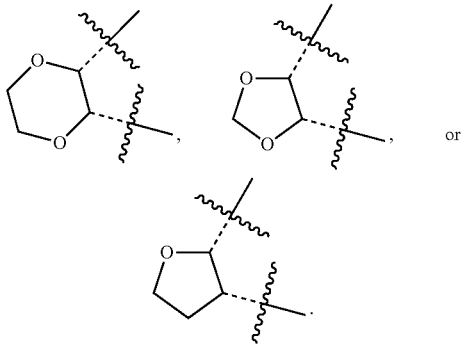

In some embodiments, each occurrence of $R^f$ is independently —$CH_3$, —$OCH_3$, —F, —Cl, —CN, —$CF_3$, —$NO_2$, —$OCF_3$, —$OCH(CH_3)_2$, or —$C(CH_3)_3$. In some embodiments, each occurrence of $R^f$ is independently is —F, —Cl, —CN, —$NO_2$, —$CH_3$, —$OCH_3$, —$OCF_3$, —$OCHF_2$, —$OCH_2F$, —$CHF_2$, or —$CH_2F$. In some embodiments, each occurrence of $R^f$ is independently —$CH_3$, —$OCH_3$, or —F. In some embodiments, two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$.

In some embodiments, each occurrence of $R^f$ is independently $R^{fb}$, wherein $R^{fb}$ is halo, —OH, —CN, $C_{1-4}$ aliphatic, —O—$C_{1-3}$ aliphatic, —O—$C_{1-3}$ fluoroaliphatic, —N($R^e$)$_2$, or —C(O)—N($R^e$)$_2$. In some embodiments, each occurrence of $R^f$ is independently $R^{fa}$, wherein $R^{fa}$ is halo, —OH, —CN, or $C_{1-4}$ aliphatic.

In some embodiments, $R^{bb}$ is $C_{1-3}$ aliphatic substituted with 0-5 $R^{bx}$, wherein $R^{bx}$ has the values described herein. In some embodiments, $R^{bb}$ is $C_{1-3}$ aliphatic substituted with 0-2 $R^{bx}$, wherein $R^{bx}$ has the values described herein. In some embodiments, $R^{bb}$ is —$CH_3$, —$CH_2CH_3$, —$CH_2CH_2CH_3$, —$CH(CH_3)_2$, —CH=$CH_2$, —C≡CH, or —C≡$CCH_3$.

In some embodiments, $R^{dd}$ is $C_{1-3}$ aliphatic substituted with 0-5 $R^{dx}$, wherein $R^{dx}$ has the values described herein. In some embodiments, $R^{dd}$ is $C_{1-3}$ aliphatic substituted with 0-2 $R^{dx}$, wherein $R^{dx}$ has the values described herein. In some embodiments, $R^{dd}$ is —$CH_3$, —$CH_2CH_3$, —$CH_2CH_2CH_3$, —$CH(CH_3)_2$, or —$CH_2$—CH=$CH_2$. In some embodiments, $R^{dd}$ is —$CH_3$, or —$CH_2CH_3$.

In some embodiments, $R^{ee}$ is $C_{1-3}$ aliphatic substituted with 0-5 $R^{fx}$, wherein $R^{fx}$ has the values described herein. In some embodiments, $R^{ee}$ is $C_{1-3}$ aliphatic substituted with 0-2 $R^{fx}$, wherein $R^{fx}$ has the values described herein. In some embodiments, $R^{ee}$ is $C_{1-3}$ aliphatic optionally substituted with one occurrence of —$CH_3$ or —$CH_2CH_3$ and optionally substituted with one occurrence of —OH, —CN, —$OCH_3$, —N($R^e$)$_2$, or —C(O)—N($R^e$)$_2$. In some embodiments, $R^{ee}$ is —$CH_3$, —$CH_2CH_3$, —$CH_2CH_2CH_3$, —$CH(CH_3)_2$, or —$CH_2$C≡CH. In some embodiments, $R^{ee}$ is —$CH_3$, or —$CH_2CH_3$.

In some embodiments, each occurrence of $R^{bx}$ is independently —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —$SO_2CH_3$, —$S(O)CH_3$, or —O—$CH_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{bx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{bx}$ is independently —OH, —CN, —NO$_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, $C_{1-3}$ aliphatic, or —O—$C_{1-3}$ aliphatic. In some embodiments, each occurrence of $R^{bx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$, or 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{bx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$. In some embodiments, $R^{bx}$ is —OH, —CN, —O—CH$_3$, —S—CH$_3$, —CH$_3$, —NH$_2$, or —OCH$_2$-phenyl.

In some embodiments, each occurrence of $R^{dx}$ is independently —Cl, —OH, —CN, —NO$_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{dx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{dx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$, or 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{dx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$. In some embodiments, each $R^{fx}$ is independently —Cl, —OH, —CN, —CH$_3$, —CH$_2$CH$_3$, —OCH$_3$, —N(CH$_3$)$_2$, —N(CH$_2$CH$_3$)$_2$, —C(O)N(CH$_3$)$_2$, or —C(O)NH$_2$. In some embodiments, $R^{dx}$ is —Cl.

In some embodiments, each occurrence of $R^{fx}$ is independently —OH, —CN, —NO$_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N(R$^e$)$_2$, —C(O)—N(R$^e$)$_2$, —SO$_2$CH$_3$, —S(O)CH$_3$, or —O—CH$_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{fx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{fx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$, or 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$. In some embodiments, each occurrence of $R^{fx}$ is independently —OH, —CN, $C_{1-4}$ aliphatic, —O—$C_{1-3}$ aliphatic, $C_{1-3}$ fluoroaliphatic, —N(R$^e$)$_2$, or —C(O)—N(R$^e$)$_2$. In some embodiments, each $R^{fx}$ is independently —OH, —CN, —CH$_3$, —CH$_2$CH$_3$, —OCH$_3$, —N(CH$_3$)$_2$, —N(CH$_2$CH$_3$)$_2$, —C(O)N(CH$_3$)$_2$, or —C(O)NH$_2$.

In some embodiments, $R^g$ is $C_{1-3}$ aliphatic. In some embodiments, $R^g$ is —CH$_3$, —CH$_2$CH$_3$, —CH$_2$CH$_2$CH$_3$, —CH(CH$_3$)$_2$, —CH=CH$_2$, or —C≡CH. In some embodiments, $R^g$ is —CH$_3$.

In some embodiments, $R^e$ is hydrogen or $C_{1-3}$ aliphatic. In some embodiments, $R^e$ is hydrogen, —CH$_3$, —CH$_2$CH$_3$, —CH$_2$CH$_2$CH$_3$, or —CH(CH$_3$)$_2$. In some embodiments, $R^e$ is hydrogen, —CH$_3$, —CH$_2$CH$_3$.

In some embodiments, $R^a$ is —CH$_2$OCH$_2$-phenyl, —CH$_2$CH$_2$-phenyl, thiazolyl, —O— phenyl, phenyl, oxazolyl, pyrazolyl, —OCH$_2$-phenyl, or cyclopropyl.

In some embodiments, $R^a$ is

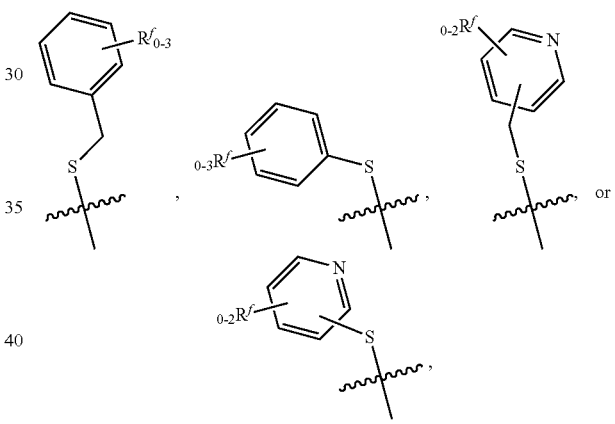

wherein $R^f$ has the value described herein.

In some embodiments, $R^a$ is

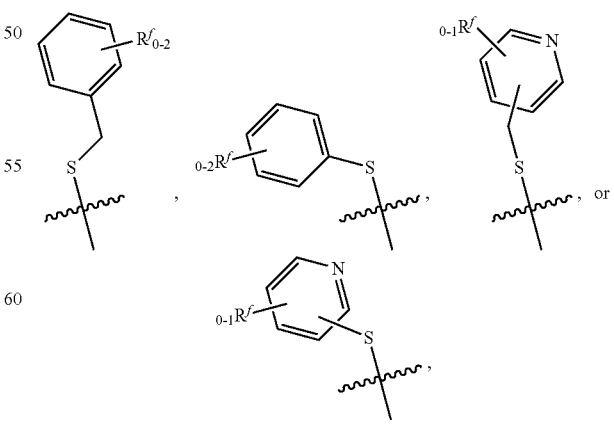

wherein $R^f$ has the value described herein.

In some embodiments, $R^a$ is

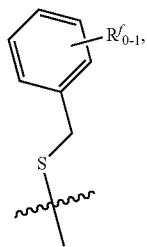

wherein $R^f$ has the value described herein.
In some embodiments, $R^a$ is

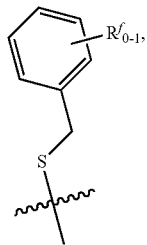

wherein $R^f$ is —F, —Cl, —CN, —CH$_3$, —OCH$_3$, —OCF$_3$, —OCHF$_2$, —OCH$_2$F, —CHF$_2$, —CF$_3$, or —CH$_2$F. In some embodiments, $R^a$ is

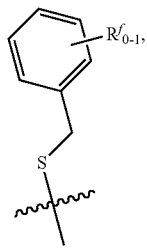

wherein $R^f$ is —F, —CH$_3$, —OCH$_3$, —OCF$_3$, or —CF$_3$.
In some embodiments, $R^a$ is

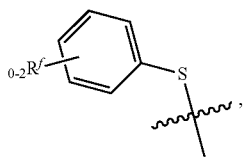

wherein $R^f$ has the value described herein. In some embodiments, $R^a$ is

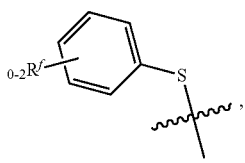

wherein each $R^f$ is independently —F, —Cl, —CN, —CH$_3$, —C(CH$_3$)$_3$, —OCH$_3$, —OCH(CH$_3$)$_3$, —OCF$_3$, —OCHF$_2$, —OCH$_2$F, —CHF$_2$, —CF$_3$, or —CH$_2$F. In some embodiments, $R^a$ is

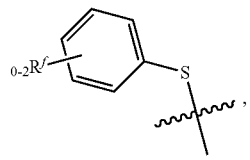

wherein each $R^f$ is independently —F, —Cl, —CH$_3$, or —OCH$_3$.
In some embodiments, $R^a$ is

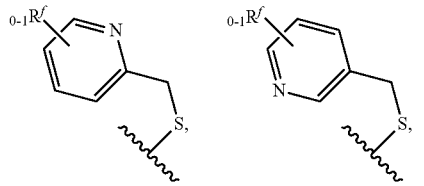 or

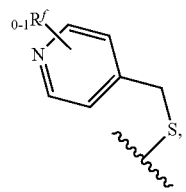

has the value described herein.
In some embodiments, $R^a$ is

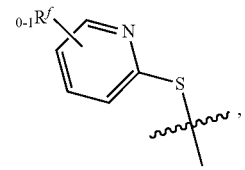

wherein $R^f$ has the value described herein. In some embodiments, $R^a$ is

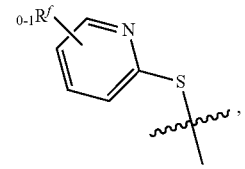

wherein $R^f$ is —F, —Cl, —CN, —NO$_2$, —CH$_3$, —OCH$_3$, or —CF$_3$. In some embodiments, $R^a$ is

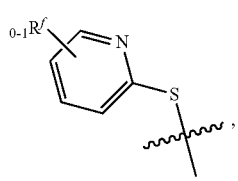
wherein $R^f$ is —Cl, —CH$_3$, or —CF$_3$. In some embodiments, $R^a$ is
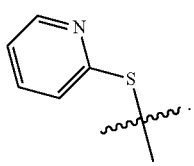 [SMILES: *Sc1ccccn1]
Representative examples of the chemical entities of formula (I) are shown below in Table 1.
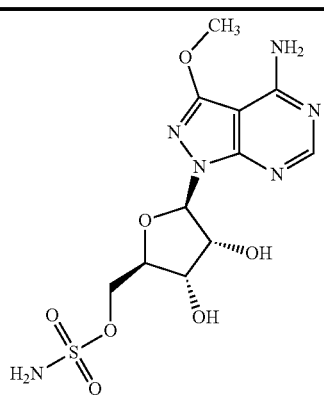
I-1
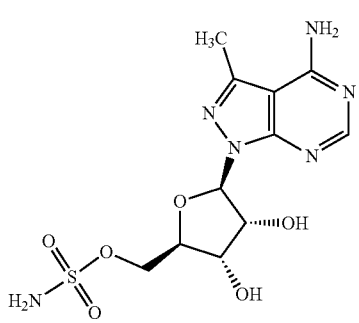 [SMILES: Cc1nn([C@@H]2O[C@H](COS(N)(=O)=O)[C@@H](O)[C@H]2O)c2ncnc(N)c12]
I-2
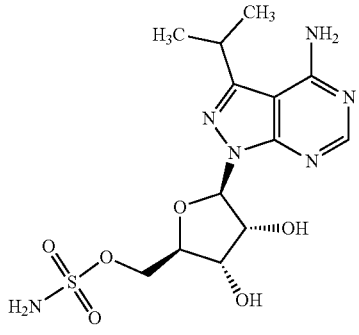 [SMILES: CC(C)c1nn([C@@H]2O[C@H](COS(N)(=O)=O)[C@@H](O)[C@H]2O)c2ncnc(N)c12]
I-3
-continued
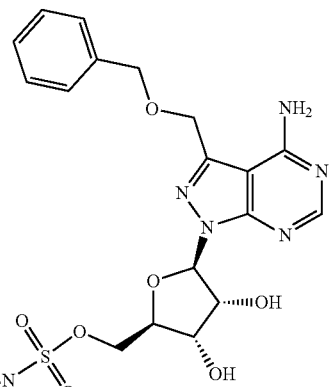
I-4
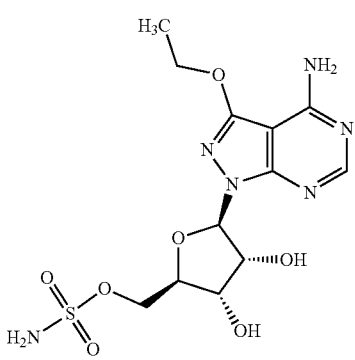 [SMILES: CCOc1nn([C@@H]2O[C@H](COS(N)(=O)=O)[C@@H](O)[C@H]2O)c2ncnc(N)c12]
I-5
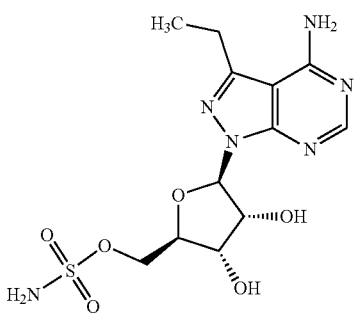 [SMILES: CCc1nn([C@@H]2O[C@H](COS(N)(=O)=O)[C@@H](O)[C@H]2O)c2ncnc(N)c12]
I-6
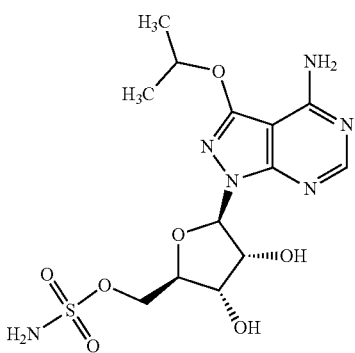 [SMILES: CC(C)Oc1nn([C@@H]2O[C@H](COS(N)(=O)=O)[C@@H](O)[C@H]2O)c2ncnc(N)c12]
I-7

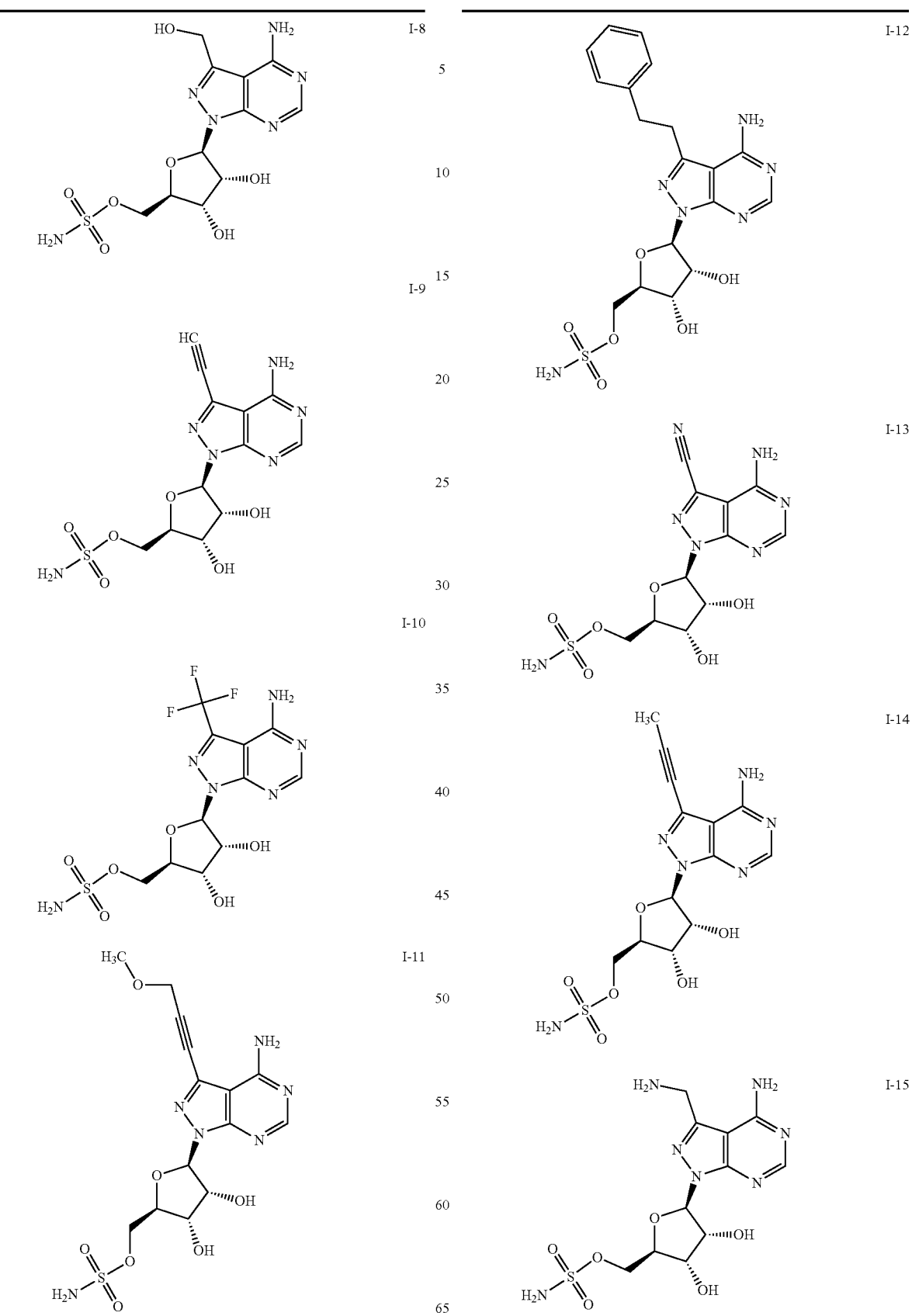

| 25 -continued | 26 -continued |
|---|---|
| 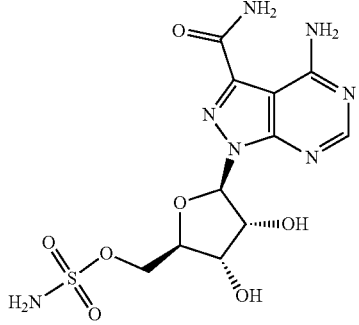 [SMILES: NC(=O)c1nn([C@@H]2O[C@H](COS(N)(=O)=O)[C@@H](O)[C@H]2O)c2ncnc(N)c12] I-16 | 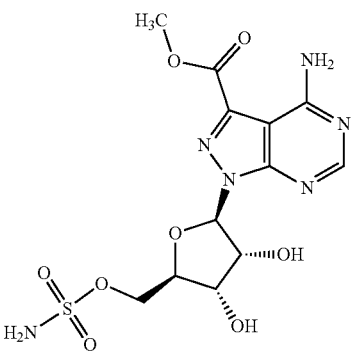 I-20 |
| 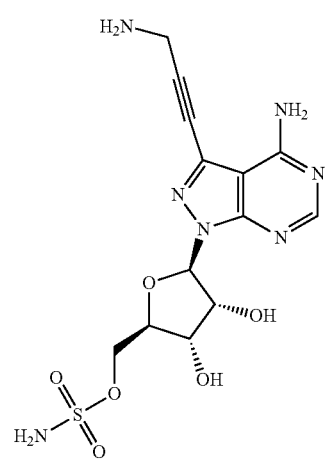 [SMILES: NCC#Cc1nn([C@@H]2O[C@H](COS(N)(=O)=O)[C@@H](O)[C@H]2O)c2ncnc(N)c12] I-17 | 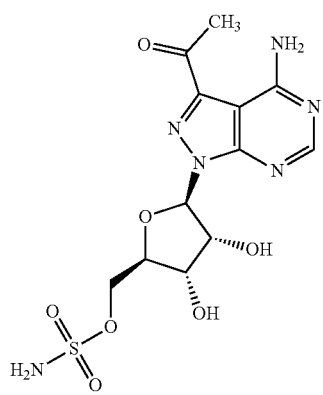 I-21 |
| 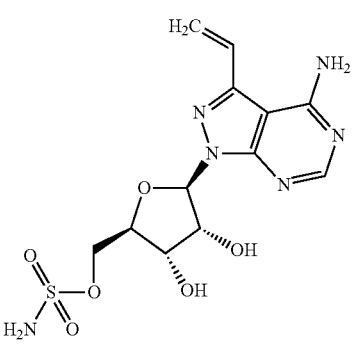 [SMILES: C=Cc1nn([C@@H]2O[C@H](COS(N)(=O)=O)[C@@H](O)[C@H]2O)c2ncnc(N)c12] I-18 | 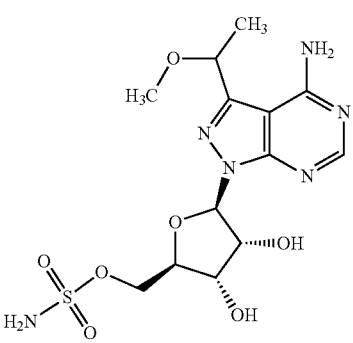 I-22 |
| 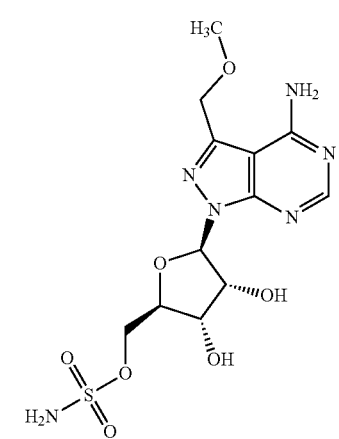 [SMILES: COCc1nn([C@@H]2O[C@H](COS(N)(=O)=O)[C@@H](O)[C@H]2O)c2ncnc(N)c12] I-19 | 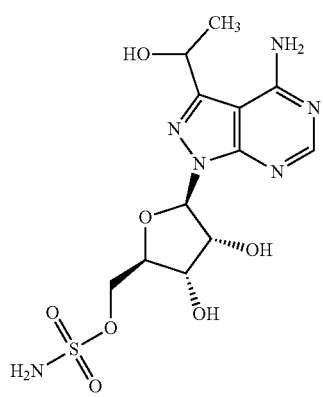 [SMILES: CC(O)c1nn([C@@H]2O[C@H](COS(N)(=O)=O)[C@@H](O)[C@H]2O)c2ncnc(N)c12] I-23a<br>I-23b |

| 27 -continued | 28 -continued |
|---|---|
| I-24 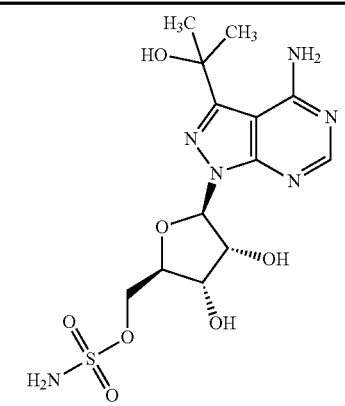 | I-28 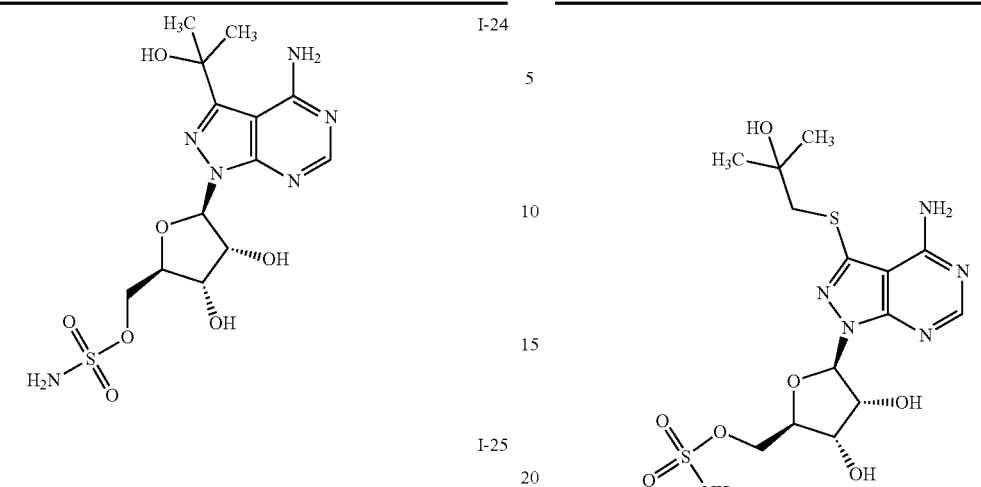 |
| I-25 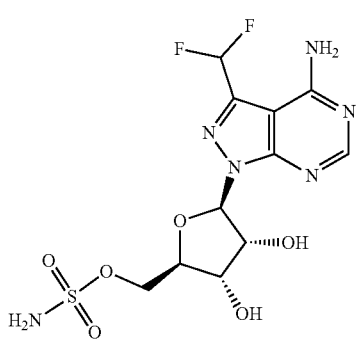 [SMILES: Nc1ncnc2c1c(C(F)F)nn2[C@@H]1O[C@H](COS(N)(=O)=O)[C@@H](O)[C@H]1O] | I-29 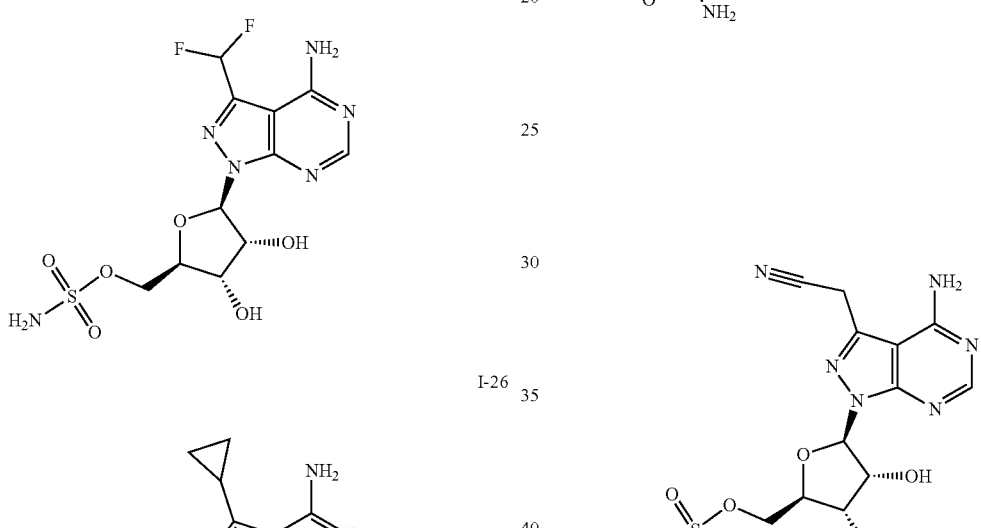 |
| I-26 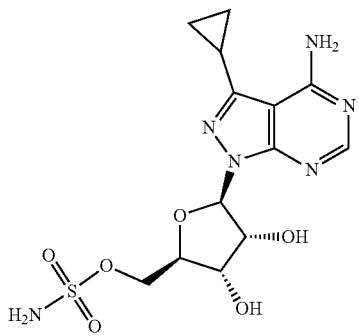 [SMILES: Nc1ncnc2c1c(C1CC1)nn2[C@@H]1O[C@H](COS(N)(=O)=O)[C@@H](O)[C@H]1O] | |
| I-27 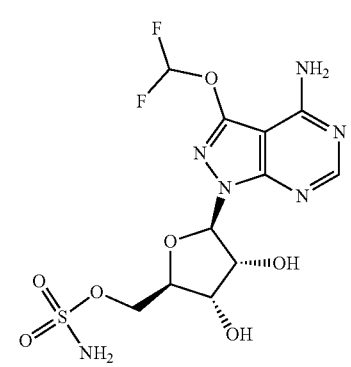 [SMILES: Nc1ncnc2c1c(OC(F)F)nn2[C@@H]1O[C@H](COS(N)(=O)=O)[C@@H](O)[C@H]1O] | I-30 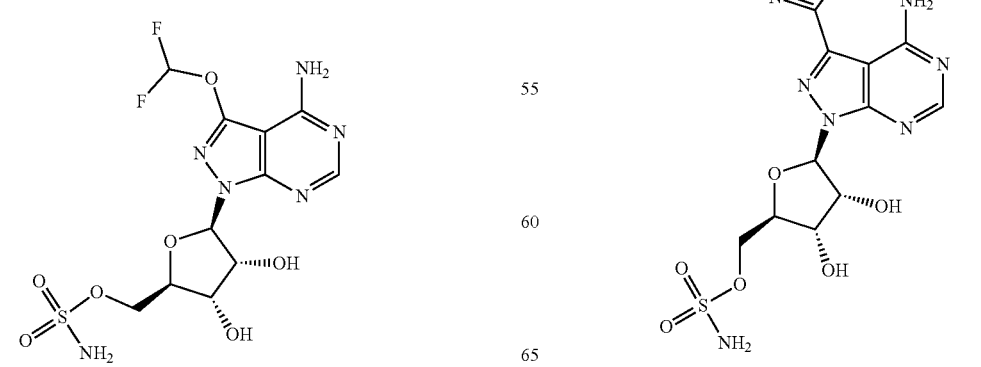 |

I-31
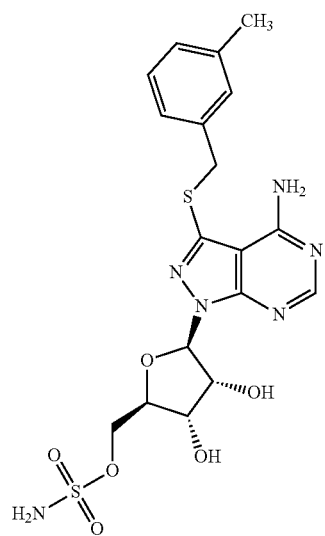 [SMILES: Cc1cccc(CSc2nn([C@@H]3O[C@H](COS(N)(=O)=O)[C@@H](O)[C@H]3O)c3ncnc(N)c23)c1]
I-32
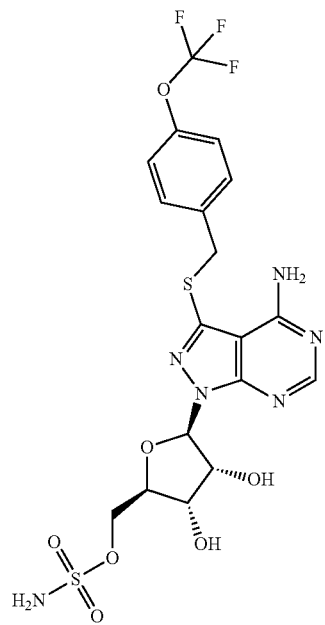 [SMILES: Nc1ncnc2c1c(SCc1ccc(OC(F)(F)F)cc1)nn2[C@@H]1O[C@H](COS(N)(=O)=O)[C@@H](O)[C@H]1O]
I-33
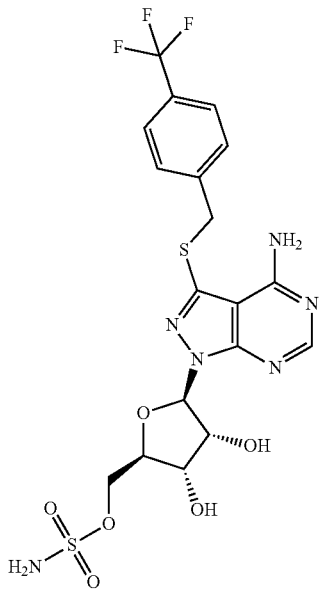 [SMILES: Nc1ncnc2c1c(SCc1ccc(C(F)(F)F)cc1)nn2[C@@H]1O[C@H](COS(N)(=O)=O)[C@@H](O)[C@H]1O]
I-34
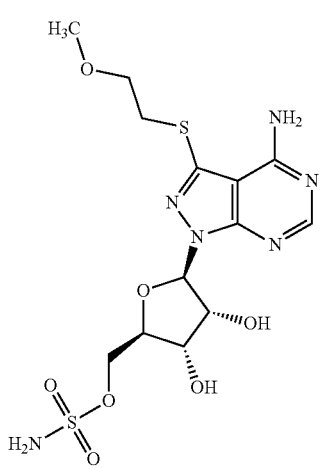 [SMILES: COCCSc1nn([C@@H]2O[C@H](COS(N)(=O)=O)[C@@H](O)[C@H]2O)c2ncnc(N)c12]
I-35

-continued
I-36
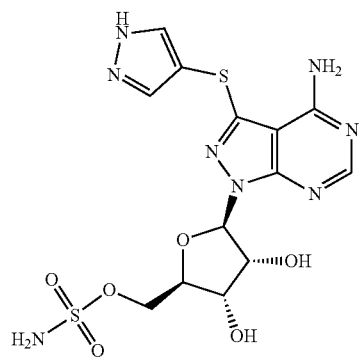 [SMILES: Nc1ncnc2c1c(Sc1cn[nH]c1)nn2[C@@H]1O[C@H](COS(N)(=O)=O)[C@@H](O)[C@H]1O]
I-37
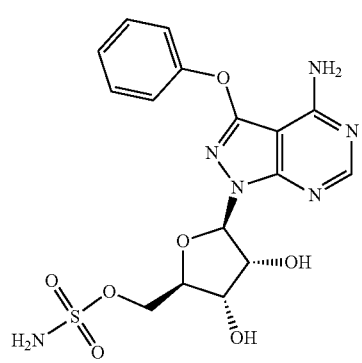 [SMILES: Nc1ncnc2c1c(Oc1ccccc1)nn2[C@@H]1O[C@H](COS(N)(=O)=O)[C@@H](O)[C@H]1O]
I-38
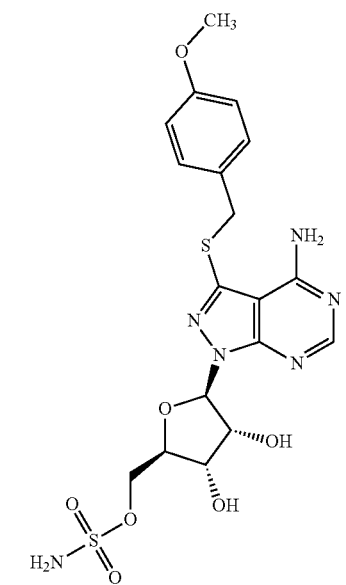 [SMILES: COc1ccc(CSc2nn([C@@H]3O[C@H](COS(N)(=O)=O)[C@@H](O)[C@H]3O)c3ncnc(N)c23)cc1]
-continued
I-39
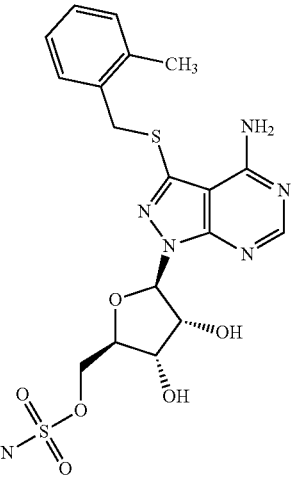
I-40
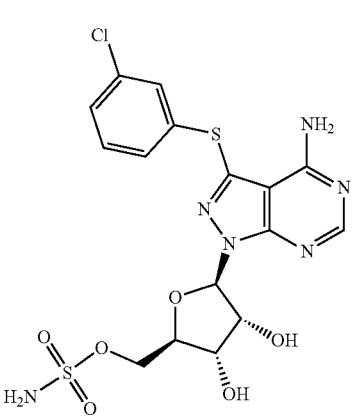 [SMILES: Nc1ncnc2c1c(Sc1cccc(Cl)c1)nn2[C@@H]1O[C@H](COS(N)(=O)=O)[C@@H](O)[C@H]1O]
I-41
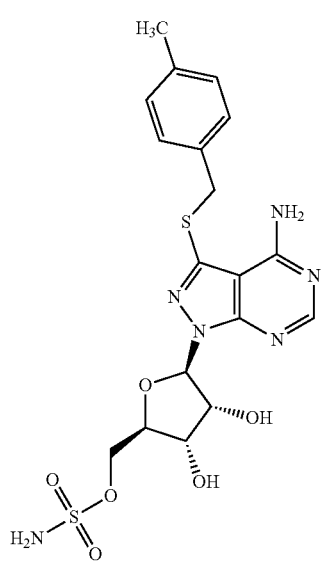 [SMILES: Cc1ccc(CSc2nn([C@@H]3O[C@H](COS(N)(=O)=O)[C@@H](O)[C@H]3O)c3ncnc(N)c23)cc1]

-continued
I-42
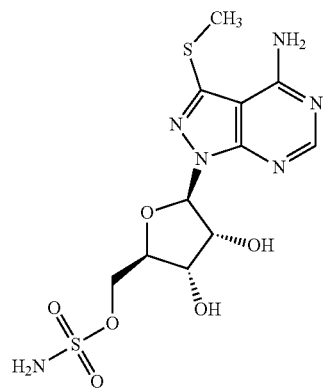 [SMILES: CSc1nn([C@@H]2O[C@H](COS(N)(=O)=O)[C@@H](O)[C@H]2O)c2ncnc(N)c12]
I-43
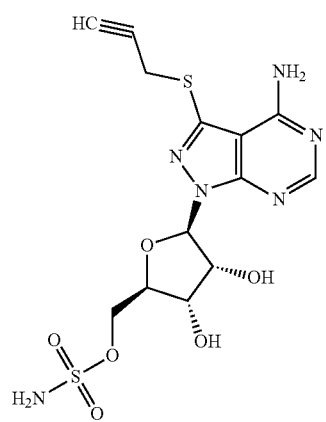 [SMILES: C#CCSc1nn([C@@H]2O[C@H](COS(N)(=O)=O)[C@@H](O)[C@H]2O)c2ncnc(N)c12]
I-44
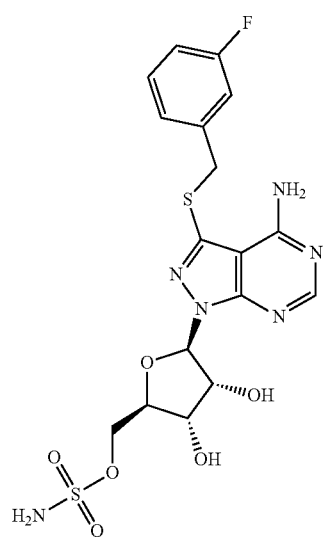 [SMILES: Nc1ncnc2c1c(SCc1cccc(F)c1)nn2[C@@H]1O[C@H](COS(N)(=O)=O)[C@@H](O)[C@H]1O]
-continued
I-45
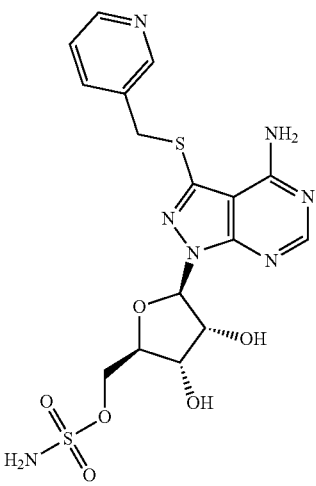 [SMILES: Nc1ncnc2c1c(SCc1cccnc1)nn2[C@@H]1O[C@H](COS(N)(=O)=O)[C@@H](O)[C@H]1O]
I-46
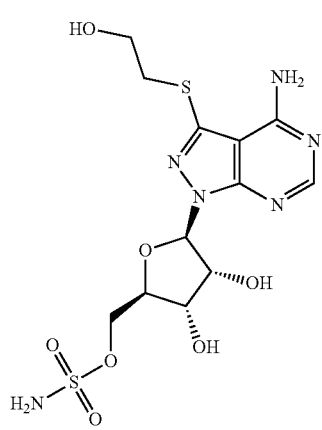 [SMILES: Nc1ncnc2c1c(SCCO)nn2[C@@H]1O[C@H](COS(N)(=O)=O)[C@@H](O)[C@H]1O]
I-47
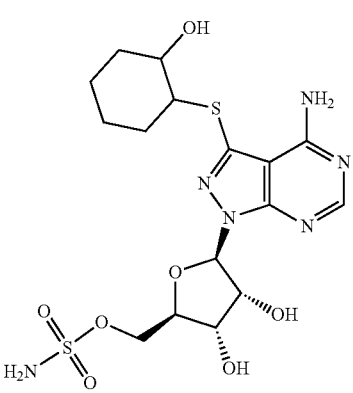 [SMILES: Nc1ncnc2c1c(SC1CCCCC1O)nn2[C@@H]1O[C@H](COS(N)(=O)=O)[C@@H](O)[C@H]1O]
I-48
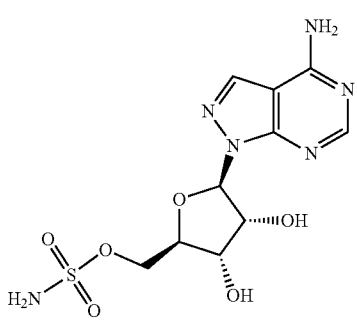 [SMILES: Nc1ncnc2c1cnn2[C@@H]1O[C@H](COS(N)(=O)=O)[C@@H](O)[C@H]1O]

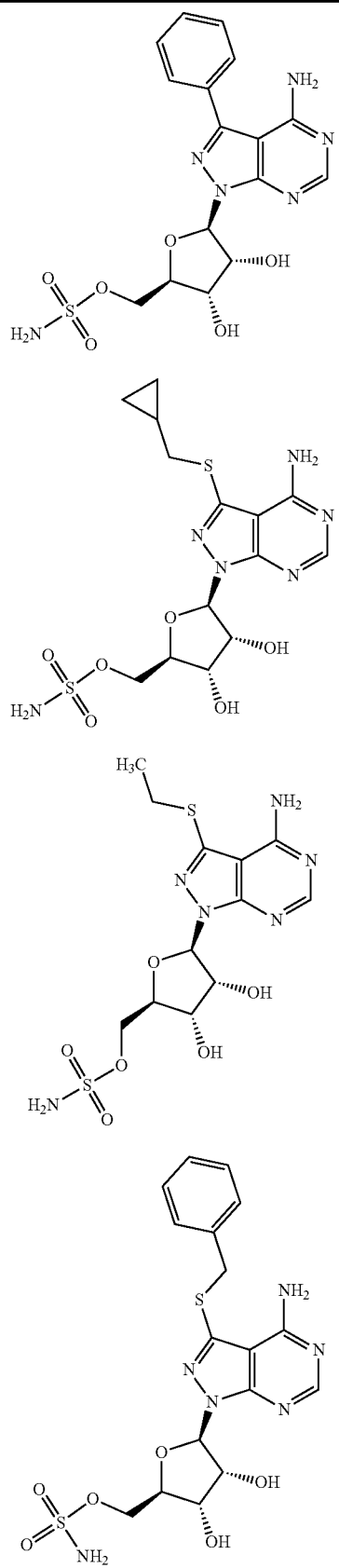
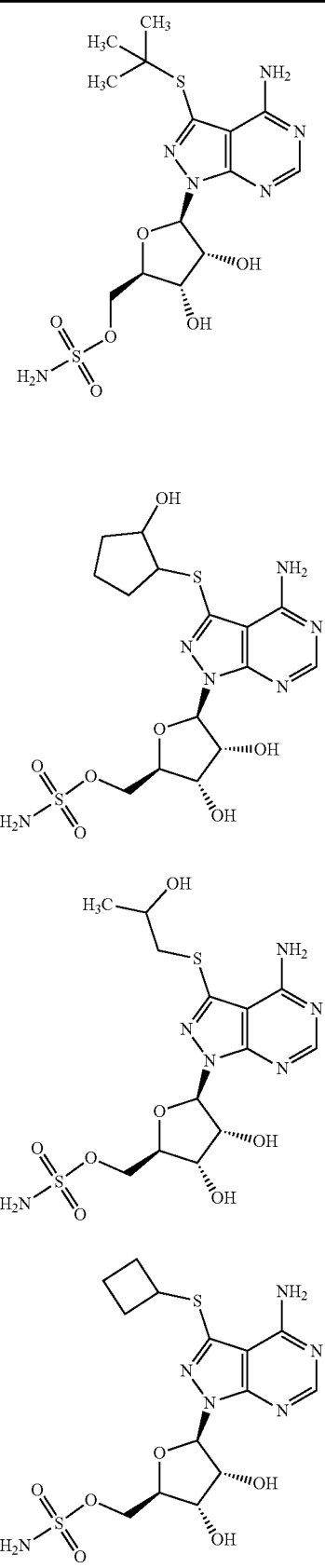

I-57
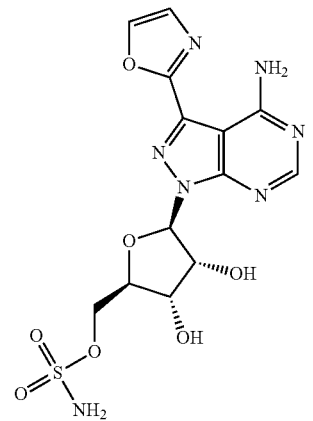 [SMILES: Nc1ncnc2c1c(-c1ncco1)nn2[C@@H]1O[C@H](COS(N)(=O)=O)[C@@H](O)[C@H]1O]
I-58
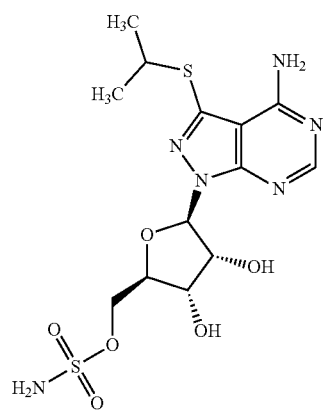 [SMILES: CC(C)Sc1nn([C@@H]2O[C@H](COS(N)(=O)=O)[C@@H](O)[C@H]2O)c2ncnc(N)c12]
I-59
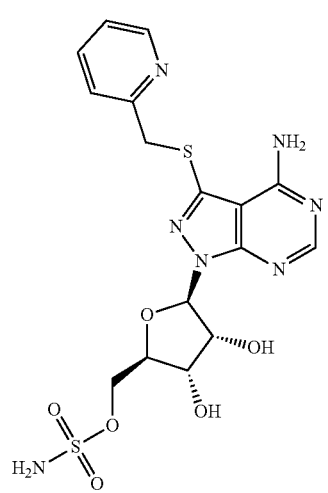 [SMILES: Nc1ncnc2c1c(SCc1ccccn1)nn2[C@@H]1O[C@H](COS(N)(=O)=O)[C@@H](O)[C@H]1O]
I-60
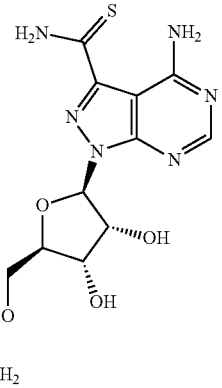
I-61
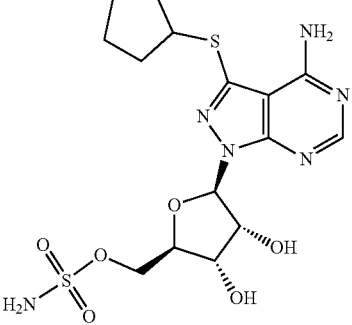
I-62
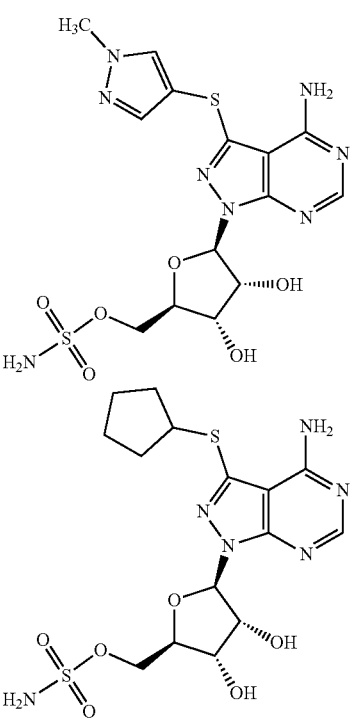
I-63
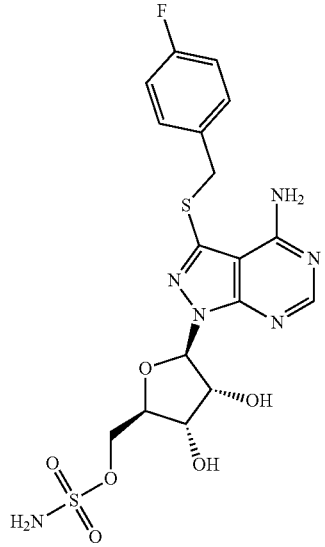 [SMILES: Nc1ncnc2c1c(SCc1ccc(F)cc1)nn2[C@@H]1O[C@H](COS(N)(=O)=O)[C@@H](O)[C@H]1O]

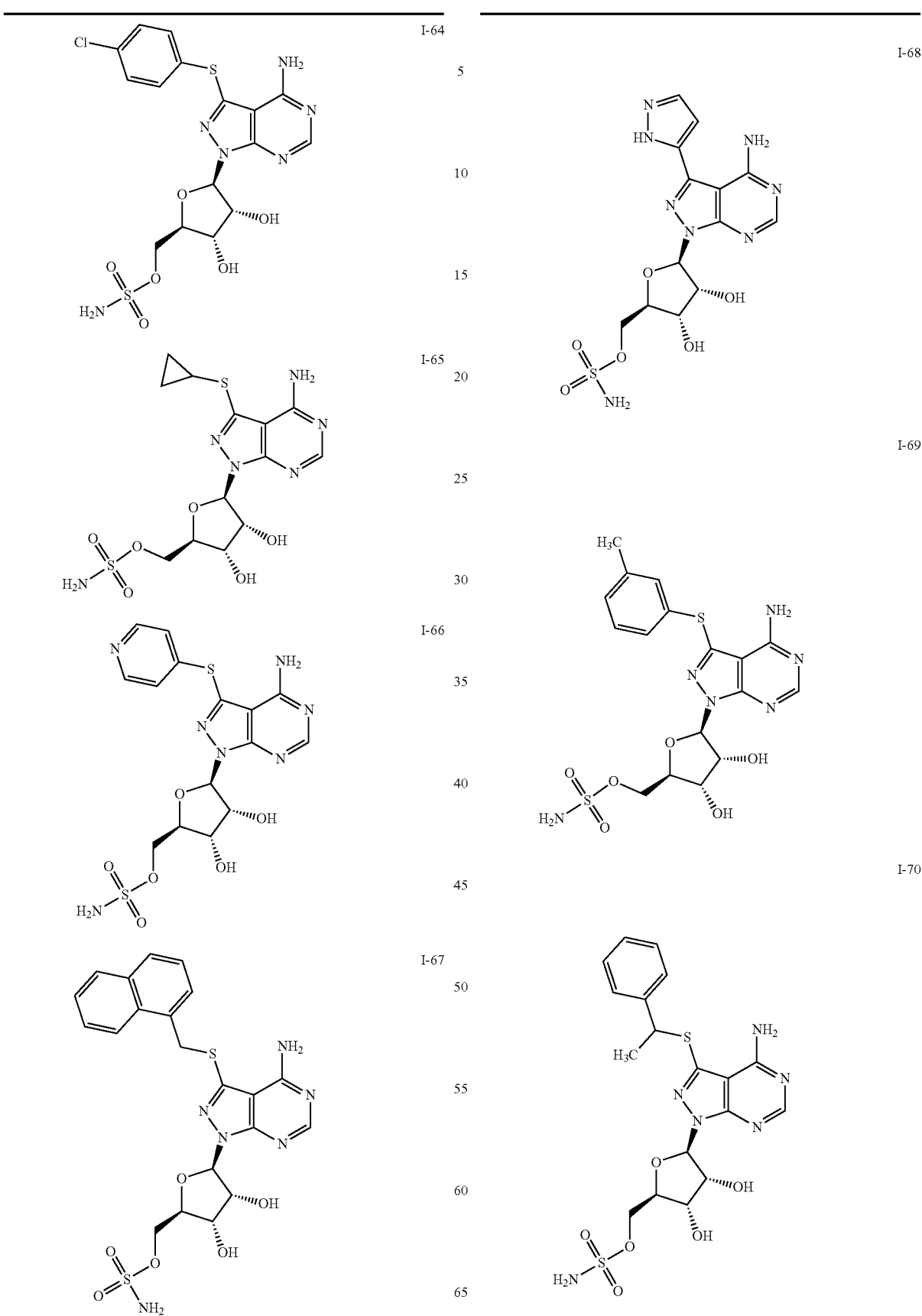

| 41 -continued | 42 -continued |
|---|---|
| I-71 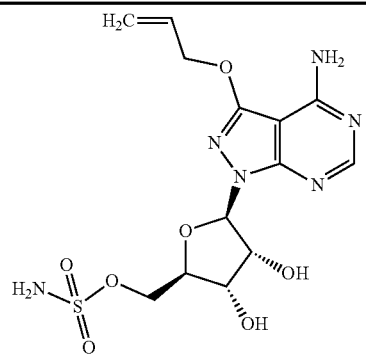 | I-75 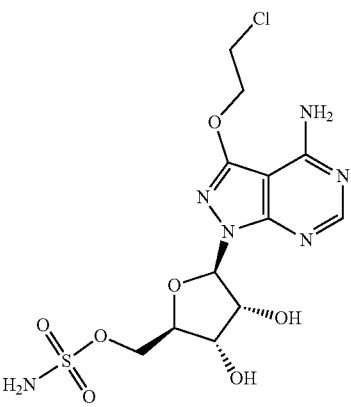 |
| I-72 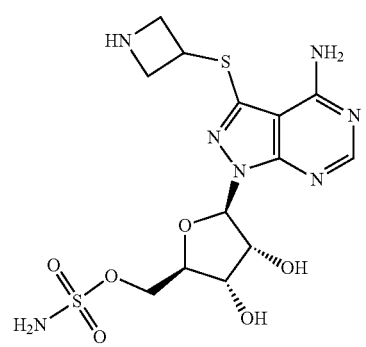 [SMILES: Nc1ncnc2c1c(SC1CNC1)nn2[C@@H]1O[C@H](COS(N)(=O)=O)[C@@H](O)[C@H]1O] | I-76 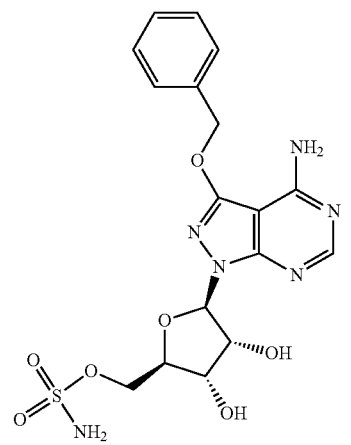 |
| I-73 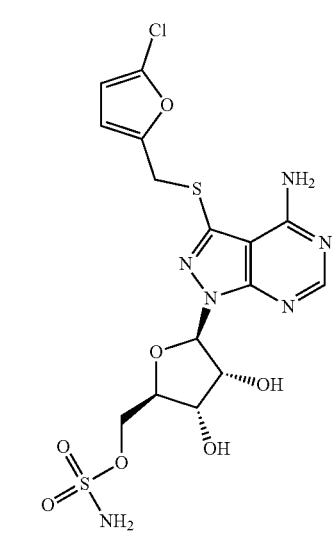 [SMILES: Nc1ncnc2c1c(SCc1ccc(Cl)o1)nn2[C@@H]1O[C@H](COS(N)(=O)=O)[C@@H](O)[C@H]1O] | I-77 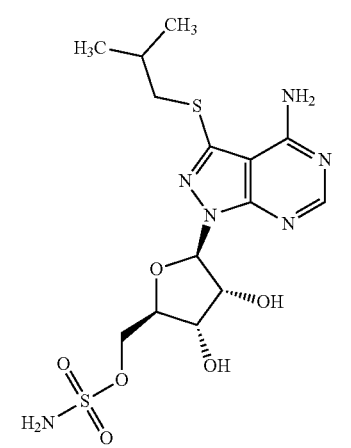 |
| I-74 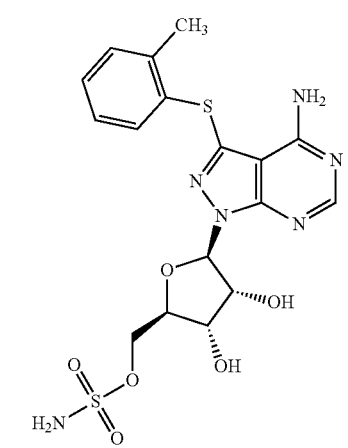 [SMILES: Cc1ccccc1Sc1nn([C@@H]2O[C@H](COS(N)(=O)=O)[C@@H](O)[C@H]2O)c2ncnc(N)c12] | |

-continued
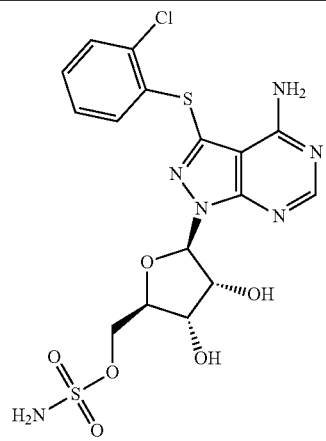
I-78
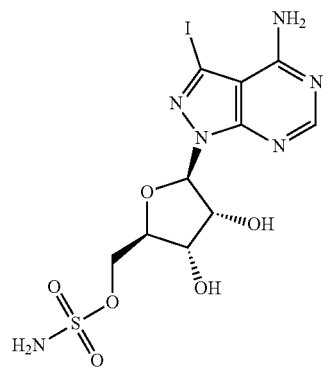 [SMILES: Nc1ncnc2c1c(I)nn2[C@@H]1O[C@H](COS(N)(=O)=O)[C@@H](O)[C@H]1O]
I-79
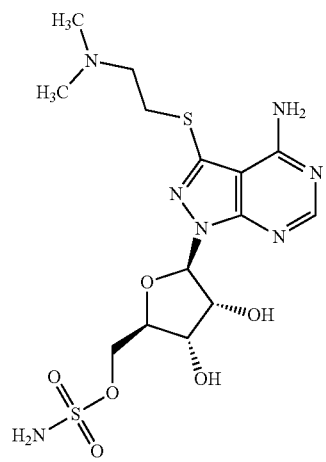 [SMILES: CN(C)CCSc1nn([C@@H]2O[C@H](COS(N)(=O)=O)[C@@H](O)[C@H]2O)c2ncnc(N)c12]
I-80
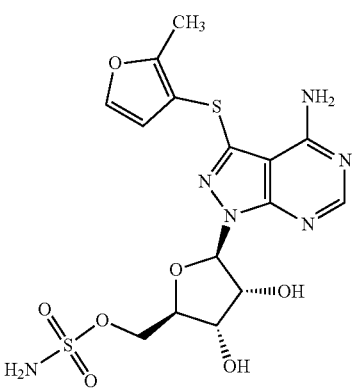 [SMILES: Cc1occc1Sc1nn([C@@H]2O[C@H](COS(N)(=O)=O)[C@@H](O)[C@H]2O)c2ncnc(N)c12]
I-81
-continued
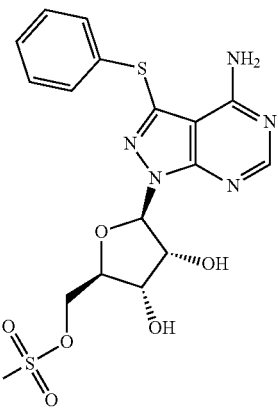
I-82
I-83
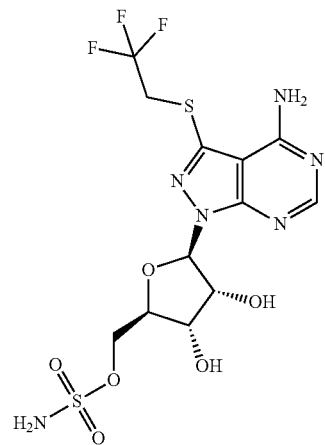 [SMILES: Nc1ncnc2c1c(SCC(F)(F)F)nn2[C@@H]1O[C@H](COS(N)(=O)=O)[C@@H](O)[C@H]1O]
I-84
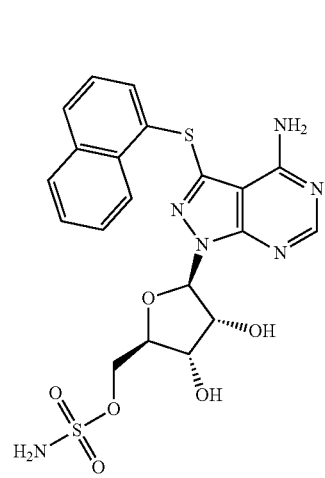 [SMILES: Nc1ncnc2c1c(Sc1cccc3ccccc13)nn2[C@@H]1O[C@H](COS(N)(=O)=O)[C@@H](O)[C@H]1O]

| 45 -continued | 46 -continued |
|---|---|
| I-85 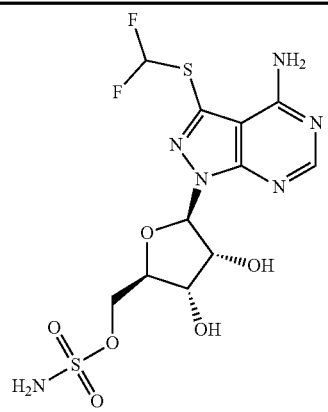 | I-89 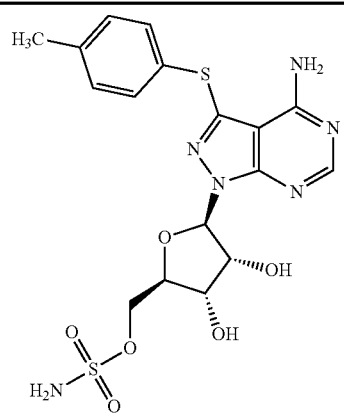 |
| I-86 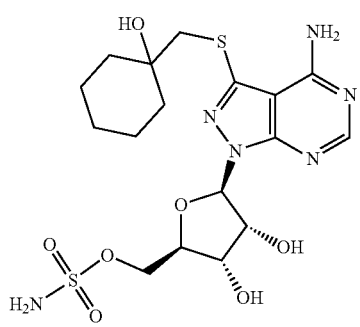 [SMILES: Nc1ncnc2c1c(SCC1(O)CCCCC1)nn2[C@@H]1O[C@H](COS(N)(=O)=O)[C@@H](O)[C@H]1O] | I-90 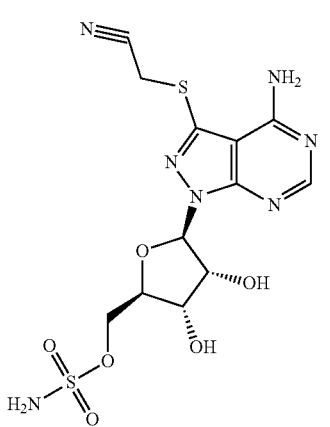 |
| I-87 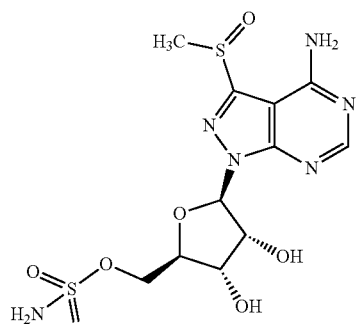 | I-91 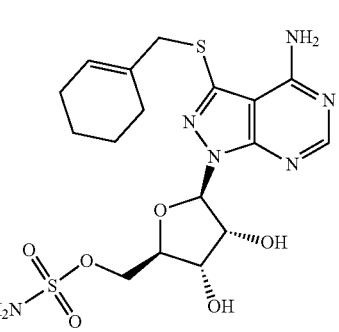 |
| I-88 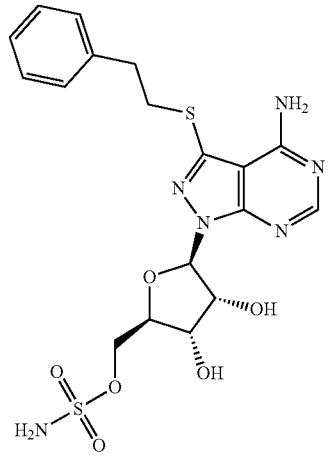 [SMILES: Nc1ncnc2c1c(SCCc1ccccc1)nn2[C@@H]1O[C@H](COS(N)(=O)=O)[C@@H](O)[C@H]1O] | I-92 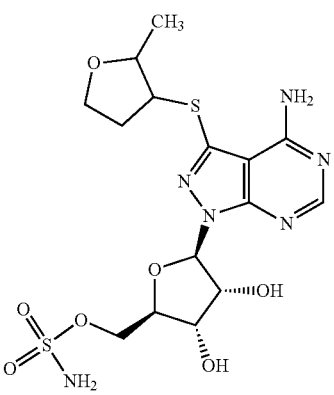 [SMILES: CC1OCCC1Sc1nn([C@@H]2O[C@H](COS(N)(=O)=O)[C@@H](O)[C@H]2O)c2ncnc(N)c12] |

I-93 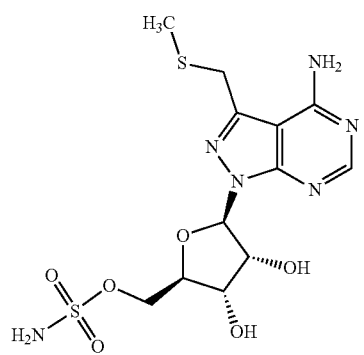 [SMILES: CSCc1nn([C@@H]2O[C@H](COS(N)(=O)=O)[C@@H](O)[C@H]2O)c2ncnc(N)c12]
I-94 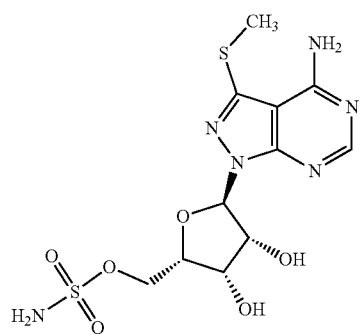 [SMILES: CSc1nn([C@@H]2O[C@@H](COS(N)(=O)=O)[C@@H](O)[C@H]2O)c2ncnc(N)c12]
I-95 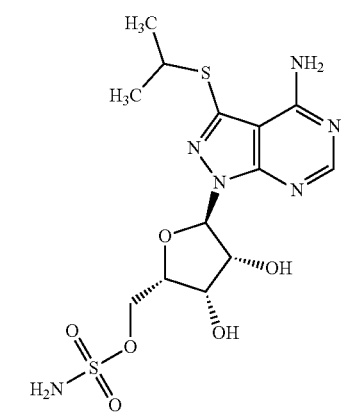 [SMILES: CC(C)Sc1nn([C@@H]2O[C@@H](COS(N)(=O)=O)[C@@H](O)[C@H]2O)c2ncnc(N)c12]
I-96 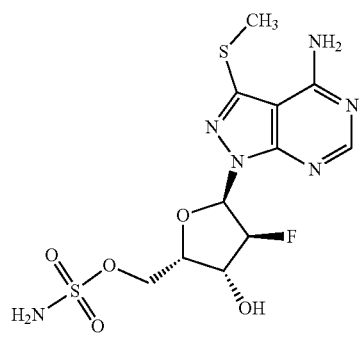 [SMILES: CSc1nn([C@@H]2O[C@@H](COS(N)(=O)=O)[C@@H](O)[C@@H]2F)c2ncnc(N)c12]
I-97 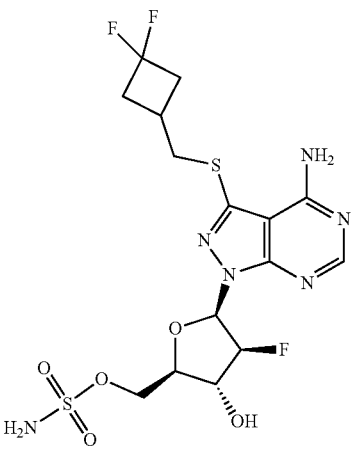 [SMILES: Nc1ncnc2c1c(SCC1CC(F)(F)C1)nn2[C@@H]1O[C@H](COS(N)(=O)=O)[C@@H](O)[C@@H]1F]
I-98 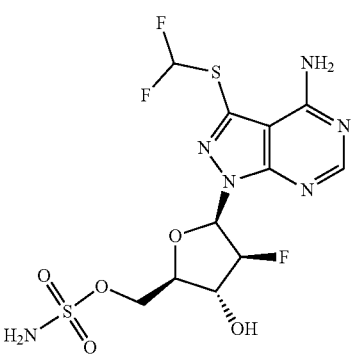
I-99 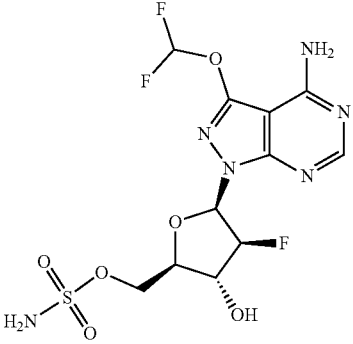 [SMILES: Nc1ncnc2c1c(OC(F)F)nn2[C@@H]1O[C@H](COS(N)(=O)=O)[C@@H](O)[C@@H]1F]
I-100 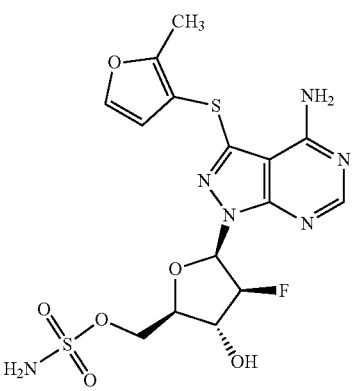 [SMILES: Cc1occc1Sc1nn([C@@H]2O[C@H](COS(N)(=O)=O)[C@@H](O)[C@@H]2F)c2ncnc(N)c12]

-continued
I-101
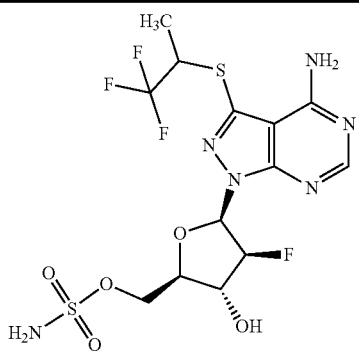
I-102
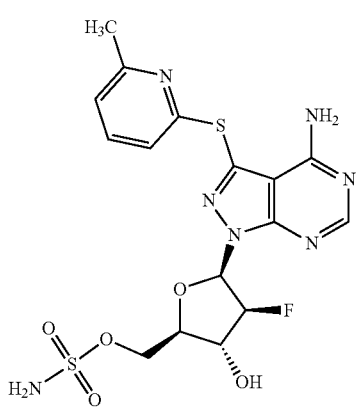 [SMILES: Cc1cccc(Sc2nn([C@@H]3O[C@H](COS(N)(=O)=O)[C@@H](O)[C@@H]3F)c3ncnc(N)c23)n1]
I-103
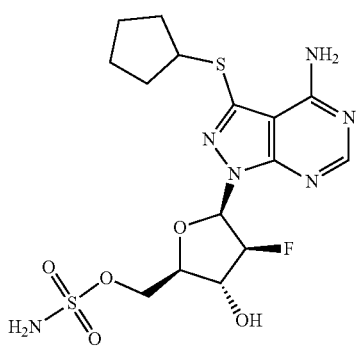 [SMILES: Nc1ncnc2c1c(SC1CCCC1)nn2[C@@H]1O[C@H](COS(N)(=O)=O)[C@@H](O)[C@@H]1F]
I-104
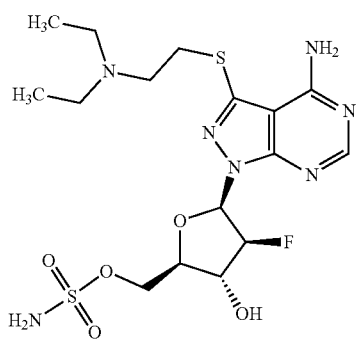 [SMILES: CCN(CC)CCSc1nn([C@@H]2O[C@H](COS(N)(=O)=O)[C@@H](O)[C@@H]2F)c2ncnc(N)c12]
-continued
I-105
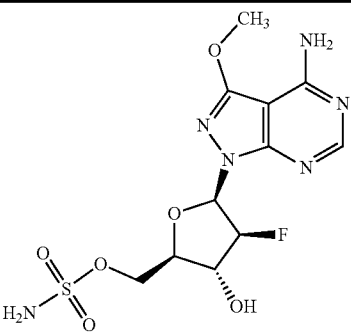
I-106
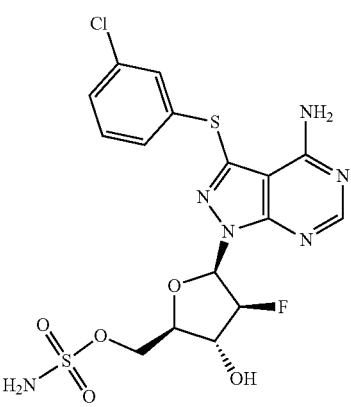 [SMILES: Nc1ncnc2c1c(Sc1cccc(Cl)c1)nn2[C@@H]1O[C@H](COS(N)(=O)=O)[C@@H](O)[C@@H]1F]
I-107
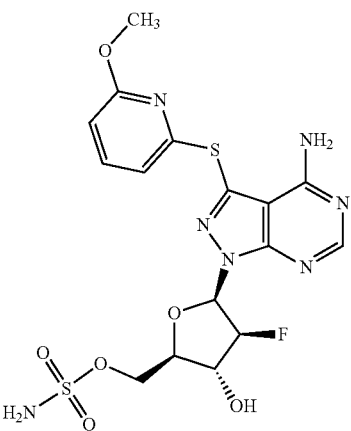 [SMILES: COc1cccc(Sc2nn([C@@H]3O[C@H](COS(N)(=O)=O)[C@@H](O)[C@@H]3F)c3ncnc(N)c23)n1]
I-108
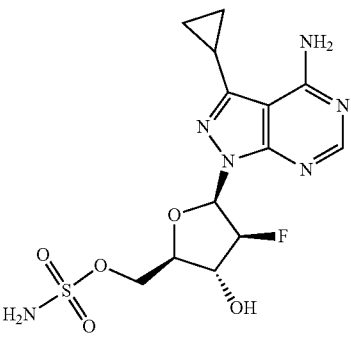 [SMILES: Nc1ncnc2c1c(C1CC1)nn2[C@@H]1O[C@H](COS(N)(=O)=O)[C@@H](O)[C@@H]1F]

| 51 -continued | 52 -continued |
|---|---|
| I-109 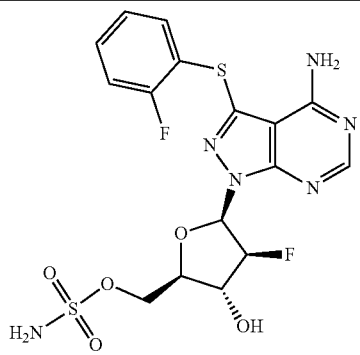 | I-113 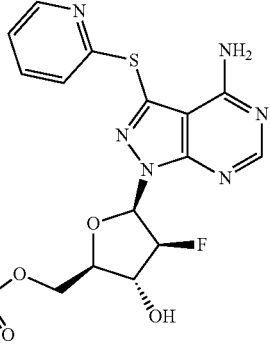 |
| I-110 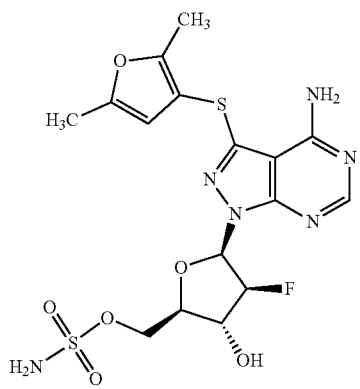 [SMILES: Cc1cc(Sc2nn([C@@H]3O[C@H](COS(N)(=O)=O)[C@@H](O)[C@@H]3F)c3ncnc(N)c23)c(C)o1] | I-114 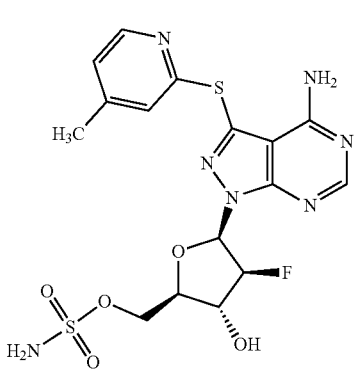 |
| I-111 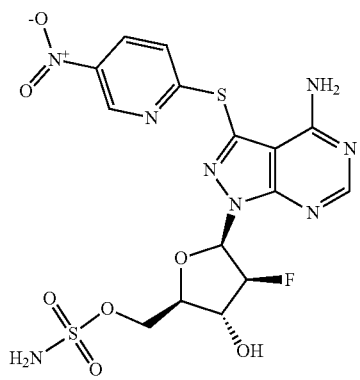 | I-115 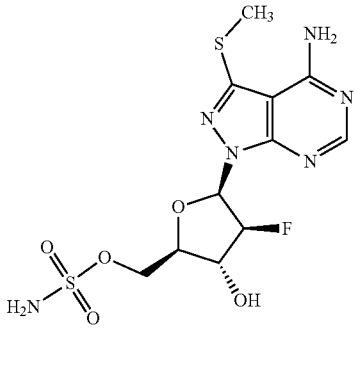 [SMILES: CSc1nn([C@@H]2O[C@H](COS(N)(=O)=O)[C@@H](O)[C@@H]2F)c2ncnc(N)c12] |
| I-112 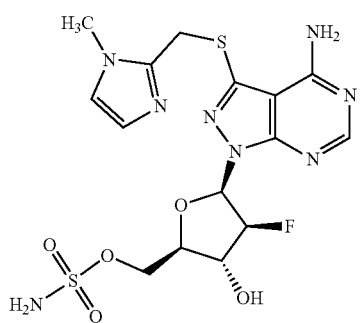 [SMILES: Cn1ccnc1CSc1nn([C@@H]2O[C@H](COS(N)(=O)=O)[C@@H](O)[C@@H]2F)c2ncnc(N)c12] | I-116 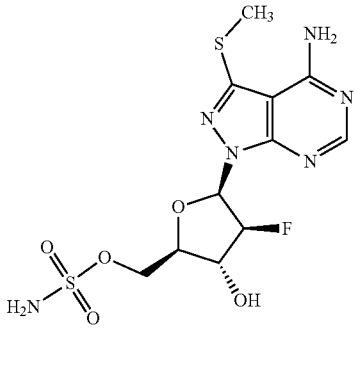 [SMILES: CSc1nn([C@@H]2O[C@H](COS(N)(=O)=O)[C@@H](O)[C@@H]2F)c2ncnc(N)c12] |

| 53 -continued | 54 -continued |
|---|---|
| I-117 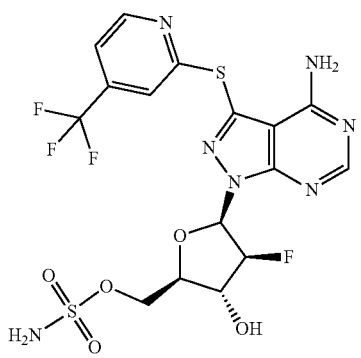 [SMILES: Nc1ncnc2c1c(Sc1cc(C(F)(F)F)ccn1)nn2[C@@H]1O[C@H](COS(N)(=O)=O)[C@@H](O)[C@@H]1F] | I-121 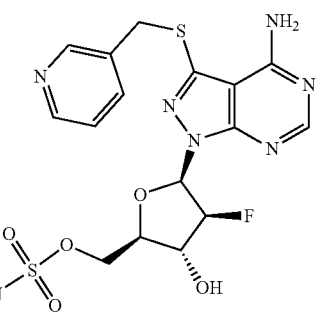 |
| I-118 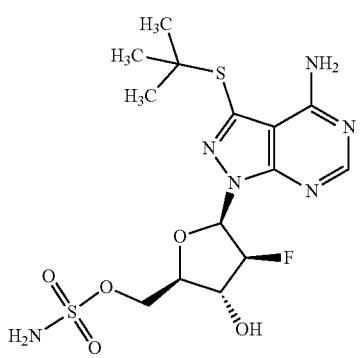 [SMILES: CC(C)(C)Sc1nn([C@@H]2O[C@H](COS(N)(=O)=O)[C@@H](O)[C@@H]2F)c2ncnc(N)c12] | I-122 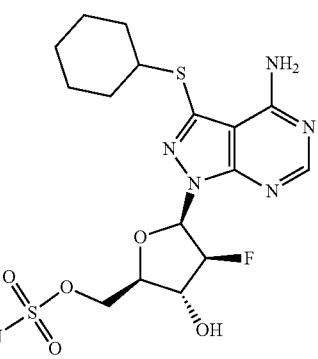 |
| I-119 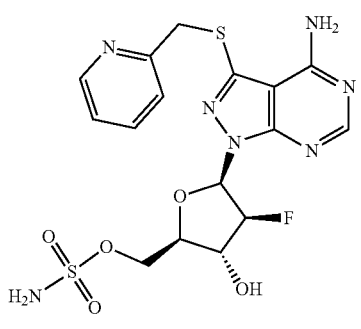 [SMILES: Nc1ncnc2c1c(SCc1ccccn1)nn2[C@@H]1O[C@H](COS(N)(=O)=O)[C@@H](O)[C@@H]1F] | I-123 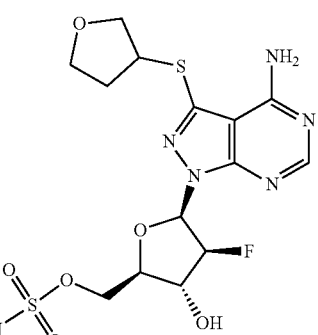 |
| I-120 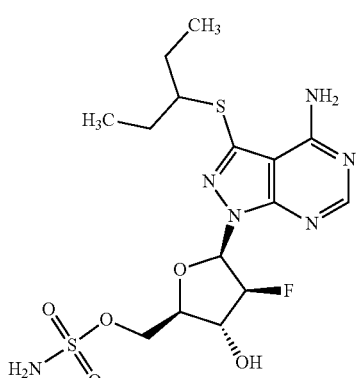 | I-124 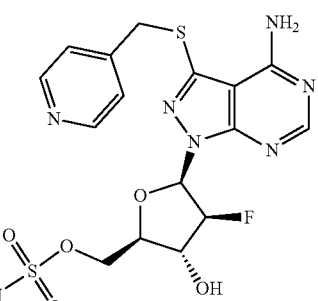 |

| 55 -continued | 56 -continued |
|---|---|
| 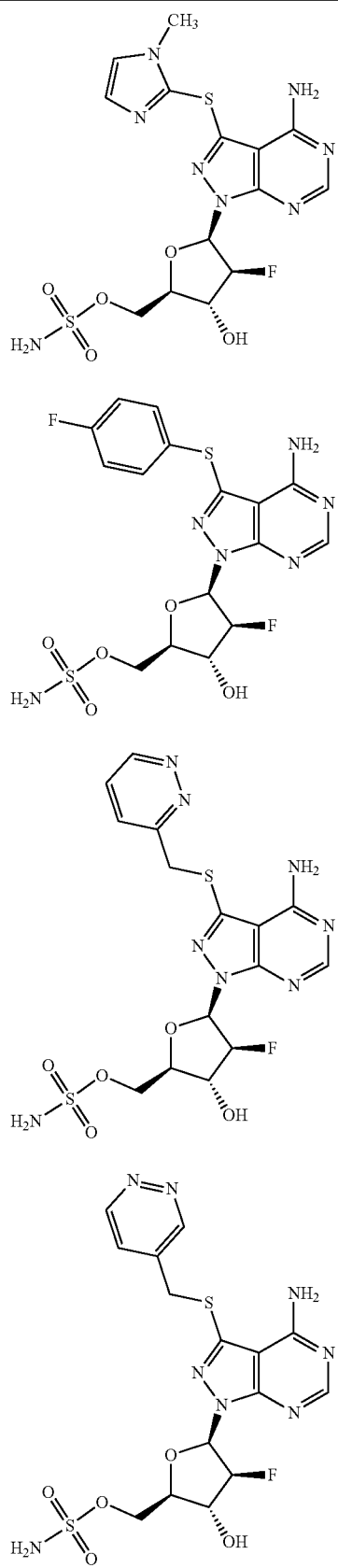 | 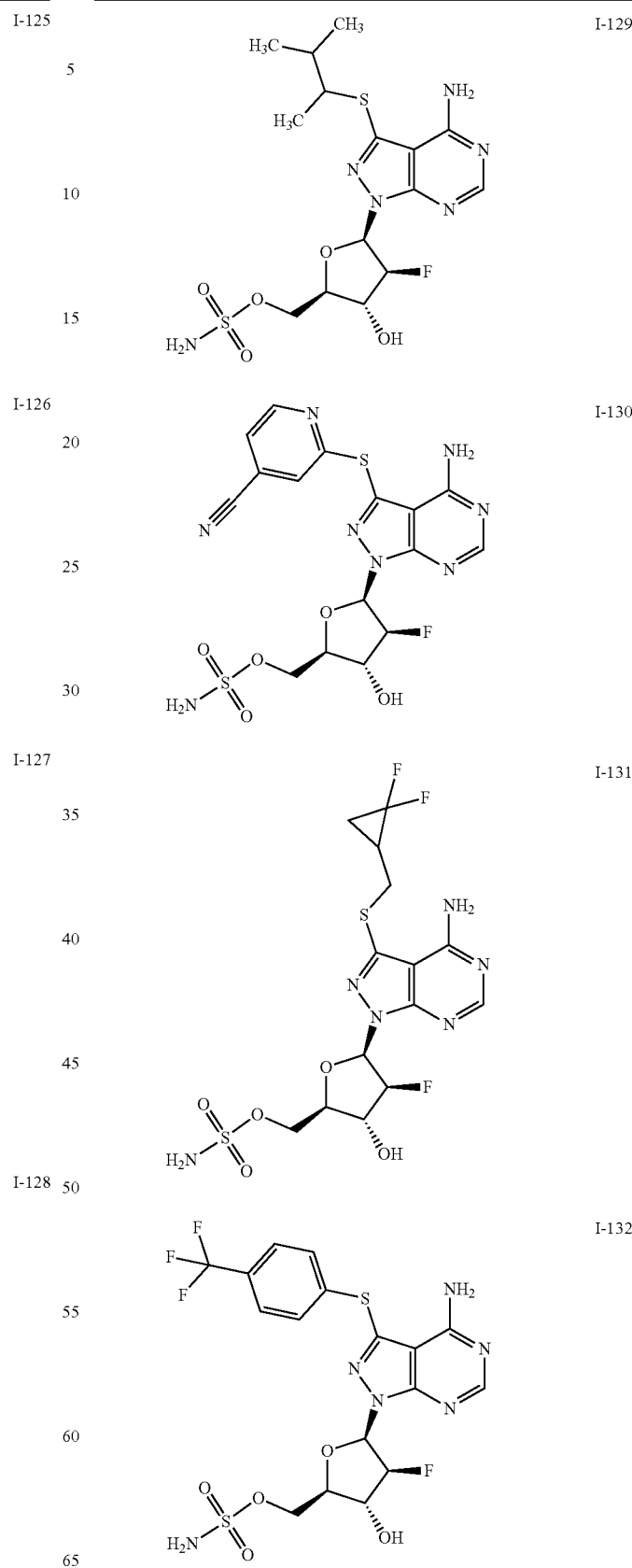 |

-continued
I-133
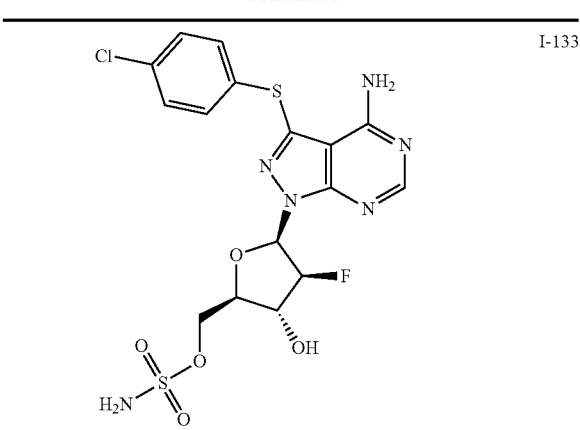
I-134
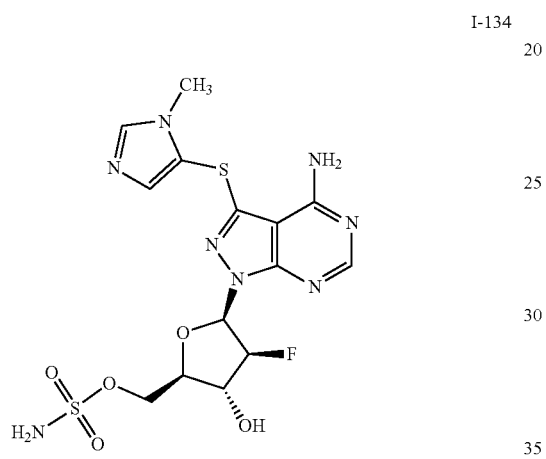
I-135
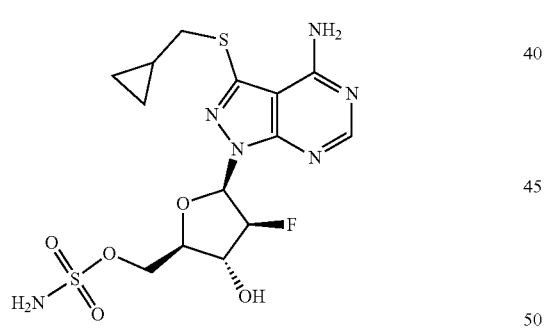
I-136
I-136a
I-136b
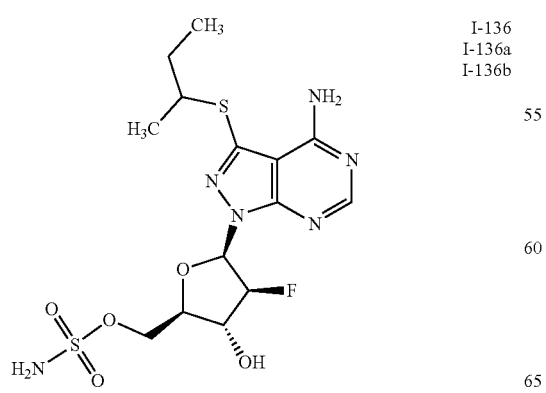
-continued
I-137
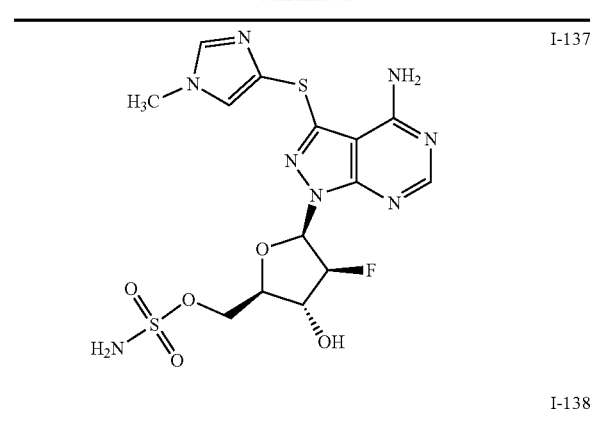
I-138
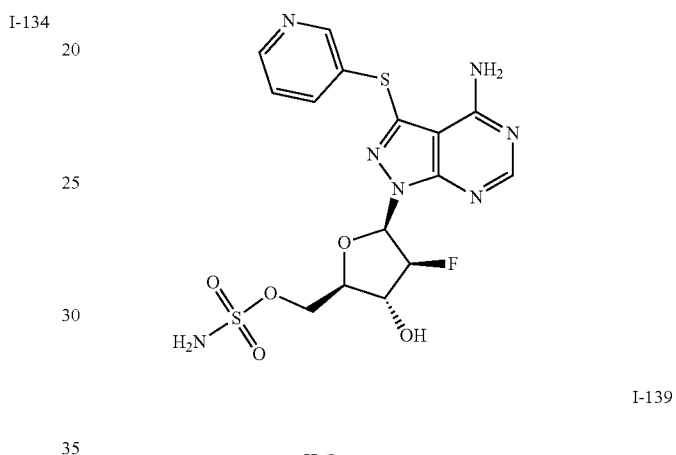
I-139
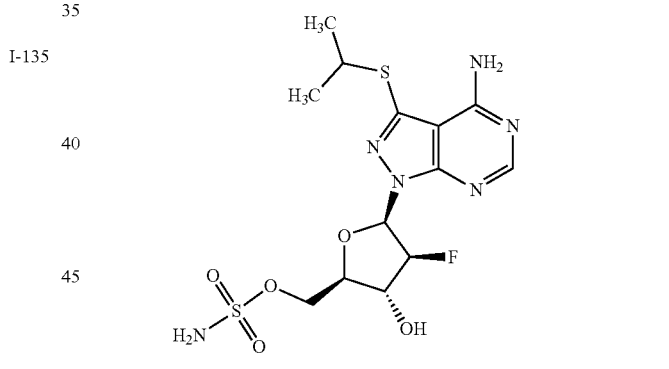
I-140
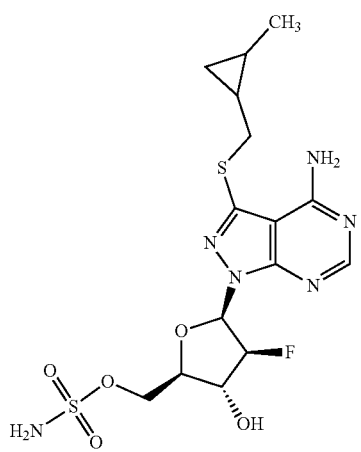 [SMILES: CC1CC1CSc1nn([C@@H]2O[C@H](COS(N)(=O)=O)[C@@H](O)[C@@H]2F)c2ncnc(N)c12]

I-141 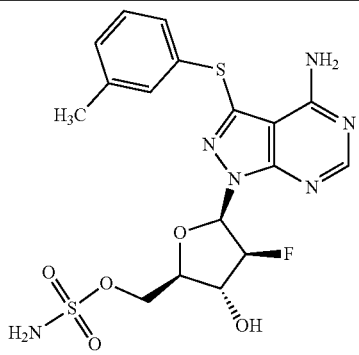
I-142 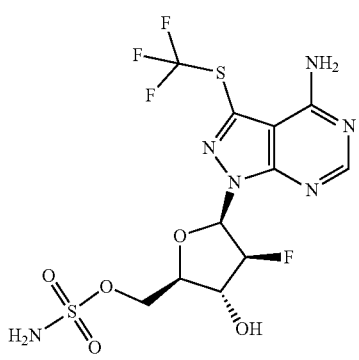 [SMILES: Nc1ncnc2c1c(SC(F)(F)F)nn2[C@@H]1O[C@H](COS(N)(=O)=O)[C@@H](O)[C@@H]1F]
I-143 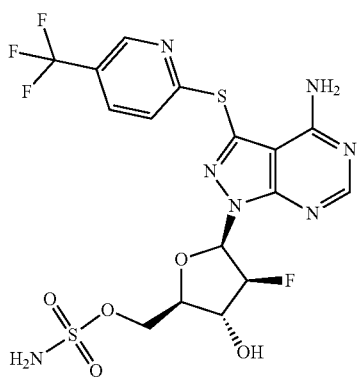
I-144 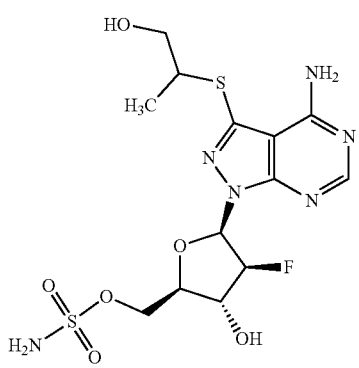 [SMILES: CC(CO)Sc1nn([C@@H]2O[C@H](COS(N)(=O)=O)[C@@H](O)[C@@H]2F)c2ncnc(N)c12]
I-145 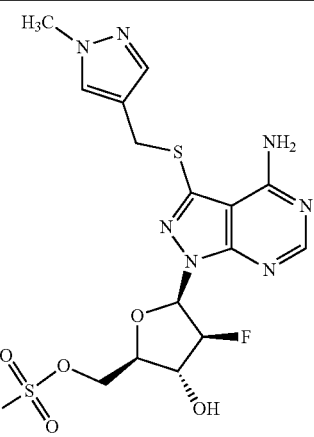
I-146 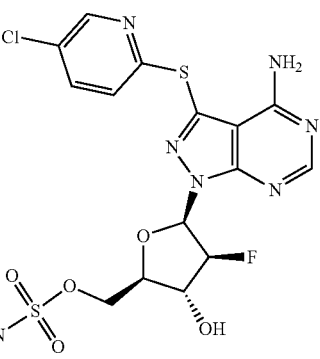
I-147 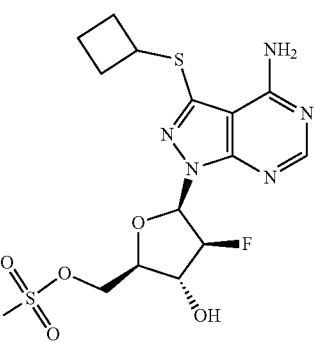
I-148 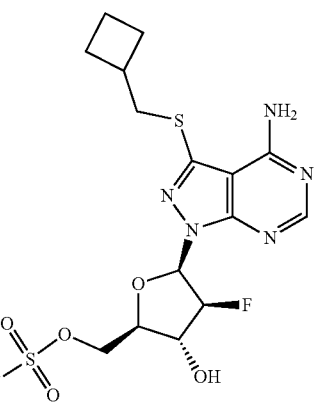

-continued
I-149
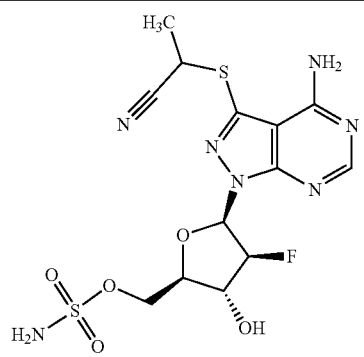
I-150
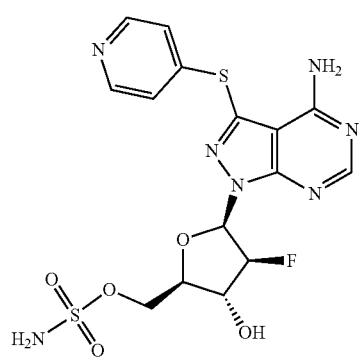 [SMILES: Nc1ncnc2c1c(Sc1ccncc1)nn2[C@@H]1O[C@H](COS(N)(=O)=O)[C@@H](O)[C@@H]1F]
I-151
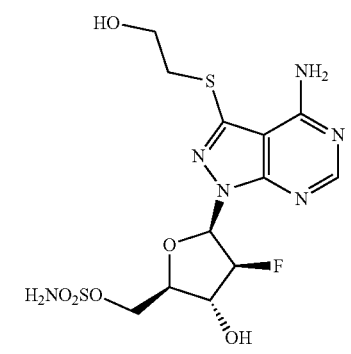
I-152
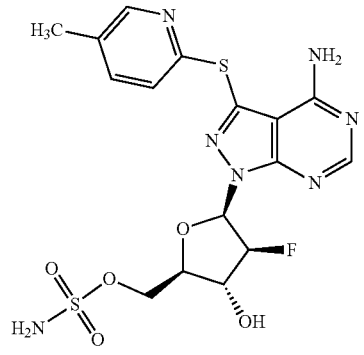 [SMILES: Cc1ccc(Sc2nn([C@@H]3O[C@H](COS(N)(=O)=O)[C@@H](O)[C@@H]3F)c3ncnc(N)c23)nc1]
-continued
I-153
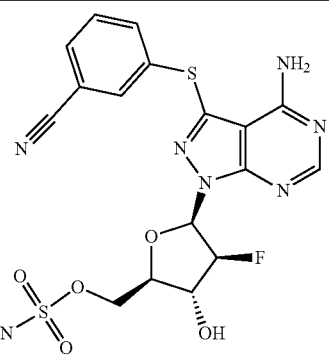
I-154
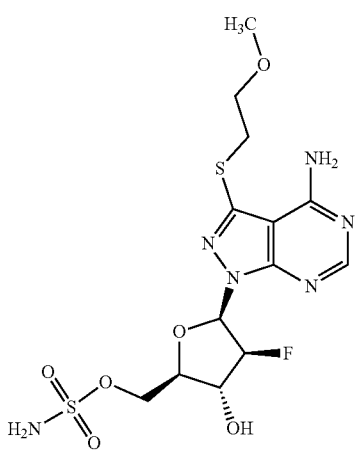 [SMILES: COCCSc1nn([C@@H]2O[C@H](COS(N)(=O)=O)[C@@H](O)[C@@H]2F)c2ncnc(N)c12]
I-155
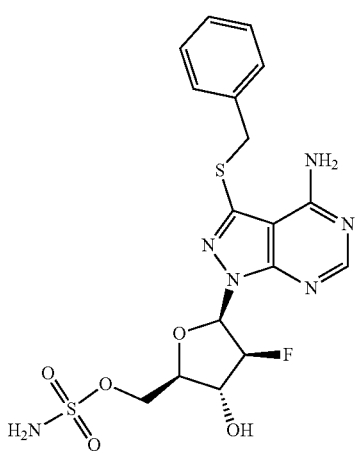 [SMILES: Nc1ncnc2c1c(SCc1ccccc1)nn2[C@@H]1O[C@H](COS(N)(=O)=O)[C@@H](O)[C@@H]1F]
I-156
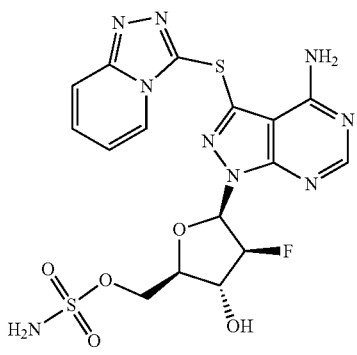 [SMILES: Nc1ncnc2c1c(Sc1nnc3ccccn13)nn2[C@@H]1O[C@H](COS(N)(=O)=O)[C@@H](O)[C@@H]1F]

| 63 -continued | | 64 -continued | |
|---|---|---|---|
| 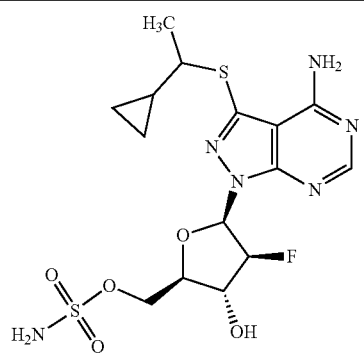 | I-157 | 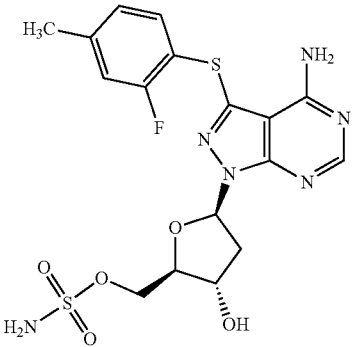 | I-161 |
| 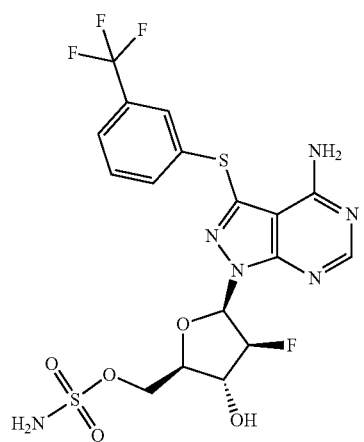 [SMILES: Nc1ncnc2c1c(Sc1cccc(C(F)(F)F)c1)nn2[C@@H]1O[C@H](COS(N)(=O)=O)[C@@H](O)[C@@H]1F] | I-158 | 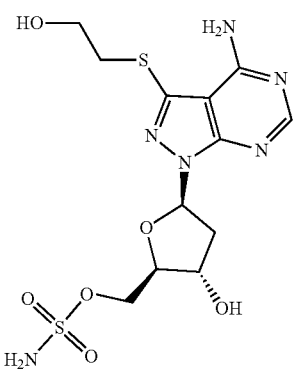 | I-162 |
| 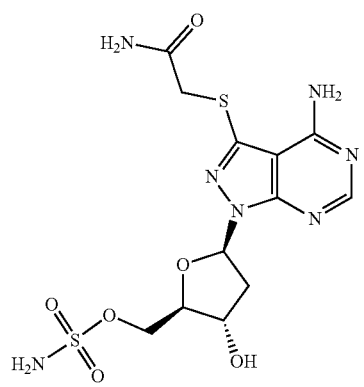 [SMILES: NC(=O)CSc1nn([C@H]2C[C@H](O)[C@@H](COS(N)(=O)=O)O2)c2ncnc(N)c12] | I-159 | 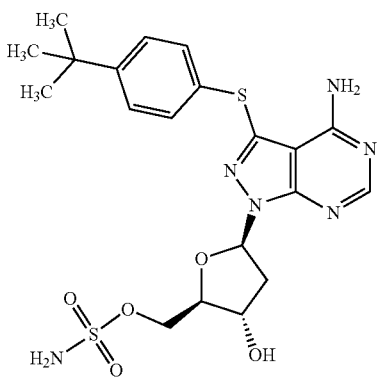 | I-163 |
| 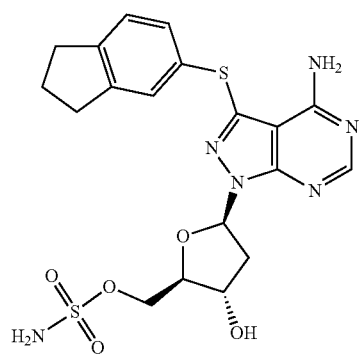 [SMILES: Nc1ncnc2c1c(Sc1ccc3c(c1)CCC3)nn2[C@H]1C[C@H](O)[C@@H](COS(N)(=O)=O)O1] | I-160 | 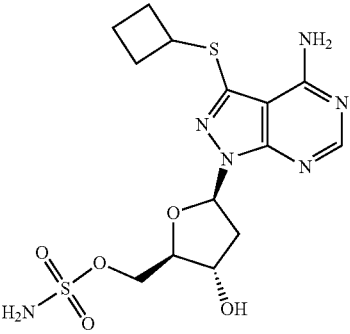 [SMILES: Nc1ncnc2c1c(SC1CCC1)nn2[C@H]1C[C@H](O)[C@@H](COS(N)(=O)=O)O1] | I-164 |

| 65 -continued | 66 -continued |
|---|---|
| I-165 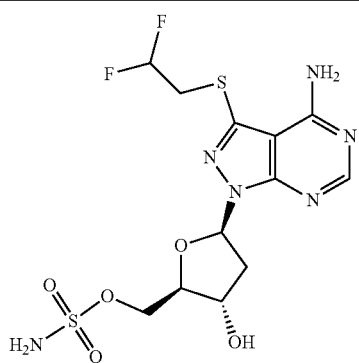 | I-169 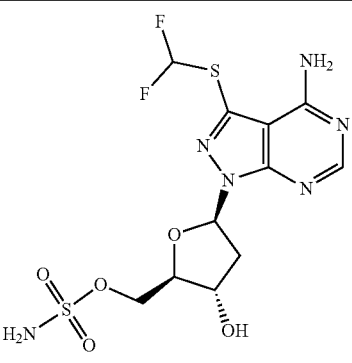 |
| I-166 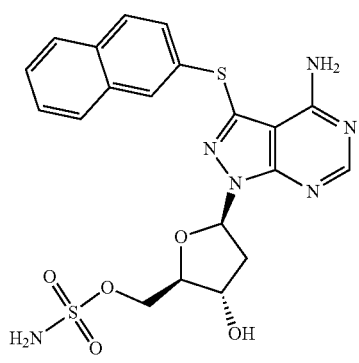 [SMILES: Nc1ncnc2c1c(Sc1ccc3ccccc3c1)nn2[C@H]1C[C@H](O)[C@@H](COS(N)(=O)=O)O1] | I-170 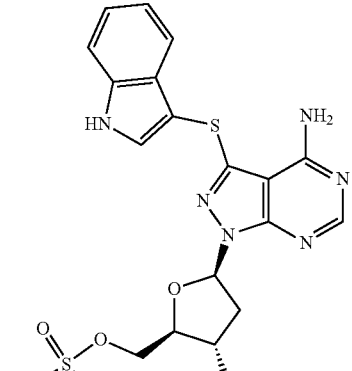 |
| I-167 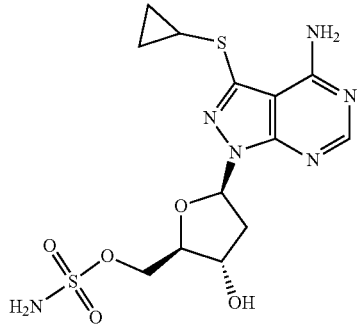 [SMILES: Nc1ncnc2c1c(SC1CC1)nn2[C@H]1C[C@H](O)[C@@H](COS(N)(=O)=O)O1] | I-171 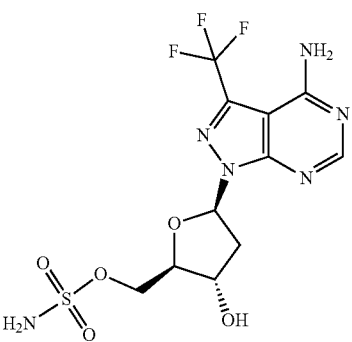 |
| I-168 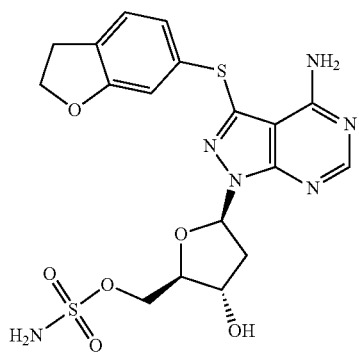 [SMILES: Nc1ncnc2c1c(Sc1ccc3c(c1)OCC3)nn2[C@H]1C[C@H](O)[C@@H](COS(N)(=O)=O)O1] | I-172 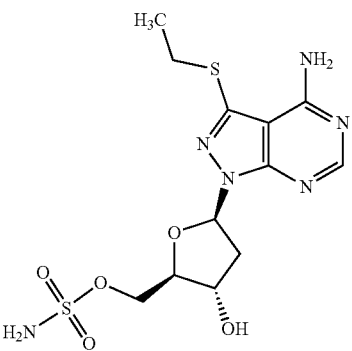 [SMILES: CCSc1nn([C@H]2C[C@H](O)[C@@H](COS(N)(=O)=O)O2)c2ncnc(N)c12] |

67
-continued
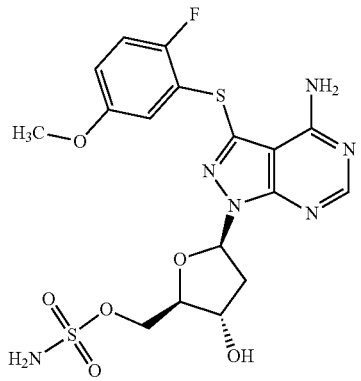 [SMILES: COc1ccc(F)c(Sc2nn([C@H]3C[C@H](O)[C@@H](COS(N)(=O)=O)O3)c3ncnc(N)c23)c1]
I-173
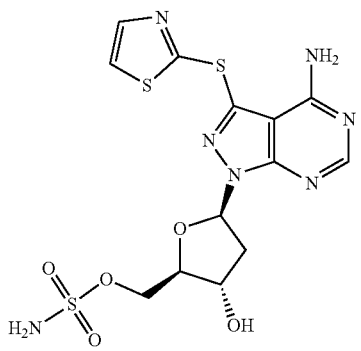 [SMILES: Nc1ncnc2c1c(Sc1nccs1)nn2[C@H]1C[C@H](O)[C@@H](COS(N)(=O)=O)O1]
I-174
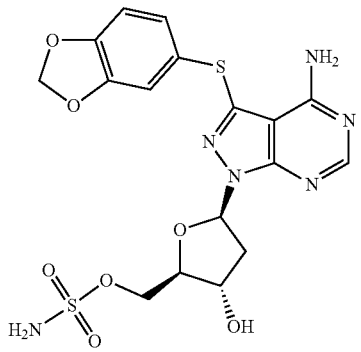 [SMILES: Nc1ncnc2c1c(Sc1ccc3c(c1)OCO3)nn2[C@H]1C[C@H](O)[C@@H](COS(N)(=O)=O)O1]
I-175
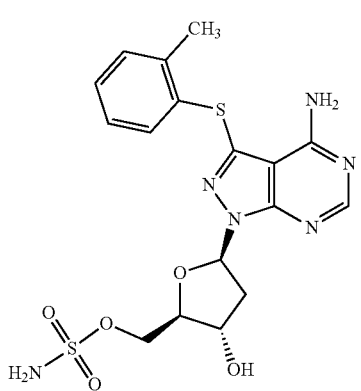 [SMILES: Cc1ccccc1Sc1nn([C@H]2C[C@H](O)[C@@H](COS(N)(=O)=O)O2)c2ncnc(N)c12]
I-176
68
-continued
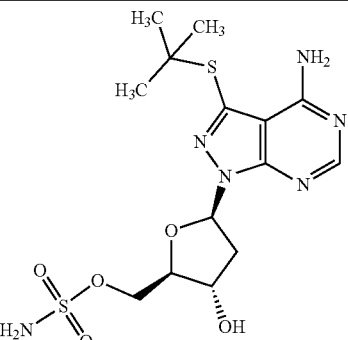
I-177
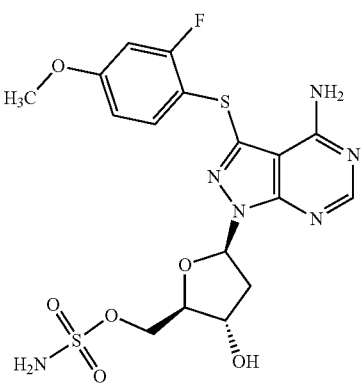 [SMILES: COc1ccc(Sc2nn([C@H]3C[C@H](O)[C@@H](COS(N)(=O)=O)O3)c3ncnc(N)c23)c(F)c1]
I-178
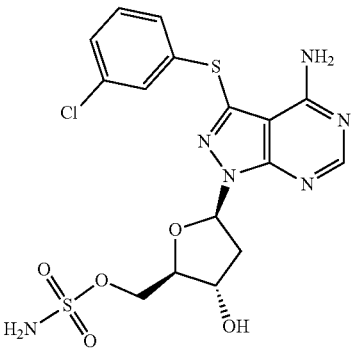 [SMILES: Nc1ncnc2c1c(Sc1cccc(Cl)c1)nn2[C@H]1C[C@H](O)[C@@H](COS(N)(=O)=O)O1]
I-179
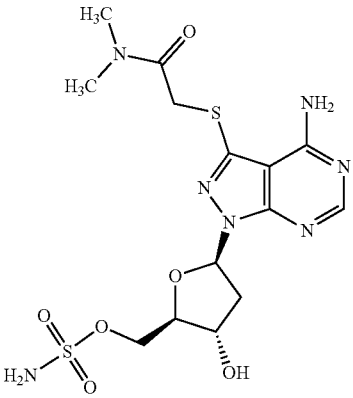 [SMILES: CN(C)C(=O)CSc1nn([C@H]2C[C@H](O)[C@@H](COS(N)(=O)=O)O2)c2ncnc(N)c12]
I-180

| 69 -continued | | 70 -continued | |
|---|---|---|---|
| 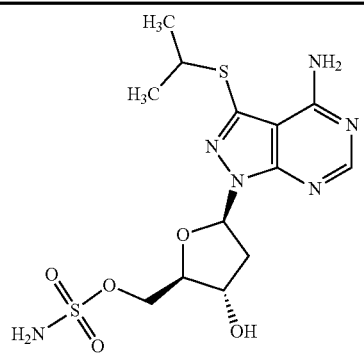 | I-181 | 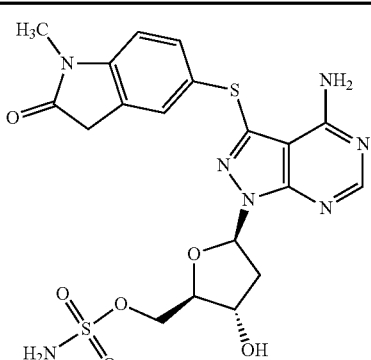 | I-185 |
| 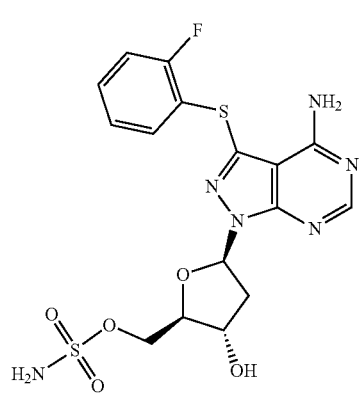 [SMILES: Nc1ncnc2c1c(Sc1ccccc1F)nn2[C@H]1C[C@H](O)[C@@H](COS(N)(=O)=O)O1] | I-182 | 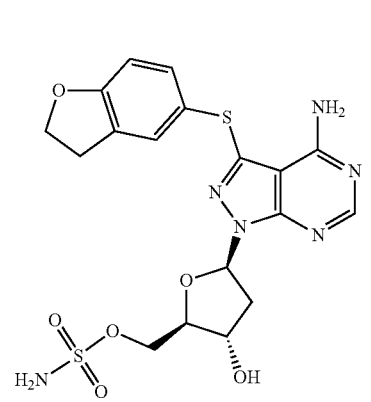 | I-186 |
| 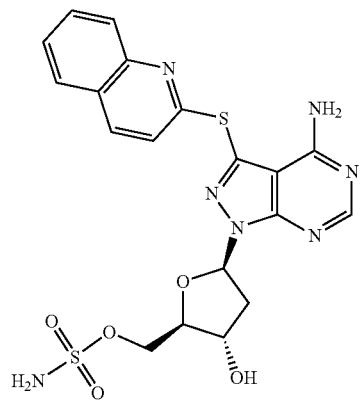 [SMILES: Nc1ncnc2c1c(Sc1ccc3ccccc3n1)nn2[C@H]1C[C@H](O)[C@@H](COS(N)(=O)=O)O1] | I-183 | 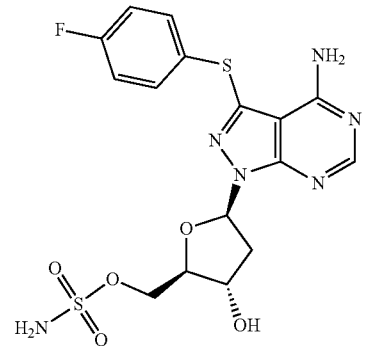 | I-187 |
| 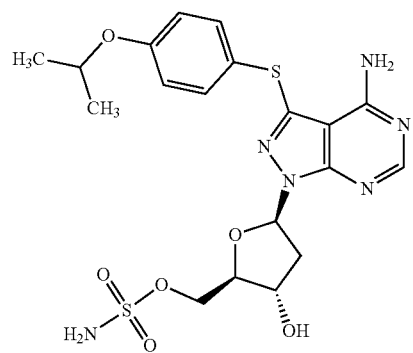 [SMILES: CC(C)Oc1ccc(Sc2nn([C@H]3C[C@H](O)[C@@H](COS(N)(=O)=O)O3)c3ncnc(N)c23)cc1] | I-184 | 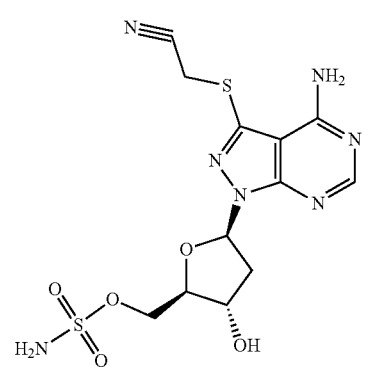 [SMILES: N#CCSc1nn([C@H]2C[C@H](O)[C@@H](COS(N)(=O)=O)O2)c2ncnc(N)c12] | I-188 |

I-189 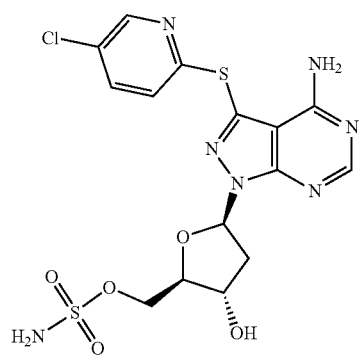 [SMILES: Nc1ncnc2c1c(Sc1ccc(Cl)cn1)nn2[C@H]1C[C@H](O)[C@@H](COS(N)(=O)=O)O1]
I-190 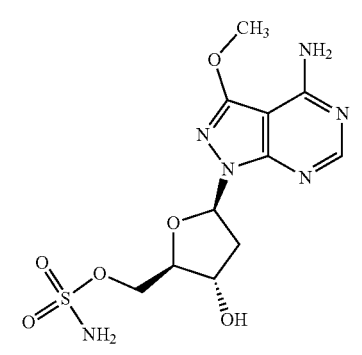 [SMILES: COc1nn([C@H]2C[C@H](O)[C@@H](COS(N)(=O)=O)O2)c2ncnc(N)c12]
I-191 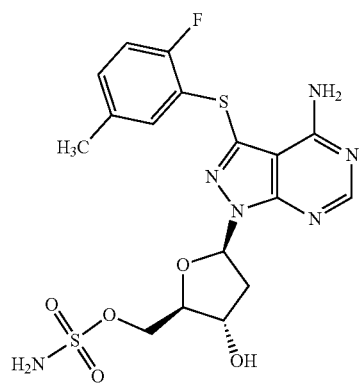 [SMILES: Cc1ccc(F)c(Sc2nn([C@H]3C[C@H](O)[C@@H](COS(N)(=O)=O)O3)c3ncnc(N)c23)c1]
I-192 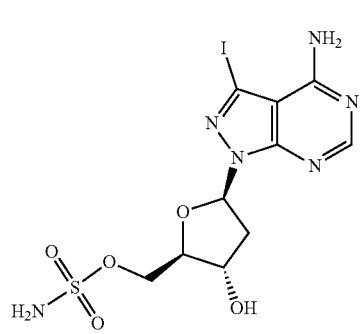 [SMILES: Nc1ncnc2c1c(I)nn2[C@H]1C[C@H](O)[C@@H](COS(N)(=O)=O)O1]
I-193 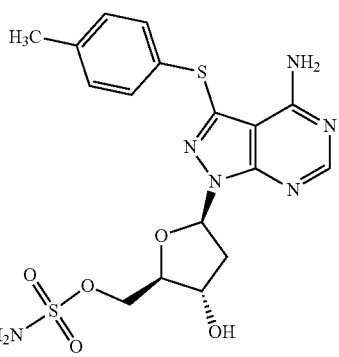
I-194 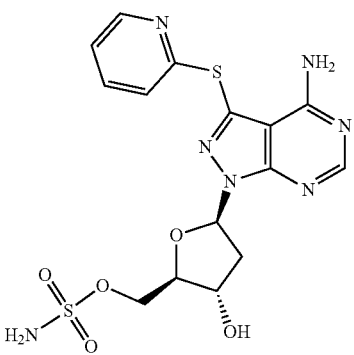 [SMILES: Nc1ncnc2c1c(Sc1ccccn1)nn2[C@H]1C[C@H](O)[C@@H](COS(N)(=O)=O)O1]
I-195 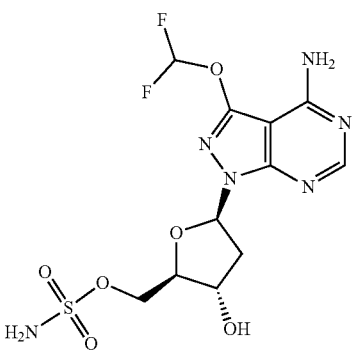 [SMILES: Nc1ncnc2c1c(OC(F)F)nn2[C@H]1C[C@H](O)[C@@H](COS(N)(=O)=O)O1]
I-196 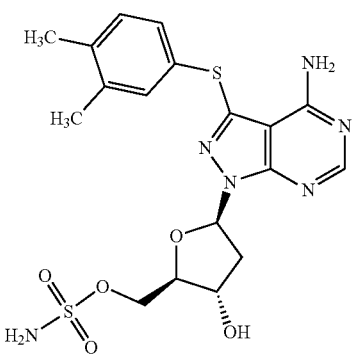 [SMILES: Cc1ccc(Sc2nn([C@H]3C[C@H](O)[C@@H](COS(N)(=O)=O)O3)c3ncnc(N)c23)cc1C]

-continued
I-197
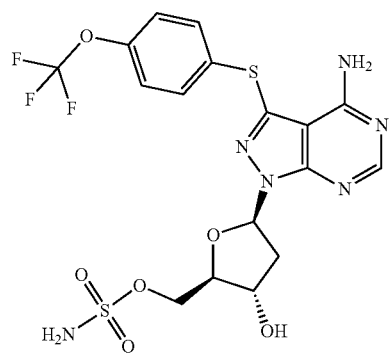 [SMILES: Nc1ncnc2c1c(Sc1ccc(OC(F)(F)F)cc1)nn2[C@H]1C[C@H](O)[C@@H](COS(N)(=O)=O)O1]
I-198
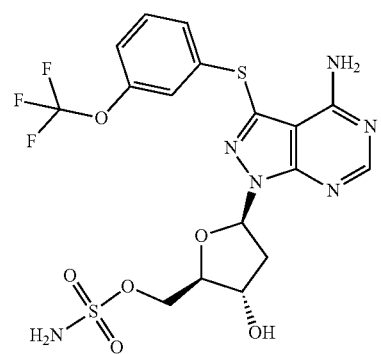 [SMILES: Nc1ncnc2c1c(Sc1cccc(OC(F)(F)F)c1)nn2[C@H]1C[C@H](O)[C@@H](COS(N)(=O)=O)O1]
I-199
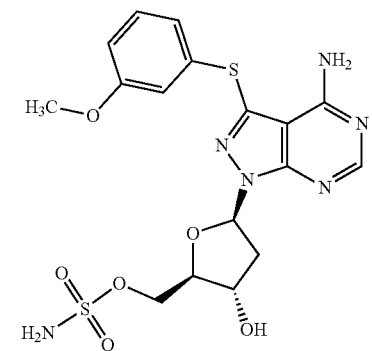 [SMILES: COc1cccc(Sc2nn([C@H]3C[C@H](O)[C@@H](COS(N)(=O)=O)O3)c3ncnc(N)c23)c1]
I-200
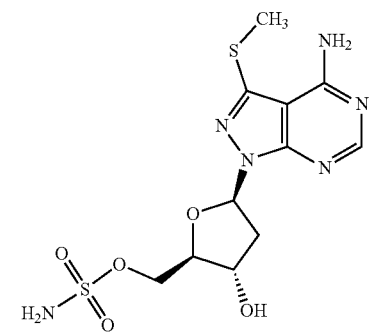 [SMILES: CSc1nn([C@H]2C[C@H](O)[C@@H](COS(N)(=O)=O)O2)c2ncnc(N)c12]
-continued
I-201
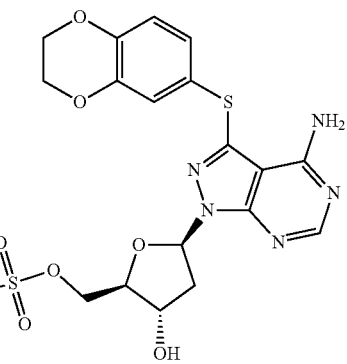
I-202
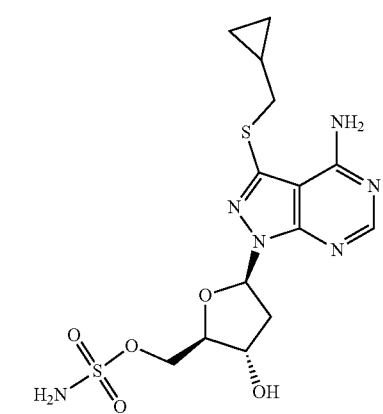 [SMILES: Nc1ncnc2c1c(SCC1CC1)nn2[C@H]1C[C@H](O)[C@@H](COS(N)(=O)=O)O1]
I-203
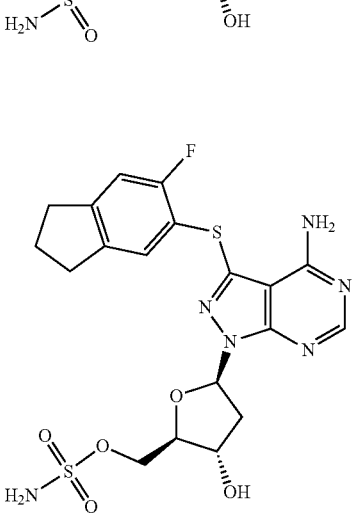
I-204
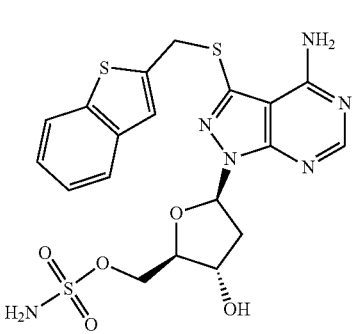 [SMILES: Nc1ncnc2c1c(SCc1cc3ccccc3s1)nn2[C@H]1C[C@H](O)[C@@H](COS(N)(=O)=O)O1]

75
-continued
I-205
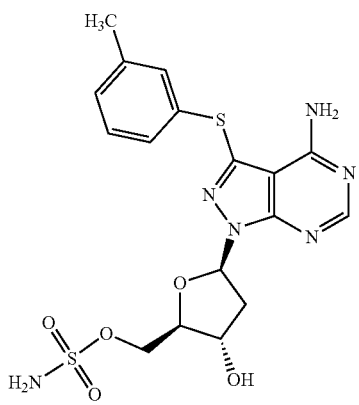 [SMILES: Cc1cccc(Sc2nn([C@H]3C[C@H](O)[C@@H](COS(N)(=O)=O)O3)c3ncnc(N)c23)c1]
I-206
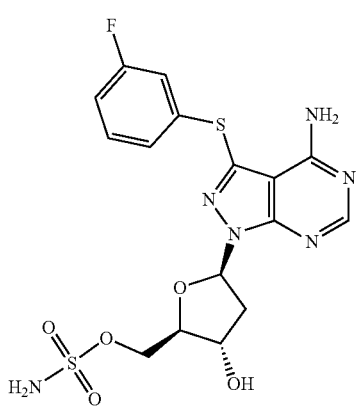 [SMILES: Nc1ncnc2c1c(Sc1cccc(F)c1)nn2[C@H]1C[C@H](O)[C@@H](COS(N)(=O)=O)O1]
I-207
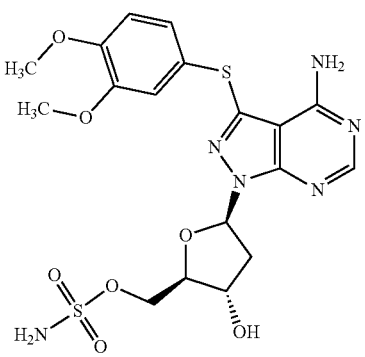 [SMILES: COc1ccc(Sc2nn([C@H]3C[C@H](O)[C@@H](COS(N)(=O)=O)O3)c3ncnc(N)c23)cc1OC]
I-208
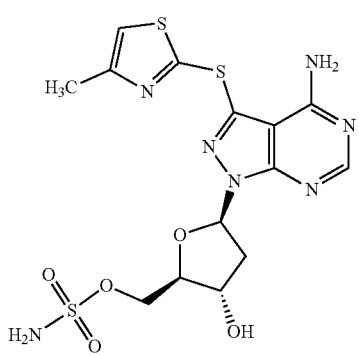 [SMILES: Cc1csc(Sc2nn([C@H]3C[C@H](O)[C@@H](COS(N)(=O)=O)O3)c3ncnc(N)c23)n1]
76
-continued
I-209
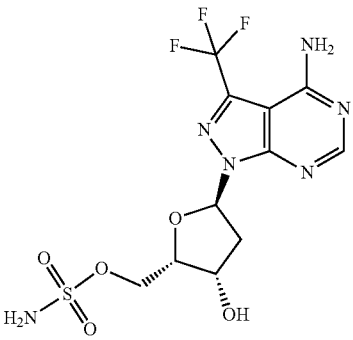 [SMILES: Nc1ncnc2c1c(C(F)(F)F)nn2[C@H]1C[C@H](O)[C@H](COS(N)(=O)=O)O1]
I-210
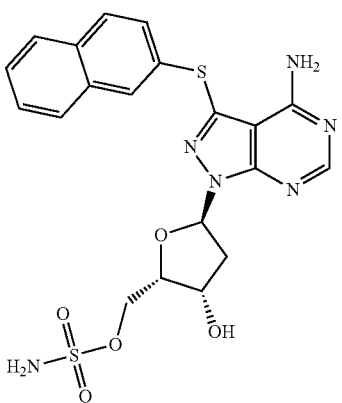 [SMILES: Nc1ncnc2c1c(Sc1ccc3ccccc3c1)nn2[C@H]1C[C@H](O)[C@H](COS(N)(=O)=O)O1]
I-211
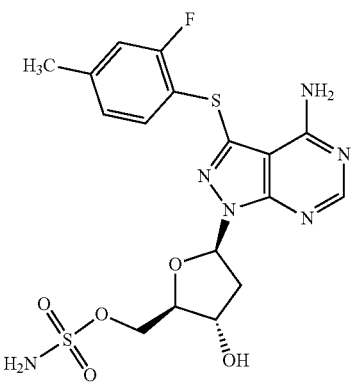 [SMILES: Cc1ccc(Sc2nn([C@H]3C[C@H](O)[C@@H](COS(N)(=O)=O)O3)c3ncnc(N)c23)c(F)c1]
I-212
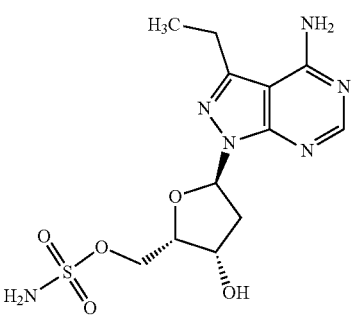 [SMILES: CCc1nn([C@H]2C[C@H](O)[C@H](COS(N)(=O)=O)O2)c2ncnc(N)c12]

-continued
I-213
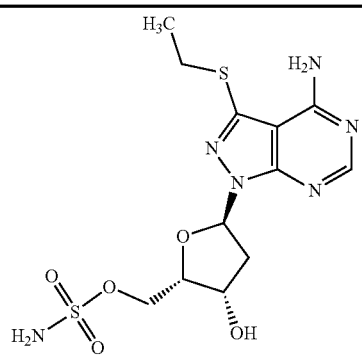
I-214
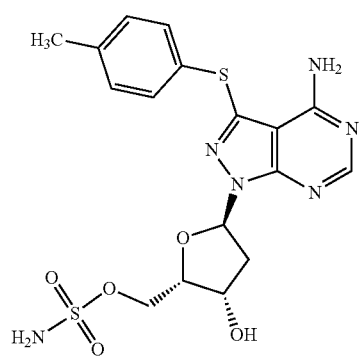 [SMILES: Cc1ccc(Sc2nn([C@H]3C[C@H](O)[C@H](COS(N)(=O)=O)O3)c3ncnc(N)c23)cc1]
I-215
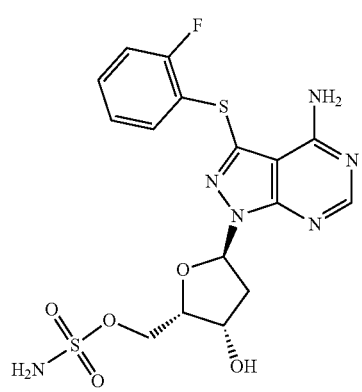 [SMILES: Nc1ncnc2c1c(Sc1ccccc1F)nn2[C@H]1C[C@H](O)[C@H](COS(N)(=O)=O)O1]
I-216
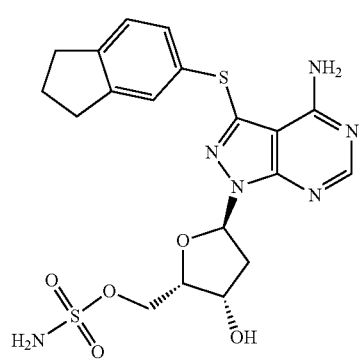 [SMILES: Nc1ncnc2c1c(Sc1ccc3c(c1)CCC3)nn2[C@H]1C[C@H](O)[C@H](COS(N)(=O)=O)O1]
-continued
I-217
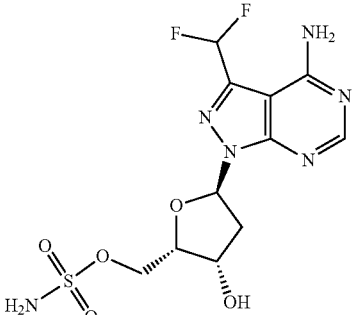
I-218
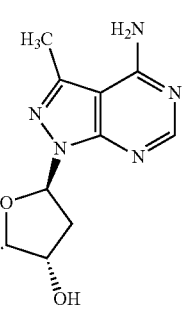
I-219
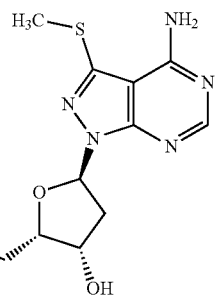
I-220
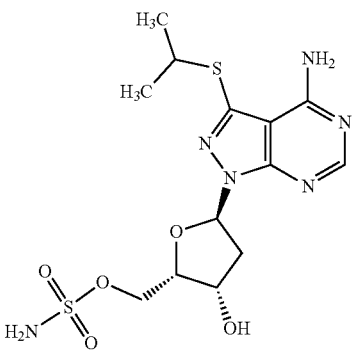 [SMILES: CC(C)Sc1nn([C@H]2C[C@H](O)[C@H](COS(N)(=O)=O)O2)c2ncnc(N)c12]

-continued

I-221
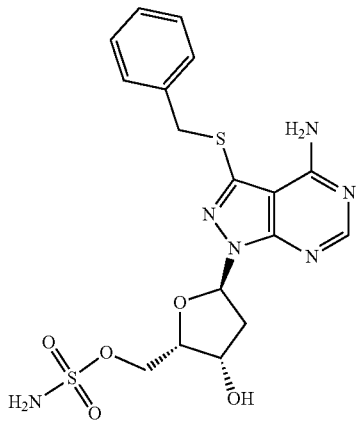 [SMILES: Nc1ncnc2c1c(SCc1ccccc1)nn2[C@H]1C[C@H](O)[C@H](COS(N)(=O)=O)O1]

I-222
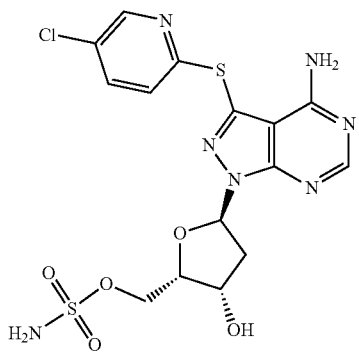

I-223
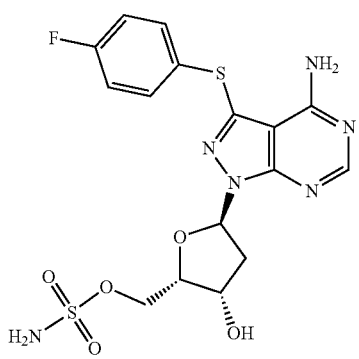 [SMILES: Nc1ncnc2c1c(Sc1ccc(F)cc1)nn2[C@H]1C[C@H](O)[C@H](COS(N)(=O)=O)O1]

-continued

I-224
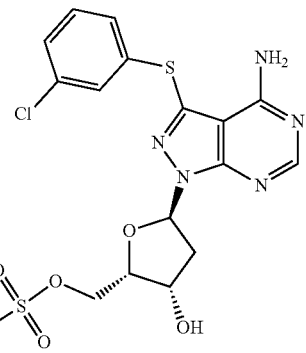

I-225
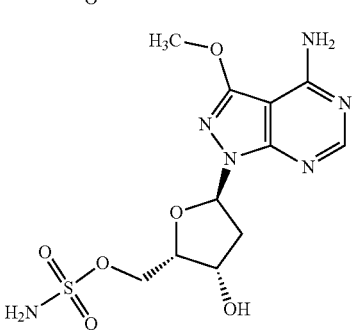

I-226
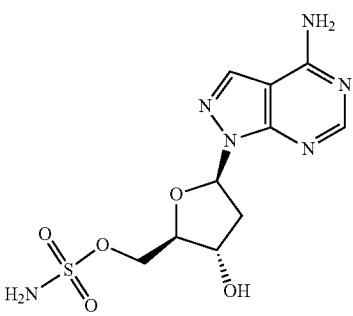 [SMILES: Nc1ncnc2c1cnn2[C@H]1C[C@H](O)[C@@H](COS(N)(=O)=O)O1]

I-227
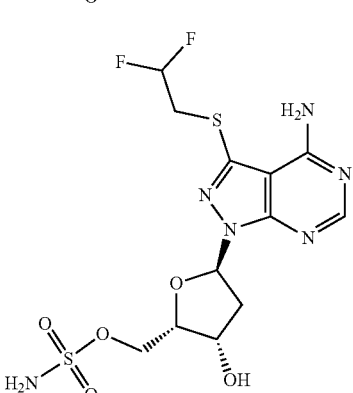

The chemical entities in Table 1 may also be identified by the following chemical names:

| Compound | Name |
|---|---|
| I-1 | [(2R,3S,4R,5R)-5-(4-amino-3-methoxy-1H-pyrazolo[3,4-d]pyrimidin-1-yl)-3,4-dihydroxytetrahydrofuran-2-yl]methyl sulfamate |
| I-2 | [(2R,3S,4R,5R)-5-(4-amino-3-methyl-1H-pyrazolo[3,4-d]pyrimidin-1-yl)-3,4-dihydroxytetrahydrofuran-2-yl]methyl sulfamate |
| I-3 | [(2R,3S,4R,5R)-5-(4-amino-3-isopropyl-1H-pyrazolo[3,4-d]pyrimidin-1-yl)-3,4-dihydroxytetrahydrofuran-2-yl]methyl sulfamate |

-continued

| Compound | Name |
|---|---|
| I-4 | [(2R,3S,4R,5R)-5-{4-amino-3-[(benzyloxy)methyl]-1H-pyrazolo[3,4-d]pyrimidin-1-yl}-3,4-dihydroxytetrahydrofuran-2-yl]methyl sulfamate |
| I-5 | [(2R,3S,4R,5R)-5-(4-amino-3-ethoxy-1H-pyrazolo[3,4-d]pyrimidin-1-yl)-3,4-dihydroxytetrahydrofuran-2-yl]methyl sulfamate |
| I-6 | [(2R,3S,4R,5R)-5-(4-amino-3-ethyl-1H-pyrazolo[3,4-d]pyrimidin-1-yl)-3,4-dihydroxytetrahydrofuran-2-yl]methyl sulfamate |
| I-7 | [(2R,3S,4R,5R)-5-(4-amino-3-isopropoxy-1H-pyrazolo[3,4-d]pyrimidin-1-yl)-3,4-dihydroxytetrahydrofuran-2-yl]methyl sulfamate |
| I-8 | {(2R,3S,4R,5R)-5-[4-amino-3-(hydroxymethyl)-1H-pyrazolo[3,4-d]pyrimidin-1-yl]-3,4-dihydroxytetrahydrofuran-2-yl}methyl sulfamate |
| I-9 | [(2R,3S,4R,5R)-5-(4-amino-3-ethynyl-1H-pyrazolo[3,4-d]pyrimidin-1-yl)-3,4-dihydroxytetrahydrofuran-2-yl]methyl sulfamate |
| I-10 | {(2R,3S,4R,5R)-5-[4-amino-3-(trifluoromethyl)-1H-pyrazolo[3,4-d]pyrimidin-1-yl]-3,4-dihydroxytetrahydrofuran-2-yl}methyl sulfamate |
| I-11 | {(2R,3S,4R,5R)-5-[4-amino-3-(3-methoxyprop-1-yn-1-yl)-1H-pyrazolo[3,4-d]pyrimidin-1-yl]-3,4-dihydroxytetrahydrofuran-2-yl}methyl sulfamate |
| I-12 | {(2R,3S,4R,5R)-5-[4-amino-3-(2-phenylethyl)-1H-pyrazolo[3,4-d]pyrimidin-1-yl]-3,4-dihydroxytetrahydrofuran-2-yl}methyl sulfamate |
| I-13 | [(2R,3S,4R,5R)-5-(4-amino-3-cyano-1H-pyrazolo[3,4-d]pyrimidin-1-yl)-3,4-dihydroxytetrahydrofuran-2-yl]methyl sulfamate |
| I-14 | {(2R,3S,4R,5R)-5-[4-amino-3 -(prop-1-yn-1-yl)-1H-pyrazolo[3,4-d]pyrimidin-1-yl]-3,4-dihydroxytetrahydrofuran-2-yl}methyl sulfamate |
| I-15 | {(2R,3S,4R,5R)-5-[4-amino-3-(aminomethyl)-1H-pyrazolo[3,4-d]pyrimidin-1-yl]-3,4-dihydroxytetrahydrofuran-2-yl}methyl sulfamate |
| I-16 | [(2R,3S,4R,5R)-5-(4-amino-3-carbamoyl-1H-pyrazolo[3,4-d]pyrimidin-1-yl)-3,4-dihydroxytetrahydrofuran-2-yl]methyl sulfamate |
| I-17 | {(2R,3S,4R,5R)-5-[4-amino-3-(3-aminoprop-1-yn-1-yl)-1H-pyrazolo[3,4-d]pyrimidin-1-yl]-3,4-dihydroxytetrahydrofuran-2-yl}methyl sulfamate |
| I-18 | [(2R,3S,4R,5R)-5-(4-amino-3-vinyl-1H-pyrazolo[3,4-d]pyrimidin-1-yl)-3,4-dihydroxytetrahydrofuran-2-yl]methyl sulfamate |
| I-19 | {(2R,3S,4R,5R)-5-[4-amino-3-(methoxymethyl)-1H-pyrazolo[3,4-d]pyrimidin-1-yl]-3,4-dihydroxytetrahydrofuran-2-yl}methyl sulfamate |
| I-20 | methyl 4-amino-1-{(2R,3R,4S,5R)-3,4-dihydroxy-5-[(sulfamoyloxy)methyl]tetrahydrofuran-2-yl}-1H-pyrazolo[3,4-d]pyrimidine-3-carboxylate |
| I-21 | [(2R,3S,4R,5R)-5-(3-acetyl-4-amino-1H-pyrazolo[3,4-d]pyrimidin-1-yl)-3,4-dihydroxytetrahydrofuran-2-yl]methyl sulfamate |
| I-22 | [(2R,3S,4R,5R)-5-{4-amino-3-[(1R)-1-methoxyethyl]-1H-pyrazolo[3,4-d]pyrimidin-1-yl}-3,4-dihydroxytetrahydrofuran-2-yl]methyl sulfamate and [(2R,3S,4R,5R)-5-{4-amino-3-[(1S)-1-methoxyethyl]-1H-pyrazolo[3,4-d]pyrimidin-1-yl}-3,4-dihydroxytetrahydrofuran-2-yl]methyl sulfamate |
| I-23a | [(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl sulfamate or [(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl sulfamate |
| I-23b | [(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl sulfamate or [(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl sulfamate |
| I-24 | {(2R,3S,4R,5R)-5-[4-amino-3-(2-hydroxypropan-2-yl)-1H-pyrazolo[3,4-d]pyrimidin-1-yl]-3,4-dihydroxytetrahydrofuran-2-yl}methyl sulfamate |
| I-25 | {(2R,3S,4R,5R)-5-[4-amino-3-(difluoromethyl)-1H-pyrazolo[3,4-d]pyrimidin-1-yl]-3,4-dihydroxytetrahydrofuran-2-yl}methyl sulfamate |
| I-26 | [(2R,3S,4R,5R)-5-(4-amino-3-cyclopropyl-1H-pyrazolo[3,4-d]pyrimidin-1-yl)-3,4-dihydroxytetrahydrofuran-2-yl]methyl sulfamate |
| I-27 | {(2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl sulfamate |
| I-28 | [(2R,3S,4R,5R)-5-{4-amino-3-[(2-hydroxy-2-methylpropyl)sulfanyl]-1H-pyrazolo[3,4-d]pyrimidin-1-yl}-3,4-dihydroxytetrahydrofuran-2-yl]methyl sulfamate |
| I-29 | {(2R,3S,4R,5R)-5-[4-amino-3-(cyanomethyl)-1H-pyrazolo[3,4-d]pyrimidin-1-yl]-3,4-dihydroxytetrahydrofuran-2-yl}methyl sulfamate |
| I-30 | {(2R,3S,4R,5R)-5-[4-amino-3-(1,3-thiazol-2-yl)-1H-pyrazolo[3,4-d]pyrimidin-1-yl]-3,4-dihydroxytetrahydrofuran-2-yl}methyl sulfamate |
| I-31 | [(2R,3S,4R,5R)-5-{4-amino-3-[(3-methylbenzyl)sulfanyl]-1H-pyrazolo[3,4-d]pyrimidin-1-yl}-3,4-dihydroxytetrahydrofuran-2-yl]methyl sulfamate |
| I-32 | [(2R,3S,4R,5R)-5-(4-amino-3-{[4-(trifluoromethoxy)benzyl]sulfanyl}-1H-pyrazolo[3,4-d]pyrimidin-1-yl)-3,4-dihydroxytetrahydrofuran-2-yl]methyl sulfamate |
| I-33 | [(2R,3S,4R,5R)-5-(4-amino-3-{[4-(trifluoromethyl)benzyl]sulfanyl}-1H-pyrazolo[3,4-d]pyrimidin-1-yl)-3,4-dihydroxytetrahydrofuran-2-yl]methyl sulfamate |
| I-34 | [(2R,3S,4R,5R)-5-{4-amino-3-[(2,4-dichlorophenyl)sulfanyl]-1H-pyrazolo[3,4-d]pyrimidin-1-yl}-3,4-dihydroxytetrahydrofuran-2-yl]methyl sulfamate |
| I-35 | [(2R,3S,4R,5R)-5-{4-amino-3-[(2-methoxyethyl)sulfanyl]-1H-pyrazolo[3,4-d]pyrimidin-1-yl}-3,4-dihydroxytetrahydrofuran-2-yl]methyl sulfamate |

-continued

| Compound | Name |
|---|---|
| I-36 | {(2R,3S,4R,5R)-5-[4-amino-3-(1H-pyrazol-4-ylsulfanyl)-1H-pyrazolo[3,4-d]pyrimidin-1-yl]-3,4-dihydroxytetrahydrofuran-2-yl}methyl sulfamate |
| I-37 | [(2R,3S,4R,5R)-5-(4-amino-3-phenoxy-1H-pyrazolo[3,4-d]pyrimidin-1-yl)-3,4-dihydroxytetrahydrofuran-2-yl]methyl sulfamate |
| I-38 | [(2R,3S,4R,5R)-5-{4-amino-3-[(4-methoxybenzyl)sulfanyl]-1H-pyrazolo[3,4-d]pyrimidin-1-yl}-3,4-dihydroxytetrahydrofuran-2-yl]methyl sulfamate |
| I-39 | [(2R,3S,4R,5R)-5-{4-amino-3-[(2-methylbenzyl)sulfanyl]-1H-pyrazolo[3,4-d]pyrimidin-1-yl}-3,4-dihydroxytetrahydrofuran-2-yl]methyl sulfamate |
| I-40 | [(2R,3S,4R,5R)-5-{4-amino-3-[(3-chlorophenyl)sulfanyl]-1H-pyrazolo[3,4-d]pyrimidin-1-yl}-3,4-dihydroxytetrahydrofuran-2-yl]methyl sulfamate |
| I-41 | [(2R,3S,4R,5R)-5-{4-amino-3-[(4-methylbenzyl)sulfanyl]-1H-pyrazolo[3,4-d]pyrimidin-1-yl}-3,4-dihydroxytetrahydrofuran-2-yl]methyl sulfamate |
| I-42 | {(2R,3S,4R,5R)-5-[4-amino-3-(methylsulfanyl)-1H-pyrazolo[3,4-d]pyrimidin-1-yl]-3,4-dihydroxytetrahydrofuran-2-yl}methyl sulfamate |
| I-43 | {(2R,3S,4R,5R)-5-[4-amino-3-(prop-2-yn-1-ylsulfanyl)-1H-pyrazolo[3,4-d]pyrimidin-1-yl]-3,4-dihydroxytetrahydrofuran-2-yl}methyl sulfamate |
| I-44 | [(2R,3S,4R,5R)-5-{4-amino-3-[(3-fluorobenzyl)sulfanyl]-1H-pyrazolo[3,4-d]pyrimidin-1-yl}-3,4-dihydroxytetrahydrofuran-2-yl]methyl sulfamate |
| I-45 | [(2R,3S,4R,5R)-5-{4-amino-3-[(pyridin-3-ylmethyl)sulfanyl]-1H-pyrazolo[3,4-d]pyrimidin-1-yl}-3,4-dihydroxytetrahydrofuran-2-yl]methyl sulfamate |
| I-46 | [(2R,3S,4R,5R)-5-{4-amino-3-[(2-hydroxyethyl)sulfanyl]-1H-pyrazolo[3,4-d]pyrimidin-1-yl}-3,4-dihydroxytetrahydrofuran-2-yl]methyl sulfamate |
| I-47 | [(2R,3S,4R,5R)-5-(4-amino-3-{[(1R,2R)-2-hydroxycyclohexyl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(1S,2S)-2-hydroxycyclohexyl]sulfanyl}-1H-pyrazolo[3,4-d]pyrimidin-1-yl)-3,4-dihydroxytetrahydrofuran-2-yl]methyl sulfamate |
| I-48 | [(2R,3S,4R,5R)-5-(4-amino-1H-pyrazolo[3,4-d]pyrimidin-1-yl)-3,4-dihydroxytetrahydrofuran-2-yl]methyl sulfamate |
| I-49 | [(2R,3S,4R,5R)-5-(4-amino-3-phenyl-1H-pyrazolo[3,4-d]pyrimidin-1-yl)-3,4-dihydroxytetrahydrofuran-2-yl]methyl sulfamate |
| I-50 | [(2R,3S,4R,5R)-5-{4-amino-3-[(cyclopropylmethyl)sulfanyl]-1H-pyrazolo[3,4-d]pyrimidin-1-yl}-3,4-dihydroxytetrahydrofuran-2-yl]methyl sulfamate |
| I-51 | {(2R,3S,4R,5R)-5-[4-amino-3-(ethylsulfanyl)-1H-pyrazolo[3,4-d]pyrimidin-1-yl]-3,4-dihydroxytetrahydrofuran-2-yl}methyl sulfamate |
| I-52 | {(2R,3S,4R,5R)-5-[4-amino-3-(benzylsulfanyl)-1H-pyrazolo[3,4-d]pyrimidin-1-yl]-3,4-dihydroxytetrahydrofuran-2-yl}methyl sulfamate |
| I-53 | {(2R,3S,4R,5R)-5-[4-amino-3-(tert-butylsulfanyl)-1H-pyrazolo[3,4-d]pyrimidin-1-yl]-3,4-dihydroxytetrahydrofuran-2-yl}methyl sulfamate |
| I-54 | [(2R,3S,4R,5R)-5-(4-amino-3-{[(1R,2R)-2-hydroxycyclopentyl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(1S,2S)-2-hydroxycyclopentyl]sulfanyl}-1H-pyrazolo[3,4-d]pyrimidin-1-yl)-3,4-dihydroxytetrahydrofuran-2-yl]methyl sulfamate |
| I-55a | [(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate or [(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl sulfamate |
| I-55b | [(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate or [(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl sulfamate |
| I-56 | {(2R,3S,4R,5R)-5-[4-amino-3-(cyclobutylsulfanyl)-1H-pyrazolo[3,4-d]pyrimidin-1-yl]-3,4-dihydroxytetrahydrofuran-2-yl}methyl sulfamate |
| I-57 | {(2R,3S,4R,5R)-5-[4-amino-3-(1,3-oxazol-2-yl)-1H-pyrazolo[3,4-d]pyrimidin-1-yl]-3,4-dihydroxytetrahydrofuran-2-yl}methyl sulfamate |
| I-58 | {(2R,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl sulfamate |
| I-59 | [(2R,3S,4R,5R)-5-{4-amino-3-[(pyridin-2-ylmethyl)sulfanyl]-1H-pyrazolo[3,4-d]pyrimidin-1-yl}-3,4-dihydroxytetrahydrofuran-2-yl]methyl sulfamate |
| I-60 | [(2R,3S,4R,5R)-5-(4-amino-3-carbamothioyl-1H-pyrazolo[3,4-d]pyrimidin-1-yl)-3,4-dihydroxytetrahydrofuran-2-yl]methyl sulfamate |
| I-61 | [(2R,3S,4R,5R)-5-{4-amino-3-[(1-methyl-1H-pyrazol-4-yl)sulfanyl]-1H-pyrazolo[3,4-d]pyrimidin-1-yl}-3,4-dihydroxytetrahydrofuran-2-yl]methyl sulfamate |
| I-62 | {(2R,3S,4R,5R)-5-[4-amino-3-(cyclopentylsulfanyl)-1H-pyrazolo[3,4-d]pyrimidin-1-yl]-3,4-dihydroxytetrahydrofuran-2-yl}methyl sulfamate |
| I-63 | [(2R,3S,4R,5R)-5-{4-amino-3-[(4-fluorobenzyl)sulfanyl]-1H-pyrazolo[3,4-d]pyrimidin-1-yl}-3,4-dihydroxytetrahydrofuran-2-yl]methyl sulfamate |
| I-64 | [(2R,3S,4R,5R)-5-{4-amino-3-[(4-chlorophenyl)sulfanyl]-1H-pyrazolo[3,4-d]pyrimidin-1-yl}-3,4-dihydroxytetrahydrofuran-2-yl]methyl sulfamate |
| I-65 | {(2R,3S,4R,5R)-5-[4-amino-3-(cyclopropylsulfanyl)-1H-pyrazolo[3,4-d]pyrimidin-1-yl]-3,4-dihydroxytetrahydrofuran-2-yl}methyl sulfamate |
| I-66 | {(2R,3S,4R,5R)-5-[4-amino-3-(pyridin-4-ylsulfanyl)-1H-pyrazolo[3,4-d]pyrimidin-1-yl]-3,4-dihydroxytetrahydrofuran-2-yl}methyl sulfamate |
| I-67 | [(2R,3S,4R,5R)-5-{4-amino-3-[(1-naphthylmethyl)sulfanyl]-1H-pyrazolo[3,4-d]pyrimidin-1-yl}-3,4-dihydroxytetrahydrofuran-2-yl]methyl sulfamate |
| I-68 | {(2R,3S,4R,5R)-5-[4-amino-3-(1H-pyrazol-5-yl)-1H-pyrazolo[3,4-d]pyrimidin-1-yl]-3,4-dihydroxytetrahydrofuran-2-yl}methyl sulfamate |

| Compound | Name |
|---|---|
| I-69 | [(2R,3S,4R,5R)-5-{4-amino-3-[(3-methylphenyl)sulfanyl]-1H-pyrazolo[3,4-d]pyrimidin-1-yl}-3,4-dihydroxytetrahydrofuran-2-yl]methyl sulfamate |
| I-70 | [(2R,3S,4R,5R)-5-(4-amino-3-{[(1R)-1-phenylethyl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(1S)-1-phenylethyl]sulfanyl}-1H-pyrazolo[3,4-d]pyrimidin-1-yl)-3,4-dihydroxytetrahydrofuran-2-yl]methyl sulfamate |
| I-71 | {(2R,3S,4R,5R)-5-[3-(allyloxy)-4-amino-1H-pyrazolo[3,4-d]pyrimidin-1-yl]-3,4-dihydroxytetrahydrofuran-2-yl}methyl sulfamate |
| I-72 | {(2R,3S,4R,5R)-5-[4-amino-3-(azetidin-3-ylsulfanyl)-1H-pyrazolo[3,4-d]pyrimidin-1-yl]-3,4-dihydroxytetrahydrofuran-2-yl}methyl sulfamate |
| I-73 | [(2R,3S,4R,5R)-5-(4-amino-3-{[(5-chloro-2-furyl)methyl]sulfanyl}-1H-pyrazolo[3,4-d]pyrimidin-1-yl)-3,4-dihydroxytetrahydrofuran-2-yl]methyl sulfamate |
| I-74 | [(2R,3S,4R,5R)-5-{4-amino-3-[(2-methylphenyl)sulfanyl]-1H-pyrazolo[3,4-d]pyrimidin-1-yl}-3,4-dihydroxytetrahydrofuran-2-yl]methyl sulfamate |
| I-75 | {(2R,3S,4R,5R)-5-[4-amino-3-(2-chloroethoxy)-1H-pyrazolo[3,4-d]pyrimidin-1-yl]-3,4-dihydroxytetrahydrofuran-2-yl}methyl sulfamate |
| I-76 | {(2R,3S,4R,5R)-5-[4-amino-3-(benzyloxy)-1H-pyrazolo[3,4-d]pyrimidin-1-yl]-3,4-dihydroxytetrahydrofuran-2-yl}methyl sulfamate |
| I-77 | {(2R,3S,4R,5R)-5-[4-amino-3-(isobutylsulfanyl)-1H-pyrazolo[3,4-d]pyrimidin-1-yl]-3,4-dihydroxytetrahydrofuran-2-yl}methyl sulfamate |
| I-78 | [(2R,3S,4R,5R)-5-[4-amino-3-(2-chlorophenyl)sulfanyl]-1H-pyrazolo[3,4-d]pyrimidin-1-yl]-3,4-dihydroxytetrahydrofuran-2-yl]methyl sulfamate |
| I-79 | [(2R,3S,4R,5R)-5-(4-amino-3-iodo-1H-pyrazolo[3,4-d]pyrimidin-1-yl)-3,4-dihydroxytetrahydrofuran-2-yl]methyl sulfamate |
| I-80 | [(2R,3S,4R,5R)-5-(4-amino-3-{[2-(dimethylamino)ethyl]sulfanyl}-1H-pyrazolo[3,4-d]pyrimidin-1-yl)-3,4-dihydroxytetrahydrofuran-2-yl]methyl sulfamate |
| I-81 | [(2R,3S,4R,5R)-5-{4-amino-3-[(2-methyl-3-furyl)sulfanyl]-1H-pyrazolo[3,4-d]pyrimidin-1-yl}-3,4-dihydroxytetrahydrofuran-2-yl]methyl sulfamate |
| I-82 | {(2R,3S,4R,5R)-5-[4-amino-3-(phenylsulfanyl)-1H-pyrazolo[3,4-d]pyrimidin-1-yl]-3,4-dihydroxytetrahydrofuran-2-yl}methyl sulfamate |
| I-83 | [(2R,3S,4R,5R)-5-{4-amino-3-[(2,2,2-trifluoroethyl)sulfanyl]-1H-pyrazolo[3,4-d]pyrimidin-1-yl}-3,4-dihydroxytetrahydrofuran-2-yl]methyl sulfamate |
| I-84 | {(2R,3S,4R,5R)-5-[4-amino-3-(1-naphthylsulfanyl)-1H-pyrazolo[3,4-d]pyrimidin-1-yl]-3,4-dihydroxytetrahydrofuran-2-yl}methyl sulfamate |
| I-85 | [(2R,3S,4R,5R)-5-{4-amino-3-[(difluoromethyl)sulfanyl]-1H-pyrazolo[3,4-d]pyrimidin-1-yl}-3,4-dihydroxytetrahydrofuran-2-yl]methyl sulfamate |
| I-86 | [(2R,3S,4R,5R)-5-(4-amino-3-{[(1-hydroxycyclohexyl)methyl]sulfanyl}-1H-pyrazolo[3,4-d]pyrimidin-1-yl)-3,4-dihydroxytetrahydrofuran-2-yl]methyl sulfamate |
| I-87 | {(2R,3S,4R,5R)-5-[4-amino-3-(methylsulfinyl)-1H-pyrazolo[3,4-d]pyrimidin-1-yl]-3,4-dihydroxytetrahydrofuran-2-yl}methyl sulfamate |
| I-88 | [(2R,3S,4R,5R)-5-{4-amino-3-[(2-phenylethyl)sulfanyl]-1H-pyrazolo[3,4-d]pyrimidin-1-yl}-3,4-dihydroxytetrahydrofuran-2-yl]methyl sulfamate |
| I-89 | [(2R,3S,4R,5R)-5-{4-amino-3-[(4-methylphenyl)sulfanyl]-1H-pyrazolo[3,4-d]pyrimidin-1-yl}-3,4-dihydroxytetrahydrofuran-2-yl]methyl sulfamate |
| I-90 | [(2R,3S,4R,5R)-5-{4-amino-3-[(cyanomethyl)sulfanyl]-1H-pyrazolo[3,4-d]pyrimidin-1-yl}-3,4-dihydroxytetrahydrofuran-2-yl]methyl sulfamate |
| I-91 | [(2R,3S,4R,5R)-5-{4-amino-3-[(cyclohex-1-en-1-ylmethyl)sulfanyl]-1H-pyrazolo[3,4-d]pyrimidin-1-yl}-3,4-dihydroxytetrahydrofuran-2-yl]methyl sulfamate |
| I-92 | [(2R,3S,4R,5R)-5-(4-amino-3-{[(2S,3R)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(2R,3R)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(2R,3S)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(2S,3S)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate |
| I-93 | [(2R,3S,4R,5R)-5-{4-amino-3-[(methylsulfanyl)methyl]-1H-pyrazolo[3,4-d]pyrimidin-1-yl}-3,4-dihydroxytetrahydrofuran-2-yl]methyl sulfamate |
| I-94 | {(2S,3S,4R,5R)-5-[4-amino-3-(methylsulfanyl)-1H-pyrazolo[3,4-d]pyrimidin-1-yl]-3,4-dihydroxytetrahydrofuran-2-yl}methyl sulfamate |
| I-95 | {(2S,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl sulfamate |
| I-96 | {(2S,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl sulfamate |
| I-97 | [(2R,3R,4S,5R)-5-(4-amino-3-{[(3,3-difluorocyclobutyl)methyl]sulfanyl}-1H-pyrazolo[3,4-d]pyrimidin-1-yl)-4-fluoro-3-hydroxytetrahydrofuran-2-yl]methyl sulfamate |
| I-98 | [(2R,3R,4S,5R)-5-{4-amino-3-[(difluoromethyl)sulfanyl]-1H-pyrazolo[3,4-d]pyrimidin-1-yl}-4-fluoro-3-hydroxytetrahydrofuran-2-yl]methyl sulfamate |
| I-99 | {(2R,3R,4S,5R)-5-[4-amino-3-(difluoromethoxy)-1H-pyrazolo[3,4-d]pyrimidin-1-yl]-4-fluoro-3-hydroxytetrahydrofuran-2-yl}methyl sulfamate |
| I-100 | [(2R,3R,4S,5R)-5-{4-amino-3-[(2-methyl-3-furyl)sulfanyl]-1H-pyrazolo[3,4-d]pyrimidin-1-yl}-4-fluoro-3-hydroxytetrahydrofuran-2-yl]methyl sulfamate |

| Compound | Name |
|---|---|
| I-101 | [(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-hydroxytetrahydrofuran-2-yl]methyl sulfamate and [(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-hydroxytetrahydrofuran-2-yl]methyl sulfamate |
| I-102 | [(2R,3R,4S,5R)-5-{4-amino-3-[(6-methylpyridin-2-yl)sulfanyl]-1H-pyrazolo[3,4-d]pyrimidin-1-yl}-4-fluoro-3-hydroxytetrahydrofuran-2-yl]methyl sulfamate |
| I-103 | {(2R,3R,4S,5R)-5-[4-amino-3-(cyclopentylsulfanyl)-1H-pyrazolo[3,4-d]pyrimidin-1-yl]-4-fluoro-3-hydroxytetrahydrofuran-2-yl}methyl sulfamate |
| I-104 | [(2R,3R,4S,5R)-5-(4-amino-3-{[2-(diethylamino)ethyl]sulfanyl}-1H-pyrazolo[3,4-d]pyrimidin-1-yl)-4-fluoro-3-hydroxytetrahydrofuran-2-yl]methyl sulfamate |
| I-105 | [(2R,3R,4S,5R)-5-(4-amino-3-methoxy-1H-pyrazolo[3,4-d]pyrimidin-1-yl)-4-fluoro-3-hydroxytetrahydrofuran-2-yl]methyl sulfamate |
| I-106 | [(2R,3R,4S,5R)-5-{4-amino-3-[(3-chlorophenyl)sulfanyl]-1H-pyrazolo[3,4-d]pyrimidin-1-yl}-4-fluoro-3-hydroxytetrahydrofuran-2-yl]methyl sulfamate |
| I-107 | [(2R,3R,4S,5R)-5-{4-amino-3-[(6-methoxypyridin-2-yl)sulfanyl]-1H-pyrazolo[3,4-d]pyrimidin-1-yl}-4-fluoro-3-hydroxytetrahydrofuran-2-yl]methyl sulfamate |
| I-108 | [(2R,3R,4S,5R)-5-(4-amino-3-cyclopropyl-1H-pyrazolo[3,4-d]pyrimidin-1-yl)-4-fluoro-3-hydroxytetrahydrofuran-2-yl]methyl sulfamate |
| I-109 | [(2R,3R,4S,5R)-5-{4-amino-3-[(2-fluorophenyl)sulfanyl]-1H-pyrazolo[3,4-d]pyrimidin-1-yl}-4-fluoro-3-hydroxytetrahydrofuran-2-yl]methyl sulfamate |
| I-110 | [(2R,3R,4S,5R)-5-{4-amino-3-[(2,5-dimethyl-3-furyl)sulfanyl]-1H-pyrazolo[3,4-d]pyrimidin-1-yl}-4-fluoro-3-hydroxytetrahydrofuran-2-yl]methyl sulfamate |
| I-111 | [(2R,3R,4S,5R)-5-{4-amino-3-[(5-nitropyridin-2-yl)sulfanyl]-1H-pyrazolo[3,4-d]pyrimidin-1-yl}-4-fluoro-3-hydroxytetrahydrofuran-2-yl]methyl sulfamate |
| I-112 | [(2R,3R,4S,5R)-5-(4-amino-3-{[(1-methyl-1H-imidazol-2-yl)methyl]sulfanyl}-1H-pyrazolo[3,4-d]pyrimidin-1-yl)-4-fluoro-3-hydroxytetrahydrofuran-2-yl]methyl sulfamate |
| I-113 | {(2R,3R,4S,5R)-5-[4-amino-3-(pyridin-2-ylsulfanyl)-1H-pyrazolo[3,4-d]pyrimidin-1-yl]-4-fluoro-3-hydroxytetrahydrofuran-2-yl}methyl sulfamate |
| I-114 | [(2R,3R,4S,5R)-5-{4-amino-3-[(4-methylpyridin-2-yl)sulfanyl]-1H-pyrazolo[3,4-d]pyrimidin-1-yl}-4-fluoro-3-hydroxytetrahydrofuran-2-yl]methyl sulfamate |
| I-115 | {(2R,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl sulfamate |
| I-116 | [(2R,3R,4S,5R)-5-{4-amino-3-[(3-fluorophenyl)sulfanyl]-1H-pyrazolo[3,4-d]pyrimidin-1-yl}-4-fluoro-3-hydroxytetrahydrofuran-2-yl]methyl sulfamate |
| I-117 | [(2R,3R,4S,5R)-5-(4-amino-3-{[4-(trifluoromethyl)pyridin-2-yl]sulfanyl}-1H-pyrazolo[3,4-d]pyrimidin-1-yl)-4-fluoro-3-hydroxytetrahydrofuran-2-yl]methyl sulfamate |
| I-118 | {(2R,3R,4S,5R)-5-[4-amino-3-(tert-butylsulfanyl)-1H-pyrazolo[3,4-d]pyrimidin-1-yl]-4-fluoro-3-hydroxytetrahydrofuran-2-yl}methyl sulfamate |
| I-119 | [(2R,3R,4S,5R)-5-{4-amino-3-[(pyridin-2-ylmethyl)sulfanyl]-1H-pyrazolo[3,4-d]pyrimidin-1-yl}-4-fluoro-3-hydroxytetrahydrofuran-2-yl]methyl sulfamate |
| I-120 | {(2R,3R,4S,5R)-5-[4-amino-3-(pentan-3-ylsulfanyl)-1H-pyrazolo[3,4-d]pyrimidin-1-yl]-4-fluoro-3-hydroxytetrahydrofuran-2-yl}methyl sulfamate |
| I-121 | [(2R,3R,4S,5R)-5-{4-amino-3-[(pyridin-3-ylmethyl)sulfanyl]-1H-pyrazolo[3,4-d]pyrimidin-1-yl}-4-fluoro-3-hydroxytetrahydrofuran-2-yl]methyl sulfamate |
| I-122 | {(2R,3R,4S,5R)-5-[4-amino-3-(cyclohexylsulfanyl)-1H-pyrazolo[3,4-d]pyrimidin-1-yl]-4-fluoro-3-hydroxytetrahydrofuran-2-yl}methyl sulfamate |
| I-123 | [(2R,3R,4S,5R)-5-{4-amino-3-[(3R)-tetrahydrofuran-3-ylsulfanyl]-1H-pyrazolo[3,4-d]pyrimidin-1-yl}-4-fluoro-3-hydroxytetrahydrofuran-2-yl]methyl sulfamate and [(2R,3R,4S,5R)-5-{4-amino-3-[(3S)-tetrahydrofuran-3-ylsulfanyl]-1H-pyrazolo[3,4-d]pyrimidin-1-yl}-4-fluoro-3-hydroxytetrahydrofuran-2-yl]methyl sulfamate |
| I-124 | [(2R,3R,4S,5R)-5-{4-amino-3-[(pyridin-4-ylmethyl)sulfanyl]-1H-pyrazolo[3,4-d]pyrimidin-1-yl}-4-fluoro-3-hydroxytetrahydrofuran-2-yl]methyl sulfamate |
| I-125 | [(2R,3R,4S,5R)-5-{4-amino-3-[(1-methyl-1H-imidazol-2-yl)sulfanyl]-1H-pyrazolo[3,4-d]pyrimidin-1-yl}-4-fluoro-3-hydroxytetrahydrofuran-2-yl]methyl sulfamate |
| I-126 | [(2R,3R,4S,5R)-5-{4-amino-3-[(4-fluorophenyl)sulfanyl]-1H-pyrazolo[3,4-d]pyrimidin-1-yl}-4-fluoro-3-hydroxytetrahydrofuran-2-yl]methyl sulfamate |
| I-127 | [(2R,3R,4S,5R)-5-{4-amino-3-[(pyridazin-3-ylmethyl)sulfanyl]-1H-pyrazolo[3,4-d]pyrimidin-1-yl}-4-fluoro-3-hydroxytetrahydrofuran-2-yl]methyl sulfamate |
| I-128 | [(2R,3R,4S,5R)-5-{4-amino-3-[(pyridazin-4-ylmethyl)sulfanyl]-1H-pyrazolo[3,4-d]pyrimidin-1-yl}-4-fluoro-3-hydroxytetrahydrofuran-2-yl]methyl sulfamate |
| I-129 | [(2R,3R,4S,5R)-5-(4-amino-3-{[(2R)-3-methylbutan-2-yl]sulfanyl}-1H-pyrazolo[3,4-d]pyrimidin-1-yl)-4-fluoro-3-hydroxytetrahydrofuran-2-yl]methyl sulfamate and [(2R,3R,4S,5R)-5-(4-amino-3-{[(2S)-3-methylbutan-2-yl]sulfanyl}-1H-pyrazolo[3,4-d]pyrimidin-1-yl)-4-fluoro-3-hydroxytetrahydrofuran-2-yl]methyl sulfamate |
| I-130 | [(2R,3R,4S,5R)-5-{4-amino-3-[(4-cyanopyridin-2-yl)sulfanyl]-1H-pyrazolo[3,4-d]pyrimidin-1-yl}-4-fluoro-3-hydroxytetrahydrofuran-2-yl]methyl sulfamate |
| I-131 | {(2R,3R,4S,5R)-5-[4-amino-3-({[(1R)-2,2-difluorocyclopropyl]methyl}sulfanyl)-1H-pyrazolo[3,4-d]pyrimidin-1-yl]-4-fluoro-3-hydroxytetrahydrofuran-2-yl}methyl sulfamate and {(2R,3R,4S,5R)-5-[4-amino-3-({[(1S)-2,2-difluorocyclopropyl]methyl}sulfanyl)-1H-pyrazolo[3,4-d]pyrimidin-1-yl]-4-fluoro-3-hydroxytetrahydrofuran-2-yl}methyl sulfamate |
| I-132 | [(2R,3R,4S,5R)-5-(4-amino-3-{[4-(trifluoromethyl)phenyl]sulfanyl}-1H-pyrazolo[3,4-d]pyrimidin-1-yl)-4-fluoro-3-hydroxytetrahydrofuran-2-yl]methyl sulfamate |

-continued

| Compound | Name |
|---|---|
| I-133 | [(2R,3R,4S,5R)-5-{4-amino-3-[(4-chlorophenyl)sulfanyl]-1H-pyrazolo[3,4-d]pyrimidin-1-yl}-4-fluoro-3-hydroxytetrahydrofuran-2-yl]methyl sulfamate |
| I-134 | [(2R,3R,4S,5R)-5-{4-amino-3-[(1-methyl-1H-imidazol-5-yl)sulfanyl]-1H-pyrazolo[3,4-d]pyrimidin-1-yl}-4-fluoro-3-hydroxytetrahydrofuran-2-yl]methyl sulfamate |
| I-135 | [(2R,3R,4S,5R)-5-{4-amino-3-[(cyclopropylmethyl)sulfanyl]-1H-pyrazolo[3,4-d]pyrimidin-1-yl}-4-fluoro-3-hydroxytetrahydrofuran-2-yl]methyl sulfamate |
| I-136 | [(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate and [(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate |
| I-136a | [(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate or [(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate |
| I-136b | [(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate or [(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate |
| I-137 | [(2R,3R,4S,5R)-5-{4-amino-3-[(1-methyl-1H-imidazol-4-yl)sulfanyl]-1H-pyrazolo[3,4-d]pyrimidin-1-yl}-4-fluoro-3-hydroxytetrahydrofuran-2-yl]methyl sulfamate |
| I-138 | {(2R,3R,4S,5R)-5-[4-amino-3-(pyridin-3-ylsulfanyl)-1H-pyrazolo[3,4-d]pyrimidin-1-yl]-4-fluoro-3-hydroxytetrahydrofuran-2-yl}methyl sulfamate |
| I-139 | {(2R,3R,4S,5R)-5-[4-amino-3-(isopropylsulfanyl)-1H-pyrazolo[3,4-d]pyrimidin-1-yl]-4-fluoro-3-hydroxytetrahydrofuran-2-yl}methyl sulfamate |
| I-140 | {(2R,3R,4S,5R)-5-[4-amino-3-({[(1R,2R)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate and {(2R,3R,4S,5R)-5-[4-amino-3-({[(1S,2R)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate and {(2R,3R,4S,5R)-5-[4-amino-3-({[(1R,2S)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate and {(2R,3R,4S,5R)-5-[4-amino-3-({[(1S,2S)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate |
| I-141 | [(2R,3R,4S,5R)-5-{4-amino-3-[(3-methylphenyl)sulfanyl]-1H-pyrazolo[3,4-d]pyrimidin-1-yl}-4-fluoro-3-hydroxytetrahydrofuran-2-yl]methyl sulfamate |
| I-142 | [(2R,3R,4S,5R)-5-{4-amino-3-[(trifluoromethyl)sulfanyl]-1H-pyrazolo[3,4-d]pyrimidin-1-yl}-4-fluoro-3-hydroxytetrahydrofuran-2-yl]methyl sulfamate |
| I-143 | [(2R,3R,4S,5R)-5-(4-amino-3-{[5-(trifluoromethyl)pyridin-2-yl]sulfanyl}-1H-pyrazolo[3,4-d]pyrimidin-1-yl)-4-fluoro-3-hydroxytetrahydrofuran-2-yl]methyl sulfamate |
| I-144 | [(2R,3R,4S,5R)-5-(4-amino-3-{[(2R)-1-hydroxypropan-2-yl]sulfanyl}-1H-pyrazolo[3,4-d]pyrimidin-1-yl)-4-fluoro-3-hydroxytetrahydrofuran-2-yl]methyl sulfamate and [(2R,3R,4S,5R)-5-(4-amino-3-{[(2S)-1-hydroxypropan-2-yl]sulfanyl}-1H-pyrazolo[3,4-d]pyrimidin-1-yl)-4-fluoro-3-hydroxytetrahydrofuran-2-yl]methyl sulfamate |
| I-145 | [(2R,3R,4S,5R)-5-(4-amino-3-{[(1-methyl-1H-pyrazol-4-yl)methyl]sulfanyl}-1H-pyrazolo[3,4-d]pyrimidin-1-yl)-4-fluoro-3-hydroxytetrahydrofuran-2-yl]methyl sulfamate |
| I-146 | [(2R,3R,4S,5R)-5-{4-amino-3-[(5-chloropyridin-2-yl)sulfanyl]-1H-pyrazolo[3,4-d]pyrimidin-1-yl}-4-fluoro-3-hydroxytetrahydrofuran-2-yl]methyl sulfamate |
| I-147 | {(2R,3R,4S,5R)-5-[4-amino-3-(cyclobutylsulfanyl)-1H-pyrazolo[3,4-d]pyrimidin-1-yl]-4-fluoro-3-hydroxytetrahydrofuran-2-yl}methyl sulfamate |
| I-148 | [(2R,3R,4S,5R)-5-{4-amino-3-[(cyclobutylmethyl)sulfanyl]-1H-pyrazolo[3,4-d]pyrimidin-1-yl}-4-fluoro-3-hydroxytetrahydrofuran-2-yl]methyl sulfamate |
| I-149 | [(2R,3R,4S,5R)-5-(4-amino-3-{[(1R)-1-cyanoethyl]sulfanyl}-1H-pyrazolo[3,4-d]pyrimidin-1-yl)-4-fluoro-3-hydroxytetrahydrofuran-2-yl]methyl sulfamate and [(2R,3R,4S,5R)-5-(4-amino-3-{[(1S)-1-cyanoethyl]sulfanyl}-1H-pyrazolo[3,4-d]pyrimidin-1-yl)-4-fluoro-3-hydroxytetrahydrofuran-2-yl]methyl sulfamate |
| I-150 | {(2R,3R,4S,5R)-5-[4-amino-3-(pyridin-4-ylsulfanyl)-1H-pyrazolo[3,4-d]pyrimidin-1-yl]-4-fluoro-3-hydroxytetrahydrofuran-2-yl}methyl sulfamate |
| I-151 | [(2R,3R,4S,5R)-5-{4-amino-3-[(2-hydroxyethyl)sulfanyl]-1H-pyrazolo[3,4-d]pyrimidin-1-yl}-4-fluoro-3-hydroxytetrahydrofuran-2-yl]methyl sulfamate |
| I-152 | [(2R,3R,4S,5R)-5-{4-amino-3-[(5-methylpyridin-2-yl)sulfanyl]-1H-pyrazolo[3,4-d]pyrimidin-1-yl}-4-fluoro-3-hydroxytetrahydrofuran-2-yl]methyl sulfamate |
| I-153 | [(2R,3R,4S,5R)-5-{4-amino-3-[(3-cyanophenyl)sulfanyl]-1H-pyrazolo[3,4-d]pyrimidin-1-yl}-4-fluoro-3-hydroxytetrahydrofuran-2-yl]methyl sulfamate |
| I-154 | [(2R,3R,4S,5R)-5-{4-amino-3-[(2-methoxyethyl)sulfanyl]-1H-pyrazolo[3,4-d]pyrimidin-1-yl}-4-fluoro-3-hydroxytetrahydrofuran-2-yl]methyl sulfamate |
| I-155 | {(2R,3R,4S,5R)-5-[4-amino-3-(benzylsulfanyl)-1H-pyrazolo[3,4-d]pyrimidin-1-yl]-4-fluoro-3-hydroxytetrahydrofuran-2-yl}methyl sulfamate |
| I-156 | {(2R,3R,4S,5R)-5-[4-amino-3-([1,2,4]triazolo[4,3-a]pyridin-3-ylsulfanyl)-1H-pyrazolo[3,4-d]pyrimidin-1-yl]-4-fluoro-3-hydroxytetrahydrofuran-2-yl}methyl sulfamate |
| I-157 | [(2R,3R,4S,5R)-5-(4-amino-3-{[(1R)-1-cyclopropylethyl]sulfanyl}-1H-pyrazolo[3,4-d]pyrimidin-1-yl)-4-fluoro-3-hydroxytetrahydrofuran-2-yl]methyl sulfamate and [(2R,3R,4S,5R)-5-(4-amino-3-{[(1S)-1-cyclopropylethyl]sulfanyl}-1H-pyrazolo[3,4-d]pyrimidin-1-yl)-4-fluoro-3-hydroxytetrahydrofuran-2-yl]methyl sulfamate |

-continued

| Compound | Name |
|---|---|
| I-158 | [(2R,3R,4S,5R)-5-(4-amino-3-{[3-(trifluoromethyl)phenyl]sulfanyl}-1H-pyrazolo[3,4-d]pyrimidin-1-yl)-4-fluoro-3-hydroxytetrahydrofuran-2-yl]methyl sulfamate |
| I-159 | [(2R,3S,5R)-5-{4-amino-3-[(2-amino-2-oxoethyl)sulfanyl]-1H-pyrazolo[3,4-d]pyrimidin-1-yl}-3-hydroxytetrahydrofuran-2-yl]methyl sulfamate |
| I-160 | {(2R,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl sulfamate |
| I-161 | [(2R,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl sulfamate |
| I-162 | [(2R,3S,5R)-5-{4-amino-3-[(2-hydroxyethyl)sulfanyl]-1H-pyrazolo[3,4-d]pyrimidin-1-yl}-3-hydroxytetrahydrofuran-2-yl]methyl sulfamate |
| I-163 | [(2R,3S,5R)-5-{4-amino-3-[(4-tert-butylphenyl)sulfanyl]-1H-pyrazolo[3,4-d]pyrimidin-1-yl}-3-hydroxytetrahydrofuran-2-yl]methyl sulfamate |
| I-164 | {(2R,3S,5R)-5-[4-amino-3-(cyclobutylsulfanyl)-1H-pyrazolo[3,4-d]pyrimidin-1-yl]-3-hydroxytetrahydrofuran-2-yl}methyl sulfamate |
| I-165 | [(2R,3S,5R)-5-{4-amino-3-[(2,2-difluoroethyl)sulfanyl]-1H-pyrazolo[3,4-d]pyrimidin-1-yl}-3-hydroxytetrahydrofuran-2-yl]methyl sulfamate |
| I-166 | {(2R,3S,5R)-5-[4-amino-3-(2-naphthylsulfanyl)-1H-pyrazolo[3,4-d]pyrimidin-1-yl]-3-hydroxytetrahydrofuran-2-yl}methyl sulfamate |
| I-167 | {(2R,3S,5R)-5-[4-amino-3-(cyclopropylsulfanyl)-1H-pyrazolo[3,4-d]pyrimidin-1-yl]-3-hydroxytetrahydrofuran-2-yl}methyl sulfamate |
| I-168 | {(2R,3S,5R)-5-[4-amino-3-(2,3-dihydro-1-benzofuran-6-ylsulfanyl)-1H-pyrazolo[3,4-d]pyrimidin-1-yl]-3-hydroxytetrahydrofuran-2-yl}methyl sulfamate |
| I-169 | [(2R,3S,5R)-5-{4-amino-3-[(difluoromethyl)sulfanyl]-1H-pyrazolo[3,4-d]pyrimidin-1-yl}-3-hydroxytetrahydrofuran-2-yl]methyl sulfamate |
| I-170 | {(2R,3S,5R)-5-[4-amino-3-(1H-indol-3-ylsulfanyl)-1H-pyrazolo[3,4-d]pyrimidin-1-yl]-3-hydroxytetrahydrofuran-2-yl}methyl sulfamate |
| I-171 | {(2R,3S,5R)-5-[4-amino-3-(trifluoromethyl)-1H-pyrazolo[3,4-d]pyrimidin-1-yl]-3-hydroxytetrahydrofuran-2-yl}methyl sulfamate |
| I-172 | {(2R,3S,5R)-5-[4-amino-3-(ethylsulfanyl)-1H-pyrazolo[3,4-d]pyrimidin-1-yl]-3-hydroxytetrahydrofuran-2-yl}methyl sulfamate |
| I-173 | [(2R,3S,5R)-5-{4-amino-3-[(2-fluoro-5-methoxyphenyl)sulfanyl]-1H-pyrazolo[3,4-d]pyrimidin-1-yl}-3-hydroxytetrahydrofuran-2-yl]methyl sulfamate |
| I-174 | {(2R,3S,5R)-5-[4-amino-3-(1,3-thiazol-2-ylsulfanyl)-1H-pyrazolo[3,4-d]pyrimidin-1-yl]-3-hydroxytetrahydrofuran-2-yl}methyl sulfamate |
| I-175 | {(2R,3S,5R)-5-[4-amino-3-(1,3-benzodioxol-5-ylsulfanyl)-1H-pyrazolo[3,4-d]pyrimidin-1-yl]-3-hydroxytetrahydrofuran-2-yl}methyl sulfamate |
| I-176 | [(2R,3S,5R)-5-{4-amino-3-[(2-methylphenyl)sulfanyl]-1H-pyrazolo[3,4-d]pyrimidin-1-yl}-3-hydroxytetrahydrofuran-2-yl]methyl sulfamate |
| I-177 | {(2R,3S,5R)-5-[4-amino-3-(tert-butylsulfanyl)-1H-pyrazolo[3,4-d]pyrimidin-1-yl]-3-hydroxytetrahydrofuran-2-yl}methyl sulfamate |
| I-178 | [(2R,3S,5R)-5-{4-amino-3-[(2-fluoro-4-methoxyphenyl)sulfanyl]-1H-pyrazolo[3,4-d]pyrimidin-1-yl}-3-hydroxytetrahydrofuran-2-yl]methyl sulfamate |
| I-179 | [(2R,3S,5R)-5-{4-amino-3-[(3-chlorophenyl)sulfanyl]-1H-pyrazolo[3,4-d]pyrimidin-1-yl}-3-hydroxytetrahydrofuran-2-yl]methyl sulfamate |
| I-180 | [(2R,3S,5R)-5-(4-amino-3-{[2-(dimethylamino)-2-oxoethyl]sulfanyl}-1H-pyrazolo[3,4-d]pyrimidin-1-yl)-3-hydroxytetrahydrofuran-2-yl]methyl sulfamate |
| I-181 | {(2R,3S,5R)-5-[4-amino-3-(isopropylsulfanyl)-1H-pyrazolo[3,4-d]pyrimidin-1-yl]-3-hydroxytetrahydrofuran-2-yl}methyl sulfamate |
| I-182 | [(2R,3S,5R)-5-{4-amino-3-[(2-fluorophenyl)sulfanyl]-1H-pyrazolo[3,4-d]pyrimidin-1-yl}-3-hydroxytetrahydrofuran-2-yl]methyl sulfamate |
| I-183 | {(2R,3S,5R)-5-[4-amino-3-(quinolin-2-ylsulfanyl)-1H-pyrazolo[3,4-d]pyrimidin-1-yl]-3-hydroxytetrahydrofuran-2-yl}methyl sulfamate |
| I-184 | [(2R,3S,5R)-5-{4-amino-3-[(4-isopropoxyphenyl)sulfanyl]-1H-pyrazolo[3,4-d]pyrimidin-1-yl}-3-hydroxytetrahydrofuran-2-yl]methyl sulfamate |
| I-185 | [(2R,3S,5R)-5-{4-amino-3-[(1-methyl-2-oxo-2,3-dihydro-1H-indol-5-yl)sulfanyl]-1H-pyrazolo[3,4-d]pyrimidin-1-yl}-3-hydroxytetrahydrofuran-2-yl]methyl sulfamate |
| I-186 | {(2R,3S,5R)-5-[4-amino-3-(2,3-dihydro-1-benzofuran-5-ylsulfanyl)-1H-pyrazolo[3,4-d]pyrimidin-1-yl]-3-hydroxytetrahydrofuran-2-yl}methyl sulfamate |
| I-187 | [(2R,3S,5R)-5-{4-amino-3-[(4-fluorophenyl)sulfanyl]-1H-pyrazolo[3,4-d]pyrimidin-1-yl}-3-hydroxytetrahydrofuran-2-yl]methyl sulfamate |
| I-188 | [(2R,3S,5R)-5-{4-amino-3-[(cyanomethyl)sulfanyl]-1H-pyrazolo[3,4-d]pyrimidin-1-yl}-3-hydroxytetrahydrofuran-2-yl]methyl sulfamate |
| I-189 | [(2R,3S,5R)-5-{4-amino-3-[(5-chloropyridin-2-yl)sulfanyl]-1H-pyrazolo[3,4-d]pyrimidin-1-yl}-3-hydroxytetrahydrofuran-2-yl]methyl sulfamate |
| I-190 | [(2R,3S,5R)-5-(4-amino-3-methoxy-1H-pyrazolo[3,4-d]pyrimidin-1-yl)-3-hydroxytetrahydrofuran-2-yl]methyl sulfamate |
| I-191 | [(2R,3S,5R)-5-{4-amino-3-[(2-fluoro-5-methylphenyl)sulfanyl]-1H-pyrazolo[3,4-d]pyrimidin-1-yl}-3-hydroxytetrahydrofuran-2-yl]methyl sulfamate |
| I-192 | [(2R,3S,5R)-5-(4-amino-3-iodo-1H-pyrazolo[3,4-d]pyrimidin-1-yl)-3-hydroxytetrahydrofuran-2-yl]methyl sulfamate |
| I-193 | [(2R,3S,5R)-5-{4-amino-3-[(4-methylphenyl)sulfanyl]-1H-pyrazolo[3,4-d]pyrimidin-1-yl}-3-hydroxytetrahydrofuran-2-yl]methyl sulfamate |
| I-194 | {(2R,3S,5R)-5-[4-amino-3-(pyridin-2-ylsulfanyl)-1H-pyrazolo[3,4-d]pyrimidin-1-yl]-3-hydroxytetrahydrofuran-2-yl}methyl sulfamate |
| I-195 | {(2R,3S,5R)-5-[4-amino-3-(difluoromethoxy)-1H-pyrazolo[3,4-d]pyrimidin-1-yl]-3-hydroxytetrahydrofuran-2-yl}methyl sulfamate |

| Compound | Name |
|---|---|
| I-196 | [(2R,3S,5R)-5-{4-amino-3-[(3,4-dimethylphenyl)sulfanyl]-1H-pyrazolo[3,4-d]pyrimidin-1-yl}-3-hydroxytetrahydrofuran-2-yl]methyl sulfamate |
| I-197 | [(2R,3S,5R)-5-(4-amino-3-{[4-(trifluoromethoxy)phenyl]sulfanyl}-1H-pyrazolo[3,4-d]pyrimidin-1-yl)-3-hydroxytetrahydrofuran-2-yl]methyl sulfamate |
| I-198 | [(2R,3S,5R)-5-(4-amino-3-{[3-(trifluoromethoxy)phenyl]sulfanyl}-1H-pyrazolo[3,4-d]pyrimidin-1-yl)-3-hydroxytetrahydrofuran-2-yl]methyl sulfamate |
| I-199 | [(2R,3S,5R)-5-{4-amino-3-[(3-methoxyphenyl)sulfanyl]-1H-pyrazolo[3,4-d]pyrimidin-1-yl}-3-hydroxytetrahydrofuran-2-yl]methyl sulfamate |
| I-200 | {(2R,3S,5R)-5-[4-amino-3-(methylsulfanyl)-1H-pyrazolo[3,4-d]pyrimidin-1-yl]-3-hydroxytetrahydrofuran-2-yl}methyl sulfamate |
| I-201 | {(2R,3S,5R)-5-[4-amino-3-(2,3-dihydro-1,4-benzodioxin-6-ylsulfanyl)-1H-pyrazolo[3,4-d]pyrimidin-1-yl]-3-hydroxytetrahydrofuran-2-yl}methyl sulfamate |
| I-202 | [(2R,3S,5R)-5-{4-amino-3-[(cyclopropylmethyl)sulfanyl]-1H-pyrazolo[3,4-d]pyrimidin-1-yl}-3-hydroxytetrahydrofuran-2-yl]methyl sulfamate |
| I-203 | [(2R,3S,5R)-5-{4-amino-3-[(6-fluoro-2,3-dihydro-1H-inden-5-yl)sulfanyl]-1H-pyrazolo[3,4-d]pyrimidin-1-yl}-3-hydroxytetrahydrofuran-2-yl]methyl sulfamate |
| I-204 | [(2R,3S,5R)-5-{4-amino-3-[(1-benzothiophen-2-ylmethyl)sulfanyl]-1H-pyrazolo[3,4-d]pyrimidin-1-yl}-3-hydroxytetrahydrofuran-2-yl]methyl sulfamate |
| I-205 | [(2R,3S,5R)-5-{4-amino-3-[(3-methylphenyl)sulfanyl]-1H-pyrazolo[3,4-d]pyrimidin-1-yl}-3-hydroxytetrahydrofuran-2-yl]methyl sulfamate |
| I-206 | [(2R,3S,5R)-5-{4-amino-3-[(3-fluorophenyl)sulfanyl]-1H-pyrazolo[3,4-d]pyrimidin-1-yl}-3-hydroxytetrahydrofuran-2-yl]methyl sulfamate |
| I-207 | [(2R,3S,5R)-5-{4-amino-3-[(3,4-dimethoxyphenyl)sulfanyl]-1H-pyrazolo[3,4-d]pyrimidin-1-yl}-3-hydroxytetrahydrofuran-2-yl]methyl sulfamate |
| I-208 | [(2R,3S,5R)-5-{4-amino-3-[(4-methyl-1,3-thiazol-2-yl)sulfanyl]-1H-pyrazolo[3,4-d]pyrimidin-1-yl}-3-hydroxytetrahydrofuran-2-yl]methyl sulfamate |
| I-209 | {(2S,3S,5R)-5-[4-amino-3-(trifluoromethyl)-1H-pyrazolo[3,4-d]pyrimidin-1-yl]-3-hydroxytetrahydrofuran-2-yl}methyl sulfamate |
| I-210 | {(2S,3S,5R)-5-[4-amino-3-(2-naphthylsulfanyl)-1H-pyrazolo[3,4-d]pyrimidin-1-yl]-3-hydroxytetrahydrofuran-2-yl}methyl sulfamate |
| I-211 | [(2S,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl sulfamate |
| I-212 | [(2S,3S,5R)-5-(4-amino-3-ethyl-1H-pyrazolo[3,4-d]pyrimidin-1-yl)-3-hydroxytetrahydrofuran-2-yl]methyl sulfamate |
| I-213 | {(2S,3S,5R)-5-[4-amino-3-(ethylsulfanyl)-1H-pyrazolo[3,4-d]pyrimidin-1-yl]-3-hydroxytetrahydrofuran-2-yl}methyl sulfamate |
| I-214 | [(2S,3S,5R)-5-{4-amino-3-[(4-methylphenyl)sulfanyl]-1H-pyrazolo[3,4-d]pyrimidin-1-yl}-3-hydroxytetrahydrofuran-2-yl]methyl sulfamate |
| I-215 | [(2S,3S,5R)-5-{4-amino-3-[(2-fluorophenyl)sulfanyl]-1H-pyrazolo[3,4-d]pyrimidin-1-yl}-3-hydroxytetrahydrofuran-2-yl]methyl sulfamate |
| I-216 | {(2S,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl sulfamate |
| I-217 | {(2S,3S,5R)-5-[4-amino-3-(difluoromethyl)-1H-pyrazolo[3,4-d]pyrimidin-1-yl]-3-hydroxytetrahydrofuran-2-yl}methyl sulfamate |
| I-218 | [(2S,3S,5R)-5-(4-amino-3-methyl-1H-pyrazolo[3,4-d]pyrimidin-1-yl)-3-hydroxytetrahydrofuran-2-yl]methyl sulfamate |
| I-219 | {(2S,3S,5R)-5-[4-amino-3-(methylsulfanyl)-1H-pyrazolo[3,4-d]pyrimidin-1-yl]-3-hydroxytetrahydrofuran-2-yl}methyl sulfamate |
| I-220 | {(2S,3S,5R)-5-[4-amino-3-(isopropylsulfanyl)-1H-pyrazolo[3,4-d]pyrimidin-1-yl]-3-hydroxytetrahydrofuran-2-yl}methyl sulfamate |
| I-221 | {(2S,3S,5R)-5-[4-amino-3-(benzylsulfanyl)-1H-pyrazolo[3,4-d]pyrimidin-1-yl]-3-hydroxytetrahydrofuran-2-yl}methyl sulfamate |
| I-222 | [(2S,3S,5R)-5-{4-amino-3-[(5-chloropyridin-2-yl)sulfanyl]-1H-pyrazolo[3,4-d]pyrimidin-1-yl}-3-hydroxytetrahydrofuran-2-yl]methyl sulfamate |
| I-223 | [(2S,3S,5R)-5-{4-amino-3-[(4-fluorophenyl)sulfanyl]-1H-pyrazolo[3,4-d]pyrimidin-1-yl}-3-hydroxytetrahydrofuran-2-yl]methyl sulfamate |
| I-224 | [(2S,3S,5R)-5-{4-amino-3-[(3-chlorophenyl)sulfanyl]-1H-pyrazolo[3,4-d]pyrimidin-1-yl}-3-hydroxytetrahydrofuran-2-yl]methyl sulfamate |
| I-225 | [(2S,3S,5R)-5-(4-amino-3-methoxy-1H-pyrazolo[3,4-d]pyrimidin-1-yl)-3-hydroxytetrahydrofuran-2-yl]methyl sulfamate |
| I-226 | [(2S,3S,5R)-5-(4-amino-1H-pyrazolo[3,4-d]pyrimidin-1-yl)-3-hydroxytetrahydrofuran-2-yl]methyl sulfamate |
| I-227 | [(2S,3S,5R)-5-{4-amino-3-[(2,2-difluoroethyl)sulfanyl]-1H-pyrazolo[3,4-d]pyrimidin-1-yl}-3-hydroxytetrahydrofuran-2-yl]methyl sulfamate |

These and other compounds of the chemical entities of the present disclosure can be made with reference to the procedures described in the Examples.

The chemical entities of this disclosure are useful inhibitors of ATG7 activity.

Compositions

Some embodiments of this disclosure relate to a composition comprising a chemical entity of this disclosure and a pharmaceutically acceptable carrier.

If a pharmaceutically acceptable salt is the chemical entity of the disclosure utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy*, 20th Ed., A. Gennaro (ed.), Lippincott Williams & Wilkins (2000) ("*Remington's*").

Examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of the disclosure preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent. Many such pharmaceutically acceptable carriers are known in the art. See, e.g., *Remington's; Handbook of Pharmaceutical Excipients,* 6th Ed., R. C. Rowe et al. (eds.), Pharmaceutical Press (2009).

The pharmaceutical compositions of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this disclosure are formulated for pharmaceutical administration to a mammal, preferably a human being. Such pharmaceutical compositions of the present disclosure may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the disclosure may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons such as mineral oil and petrolatum; and water may also be used in suspension formulations.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this disclosure may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. In such solid dosage forms, the active chemical entity is mixed with at least one inert, pharmaceutically acceptable excipient or carrier such as sodium citrate or dicalcium phosphate and/or a) fillers or extenders such as starches, lactose, sucrose, glucose, mannitol, micro-crystalline cellulose and silicic acid, b) binders such as, for example, carboxymethylcellulose, alginates, gelatin, sucrose, and acacia, c) humectants such as glycerol, d) disintegrating agents such as agar-agar, calcium carbonate, polyvinylpyrrolidinone, croscarmellose, sodium starch glycolate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, sodium stearyl fumarate, solid polyethylene glycols, sodium lauryl sulfate, silicon dioxide and mixtures thereof. In the case of capsules, tablets and pills, the dosage form may also comprise buffering agents.

The active chemical entity can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, the pharmaceutical compositions of this disclosure may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this disclosure include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this disclosure are particularly useful in therapeutic applications relating to disorders as described herein (e.g., proliferation disorders, e.g., cancers, inflammatory, neurodegenerative disorders). The term "subject" as used herein, means an animal, preferably a mammal, more preferably a human. The term "patient" as used herein, means a human. Preferably, the composition is formulated for administration to a patient or subject having or at risk of developing or experiencing a recurrence of the relevant disorder being treated. Preferred pharmaceutical compositions of the disclosure are those formulated for oral, intravenous, or subcutaneous administration. However, any of the above dosage forms containing a therapeutically effective amount of a chemical entity of the disclosure are well within the bounds of routine experimentation and therefore, well within the scope of the instant disclosure. In certain embodiments, the pharmaceutical composition of the disclosure may further comprise another therapeutic agent. Preferably, such other therapeutic agent is one normally administered to patients with the disorder, disease or condition being treated.

By "therapeutically effective amount" is meant an amount of the chemical entity or composition sufficient, upon single or multiple dose administration, to cause a detectable decrease in ATG7 activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of ATG7 inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific chemical entity employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this disclosure typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

Uses

As discussed above, the present disclosure provides chemical entities that are useful as inhibitors of ATG7, and thus the present chemical entities can be useful for treating proliferative, inflammatory, cardiovascular and neurodegenerative disorders.

The chemical entities and pharmaceutical compositions of the present disclosure can be useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors (hematologic malignancies). The term "cancer" encompasses diseases of skin, tissues, organs, bone, cartilage, blood, and vessels. The term "cancer" further encompasses primary and metastatic cancers.

In some embodiments, therefore, the present disclosure provides the chemical entity of formula (I), or a pharmaceutically acceptable salt thereof, for use in treating cancer. In some embodiments, the present disclosure provides a pharmaceutical composition (as described herein) for the treatment of cancer comprising the chemical entity of formula (I), or a pharmaceutically acceptable salt thereof. In some embodiments, the present disclosure provides the use of the chemical entity of formula (I), or a pharmaceutically acceptable salt thereof, for the preparation of a pharmaceutical composition (as described herein) for the treatment of cancer. In some embodiments, the present disclosure provides the use of an effective amount of the chemical entity of formula (I), or a pharmaceutically acceptable salt thereof, for the treatment of cancer. In some embodiments, the present disclosure provides the chemical entity of formula (I), or a pharmaceutically acceptable salt thereof, for the preparation of a medicament for use in treating cancer.

Non-limiting examples of solid tumors that can be treated with the disclosed inhibitors include pancreatic cancer; bladder cancer including invasive bladder cancer; colorectal cancer; thyroid cancer, gastric cancer, breast cancer, including metastatic breast cancer; prostate cancer, including androgen-dependent and androgen-independent prostate cancer; renal cancer, including, e.g., metastatic renal cell carcinoma; liver cancer including e.g. hepatocellular cancer and intrahepatic bile duct; lung and bronchus cancer, including non-small cell lung cancer (NSCLC), squamous lung cancer, brochioloalveolar carcinoma (BAC), adenocarcinoma of the lung, and small cell lung cancer (SCLC); ovarian cancer, including, e.g., progressive epithelial or primary peritoneal cancer; cervical cancer; uterine cancer including e.g. uterine corpus and uterine cervix; endometrial cancer; gastric cancer; esophageal cancer; head and neck cancer, including, e.g., squamous cell carcinoma of the head and neck, nasopharyngeal cancer, oral cavity and pharynx; melanoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine, including metastatic neuroendocrine tumors; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); small lymphocytic lymphoma (SLL); marginal zone lymphoma; smoldering multiple myeloma; and myeloproliferative syndromes.

In some embodiments, chemical entities of the present disclosure are suitable for the treatment of breast cancer, lung cancer, ovarian cancer, multiple myeloma, acute myeloid leukemia or acute lymphoblastic leukemia. In some embodiments, chemical entities of the present disclosure are suitable for the treatment of NHL. In some embodiments, chemical entities of the present disclosure are suitable for the treatment of indolent NHL. In some embodiments, chemical entities of the present disclosure are suitable for the treatment of follicular lymphoma, small lymphocytic lymphoma, mantle cell lymphoma or marginal zone lymphoma. In some embodiments, chemical entities of the present disclosure are suitable for the treatment of diffuse large B-cell lymphoma (DLBCL) or chronic lymphocytic lymphoma (CLL). In some embodiments, chemical entities of the present disclosure are suitable for the treatment of multiple myeloma. In some embodiments, chemical entities of the present disclosure are suitable for the treatment of ALL, AML, or MDS.

Depending on the particular disorder or condition to be treated, in some embodiments, the ATG7 inhibitor of the disclosure is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The ATG7 inhibitor of the disclosure may be administered with the other therapeutic agent in a single dosage form or as a separate dosage form. When administered as a separate dosage form, the other therapeutic agent may be administered prior to, at the same time as, or following administration of the ATG7 inhibitor of the disclosure.

In some embodiments, the ATG7 enzyme inhibitor of the disclosure is administered in conjunction with a therapeutic agent selected from cytotoxic agents, radiotherapy, and immunotherapy appropriate for treatment of proliferative disorders and cancer. Examples of cytotoxic agents suitable for use in combination with the ATG7 inhibitors of the disclosure include: antimetabolites, topoisomerase inhibitors, vinca alkaloids, taxanes, platinum agents, antibiotics, alkylating agents and cyclophosphamide, protein tyrosine kinase inhibitors, proteasome inhibitors, antibodies, mitoxantrone; dexamethasone, prednisone, and temozolomide.

Other examples of agents the inhibitors of the disclosure may be combined with include anti-inflammatory agents, immunomodulatory and immunosuppressive agents, antibacterial and antiviral agents, and agents for Alzheimer's treatment.

In some embodiments, the ATG7 enzyme inhibitor of the disclosure is administered in conjunction with mTor inhibitors, such as rapamycin and its analogs (temsirolimus, everolimus, ridaforolimus, and sirolimus), dactolisib, BGT226, SF1126, PKI-587, NVPBE235, sapanisertib (MLN0128), AZD8055, and AZD2014.

In order that this disclosure is more fully understood, the following preparative and testing examples are set forth. These examples are for the purpose of illustration only and are not intended to be construed as limiting the scope of the disclosure in any way.

General Synthetic Methods and Intermediates

The compounds of the present disclosure can be prepared by methods known to one of ordinary skill in the art and/or by reference to the schemes shown below and the synthetic examples. Exemplary synthetic routes are set forth in Schemes below, and in the Examples.

Scheme 1: General route for preparing substituted pyrazolopyrimidines

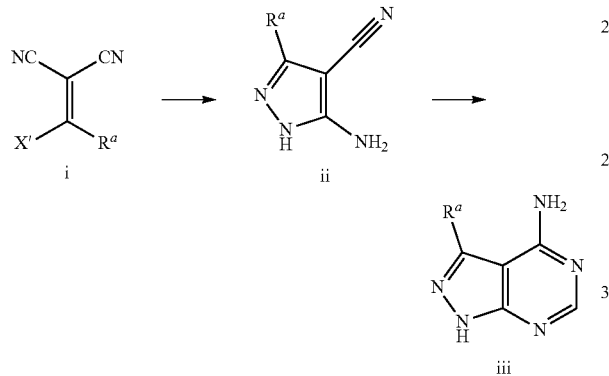

Scheme 1 shows a general route for the preparation of compounds of formula iii from commercially available, or readily derivable, dicyanoethylenes of the formula i (X' is a leaving group, such as CN, —O-T$_1$-R$^b$, —O—R$^{dd}$, or —S—R$^{ee}$). The cyanoethylene derivatives are reacted with hydrazine hydrate or a protected derivative of hydrazine to provide tri-substituted pyrazoles of the formula ii (R$^a$=—C$_{1-3}$fluoroaliphatic, R$^{bb}$, —O—R$^{dd}$, —S—R$^{ee}$). In the case where R$^a$ is cyano, tetracyanoethylene is reacted with a protected hydrazine to provide the aminopyrazole ii. In either case, the resulting aminopyrazole ii is heated in the presence of formamide to provide pyrazolopyridine iii.

Scheme 2: General route for the preparation and functionalization of halopyrazolopyrimidines

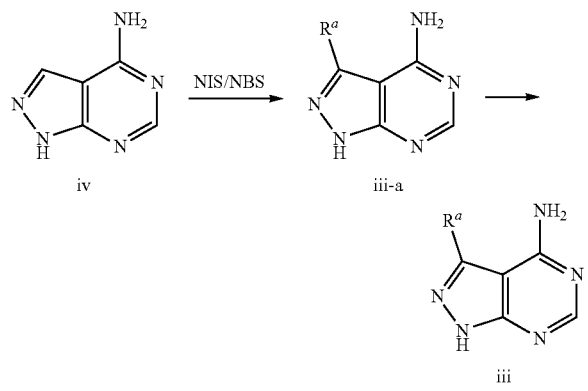

The preparation of pyrazolopyrimidines of formula iii-a where R$^a$=iodine or bromine is accomplished by treatment of pyrazolopyrimidine iv with N-iodosuccinimide or N-bromosuccinimide, respectively as illustrated in Scheme 2. Iodides of formula iii-a are versatile intermediates that can be converted to a number of different intermediates of formula iii. Palladium-mediated carbon-carbon bond forming reactions such as Suzuki, Sonagashira, Heck and Stille reactions, optionally followed by functionality modifications such as reduction or substitution, provide a variety of different substituents R$^a$ (R$^a$=-T$_1$-R$^b$, or R$^{bb}$).

Scheme 3: General route for glycosylation of pyrazolopyrimidines

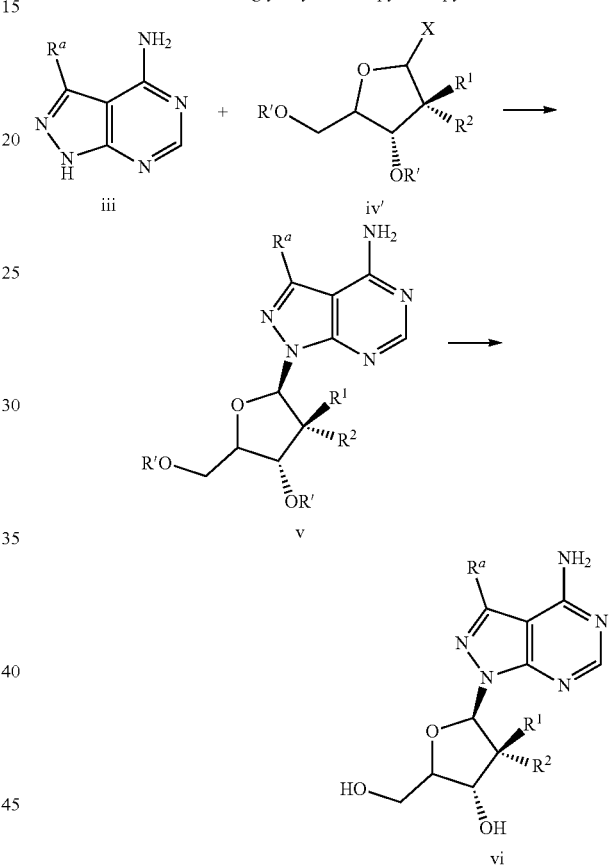

Scheme 3 illustrates the general synthesis of glycosylated pyrazolopyrimidines of formula v and vi (Vorbiggen, H.; Ruh-Pohlenz, C. Handbook of Nucleoside Synthesis; Organic Reactions; John Wiley & Sons; New York, 2001). Compounds of formula iv' are protected sugar derivatives where R'=acetate or benzoate or other ester and X=OCOCH$_3$ or halide. Conditions for the glycosylation vary depending on the character of R$^1$ and R$^2$. When R$^1$=H, R$^2$=OR' and X=OAc, reaction of compounds iii and iv' in the presence of a Lewis acid (such as BF$_3$—OEt$_2$) provides compounds of formula v and treatment with an alkyoxide base in an alcoholic solvent (NaOMe in MeOH, for example) provides the deprotected glycosides of formula vi. When R$^1$ and R$^2$=H, or R$^1$=F and R$^2$=H, optimal glycosylation conditions require a halogenated sugar derivative (compounds of formula iv' where X=chlorine or bromine). In these cases, deprotonation of compounds of formula iii with strong base such as NaH or potassium tert-butoxide in an ethereal solvent like THF with additional solvents such as acetonitrile, methylene chloride and DMF added to improve solubility followed by combination with protected sugar derivatives of formula iv' provides compounds of formula v. Alternatively potassium hydroxide and tris(3, 6-dioxaheptyl)amine in acetonitrile can be used to generate the deprotonated pyrazolopyrimidine base. In a more specific example, deprotonation of compounds of formula iii with strong base such as NaH or potassium tert-butoxide is followed by treatment with the protected sugar derivatives of formula iv' where $R^1$=H, $R^2$ and the adjacent 3' oxygen are tied together in a dimethyl acetonide, and X=chlorine or bromine, provides compounds of formula v.

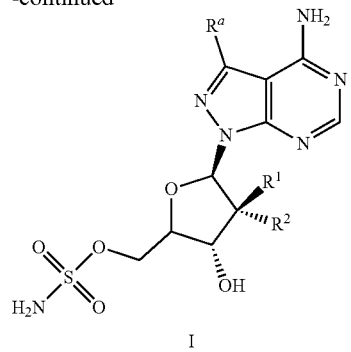

I

The general conversion of alcohols of formula vi to sulfamates of formula I is illustrated in Scheme 4. When $R^1$=H and $R^2$=OH, protection of the two secondary alcohols as an acetonide can be achieved with 2,2-dimethoxypropane or a similar acetal and a catalytic amount of acid, such as p-toluene sulfonic acid, to give alcohols of formula vii. When $R^1$ and $R^2$=H, protection of both free alcohols with a trialkylsilyl halide under standard conditions (TBSCl or TIPSCl, DMAP, imidazole, DMF, for example) followed by selective deprotection of the primary alcohol using HCl in ethanol at low temperature provides alcohols of formula vii. Alcohols of formula vii can be converted to sulfamates of formula viii by reaction with an appropriate sulfamating reagent (Method A, for example chlorosulfonamide or see PCT publication WO2009/042013). Removal of the remaining protecting groups either under acidic conditions such as formic acid or HCl or with a fluoride source such as HF.Et$_3$N results in compounds of formula I.

Scheme 4: General route for preparation of pyrazolopyrimidine sulfamates

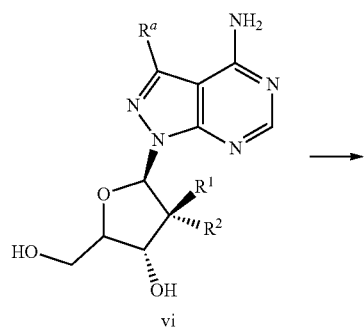

vi

Scheme 5: General route for preparation of pyrazolopyrimidine deoxylyxose-derived sulfamates

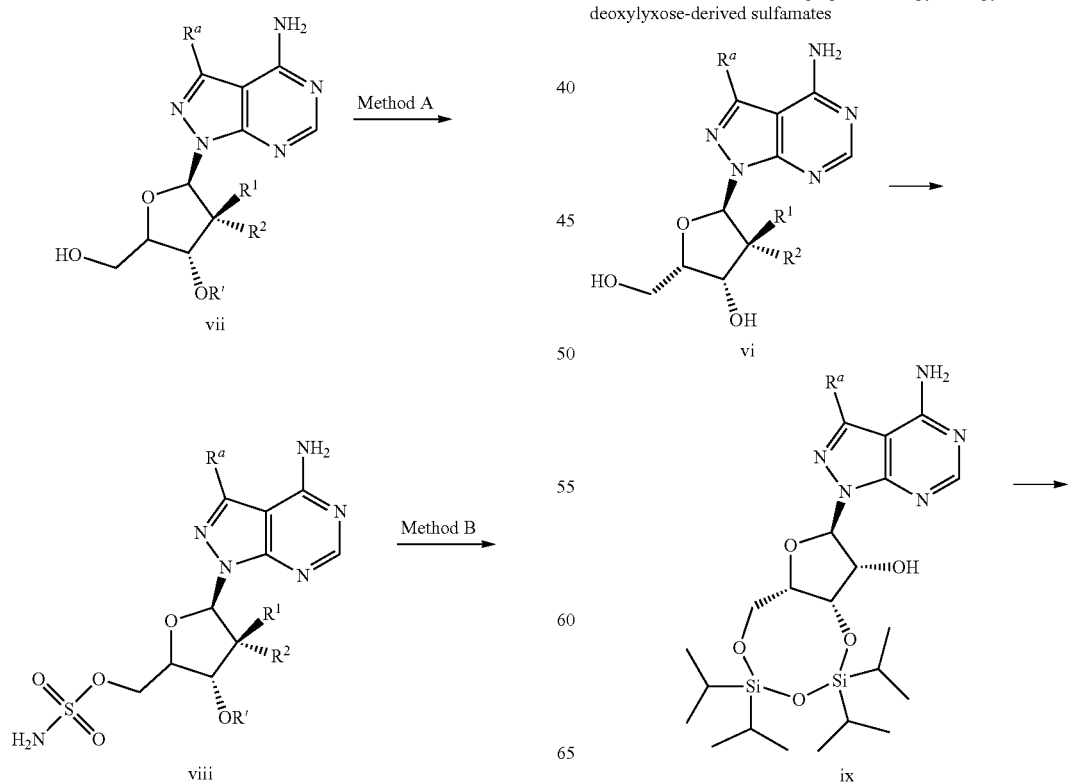

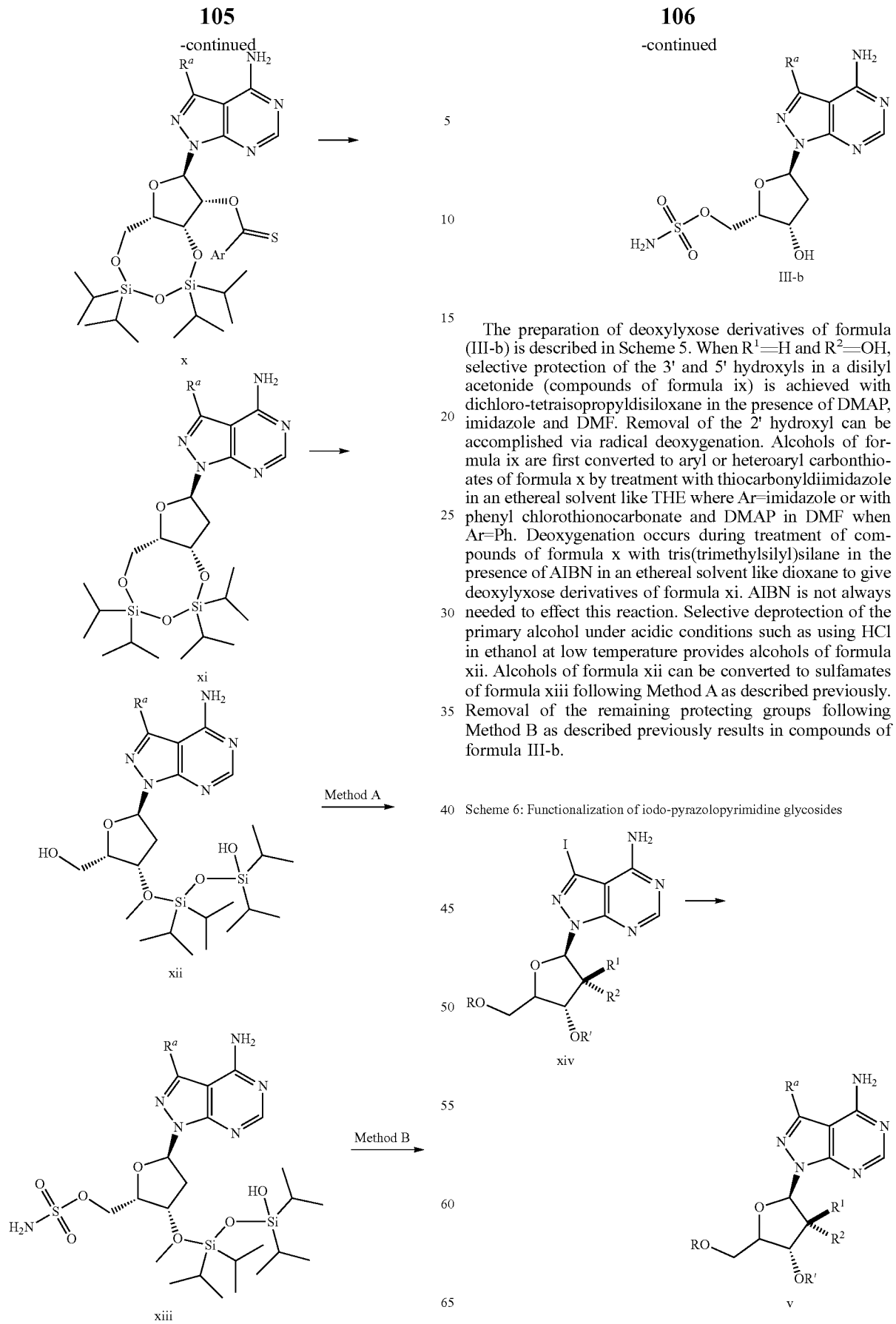

The preparation of deoxylyxose derivatives of formula (III-b) is described in Scheme 5. When $R^1$=H and $R^2$=OH, selective protection of the 3' and 5' hydroxyls in a disilyl acetonide (compounds of formula ix) is achieved with dichloro-tetraisopropyldisiloxane in the presence of DMAP, imidazole and DMF. Removal of the 2' hydroxyl can be accomplished via radical deoxygenation. Alcohols of formula ix are first converted to aryl or heteroaryl carbonthioates of formula x by treatment with thiocarbonyldiimidazole in an ethereal solvent like THF where Ar=imidazole or with phenyl chlorothionocarbonate and DMAP in DMF when Ar=Ph. Deoxygenation occurs during treatment of compounds of formula x with tris(trimethylsilyl)silane in the presence of AIBN in an ethereal solvent like dioxane to give deoxylyxose derivatives of formula xi. AIBN is not always needed to effect this reaction. Selective deprotection of the primary alcohol under acidic conditions such as using HCl in ethanol at low temperature provides alcohols of formula xii. Alcohols of formula xii can be converted to sulfamates of formula xiii following Method A as described previously. Removal of the remaining protecting groups following Method B as described previously results in compounds of formula III-b.

Scheme 6: Functionalization of iodo-pyrazolopyrimidine glycosides

Iodides of formula xiv are versatile intermediates that can be converted to a number of different intermediates of formula v. Palladium-mediated carbon-carbon bond forming transformations such as Suzuki, Sonagashira, Heck and Stille reactions provide a variety of different substituents $R^a$ ($R^a$=CN, —CO$_2$CH$_3$, -T$_1$-R$^b$, or R$^{bb}$,) in compounds of formula v. Additionally, other metal-mediated carbon-nitrogen (Buchwald or Hartwig reactions), carbon-sulfur and carbon-oxygen forming reactions can be used to prepare aryl and alkyl amino, thio and oxo-pyrazolopyrimidine derivatives of formula v ($R^a$=—O-T$_1$-R$^b$, —O—R$^{dd}$, —S-T$_1$-R$^c$, or —S—R$^{ee}$). Further elaboration of these substituents via reduction, oxidation, substitution, addition, alkylation, fluorination provide even more diversity in $R^a$ ($R^a$=C$_{1-3}$fluoroaliphatic, R$^{bb}$, —C(O)CH$_3$. —C(S)NH$_2$, —C(O)NH$_2$). Compounds of formula v can then be converted to the desired pyrazolopyrimidine sulfamates as described in Schemes 3 and 4.

Scheme 7: Alternative preparation of alkoxy-pyrazolopyrimidine glycosides

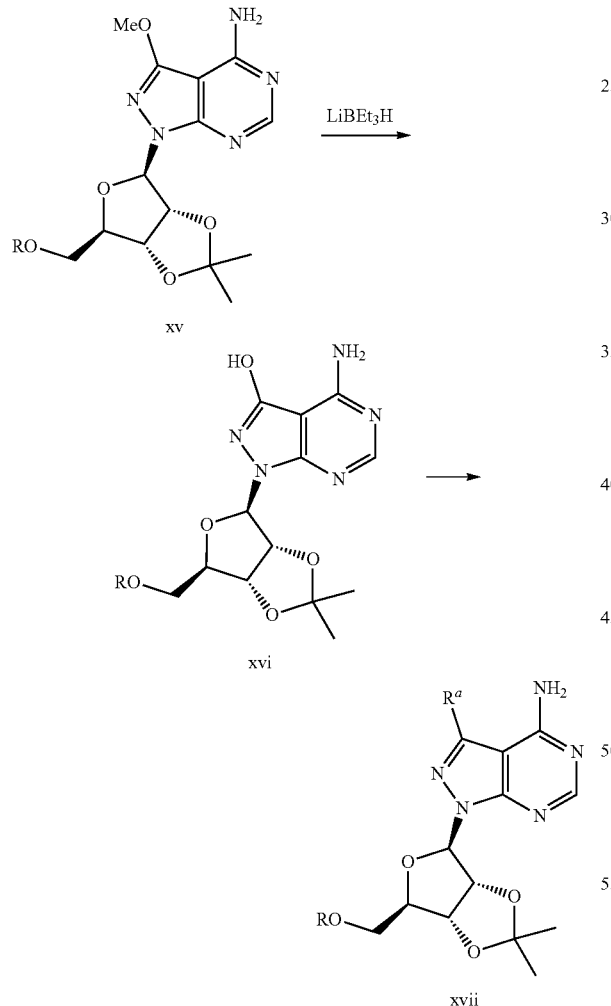

Certain $R^a$ substituents cannot be introduced using the iodides of formula xiv in Scheme 6 or are more easily introduced via an alkylation of the alcohols of formula xvi. Alcohols of formula xvi are prepared from methyl ethers of formula xv by treatment with super-hydride (lithium triethylborohydride) in THF at reflux. Alkylation of compounds of formula xvi with 1,2 dichloroethane or methyl chlorodifluoroacetate in the presence of potassium carbonate provides ethers of formula xvii when $R^a$=—O—C$_{1-3}$fluoroaliphatic or —O—R$^{dd}$ such as —OCH$_2$CH$_2$Cl or —OCHF$_2$ respectively. Compounds of formula xvii can then be converted to the desired pyrazolopyrimidine sulfamates as described in Schemes 3 and 4.

Scheme 8: Preparation of thio-pyrazolopyrimidine glycosides

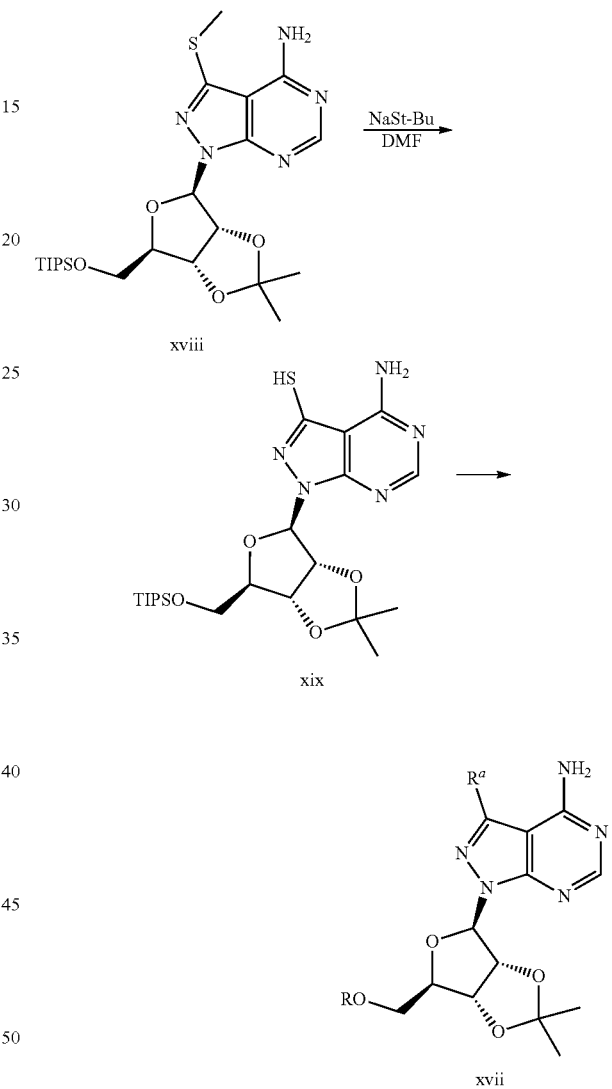

Certain sulfur containing $R^a$ substituents cannot be introduced using the iodides of formula xiv in Scheme 6 or are more easily introduced via an alkylation of the thiols of formula xix or the sodium salt of compounds of formula xix. Thiols of formula xix are prepared by treating methyl sulfides of formula xvii with sodium tert-butyl thiolate in DMF. Thiols of formula xix are then alkylated with a variety of alkyl halides to give xvii where $R^a$=—S-T$_1$-R$^c$, or —S—R$^{ee}$. Alternatively, thiols of formula xix are reacted with a palladium catalyst and an alkyl, aryl or heteroaryl bromide or iodide to give compounds of formula xvii where $R^a$=—S-T$_1$-R$^c$.

Scheme 9: Alternative preparation of thio-pyrazolopyrimidine glycosides

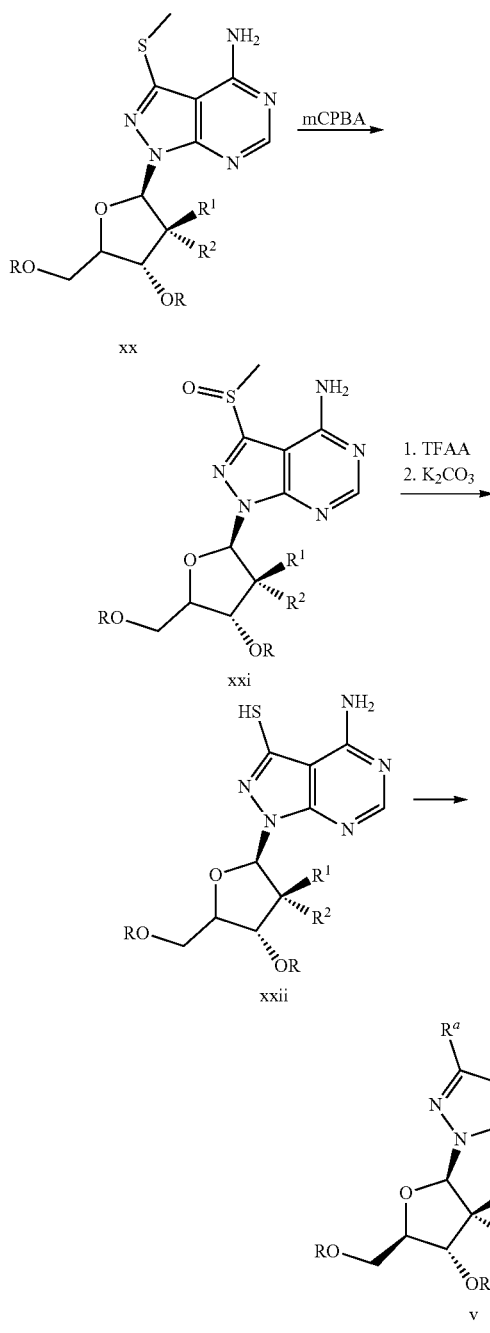

An alternative procedure to prepare pyrazolopyrimidine glycosides of formula v where $R^a$ contains sulfur is shown in Scheme 9. When $R^1$ and $R^2$=H or when $R^1$=F and $R^2$=H, $R^a$ substituents are introduced via an alkylation or palladium mediated coupling of the thiols of formula xxii. Thiols of formula xxii are prepared by oxidizing methyl sulfides of formula xx with mCPBA to give sulfoxides of formula xxi. Sulfoxides of formula xxi are then treated with trifluoroacetic anhydride followed by potassium carbonate to give sulfides of formula xxii. Alkylation of sulfides of formula xxii with a variety of alkyl halides give compounds of formula xvii where $R^a$=—S—$C_{1-3}$fluoroaliphatic, —S-$T_1$-$R^c$ or —S—$R^{ee}$. Alternatively, thiols of formula xxii can be reacted with a palladium catalyst and an alkyl, aryl or heteroaryl bromide or iodide to give compounds of formula v where $R^a$=—S-$T_1$-$R^c$. Compounds of formula v can then be converted to the desired pyrazolopyrimidine sulfamates as described in Schemes 3 and 4.

Preparation of Exemplary Chemical Entities

| | Definitions |
|---|---|
| AA | ammonium acetate |
| ATP | adenosine triphosphate |
| AIBN | 2,2'-azobis(2-methylpropionitrile) |
| BrettPhos Pd G3 | [(2-di-cyclohexylphosphino-3,6-dimethoxy-2',4',6'-triisopropyl-1,1'-biphenyl)-2-(2'-amino-1,1'-biphenyl)]palladium(II) methanesulfonate (CAS 1470372-59-8) |
| Conc | Concentrated |
| DAST | (diethylamino)sulfur trifluoride |
| DCE | dichloroethane |
| DCM | dichloromethane |
| DHP | dihydropyran |
| DIPEA | diisopropylethyl amine |
| DMF | N,N-dimethylformamide |
| DMFDMA | N,N-dimethylformamide dimethyl acetal |
| DMAP | N,N-dimethylpyridin-4-amine |
| DMSO | dimethylsulfoxide |
| EDC | N-(3-dimethylaminopropyl)-N'-ethylcarbodiimide hydrochloride |
| EDTA | ethylenediaminetetraacetic acid |
| EtOAc | ethyl acetate |
| EtOH | ethanol |
| FA | formic acid |
| FBS | fetal bovine serum |
| h | hours |
| HATU | N,N,N',N'-tetramethyl-O-(7-azabenzotriazole-1-yl)uronium hexafluorophosphate |
| HBTU | O-benzotriazol-1-yl-N,N,N',N'-tetramethyluronium hexafluorophosphate |
| HEPES | N-(2-hydroxyethyl)piperazine-N'-(2-ethanesulfonic acid) |
| HOBT | 1-hydroxybenztriazole hydrate |
| HRMS | high resolution mass spectrum |
| Int | intermediate |
| IPA | isopropyl alcohol |
| IBX | 2-iodoxybenzoic acid |
| LAH | lithium aluminum hydride |
| LCMS | liquid chromatography mass spectrum |
| m/z | mass to charge |
| mCPBA | 3-chloroperoxybenzoic acid |
| Me | methyl |
| MEM | minimum essential media |
| MeOH | methanol |
| min | minutes |
| mL | milliliters |
| MS | mass spectrum |
| MTBE | methyl tert-butyl ether |
| MWI | microwave irradiation |
| NaHMDS | sodium bis(trimethylsilyl)amide |
| NMM | N-methyl morpholine |
| NMR | nuclear magnetic resonance spectroscopy |
| ON | overnight |
| PPTS | pyridinium p-toluenesulfonate |
| PBS | phosphate buffered saline |
| RuPhos Pd G2 | chloro(2-dicyclohexylphosphino-2',6'-diisopropoxy-1,1'-biphenyl)[2-(2'-amino-1,1'-biphenyl)]palladium(II) (CAS 1375325-68-0) |
| rt | room temperature |
| SelectFluor | 1-chloromethyl-4-fluoro-1,4-diazoniabicyclo[2.2.2]octane bis(tetrafluoroborate) |
| SFC | supercritical fluid chromatography |
| TCDI | 1,1'-thiocarbonyldiimidazole |
| TBAB | tetrabutylammonium bromide |
| TBAI | tetra-n-butylammonium iodide |
| TBS | t-butyl dimethyl silyl |
| TEA | triethylamine |
| TFA | trifluoroacetic acid |
| TFAA | trifluoroacetic anhydride |
| TFFH | 1,1,3,3-tetramethylfluoroformamidinium hexafluorophosphate |
| THF | tetrahydrofuran |

-continued

| Definitions | |
|---|---|
| TIPS | tri-isopropyl silyl |
| TMEDA | N,N,N',N'-tetramethyl-ethane-1,2-diamine |
| TTMSS | tris(trimethylsilyl)silane |
| Xantphos | 4,5-bis(diphenylphosphino)-9,9-dimethylxanthene |
| XPhos | 2-dicyclohexylphosphino-2',4',6'-triisopropylbiphenyl |
| XPhos Pd G2 | chloro(2-dicyclohexylphosphino-2',4',6'-triisopropyl-1,1'-biphenyl)(2'-amino-1,1'-biphenyl-2-yl) palladium(II) |
| XPhos Precatalyst | chloro(2-dicyclohexylphosphino-2',4',6'-triisopropyl-1,1'-biphenyl)[2-(2-aminoethyl)phenyl)]palladium(II), (CAS# 1028206-56-5) |

Analytical Methods
NMR Conditions:

$^1$H NMR spectra are run on a 400 MHz Bruker or Varian spectrometer unless otherwise stated.

LCMS Conditions:

LCMS spectra were recorded on a Hewlett-Packard HP1100 or Agilent 1100 Series LC system connected to a Micromass mass spectromteter using reverse phase C18 columns. Various gradients and run times were selected in order to best characterize the compounds. Mobile phases were based on ACN/water gradients and contained either 0.1% formic acid (methods indicated as FA) or 10 mM ammonium acetate (methods indicated as AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run.

In some cases, LCMS spectra were recorded on a Hewlett-Packard HP1100 or Agilent 1100 Series LC system connected to a Micromass mass spectromteter using reverse phase C18 columns. In other cases, LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase C18 columns. Various gradients and run times were selected in order to best characterize the compounds. Mobile phases were based on ACN/water gradients and contained either 0.1% formic acid (methods indicated as FA) or 10 mM ammonium acetate (methods indicated as AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run. Another example of a solvent gradient that was used was 95% mobile phase A (mobile phase A=99% water+1% ACN+0.1% formic acid) to 100% mobile phase B (mobile phase B=95% ACN+5% water+0.1% formic acid) at a flow rate of 0.5 mL/min for a 5 min run.

One of ordinary skill in the art will recognize that modifications of the gradient, column length, and flow rate are possible and that some conditions may be suitable for compound characterization than others, depending on the chemical species being analyzed.

Preparative HPLC:

Preparative HPLC is conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

One of ordinary skill in the art will recognize that modifications of the gradient, column length, and flow rate are possible and that some conditions may be suitable for compound characterization than others, depending on the chemical species being analyzed.

Preparative SFC:

Preparative SFC is conducted using 10, 20 or 30 mm×250 mm ChiralPak columns (typically IA, IB, IC, ID, IE and IF) eluting with appropriate percentages of supercritical carbon dioxide and alcohol containing 0.3% diethyl amine or 0.3% triethylamine or 0.3% formic acid or without any acid or base additives. Isocratic conditions with flow rates in the range of 10-100 mL/min and a column temperature of 40° C. are typical. Preparative SFC is conducted on A Jasco SFC prep purification system with UV/visible triggered fraction collection set to between 200 nm and 400 nm and back pressure regulation set to 10 MPa.

One of ordinary skill in the art will recognize that modifications of the gradient, column length, and flow rate are possible and that some conditions may be suitable for compound characterization than others, depending on the chemical species being analyzed.

X-Ray Powder Diffraction (XRPD) Conditions:

XRPD is performed using a Bruker AXS D8 Advance X-ray Diffractometer using CuKa radiation (40 kV, 40 mA), θ-2θ goniometer, and divergence of V4 and receiving slits, a Ge monochormator and a Lynxeye detector. Samples are run under ambient conditions as flat plate specimens using powder. The sample is gently packed into a cavity cut into polished, zero-background (510) silicon wafer. The sample is rotated in its own plane during analysis. The data are collected on an angular range of 2 to 42°2θ, with a step size of 0.05°2θ and a collection time of 0.5 s/step. Data collection is performed using Diffrac Plus XRD Commander v2.6.1 software. Data analysis and presentation is performed using Diffrac Plus EVA v13.0.0.2 or v15.0.0.0 software.

Example 1: [(2R,3S,4R,5R)-5-(4-amino-3-ethoxy-1H-pyrazolo[3,4-d]pyrimidin-1-yl)-3,4-dihydroxytetrahydrofuran-2-yl]methyl Sulfamate Compound I-5

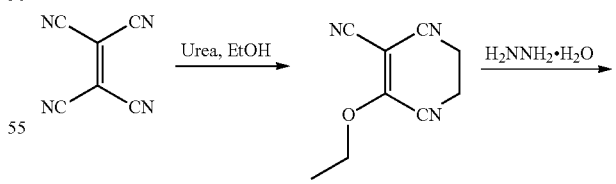

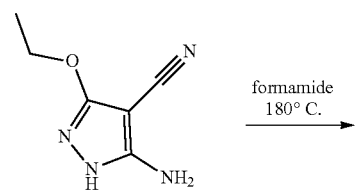

-continued

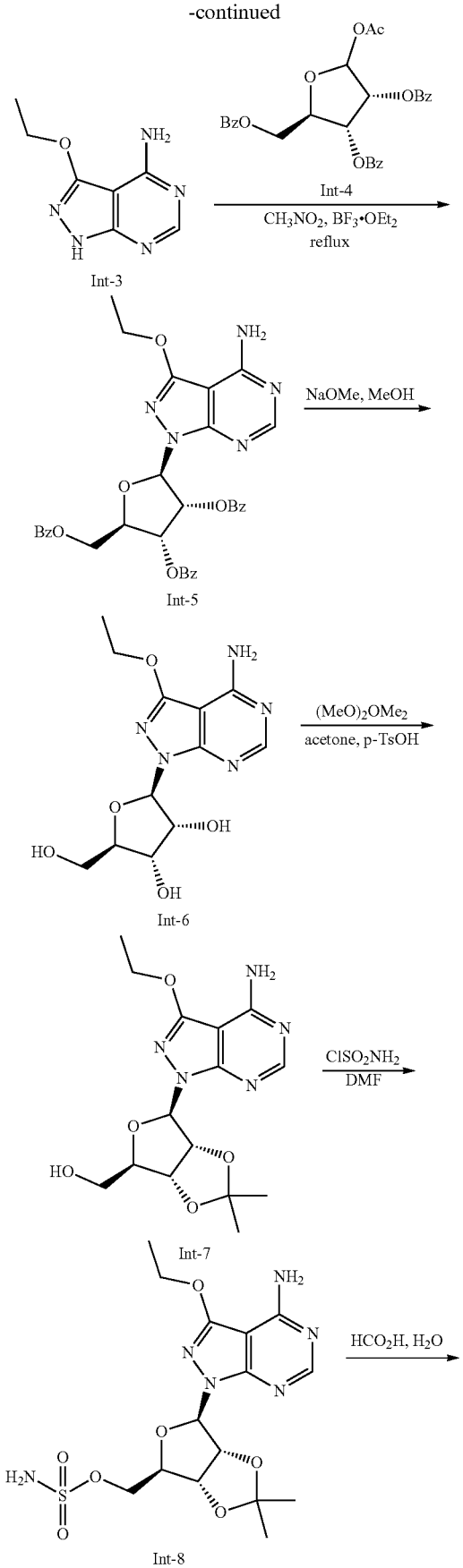

-continued

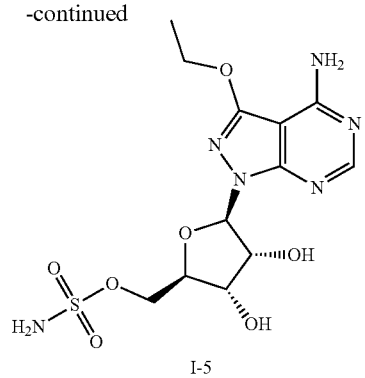

I-5

Step 1: (diethoxymethylene)malononitrile

Tetracyanoethylene (25.0 g, 195 mmol) was dissolved in a solution of urea (3.9 g, 65 mmol) in ethanol (95 mL). The resulting brown mixture was stirred at 50° C. for 45 minutes and cooled to rt. The mixture was partitioned between ether (750 mL) and saturated aqueous sodium bicarbonate solution. The phases were separated and the extracts washed with brine, dried over sodium sulfate, filtered and concentrated under reduced pressure to afford a brown oil. The oil was dissolved in ether (150 mL) and cooled in a dry ice/acetone bath. After several hours, a precipitate formed which was subsequently isolated by suction filtration to give (diethoxymethylene)malononitrile (24.4 g, 75%). $^1$H NMR (300 MHz, $d_6$-DMSO) δ 4.54 (q, J=7.0 Hz, 1H), 1.33 (t, J=7.0 Hz, 3H).

Step 2: 5-amino-3-ethoxy-1H-pyrazole-4-carbonitrile

To a rapidly stirred suspension of (diethoxymethylene)malononitrile (24.45 g, 147.1 mmol) in water (360 mL) was added hydrazine hydrate (8.6 mL, 180 mmol). Upon mixing, the reaction produced to a uniform orange/yellow suspension. After stirring at rt for 2 h, the solids were isolated by suction filtration to give 5-amino-3-ethoxy-1H-pyrazole-4-carbonitrile (17.47 g, 78%). LCMS (AA): m/z 153 (M+H); $^1$H NMR (300 MHz, $d_6$-DMSO) δ 10.99 (br s, 1H), 6.32 (br s, 2H), 4.11 (q, J=7.0 Hz, 2H), 1.27 (t, J=7.1 Hz, 3H).

Step 3: 3-ethoxy-1H-pyrazolo[3,4-d]pyrimidin-4-amine Intermediate 3

5-Amino-3-ethoxy-1H-pyrazole-4-carbonitrile (8.0 g, 52 mmol) was suspended in formamide (13 mL) in a 100 mL round bottom flask fitted with a stirbar and reflux condenser. The mixture was heated in an oil bath at 150° C. for 0.5 h then 200° C. for 1.5 h before cooling to rt. On cooling, a precipitate formed. Water (50 mL) was added to the solid cake and the solids were isolated by suction filtration. The solids were washed with additional cold water and dried for a few minutes under suction. The filtrate was extracted with ethyl acetate (2×200 mL). The extracts were combined and washed with brine, dried over sodium sulfate, filtered and concentrated under reduced pressure. The residue was combined with the solids collected by filtration. The mixture was recrystallized from hot aqueous MeOH (18 mL water, ca. 30 mL MeOH) to afford the 3-ethoxy-1H-pyrazolo[3,4-d]pyrimidin-4-amine as an off-white solid (1.95 g, 21%). LCMS (AA): m/z 180 (M+H); $^1$H NMR (300 MHz, d$_6$-DMSO) δ 12.28 (br s, 1H), 8.06 (s, 1H), 4.31 (q, J=7.0 Hz, 2H), 1.38 (t, J=7.0 Hz, 3H).

Step 4: (2R,3R,4R,5R)-2-(4-amino-3-ethoxy-1H-pyrazolo[3,4-d]pyrimidin-1-yl)-5-[(benzoyloxy)methyl]tetrahydrofuran-3,4-diyl Dibenzoate Intermediate 5

β-D-Ribofuranose 1-acetate 2,3,5-tribenzoate (Intermediate 4, 3.66 g, 7.26 mmol) and Intermediate 3 (1.00 g, 5.58 mmol) were combined in a 250 mL, 3 neck flask fitted with a stirbar and reflux condenser. Nitromethane (42 mL) was added to the flask by syringe. The resulting suspension was warmed to reflux in an oil bath. Boron trifluoride etherate (1.2 mL, 9.8 mmol) was then added dropwise to the heated mixture by syringe. The reaction mixture turned homogeneous during completion of BF$_3$ addition. Upon completion of addition, heating was continued 45 min. The dark brown mixture was cooled to rt, poured into ethyl acetate (100 mL) and washed with half-saturated aqueous sodium bicarbonate solution (100 mL). The mixture was filtered and then the phases were separated. The aqueous phase was extracted with additional ethyl acetate (2×100 mL). The extracts were combined, washed with water and brine then dried over sodium sulfate, filtered and concentrated under reduced pressure. The crude product was adsorbed onto 4 g celite and purified by silica gel chromatography (80 g silica, 80/20 hexanes/ethyl acetate to ethyl acetate gradient) to afford pure (2R,3R,4R,5R)-2-(4-amino-3-ethoxy-1H-pyrazolo[3,4-d]pyrimidin-1-yl)-5-[(benzoyloxy)methyl]tetrahydrofuran-3,4-diyl dibenzoate (2.838 g, 82%). LCMS (AA): m/z 624 (M+H); $^1$H NMR (300 MHz, CDCl$_3$) δ 8.32 (s, 1H), 8.11-8.04 (m, 2H), 8.03-7.90 (m, 4H), 7.54 (s, 3H), 7.45-7.31 (m, 6H), 6.76 (d, J=3.8 Hz, 1H), 6.42-6.33 (m, 1H), 6.24 (t, J=5.2 Hz, 1H), 5.61-5.49 (m, 2H), 4.84-4.70 (m, 2H), 4.60 (dd, J=12.8, 6.0 Hz, 1H), 4.42-4.20 (m, 2H), 1.39 (t, J=7.1 Hz, 3H).

Step 5: (2R,3R,4S,5R)-2-(4-amino-3-ethoxy-1H-pyrazolo[3,4-d]pyrimidin-1-yl)-5-(hydroxymethyl)tetrahydrofuran-3,4-diol Intermediate 6

Intermediate 5 (2.838 g, 4.551 mmol) was dissolved in MeOH (120 mL). To this solution was added 0.50 M sodium methoxide in MeOH (1.8 mL, 0.92 mmol) solution. pH was approximately 9. After stirring at rt overnight remaining base was neutralized by the addition of Amberlite CG-50 weakly acidic resin (1 g). After 0.5 h, the mixture was filtered through Celite and the filtrate concentrated under reduced pressure. The crude product was suspended in ether (sonicate and scrape), filtered and dried in vacuo to afford (2R,3R,4S,5R)-2-(4-amino-3-ethoxy-1H-pyrazolo[3,4-d]pyrimidin-1-yl)-5-(hydroxymethyl)tetrahydrofuran-3,4-diol (Intermediate 6, 1.129 g, 80%). LCMS (AA): m/z 312 (M+H); $^1$H NMR (300 MHz, d$_6$-DMSO) δ 8.13 (s, 1H), 5.98 (d, J=4.3 Hz, 1H), 5.31 (d, J=5.6 Hz, 1H), 5.04 (d, J=5.7 Hz, 1H), 4.75 (t, J=5.8 Hz, 1H), 4.48 (dd, J=9.9, 5.0 Hz, 1H), 4.32 (q, J=7.0 Hz, 2H), 4.18 (dd, J=10.1, 5.1 Hz, 1H), 3.90-3.79 (m, 1H), 3.63-3.51 (m, 1H), 3.48-3.38 (m, 1H), 1.40 (t, J=7.0 Hz, 3H).

Step 6: [(3aR,4R,6R,6aR)-6-(4-amino-3-ethoxy-1H-pyrazolo[3,4-d]pyrimidin-1-yl)-2,2-dimethyltetrahydrofuro[3,4-d][1,3]dioxol-4-yl]methanol Intermediate 7

Intermediate 6 (1.129 g, 3.626 mmol), acetone (60 mL), 2,2-dimethoxypropane (2.2 mL, 18 mmol) and p-toluenesulfonic acid monohydrate (0.690 g, 3.63 mmol) were combined in a flask and stirred at rt for 24 h. The reaction mixture was concentrated under reduced pressure and partitioned between saturated aqueous sodium bicarbonate solution (75 mL) and ethyl acetate (200 mL). The aqueous phase was extracted with additional ethyl acetate. The extracts were combined, washed with brine and dried over sodium sulfate. The crude product appeared to contain trace methyl benzoate from the previous step. The residue was adsorbed onto Celite (3 g) and eluted through a silica column (40 g, ethyl acetate to 95/5 ethyl acetate/ethanol gradient) to afford pure [(3aR,4R,6R,6aR)-6-(4-amino-3-ethoxy-1H-pyrazolo[3,4-d]pyrimidin-1-yl)-2,2-dimethyltetrahydrofuro[3,4-d][1,3]dioxol-4-yl]methanol (Intermediate 7, 0.950 g, 75%). LCMS (AA): m/z 352 (M+H); $^1$H NMR (400 MHz, d$_6$-DMSO) δ 8.15 (s, 1H), 7.99-7.63 (br s, 1H), 6.85-6.52 (br s, 1H), 6.20 (d, J=2.0 Hz, 1H), 5.19 (dd, J=6.1, 2.0 Hz, 1H), 4.92 (t, J=5.9 Hz, 1H), 4.88 (dd, J=6.1, 2.1 Hz, 1H), 4.42-4.25 (m, 2H), 4.13-4.06 (m, 1H), 3.57 (ddd, J=11.3, 7.1, 6.1 Hz, 1H), 3.43 (dt, J=11.4, 5.9 Hz, 1H), 1.50 (s, 3H), 1.41 (t, J=7.0 Hz, 3H), 1.31 (s, 3H).

Step 7: [(3aR,4R,6R,6aR)-6-(4-amino-3-ethoxy-1H-pyrazolo[3,4-d]pyrimidin-1-yl)-2,2-dimethyltetrahydrofuro[3,4-d][1,3]dioxol-4-yl]methyl Sulfamate Intermediate 8

Intermediate 7 (0.360 g, 1.02 mmol) was dissolved in DMF (3.5 mL). Chlorosulfonamide (0.355 g, 3.07 mmol) was added and the mixture was stirred at rt for 2 h. The mixture was poured into saturated aqueous sodium bicarbonate solution (75 mL) and extracted with ethyl acetate (100+75 mL). The extracts were combined, washed with water and brine and then dried over sodium sulfate, filtered and concentrated under reduced pressure. The crude [(3aR,4R,6R,6aR)-6-(4-amino-3-ethoxy-1H-pyrazolo[3,4-d]pyrimidin-1-yl)-2,2-dimethyltetrahydrofuro[3,4-d][1,3]dioxol-4-yl]methyl sulfamate was used as obtained in the following step (Intermediate 8, 0.453 g, 100%). LCMS (AA): m/z 431 (M+H); $^1$H NMR (400 MHz, DMSO) δ 8.16 (s, 1H), 7.91-7.70 (m, 1H), 7.55 (s, 2H), 6.94-6.54 (m, 1H), 6.28 (d, J=1.1 Hz, 1H), 5.19 (dd, J=6.0, 1.2 Hz, 1H), 4.97 (dd, J=6.0, 2.0 Hz, 1H), 4.35 (s, 4H), 4.08 (dd, J=9.6, 6.4 Hz, 1H), 1.51 (s, 3H), 1.40 (t, J=7.0 Hz, 3H), 1.33 (s, 3H).

Step 8: [(2R,3S,4R,5R)-5-(4-amino-3-ethoxy-1H-pyrazolo[3,4-d]pyrimidin-1-yl)-3,4-dihydroxytetrahydrofuran-2-yl]methyl Sulfamate I-5

Intermediate 8 (0.453 g, 1.05 mmol) was dissolved in a mixture of formic acid (10 mL) and water (10 mL) and stirred overnight at rt. The mixture was twice diluted with toluene (100 mL) and concentrated to ¼ volume. Subsequently, the moist mixture was coevaporated from acetonitrile until dry. The resulting white solid was dissolved in acetonitrile, adsorbed onto 3.5 g celite and eluted through a C18 cartridge (86 g, 95/5 to 30/70 water/acetonitrile gradient, with 10 mM ammonium acetate). Product-containing fractions were concentrated under reduced pressure. Water was removed through acetonitrile then toluene azeotrope. LCMS (AA): m/z 391 (M+H); $^1$H NMR (300 MHz, CD$_3$OD) δ 8.13 (s, 1H), 6.20 (d, J=3.0 Hz, 1H), 4.62-4.57 (m, 1H), 4.55 (t, J=5.0 Hz, 1H), 4.50-4.41 (m, 2H), 4.38-4.29 (m, 1H), 4.24 (d, J=5.8 Hz, 1H), 4.20 (d, J=3.6 Hz, 1H), 1.47 (t, J=7.1 Hz, 3H).

Example 2

The following compounds were prepared following the procedures detailed in Example 1, substituting the appropriate alcohol for ethanol in Step 1.

| Compound | Alcohol | LCMS | 1H-NMR |
|---|---|---|---|
| I-1 | methanol | LCMS (FA): m/z 377 (M + H) | (400 MHz, $d_6$-DMSO) δ 8.14 (s, 1H), 7.75 (br s, 1H), 7.62-7.37 (br m, 2H), 6.78 (br s, 1H), 6.06 (d, J = 3.1 Hz, 1H), 5.54 (br s, 1H), 5.32 (br s, 1H), 4.42 (s, 1H), 4.34 (br t, J = 4.3 Hz, 1H), 4.21 (q, J = 6.9 Hz, 1H), 4.11-4.02 (m, 2H), 3.97 (s, 3H). |
| I-7 | isopropanol | LCMS (AA): m/z 405 (M + H) | (300 MHz, $CD_3OD$) δ 8.13 (s, 1H), 6.20 (d, J = 2.9 Hz, 1H), 5.21-5.08 (m, 1H), 4.63-4.44 (m, 2H), 4.34 (dd, J = 13.0, 6.2 Hz, 1H), 4.28-4.13 (m, 2H), 1.46 (s, 3H), 1.44 (s, 3H). |
| I-37 | phenol | LCMS (FA): m/z 439 (M + H) | (400 MHz, $d_6$-DMSO) δ 8.25-8.34 (m, 2H), 7.49 (d, J = 8.5 Hz, 2H), 6.93 (d, J = 8.8 Hz, 2H), 6.22 (d, J = 3.3 Hz, 1H), 4.52 (dd, J = 4.8, 3.5 Hz, 1H), 4.36-4.41 (m, 1H), 4.24 (dd, J = 10.0, 3.0 Hz, 1H), 4.09-4.15 (m, 1H), 4.02-4.08 (m, 1H). |

Example 3: [(2R,3S,4R,5R)-5-(4-amino-3-methyl-1H-pyrazolo[3,4-d]pyrimidin-1-yl)-3,4-dihydroxytetrahydrofuran-2-yl]methyl Sulfamate Compound I-2

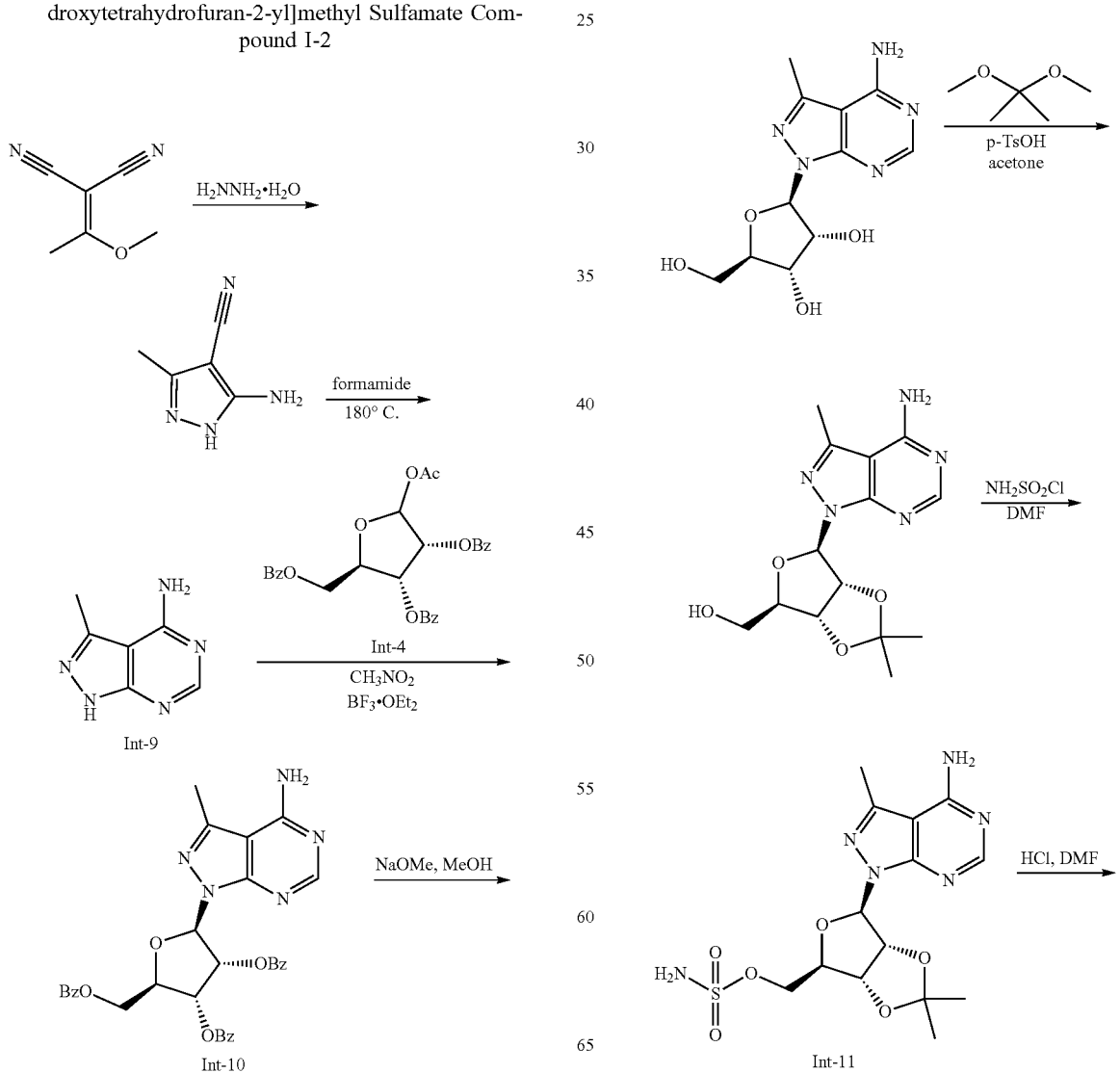

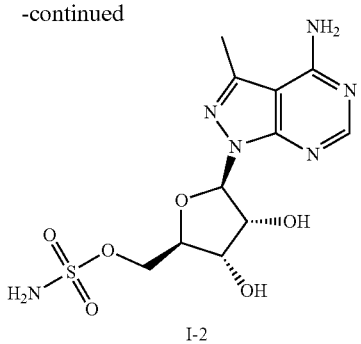

I-2

Step 1: 5-amino-3-methyl-1H-pyrazole-4-carbonitrile

Hydrazine hydrate (4.5 mL, 92 mmol) was placed in a 50 mL round bottom flask. While stirring at rt, (1-ethoxyethylidene)malononitrile (5.0 g, 37 mmol) was added in portions. After half the material had been added, the flask was placed in an ice-water bath. Upon completion of addition, a precipitate had begun to form and the reaction flask was removed from the ice-water bath and heated at reflux for 2 h, then cooled to rt. The resulting solution was briefly cooled in an ice-water bath and then sonicated for a few moments to induce crystallization. Solids were collected by filtration, washed with water and then dried in vacuo to give 5-amino-3-methyl-1H-pyrazole-4-carbonitrile (2.69 g, 60%). $^1$H NMR (300 MHz, $d_6$-DMSO) δ 3.31 (s, 3H).

Step 2: 3-methyl-1H-pyrazolo[3,4-d]pyrimidin-4-amine Intermediate 9

5-Amino-3-methyl-1H-pyrazole-4-carbonitrile (2.7 g, 22) was suspended in formamide (5.5 mL, 140 mmol) in a 50 mL round bottom flask fitted with a stirbar and reflux condenser. The mixture was heated in an oil bath at 180° C. for 0.5 h. The mixture turned homogeneous and dark orange/red. The temperature of the oil bath was increased to 200° C. and stirred for 1 h. Midway through heating, a cream-colored precipitate formed. After cooling to rt, cold water (10 mL) was added and the mixture was filtered. The solids were washed with additional cold water and dried for a few minutes under suction. The still-wet solids were suspended in water (50 mL), acidified with conc. HCl, and heated in an oil bath until homogeneous (brown solution). A tipful of decolorizing carbon was added and the mixture heated near reflux for a few minutes. The mixture was filtered to remove the carbon. The resulting solution was basified with concentrated ammonium hydroxide solution while still hot. The solution was then cooled to rt and a creamy white precipitate formed. The solids were isolated by suction filtration and dried under suction. Remaining water was removed by azeotropic coevaporation from toluene (twice) to afford the dried product, 3-methyl-1H-pyrazolo[3,4-d]pyrimidin-4-amine (2.89 g, 88%). $^1$H NMR (300 MHz, $d_4$-acetic acid) δ 8.43 (s, 1H), 2.73 (s, 3H).

Step 3: (2R,3R,4R,5R)-2-(4-amino-3-methyl-1H-pyrazolo[3,4-d]pyrimidin-1-yl)-5-[(benzoyloxy)methyl]tetrahydrofuran-3,4-diyl Dibenzoate Intermediate 10

The titled compound was prepared following the procedure described in Example 1 Step 4, substituting Intermediate 9 for Intermediate 3 (53%). $^1$H NMR (300 MHz, CDCl$_3$) δ 8.34 (s, 1H), 8.16-8.07 (m, 2H), 8.02-7.87 (m, 4H), 7.59-7.49 (m, 3H), 7.45-7.30 (m, 6H), 6.80 (d, J=3.5 Hz, 1H), 6.41 (dd, J=5.3, 3.5 Hz, 1H), 6.31 (dd, J=5.6, 5.6 Hz, 1H), 4.85-4.72 (m, 2H), 4.61 (dd, J=11.6, 4.4 Hz, 1H), 2.54 (s, 3H).

Step 4: (2R,3R,4S,5R)-2-(4-amino-3-methyl-1H-pyrazolo[3,4-d]pyrimidin-1-yl)-5-(hydroxymethyl)tetrahydrofuran-3,4-diol (2R,3R,4R,5R)-2-(4-amino-3-methyl-1H-pyrazolo[3,4-d]pyrimidin-1-yl)-5-[(benzoyloxy)methyl]tetrahydrofuran-3,4-diyl dibenzoate (Intermediate 10, 2.21 g, 3.72) was dissolved in MeOH (100 mL). To this solution was added a 0.50 M of sodium methoxide in MeOH (1.5 mL, 0.75 mmol) solution in 0.5 mL increments until pH was 9. The reaction mixture was stirred at rt overnight and then the reaction was quenched by the addition of Amberlyst 15 beads (4.00 g, 15-20 meq, strongly acidic). After gently stirring for 0.5 h, the mixture was filtered. The filtrate was then stirred with 4.12 g (3.14 meq/g) MP-carbonate resin beads for 0.5 h. After filtration and concentration, the biphasic mixture was suspended in ether and the solid product, (2R,3R,4S,5R)-2-(4-amino-3-methyl-1H-pyrazolo[3,4-d]pyrimidin-1-yl)-5-(hydroxymethyl)tetrahydrofuran-3,4-diol, was isolated by suction filtration (0.28 g, 27%). LCMS (AA): m/z 282 (M+H); $^1$H NMR (400 MHz, $d_6$-DMSO) δ 8.14 (s, 1H), 6.01 (d, J=4.8 Hz, 1H), 5.38-5.20 (m, 2H), 5.17-5.02 (m, 1H), 4.91-4.80 (m, 1H), 4.55 (t, J=4.9 Hz, 1H), 4.16 (t, J=4.7 Hz, 1H), 3.86 (dd, J=8.6, 3.4 Hz, 2H), 3.62-3.49 (m, 1H), 3.47-3.36 (m, 2H), 2.52 (s, 3H).

Step 5: [(3aR,4R,6R,6aR)-6-(4-amino-3-methyl-1H-pyrazolo[3,4-d]pyrimidin-1-yl)-2,2-dimethyltetrahydrofuro[3,4-d][1,3]dioxol-4-yl]methanol The titled compound was prepared following the procedure described in Example 1 Step 6, substituting (2R,3R,4S,5R)-2-(4-amino-3-methyl-1H-pyrazolo[3,4-d]pyrimidin-1-yl)-5-(hydroxymethyl)tetrahydrofuran-3,4-diol for Intermediate 6 (76%). LCMS (AA): m/z 322 (M+H); $^1$H NMR (300 MHz, $d_6$-DMSO) δ 8.34-8.19 (m, 1H), 6.24 (s, 1H), 5.26 (d, J=4.6 Hz, 1H), 4.92 (d, J=6.8 Hz, 1H), 4.16-4.06 (m, 1H), 3.52 (dd, J=11.3, 7.4 Hz, 1H), 3.37 (dd, J=11.3, 5.9 Hz, 1H), 2.55 (s, 3H), 1.51 (s, 3H), 1.32 (s, 3H).

Step 6: [(3aR,4R,6R,6aR)-6-(4-amino-3-methyl-1H-pyrazolo[3,4-d]pyrimidin-1-yl)-2,2-dimethyltetrahydrofuro[3,4-d][1,3]dioxol-4-yl]methyl Sulfamate Intermediate 11

The titled compound was prepared following the procedure described in Example 1 Step 7, substituting [(3aR,4R,6R,6aR)-6-(4-amino-3-methyl-1H-pyrazolo[3,4-d]pyrimidin-1-yl)-2,2-dimethyltetrahydrofuro[3,4-d][1,3]dioxol-4-yl]methanol for Intermediate 7. LCMS (AA): m/z 401 (M+H); $^1$H NMR (300 MHz, $d_6$-DMSO) δ 7.94 (s, 1H), 7.65-7.34 (m, 3H), 6.31 (s, 1H), 5.28 (d, J=6.1 Hz, 1H), 4.99 (dd, J=6.1, 2.2 Hz, 1H), 4.34 (dd, J=6.8, 4.6 Hz, 1H), 4.20 (dd, J=10.3, 6.5 Hz, 1H), 4.05 (dd, J=10.3, 7.2 Hz, 1H), 2.54 (s, 3H), 1.51 (s, 3H), 1.33 (s, 3H).

Step 7: [(2R,3S,4R,5R)-5-(4-amino-3-methyl-1H-pyrazolo[3,4-d]pyrimidin-1-yl)-3,4-dihydroxytetrahydrofuran-2-yl]methyl Sulfamate Compound I-2

[(3aR,4R,6R,6aR)-6-(4-amino-3-methyl-1H-pyrazolo[3,4-d]pyrimidin-1-yl)-2,2-dimethyltetrahydrofuro[3,4-d][1,3]dioxol-4-yl]methyl sulfamate (Intermediate 11, 0.085 g, 0.21) was dissolved in DMF (1 mL) to which 6.0 M aqueous hydrochloric acid (0.26 mL, 1.6 mmol) was added. The solution was stirred at rt. After 24 h, additional HCl was added (6M, 0.5 mL). Stirring was continued at rt for 24 h then the reaction mixture was concentrated under reduced pressure. The crude material was purified by preparative reverse phase HPLC (37 mg, 46%). LCMS (AA): m/z 361 (M+H); $^1$H NMR (300 MHz, d$_6$-DMSO) δ 8.15 (s, 1H), 7.60-7.14 (br m, 4H), 6.08 (d, J=3.6 Hz, 1H), 5.61-5.44 (m, 1H), 5.40-5.24 (m, 1H), 4.54-4.40 (m, 1H), 4.30 (t, J=5.2 Hz, 1H), 4.21 (dd, J=9.7, 2.9 Hz, 1H), 4.14-3.91 (m, 2H), 2.53 (s, 3H).

Example 4

The compounds listed below were prepared as described in Example 3 starting with Step 3 substituting the base listed in the table for Intermediate 9.

| Compound | Base | LCMS | $^1$H-NMR |
|---|---|---|---|
| I-48 | 1H-pyrazolo[3,4-d]pyrimidin-4-amine | LCMS (AA): m/z 347 (M + H) | (400 MHz, CD$_3$OD) δ 8.19 (s, 1H), 8.14 (s, 1H), 6.30 (d, J = 3.3 Hz, 1H), 4.69 (dd, J = 5.0, 3.5 Hz, 1H), 4.54-4.58 (m, 1H), 4.34 (dd, J = 10.0, 3.3 Hz, 1H), 4.23-4.29 (m, 1H), 4.17-4.23 (m, 1H). |

Example 5: methyl 4-amino-1-{(2R,3S,4R,5R)-3,4-dihydroxy-5-[(sulfamoyloxy)methyl]tetrahydrofuran-2-yl}-1H-pyrazolo[3,4-d]pyrimidine-3-carboxylate Compound I-20

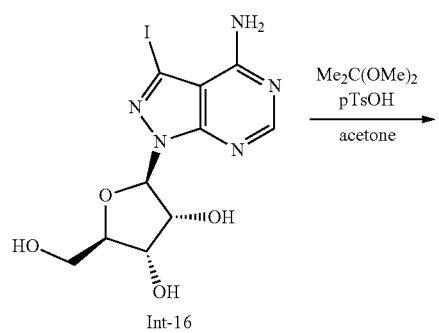

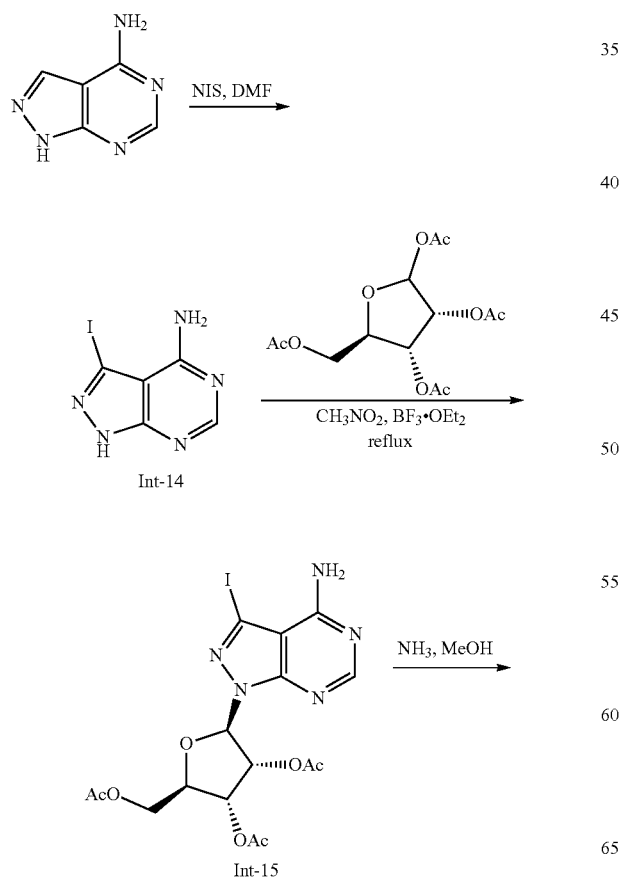

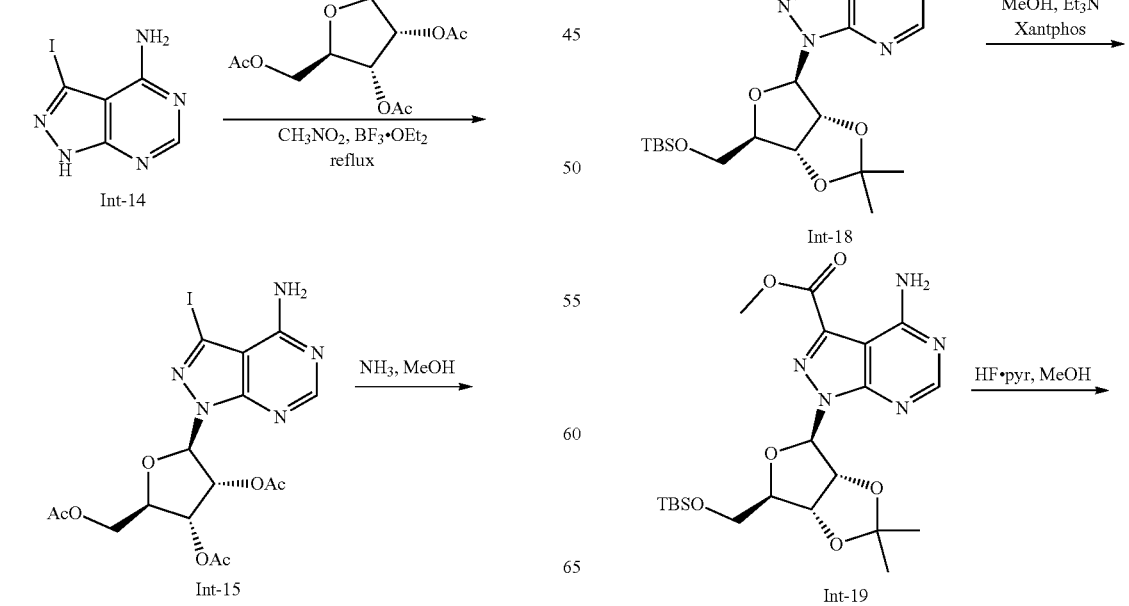

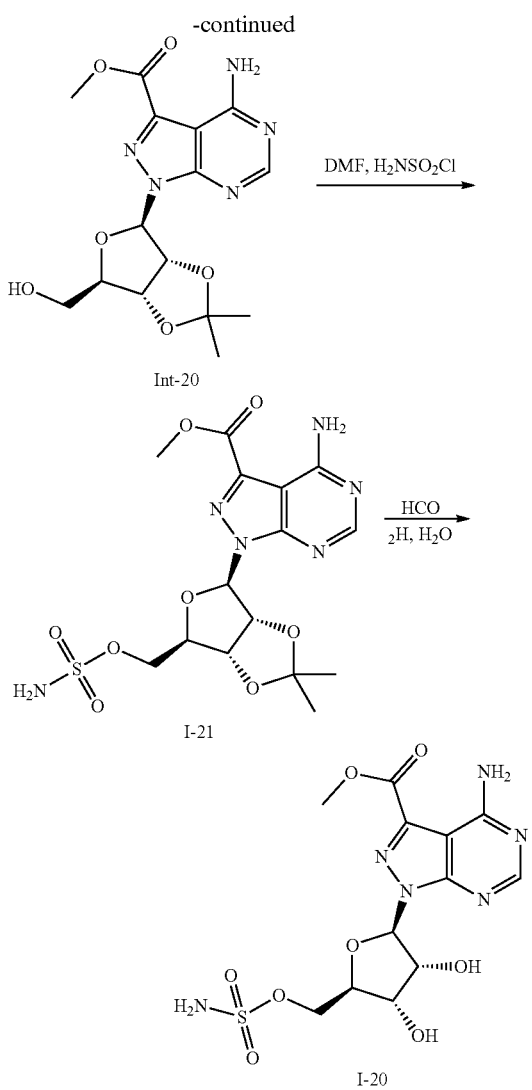

Int-20

I-21

I-20

Step 1: 4-amino-3-iodo-1H-pyrazolo[3,4-d]pyrimidine Intermediate 14

To a solution of 4-aminopyrazolo[3,4-d]pyrimidine (5.00 g, 37.0 mmol) in DMF (130 mL) was added N-iodosuccinimide (10.83 g, 48.14 mmol). The reaction mixture was heated overnight at 50° C. Additional N-iodosuccinimide (1.67 g, 7.41 mmol) was added and heating was continued at 50° C. for a second night. The mixture was then allowed to cool to rt and concentrated to one half volume under reduced pressure. Water was added and the resulting precipitate was collected by suction filtration. The solids were washed with water and ethanol, then dried in vacuo at 40° C. to afford the product, 4-amino-3-iodo-1H-pyrazolo[3,4-d]pyrimidine (Intermediate 14, 8.66 g, 90%). LCMS (AA): m/z 262 (M+H); $^1$H NMR (400 MHz, $d_6$-DMSO) δ 13.80 (s, 1H), 8.16 (s, 1H).

Step 2: (2R,3R,4R,5R)-2-(acetoxymethyl)-5-(4-amino-3-iodo-1H-pyrazolo[3,4-d]pyrimidin-1-yl)tetrahydrofuran-3,4-diyl Diacetate Intermediate 15

1,2,3,5-Tetra-O-acetyl-β-D-ribofuranose (1.38 g, 4.33 mmol), Intermediate 14 (0.870 g, 3.33 mmol) and nitromethane (11 mL) were combined in a 3-neck flask fitted with a stirbar and reflux condenser. The mixture was warmed to reflux in an oil bath. Boron trifluoride etherate (0.739 mL, 5.83 mmol) was then added dropwise to the heated mixture by syringe. The reaction mixture turned homogeneous after completion of BF$_3$ addition and was allowed to stir at reflux for 45 min, during which time the mixture turned dark brown. After cooling to rt, the reaction mixture was quenched with saturated aqueous sodium bicarbonate solution, then diluted with ethyl acetate. The mixture was twice extracted into ethyl acetate. The extracts were combined, washed with water and brine then dried over sodium sulfate, filtered and concentrated under reduced pressure. The crude product was purified by silica gel chromatography (40 g silica, DCM to 93/7 DCM/MeOH gradient) to afford pure (2R,3R,4R,5R)-2-(acetoxymethyl)-5-(4-amino-3-iodo-1H-pyrazolo[3,4-d]pyrimidin-1-yl)tetrahydrofuran-3,4-diyl diacetate (1.29 g, 75%). LCMS (AA): m/z 520 (M+H); $^1$H NMR (300 MHz, CDCl$_3$) δ 8.35 (s, 1H), 6.50 (d, J=4.0 Hz, 1H), 6.05 (br s, 2H), 5.96 (dd, J=5.3, 4.0 Hz, 1H), 5.74 (t, J=5.3 Hz, 1H), 4.56-4.34 (m, 2H), 4.18 (dd, J=11.9, 4.7 Hz, 1H), 2.23-2.04 (m, 9H).

Step 3: (2R,3R,4S,5R)-2-(4-amino-3-iodo-1H-pyrazolo[3,4-d]pyrimidin-1-yl)-5-(hydroxymethyl)tetrahydrofuran-3,4-diol Intermediate 16

(2R,3R,4R,5R)-2-(acetoxymethyl)-5-(4-amino-3-iodo-1H-pyrazolo[3,4-d]pyrimidin-1-yl)tetrahydrofuran-3,4-diyl diacetate (Intermediate 15, 1.29 g, 2.48 mmol) was dissolved in MeOH (30 mL). To this solution was added a solution of ammonia in MeOH (7.0 M, 10.0 mL). Reaction was complete after stirring at rt overnight. The mixture was concentrated under reduced pressure and used without further purification in the following step (0.85 g, 88%). LCMS (AA): m/z 394 (M+H); $^1$H NMR (400 MHz, $d_6$-DMSO) δ 8.23 (s, 1H), 6.03 (d, J=5.0 Hz, 1H), 5.39 (d, J=6.0 Hz, 1H), 5.16 (d, J=5.4 Hz, 1H), 4.83 (t, J=5.8 Hz, 1H), 4.57 (dd, J=10.8, 5.2 Hz, 1H), 4.16 (dd, J=9.6, 5.0 Hz, 1H), 3.89 (dd, J=9.9, 4.6 Hz, 1H), 3.55 (dt, J=10.1, 5.0 Hz, 1H), 3.43 (dd, J=11.8, 5.9 Hz, 1H).

Step 4: [(3aR,4R,6R,6aR)-6-(4-amino-3-iodo-1H-pyrazolo[3,4-d]pyrimidin-1-yl)-2,2-dimethyltetrahydrofuro[3,4-d][1,3]dioxol-4-yl]methanol Intermediate 17

The titled compound was prepared following the procedure described in Example 1 Step 6, substituting Intermediate 16 for Intermediate 6 (81%). LCMS (AA): m/z 434 (M+H); $^1$H NMR (400 MHz, CD$_3$OD) δ 8.22 (s, 1H), 6.39 (d, J=1.7 Hz, 1H), 5.33 (dd, J=6.0, 1.7 Hz, 1H), 4.98 (dd, J=6.0, 2.1 Hz, 1H), 4.27 (td, J=6.1, 2.1 Hz, 1H), 3.66 (dd, J=11.6, 6.1 Hz, 1H), 3.56 (dd, J=11.7, 6.1 Hz, 1H), 1.57 (s, 3H), 1.38 (s, 3H).

Step 5: 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-iodo-1H-pyrazolo[3,4-d]pyrimidin-4-amine Intermediate 18

To a solution of [(3aR,4R,6R,6aR)-6-(4-amino-3-iodo-1H-pyrazolo[3,4-d]pyrimidin-1-yl)-2,2-dimethyltetrahydrofuro[3,4-d][1,3]dioxol-4-yl]methanol (Intermediate 17, 6.00 g, 13.8 mmol) in methylene chloride (100 mL) was added 1H-imidazole (2.357 g, 34.62 mmol), DMAP (80 mg, 0.7 mmol) and tert-butyldimethylsilyl chloride (3.131 g, 20.78 mmol). The solution was allowed to stir at rt under atmosphere of nitrogen overnight. Saturated aqueous ammonium chloride solution was added and the mixture was extracted twice with methylene chloride. The combined extracts were washed with saturated aqueous sodium bicarbonate and brine, then dried over sodium sulfate, filtered and concentrated. The crude material was purified by silica gel chromatography (220 g silica, methylene chloride to 50/50 methylene chloride/ethyl acetate gradient) to afford the product, 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-iodo-1H-pyrazolo[3,4-d]pyrimidin-4-amine, as a white solid (5.75 g, 76%). LCMS (AA): m/z 548 (M+H); $^1$H NMR (400 MHz, CDCl$_3$) δ 8.36 (s, 1H), 6.50 (d, J=1.9 Hz, 1H), 6.12-5.85 (m, 2H), 5.43 (dd, J=6.1, 1.9 Hz, 1H), 4.99 (dd, J=6.1, 2.1 Hz, 1H), 4.31 (ddd, J=7.7, 5.6, 2.1 Hz, 1H), 3.70 (dd, J=10.5, 7.7 Hz, 1H), 3.59 (dd, J=10.5, 5.6 Hz, 1H), 1.60 (s, 3H), 1.40 (s, 3H), 0.90-0.85 (m, 10H), 0.01 (s, 3H), 0.01 (s, 3H).

Step 6: methyl 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carboxylate Intermediate 19

To a 2-neck, round bottom flask fitted with a stirbar, reflux condenser and 3-way valve was added Intermediate 18 (1.00 g, 1.83 mmol), palladium acetate (8 mg, 0.04 mmol) and 4,5-bis(diphenylphosphino)-9,9-dimethylxanthene (Xantphos, 42 mg, 0.073 mmol). The flask was evacuated and backfilled with argon from a balloon. To the solids were added MeOH (10 mL) and triethylamine (2.5 mL, 18 mmol) by syringe. The reaction was again gently evacuated and backfilled with argon. Carbon monoxide gas was bubbled through the reaction mixture for 5 min. The reaction mixture was heated at 60° C. under a carbon monoxide balloon for 2 h. The reaction was sluggish. Carbon monoxide was subsequently bubbled through the heated reaction mixture for 1 h and then the mixture was allowed to stir under an atmosphere of carbon monoxide overnight. The mixture was cooled to rt and partitioned between water and ethyl acetate (50 mL, 100 mL, respectively). The phases were separated and the aqueous phase was extracted with 2×50 mL ethyl acetate. The extracts were combined, washed with brine and dried over sodium sulfate. The extracts were cloudy and yellow throughout the workup and were twice filtered through celite to afford a clear, pale yellow solution. After concentration under reduced pressure the crude product was purified by silica gel chromatography (40 g, 90/10 to 40/60 hexane/ethyl acetate gradient) to afford methyl 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carboxylate (Intermediate 19, 744 mg, 85%). $^1$H NMR (400 MHz, CDCl$_3$) δ 8.39 (s, 1H), 8.24 (s, 1H), 6.61 (d, J=1.9 Hz, 1H), 5.83 (s, 1H), 5.51 (dd, J=6.2, 1.9 Hz, 1H), 5.05 (dd, J=6.2, 2.1 Hz, 1H), 4.35 (ddd, J=7.8, 5.5, 2.1 Hz, 1H), 4.03 (s, 3H), 3.76 (dd, J=10.4, 8.1 Hz, 1H), 3.61 (dd, J=10.4, 5.5 Hz, 1H), 1.61 (s, 3H), 1.41 (s, 3H), 0.87 (d, J=2.8 Hz, 9H), 0.04--0.03 (m, 6H).

Step 7: methyl 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carboxylate Intermediate 20

To a polypropylene vial was added Intermediate 19 (0.175 g, 0.365 mmol), MeOH (7.0 mL) and pyridine hydrofluoride (0.33 mL). The vial was capped and the reaction was stirred at rt overnight. Excess acid was carefully quenched by the addition of saturated aqueous sodium bicarbonate solution. The mixture was extracted twice with ethyl acetate. The extracts were combined, washed with brine, dried over sodium sulfate, filtered and concentrated under reduced pressure to afford the crude product which was used without further purification (136 mg, 100%). LCMS (AA): m/z 366 (M+H).

Step 8: methyl 4-amino-1-{(3aR,4R,6R,6aR)-2,2-dimethyl-6-[(sulfamoyloxy)methyl]tetrahydrofuro[3,4-d][1,3]dioxol-4-yl}-1H-pyrazolo[3,4-d]pyrimidine-3-carboxylate Intermediate 21

The titled compound was prepared following the procedure described in Example 1 Step 7, substituting methyl 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carboxylate for Intermediate 7 (89%). LCMS (AA): m/z 445 (M+H).

Step 9: methyl 4-amino-1-{(2R,3R,4S,5R)-3,4-dihydroxy-5-[(sulfamoyloxy)methyl]tetrahydrofuran-2-yl}-1H-pyrazolo[3,4-d]pyrimidine-3-carboxylate 1-20

The titled compound was prepared following the procedure detailed in Example 1 Step 8, substituting Intermediate 21 for Intermediate 8 (70%). LCMS (AA): m/z 405 (M+H); $^1$H NMR (400 MHz, CD$_3$OD) δ 8.25 (s, 1H), 6.38 (d, J=3.6 Hz, 1H), 4.73 (dd, J=5.0, 3.6 Hz, 1H), 4.59 (t, J=5.2 Hz, 1H), 4.36 (dd, J=10.3, 3.1 Hz, 1H), 4.31-4.20 (m, 2H), 4.01 (s, 3H).

Example 6: {(2R,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl Sulfamate Compound I-58

Step 1: (2R,3R,4R,5R)-2-(acetoxymethyl)-5-[4-amino-3-(isopropylsulfanyl)-1H-pyrazolo[3,4-d]pyrimidin-1-yl]tetrahydrofuran-3,4-diyl Diacetate The titled compound was prepared as described in Example 5 Step 2 substituting 3-(isopropylsulfanyl)-1H-pyrazolo[3,4-d]pyrimidin-4-amine (Intermediate 99, prepared as described in Example 65, step 2) for Intermediate 14 (68%). LCMS (FA): m/z 468 (M+H).

Step 2: (2R,3R,4S,5R)-2-[4-amino-3-(isopropylsulfanyl)-1H-pyrazolo[3,4-d]pyrimidin-1-yl]-5-(hydroxymethyl)tetrahydrofuran-3,4-diol The titled compound was prepared as described in Example 5 Step 3 using (2R,3R,4R,5R)-2-(acetoxymethyl)-5-[4-amino-3-(isopropylsulfanyl)-1H-pyrazolo[3,4-d]pyrimidin-1-yl]tetrahydrofuran-3,4-diyl diacetate in place of Intermediate 15 (100%). LCMS (FA): m/z 342 (M+H).

Steps 3-5: {(2R,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl Sulfamate Compound I-58

The titled compound was prepared as described in Example 1 Steps 6, 7 and 8 substituting (2R,3R,4S,5R)-2-

[4-amino-3-(isopropylsulfanyl)-1H-pyrazolo[3,4-d]pyrimidin-1-yl]-5-(hydroxymethyl)tetrahydrofuran-3,4-diol for Intermediate 6. LCMS (FA): m/z 421 (M+H); $^1$H NMR (400 MHz, d$_6$-DMSO) δ 8.23 (s, 1H), 7.53 (s, 2H), 6.16 (d, J=3.0 Hz, 1H), 5.65 (d, J=5.3 Hz, 1H), 5.42 (d, J=6.3 Hz, 1H), 4.45-4.50 (m, 1H), 4.34-4.40 (m, 1H), 4.25 (dd, J=10.4, 3.3 Hz, 1H), 4.10-4.16 (m, 1H), 4.02 (dd, J=10.4, 7.5 Hz, 1H), 3.60-3.71 (m, 1H), 1.36 (d, J=3.5 Hz, 3H), 1.35 (d, J=3.5 Hz, 3H).

Example 7: [(2R,3S,4R,5R)-5-{4-amino-3-[(methylsulfanyl)methyl]-1H-pyrazolo[3,4-d]pyrimidin-1-yl}-3,4-dihydroxytetrahydrofuran-2-yl]methyl Sulfamate Compound I-93

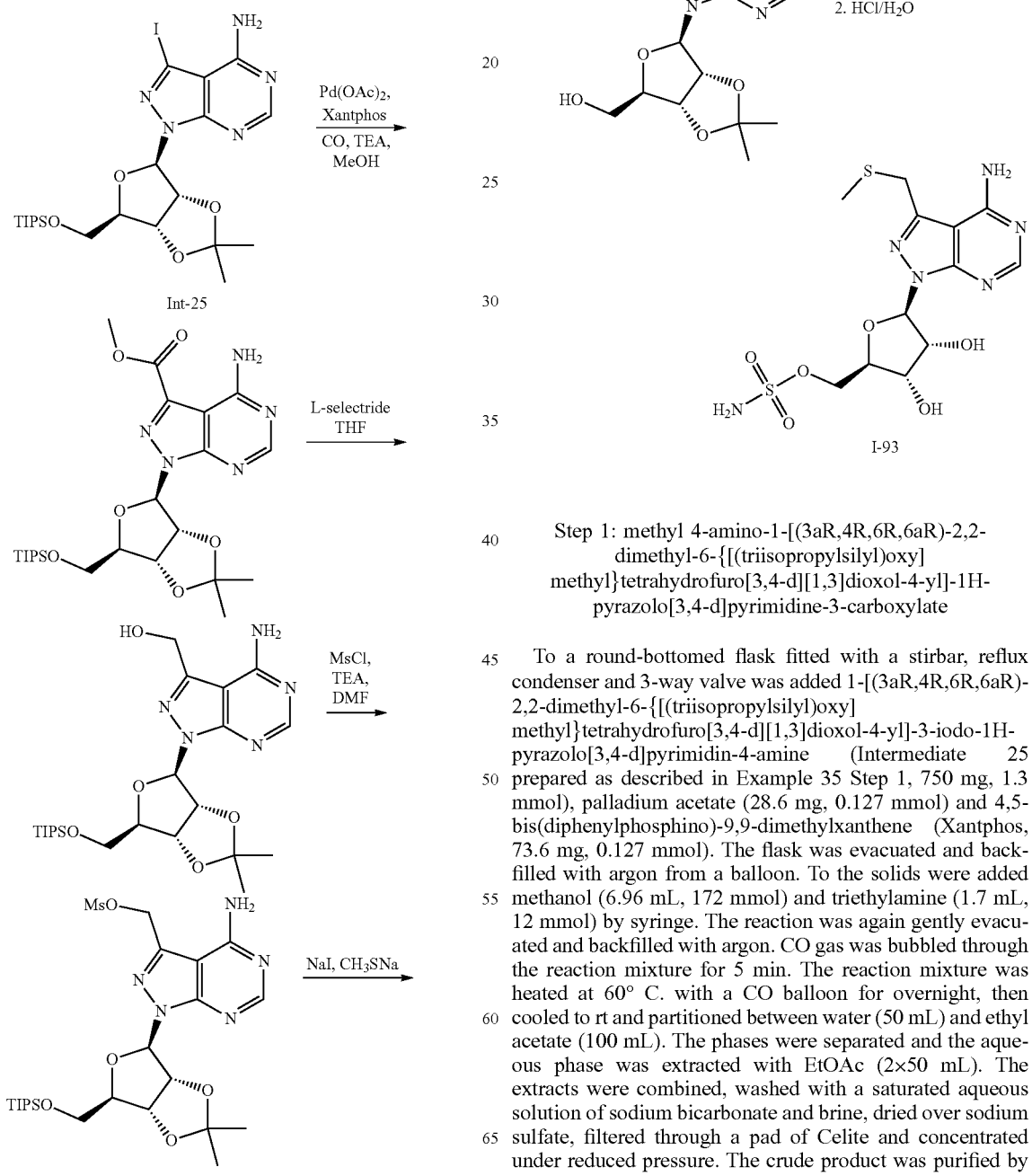

Step 1: methyl 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carboxylate To a round-bottomed flask fitted with a stirbar, reflux condenser and 3-way valve was added 1-[(3aR,4R,6R,6aR)-2,2-dimethyl-6-{[(triisopropylsilyl)oxy]methyl}tetrahydrofuro[3,4-d][1,3]dioxol-4-yl]-3-iodo-1H-pyrazolo[3,4-d]pyrimidin-4-amine (Intermediate 25 prepared as described in Example 35 Step 1, 750 mg, 1.3 mmol), palladium acetate (28.6 mg, 0.127 mmol) and 4,5-bis(diphenylphosphino)-9,9-dimethylxanthene (Xantphos, 73.6 mg, 0.127 mmol). The flask was evacuated and backfilled with argon from a balloon. To the solids were added methanol (6.96 mL, 172 mmol) and triethylamine (1.7 mL, 12 mmol) by syringe. The reaction was again gently evacuated and backfilled with argon. CO gas was bubbled through the reaction mixture for 5 min. The reaction mixture was heated at 60° C. with a CO balloon for overnight, then cooled to rt and partitioned between water (50 mL) and ethyl acetate (100 mL). The phases were separated and the aqueous phase was extracted with EtOAc (2×50 mL). The extracts were combined, washed with a saturated aqueous solution of sodium bicarbonate and brine, dried over sodium sulfate, filtered through a pad of Celite and concentrated under reduced pressure. The crude product was purified by silica gel chromatography to give methyl 4-amino-1-[(3aR, 4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carboxylate (488 mg, 74%). LCMS (FA): m/z 522 (M+H).

Step 2: {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methanol Into a solution of methyl 4-amino-1-[(3aR,4R,6R,6aR)-2,2-dimethyl-6-{[(triisopropylsilyl)oxy]methyl}tetrahydrofur[3,4-d][1,3]dioxol-4-yl]-1H-pyrazolo[3,4-d]pyrimidine-3-carboxylate (488 mg, 0.935 mmol) in THF (20.2 mL, 249 mmol) was added a solution of L-Selectride (R) in THF (1.0 M, 9.354 mL, 9.354 mmol). The mixture was stirred at rt overnight. Water was added to the reaction mixture and the resulting solution was stirred for 20 min at rt. EtOAc was added and the phases were separated. The aqueous phase was extracted with EtOAc three times. The extracts were combined, washed with water and brine, dried over sodium sulfate, filtered and concentrated under reduced pressure. The crude material was purified by silica gel chromatography to give {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methanol (462 mg, 73%). LCMS (FA): m/z 494 (M+H).

Step 3: {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methyl Methanesulfonate To a solution of {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methanol (340 mg, 0.69 mmol) in methylene chloride (11 mL) and triethylamine (0.288 mL, 2.07 mmol) was added methanesulfonyl chloride (0.107 mL, 1.38 mmol) at 0° C. After 1 h, the reaction mixture was partioned between water and DCM. The organic phase was collected, washed with brine, dried over sodium sulfate and concentrated under reduced pressure. The crude material was purified by silica gel chromatography to give {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methyl methanesulfonate (130 mg, 33%). LCMS (FA): m/z 572 (M+H).

Step 4: 1-[(3aR,4R,6R,6aR)-2,2-dimethyl-6-{[(triisopropylsilyl)oxy]methyl}tetrahydrofuro[3,4-d][1,3]dioxol-4-yl]-3-[(methylsulfanyl)methyl]-1H-pyrazolo[3,4-d]pyrimidin-4-amine To a solution of {4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}methyl methanesulfonate (130 mg, 0.23 mmol) and sodium iodide (17.0 mg, 0.114 mmol) in DMF (1.76 mL, 22.7 mmol) was added sodium methyl mercaptide (47.8 mg, 0.682 mmol). The mixture was stirred for 2 h and then quenched with an aqueous saturated solution of NaHCO$_3$. The phases were separated and the aqueous phase was extracted with EtOAc (3×). The organic extracts were combined, washed with water and brine, dried over sodium sulfate, filtered and concentrated under reduced pressure.

The crude material was purified by silica gel chromatography to give 1-[(3aR,4R,6R,6aR)-2,2-dimethyl-6-{[(triisopropylsilyl)oxy]methyl}tetrahydrofuro[3,4-d][1,3]dioxol-4-yl]-3-[(methylsulfanyl)methyl]-1H-pyrazolo[3,4-d]pyrimidin-4-amine (120 mg, 60%). LCMS (FA): m/z 524 (M+H).

Steps 5-7: [(2R,3S,4R,5R)-5-{4-amino-3-[(methylsulfanyl)methyl]-1H-pyrazolo[3,4-d]pyrimidin-1-yl}-3,4-dihydroxytetrahydrofuran-2-yl]methyl Sulfamate I-93

The titled compound was prepared following the procedures described in Example 5 Step 7, Example 1 Step 7 and Example 3 Step 7 substituting 1-[(3aR,4R,6R,6aR)-2,2-dimethyl-6-{[(triisopropylsilyl)oxy]methyl}tetrahydrofuro[3,4-d][1,3]dioxol-4-yl]-3-[(methylsulfanyl)methyl]-1H-pyrazolo[3,4-d]pyrimidin-4-amine for methyl 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carboxylate. LCMS (FA): m/z 407 (M+H); $^1$H NMR (400 MHz, d$_6$-DMSO) δ 8.20 (s, 1H), 7.51 (s, 2H), 6.13 (d, J=3.3 Hz, 1H), 5.58 (br d, J=4.6 Hz, 1H), 5.37 (br d, J=5.6 Hz, 1H), 4.45-4.54 (m, 1H), 4.31-4.39 (m, 1H), 4.24 (dd, J=10.4, 3.4 Hz, 1H), 4.07-4.14 (m, 1H), 4.04 (d, J=5.5 Hz, 2H), 4.00 (dd, J=7.1, 3.2 Hz, 1H), 1.94 (s, 3H).

Example 8: {(2R,3S,4R,5R)-5-[4-amino-3-(methylsulfanyl)-1H-pyrazolo[3,4-d]pyrimidin-1-yl]-3,4-dihydroxytetrahydrofuran-2-yl}methyl Sulfamate Compound I-42

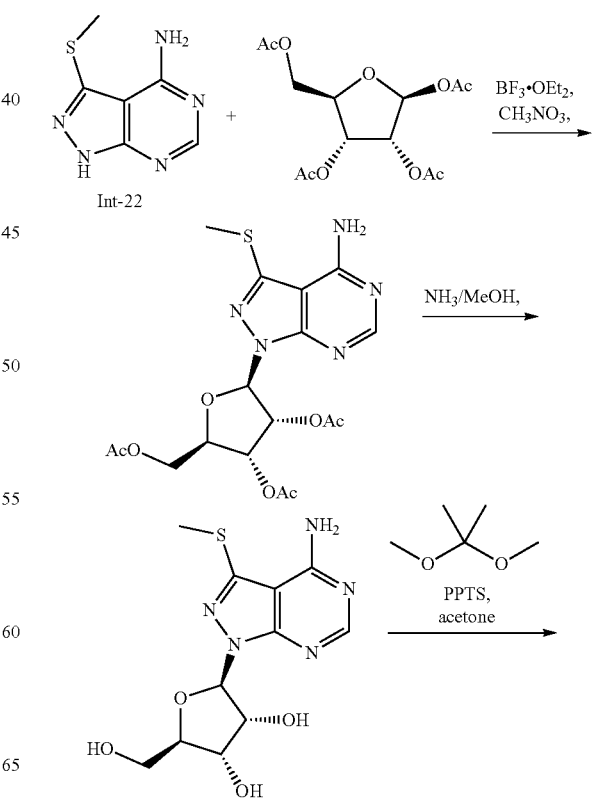

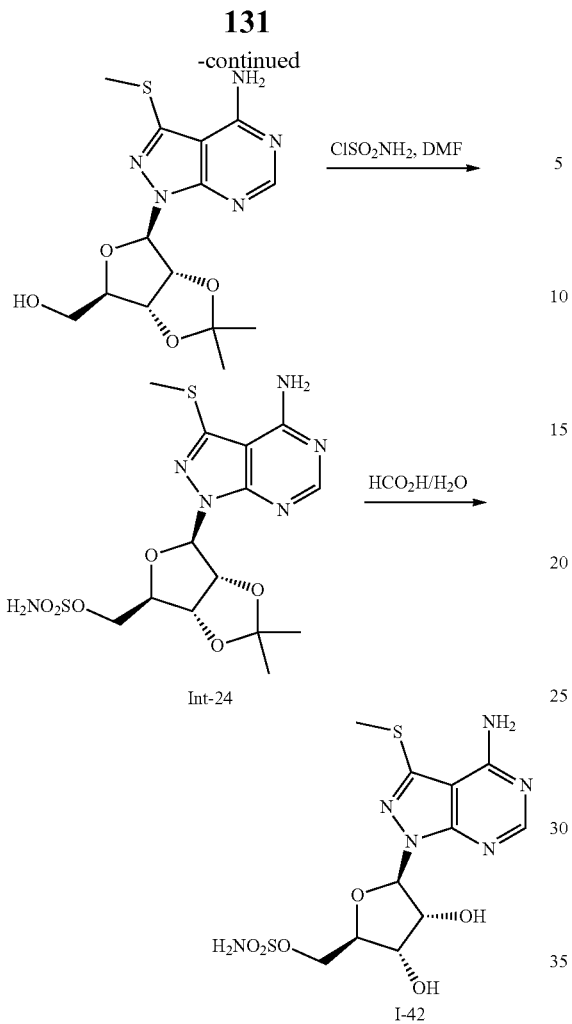

The titled compound was prepared starting with Example 5 Step 2. 3-(Methylsulfanyl)-1H-pyrazolo[3,4-d]pyrimidin-4-amine (Intermediate 22, prepared from commercially available 2-(bis(methylthio)methylene)malononitrile following procedures outlined in Example 48 Steps 2 and 3) was used in place of Intermediate 14 to give (2R,3R,4R,5R)-2-(acetoxymethyl)-5-(4-amino-3-(methylthio)-1H-pyrazolo[3,4-d]pyrimidin-1-yl)tetrahydrofuran-3,4-diyl diacetate which was then taken on through steps 4-7 of Example 3. LCMS (FA): m/z 393 (M+H). $^1$H NMR (400 MHz, CD$_3$OD) δ 8.18 (s, 1H), 6.27 (d, J=3.1 Hz, 1H), 4.66-4.72 (m, 1H), 4.60 (br t, J=5.1 Hz, 1H), 4.31-4.41 (m, 1H), 4.19-4.30 (m, 2H), 2.69 (s, 3H).

Example 9: {(2R,3S,4R,5R)-5-[4-amino-3-(methylsulfinyl)-1H-pyrazolo[3,4-d]pyrimidin-1-yl]-3,4-dihydroxytetrahydrofuran-2-yl}methyl Sulfamate Compound I-87

Intermediate 24 (product of Example 8 Step 4, {(3aR,4R,6R,6aR)-6-[4-amino-3-(methylsulfanyl)-1H-pyrazolo[3,4-d]pyrimidin-1-yl]-2,2-dimethyltetrahydrofuro[3,4-d][1,3]dioxol-4-yl}methyl sulfamate (50 mg, 0.1 mmol)) was dissolved in acetonitrile (10 mL) and water (20 mL) and a solution of sodium metaperiodate in water (0.06 M, 0.92 mL, 0.053 mmol) was added. Upon full consumption of starting material, water and EtOAc were added and the two layers were separated. The organic layer was concentrated, and the residue was treated with 0.89 mL trifluoroacetic acid (0.89 mL, 12 mmol) and water (0.21 mL). The resulting mixture was stirred for 30 min, and then concentrated under reduced pressure. The crude material was purified by preparative reverse phase HPLC to give a mixture of 2 diastereomers: {(2R,3S,4R,5R)-5-[4-amino-3-(methylsulfinyl)-1H-pyrazolo[3,4-d]pyrimidin-1-yl]-3,4-dihydroxytetrahydrofuran-2-yl}methyl sulfamate and {(2R,3S,4R,5R)-5-[4-amino-3-(methylsulfinyl)-1H-pyrazolo[3,4-d]pyrimidin-1-yl]-3,4-dihydroxytetrahydrofuran-2-yl}methyl sulfamate (11 mg, 20%). LCMS (FA): m/z 409 (M+H); $^1$H NMR (400 MHz, d$_6$-DMSO) δ 8.36 (d, J=1.0 Hz, 1H), 7.52 (d, J=10.7 Hz, 2H), 6.23 (dd, J=11.4, 3.3 Hz, 1H), 4.51 (br d, J=15.3 Hz, 1H), 4.28-4.43 (m, 1H), 4.11-4.26 (m, 2H), 4.02-4.09 (m, 1H), 3.01 (d, J=0.8 Hz, 3H).

Example 10: [(2R,3S,4R,5R)-5-(4-amino-3-phenyl-1H-pyrazolo[3,4-d]pyrimidin-1-yl)-3,4-dihydroxytetrahydrofuran-2-yl]methyl Sulfamate Compound I-49

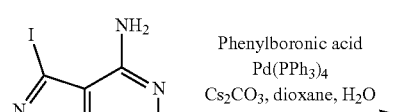

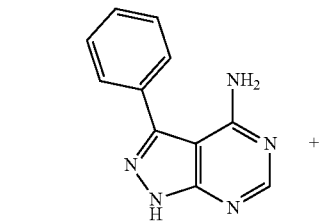

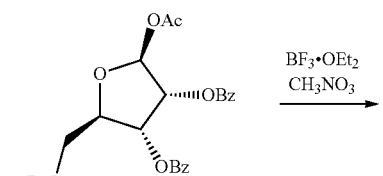

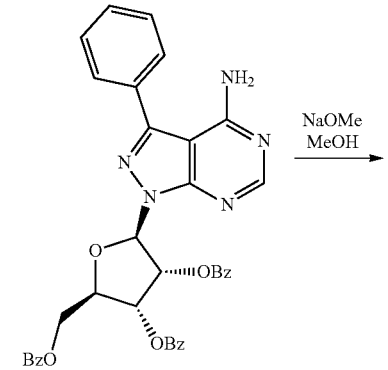

-continued

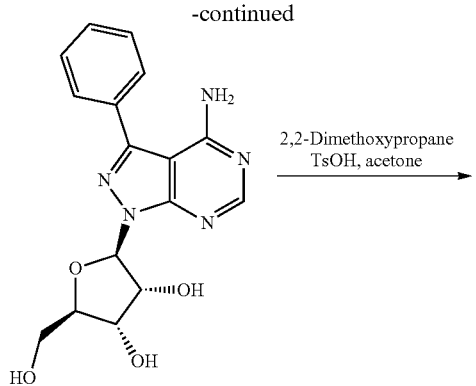

Step 1: 3-phenyl-1H-pyrazolo[3,4-d]pyrimidin-4-amine

To a solution of Intermediate 14 (0.400 g, 1.53 mmol) in 1,4-dioxane (4.5 mL) and water (1.2 mL) was added phenylboronic acid (0.260 g, 2.13 mmol), cesium carbonate (1.50 g, 4.60 mmol) and tetrakis(triphenylphosphine)palladium(0) (0.089 g, 0.077 mmol). The mixture was degassed and was subjected to microwave irradiation at 170° C. for 3 h. The mixture was then allowed to cool to rt and diluted with water and extracted twice with ethyl acetate. The extracts were combined, washed with brine, dried over sodium sulfate, filtered and concentrated under reduced pressure. Ethyl acetate was added. The resulting precipitate was collected by suction filtration and then dried in vacuo at 40° C. to afford the title compound (0.200 g, 62%). LCMS (AA) m/z 212 (M+H).

Steps 2-6: [(2R,3S,4R,5R)-5-(4-amino-3-phenyl-1H-pyrazolo[3,4-d]pyrimidin-1-yl)-3,4-dihydroxytetrahydrofuran-2-yl]methyl Sulfamate I-49

The titled compound was prepared by using 3-phenyl-1H-pyrazolo[3,4-d]pyrimidin-4-amine as a substitute for Intermediate 14 in Step 2 of Example 5 and then using the resulting compound in the Steps 3-4 of Example 5 and Step 6-7 of Example 3. LCMS (FA): m/z 423 (M+H); $^1$H NMR (400 MHz, $d_6$-DMSO) δ 8.29 (s, 1H), 7.68-7.72 (m, 2H), 7.51-7.60 (m, 3H), 6.25 (d, J=3.3 Hz, 1H), 4.55 (dd, J=4.8, 3.3 Hz, 1H), 4.37-4.44 (m, 1H), 4.24 (dd, J=10.2, 3.1 Hz, 1H), 4.10-4.17 (m, 1H), 4.03-4.10 (m, 1H).

Example 11: [(2R,3S,4R,5R)-5-(4-amino-3-cyano-1H-pyrazolo[3,4-d]pyrimidin-1-yl)-3,4-dihydroxytetrahydrofuran-2-yl]methyl Sulfamate Compound I-13

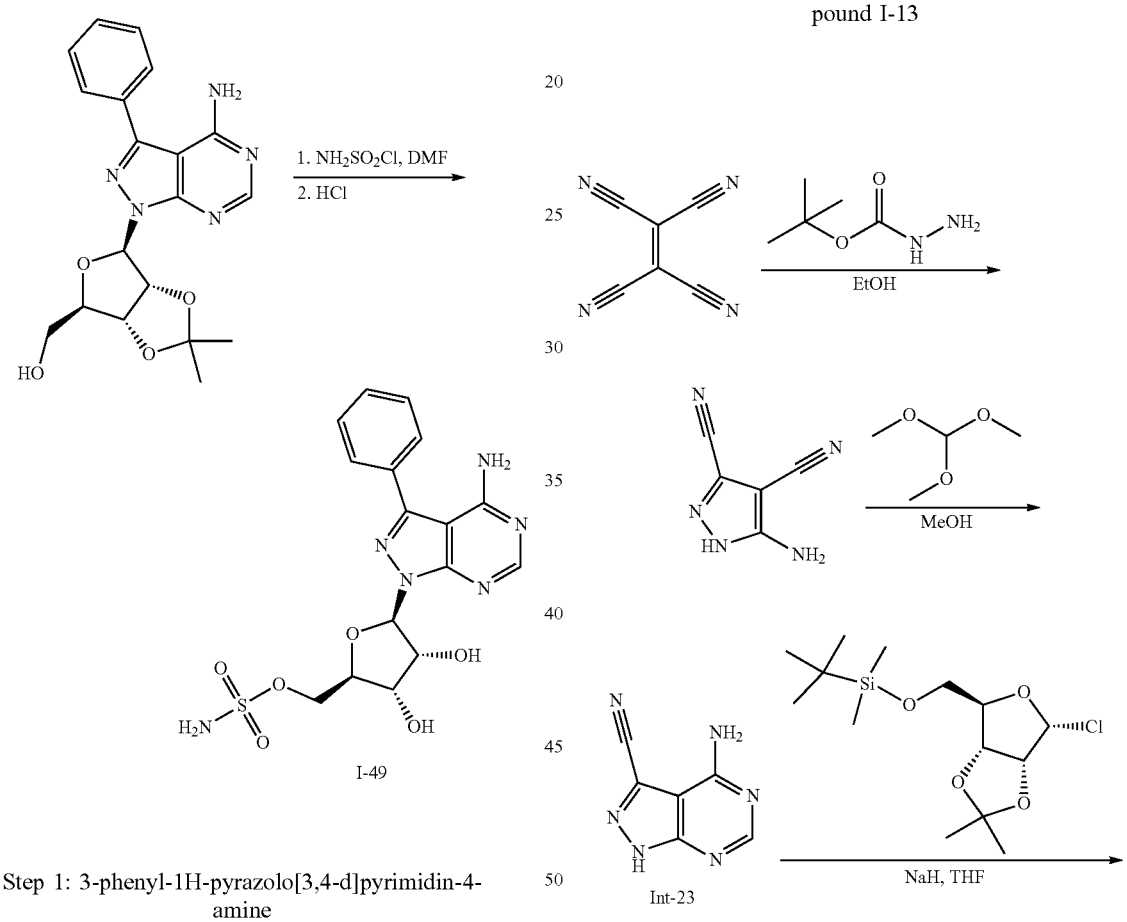

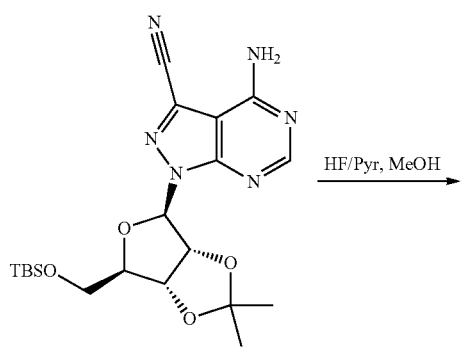

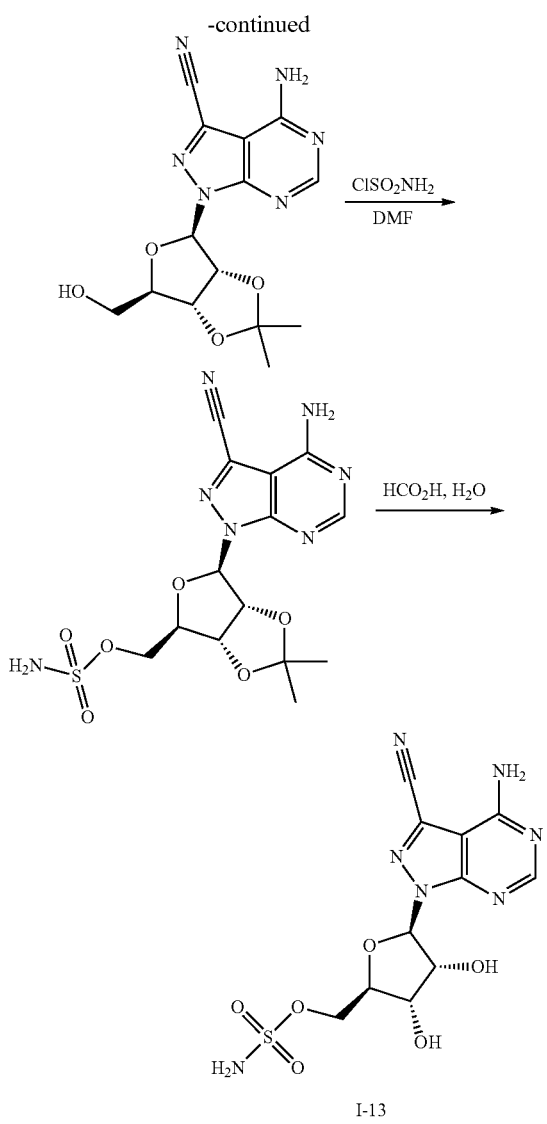

I-13

Step 1: 5-amino-1H-pyrazole-3,4-dicarbonitrile tert-Butyl carbazate (7.5 g, 57 mmol) was dissolved in ethanol (45 mL) and the resulting solution was cooled in an ice-water bath. Tetracyanoethylene (7.27 g, 56.7 mmol) was added in portions over several minutes. The mixture was stirred in the ice-water bath for 10 min and then allowed to warm to rt and stirred until the tetracyanoethylene dissolved. Once dissolved the mixture was warmed to reflux and stirred for 4 h. The mixture was then cooled to rt and concentrated under reduced pressure to afford a sticky orange solid which was used as is in the following step. LCMS (AA): m/z 132 (M−H).

Step 2: 4-amino-1H-pyrazolo[3,4-d]pyrimidine-3-carbonitrile Intermediate 23

5-Amino-1H-pyrazole-3,4-dicarbonitrile (7.6 g, 57 mmol) was suspended in trimethylorthoformate (60 mL) in a round bottom flask fitted with a stirbar and reflux condenser. The flask was placed in an oil bath and the mixture was heated at reflux overnight. After cooling to rt the following morning, the reaction solution was concentrated under reduced pressure to afford an orange oil. The oil was dried under high vacuum with stirring for 2 h. The residue was dissolved in MeOH (25 mL) and cooled under nitrogen in an ice-water bath. A solution of ammonia in MeOH (7.0 M, 65 mL, 460 mmol) was added. The resulting slightly opaque solution was warmed to rt and stirred overnight. The solids produced were isolated by suction filtration, washed with MeOH and dried under suction. The tan powder was transferred to a round bottom flask and dried under high vacuum and used without further purification (6.20 g, 68%, 2 steps). LCMS (AA): m/z 161 (M+H); $^1$H NMR (300 MHz, $d_6$-DMSO) δ 8.04 (s, 1H).

Step 3: 4-amino-1-[(3aR,4R,6R,6aR)-6-({[tert-butyl (dimethyl)silyl]oxy}methyl)-2,2-dimethyltetrahydrofuro[3,4-d][1,3]dioxol-4-yl]-1H-pyrazolo[3,4-d]pyrimidine-3-carbonitrile A degassed solution of azeotropically dried (with toluene) 5-O-(tert-butyldimethylsilyl)-2,3-O-isopropylidene-D-ribofuranose (1.520 g, 4.992 mmol; ref.: Chu, C K, *J. Med. Chem.*, 2008, 15, 3934) and carbon tetrachloride (0.72 mL, 7.5 mmol) in tetrahydrofuran (25 mL) was cooled in a dry ice/acetone bath under argon. Hexamethylphosphorous triamide (1.18 mL, 6.49 mmol) was added to the cooled solution and the mixture was allowed to stir at −78° C. for 0.5 h, at which time the mixture solidified into a stiff, slightly opaque mixture. The flask was warmed to −40° C. (acetonitrile/dry ice), stirred for 1 h and then warmed in an ice-water bath.

In a separate flask, a suspension of 4-amino-1H-pyrazolo [3,4-d]pyrimidine-3-carbonitrile (Intermediate 23, 0.879 g, 5.49 mmol) in THF (13 mL) and DMF (13 mL) with hexamethylphosphoramide (2.5 mL) was prepared and stirred under argon at 0° C. Sodium hydride (0.240 g, 5.99 mmol) was added and the mixture slowly turned homogeneous and was allowed to stir for 1.25 h at 0° C.

The ice water-cooled chloro-ribose solution was added to the 0° C. solution of sodium-4-amino-1H-pyrazolo[3,4-d] pyrimidine-3-carbonitrile via canula. THF (5 mL) was used as a wash to transfer any remaining residue. The mixture was allowed to warm to rt and stirred for 48 h. The mixture was poured into 50% saturated ammonium chloride solution (100 mL) and extracted with ethyl acetate (3×150 mL). The extracts were combined, washed with water (200 mL) and brine. The combined extracts were dried over sodium sulfate, filtered and concentrated under reduced pressure to afford a yellow, waxy oil which was dissolved in MeOH/ethyl acetate and adsorbed onto celite. The crude mixture was purified by silica gel chromatography (80 g, 80/20 to 50/50 hexanes/ethyl acetate gradient) to afford 4-amino-1-[(3aR,4R,6R,6aR)-6-({[tert-butyl(dimethyl)silyl] oxy}methyl)-2,2-dimethyltetrahydrofuro[3,4-d][1,3]dioxol-4-yl]-1H-pyrazolo[3,4-d]pyrimidine-3-carbonitrile (382 mg, 17%). LCMS (AA): m/z 447 (M+H); $^1$H NMR (400 MHz, $CD_3OD$) δ 8.33 (s, 1H), 6.52 (d, J=1.3 Hz, 1H), 5.42 (dd, J=6.0, 1.4 Hz, 1H), 5.00 (dd, J=6.0, 2.2 Hz, 1H), 4.28 (ddd, J=6.6, 6.6, 2.3 Hz, 1H), 3.70 (dd, J=10.7, 6.7 Hz, 1H), 3.60 (dd, J=10.7, 6.6 Hz, 1H), 1.57 (s, 3H), 1.39 (s, 3H), 0.86-0.83 (m, 9H), −0.03 (s, 3H), −0.04 (s, 3H).

Step 4: 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carbonitrile A solution of 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carbonitrile (0.330 g, 0.739 mmol) in MeOH (29 mL) was transferred to a polypropylene conical vial fitted with a stirbar. Pyridine hydrofluoride (0.73 mL, 8.1 mmol) was added and the reaction mixture stirred at rt overnight. The mixture was transferred to a separatory funnel with 50 mL saturated aqueous sodium bicarbonate solution and ethyl acetate. A white precipitate formed on shaking. The solids were removed by filtration and discarded. The aqueous phase was extracted with additional ethyl acetate. The extracts were combined, washed with brine and dried over sodium sulfate. The extracts were filtered and concentrated under reduced pressure to afford 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carbonitrile as a white solid which was used as obtained (220 mg, 90%). LCMS (AA): m/z 333 (M+H); $^1$H NMR (300 MHz, CD$_3$OD) δ 8.33 (s, 1H), 6.51 (d, J=1.7 Hz, 1H), 5.39 (dd, J=6.0, 1.6 Hz, 1H), 5.01 (dd, J=6.0, 2.1 Hz, 1H), 4.31 (td, J=6.3, 2.3 Hz, 1H), 3.65 (dd, J=11.7, 6.2 Hz, 1H), 3.57 (dd, J=11.7, 6.6 Hz, 1H), 1.58 (s, 3H), 1.38 (s, 3H).

Step 5: [(3aR,4R,6R,6aR)-6-(4-amino-3-cyano-1H-pyrazolo[3,4-d]pyrimidin-1-yl)-2,2-dimethyltetrahydrofuro[3,4-d][1,3]dioxol-4-yl]methyl Sulfamate 4-Amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carbonitrile (0.330 g, 0.993 mmol) was azeotropically dried in toluene/THF and then further dried in vacuo prior to use. The dried solid was dissolved in DMF (7 mL). Chlorosulfonamide (0.344 g, 2.98 mmol) was added and the mixture was stirred at rt 1.5 h. The mixture was poured into saturated aqueous sodium bicarbonate solution (50 mL) and extracted with ethyl acetate (100+75 mL). The extracts were combined, washed with water (2×) and brine and then dried over sodium sulfate, filtered and concentrated under reduced pressure. The crude material was used as obtained (240 mg, 59%). LCMS (AA): m/z 412 (M+H); $^1$H NMR (300 MHz, CD$_3$OD) δ 8.33 (s, 1H), 6.57 (s, 1H), 5.44 (dd, J=5.9, 1.1 Hz, 1H), 5.09 (dd, J=5.9, 2.4 Hz, 1H), 4.51 (td, J=7.1, 2.4 Hz, 1H), 4.22 (dd, J=10.6, 6.1 Hz, 1H), 4.12 (dd, J=10.5, 7.2 Hz, 1H), 1.58 (s, 3H), 1.39 (s, 3H).

Step 6: [(2R,3S,4R,5R)-5-(4-amino-3-cyano-1H-pyrazolo[3,4-d]pyrimidin-1-yl)-3,4-dihydroxytetrahydrofuran-2-yl]methyl Sulfamate I-13

[(3aR,4R,6R,6aR)-6-(4-Amino-3-cyano-1H-pyrazolo[3,4-d]pyrimidin-1-yl)-2,2-dimethyltetrahydrofuro[3,4-d][1,3]dioxol-4-yl]methyl sulfamate (0.240 g, 0.583 mmol) was dissolved in a mixture of formic acid (6 mL) and water (6 mL) and stirred at rt for 48 h. The reaction mixture was diluted with toluene (100 mL) and concentrated to ¼ volume. Toluene coevaporations were repeated until dry. The resulting white solid was dissolved in acetonitrile and MeOH and adsorbed onto 2.5 g celite. The mixture was purified by C18 chromatography (86 g, 95/5 to 30/70 water/acetonitrile gradient with 10 mM ammonium acetate). Product containing fractions were concentrated under reduced pressure. Water was removed through acetonitrile then toluene azeotrope to afford [(2R,3S,4R,5R)-5-(4-amino-3-cyano-1H-pyrazolo[3,4-d]pyrimidin-1-yl)-3,4-dihydroxytetrahydrofuran-2-yl]methyl sulfamate (90 mg, 42%). LCMS (AA): m/z 372 (M+H); $^1$H NMR (400 MHz, d$_6$-DMSO) δ 8.35 (s, 1H), 7.51 (br s, 2H), 6.22 (d, J=3.6 Hz, 1H), 5.71 (d, J=5.4 Hz, 1H), 5.48 (d, J=5.9 Hz, 1H), 4.52 (dd, J=8.9, 5.0 Hz, 1H), 4.32 (dd, J=9.8, 4.8 Hz, 1H), 4.22 (dd, J=10.4, 3.5 Hz, 1H), 4.19-4.11 (m, 1H), 4.04 (dd, J=10.4, 6.8 Hz, 1H).

Example 12: {(2R,3S,4R,5R)-5-[4-amino-3-(aminomethyl)-1H-pyrazolo[3,4-d]pyrimidin-1-yl]-3,4-dihydroxytetrahydrofuran-2-yl}methyl Sulfamate Compound I-15

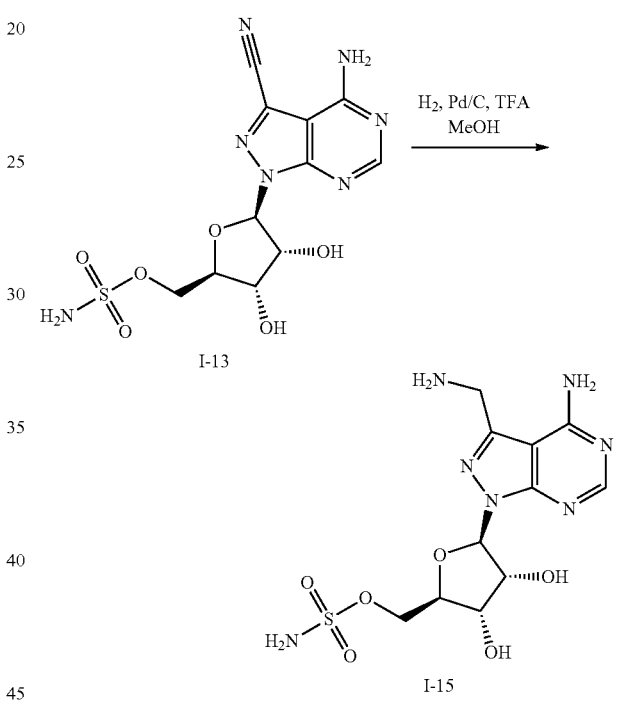

To a degassed solution of [(2R,3S,4R,5R)-5-(4-amino-3-cyano-1H-pyrazolo[3,4-d]pyrimidin-1-yl)-3,4-dihydroxytetrahydrofuran-2-yl]methyl sulfamate (0.070 g, 0.19 mmol, I-13) and TFA (0.07 mL, 0.94 mmol) in MeOH (7.0 mL) under argon was added Pd (10% on carbon, 0.010 g). The reaction flask was evacuated and backfilled with hydrogen from a balloon, and the mixture stirred at rt for 4 h. The reaction mixture was filtered through a MillexGV 0.22 uM syringe frit and concentrated under reduced pressure. The residue was adsorbed onto 1.5 g of celite and purified by C18 chromatography (86 g cartridge, 95/5 to 50/50 water/ACN with 10 mM ammonium acetate) to afford {(2R,3S,4R,5R)-5-[4-amino-3-(aminomethyl)-1H-pyrazolo[3,4-d]pyrimidin-1-yl]-3,4-dihydroxytetrahydrofuran-2-yl}methyl sulfamate (41 mg, 51%). LCMS (AA): m/z 376 (M+H); $^1$H NMR (400 MHz, CD$_3$OD) δ 8.20 (s, 1H), 6.30 (d, J=3.3 Hz, 1H), 4.71 (dd, J=5.0, 3.3 Hz, 1H), 4.64 (t, J=5.1 Hz, 1H), 4.47 (s, 2H), 4.36-4.30 (m, 1H), 4.29-4.22 (m, 2H).

Example 13: [(2R,3S,4R,5R)-5-(4-amino-3-carbamoyl-1H-pyrazolo[3,4-d]pyrimidin-1-yl)-3,4-dihydroxytetrahydrofuran-2-yl]methyl Sulfamate Compound I-16

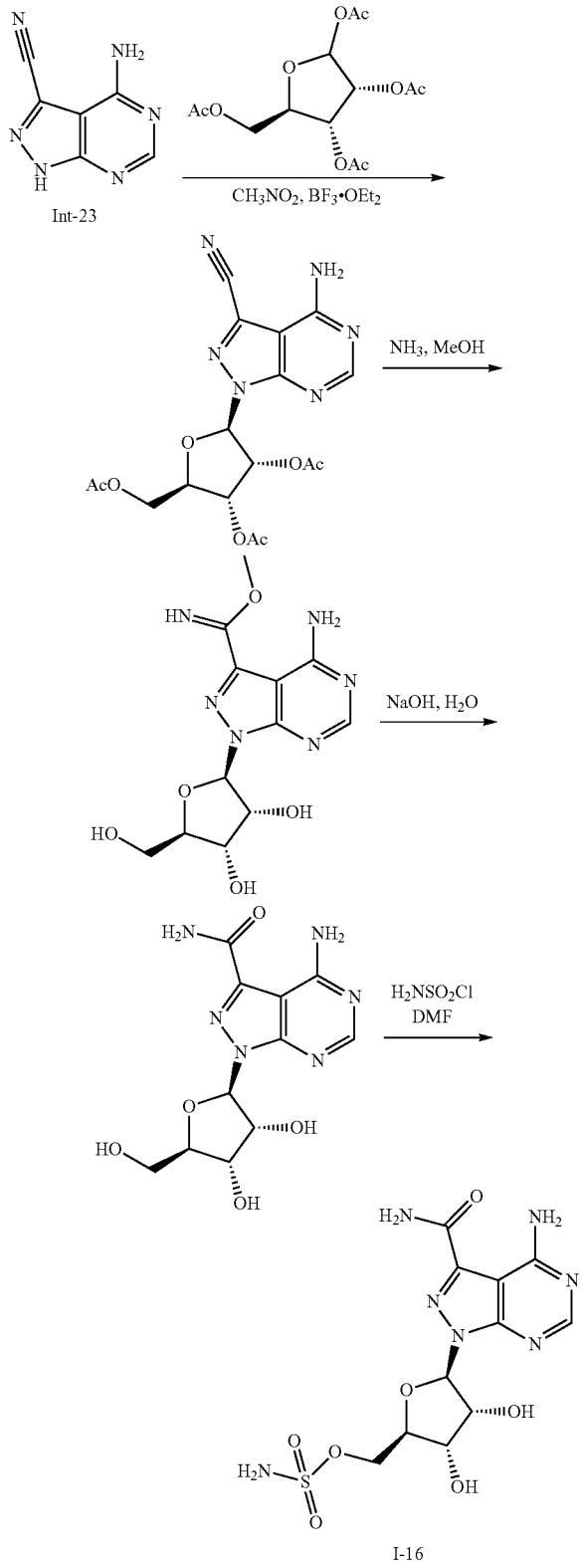

Step 1: (2R,3R,4R,5R)-2-(acetoxymethyl)-5-(4-amino-3-cyano-1H-pyrazolo[3,4-d]pyrimidin-1-yl)tetrahydrofuran-3,4-diyl Diacetate The titled compound was prepared following the procedure described in Example 5 Step 2, substituting Intermediate 23 for Intermediate 14. The crude compound was purified by silica gel chromatography (80/20 hexanes/ethyl acetate to ethyl acetate gradient) to afford the pure product (48%). LCMS (AA): m/z 419 (M+H); $^1$H NMR (400 MHz, CD$_3$OD) δ 8.33 (s, 1H), 6.53 (d, J=3.8 Hz, 1H), 5.95 (dd, J=5.3, 3.9 Hz, 1H), 5.74 (t, J=5.4 Hz, 1H), 4.50-4.40 (m, 2H), 4.19 (td, J=5.1, 1.4 Hz, 1H), 2.13 (s, 3H), 2.08 (s, 3H), 2.07 (s, 3H).

Step 2: methyl 4-amino-1-[(2R,3R,4S,5R)-3,4-dihydroxy-5-(hydroxymethyl) tetrahydrofuran-2-yl]-1H-pyrazolo[3,4-d]pyrimidine-3-carboximidoate The titled compound was prepared following the procedure described in Example 5 Step 3, substituting (2R,3R,4R,5R)-2-(acetoxymethyl)-5-(4-amino-3-cyano-1H-pyrazolo[3,4-d]pyrimidin-1-yl)tetrahydrofuran-3,4-diyl diacetate for Intermediate 15. The crude material was used without further purification. LCMS (AA): m/z 325 (M+H).

Step 3: 4-amino-1-[(2R,3R,4S,5R)-3,4-dihydroxy-5-(hydroxymethyl)tetrahydrofuran-2-yl]-1H-pyrazolo[3,4-d]pyrimidine-3-carboxamide Methyl 4-amino-1-[(2R,3R,4S,5R)-3,4-dihydroxy-5-(hydroxymethyl)tetrahydrofuran-2-yl]-1H-pyrazolo[3,4-d]pyrimidine-3-carboximidoate (1.02 g, 3.14 mmol) was dissolved in water (15 mL). A solution of sodium hydroxide in water (1.00 M, 0.638 mL, 0.638 mmol) was added and the yellow/brown solution was allowed to stir at rt for 36 h. The mixture was concentrated under reduced pressure and then azeotropically dried with acetonitrile. The crude product was used as obtained (0.950 g, 97%). LCMS (AA): m/z 311 (M+H); $^1$H NMR (400 MHz, d$_6$-DMSO) δ 8.19 (s, 1H), 6.11 (d, J=4.8 Hz, 1H), 4.67 (t, J=4.9 Hz, 1H), 4.28 (t, J=4.6 Hz, 1H), 3.91 (dd, J=9.9, 4.6 Hz, 1H), 3.61 (dd, J=11.9, 4.5 Hz, 1H), 3.46 (dd, J=11.9, 5.8 Hz, 1H).

Step 4: [(2R,3S,4R,5R)-5-(4-amino-3-carbamoyl-1H-pyrazolo[3,4-d]pyrimidin-1-yl)-3,4-dihydroxytetrahydrofuran-2-yl]methyl Sulfamate I-16

To a solution of 4-amino-1-[(2R,3R,4S,5R)-3,4-dihydroxy-5-(hydroxymethyl)tetrahydrofuran-2-yl]-1H-pyrazolo[3,4-d]pyrimidine-3-carboxamide (150 mg, 0.49 mmol) in DMF (9.0 mL) cooled in an ice water bath was added chlorosulfonamide (71 mg, 0.61 mmol) and the reaction mixture was stirred at rt for 1 h. Poly(4-vinylpyridine) (1.00 g, 3.17 mmol) and MeOH (1.0 mL) were added to the reaction mixture which was stirred for 10 min, filtered and concentrated to dryness. The residue was dissolved in MeOH and adsorbed onto celite (3 g). The crude material was purified by C18 reverse phase chromatography (86 g cartridge, 95/5 to 20/80 water/acetonitrile w/10 mM ammonium acetate gradient). The resulting product was impure and was repurified by HPLC to give pure [(2R,3S,4R,5R)-5-(4-amino-3-carbamoyl-1H-pyrazolo[3,4-d]pyrimidin-1-yl)-3,4-dihydroxytetrahydrofuran-2-yl]methyl sulfamate (35 mg, 18%). LCMS (AA): m/z 390 (M+H); $^1$H NMR (400 MHz, d$_6$-DMSO) δ 8.84 (d, J=3.5 Hz, 1H), 8.24 (s, 1H), 8.17 (s, 1H), 8.08 (d, J=3.8 Hz, 1H), 8.02 (s, 1H), 6.21 (d, J=3.5

Hz, 1H), 4.56 (dd, J=4.7, 3.7 Hz, 1H), 4.47 (t, J=5.1 Hz, 1H), 4.25 (dd, J=9.7, 2.4 Hz, 1H), 4.12 (s, 2H).

Example 14: {(2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl Sulfamate Compound I-27

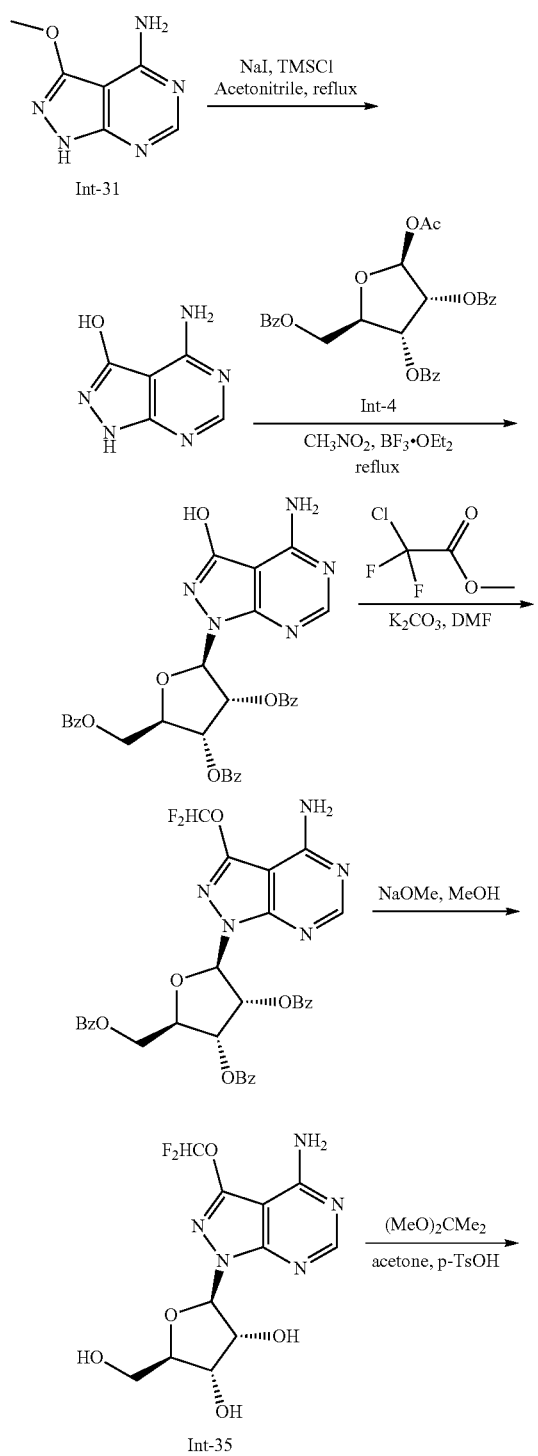

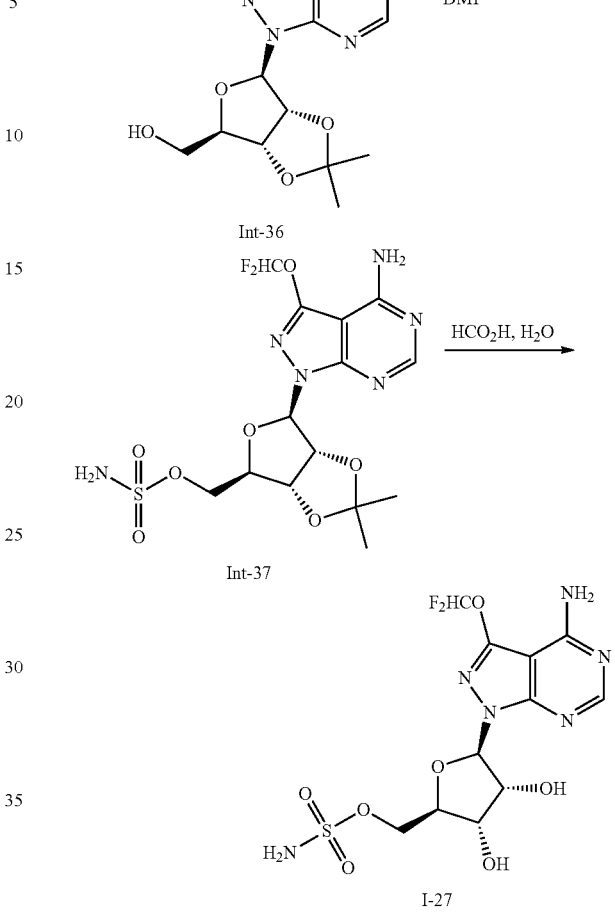

Step 1: 4-amino-1H-pyrazolo[3,4-d]pyrimidin-3-ol

To a mixture of Intermediate 31 (prepared following procedures detailed in Example 1, Steps 1-3, using MeOH in place of ethanol in step 1. LCMS (AA): m/z 166 (M+H); $^1$H NMR (400 MHz, d$_6$-DMSO) δ 12.33 (s, 1H), 8.07 (s, 1H), 3.95 (s, 3H), 1.00 g, 6.05 mmol) in acetonitrile (170 mL), was added chlorotrimethylsilane (1.15 mL, 9.08 mmol) and sodium iodide (1.36 g, 9.08 mmol). The reaction mixture was heated at 90° C. for 18 h. Additional portions of chlorotrimethylsilane (1.57 mL, 9.08 mmol) and sodium iodide (1.36 g, 9.08 mmol) were added and heating was continued for 3 days. Approximately 75 mL acetonitrile was added to the cooled reaction mixture and the solids were isolated by filtration, washed with water and hexane, coevaporated with toluene and dried under vacuum to provide 4-amino-1H-pyrazolo[3,4-d]pyrimidin-3-ol as a beige solid (430 mg, 47%) LCMS (AA): m/z 152 (M+H); $^1$H NMR (400 MHz, d$_6$-DMSO) δ 11.38 (s, 1H), 8.01 (s, 1H), 7.62 (s, 1H), 6.82 (s, 1H).

Step 2: (2R,3R,4R,5R)-2-(4-amino-3-hydroxy-1H-pyrazolo[3,4-d]pyrimidin-1-yl)-5-[(benzoyloxy)methyl]tetrahydrofuran-3,4-diyl Dibenzoate The titled compound was prepared from 4-amino-1H-pyrazolo[3,4-d]pyrimidin-3-ol following the procedure detailed in Example 5 Step 2 (23%) LCMS (AA): m/z 596 (M+H); $^1$H NMR (400 MHz, d$_6$-DMSO) δ 11.77 (s, 1H), 8.13 (s, 1H), 8.00-7.91 (m, 4H), 7.90-7.86 (m, 2H), 7.70-7.60 (m, 3H), 7.55-7.39 (m, 6H), 6.54 (d, J=2.3 Hz, 1H), 6.20-6.14 (m, 1H), 6.14-6.08 (m, 1H), 4.83-4.77 (m, 1H), 4.56 (ddd, J=16.9, 12.0, 4.5 Hz, 2H).

Step 3: (2R,3R,4R,5R)-2-[4-amino-3-(difluoromethoxy)-1H-pyrazolo[3,4-d]pyrimidin-1-yl]-5-[(benzoyloxy)methyl]tetrahydrofuran-3,4-diyl Dibenzoate To a solution of (2R,3R,4R,5R)-2-(4-amino-3-hydroxy-1H-pyrazolo[3,4-d]pyrimidin-1-yl)-5-[(benzoyloxy)methyl] tetrahydrofuran-3,4-diyl dibenzoate (100 mg, 0.17 mmol) in DMF (2.0 mL), was added potassium carbonate (70 mg, 0.50 mmol) and methyl chlorodifluoroacetate (53 uL, 0.50 mmol). The reaction mixture was stirred at rt for 90 min and then heated at 80° C. for 30 min. The reaction mixture was cooled to rt, diluted with EtOAc and neutralized by the addition of 1N HCl. The mixture was extracted with EtOAc (3×), and the combined organic phases were washed with water (3×) then brine, dried (Na$_2$SO$_4$), filtered and evaporated. The residue was purified by silica gel chromatography (0% to 5% MeOH/DCM) to provide (2R,3R,4R,5R)-2-[4-amino-3-(difluoromethoxy)-1H-pyrazolo[3,4-d]pyrimidin-1-yl]-5-[(benzoyloxy)methyl]tetrahydrofuran-3,4-diyl dibenzoate as a yellow solid (87 mg, 80%). LCMS (AA): m/z 646 (M+H); $^1$H NMR (400 MHz, CDCl$_3$) δ 8.36 (s, 1H), 8.12-8.07 (m, 2H), 8.02 (s, 1H), 7.99-7.94 (m, 4H), 7.62-7.51 (m, 3H), 7.48-7.34 (m, 5H), 6.96 (t, J=71.6 Hz, 1H), 6.77 (d, J=4.4 Hz, 1H), 6.39-6.35 (m, 1H), 6.16 (t, J=5.2 Hz, 1H), 4.84-4.72 (m, 2H), 4.65-4.53 (m, 1H).

Step 4: (2R,3R,4S,5R)-2-[4-amino-3-(difluoromethoxy)-1H-pyrazolo[3,4-d]pyrimidin-1-yl]-5-(hydroxymethyl)tetrahydrofuran-3,4-diol Intermediate 35

The titled compound was prepared from (2R,3R,4R,5R)-2-[4-amino-3-(difluoromethoxy)-1H-pyrazolo[3,4-d]pyrimidin-1-yl]-5-[(benzoyloxy)methyl]tetrahydrofuran-3,4-diyl dibenzoate following the procedure outlined in Example 1 Step 5 (49%). LCMS (AA): m/z 334 (M+H); $^1$H NMR (400 MHz, CD$_3$OD) δ 8.19 (s, 1H), 7.36 (t, J=71.8 Hz, 1H), 6.19 (d, J=4.2 Hz, 1H), 4.68-4.65 (m, 1H), 4.42 (t, J=5.0 Hz, 1H), 4.09-4.04 (m, 1H), 3.78 (dd, J=12.2, 3.5 Hz, 1H), 3.66 (dd, J=12.2, 5.1 Hz, 1H).

Step 5: {(3aR,4R,6R,6aR)-6-[4-amino-3-(difluoromethoxy)-1H-pyrazolo[3,4-d]pyrimidin-1-yl]-2,2-dimethyltetrahydrofuro[3,4-d][1,3]dioxol-4-yl}methanol Intermediate 36

The titled compound was prepared from (2R,3R,4S,5R)-2-[4-amino-3-(difluoromethoxy)-1H-pyrazolo[3,4-d]pyrimidin-1-yl]-5-(hydroxymethyl)tetrahydrofuran-3,4-diol following the procedure detailed in Example 1 Step 6 (51%). LCMS (AA): m/z 374 (M+H); $^1$H NMR (400 MHz, CDCl$_3$) δ 8.27 (s, 1H), 7.15 (t, J=71.6 Hz, 1H), 6.32 (d, J=3.5 Hz, 1H), 5.21 (dd, J=5.9, 3.5 Hz, 1H), 5.01 (dd, J=6.0, 1.4 Hz, 1H), 4.81 (s, 1H), 4.51-4.46 (m, 1H), 3.88 (dd, J=12.6, 2.2 Hz, 1H), 3.81-3.73 (m, 1H), 1.63 (s, 3H), 1.38 (s, 3H).

Steps 6 and 7: {(2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl Sulfamate Compound I-27

The titled compound was prepared from Intermediate 36 following the procedures outlined in Example 1 Steps 7 and 8 (44% over 2 steps). LCMS (AA): m/z 413 (M+H); $^1$H NMR (400 MHz, CD$_3$OD) δ 9.77 (s, 1H), 8.98 (dd, J=73.1, 70.4 Hz, 1H), 7.82 (d, J=2.6 Hz, 1H), 6.16 (p, J=5.0 Hz, 2H), 5.88 (dd, J=12.7, 5.5 Hz, 1H), 5.82-5.75 (m, 2H).

Example 15: Alternate Synthesis of {(2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl Sulfamate Compound I-27

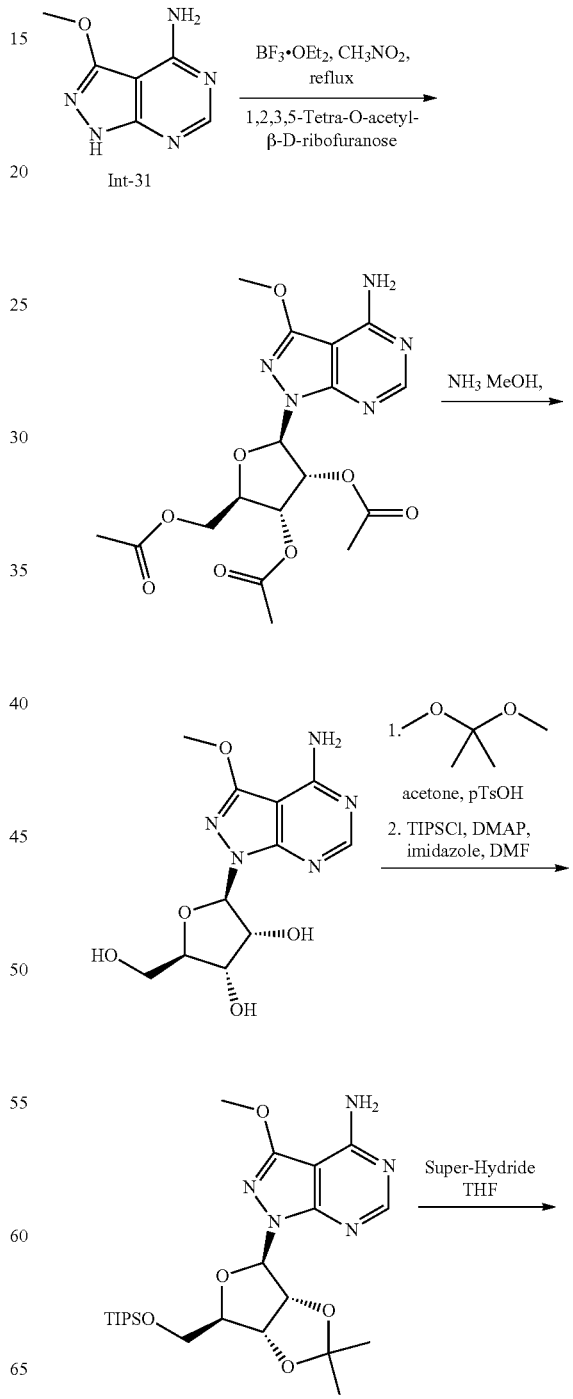

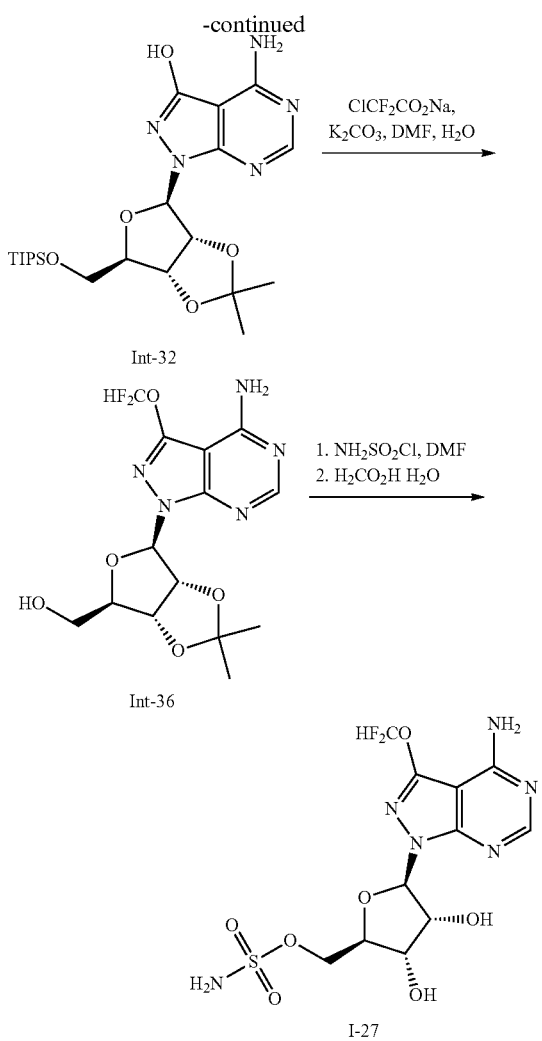

Step 1: (2R,3R,4R,5R)-2-(Acetoxymethyl)-5-(4-amino-3-methoxy-1H-pyrazolo[3,4-d]pyrimidin-1-yl)tetrahydrofuran-3,4-diyl Diacetate The title compound was prepared following the procedure described in Example 5 Step 2, substituting Intermediate 31 for Intermediate 14 LCMS (FA): m/z=424 (M+H); $^1$H NMR (400 MHz, CDCl$_3$) δ 8.32 (s, 1H), 6.48 (d, J=3.5 Hz, 1H), 5.86-5.98 (m, 1H), 5.77 (br t, J=5.2 Hz, 2H), 5.35-5.99 (m, 1H), 4.35-4.50 (m, 2H), 4.21-4.30 (m, 1H), 4.10 (s, 3H), 2.08-2.18 (m, 9H).

Step 2: (2R,3R,4S,5R)-2-(4-amino-3-methoxy-1H-pyrazolo[3,4-d]pyrimidin-1-yl)-5-(hydroxymethyl)tetrahydrofuran-3,4-diol The title compound was prepared following the procedure described in Example 5 Step 3, substituting (2R,3R,4R,5R)-2-(acetoxymethyl)-5-(4-amino-3-methoxy-1H-pyrazolo[3,4-d]pyrimidin-1-yl)tetrahydrofuran-3,4-diyl diacetate for Intermediate 15. LCMS (FA): m/z=298 (M+H); $^1$H NMR (400 MHz, d$_6$-DMSO) δ 8.14 (s, 1H), 5.99 (d, J=4.3 Hz, 1H), 4.93-5.39 (m, 2H), 4.74 (br s, 1H), 4.52 (t, J=4.5 Hz, 1H), 4.19 (t, J=4.6 Hz, 1H), 3.97 (s, 3H), 3.80-3.91 (m, 1H), 3.58 (br d, J=11.7 Hz, 1H), 3.41-3.52 (m, 1H).

Step 3: [(3aR,4R,6R,6aR)-6-(4-amino-3-methoxy-1H-pyrazolo[3,4-d]pyrimidin-1-yl)-2,2-dimethyltetrahydrofuro[3,4-d][1,3]dioxol-4-yl]methanol The title compound was prepared following the procedure described in Example 1 Step 6, substituting (2R,3R,4S,5R)-2-(4-amino-3-methoxy-1H-pyrazolo[3,4-d]pyrimidin-1-yl)-5-(hydroxymethyl)tetrahydrofuran-3,4-diol for Intermediate 16. LCMS (FA): m/z=338 (M+H); $^1$H NMR (400 MHz, d$_6$-DMSO) δ 8.16 (s, 1H), 7.80 (br s, 1H), 6.86 (br s, 1H), 6.20 (d, J=2.0 Hz, 1H), 5.22 (dd, J=6.0, 2.3 Hz, 1H), 4.84-5.00 (m, 2H), 4.04-4.19 (m, 1H), 3.98 (s, 3H), 3.59 (dt, J=11.2, 6.6 Hz, 1H), 3.44 (dt, J=11.3, 5.9 Hz, 1H), 1.51 (s, 3H), 1.33 (s, 3H).

Step 4: 1-[(3aR,4R,6R,6aR)-2,2-dimethyl-6-{[(triisopropylsilyl)oxy]methyl)}tetrahydrofuro[3,4-d][1,3]dioxol-4-yl]-3-methoxy-1H-pyrazolo[3,4-d]pyrimidin-4-amine To a stirred solution of [(3aR,4R,6R,6aR)-6-(4-amino-3-methoxy-1H-pyrazolo[3,4-d]pyrimidin-1-yl)-2,2-dimethyltetrahydrofuro[3,4-d][1,3]dioxol-4-yl]methanol (3.31 g, 9.81 mmol) in DMF (43 mL) was added 1H-imidazole (2.20 g, 32.4 mmol), DMAP (240 mg, 2.0 mmol) and triisopropylsilyl chloride (6.24 mL, 29.4 mmol) at rt under an atmosphere of dry nitrogen. The reaction mixture was allowed to stir at rt for 3 h, until complete. The reaction mixture was allowed to cool in an ice-water bath and saturated ammonium chloride solution was introduced. After stirring several minutes, the mixture was extracted twice with EtOAc. The combined extracts were washed with water and brine, dried over sodium sulfate, filtered and concentrated under reduced pressure. The crude product was purified by silica gel chromatography to afford 1-[(3aR,4R,6R,6aR)-2,2-dimethyl-6-{[(triisopropylsilyl)oxy]methyl}tetrahydrofuro[3,4-d][1,3]dioxol-4-yl]-3-methoxy-1H-pyrazolo[3,4-d]pyrimidin-4-amine as a white solid (4.30 g, 89%). LCMS (FA): m/z=494; $^1$H NMR (400 MHz, CDCl$_3$) δ 8.33 (s, 1H), 6.47 (d, J=2.0 Hz, 1H), 5.66 (br s, 2H), 5.43 (dd, J=6.1, 1.9 Hz, 1H), 5.03 (dd, J=6.2, 1.9 Hz, 1H), 4.32 (ddd, J=8.0, 5.7, 2.0 Hz, 1H), 4.06 (s, 3H), 3.87 (dd, J=10.0, 8.3 Hz, 1H), 3.74 (dd, J=10.1, 5.5 Hz, 1H), 1.63 (s, 3H), 1.43 (s, 3H), 1.05 (br d, J=1.5 Hz, 21H).

Step 5: 4-Amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-ol Intermediate 32

To a solution of 1-[(3aR,4R,6R,6aR)-2,2-dimethyl-6-{[(triisopropylsilyl)oxy]methyl}tetrahydrofuro[3,4-d][1,3]dioxol-4-yl]-3-methoxy-1H-pyrazolo[3,4-d]pyrimidin-4-amine (1.50 g, 3.04 mmol) in THF (45 mL) at rt was added a solution of lithium triethylborohydride in THF (1.0 M, 45 mL, 45 mmol) dropwise. Upon completion of addition, the reaction mixture was allowed to stir at 80° C. for 2 h in a heated oil bath. Upon completion of reaction, the flask was allowed to cool in an ice-water bath. Excess hydride reagent was carefully quenched by the slow addition of water (23 mL) over the period of 1 h. The reaction mixture was made neutral by the addition of a saturated aqueous ammonium chloride solution (250 mL). The mixture was transferred to a separatory funnel and twice extracted with EtOAc. The combined extracts were washed with saturated sodium bicarbonate solution and brine, dried over sodium sulfate, filtered and concentrated under reduced pressure. The crude product was purified by silica gel chromatography to afford 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-ol as a white solid (Intermediate 32, 1.13 g, 78%). LCMS (FA): m/z 480. $^1$H NMR (400 MHz, CDCl$_3$) δ 8.27 (s, 1H), 6.11-6.15 (m, 1H), 6.06 (br s, 2H), 4.93-4.98 (m, 1H), 4.85-4.92 (m, 1H), 4.19-4.30 (m, 1H), 3.86-3.96 (m, 1H), 3.75-3.84 (m, 1H), 1.51 (s, 3H), 1.30 (s, 3H), 1.10-1.23 (m, 3H), 1.02 (dd, J=7.2, 5.5 Hz, 18H).

Step 6: {(3aR,4R,6R,6aR)-6-[4-amino-3-(difluoromethoxy)-1H-pyrazolo[3,4-d]pyrimidin-1-yl]-2,2-dimethyltetrahydrofuro[3,4-d][1,3]dioxol-4-yl}methanol Intermediate 36

To round-bottom flask was added 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-ol (Intermediate 32, 3.29 g, 6.86 mmol), potassium carbonate (3.13 g, 22.6 mmol), and sodium chlorodifluoroacetate (3.45 g, 22.6 mmol). The flask was evacuated and backfilled with argon. DMF (60 mL) was introduced, followed by water (5.9 mL). The resulting mixture was degassed by active argon bubbling through the stirred reaction mixture. The degassed reaction mixture was stirred vigorously and placed in a pre-heated (80° C.) oil bath and stirred overnight. Upon completion, the reaction mixture was allowed to cool to rt. The heterogeneous mixture was partitioned between EtOAc (150 mL) and water (100 mL) to which was added 60 mL saturated aqueous ammonium chloride solution. The phases were separated and the washings were extracted with additional EtOAc (50 mL). The extracts were combined, washed with water and brine, then dried over sodium sulfate, filtered and concentrated under reduced pressure. The crude product was purified by silica gel chromatography to afford {(3aR,4R,6R,6aR)-6-[4-amino-3-(difluoromethoxy)-1H-pyrazolo[3,4-d]pyrimidin-1-yl]-2,2-dimethyltetrahydrofuro[3,4-d][1,3]dioxol-4-yl}methanol (1.79 g, 70%) identical in all respects to that produced in Example 8 Step 5.

Steps 7 and 8: 2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl Sulfamate Compound I-27

The titled compound was prepared from Intermediate 36 as described in Example 1 Steps 7 and 8.

Example 16: {(2R,3S,4R,5R)-5-[4-amino-3-(2-chloroethoxy)-1H-pyrazolo[3,4-d]pyrimidin-1-yl]-3,4-dihydroxytetrahydrofuran-2-yl}methyl Sulfamate Compound I-75

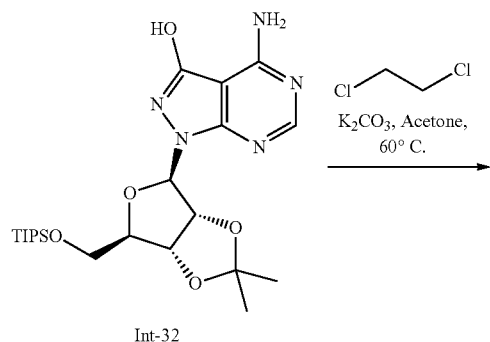

-continued

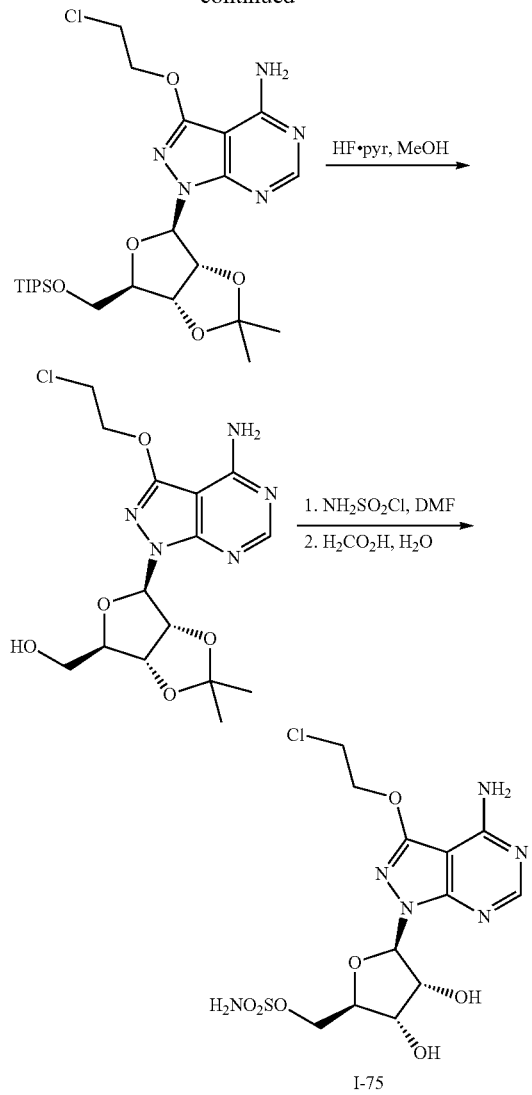

Step 1: 3-(2-chloroethoxy)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine Into a suspension of Intermediate 32 (0.150 g, 0.313 mmol) in acetone (8.99 mL) was added potassium carbonate (142.5 mg, 1.03 mmol) and 1,2-dichloroethane (0.246 mL). The reaction mixture was allowed to heat at 60° C. overnight. After completion of the reaction, acetone was removed under reduced pressure and the residue was extracted into ethyl acetate (2×50 mL). The extracts were combined, washed with brine then dried over sodium sulfate, filtered and concentrated under reduced pressure. The crude product was purified by silica gel chromatography (gradient of 0-30% EtOAc in hexanes) to afford the product as a white solid (154 mg, 91%). LCMS (FA): m/z=542 (M+H); $^1$H NMR (400 MHz, CDCl$_3$) δ 8.33 (s, 1H), 6.44 (d, J=2.3 Hz, 1H), 5.58 (s, 2H), 5.39 (dd, J=6.3, 2.3 Hz, 1H), 5.00 (dd, J=6.3, 2.0 Hz, 1H), 4.53-4.70 (m, 2H), 4.28-4.34 (m, 1H), 3.89 (t, J=5.5 Hz, 2H), 3.78-3.85 (m, 1H), 3.69-3.75 (m, 1H), 1.61 (s, 3H), 1.41 (s, 3H), 0.98-1.09 (m, 21H).

Step 2: {(3aR,4R,6R,6aR)-6-[4-amino-3-(2-chloro-ethoxy)-1H-pyrazolo[3,4-d]pyrimidin-1-yl]-2,2-dimethyltetrahydrofuro[3,4-d][1,3]dioxol-4-yl}methanol The titled compound was prepared as described in Example 5 Step 7 substituting 3-(2-chloroethoxy)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine for methyl 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carboxylate (93%). LCMS (FA): m/z=386 (M+H).

Step 3: {(3aR,4R,6R,6aR)-6-[4-amino-3-(2-chloro-ethoxy)-1H-pyrazolo[3,4-d]pyrimidin-1-yl]-2,2-dimethyltetrahydrofuro[3,4-d][1,3]dioxol-4-yl}methyl Sulfamate The title compound was prepared as described in Example 1 Step 7 substituting {(3aR,4R,6R,6aR)-6-[4-amino-3-(2-chloroethoxy)-1H-pyrazolo[3,4-d]pyrimidin-1-yl]-2,2-dimethyltetrahydrofuro[3,4-d][1,3]dioxol-4-yl}methanol for Intermediate 7 (90%). LCMS (FA): m/z=465 (M+H).

Step 4: {(2R,3S,4R,5R)-5-[4-amino-3-(2-chloroethoxy)-1H-pyrazolo[3,4-d]pyrimidin-1-yl]-3,4-dihydroxytetrahydrofuran-2-yl}methyl Sulfamate The title compound was prepared as described in Example 1 Step 8 substituting {(3aR,4R,6R,6aR)-6-[4-amino-3-(2-chloroethoxy)-1H-pyrazolo[3,4-d]pyrimidin-1-yl]-2,2-dimethyltetrahydrofuro[3,4-d][1,3]dioxol-4-yl}methyl sulfamate for {(2R,3S,4R,5R)-5-[4-amino-3-(2-chloroethoxy)-1H-pyrazolo[3,4-d]pyrimidin-1-yl]-3,4-dihydroxytetrahydrofuran-2-yl}methyl sulfamate (94%). LCMS (FA): m/z 425 (M+H); $^1$H NMR (400 MHz, $d_6$-DMSO) δ 8.18 (s, 1H), 7.72-7.96 (m, 1H), 7.49 (br s, 2H), 6.63 (br s, 1H), 6.06 (d, J=3.1 Hz, 1H), 5.55 (br s, 1H), 5.31 (br s, 1H), 4.56 (t, J=5.2 Hz, 2H), 4.39-4.47 (m, 1H), 4.31 (br t, J=4.9 Hz, 1H), 4.17-4.25 (m, 1H), 3.99-4.09 (m, 4H).

Example 16a: {(2R,3S,4R,5R)-5-[3-(allyloxy)-4-amino-1H-pyrazolo[3,4-d]pyrimidin-1-yl]-3,4-dihydroxytetrahydrofuran-2-yl}methyl Sulfamate Compound I-71

The title compound was prepared as described in Example 16 utilizing 3-bromoprop-1-ene instead of 1,2-dichloroethane in Step 1. LCMS (FA): m/z 403 (M+H); $^1$H NMR (400 MHz, CD$_3$OD) δ 8.15 (s, 1H), 6.10-6.27 (m, 2H), 5.47 (br d, J=15.9 Hz, 1H), 5.33 (br d, J=11.0 Hz, 1H), 4.93 (br d, J=5.8 Hz, 2H), 4.58 (br s, 2H), 4.34 (br d, J=7.0 Hz, 1H), 4.17-4.27 (m, 2H).

Example 17: [(2R,3S,4R,5R)-5-(4-amino-3-isopropyl-1H-pyrazolo[3,4-d]pyrimidin-1-yl)-3,4-dihydroxytetrahydrofuran-2-yl]methyl Sulfamate Compound I-3

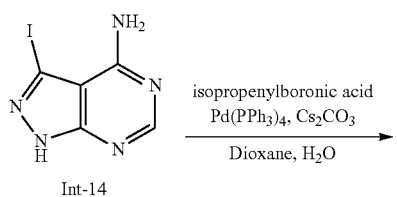

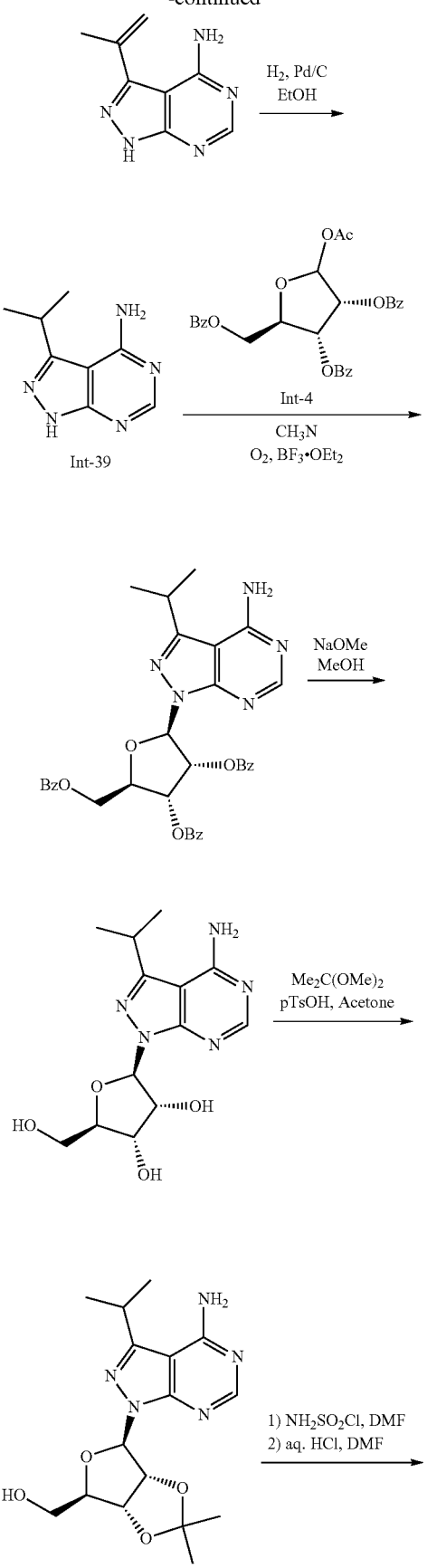

151

-continued

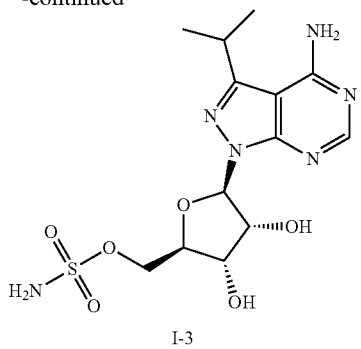

I-3

Step 1: 3-isopropenyl-1H-pyrazolo[3,4-d]pyrimidin-4-amine

To a solution of Intermediate 14 (0.600 g, 2.30 mmol) in 1,4-dioxane (8.0 mL) and water (2.8 mL) was added isopropenylboronic acid (0.274 g, 3.20 mmol), cesium carbonate (2.25 g, 6.90 mmol) and tetrakis(triphenylphosphine)palladium(0) (0.133 g, 0.115 mmol). The reaction mixture was subjected to microwave irradiation at 170° C. for 2 h. The mixture was then allowed to cool to rt and precipitated solids were removed by filtration. The filtrate was diluted with water and extracted twice with ethyl acetate. The extracts were combined, washed with brine, dried over sodium sulfate, filtered and concentrated under reduced pressure. DCM was added and the resulting precipitate was collected by suction filtration, and then dried in vacuo at 40° C. to afford 3-isopropenyl-1H-pyrazolo[3,4-d]pyrimidin-4-amine (0.27 g, 67%). LCMS (FA): m/z 176 (M+H); $^1$H NMR (300 MHz, $d_6$-DMSO) δ 8.16 (s, 1H), 5.48-5.44 (m, 1H), 5.29 (s, 1H), 2.18 (s, 3H).

Step 2: 3-isopropyl-1H-pyrazolo[3,4-d]pyrimidin-4-amine Intermediate 39

To a solution of 3-isopropenyl-1H-pyrazolo[3,4-d]pyrimidin-4-amine (0.245 g, 1.40 mmol) in ethanol (20 mL) was added Pd/C (0.025 g, 10 wt. %). The mixture was allowed to stir under an atmosphere of hydrogen for 3 days. The mixture was diluted with ethanol and filtered through Celite. The filtrate was concentrated under reduced pressure and then dried in vacuo at 40° C. to afford 3-isopropyl-1H-pyrazolo[3,4-d]pyrimidin-4-amine (Intermediate 39, 0.24 g, 95%). LCMS (FA): m/z 178 (M+H); $^1$H NMR (400 MHz, $d_6$-DMSO) δ 8.08 (s, 1H), 7.10 (br s, 2H), 3.52-3.44 (m, 1H), 1.25 (d, 6H).

Step 3: (2R,3R,4R,5R)-2-(4-amino-3-isopropyl-1H-pyrazolo[3,4-d]pyrimidin-1-yl)-5-[(benzoyloxy)methyl]tetrahydrofuran-3,4-diyl Dibenzoate The titled compound was prepared following the procedure detailed in Example 1 Step 4, substituting Intermediate 39 for Intermediate 3 (62%). LCMS (FA): m/z 622 (M+H); $^1$H NMR (300 MHz, $d_6$-DMSO) δ 8.17 (s, 1H), 7.98-7.88 (m, 6H), 7.68-7.61 (m, 3H), 7.51-7.42 (m, 6H), 6.64 (d, J=3.3 Hz, 1H), 6.32-6.26 (m, 1H), 6.25-6.19 (m, 1H), 4.84 (dd, J=9.6, 4.7 Hz, 1H), 4.69-4.51 (m, 2H), 3.58-3.45 (m, 1H), 1.26-1.15 (m, 6H).

Step 4: (2R,3R,4S,5R)-2-(4-amino-3-isopropyl-1H-pyrazolo[3,4-d]pyrimidin-1-yl)-5-(hydroxymethyl)tetrahydrofuran-3,4-diol The titled compound was prepared following the procedure detailed in Example 1 Step 5, substituting (2R,3R,4R,5R)-2-(4-amino-3-isopropyl-1H-pyrazolo[3,4-d]pyrimidin-1-yl)-5-[(benzoyloxy)methyl]tetrahydrofuran-3,4-diyl dibenzoate for Intermediate 5 (72%). LCMS (FA): m/z 310 (M+H); $^1$H NMR (400 MHz, $d_6$-DMSO) δ 8.15 (s, 1H), 6.05 (d, J=4.3 Hz, 1H), 5.35 (d, J=4.9 Hz, 1H), 5.10 (d, J=5.2 Hz, 1H), 4.85 (dd, J=6.7, 5.1 Hz, 1H), 4.55 (dd, J=4.4, 4.0 Hz, 1H), 4.24 (dd, J=9.1, 4.4 Hz, 1H), 3.89 (dd, J=9.8, 4.6 Hz, 1H), 3.59 (dt, J=11.7, 4.6 Hz, 1H), 3.52 (dt, J=13.5, 6.8 Hz, 1H), 3.47-3.40 (m, 1H), 1.27-1.2 (m, 6H).

Step 5: [(3aR,4R,6R,6aR)-6-(4-amino-3-isopropyl-1H-pyrazolo[3,4-d]pyrimidin-1-yl)-2,2-dimethyltetrahydrofuro[3,4-d][1,3]dioxol-4-yl]methanol The titled compound was prepared following the procedure detailed in Example 1, step 6, substituting (2R,3R,4S,5R)-2-(4-amino-3-isopropyl-1H-pyrazolo[3,4-d]pyrimidin-1-yl)-5-(hydroxymethyl)tetrahydrofuran-3,4-diol for Intermediate 6 (65%). LCMS (FA): m/z 350 (M+H); $^1$H NMR (300 MHz, $d_6$-DMSO) δ 8.16 (s, 1H), 6.26 (d, J=1.8 Hz, 1H), 5.23 (dd, J=6.0, 1.7 Hz, 1H), 4.94 (d, J=6.0 Hz, 1H), 4.13 (t, J=6.2 Hz, 1H), 3.62-3.47 (m, 2H), 3.43-3.36 (m, 1H), 1.51 (s, 3H), 1.32 (s, 3H), 1.26 (d, J=6.7 Hz, 6H).

Steps 6 and 7: [(2R,3S,4R,5R)-5-(4-amino-3-isopropyl-1H-pyrazolo[3,4-d]pyrimidin-1-yl)-3,4-dihydroxytetrahydrofuran-2-yl]methyl Sulfamate Compound I-3

The titled compound was prepared following the procedure detailed in Example 1 Step 7 and Example 3 Step 7, substituting [(3aR,4R,6R,6aR)-6-(4-amino-3-isopropyl-1H-pyrazolo[3,4-d]pyrimidin-1-yl)-2,2-dimethyltetrahydrofuro[3,4-d][1,3]dioxol-4-yl]methanol for Intermediate 7 (75%). LCMS (FA): m/z 389 (M+H); $^1$H NMR (300 MHz, $d_6$-DMSO) δ 8.16 (s, 1H), 6.12 (d, J=2.3 Hz, 1H), 4.44-4.39 (m, 2H), 4.26-4.21 (m, 1H), 4.11-4.02 (m, 2H), 3.56-3.47 (m, 1H), 1.26 (d, J=6.7 Hz, 6H).

Example 18: [(2R,3S,4R,5R)-5-(4-amino-3-ethyl-1H-pyrazolo[3,4-d]pyrimidin-1-yl)-3,4-dihydroxytetrahydrofuran-2-yl]methyl Sulfamate Compound I-6

The titled compound was prepared following the procedures detailed in Example 17, substituting vinylboronic acid dibutyl ester for isopropenylboronic acid in Step 1. LCMS (FA): m/z 375 (M+H); $^1$H NMR (400 MHz, $d_6$-DMSO) δ 8.16 (s, 1H), 6.10 (d, J=3.3 Hz, 1H), 5.53 (d, J=5.3 Hz, 1H), 5.34 (d, J=5.7 Hz, 1H), 4.46 (dd, J=8.4, 5.0 Hz, 1H), 4.35 (dd, J=10.3, 5.2 Hz, 1H), 4.22 (dd, J=9.9, 2.9 Hz, 1H), 4.10-3.99 (m, 2H), 2.99-2.91 (m, 2H), 1.22 (t, J=7.5 Hz, 3H).

Example 19: [(2R,3S,4R,5R)-5-{4-amino-3-[(benzyloxy)methyl]-1H-pyrazolo[3,4-d]pyrimidin-1-yl}-3,4-dihydroxytetrahydrofuran-2-yl]methyl Sulfamate Compound I-4

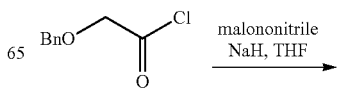

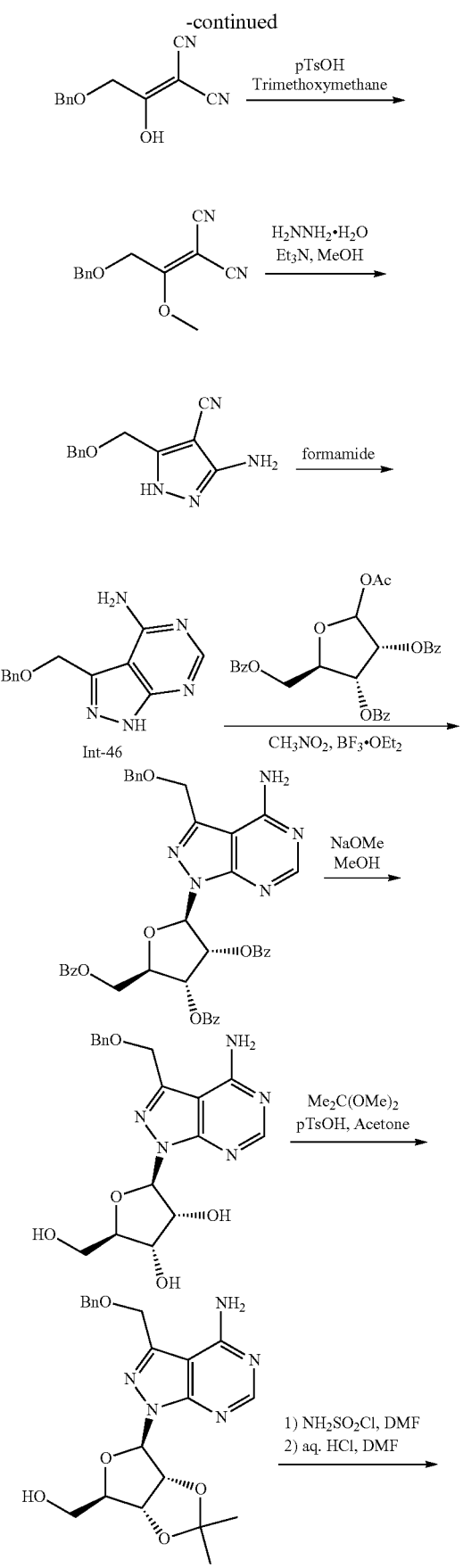

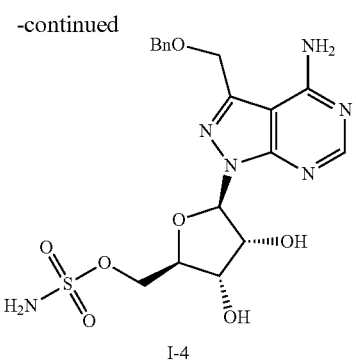

I-4

Step 1: [2-(benzyloxy)-1-hydroxyethylidene]malononitrile

To a solution of malononitrile (0.539 g, 8.16 mmol) in THF (15 mL) at 0° C. was added 60% NaH (0.674 g, 16.8 mmol) and the resulting mixture was stirred for 10 min. Benzyloxyacetyl chloride (1.28 mL, 8.11 mmol) was subsequently added dropwise to the cooled reaction mixture. Upon completion of addition, the mixture was warmed to rt and stirred for 3 hours. The reaction mixture was quenched with 1N HCl solution and then diluted with ethyl acetate. The mixture was twice extracted into ethyl acetate. The extracts were combined, washed with water and brine, then dried over sodium sulfate, filtered and concentrated under reduced pressure. The crude product was purified by silica gel chromatography (40 g silica, DCM to 85/15 DCM/MeOH gradient) to afford pure [2-(benzyloxy)-1-hydroxyethylidene]malononitrile (1.30 g, 75%). LCMS (FA): m/z 213 (M–H); $^1$H NMR (400 MHz, CD$_3$OD) δ 7.40-7.26 (m, 5H), 4.59 (s, 2H), 4.36 (s, 2H).

Step 2: [2-(benzyloxy)-1-methoxyethylidene]malononitrile

To a solution of [2-(benzyloxy)-1-hydroxyethylidene]malononitrile (1.47 g, 6.86 mmol) in trimethoxymethane (12 mL) was added p-toluenesulfonic acid monohydrate (0.65 g, 3.43 mmol). The resulting mixture was heated overnight at reflux. The reaction mixture was concentrated under reduced pressure and the crude residue was purified by silica gel chromatography (80 g silica, hexanes to 60/40 hexanes/ethyl acetate gradient) to afford pure [2-(benzyloxy)-1-methoxyethylidene]malononitrile (0.88 g, 56%). LCMS (FA): m/z 227 (M–H); $^1$H NMR (400 MHz, CDCl$_3$) δ 7.43-7.33 (m, 5H), 4.62 (s, 2H), 4.44 (s, 2H), 4.20 (s, 3H).

Step 3: 5-amino-3-[(benzyloxy)methyl]-1H-pyrazole-4-carbonitrile

To a solution of [2-(benzyloxy)-1-methoxyethylidene]malononitrile (0.745 g, 3.26 mmol) in MeOH (11 mL) was added hydrazine monohydrate (0.38 mL, 7.52 mmol) and triethylamine (0.90 mL, 6.44 mmol). The reaction mixture was stirred at rt for 2 hours. The solution was concentrated to dryness, water was added and the mixture was extracted twice with ethyl acetate. The extracts were combined, washed with brine, dried over sodium sulfate, filtered and concentrated to afford 5-amino-3-[(benzyloxy)methyl]-1H-pyrazole-4-carbonitrile which was used as obtained (0.64 g, 85%). LCMS (FA): m/z 229 (M+H); $^1$H NMR (300 MHz, d$_6$-DMSO) δ 7.36-7.27 (m, 5H), 4.48 (s, 2H), 4.35 (s, 2H).

Step 4: 3-[(benzyloxy)methyl]-1H-pyrazolo[3,4-d]pyrimidin-4-amine Intermediate-46

The titled compound was prepared following the procedure detailed in Example 1 Step 3, substituting 5-amino-3-[(benzyloxy)methyl]-1H-pyrazole-4-carbonitrile for 5-amino-3-ethoxy-1H-pyrazole-4-carbonitrile (89%). LCMS (FA): m/z 256 (M+H); $^1$H NMR (400 MHz, $d_6$-DMSO) δ 13.29 (br s, 1H), 8.15 (s, 1H), 7.38-7.28 (m, 5H), 4.82 (s, 2H), 4.57 (s, 2H).

Step 5: (2R,3R,4R,5R)-2-{4-amino-3-[(benzyloxy)methyl]-1H-pyrazolo[3,4-d]pyrimidin-1-yl}-5-[(benzoyloxy)methyl]tetrahydrofuran-3,4-diyl Dibenzoate The titled compound was prepared following the procedure detailed in Example 1 Step 4, substituting Intermediate 46 for Intermediate 3 (67%). LCMS (FA): m/z 700 (M+H); $^1$H NMR (400 MHz, $d_6$-DMSO) δ 8.23 (s, 1H), 8.04-8.00 (m, 2H), 7.94-7.87 (m, 4H), 7.68-7.60 (m, 3H), 7.51-7.43 (m, 6H), 7.37-7.30 (m, 5H), 6.69 (d, J=3.8 Hz, 1H), 6.34 (dd, J=5.4, 3.9 Hz, 1H), 6.16 (t, J=5.6 Hz, 1H), 4.87 (dt, J=5.8, 3.7 Hz, 1H), 4.72 (s, 2H), 4.68 (dd, J=12.3, 3.2 Hz, 1H), 4.57-4.51 (m, 3H).

Step 6: (2R,3R,4S,5R)-2-{4-amino-3-[(benzyloxy)methyl]-1H-pyrazolo[3,4-d]pyrimidin-1-yl}-5-(hydroxymethyl)tetrahydrofuran-3,4-diol The titled compound was prepared following the procedure detailed in Example 1 Step 5, substituting (2R,3R,4R,5R)-2-{4-amino-3-[(benzyloxy)methyl]-1H-pyrazolo[3,4-d]pyrimidin-1-yl}-5-[(benzoyloxy)methyl]tetrahydrofuran-3,4-diyl dibenzoate for Intermediate 5 (84%). LCMS (FA): m/z 388 (M+H); $^1$H NMR (400 MHz, $d_6$-DMSO) δ 8.21 (s, 1H), 7.42-7.28 (m, 5H), 6.06 (d, J=4.8 Hz, 1H), 5.36 (d, J=5.6 Hz, 1H), 5.14 (d, J=5.0 Hz, 1H), 4.88-4.82 (m, 3H), 4.62-4.56 (m, 3H), 4.18 (dd, J=9.0, 4.5 Hz, 1H), 3.89 (dd, J=9.7, 4.6 Hz, 1H), 3.56 (dt, J=9.7, 4.8 Hz, 1H), 3.43 (dt, J=11.8, 6.0 Hz, 1H).

Step 7: [(3aR,4R,6R,6aR)-6-{4-amino-3-[(benzyloxy)methyl]-1H-pyrazolo[3,4-d]pyrimidin-1-yl}-2,2-dimethyltetrahydrofuro[3,4-d][1,3]dioxol-4-yl]methanol Intermediate-49

The titled compound was prepared following the procedure detailed in Example 1 Step 6, substituting (2R,3R,4S,5R)-2-{4-amino-3-[(benzyloxy)methyl]-1H-pyrazolo[3,4-d]pyrimidin-1-yl}-5-(hydroxymethyl)tetrahydrofuran-3,4-diol for Intermediate 6 (56%). LCMS (FA): m/z 428 (M+H); $^1$H NMR (400 MHz, CDCl$_3$) δ 8.33 (s, 1H), 7.41-7.31 (m, 5H), 6.41 (d, J=3.7 Hz, 1H), 5.60 (dd, J=11.4, 2.2 Hz, 1H), 5.19 (dd, J=5.9, 3.7 Hz, 1H), 5.09 (dd, J=5.9, 1.0 Hz, 1H), 4.88 (s, 2H), 4.61 (s, 2H), 4.54 (s, 1H), 3.95 (dt, J=12.7, 2.0 Hz, 1H), 3.76 (ddd, J 2.5, 11.5, 12.7 Hz, 1H), 1.65 (s, 3H), 1.38 (s, 3H).

Steps 8 and 9: [(2R,3S,4R,5R)-5-{4-amino-3-[(benzyloxy)methyl]-1H-pyrazolo[3,4-d]pyrimidin-1-yl}-3,4-dihydroxytetrahydrofuran-2-yl]methyl Sulfamate Compound I-4

The titled compound was prepared following the procedures detailed in Example 1 Step 7 and Example 3 Step 7 substituting [(3aR,4R,6R,6aR)-6-{4-amino-3-[(benzyloxy)methyl]-1H-pyrazolo[3,4-d]pyrimidin-1-yl}-2,2-dimethyltetrahydrofuro[3,4-d][1,3]dioxol-4-yl]methanol for Intermediate 7 (81%). LCMS (FA): m/z 467 (M+H); $^1$H NMR (400 MHz, $d_6$-DMSO) δ 8.22 (s, 1H), 7.39-7.28 (m, 5H), 6.13 (d, J=3.6 Hz, 1H), 5.58 (d, J=5.5 Hz, 1H), 5.39 (d, J=6.1 Hz, 1H), 4.86 (d, J=12.7 Hz, 1H), 4.83 (d, J=12.7 Hz, 1H), 4.62 (d, J=11.5 Hz, 1H), 4.58 (d, J=11.5 Hz, 1H), 4.50 (dd, J=8.9, 5.2 Hz, 1H), 4.32 (dd, J=11.0, 5.6 Hz, 1H), 4.21 (dd, J=10.3, 3.4 Hz, 1H), 4.12-4.07 (m, 1H), 4.02 (dd, J=10.2, 7.2 Hz, 1H).

Example 20: {(2R,3S,4R,5R)-5-[4-amino-3-(hydroxymethyl)-1H-pyrazolo[3,4-d]pyrimidin-1-yl]-3,4-dihydroxytetrahydrofuran-2-yl}methyl Sulfamate Compound I-8

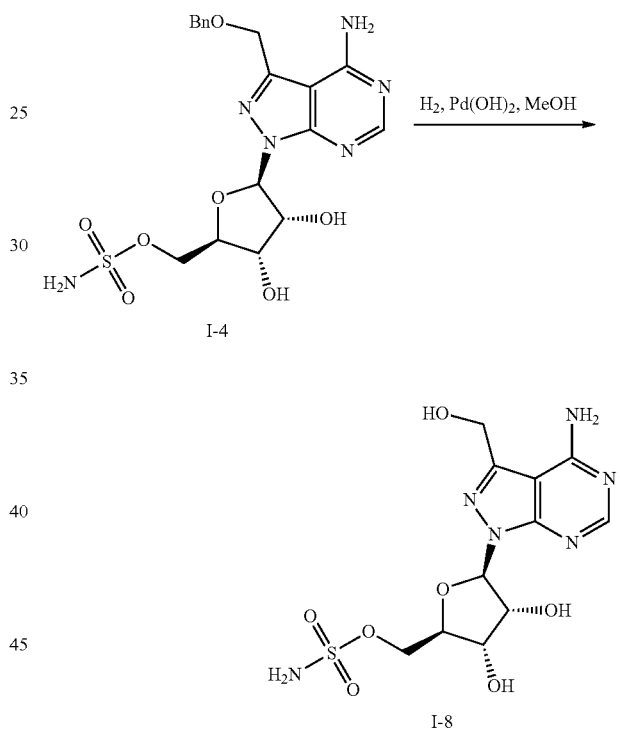

To a solution of [(2R,3S,4R,5R)-5-{4-amino-3-[(benzyloxy)methyl]-1H-pyrazolo[3,4-d]pyrimidin-1-yl}-3,4-dihydroxytetrahydrofuran-2-yl]methyl sulfamate (0.15 g, 0.32 mmol) in MeOH (5 mL) was added palladium hydroxide on carbon (0.015 g, 20 wt. %). The mixture was allowed to stir under an atmosphere of hydrogen at 35° C. for 7 days. The mixture was diluted with MeOH and filtered through Celite. The filtrate was concentrated under reduced pressure and then dried in vacuo at 40° C. to afford {(2R,3S,4R,5R)-5-[4-amino-3-(hydroxymethyl)-1H-pyrazolo[3,4-d]pyrimidin-1-yl]-3,4-dihydroxytetrahydrofuran-2-yl}methyl sulfamate (0.096 g, 79%). LCMS (FA): m/z 377 (M+H); $^1$H NMR (400 MHz, $d_6$-DMSO) δ 8.21 (s, 1H), 6.11 (d, J=3.7 Hz, 1H), 4.74 (s, 2H), 4.47 (dd, J=3.9, 4.9 1H), 4.28 (t, J=5.3 Hz, 1H), 4.21 (dd, J=10.3, 3.4 Hz, 1H), 4.11-4.05 (m, 1H), 3.99 (dd, J=10.3, 7.3 Hz, 1H).

Example 21 [(2R,3S,4R,5R)-5-(4-amino-3-ethynyl-1H-pyrazolo[3,4-d]pyrimidin-1-yl)-3,4-dihydroxytetrahydrofuran-2-yl]methyl Sulfamate Compound I-9

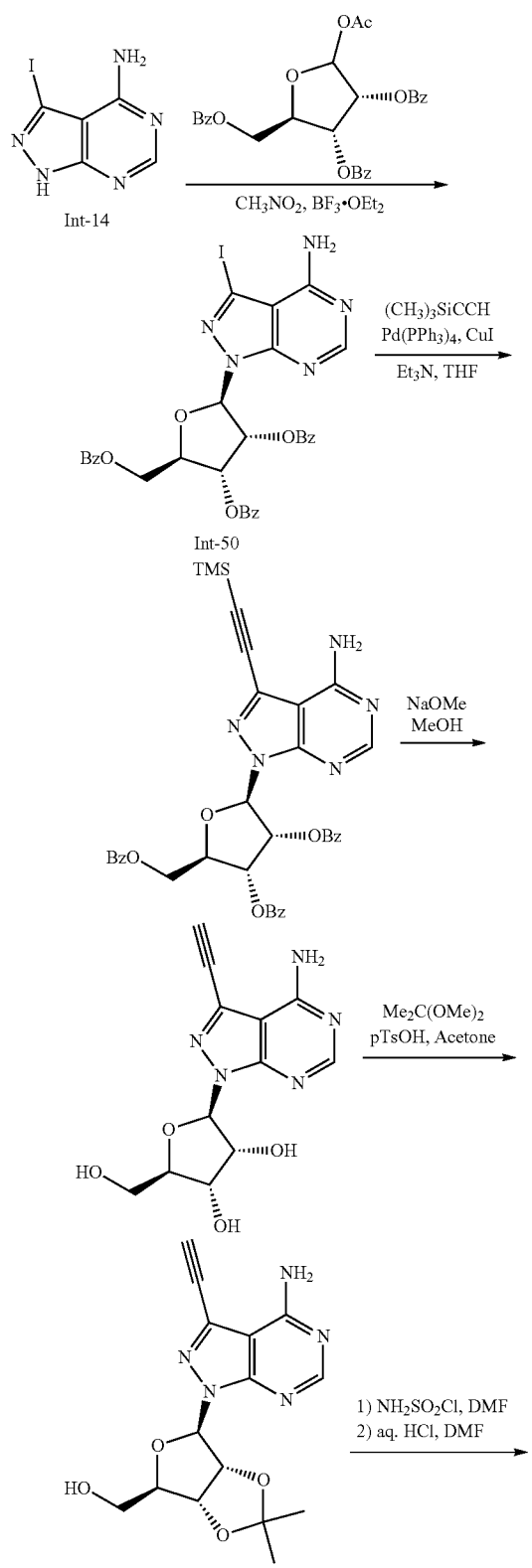

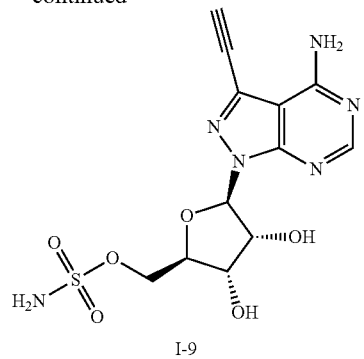

Step 1: (2R,3R,4R,5R)-2-(4-amino-3-iodo-1H-pyrazolo[3,4-d]pyrimidin-1-yl)-5-[(benzoyloxy)methyl]tetrahydrofuran-3,4-diyl Dibenzoate Intermediate 50

The titled compound was prepared following the procedure detailed in Example 5 Step 2, substituting 1-O-acetyl-2,3,5-tri-O-benzoyl-β-D-ribofuranose for 1,2,3,5-tetra-O-acetyl-(β-D-ribofuranose (55%). LCMS (FA): m/z 706 (M+H); $^1$H NMR (400 MHz, CDCl$_3$) δ 8.35 (s, 1H), 8.14-8.10 (m, 2H), 8.00-7.94 (m, 4H), 7.58-7.52 (m, 3H), 7.48-7.42 (m, 2H), 7.41-7.34 (m, 4H), 6.78 (d, J=3.6 Hz, 1H), 6.42 (dd, J=5.4, 3.6 Hz, 1H), 6.25 (t, J=5.6 Hz, 1H), 4.84-4.74 (m, 2H), 4.63 (dd, J=12.1, 4.6 Hz, 1H).

Step 2: (2R,3R,4R,5R)-2-{4-amino-3-[(trimethylsilyl)ethynyl]-1H-pyrazolo[3,4-d]pyrimidin-1-yl}-5-[(benzoyloxy)methyl]tetrahydrofuran-3,4-diyl Dibenzoate The titled compound was prepared following the procedure detailed in Example 26 Step 1, substituting (trimethylsilyl)acetylene for methyl propargyl ether (76%). LCMS (FA): m/z 676 (M+H); $^1$H NMR (400 MHz, CDCl$_3$) δ 8.37 (s, 1H), 8.14-8.09 (m, 2H), 8.00-7.92 (m, 4H), 7.59-7.50 (m, 3H), 7.47-7.32 (m, 6H), 6.82 (d, J=3.2 Hz, 1H), 6.39 (dd, J=5.4, 3.2 Hz, 1H), 6.32-6.26 (m, 1H), 4.85-4.80 (m, 1H), 4.73 (dd, J=12.1, 3.8 Hz, 1H), 4.65 (dd, J=12.1, 4.8 Hz, 1H), 0.34 (s, 9H).

Step 3: (2R,3R,4S,5R)-2-(4-amino-3-ethynyl-1H-pyrazolo[3,4-d]pyrimidin-1-yl)-5-(hydroxymethyl)tetrahydrofuran-3,4-diol The titled compound was prepared following the procedure detailed in Example 1 Step 5, substituting (2R,3R,4R,5R)-2-{4-amino-3-[(trimethylsilyl)ethynyl]-1H-pyrazolo[3,4-d]pyrimidin-1-yl}-5-[(benzoyloxy)methyl]tetrahydrofuran-3,4-diyl dibenzoate for Intermediate 5 (80%). LCMS (FA): m/z 292 (M+H); $^1$H NMR (300 MHz, d$_6$-DMSO) δ 8.26 (s, 1H), 6.09 (d, J=4.8 Hz, 1H), 4.71 (s, 1H), 4.57 (t, J=4.9 Hz, 1H), 4.18 (t, J=4.6 Hz, 1H), 3.91 (dd, J=9.8, 4.5 Hz, 1H), 3.56 (dd, J=11.6, 4.5 Hz, 1H), 3.43 (dd, J=11.8, 5.7 Hz, 1H).

Step 4: [(3aR,4R,6R,6aR)-6-(4-amino-3-ethynyl-1H-pyrazolo[3,4-d]pyrimidin-1-yl)-2,2-dimethyltetrahydrofuro[3,4-d][1,3]dioxol-4-yl]methanol The titled compound was prepared following the procedure detailed in Example 1, step 6, substituting (2R,3R,4S, 5R)-2-(4-amino-3-ethynyl-1H-pyrazolo[3,4-d]pyrimidin-1-yl)-5-(hydroxymethyl)tetrahydrofuran-3,4-diol for Intermediate 6 (90%). LCMS (FA): m/z 332 (M+H); $^1$H NMR (400 MHz, d$_6$-DMSO) δ 8.26 (s, 1H), 6.30 (d, J=1.8 Hz, 1H), 5.30 (dd, J=6.1, 1.8 Hz, 1H), 4.96-4.91 (m, 2H), 4.73 (s, 1H), 4.15-4.08 (m, 1H), 3.53-3.45 (m, 1H), 3.36 (dd, J=11.3, 5.7 Hz, 1H), 1.51 (s, 3H), 1.32 (s, 3H).

Step 5: [(2R,3S,4R,5R)-5-(4-amino-3-ethynyl-1H-pyrazolo[3,4-d]pyrimidin-1-yl)-3,4-dihydroxytetrahydrofuran-2-yl]methyl Sulfamate Compound I-9

The titled compound was prepared following the procedures detailed in Example 1 Step 7 and Example 3 Step 7, substituting [(3aR,4R,6R,6aR)-6-(4-amino-3-ethynyl-1H-pyrazolo[3,4-d]pyrimidin-1-yl)-2,2-dimethyltetrahydrofuro[3,4-d][1,3]dioxol-4-yl]methanol for Intermediate 7 (85%). LCMS (FA): m/z 371 (M+H); $^1$H NMR (400 MHz, d$_6$-DMSO) δ 8.26 (s, 1H), 6.15 (d, J=3.8 Hz, 1H), 5.63 (d, J=5.5 Hz, 1H), 5.43 (d, J=5.8 Hz, 1H), 4.72 (s, 1H), 4.49 (dd, J=9.0, 5.1 Hz, 1H), 4.29 (dd, J=10.4, 5.2 Hz, 1H), 4.22 (dd, J=10.4, 3.6 Hz, 1H), 4.14-4.09 (m, 1H), 4.01 (dd, J=10.4, 7.2 Hz, 1H).

Example 22: {(2R,3S,4R,5R)-5-[4-amino-3-(trifluoromethyl)-1H-pyrazolo[3,4-d]pyrimidin-1-yl]-3,4-dihydroxytetrahydrofuran-2-yl}methyl Sulfamate Compound I-10

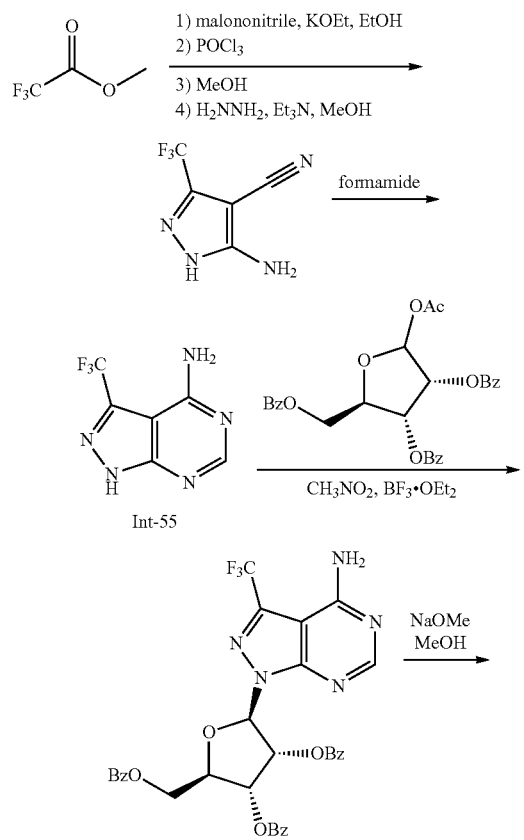

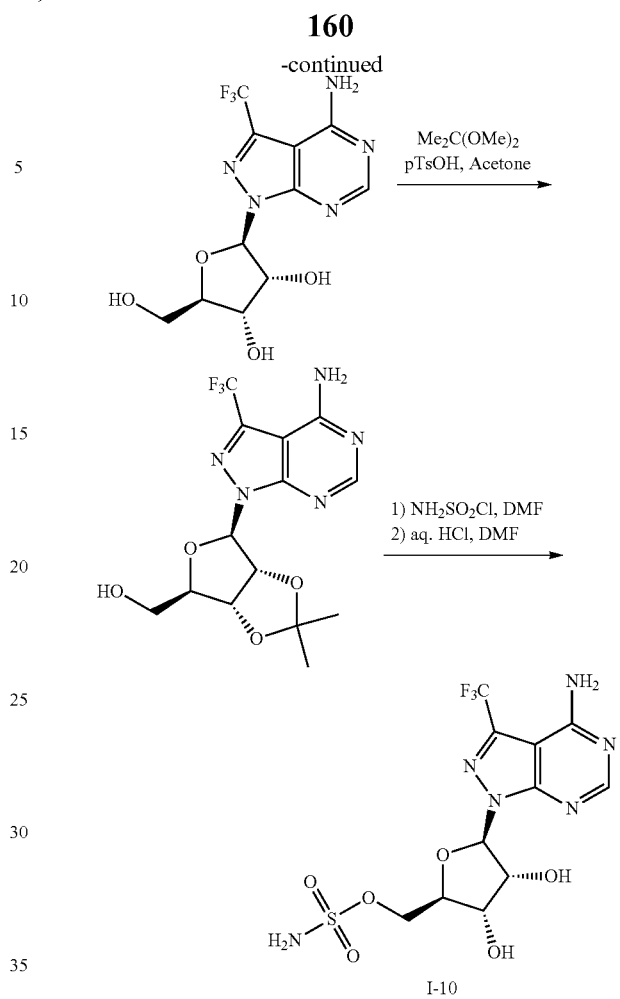

Step 1: 5-amino-3-(trifluoromethyl)-1H-pyrazole-4-carbonitrile

To a solution of 24% potassium ethoxide in ethanol (12.0 mL, 30.5 mmol) was added EtOH (11 mL) followed by malononitrile (1.92 mL, 30.5 mmol) in ethanol (4.5 mL) and methyltrifluoroacetate (3.38 mL, 33.6 mmol). The mixture was stirred at rt for 3 hours, after which time the volatiles were evaporated to obtain a white solid. To this white solid was added phosphoryl chloride (15.0 mL, 161 mmol) and the mixture was heated at 110° C. for 50 min. The mixture was then allowed to cool to rt and most of the phosphoryl chloride was removed under reduced pressure. The mixture was then cooled to 0° C. and the remaining phosphoryl chloride was quenched by the addition of MeOH. Volatiles were evaporated to obtain a yellow solid. To this yellow solid was added MeOH (64 mL), hydrazine monohydrate (3.45 mL, 68.9 mmol) and triethylamine (8.36 mL, 60.0 mmol). The mixture was stirred at rt for 3 hours. The solvents were evaporated and the residue was purified by silica gel chromatography (220 g silica, DCM to 90/10 DCM/MeOH gradient) to afford pure 5-amino-3-(trifluoromethyl)-1H-pyrazole-4-carbonitrile (0.60 g, 11%). LCMS (FA) m/z 175 (M+H).

Step 2: 3-(trifluoromethyl)-1H-pyrazolo[3,4-d]pyrimidin-4-amine Intermediate 55

The titled compound was prepared following the procedure detailed in Example 1 Step 3, substituting 5-amino-3-

(trifluoromethyl)-1H-pyrazole-4-carbonitrile for 5-amino-3-ethoxy-1H-pyrazole-4-carbonitrile (61%). LCMS (FA) m/z 204 (M+H); $^1$H NMR (400 MHz, d$_6$-DMSO) δ 14.32 (br s, 1H), 8.29 (s, 1H).

Step 3: (2R,3R,4R,5R)-2-[4-amino-3-(trifluoromethyl)-1H-pyrazolo[3,4-d]pyrimidin-1-yl]-5-[(benzoyloxy)methyl]tetrahydrofuran-3,4-diyl Dibenzoate The titled compound was prepared following the procedure detailed in Example 1 Step 4, substituting Intermediate 55 for Intermediate 3 (48%). LCMS (FA) m/z 648 (M+H); $^1$H NMR (400 MHz, CDCl$_3$) δ 8.43 (s, 1H), 8.11-8.08 (m, 2H), 7.99-7.94 (m, 4H), 7.59-7.52 (m, 3H), 7.44-7.34 (m, 6H), 6.88 (d, J=3.7 Hz, 1H), 6.44 (dd, J=5.5, 3.7 Hz, 1H), 6.25 (t, J=5.7 Hz, 1H), 4.86 (dd, J=9.7, 4.5 Hz, 1H), 4.77 (dd, J=12.2, 3.7 Hz, 1H), 4.65 (dd, J=12.2, 4.7 Hz, 1H).

Step 4: (2R,3R,4S,5R)-2-[4-amino-3-(trifluoromethyl)-1H-pyrazolo[3,4-d]pyrimidin-1-yl]-5-(hydroxymethyl)tetrahydrofuran-3,4-diol The titled compound was prepared following the procedure detailed in Example 1 Step 5, substituting (2R,3R,4R,5R)-2-[4-amino-3-(trifluoromethyl)-1H-pyrazolo[3,4-d]pyrimidin-1-yl]-5-[(benzoyloxy)methyl]tetrahydrofuran-3,4-diyl dibenzoate for Intermediate 5 (89%). LCMS (FA) m/z 336 (M+H); $^1$H NMR (400 MHz, d$_6$-DMSO) δ 8.35 (s, 1H), 6.17 (d, J=4.8 Hz, 1H), 5.50 (s, 1H), 5.25 (s, 1H), 4.87-4.79 (m, 1H), 4.60 (t, J=4.9 Hz, 1H), 4.20 (t, J=4.6 Hz, 1H), 3.93 (dd, J=9.9, 4.7 Hz, 1H), 3.60-3.53 (m, 1H), 3.47-3.39 (m, 1H).

Step 5: {(3aR,4R,6R,6aR)-6-[4-amino-3-(trifluoromethyl)-1H-pyrazolo[3,4-d]pyrimidin-1-yl]-2,2-dimethyltetrahydrofuro[3,4-d][1,3]dioxol-4-yl}methanol The titled compound was prepared following the procedure detailed in Example 1 Step 6, substituting (2R,3R,4S,5R)-2-[4-amino-3-(trifluoromethyl)-1H-pyrazolo[3,4-d]pyrimidin-1-yl]-5-(hydroxymethyl)tetrahydrofuran-3,4-diol for Intermediate 6 (73%). LCMS (FA) m/z 376 (M+H); 1H NMR (400 MHz, d$_6$-DMSO) δ 8.36 (s, 1H), 6.39 (d, J=1.9 Hz, 1H), 5.33 (dd, J=6.1, 2.0 Hz, 1H), 4.97-4.91 (m, 2H), 4.19-4.14 (m, 1H), 3.54-3.46 (m, 1H), 3.42-3.35 (m, 1H), 1.52 (s, 3H), 1.33 (s, 3H).

Steps 6 and 7: {(2R,3S,4R,5R)-5-[4-amino-3-(trifluoromethyl)-1H-pyrazolo[3,4-d]pyrimidin-1-yl]-3,4-dihydroxytetrahydrofuran-2-yl}methyl Sulfamate Compound I-10

The titled compound was prepared following the procedures detailed in Example 1 Step 7 and Example 3 Step 7, substituting {(3aR,4R,6R,6aR)-6-[4-amino-3-(trifluoromethyl)-1H-pyrazolo[3,4-d]pyrimidin-1-yl]-2,2-dimethyltetrahydrofuro[3,4-d][1,3]dioxol-4-yl}methanol for Intermediate 7 (69%). LCMS (FA) m/z 415 (M+H); $^1$H NMR (400 MHz, d$_6$-DMSO) δ 8.36 (s, 1H), 6.23 (d, J=3.6 Hz, 1H), 4.56-4.50 (m, 1H), 4.31 (t, J=5.2 Hz, 1H), 4.23 (dd, J=10.4, 3.4 Hz, 1H), 4.18-4.13 (m, 1H), 4.03 (dd, J=10.4, 7.1 Hz, 1H).

Example 23: [(2R,3S,4R,5R)-5-(4-amino-3-vinyl-1H-pyrazolo[3,4-d]pyrimidin-1-yl)-3,4-dihydroxytetrahydrofuran-2-yl]methyl Sulfamate Compound I-18

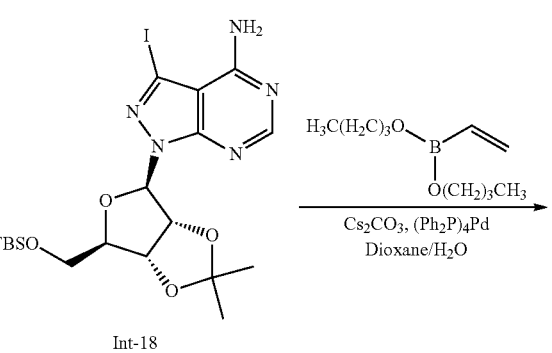

Int-18

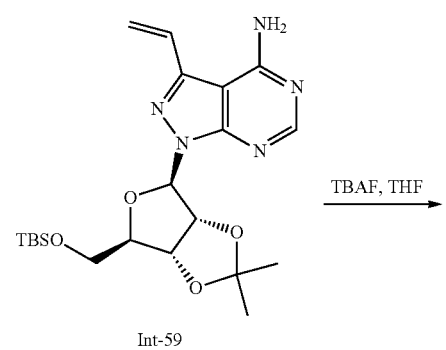

Int-59

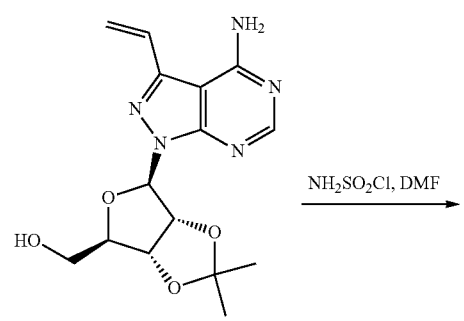

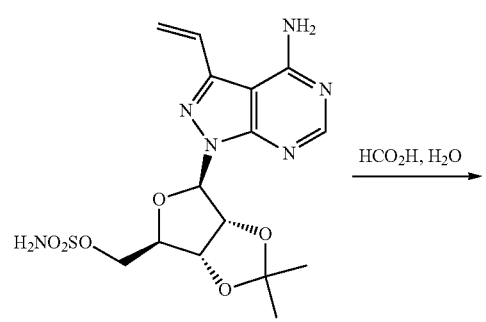

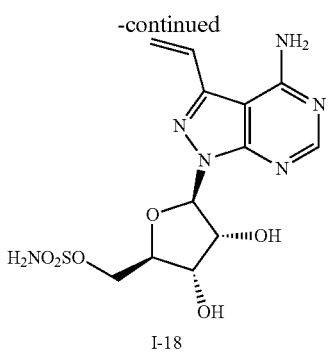

I-18

Step 1: 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-vinyl-1H-pyrazolo[3,4-d]pyrimidin-4-amine Intermediate 59

The titled compound was prepared following the procedure detailed in Example 17 Step 1 substituting vinylboronic acid dibutyl ester for isopropenyl boronic acid (74%). LCMS (AA): m/z 448 (M+H); $^1$H NMR (400 MHz, CDCl$_3$) δ 8.36 (s, 1H), 6.92 (dd, J=17.7, 11.2 Hz, 1H), 6.57 (d, J=1.8 Hz, 1H), 6.27 (br s, 2H), 6.00 (dd, J=17.7, 1.0 Hz, 1H), 5.73 (dd, J=11.3, 1.0 Hz, 1H), 5.44 (dd, J=6.1, 1.8 Hz, 1H), 5.00 (dd, J=6.2, 2.2 Hz, 1H), 4.31 (ddd, J=7.8, 5.7, 2.2 Hz, 1H), 3.72 (dd, J=10.5, 7.7 Hz, 1H), 3.60 (dd, J=10.5, 5.6 Hz, 1H), 1.61 (s, 3H), 1.40 (s, 3H), 0.86 (s, 9H), −0.02 (s, 6H).

Step 2: [(3aR,4R,6R,6aR)-6-(4-amino-3-vinyl-1H-pyrazolo[3,4-d]pyrimidin-1-yl)-2,2-dimethyltetrahydrofuro[3,4-d][1,3]dioxol-4-yl]methanol To a solution of Intermediate 59 (0.150 g, 0.335 mmol) in THF (4.5 mL) was added a solution of tetra-n-butylammonium fluoride (1.0M in THF, 0.37 mL, 0.37 mmol) and the reaction mixture was stirred at rt for 2 h. The reaction mixture was quenched with saturated aqueous ammonium chloride solution and extracted into ethyl acetate (2×50 mL). The combined organic layers were then washed with brine, dried over sodium sulfate, filtered and concentrated. The crude product was purified by silica gel chromatography (12 g, DCM to 95/5 DCM/MeOH gradient) to afford product as a white solid (71 mg, 63%). $^1$H NMR (400 MHz, CD$_3$OD) δ 8.20 (s, 1H), 7.12 (dd, J=17.3, 11.1 Hz, 1H), 6.47 (d, J=2.0 Hz, 1H), 6.13 (dd, J=17.3, 1.6 Hz, 1H), 5.58 (dd, J=11.1, 1.6 Hz, 1H), 5.33 (dd, J=6.0, 2.0 Hz, 1H), 5.03 (dd, J=6.0, 2.0 Hz, 1H), 4.32 (d, J=2.1 Hz, 1H), 3.73 (dd, J=11.8, 5.6 Hz, 1H), 3.62 (dd, J=11.8, 5.6 Hz, 1H), 1.60 (s, 3H), 1.39 (s, 3H).

Step 3: [(3aR,4R,6R,6aR)-6-(4-amino-3-vinyl-1H-pyrazolo[3,4-d]pyrimidin-1-yl)-2,2-dimethyltetrahydrofuro[3,4-d][1,3]dioxol-4-yl]methyl Sulfamate The titled compound was prepared following the procedure detailed in Example 1 step 7, substituting [(3aR,4R,6R,6aR)-6-(4-amino-3-vinyl-1H-pyrazolo[3,4-d]pyrimidin-1-yl)-2,2-dimethyltetrahydrofuro[3,4-d][1,3]dioxol-4-yl]methanol for Intermediate 7. LCMS (AA): m/z 413 (M+H).

Step 4: [(2R,3S,4R,5R)-5-(4-amino-3-vinyl-1H-pyrazolo[3,4-d]pyrimidin-1-yl)-3,4-dihydroxytetrahydrofuran-2-yl]methyl Sulfamate I-18

The titled compound was prepared following the procedure detailed in Example 1 Step 8, substituting [(3aR,4R, 6R,6aR)-6-(4-amino-3-vinyl-1H-pyrazolo[3,4-d]pyrimidin-1-yl)-2,2-dimethyltetrahydrofuro[3,4-d][1,3]dioxol-4-yl] methyl sulfamate for Intermediate 8 (66%). LCMS (AA): m/z 373 (M+H); $^1$H NMR (300 MHz, CD$_3$OD) δ 8.20 (s, 1H), 7.11 (dd, J=17.3, 11.1 Hz, 1H), 6.33 (d, J=3.5 Hz, 1H), 6.16 (dd, J=17.3, 1.6 Hz, 1H), 5.57 (dd, J=11.1, 1.6 Hz, 1H), 4.70 (dd, J=5.1, 3.6 Hz, 1H), 4.61-4.56 (m, 1H), 4.40-4.35 (m, 1H), 4.30-4.20 (m, 2H).

Example 24: {(2R,3S,4R,5R)-5-[4-amino-3-(methoxymethyl)-1H-pyrazolo[3,4-d]pyrimidin-1-yl]-3,4-dihydroxytetrahydrofuran-2-yl}methyl Sulfamate Compound I-19

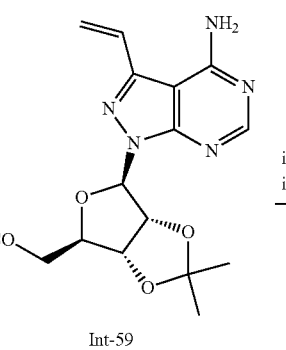

Int-59

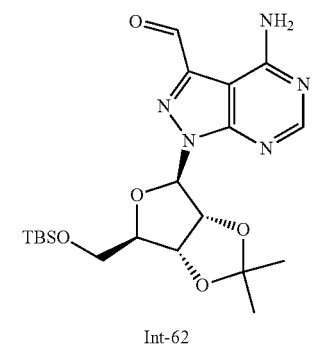

Int-62

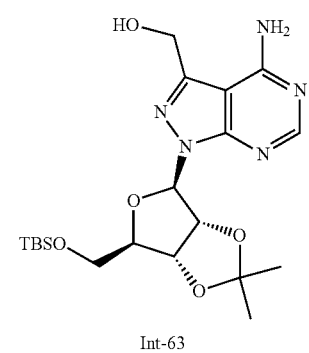

Int-63

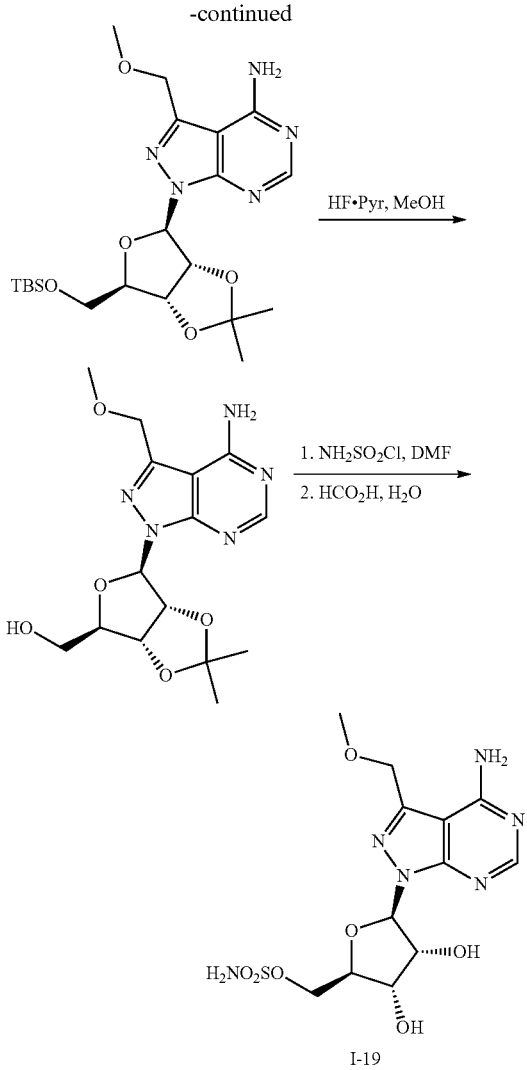

Step 1: 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carbaldehyde Intermediate 62

To a solution of Intermediate 59 (0.300 g, 0.670 mmol) in 1,4-dioxane (4.0 mL) and water (1.4 mL) was added osmium tetroxide (4% in water, 0.07 mL, 0.020 mmol). The reaction mixture was stirred at rt for 1 h then sodium metaperiodate (0.430 g, 2.01 mmol) was added and stirring was continued for 2 h. The reaction mixture was diluted with water and extracted into ethyl acetate (2×50 mL). The combined extracts were washed with brine, dried over sodium sulfate, filtered and concentrated under reduced pressure. The crude product was purified by silica gel chromatography (24 g, hexanes to 50/50 hexanes/ethyl acetate gradient) to afford the product as a white solid (279 mg, 92%). LCMS (AA): m/z 450 (M+H); $^1$H NMR (400 MHz, CDCl$_3$) δ 10.00 (s, 1H), 8.42 (s, 1H), 6.60 (d, J=2.2 Hz, 1H), 5.52 (dd, J=6.1, 2.2 Hz, 1H), 5.04 (dd, J=6.2, 2.2 Hz, 1H), 4.40-4.35 (m, 1H), 3.71 (dd, J=10.6, 7.2 Hz, 1H), 3.64 (dd, J=10.6, 5.3 Hz, 1H), 1.62 (s, 3H), 1.42 (s, 3H), 0.86 (s, 9H), −0.01 (d, J=2.2 Hz, 6H).

Step 2: {4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}methanol Intermediate 63

To a cooled (0° C.) solution of Intermediate 62 (0.295 g, 0.656 mmol) in MeOH (5.0 mL) and THF (2.5 mL) was added sodium borohydride (0.11 g, 3.0 mmol). The reaction mixture was stirred overnight with slow warming to rt under a nitrogen atmosphere. Water was carefully added and the mixture was extracted with ethyl acetate (2×50 mL). The combined extracts were washed with brine, dried over sodium sulfate, filtered and concentrated under reduced pressure. The crude product was purified by silica gel chromatography (12 g silica, DCM to 95/5 DCM/MeOH gradient) to afford 4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}methanol as a white solid (232 mg, 78%). LCMS (AA): m/z 453 (M+H); $^1$H NMR (400 MHz, CDCl$_3$) δ 8.33 (s, 1H), 6.49 (d, J=2.1 Hz, 1H), 6.46-6.35 (m, 1H), 5.41 (dd, J=6.2, 2.0 Hz, 1H), 4.98-4.94 (m, 3H), 4.31-4.25 (m, 1H), 3.69 (dd, J=10.4, 7.6 Hz, 1H), 3.60 (dd, J=10.5, 5.6 Hz, 1H), 1.60 (s, 3H), 1.40 (s, 3H), 0.87 (s, 9H), −0.01 (d, J=1.7 Hz, 6H).

Step 3: 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(methoxymethyl)-1H-pyrazolo[3,4-d]pyrimidin-4-amine To a cooled (0° C.) solution of Intermediate 63 (0.124 g, 0.274 mmol) in THF (1.4 mL) was added sodium hydride (0.013 g, 0.330 mmol). The reaction mixture was stirred for 30 min under an argon atmosphere. Methyl iodide (0.050 g, 0.357 mmol) was added to the 0° C. mixture and the reaction was allowed to proceed for 1 h. Water was added and the mixture was extracted with ethyl acetate (2×50 mL). The combined extracts were washed with brine, dried over sodium sulfate, filtered and concentrated under reduced pressure. The crude product was purified by silica gel chromatography (24 g, DCM to 95/5 DCM/MeOH gradient) to afford 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(methoxymethyl)-1H-pyrazolo[3,4-d]pyrimidin-4-amine as a white solid (77 mg, 60%). LCMS (AA): m/z 466 (M+H); $^1$H NMR (400 MHz, CDCl$_3$) δ 8.33 (s, 1H), 6.50 (d, J=2.1 Hz, 1H), 5.43 (dd, J=6.2, 2.1 Hz, 1H), 4.98 (dd, J=6.2, 2.2 Hz, 1H), 4.76 (d, J=2.6 Hz, 2H), 4.33-4.24 (m, 1H), 3.69 (dd, J=10.5, 7.5 Hz, 1H), 3.60 (dd, J=10.5, 5.4 Hz, 1H), 3.47 (s, 3H), 1.60 (s, 3H), 1.40 (s, 3H), 0.89-0.84 (m, 9H), −0.01 (d, J=2.7 Hz, 6H).

Step 4: {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methanol To a polypropylene vial was added 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(methoxymethyl)-1H-pyrazolo[3,4-d]pyrimidin-4-amine (0.116 g, 0.249 mmol), MeOH (5.0 mL) and pyridine hydrofluoride (0.22 mL). The tube was capped and the reaction mixture was stirred at rt overnight. The reaction mixture was quenched by the addition of saturated aqueous sodium bicarbonate solution and extracted with ethyl acetate (2×50 mL). The combined extracts were washed with brine, dried over sodium sulfate, filtered and concentrated under reduced pressure to afford crude {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methanol which was used as obtained (85 mg, 97%). LCMS (AA): m/z 352 (M+H); $^1$H NMR (400 MHz, CD$_3$OD) δ 8.22 (s, 1H), 6.42 (d, J=1.8 Hz, 1H), 5.36-5.32 (m, 1H), 4.99 (dd, J=6.0, 2.0 Hz, 1H), 4.78 (d, J=2.1 Hz, 2H), 4.31-4.26 (m, 1H), 3.67 (dd, J=11.8, 5.8 Hz, 1H), 3.58 (dd, J=11.7, 5.9 Hz, 1H), 3.47 (s, 3H), 1.59 (s, 4H), 1.39 (s, 3H).

Step 5: {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methyl Sulfamate The titled compound was prepared following the procedure described in Example 1 Step 7, substituting {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methanol for Intermediate 7. Crude {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methyl sulfamate was used as obtained in the following step. LCMS (AA): m/z 431 (M+H).

Step 6: {(2R,3S,4R,5R)-5-[4-amino-3-(methoxymethyl)-1H-pyrazolo[3,4-d]pyrimidin-1-yl]-3,4-dihydroxytetrahydrofuran-2-yl}methyl Sulfamate Compound I-19

The titled compound was prepared following the procedure detailed in Example 1 Step 8, substituting {(3aR,4R,6R,6aR)-6-[4-amino-3-(methoxymethyl)-1H-pyrazolo[3,4-d]pyrimidin-1-yl]-2,2-dimethyltetrahydrofuro[3,4-d][1,3]dioxol-4-yl}methyl sulfamate for Intermediate 8 (55 mg, 54%; 2 steps). LCMS (AA): m/z 391 (M+H); $^1$H NMR (300 MHz, CD$_3$OD) δ 8.21 (s, 1H), 6.29 (d, J=3.4 Hz, 1H), 4.78 (s, 2H), 4.68 (dd, J=5.1, 3.4 Hz, 1H), 4.59-4.54 (m, 1H), 4.36-4.29 (m, 1H), 4.28-4.17 (m, 2H), 3.46 (s, 3H).

Example 25: {(2R,3S,4R,5R)-5-[4-amino-3-(difluoromethyl)-1H-pyrazolo[3,4-d]pyrimidin-1-yl]-3,4-dihydroxytetrahydrofuran-2-yl}methyl Sulfamate Compound I-25

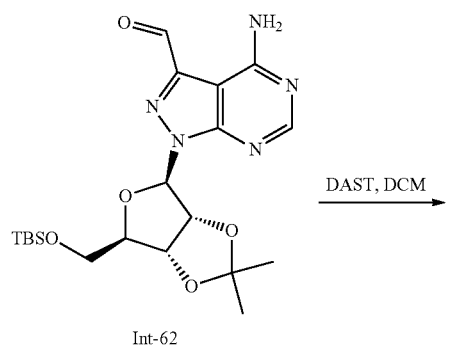

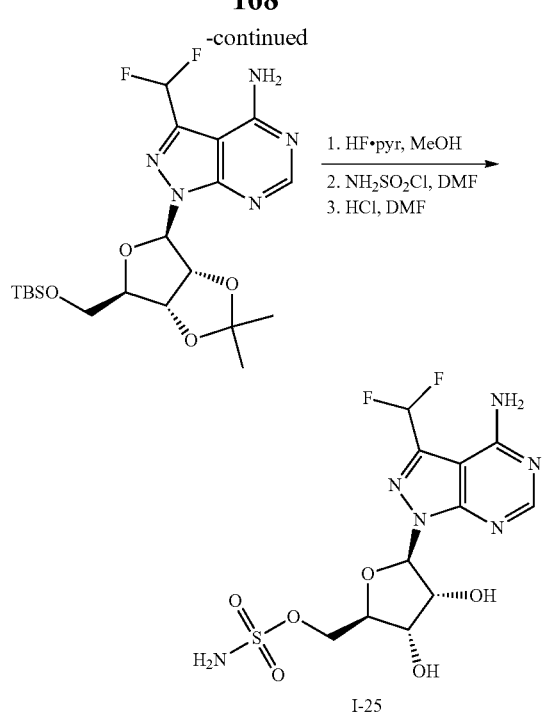

Step 1: 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine To a solution of Intermediate 62 (0.220 g, 0.49 mmol) in DCM (3 mL) was added diethylaminosulfur trifluoride (0.162 mL, 1.23 mmol) dropwise at 0° C. Upon completion of addition, the ice bath was removed and the mixture was stirred at rt for 90 min. The reaction mixture was quenched with saturated aqueous sodium bicarbonate solution and then diluted with ethyl acetate. The mixture was twice extracted into ethyl acetate. The extracts were combined, washed with water and brine then dried over sodium sulfate, filtered and concentrated under reduced pressure. The crude product was purified by silica gel chromatography (24 g silica, hexanes to 60/40 hexanes/ethyl acetate gradient) to afford 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine (0.166 g, 72%). LCMS (AA): m/z 472 (M+H); $^1$H NMR (400 MHz, CDCl$_3$) δ 8.41 (s, 1H), 6.83 (t, J=54.2 Hz, 1H), 6.55 (d, J=1.9 Hz, 1H), 5.44 (dd, J=6.1, 2.0 Hz, 1H), 4.98 (dd, J=6.1, 2.2 Hz, 1H), 4.34-4.29 (m, 1H), 3.68-3.56 (m, 2H), 1.60 (s, 3H), 1.39 (s, 3H), 0.84 (s, 9H), −0.04 (s, 6H).

Step 2: {(3aR,4R,6R,6aR)-6-[4-amino-3-(difluoromethyl)-1H-pyrazolo[3,4-d]pyrimidin-1-yl]-2,2-dimethyltetrahydrofuro[3,4-d][1,3]dioxol-4-yl}methanol The titled compound was prepared following the procedure detailed in Example 5 Step 7, substituting 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine for Intermediate 19 (78%). LCMS (AA): m/z 358 (M+H); $^1$H NMR (400 MHz, CDCl$_3$) δ 8.34 (s, 1H), 6.86 (t, J=54.0 Hz, 1H), 6.40 (d, J=3.8 Hz, 1H), 5.24 (dd, J=5.9, 3.8 Hz, 1H), 5.18 (dd, J=10.4, 2.7 Hz, 1H), 5.06 (dd, J=5.9, 1.4 Hz, 1H), 4.55-4.52 (m, 1H), 3.95-3.89 (m, 1H), 3.82-3.74 (m, 1H), 1.65 (s, 3H), 1.38 (s, 3H).

Step 3: {(2R,3S,4R,5R)-5-[4-amino-3-(difluoromethyl)-1H-pyrazolo[3,4-d]pyrimidin-1-yl]-3,4-dihydroxytetrahydrofuran-2-yl}methyl Sulfamate Compound I-25

The titled compound was prepared following the procedure detailed in Example 1 Steps 7 and Example 3 Step 7, substituting {(3aR,4R,6R,6aR)-6-[4-amino-3-(difluoromethyl)-1H-pyrazolo[3,4-d]pyrimidin-1-yl]-2,2-dimethyltetrahydrofuro[3,4-d][1,3]dioxol-4-yl}methanol for Intermediate 7 (56%). LCMS (AA): m/z 397 (M+H); $^1$H NMR (400 MHz, d$_6$-DMSO) δ 8.32 (s, 1H), 7.39 (t, J=53.3 Hz, 1H), 6.19 (d, J=3.8 Hz, 1H), 4.54-4.50 (m, 1H), 4.31 (t, J=5.3 Hz, 1H), 4.22 (dd, J=10.4, 3.5 Hz, 1H), 4.16-4.10 (m, 1H), 4.02 (dd, J=10.4, 7.2 Hz, 1H).

Example 26: {(2R,3S,4R,5R)-5-[4-amino-3-(3-methoxyprop-1-yn-1-yl)-1H-pyrazolo[3,4-d]pyrimidin-1-yl]-3,4-dihydroxytetrahydrofuran-2-yl}methyl Sulfamate Compound I-11

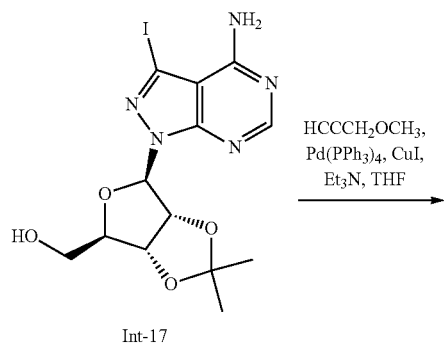

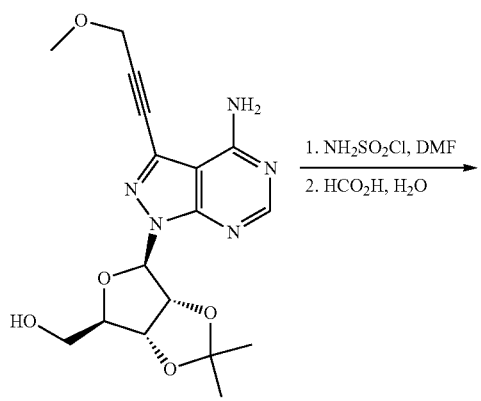

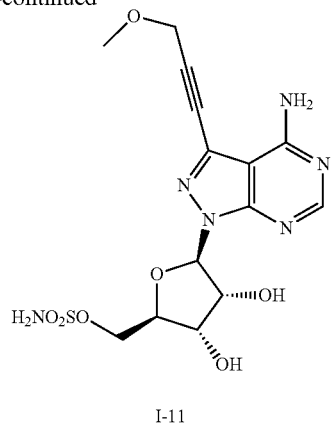

I-11

Step 1: {(3aR,4R,6R,6aR)-6-[4-amino-3-(3-methoxyprop-1-yn-1-yl)-1H-pyrazolo[3,4-d]pyrimidin-1-yl]-2,2-dimethyltetrahydrofuro[3,4-d][1,3]dioxol-4-yl}methanol A mixture of [(3aR,4R,6R,6a)-6-(4-amino-3-iodo-1H-pyrazolo[3,4-d]pyrimidin-1-yl)-2,2-dimethyltetrahydrofuro[3,4-d][1,3]dioxol-4-yl]methanol (Intermediate 17, 0.433 g, 1.00 mmol), tetrakis(triphenylphosphine)palladium(0) (0.116 g, 0.100 mmol), copper(I) iodide (0.003 g, 0.02 mmol), THF (8.0 mL), triethylamine (0.29 mL, 2.1 mmol) and methyl propargyl ether (0.15 mL, 1.8 mmol) was heated at 65° C. overnight. Additional methyl propargyl ether (0.08 mL) was added and heating was continued for 4 h. Upon completion, the reaction was allowed to cool to rt. The mixture was diluted with water and extracted with ethyl acetate (2×100 mL). The extracts were combined, washed with water and brine then dried over sodium sulfate, filtered and concentrated under reduced pressure. The crude product was purified by silica gel chromatography (24 g silica, DCM to 95/5 DCM/MeOH gradient) to afford {(3aR,4R,6R,6aR)-6-[4-amino-3-(3-methoxyprop-1-yn-1-yl)-1H-pyrazolo[3,4-d]pyrimidin-1-yl]-2,2-dimethyltetrahydrofuro[3,4-d][1,3]dioxol-4-yl}methanol as a white solid (254 mg, 68%). LCMS (AA): m/z 376 (M+H); $^1$H NMR (400 MHz, d$_6$-DMSO) δ 8.26 (s, 1H), 6.30 (d, J=1.8 Hz, 1H), 5.30 (dd, J=6.1, 1.8 Hz, 1H), 4.95-4.91 (m, 2H), 4.43 (s, 2H), 4.15-4.09 (m, 1H), 3.53-3.45 (m, 1H), 3.39-3.33 (m, 4H), 1.50 (s, 3H), 1.32 (s, 3H).

Step 2: {(3aR,4R,6R,6aR)-6-[4-amino-3-(3-methoxyprop-1-yn-1-yl)-1H-pyrazolo[3,4-d]pyrimidin-1-yl]-2,2-dimethyltetrahydrofuro[3,4-d][1,3]dioxol-4-yl}methyl Sulfamate The titled compound was prepared following the procedure detailed in Example 1 Step 7, substituting {(3aR,4R,6R,6aR)-6-[4-amino-3-(3-methoxyprop-1-yn-1-yl)-1H-pyrazolo[3,4-d]pyrimidin-1-yl]-2,2-dimethyltetrahydrofuro[3,4-d][1,3]dioxol-4-yl}methanol for Intermediate 7. The crude product was used as obtained in the following step. LCMS (AA): m/z 455 (M+H).

Step 3: {(2R,3S,4R,5R)-5-[4-amino-3-(3-methoxyprop-1-yn-1-yl)-1H-pyrazolo[3,4-d]pyrimidin-1-yl]-3,4-dihydroxytetrahydrofuran-2-yl}methyl Sulfamate Compound I-11

The titled compound was prepared following the procedure detailed in Example 1 Step 8, substituting {(3aR,4R, 6R,6aR)-6-[4-amino-3-(3-methoxyprop-1-yn-1-yl)-1H-pyrazolo[3,4-d]pyrimidin-1-yl]-2,2-dimethyltetrahydrofuro[3,4-d][1,3]dioxol-4-yl}methyl sulfamate for Intermediate 8 (99 mg, 36%; 2 steps) LCMS (AA): m/z 415 (M+H); $^1$H NMR (400 MHz, d$_6$-DMSO) δ 8.27 (s, 1H), 7.53 (bs, 2H), 6.16 (d, J=3.8 Hz, 1H), 5.63 (d, J=5.5 Hz, 1H), 5.44 (d, J=6.0 Hz, 1H), 4.53-4.48 (m, 1H), 4.30 (dd, J=11.0, 5.5 Hz, 1H), 4.22 (dd, J=10.4, 3.7 Hz, 1H), 4.15-4.09 (m, 1H), 4.01 (dd, J=10.4, 7.2 Hz, 1H), 3.36 (s, 3H).

Example 27: {(2R,3S,4R,5R)-5-[4-amino-3-(prop-1-yn-1-yl)-1H-pyrazolo[3,4-d]pyrimidin-1-yl]-3,4-dihydroxytetrahydrofuran-2-yl}methyl Sulfamate Compound I-14

The following compound was prepared following the procedures detailed in Example 26, substituting the appropriate alkyne for methyl propargyl ether in Step 1.

| Compound | Alkyne | LCMS | 1H-NMR |
|---|---|---|---|
| I-14 | prop-1-yne | LCMS (AA): m/z 385 (M + H). | (400 MHz, d$_6$-DMSO) δ 8.24 (s, 1H), 8.03 (br s, 1H), 7.54 (bs, 2H), 6.72 (br s, 1H), 6.14 (d, J = 3.4 Hz, 1H), 5.61 (d, J = 5.3 Hz, 1H), 5.42 (d, J = 5.8 Hz, 1H), 4.56-4.42 (m, 1H), 4.35-4.26 (m, 1H), 4.25-4.17 (m, 1H), 4.15-4.07 (m, 1H), 4.04-3.93 (m, 1H), 2.16 (s, 3H). |

Example 28: {(2R,3S,4R,5R)-5-[4-amino-3-(3-aminoprop-1-yn-1-yl)-1H-pyrazolo[3,4-d]pyrimidin-1-yl]-3,4-dihydroxytetrahydrofuran-2-yl}methyl Sulfamate Compound I-17

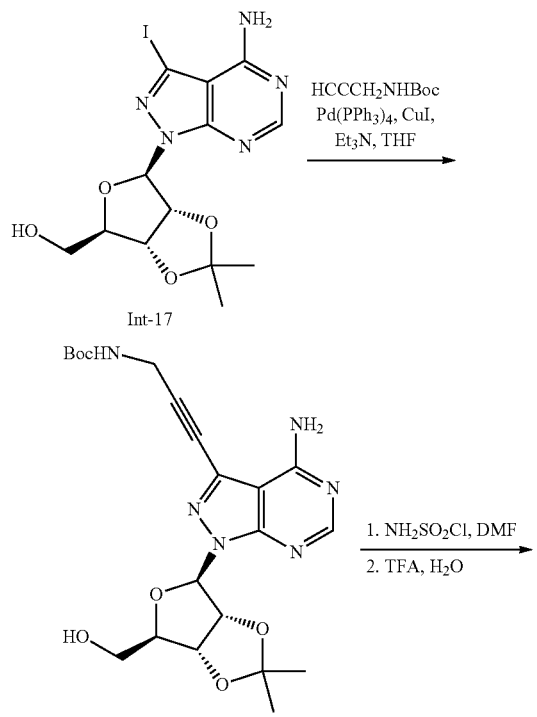

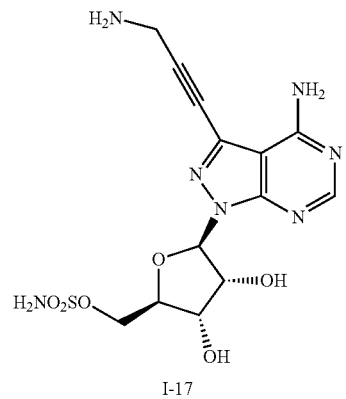

Step 1: tert-butyl (3-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}prop-2-yn-1-yl)carbamate The titled compound was prepared following the procedure detailed in Example 26 Step 1 substituting N-Boc propargylamine for methyl propargyl ether (335 mg, 73%). LCMS (AA): m/z 461 (M+H); $^1$H NMR (400 MHz, CDCl$_3$) δ 8.32 (s, 1H), 6.43 (d, J=3.4 Hz, 1H), 5.18 (dd, J=5.8, 3.5 Hz, 1H), 5.09-5.01 (m, 2H), 4.53 (s, 1H), 4.10 (d, J=5.6 Hz, 2H), 3.95-3.89 (m, 1H), 3.79-3.73 (m, 1H), 1.63 (s, 3H), 1.46 (s, 9H), 1.37 (s, 3H).

Step 2: tert-butyl [3-(4-amino-1-{(3aR,4R,6R,6aR)-2,2-dimethyl-6-[(sulfamoyloxy)methyl]tetrahydrofuro[3,4-d][1,3]dioxol-4-yl}-1H-pyrazolo[3,4-d]pyrimidin-3-yl)prop-2-yn-1-yl]carbamate The titled compound was prepared following the procedure detailed in Example 1 Step 7 substituting tert-butyl (3-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}prop-2-yn-1-yl)carbamate for Intermediate 7. The crude product was used as obtained in the following step. LCMS (AA): m/z 540 (M+H).

Step 3: {(2R,3S,4R,5R)-5-[4-amino-3-(3-aminoprop-1-yn-1-yl)-1H-pyrazolo[3,4-d]pyrimidin-1-yl]-3,4-dihydroxytetrahydrofuran-2-yl}methyl Sulfamate Compound I-17

A solution of tert-butyl [3-(4-amino-1-{(3aR,4R,6R,6aR)-2,2-dimethyl-6-[(sulfamoyloxy)methyl]tetrahydrofuro[3,4-d][1,3]dioxol-4-yl}-1H-pyrazolo[3,4-d]pyrimidin-3-yl)prop-2-yn-1-yl]carbamate (0.152 g, 0.282 mmol) in 9:1 TFA/water (10.0 mL) was stirred at rt for 1 h. The mixture was diluted with toluene (15 mL) and concentrated to ¼ volume. Subsequently, the moist mixture was repeatedly coevaporated from acetonitrile until dry. The crude material was purified by preparative reverse phase HPLC to give the titled compound (28 mg, 21%; 2 steps). LCMS (AA): m/z 400 (M+H); $^1$H NMR (400 MHz, d$_6$-DMSO) δ 8.26 (s, 1H), 6.15 (d, J=3.6 Hz, 1H), 4.49-4.45 (m, 1H), 4.31-4.27 (m, 1H), 4.22 (dd, J=10.4, 3.6 Hz, 1H), 4.15-4.09 (m, 1H), 3.99 (dd, J=10.4, 7.2 Hz, 1H), 3.79 (s, 2H).

Example 29: {(2R,3S,4R,5R)-5-[4-amino-3-(2-phenylethyl)-1H-pyrazolo[3,4-d]pyrimidin-1-yl]-3,4-dihydroxytetrahydrofuran-2-yl}methyl Sulfamate Compound I-12

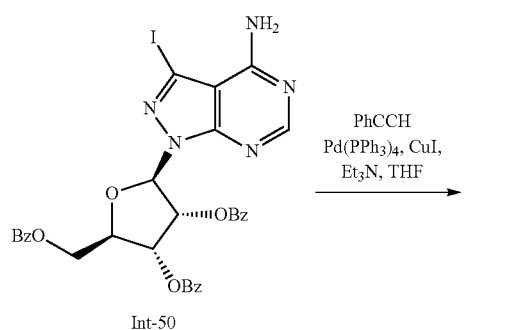

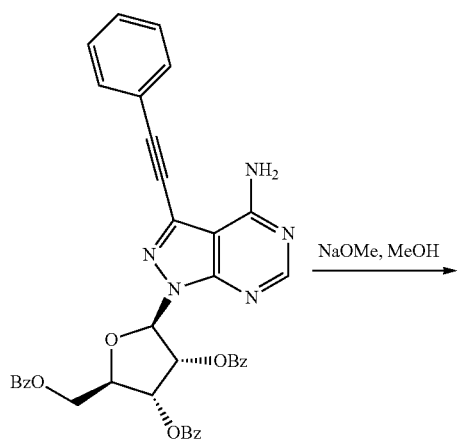

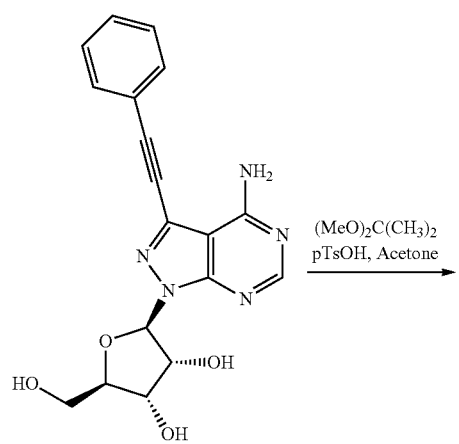

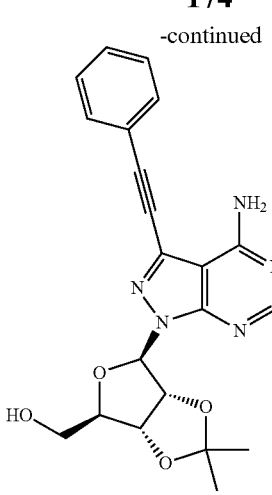

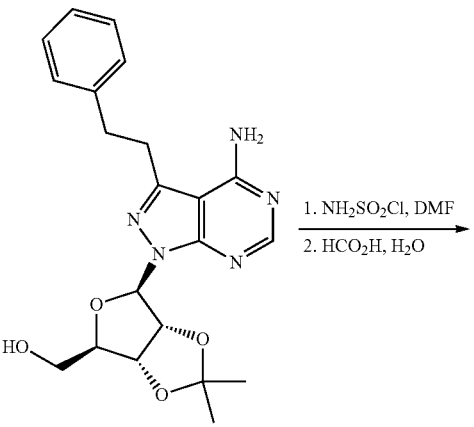

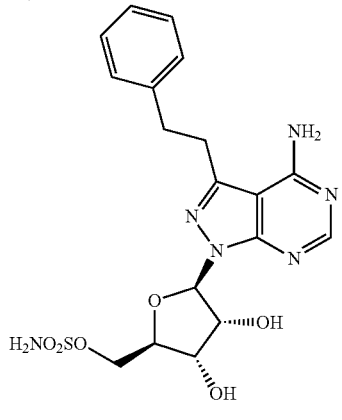

I-12

Step 1: (2R,3R,4R,5R)-2-[4-amino-3-(phenylethynyl)-1H-pyrazolo[3,4-d]pyrimidin-1-yl]-5-[(benzoyloxy)methyl]tetrahydrofuran-3,4-diyl Dibenzoate The titled compound was prepared following the procedure detailed Example 26 Step 1 substituting Intermediate 50 for Intermediate 17 and phenyl acetylene for methyl propargyl ether (909 mg, 94%). LCMS (AA): m/z 680 (M+H).

Step 2: (2R,3R,4S,5R)-2-[4-amino-3-(phenylethynyl)-1H-pyrazolo[3,4-d]pyrimidin-1-yl]-5-(hydroxymethyl)tetrahydrofuran-3,4-diol The titled compound was prepared following the procedure detailed in Example 1 Step 5, substituting (2R,3R,4R, 5R)-2-[4-amino-3-(phenylethynyl)-1H-pyrazolo[3,4-d]pyrimidin-1-yl]-5-[(benzoyloxy)methyl]tetrahydrofuran-3,4-diyl dibenzoate for Intermediate 5 (430 mg, 87%). $^1$H NMR (400 MHz, d$_6$-DMSO) δ 8.28 (s, 1H), 7.80-7.73 (m, 2H), 7.54-7.43 (m, 3H), 6.13 (d, J=4.8 Hz, 1H), 4.65-4.59 (m, 1H), 4.23-4.18 (m, 1H), 3.95-3.89 (m, 1H), 3.61-3.54 (m, 1H), 3.45 (dd, J=11.8, 5.7 Hz, 1H).

Step 3: {(3aR,4R,6R,6aR)-6-[4-amino-3-(phenylethynyl)-1H-pyrazolo[3,4-d]pyrimidin-1-yl]-2,2-dimethyltetrahydrofuro[3,4-d][1,3]dioxol-4-yl}methanol The titled compound was prepared following the procedure detailed in Example 1 Step 6, substituting (2R,3R,4S,5R)-2-[4-amino-3-(phenylethynyl)-1H-pyrazolo[3,4-d]pyrimidin-1-yl]-5-(hydroxymethyl)tetrahydrofuran-3,4-diol for Intermediate 6 (215 mg, 45%). LCMS (AA): m/z 408 (M+H).

Step 4: {(3aR,4R,6R,6aR)-6-[4-amino-3-(2-phenylethyl)-1H-pyrazolo[3,4-d]pyrimidin-1-yl]-2,2-dimethyltetrahydrofuro[3,4-d][1,3]dioxol-4-yl}methanol To a solution of {(3aR,4R,6R,6aR)-6-[4-amino-3-(phenylethynyl)-1H-pyrazolo[3,4-d]pyrimidin-1-yl]-2,2-dimethyltetrahydrofuro[3,4-d][1,3]dioxol-4-yl}methanol (0.112 g, 0.275 mmol) in ethanol (4.0 mL) was added Pd/C (10 wt. %, 0.011 g, 0.82 mmol) and the reaction mixture was stirred at rt under an atmosphere of hydrogen overnight. The reaction mixture was diluted with ethyl acetate and filtered through a pad of Celite. The filter pad was washed with ethyl acetate (3×50 mL) and the filtrate was collected and concentrated under reduced pressure. The crude product was purified by silica gel chromatography (12 g silica, DCM to 95/5 DCM/MeOH gradient) to afford {(3aR,4R,6R,6aR)-6-[4-amino-3-(2-phenylethyl)-1H-pyrazolo[3,4-d]pyrimidin-1-yl]-2,2-dimethyltetrahydrofuro[3,4-d][1,3]dioxol-4-yl}methanol (132 mg, quant.). LCMS (AA): m/z 412 (M+H); $^1$H NMR (400 MHz, CDCl$_3$) δ 8.29 (s, 1H), 7.33-7.22 (m, 3H), 7.19-7.15 (m, 2H), 6.50 (d, J=3.2 Hz, 1H), 5.63 (s, 2H), 5.16 (dd, J=5.9, 3.2 Hz, 1H), 5.10-5.07 (m, 1H), 4.57-4.53 (m, 1H), 3.94-3.89 (m, 1H), 3.76 (dd, J=12.8, 2.7 Hz, 1H), 3.27-3.09 (m, 5H), 1.65 (s, 3H), 1.39 (s, 3H).

Step 5: {(3aR,4R,6R,6aR)-6-[4-amino-3-(2-phenylethyl)-1H-pyrazolo[3,4-d]pyrimidin-1-yl]-2,2-dimethyltetrahydrofuro[3,4-d][1,3]dioxol-4-yl}methyl Sulfamate The titled compound was prepared following the procedure detailed in Example 1 Step 7, substituting {(3aR,4R,6R,6aR)-6-[4-amino-3-(2-phenylethyl)-1H-pyrazolo[3,4-d]pyrimidin-1-yl]-2,2-dimethyltetrahydrofuro[3,4-d][1,3]dioxol-4-yl}methanol for Intermediate 7 (157 mg). The crude product was used as obtained in the following step. LCMS (AA): m/z 491 (M+H).

Step 6: {(2R,3S,4R,5R)-5-[4-amino-3-(2-phenylethyl)-1H-pyrazolo[3,4-d]pyrimidin-1-yl]-3,4-dihydroxytetrahydrofuran-2-yl}methyl Sulfamate Compound I-12

The titled compound was prepared following the procedure detailed in Example 1 Step 8, substituting {(3aR,4R,6R,6aR)-6-[4-amino-3-(2-phenylethyl)-1H-pyrazolo[3,4-d]pyrimidin-1-yl]-2,2-dimethyltetrahydrofuro[3,4-d][1,3]dioxol-4-yl}methyl sulfamate for Intermediate 8 (96 mg, 67%; 2 steps). LCMS (AA): m/z 451 (M+H); $^1$H NMR (300 MHz, d$_6$-DMSO) δ 8.17 (s, 1H), 7.51 (s, 2H), 7.33-7.26 (m, 4H), 7.22-7.14 (m, 1H), 6.12 (d, J=2.7 Hz, 1H), 5.54 (d, J=5.0 Hz, 1H), 5.33 (d, J=6.2 Hz, 1H), 4.46-4.31 (m, 2H), 4.24 (dd, J=9.9, 2.6 Hz, 1H), 4.13-3.96 (m, 2H), 3.31-3.22 (m, 2H), 3.08-2.96 (m, 2H).

Example 30: [(2R,3S,4R,5R)-5-(3-acetyl-4-amino-1H-pyrazolo[3,4-d]pyrimidin-1-yl)-3,4-dihydroxytetrahydrofuran-2-yl]methyl Sulfamate Compound I-21

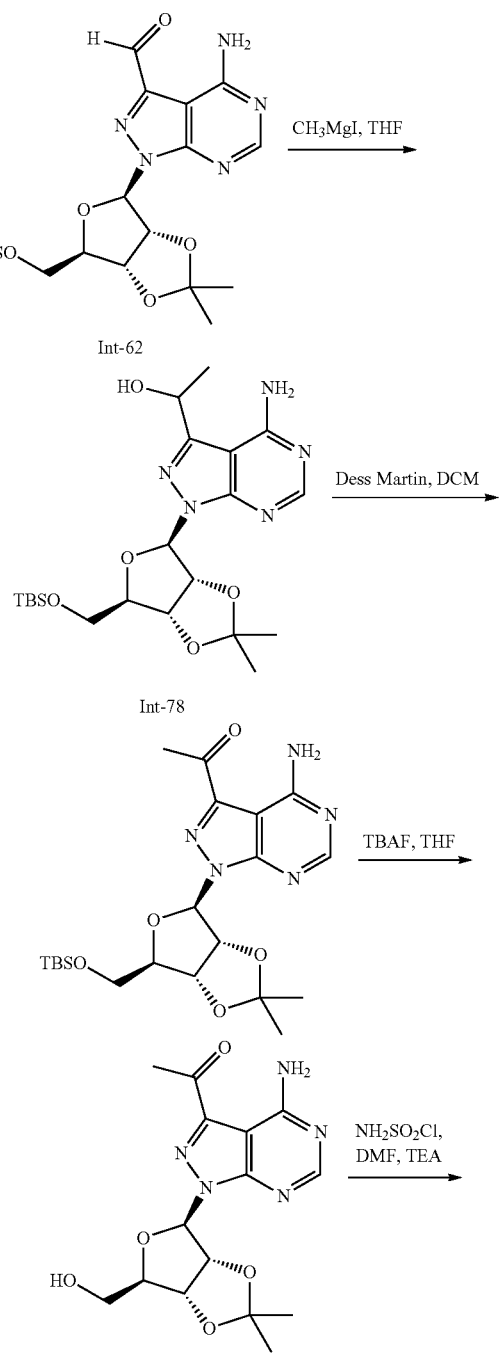

-continued

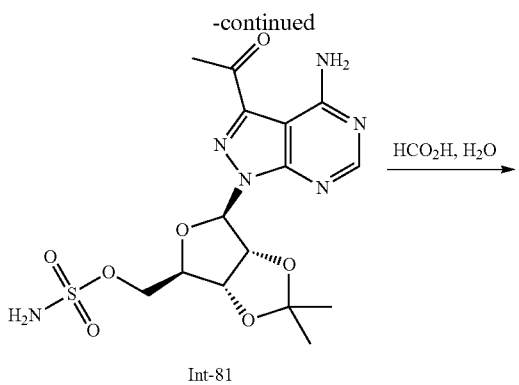

Int-81

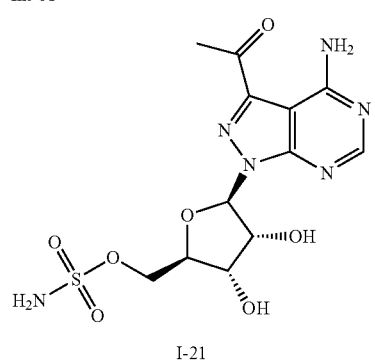

I-21

Step 1: (1S)-1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanol and (1R)-1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanol Intermediate-78

To a 0° C. solution of Intermediate 62 (0.757 g, 1.68 mmol) in THF (15 mL) was added methylmagnesium iodide (3.0 M in ether, 2.0 mL, 5.9 mmol). After 10 minutes, the reaction mixture was warmed to rt and stirred 1 h. The reaction mixture was quenched with saturated aqueous ammonium chloride solution and extracted with ethyl acetate (2×100 mL). The extracts were combined, washed with brine, dried over sodium sulfate, filtered and concentrated under reduced pressure. The crude product was purified by silica gel chromatography (40 g, DCM to 95/5 DCM/MeOH gradient) to afford 1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanol, Intermediate 78 as an inseparable mixture of diastereomers (447 mg, 93% based on recovered starting material). LCMS (AA): m/z 466 (M+H); $^1$H NMR (400 MHz, CDCl$_3$) δ 8.27 (s, 1H), 6.81 (bs, 2H), 6.53-6.45 (m, 1H), 5.42-5.38 (m, 1H), 5.23-5.15 (m, 1H), 4.99-4.94 (m, 1H), 4.31-4.26 (m, 1H), 3.74-3.67 (m, 1H), 3.66-3.54 (m, 1H), 1.60 (s, 6H), 1.40 (s, 3H), 0.86 (s, 9H), −0.01 (d, J=4.2 Hz, 6H).

Step 2: 1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanone To a solution of Intermediate 78 (0.063 g, 0.14 mmol) in DCM (2.0 mL) was added Dess-Martin periodinane (0.069 g, 0.162 mmol). The mixture was stirred at rt for 2 h. Water was added and the mixture was extracted with DCM (2×50 mL). The combined extracts were washed with brine, dried over sodium sulfate, filtered and concentrated under reduced pressure. The crude product was purified by silica gel chromatography (12 g, hexanes to 50/50 hexanes/EtOAc gradient) to afford 1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanone as a white solid (34 mg, 54%). LCMS (AA): m/z 464 (M+H); $^1$H NMR (400 MHz, CDCl$_3$) δ 8.37 (s, 1H), 6.58 (d, J=2.3 Hz, 1H), 5.49 (dd, J=6.1, 2.2 Hz, 1H), 5.03 (dd, J=6.2, 2.2 Hz, 1H), 4.42-4.34 (m, 1H), 3.73 (dd, J=10.5, 7.3 Hz, 1H), 3.66 (dd, J=10.5, 5.3 Hz, 1H), 2.73 (s, 3H), 1.62 (s, 3H), 1.42 (s, 3H), 0.86 (s, 9H), −0.01 (d, J=3.1 Hz, 6H).

Step 3: 1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanone The titled compound was prepared following the procedure detailed in Example 23 Step 2 substituting 1-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}ethanone for Intermediate 59 (30 mg, 100%). LCMS (AA): m/z 350 (M+H); $^1$H NMR (400 MHz, CDCl$_3$) δ 8.35 (s, 1H), 6.41 (d, J=4.1 Hz, 1H), 5.49-5.37 (m, 1H), 5.26 (dd, J=5.9, 4.1 Hz, 1H), 5.11 (dd, J=5.9, 1.2 Hz, 1H), 4.62-4.53 (m, 1H), 3.96 (dd, J=12.7, 1.8 Hz, 1H), 3.86-3.73 (m, 1H), 2.73 (s, 3H), 1.67 (s, 3H), 1.39 (s, 3H).

Step 4: [(3aR,4R,6R,6aR)-6-(3-acetyl-4-amino-1H-pyrazolo[3,4-d]pyrimidin-1-yl)-2,2-dimethyltetrahydrofuro[3,4-d][1,3]dioxol-4-yl]methyl Sulfamate Intermediate 81

To a solution of 1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanone (0.028 g, 0.080 mmol) in DMF (0.7 mL) and triethylamine (0.017 mL, 0.120 mmol) was added chlorosulfonamide (0.014 g, 0.120 mmol). The reaction mixture was stirred at rt for 30 min. The reaction mixture was quenched with water and extracted with ethyl acetate (2×50 mL). The extracts were combined, washed with water and brine, dried over sodium sulfate, filtered and concentrated under reduced pressure. The crude product was used as obtained in the following step. LCMS (AA): m/z 429 (M+H).

Step 5: [(2R,3S,4R,5R)-5-(3-acetyl-4-amino-1H-pyrazolo[3,4-d]pyrimidin-1-yl)-3,4-dihydroxytetrahydrofuran-2-yl]methyl Sulfamate I-21

The titled compound was prepared following the procedure detailed in Example 1 Step 8, substituting [(3aR,4R,6R,6aR)-6-(3-acetyl-4-amino-1H-pyrazolo[3,4-d]pyrimidin-1-yl)-2,2-dimethyltetrahydrofuro[3,4-d][1,3]dioxol-4-yl]methyl sulfamate for Intermediate 8 (18 mg, 58%; 2 steps). LCMS (AA): m/z 389 (M+H); $^1$H NMR (400 MHz, CD$_3$OD) δ 8.24 (s, 1H), 6.40 (d, J=2.3 Hz, 1H), 4.76-4.72 (m, 2H), 4.35 (dd, J=9.3, 2.3 Hz, 1H), 4.33-4.24 (m, 2H), 2.73 (s, 3H).

Example 31: [(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl Sulfamate and [(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl Sulfamate Compounds I-23a & I-23b

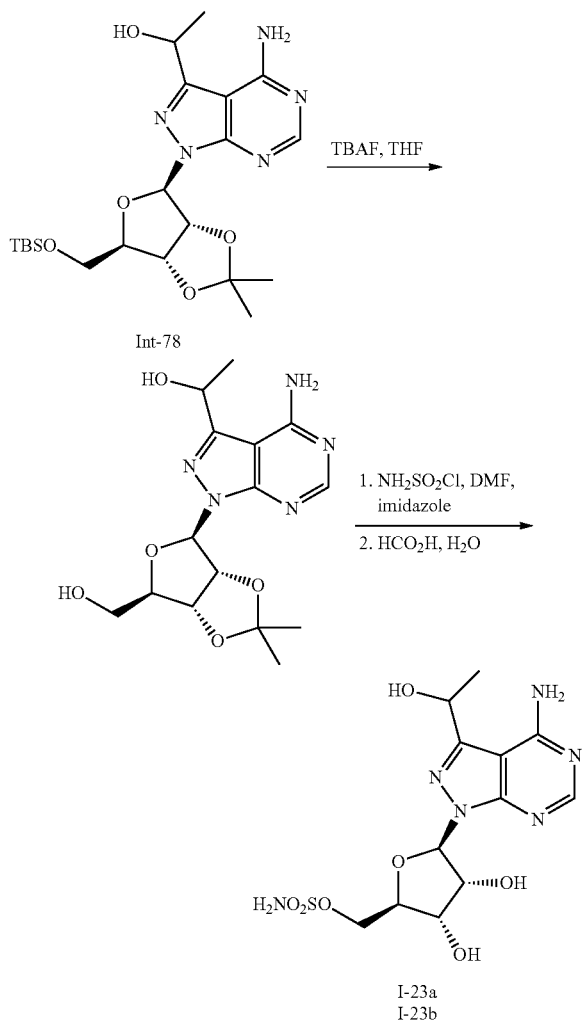

Step 1: (1S)-1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanol and (1R)-1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanol The titled compound was prepared following the procedure detailed in Example 23 Step 2 substituting Intermediate 78 for Intermediate 59 (91 mg, 81%). LCMS (AA): m/z 352 (M+H); $^1$H NMR (400 MHz, CDCl$_3$) δ 8.30 (s, 1H), 6.41 (d, J=3.5 Hz, 1H), 5.23-5.12 (m, 2H), 5.05 (d, J=5.9 Hz, 1H), 4.56-4.49 (m, 1H), 3.96-3.86 (m, 1H), 3.80-3.71 (m, 1H), 3.12-3.03 (m, 1H), 1.68-1.57 (m, 6H), 1.37 (s, 3H).

Step 2: [(3aR,4R,6R,6aR)-6-{4-amino-3-[(1S)-1-hydroxyethyl]-1H-pyrazolo[3,4-d]pyrimidin-1-yl}-2,2-dimethyltetrahydrofuro[3,4-d][1,3]dioxol-4-yl]methyl Sulfamate and [(3aR,4R,6R,6aR)-6-{4-amino-3-[(1R)-1-hydroxyethyl]-1H-pyrazolo[3,4-d]pyrimidin-1-yl}-2,2-dimethyltetrahydrofuro[3,4-d][1,3]dioxol-4-yl]methyl Sulfamate To a 0° C. solution of (1S)-1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanol and (1R)-1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanol (0.092 g, 0.262 mmol) in DMF (2.0 mL) was added 1H-imidazole (0.021 g, 0.314 mmol) and chlorosulfonamide (0.036 g, 0.314 mmol). The mixture was stirred with cooling for 0.5 h. Additional 1H-imidazole (0.007 g, 0.105 mmol) and chlorosulfonamide (0.012 g, 0.105 mmol) were added and stirring was continued for 1 h. The reaction was quenched with water and extracted with ethyl acetate (2×50 mL). The extracts were combined, washed with water and brine, dried over sodium sulfate, filtered and concentrated under reduced pressure. The crude product was used as obtained in the following step. LCMS (AA): m/z 431 (M+H).

Step 3: [(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl sulfamate or [(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl Sulfamate Compound I-23a (Peak 1) and [(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl Sulfamate or [(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl Sulfamate Compound I-23b (Peak 2)

The titled compounds were prepared following the procedure detailed in Example 1 Step 8, substituting [(3aR,4R,6R,6aR)-6-{4-amino-3-[(1S)-1-hydroxyethyl]-1H-pyrazolo[3,4-d]pyrimidin-1-yl}-2,2-dimethyltetrahydrofuro[3,4-d][1,3]dioxol-4-yl]methyl sulfamate and [(3aR,4R,6R,6aR)-6-{4-amino-3-[(1R)-1-hydroxyethyl]-1H-pyrazolo[3,4-d]pyrimidin-1-yl}-2,2-dimethyltetrahydrofuro[3,4-d][1,3]dioxol-4-yl]methyl sulfamate for [(3aR,4R,6R,6aR)-6-(4-amino-3-ethoxy-1H-pyrazolo[3,4-d]pyrimidin-1-yl)-2,2-dimethyltetrahydrofuro[3,4-d][1,3]dioxol-4-yl]methyl sulfamate. The diastereomers were separated by preparative reverse phase HPLC as Peak 1 and Peak 2. Absolute configuration of the products is unknown.

Peak 1 (Compound I-23a)

(18 mg, 18%) LCMS (AA): m/z 391 (M+H); $^1$H NMR (400 MHz, CD$_3$OD) δ 8.20 (s, 1H), 6.28 (d, J=3.4 Hz, 1H), 5.13-5.07 (m, 1H), 4.67 (dd, J=5.1, 3.4 Hz, 1H), 4.58-4.54 (m, 1H), 4.36-4.32 (m, 1H), 4.26-4.18 (m, 2H), 1.55 (d, J=6.6 Hz, 3H).

Peak 2 (Compound I-23b)

(7 mg, 7%) LCMS (AA): m/z 391 (M+H); $^1$H NMR (400 MHz, CD$_3$OD) δ 8.19 (s, 1H), 6.28 (d, J=3.2 Hz, 1H), 5.13-5.05 (m, 1H), 4.64 (dd, J=5.1, 3.2 Hz, 1H), 4.60-4.56 (m, 1H), 4.37-4.33 (m, 1H), 4.27-4.19 (m, 2H), 1.56 (d, J=6.6 Hz, 3H).

Example 32: [(2R,3S,4R,5R)-5-{4-amino-3-[(1R)-1-methoxyethyl]-1H-pyrazolo[3,4-d]pyrimidin-1-yl}-3,4-dihydroxytetrahydrofuran-2-yl]methyl Sulfamate and [(2R,3S,4R,5R)-5-{4-amino-3-[(1S)-1-methoxyethyl]-1H-pyrazolo[3,4-d]pyrimidin-1-yl}-3,4-dihydroxytetrahydrofuran-2-yl]methyl Sulfamate Compound I-22

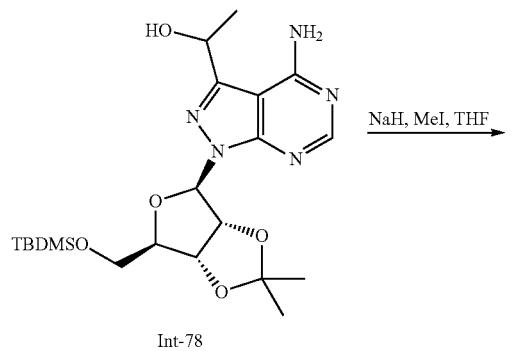

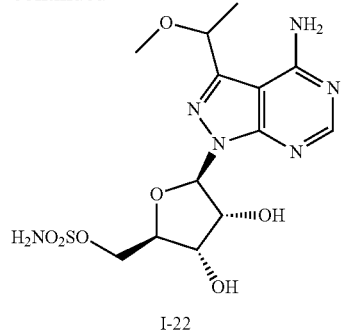

Step 1: 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-[(1S)-1-methoxyethyl]-1H-pyrazolo[3,4-d]pyrimidin-4-amine and 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-[(1R)-1-methoxyethyl]-1H-pyrazolo[3,4-d]pyrimidin-4-amine The titled compound was prepared following the procedure detailed in Example 24 Step 3 substituting Intermediate 78 for Intermediate 63 to provide the product as an inseparable mixture of diastereomers (69 mg, 47%). LCMS (AA): m/z 481 (M+H); $^1$H NMR (400 MHz, CDCl$_3$) δ 8.37-8.35 (m, 1H), 6.51-6.49 (m, 1H), 5.49-5.45 (m, 1H), 5.01-4.98 (m, 1H), 4.71-4.63 (m, 1H), 4.31-4.26 (m, 1H), 3.75-3.68 (m, 1H), 3.62-3.55 (m, 1H), 3.35-3.30 (m, 3H), 1.62-1.59 (m, 3H), 1.54-1.49 (m, 3H), 1.42-1.38 (m, 3H), 0.88-0.86 (m, 9H), 0.00--0.03 (m, 6H).

Step 2: [(3aR,4R,6R,6aR)-6-{4-amino-3-[(1S)-1-methoxyethyl]-1H-pyrazolo[3,4-d]pyrimidin-1-yl}-2,2-dimethyltetrahydrofuro[3,4-d][1,3]dioxol-4-yl]methanol and [(3aR,4R,6R,6aR)-6-{4-amino-3-[(1R)-1-methoxyethyl]-1H-pyrazolo[3,4-d]pyrimidin-1-yl}-2,2-dimethyltetrahydrofuro[3,4-d][1,3]dioxol-4-yl]methanol The titled compound was prepared following the procedure detailed in Example 23 Step 2 substituting 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-[(1S)-1-methoxyethyl]-1H-pyrazolo[3,4-d]pyrimidin-4-amine and 1-[(3aR,4R,6R,6aR)-6-({[tert-butyl(dimethyl)silyl]oxy}methyl)-2,2-dimethyltetrahydrofuro[3,4-d][1,3]dioxol-4-yl]-3-[(1R)-1-methoxyethyl]-1H-pyrazolo[3,4-d]pyrimidin-4-amine for Intermediate 59 to provide the product as an inseparable mixture of diastereomers (91 mg, 81%). LCMS (AA): m/z 366 (M+H); $^1$H NMR (400 MHz, CDCl$_3$) δ 8.37-8.34 (m, 1H), 6.42-6.39 (m, 1H), 5.67-5.59 (m, 1H), 5.24-5.19 (m, 1H), 5.12-5.07 (m, 1H), 4.73-4.67 (m, 1H), 4.55-4.53 (m, 1H), 3.97-3.92 (m, 1H), 3.80-3.72 (m, 1H), 3.37-3.33 (m, 3H), 1.68-1.62 (m, 3H), 1.54-1.50 (m, 3H), 1.39-1.37 (m, 3H).

Step 3: [(3aR,4R,6R,6aR)-6-{4-amino-3-[(1S)-1-methoxyethyl]-1H-pyrazolo[3,4-d]pyrimidin-1-yl}-2,2-dimethyltetrahydrofuro[3,4-d][1,3]dioxol-4-yl]methyl Sulfamate and [(3aR,4R,6R,6aR)-6-{4-amino-3-[(1R)-1-methoxyethyl]-1H-pyrazolo[3,4-d]pyrimidin-1-yl}-2,2-dimethyltetrahydrofuro[3,4-d][1,3]dioxol-4-yl]methyl Sulfamate The titled compound was prepared following the procedure detailed in Example 1 Step 7, substituting [(3aR,4R, 6R,6aR)-6-{4-amino-3-[(1S)-1-methoxyethyl]-1H-pyrazolo [3,4-d]pyrimidin-1-yl}-2,2-dimethyltetrahydrofuro[3,4-d] [1,3]dioxol-4-yl]methanol and [(3aR,4R,6R,6aR)-6-{4-amino-3-[(1R)-1-methoxyethyl]-1H-pyrazolo[3,4-d] pyrimidin-1-yl}-2,2-dimethyltetrahydrofuro[3,4-d][1,3] dioxol-4-yl]methanol for Intermediate 7. The crude product was used as obtained in the following step. LCMS (AA): m/z 445 (M+H).

Step 4: [(2R,3S,4R,5R)-5-{4-amino-3-[(1R)-1-methoxyethyl]-1H-pyrazolo[3,4-d]pyrimidin-1-yl}-3,4-dihydroxytetrahydrofuran-2-yl]methyl Sulfamate and [(2R,3S,4R,5R)-5-{4-amino-3-[(1S)-1-methoxyethyl]-1H-pyrazolo[3,4-d]pyrimidin-1-yl}-3,4-dihydroxytetrahydrofuran-2-yl]methyl Sulfamate Compound I-22

The titled compound was prepared following the procedure detailed in Example 1 Step 8, substituting [(3aR,4R,6R,6aR)-6-{4-amino-3-[(1S)-1-methoxyethyl]-1H-pyrazolo [3,4-d]pyrimidin-1-yl}-2,2-dimethyltetrahydrofuro[3,4-d] [1,3]dioxol-4-yl]methyl sulfamate and [(3aR,4R,6R,6aR)-6-{4-amino-3-[(1R)-1-methoxyethyl]-1H-pyrazolo[3,4-d] pyrimidin-1-yl}-2,2-dimethyltetrahydrofuro[3,4-d][1,3] dioxol-4-yl]methyl sulfamate for Intermediate 8 to provide the product as a mixture of diastereomers (30 mg, 91%; 2 steps). LCMS (AA): m/z 405 (M+H); $^1$H NMR (400 MHz, CD$_3$OD) δ 8.23-8.22 (m, 1H), 6.30-6.28 (m, 1H), 4.77-4.71 (m, 1H), 4.70-4.67 (m, 1H), 4.61-4.56 (m, 1H), 4.37-4.31 (m, 1H), 4.27-4.19 (m, 2H), 3.36-3.35 (m, 3H), 1.54-1.49 (m, 3H).

Example 33: {(2R,3S,4R,5R)-5-[4-amino-3-(2-hydroxypropan-2-yl)-1H-pyrazolo[3,4-d]pyrimidin-1-yl]-3,4-dihydroxytetrahydrofuran-2-yl}methyl Sulfamate Compound I-24

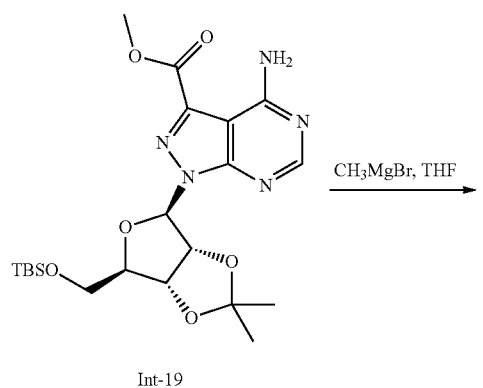

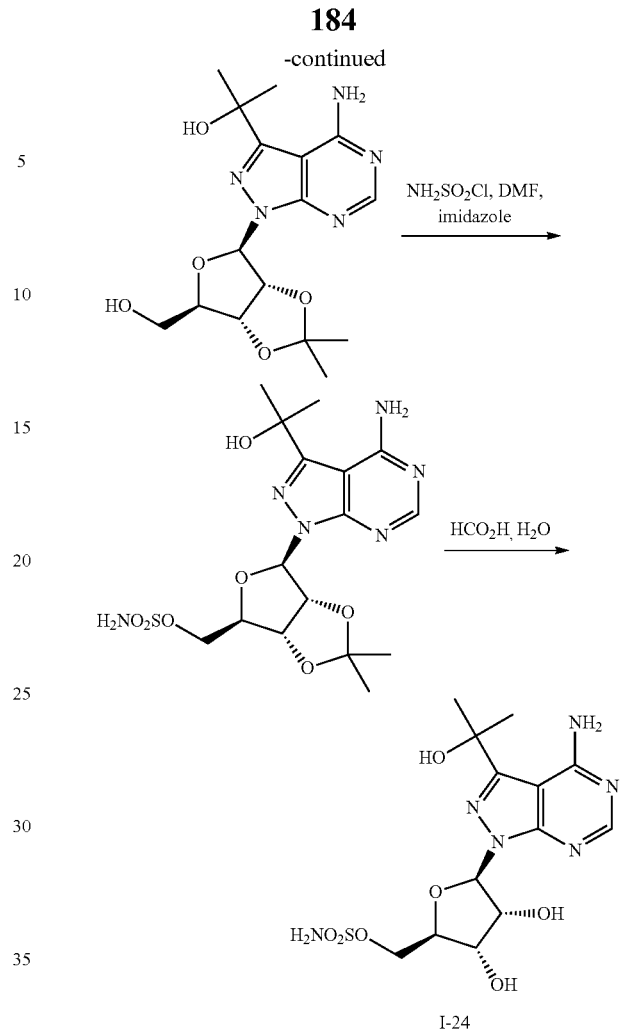

Step 1: 2-{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}propan-2-ol The titled compound was prepared following the procedure detailed in Example 30 Step 1 substituting Intermediate 19 for Intermediate 62 (371 mg, 67%). LCMS (AA): m/z 480 (M+H); $^1$H NMR (300 MHz, CDCl$_3$) δ 8.25 (s, 1H), 7.37 (br s, 2H), 6.51 (d, J=2.0 Hz, 1H), 5.39 (dd, J=6.1, 2.0 Hz, 1H), 4.97 (dd, J=6.1, 2.1 Hz, 1H), 4.36-4.27 (m, 1H), 3.74 (dd, J=10.4, 7.7 Hz, 1H), 3.61 (dd, J=10.5, 5.6 Hz, 1H), 1.73-1.68 (m, 6H), 1.61 (s, 3H), 1.41 (s, 3H), 0.87 (d, J=2.8 Hz, 9H), 0.00 (d, J=2.9 Hz, 6H).

Step 2: 2-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl})propan-2-ol The titled compound was prepared following the procedure detailed in Example 23 step 2 substituting 2-{4-amino-1-[(3aR,4R,6R,6aR)-6-({[tert-butyl(dimethyl)silyl] oxy}methyl)-2,2-dimethyltetrahydrofuro[3,4-d][1,3]dioxol-4-yl]-1H-pyrazolo[3,4-d]pyrimidin-3-yl}propan-2-ol for Intermediate 59 (37 mg, 97%). $^1$H NMR (300 MHz, CDCl$_3$) δ 8.28 (s, 1H), 7.10-6.53 (m, 2H), 6.47 (d, J=3.3 Hz, 1H), 5.20 (dd, J=5.9, 3.3 Hz, 1H), 5.07 (dd, J=5.9, 1.1 Hz, 1H), 4.56-4.51 (m, 1H), 3.91 (dd, J=12.7, 1.8 Hz, 1H), 3.76 (dd, J=12.7, 2.7 Hz, 1H), 2.79 (s, 1H), 1.71 (s, 3H), 1.68 (s, 3H), 1.65 (s, 3H), 1.38 (s, 3H).

Step 3: {(3aR,4R,6R,6aR)-6-[4-amino-3-(2-hydroxypropan-2-yl)-1H-pyrazolo[3,4-d]pyrimidin-1-yl]-2,2-dimethyltetrahydrofuro[3,4-d][1,3]dioxol-4-yl}methyl Sulfamate The titled compound was prepared following the procedure detailed in Example 31 Step 2 substituting 2-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}propan-2-ol for 1-{4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}ethanol. The crude product was used as obtained in the following step. LCMS (AA): m/z 445 (M+H).

Step 4: {(2R,3S,4R,5R)-5-[4-amino-3-(2-hydroxypropan-2-yl)-1H-pyrazolo[3,4-d]pyrimidin-1-yl]-3,4-dihydroxytetrahydrofuran-2-yl}methyl Sulfamate Compound I-24

The titled compound was prepared following the procedure detailed in Example 1 Step 8, substituting {(3aR,4R,6R,6aR)-6-[4-amino-3-(2-hydroxypropan-2-yl)-1H-pyrazolo[3,4-d]pyrimidin-1-yl]-2,2-dimethyltetrahydrofuro[3,4-d][1,3]dioxol-4-yl}methyl sulfamate for Intermediate 8 (11 mg, 28%; 2 steps). LCMS (AA): m/z 405 (M+H); $^1$H NMR (400 MHz, CD$_3$OD) δ 8.18 (s, 1H), 6.30 (d, J=2.4 Hz, 1H), 4.66-4.61 (m, 2H), 4.38-4.32 (m, 1H), 4.27-4.19 (m, 2H), 1.64 (s, 3H), 1.63 (s, 3H).

Example 34: [(2R,3S,4R,5R)-5-(4-amino-3-cyclopropyl-1H-pyrazolo[3,4-d]pyrimidin-1-yl)-3,4-dihydroxytetrahydrofuran-2-yl]methyl Sulfamate Compound I-26

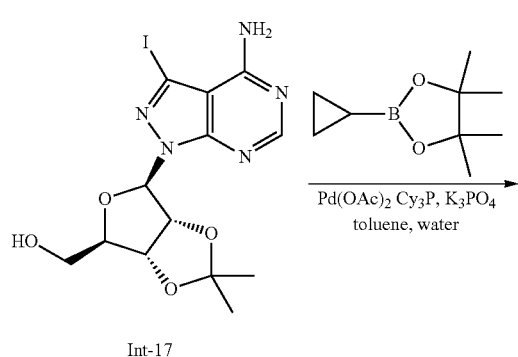

Int-17

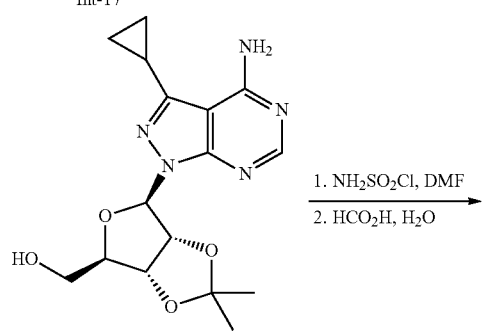

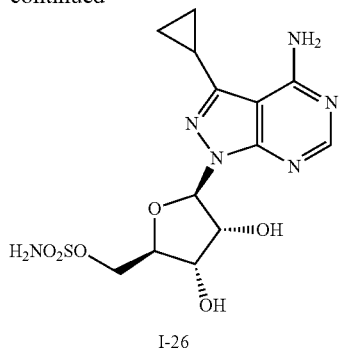

I-26

Step 1: [(3aR,4R,6R,6aR)-6-(4-amino-3-cyclopropyl-1H-pyrazolo[3,4-d]pyrimidin-1-yl)-2,2-dimethyltetrahydrofuro[3,4-d][1,3]dioxol-4-yl]methanol A mixture of Intermediate 17 (0.120 g, 0.277 mmol), cyclopropylboronic acid pinacol ester (0.047 g, 0.554 mmol) and potassium phosphate (0.176 g, 0.831 mmol) in toluene (1.2 mL) and water (0.24 mL) was flushed with argon. Palladium(II) acetate (0.012 g, 0.055 mmol) and tricyclohexylphosphine (0.031 g, 0.111 mmol) were added and the reaction mixture was heated at 100° C. with stirring overnight. The reaction mixture was cooled to rt. Water was added and the mixture was extracted with ethyl acetate (2×50 mL). The extracts were combined, washed with water and brine, dried over sodium sulfate, filtered and concentrated under reduced pressure. The crude product was purified by silica gel chromatography (24 g, DCM to 90/10 DCM/MeOH gradient) to afford the product as a white solid (47 mg, 49%). LCMS (AA): m/z 348 (M+H); $^1$H NMR (400 MHz, CDCl$_3$) δ 8.33 (s, 1H), 6.46 (d, J=3.2 Hz, 1H), 5.88 (bs, 2H), 5.15 (dd, J=5.9, 3.2 Hz, 1H), 5.10-5.06 (m, 1H), 4.56-4.51 (m, 1H), 3.93 (dd, J=12.8, 1.6 Hz, 1H), 3.75 (dd, J=12.9, 2.4 Hz, 1H), 2.09-2.00 (m, 2H), 1.12-0.99 (m, 4H).

Step 2: [(3aR,4R,6R,6aR)-6-(4-amino-3-cyclopropyl-1H-pyrazolo[3,4-d]pyrimidin-1-yl)-2,2-dimethyltetrahydrofuro[3,4-d][1,3]dioxol-4-yl]methyl Sulfamate The titled compound was prepared following the procedure detailed in Example 1 Step 7, substituting [(3aR,4R,6R,6aR)-6-(4-amino-3-cyclopropyl-1H-pyrazolo[3,4-d]pyrimidin-1-yl)-2,2-dimethyltetrahydrofuro[3,4-d][1,3]dioxol-4-yl]methanol for Intermediate 7. The crude product was used as obtained in the following step. LCMS (AA): m/z 427 (M+H).

Step 3: [(2R,3S,4R,5R)-5-(4-amino-3-cyclopropyl-1H-pyrazolo[3,4-d]pyrimidin-1-yl)-3,4-dihydroxytetrahydrofuran-2-yl]methyl Sulfamate I-26

The titled compound was prepared following the procedure detailed in Example 1 Step 8, substituting [(3aR,4R,6R,6aR)-6-(4-amino-3-cyclopropyl-1H-pyrazolo[3,4-d]pyrimidin-1-yl)-2,2-dimethyltetrahydrofuro[3,4-d][1,3]dioxol-4-yl]methyl sulfamate for Intermediate 8 (25 mg, 50%; 2 steps). LCMS (AA): m/z 387 (M+H); $^1$H NMR (400 MHz, CD$_3$OD) δ 8.15 (s, 1H), 6.23 (d, J=3.2 Hz, 1H), 4.59

(dd, J=5.1, 3.2 Hz, 1H), 4.56-4.51 (m, 1H), 4.33 (dd, J=9.8, 2.7 Hz, 1H), 4.24-4.14 (m, 2H), 2.29-2.21 (m, 1H), 1.05-1.00 (m, 4H).

Example 35: {(2R,3S,4R,5R)-5-[4-amino-3-(phenylsulfanyl)-1H-pyrazolo[3,4-d]pyrimidin-1-yl]-3,4-dihydroxytetrahydrofuran-2-yl}methyl Sulfamate Compound I-82

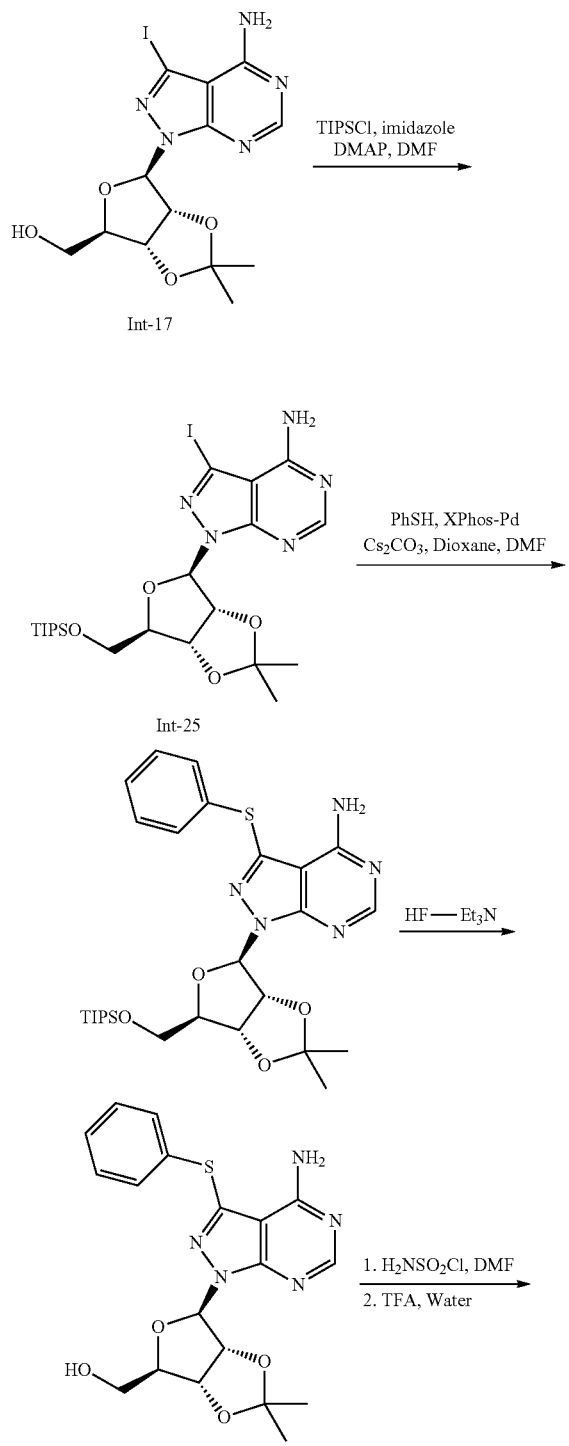

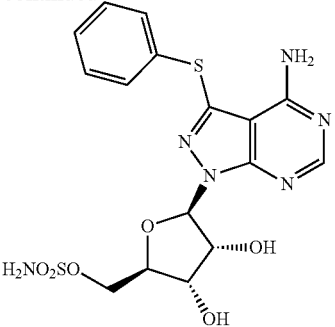

I-82

Step 1: 1-[(3aR,4R,6R,6aR)-2,2-dimethyl-6-{[(triisopropylsilyl)oxy]methyl}tetrahydrofuro[3,4-d][1,3]dioxol-4-yl]-3-iodo-1H-pyrazolo[3,4-d]pyrimidin-4-amine (Intermediate 25)

Into a stirred solution of Intermediate 17 (1.84 g, 4.25 mmol) in DMF (18.40 mL) was added 1H-imidazole (1.5 g, 23 mmol), DMAP (103.8 mg, 0.850 mmol) and triisopropylsilyl chloride (4.5 mL) at rt under an atmosphere of argon. The reaction mixture was allowed to stir at rt overnight. After completion, the reaction was quenched by the addition of a saturated $NH_4Cl$ solution at 0° C. and the mixture was extracted with EtOAc. The extracts were combined, washed with water and brine, dried over $Na_2SO_4$, filtered and concentrated under reduced pressure. The crude product was purified by silica gel chromatography (0-50% EtOAc in hexane gradient) to afford the product as a white solid (2.16 g, 86%). LCMS (FA): m/z=590 (M+H); $^1$H NMR (400 MHz, $CDCl_3$) δ 8.36 (s, 1H), 6.52 (d, J=1.6 Hz, 1H), 6.07 (br s, 2H), 5.47 (dd, J=6.1, 1.6 Hz, 1H), 5.05 (dd, J=6.1, 1.9 Hz, 1H), 4.36 (ddd, J=7.9, 5.8, 1.9 Hz, 1H), 3.79 (dd, J=10.2, 8.2 Hz, 1H), 3.66 (dd, J=10.2, 5.6 Hz, 1H), 1.61 (s, 3H), 1.41 (s, 3H), 0.95-1.09 (m, 21H).

Step 2: 1-[(3aR,4R,6R,6aR)-2,2-dimethyl-6-{[(triisopropylsilyl)oxy]methyl}tetrahydrofuro[3,4-d][1,3]dioxol-4-yl]-3-(phenylsulfanyl)-1H-pyrazolo[3,4-d]pyrimidin-4-amine Intermediate 25 (200 mg, 0.3 mmol), benzenethiol (69.7 uL, 0.678 mmol), cesium carbonate (221 mg, 0.678 mmol), and Pd-XPhos (50.1 mg, 0.068 mmol) were dissolved in dioxane (2.65 mL). The reaction mixture was degassed, purged with argon and allowed to stir at 100° C. for 5 h in an oil bath. The reaction mixture was then subjected to microwave irradiation at 150° C. for 30 min. The reaction mixture was then diluted with EtOAc, filtered and concentrated. The crude compound was purified by column chromatography to give 1-[(3aR,4R,6R,6aR)-2,2-dimethyl-6-{[(triisopropylsilyl)oxy]methyl}tetrahydrofuro[3,4-d][1,3]dioxol-4-yl]-3-(phenylsulfanyl)-1H-pyrazolo[3,4-d]pyrimidin-4-amine (547 mg, 99.7%) as a white solid. LCMS (FA): m/z=572 (M+H).

Step 3: {(3aR,4R,6R,6aR)-6-[4-amino-3-(phenylsulfanyl)-1H-pyrazolo[3,4-d]pyrimidin-1-yl]-2,2-dimethyltetrahydrofuro[3,4-d][1,3]dioxol-4-yl}methanol The titled compound was prepared as described in Example 65 Step 7 substituting 1-[(3aR,4R,6R,6aR)-2,2-dimethyl-6-{[(triisopropylsilyl)oxy]methyl}tetrahydrofuro[3,4-d][1,3]dioxol-4-yl]-3-(phenylsulfanyl)-1H-pyrazolo[3,4-d]pyrimidin-4-amine for {(2R,3R,4S,5R)-5-[4-amino-3-(isopropylsulfanyl)-1H-pyrazolo[3,4-d]pyrimidin-1-yl]-4- fluoro-3-[(triisopropylsilyl)oxy]tetrahydrofuran-2-yl}methyl sulfamate. LCMS (FA): m z=416 (M+H).

Step 4: {(3aR,4R,6R,6aR)-6-[4-amino-3-(phenylsulfanyl)-1H-pyrazolo[3,4-d]pyrimidin-1-yl]-2,2-dimethyltetrahydrofuro[3,4-d][1,3]dioxol-4-yl}methyl Sulfamate The titled compound was prepared as described in Example 1 Step 7 substituting {(3aR,4R,6R,6aR)-6-[4-amino-3-(phenylsulfanyl)-1H-pyrazolo[3,4-d]pyrimidin-1-yl]-2,2-dimethyltetrahydrofuro[3,4-d][1,3]dioxol-4-yl}methanol for Intermediate 7, which was used without further purification in the following step. LCMS (FA): m/z=495 (M+H).

Step 5: {(2R,3S,4R,5R)-5-[4-amino-3-(phenylsulfanyl)-1H-pyrazolo[3,4-d]pyrimidin-1-yl]-3,4-dihydroxytetrahydrofuran-2-yl}methyl Sulfamate I-82

To {(3aR,4R,6R,6aR)-6-[4-amino-3-(phenylsulfanyl)-1H-pyrazolo[3,4-d]pyrimidin-1-yl]-2,2-dimethyltetrahydrofuro[3,4-d][1,3]dioxol-4-yl}methyl sulfamate from Step 4 (70 mg, 0.14 mmol) was added a solution of TFA and water (0.112 mL, 10:1 TFA:water). The reaction mixture was allowed to stir for 2.5 h and then concentrated under reduced pressure. The crude material was purified by preparative reverse phase HPLC to obtain the titled compound (23 mg, 40%). LCMS (FA): m/z=455 (M+H); $^1$H NMR (400 MHz, $d_6$-DMSO) δ 8.27 (s, 1H), 7.54 (s, 2H), 7.23-7.40 (m, 5H), 6.20 (d, J=3.3 Hz, 1H), 4.45-4.65 (m, 1H), 4.33 (t, J=5.3 Hz, 1H), 4.24 (dd, J=10.5, 3.3 Hz, 1H), 4.15 (td, J=6.5, 3.5 Hz, 1H), 4.01 (dd, J=10.5, 7.5 Hz, 1H).

Example 36

The following compounds were prepared following the procedures in Example 35 using Intermediate 25 with the reagents and conditions described in the table below.

| Compound number | Reagent Used with Intermediate 25 in Transition-metal catalyzed Couplling | Transition-metal Catalyzed Coupling Conditions | Final deprotection conditions | LCMS data | $^1$H NMR Data |
|---|---|---|---|---|---|
| I-92 | 2-methyltetrahydrofuran-3-thiol | CuI, TBAB, 190° C. 1.5 h MW NaOtBu | Example 35 Step 5 | LCMS (FA): m/z 463 (M + H) | $^1$H NMR (400 MHz, $d_6$-DMSO) δ 8.22 (s, 1H), 7.53 (s, 2H), 6.04-6.21 (m, 1H), 4.42-4.52 (m, 1H), 4.34-4.41 (m, 1H), 4.16-4.31 (m, 3H), 4.10-4.15 (m, 1H), 3.86-4.07 (m, 2H), 3.65-3.77 (m, 1H), 3.51-3.62 (m, 1H), 1.90-2.10 (m, 1H), 1.17-1.27 (m, 3H). |
| I-30 | 2-(tributylstannyl)thiazole | Pd(PPh$_3$)$_4$, CuI, LiCl, dioxane | Example 35 Step 5 | LCMS (FA): m/z 430 (M + H) | $^1$H NMR (400 MHz, $d_6$-DMSO) δ 9.24 (br d, J = 2.9 Hz, 1H), 8.28-8.37 (m, 2H), 8.11 (d, J = 3.3 Hz, 1H), 7.95 (d, J = 3.3 Hz, 1H), 7.53 (s, 2H), 6.24 (d, J = 3.3 Hz, 1H), 4.49-4.68 (m, 1H), 4.43 (t, J = 5.3 Hz, 1H), 4.30 (dd, J = 10.3, 3.1 Hz, 1H), 4.06-4.22 (m, 2H). |
| I-52 | phenylmethanethiol | Xphos precatalyst, 115° C. ON Cs$_2$CO$_3$ DMF | Example 3 Step 7 | LCMS (FA): m/z 469 (M + H) | $^1$H NMR (400 MHz, CD$_3$OD) δ 8.18 (s, 1H), 7.31-7.36 (m, 2H), 7.20-7.30 (m, 3H), 6.21-6.36 (m, 1H), 4.53-4.71 (m, 2H), 4.34-4.42 (m, 3H), 4.18-4.31 (m, 2H). |
| I-57 | 2-(tributylstannyl)oxazole | Pd(PPh$_3$)$_4$, CuI, LiCl | Example 35 Step 5 | LCMS (FA): m/z 414 (M + H) | $^1$H NMR (400 MHz, $d_6$-DMSO) δ 8.29 (d, J = 0.8 Hz, 1H), 8.26 (s, 1H), 7.55 (d, J = 0.8 Hz, 1H), 6.21 (d, J = 3.5 Hz, 1H), 4.49-4.65 (m, 1H), 4.38 (t, J = 5.4 Hz, 1H), 4.24 (dd, J = 10.5, 3.3 Hz, 1H), 4.14 (td, J = 6.4, 3.3 Hz, 1H), 4.04 (dd, J = 10.3, 7.3 Hz, 1H). |
| I-68 | 1-(tetrahydro-2H-pyran-2-yl)-3-(4,4,5,5-tetramethyl-1,3,2-dioxaborolan-2-yl)-1H-pyrazole | Pd(PPh$_3$)$_4$, 100° C. ON Cs$_2$CO$_3$ | Example 35 Step 5 | LCMS (FA): m/z 413 (M + H) | $^1$H NMR (400 MHz, $d_6$-DMSO) δ 9.31 (br d, J = 3.3 Hz, 1H), 8.21 (s, 1H), 8.05 (br s, 1H), 7.95 (d, J = 2.5 Hz, 1H), 6.83 (d, J = 2.5 Hz, 1H), 6.20 (d, J = 3.8 Hz, 1H), 5.61 (br d, J = 4.0 Hz, 1H), 5.38 (br s, 1H), 4.51-4.62 (m, 1H), 4.35-4.48 (m, 1H), 4.27 (dd, J = 9.7, 2.6 Hz, 1H), 4.01-4.18 (m, 2H). |

-continued

| Compound number | Reagent Used with Intermediate 25 in Transition-metal catalyzed Couplling | Transition-metal Catalyzed Coupling Conditions | Final deprotection conditions | LCMS data | ¹H NMR Data |
|---|---|---|---|---|---|
| I-53 | potassium 2-methyl-propane-2-thiolate | (PPh$_3$)$_4$Pd, Cs$_2$CO$_3$, dioxane, 100° C. | Example 1 Step 8 | LCMS (FA) m/z 435 (M + H) | ¹H NMR (400 MHz, CD$_3$OD) δ 8.23 (s, 1H), 6.34 (d, J = 3.0 Hz, 1H), 4.69 (dd, J = 4.8, 3.1 Hz, 1H), 4.57 (t, J = 5.5 Hz, 1H), 4.34-4.40 (m, 1H), 4.26-4.32 (m, 1H), 4.18-4.24 (m, 1H), 1.43 (s, 9H). |
| I-79 | | No palladium coupling | Example 1 Step 8 | LCMS (FA) m/z 473 (M + H) | ¹H NMR (400 MHz, CD$_3$OD) δ 8.22 (s, 1H), 6.25 (d, J = 3.4 Hz, 1H), 4.68 (t, J = 4.2 Hz, 1H), 4.51 (t, J = 5.2 Hz, 1H), 4.30-4.40 (m, 1H), 4.16-4.29 (m, 2H). |
| I-84 | naphthalene-1-thiol | Pd/XPhos, Cs$_2$CO$_3$, DMF, 120° C. | Example 1 Step 8 | LCMS (FA) m/z 505 (M + H) | ¹H NMR (400 MHz, CD$_3$OD) δ 8.46 (d, J = 8.4 Hz, 1H), 8.21 (s, 1H), 7.92 (dd, J = 20.0, 8.0 Hz, 2H), 7.53-7.69 (m, 3H), 7.41-7.50 (m, 1H), 6.27 (d, J = 2.5 Hz, 1H), 4.47 (dd, J = 4.8, 2.8 Hz, 1H), 4.23-4.32 (m, 1H), 4.11-4.22 (m, 2H), 3.92 (dd, J = 10.8, 6.9 Hz, 1H). |
| I-34 | 2,4-dichloro-benzenethiol | Pd/XPhos, Cs$_2$CO$_3$, DMF, 120° C. | Example 1 Step 8 | LCMS (FA) m/z 525 (M + 2) | ¹H NMR (400 MHz, CD$_3$OD) δ 8.26 (s, 1H), 7.57 (s, 1H), 7.27 (br d, J = 8.3 Hz, 1H), 7.04 (d, J = 8.5 Hz, 1H), 6.25-6.46 (m, 1H), 4.60-4.75 (m, 1H), 4.52 (br t, J = 5.0 Hz, 1H), 4.24-4.35 (m, 2H), 4.13-4.21 (m, 1H). |
| I-40 | 3-chloro-benzenethiol | Pd/XPhos, Cs$_2$CO$_3$, DMF, 120° C. | Example 1 Step 8 | LCMS (FA) m/z 489 (M + H) | ¹H NMR (400 MHz, CD$_3$OD) δ 8.25 (s, 1H), 7.41 (t, J = 1.7 Hz, 1H), 7.21-7.36 (m, 3H), 6.35 (d, J = 3.3 Hz, 1H), 4.70 (dd, J = 5.0, 3.5 Hz, 1H), 4.53 (t, J = 5.5 Hz, 1H), 4.24-4.39 (m, 2H), 4.15-4.23 (m, 1H). |
| I-78 | 2-chloroben-zenethiol | Pd/XPhos, Cs$_2$CO$_3$, DMF, 120° C. | Example 1 Step 8 | LCMS (FA) m/z 489 (M + H) | ¹H NMR (400 MHz, CD$_3$OD) δ 8.26 (s, 1H), 7.45-7.54 (m, 1H), 7.17-7.32 (m, 2H), 7.02-7.09 (m, 1H), 6.35 (d, J = 3.0 Hz, 1H), 4.68 (dd, J = 5.0, 3.1 Hz, 1H), 4.51 (t, J = 5.4 Hz, 1H), 4.24-4.35 (m, 2H), 4.09-4.20 (m, 1H). |
| I-64 | 4-chloroben-zenethiol | Pd/XPhos, Cs$_2$CO$_3$, DMF, 120° C. | Example 1 Step 8 | LCMS (FA) m/z 489 (M + H) | ¹H NMR (400 MHz, CD$_3$OD) δ 8.23 (br s, 1H), 7.10-7.55 (m, 4H), 6.29-6.37 (m, 1H), 4.64-4.72 (m, 1H), 4.48-4.57 (m, 1H), 4.24-4.36 (m, 2H), 4.20 (br d, J = 6.4 Hz, 1H). |
| I-74 | 2-methylben-zenethiol | P Pd/XPhos, Cs$_2$CO$_3$, DMF, 120° C. | Example 1 Step 8 | LCMS (FA) m/z 469 (M + H) | ¹H NMR (400 MHz, CD$_3$OD) δ 8.22 (s, 1H), 7.30 (br d, J = 7.4 Hz, 1H), 7.11-7.26 (m, 3H), 6.27-6.34 (m, 1H), 4.53-4.60 (m, 1H), 4.39 (br t, J = 5.1 Hz, 1H), 4.23 (br d, J = 7.4 Hz, 2H), 4.01-4.07 (m, 1H), 2.47 (s, 3H). |
| I-69 | 3-methylben-zenethiol | Pd/XPhos, Cs$_2$CO$_3$, DMF, 120° C. | Example 1 Step 8 | LCMS (FA) m/z 469 (M + H) | ¹H NMR (400 MHz, CD$_3$OD) δ 8.22 (s, 1H), 7.20-7.25 (m, 2H), 7.12 (dd, J = 16.4, 7.7 Hz, 2H), 6.33 (d, J = 3.1 Hz, 1H), 4.68 (dd, J = 4.9, 3.3 Hz, 1H), 4.52 (t, J = 5.4 Hz, 1H), 4.30-4.36 (m, 1H), 4.25-4.30 (m, 1H), 4.15-4.20 (m, 1H), 2.30 (s, 3H). |

-continued

| Compound number | Reagent Used with Intermediate 25 in Transition-metal catalyzed Couplling | Transition-metal Catalyzed Coupling Conditions | Final deprotection conditions | LCMS data | $^1$H NMR Data |
|---|---|---|---|---|---|
| I-89 | 4-methylbenzenethiol | Pd/XPhos, Cs$_2$CO$_3$, DMF, 120° C. | Example 1 Step 8 | LCMS (FA) m/z 469 (M + H) | $^1$H NMR (400 MHz, CD$_3$OD) δ 8.21 (s, 1H), 7.30 (br d, J = 7.5 Hz, 2H), 7.18 (br d, J = 7.7 Hz, 2H), 6.26-6.35 (m, 1H), 4.61-4.68 (m, 1H), 4.51 (br t, J = 5.1 Hz, 1H), 4.22-4.36 (m, 2H), 4.11-4.20 (m, 1H), 2.31 (s, 3H). |
| I-33 | (4-(trifluoromethoxy)phenyl)methanethiol | Pd/XPhos, Cs$_2$CO$_3$, dioxane, 150° C. | Example 1 Step 8 | LCMS (FA) m/z 537 (M + H) | $^1$H NMR (400 MHz, CD$_3$OD) δ 8.16 (s, 1H), 7.51-7.58 (m, 4H), 6.27 (d, J = 3.1 Hz, 1H), 4.61-4.64 (m, 1H), 4.55-4.59 (m, 1H), 4.41-4.51 (m, 2H), 4.33-4.39 (m, 1H), 4.21-4.29 (m, 2H). |
| I-63 | (4-fluorophenyl)methanethiol | Pd/XPhos, Cs$_2$CO$_3$, dioxane, MW, 150° C. | Example 1 Step 8 | LCMS (FA) m/z 487 (M + H) | $^1$H NMR (400 MHz, d$_6$-DMSO) δ 8.20 (s, 1H), 7.54 (s, 2H), 7.43 (dd, J = 8.5, 5.6 Hz, 2H), 7.13 (t, J = 8.8 Hz, 2H), 6.13 (d, J = 3.1 Hz, 1H), 5.60 (d, J = 5.4 Hz, 1H), 5.38 (d, J = 6.3 Hz, 1H), 4.45-4.54 (m, 1H), 4.33-4.42 (m, 3H), 4.27 (dd, J = 10.2, 3.0 Hz, 1H), 4.01-4.18 (m, 2H). |
| I-44 | (3-fluorophenyl)methanethiol | Pd/XPhos, Cs$_2$CO$_3$, dioxane, MW, 150° C. | Example 1 Step 8 | LCMS (FA) m/z 487 (M + H) | $^1$H NMR (400 MHz, CD$_3$OD) δ 8.17 (s, 1H), 7.23-7.30 (m, 1H), 7.11 (br d, J = 7.7 Hz, 2H), 6.95 (br t, J = 9.0 Hz, 1H), 6.27 (d, J = 3.0 Hz, 1H), 4.60-4.64 (m, 1H), 4.53-4.59 (m, 1H), 4.32-4.41 (m, 3H), 4.18-4.29 (m, 2H). |
| I-31 | m-tolylmethanethiol | Pd/XPhos, Cs$_2$CO$_3$, dioxane, MW, 150° C. | Example 1 Step 8 | LCMS (FA) m/z 483 (M + H) | $^1$H NMR (400 MHz, CD$_3$OD) δ 8.15 (s, 1H), 7.06-7.16 (m, 3H), 7.02 (d, J = 7.3 Hz, 1H), 6.27 (d, J = 3.0 Hz, 1H), 4.60-4.64 (m, 1H), 4.54-4.59 (m, 1H), 4.36 (dd, J = 10.3, 3.1 Hz, 1H), 4.32 (d, J = 2.5 Hz, 2H), 4.24-4.29 (m, 1H), 4.18-4.24 (m, 1H), 2.26 (s, 3H). |
| I-32 | (4-(trifluoromethoxy)phenyl)methanethiol | Pd/XPhos, Cs$_2$CO$_3$, dioxane, MW, 150° C. | Example 1 Step 8 | LCMS (FA) m/z 553 (M + H) | $^1$H NMR (400 MHz, CD$_3$OD) δ 8.18 (s, 1H), 7.44 (d, J = 8.7 Hz, 2H), 7.17 (d, J = 8.2 Hz, 2H), 6.29 (d, J = 3.3 Hz, 1H), 4.57-4.68 (m, 2H), 4.43 (d, J = 5.0 Hz, 2H), 4.35-4.41 (m, 1H), 4.24-4.31 (m, 2H). |
| I-38 | (4-methoxyphenyl)methanethiol | Pd/XPhos, Cs$_2$CO$_3$, dioxane, MW, 150° C. | Example 1 Step 8 | LCMS (FA) m/z 499 (M + H) | $^1$H NMR (400 MHz, CD$_3$OD) δ 8.15 (s, 1H), 7.21 (br d, J = 8.5 Hz, 2H), 6.80 (br d, J = 8.5 Hz, 2H), 6.27 (d, J = 2.9 Hz, 1H), 4.61-4.68 (m, 1H), 4.57 (t, J = 5.3 Hz, 1H), 4.36 (dd, J = 10.1, 2.7 Hz, 1H), 4.32 (s, 2H), 4.19-4.29 (m, 2H), 3.74 (s, 3H). |
| I-41 | p-tolylmethanethiol | Pd/XPhos, Cs$_2$CO$_3$, dioxane, MW, 150° C. | Example 1 Step 8 | LCMS (FA) m/z 483 (M + H) | $^1$H NMR (400 MHz, CD$_3$OD) δ 8.16 (s, 1H), 7.19 (d, J = 8.0 Hz, 2H), 7.07 (d, J = 7.9 Hz, 2H), 6.27 (d, J = 3.0 Hz, 1H), 4.59-4.63 (m, 1H), 4.54-4.58 (m, 1H), 4.33-4.38 (m, 1H), 4.33 (s, 2H), 4.18-4.29 (m, 2H), 2.28 (s, 3H). |
| I-81 | 2-methylfuran-3-thiol | Pd/XPhos precatalyst, Cs$_2$CO$_3$, DMF, 145° C. | Example 35 Step 5 | LCMS (FA): m/z 459 (M + H) | $^1$H NMR (400 MHz, d$_6$-DMSO) δ 8.23 (s, 1H), 7.60 (d, J = 1.9 Hz, 1H), 7.53 (s, 2H), 6.57 (d, J = 1.9 Hz, 1H), 6.11 (d, J = 3.0 Hz, 1H), 4.37-4.43 (m, 1H), 4.22-4.28 (m, |

-continued

| Compound number | Reagent Used with Intermediate 25 in Transition-metal catalyzed Couplling | Transition-metal Catalyzed Coupling Conditions | Final deprotection conditions | LCMS data | ¹H NMR Data |
|---|---|---|---|---|---|
| | | | | | 1H), 4.19 (dd, J = 10.5, 3.4 Hz, 1H), 4.07-4.13 (m, 1H), 3.92 (dd, J = 10.5, 7.6 Hz, 1H), 2.38 (s, 3H). |

Example 37: {(2R,3S,4R,5R)-5-[4-amino-3-(benzyloxy)-1H-pyrazolo[3,4-d]pyrimidin-1-yl]-3,4-dihydroxytetrahydrofuran-2-yl}methyl Sulfamate Compound I-76

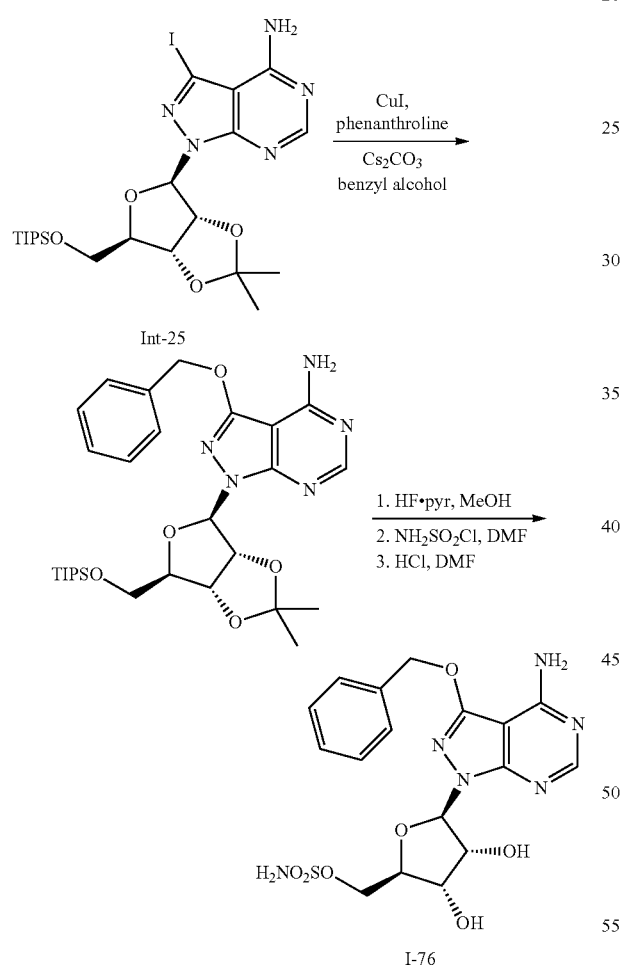

Step 1: 3-(benzyloxy)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine Into a microwave vial was added Intermediate 25 (250 mg, 0.424 mmol), copper(I) iodide (8.08 mg, 0.042 mmol), 3,4,7,8-tetramethyl-1,10-phenanthroline (20.0 mg, 0.085 mmol), cesium carbonate (0.276 g, 0.848 mmol) and benzyl alcohol (1.25 mL, 12.1 mmol). The mixture was sonicated under an atmosphere of argon. The reaction mixture was allowed to heat in an oil bath at 110° C. for 24 h. The reaction mixture was cooled to rt, diluted with DCM and filtered through a pad of silica gel. DCM was used to elute benzyl alcohol and then the product was eluted from the silica gel pad with EtOAc. The EtOAc fraction was concentrated under reduced pressure. The crude product was purified by silica gel chromatography to afford the product as green oil (73 mg, 30%). LCMS (FA) m/z 570 (M+H).

Step 2: (2R,3S,4R,5R)-5-[4-amino-3-(benzyloxy)-1H-pyrazolo[3,4-d]pyrimidin-1-yl]-3,4-dihydroxytetrahydrofuran-2-yl}methyl Sulfamate The titled compound was prepared by taking 3-(benzyloxy)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine through Step 7 of Example 5 and then Steps 7 and 8 of Example 1. LCMS (FA) m/z 453 (M+H); ¹H NMR (400 MHz, CD₃OD) δ 8.14 (s, 1H), 7.54 (d, J=7.3 Hz, 2H), 7.29-7.46 (m, 3H), 6.18-6.23 (m, 1H), 5.46 (s, 2H), 4.51-4.63 (m, 2H), 4.32 (dd, J=10.4, 3.1 Hz, 1H), 4.10-4.25 (m, 2H).

Example 38: [(2R,3S,4R,5R)-5-(4-amino-3-carbamothioyl-1H-pyrazolo[3,4-d]pyrimidin-1-yl)-3,4-dihydroxytetrahydrofuran-2-yl]methyl Sulfamate Compound I-60

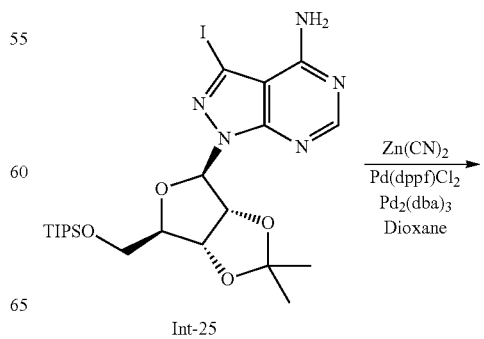

Int-25

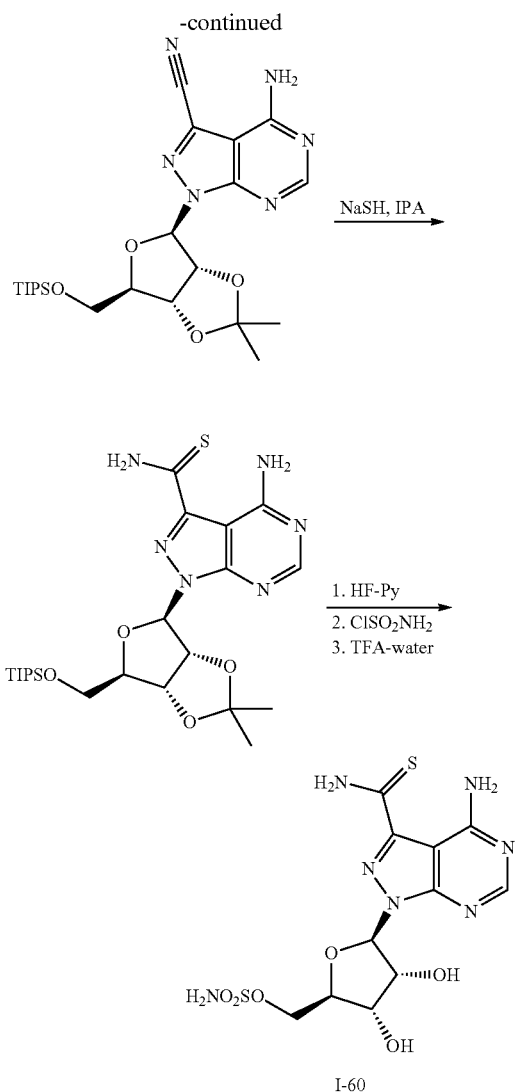

I-60

Step 1: 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carbonitrile To a solution of Intermediate 25 in DMF (3 mL) was added zinc cyanide (44 mg, 0.37 mmol), tris(dibenzylideneacetone)dipalladium (0) (16 mg, 0.017 mmol), and [1,1'-bis(diphenylphosphino)ferrocene]palladium(II)dichloride (28 mg, 0.034 mmol). The reaction mixture was degassed and purged with $N_2$.

The mixture was subjected to microwave irradiation at 190° C. for 20 min. The reaction mixture was then filtered through Celite and the filtrate concentrated under reduced pressure. The crude product was dry-loaded onto Celite and purified by column chromatography to afford 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carbonitrile (47 mg, 30%). LCMS (FA): m/z 489 (M+H).

Step 2: 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carbothioamide To a solution of 4-amino-1-[(3aR,4R,6R,6aR)-2,2-dimethyl-6-{[(triisopropylsilyl)oxy]methyl}tetrahydrofuro[3,4-d][1,3]dioxol 4-yl]-H-pyrazolo[3,4-d]pyrimidine-3-carbonitrile (60 mg, 0.10 mmol) in IPA (1 mL) was added sodium hydrogen sulfide (17 mg, 0.31 mmol) and the reaction mixture was allowed to stir at 80° C. overnight. The reaction mixture was concentrated to dryness and the crude material was purified by column chromatography to afford 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carbothioamide (33 mg, 50%). LCMS (FA): m/z 523 (M+H).

Step 3: 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carbothioamide The titled compound was prepared as described in Example 5 Step 7 substituting 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-carbothioamide for Intermediate 20. LCMS (FA): m/z 367 (M+H).

Step 4: [(3aR,4R,6R,6aR)-6-(4-amino-3-carbamothioyl-1H-pyrazolo[3,4-d]pyrimidin-1-yl)-2,2-dimethyltetrahydrofuro[3,4-d][1,3]dioxol-4-yl]methyl Sulfamate The title compound was prepared as described in Example 1 Step 7 substituting 4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidine-3-carbothioamide for Intermediate 8. LCMS (FA): m/z 446 (M+H).

Step 5: [(2R,3S,4R,5R)-5-(4-amino-3-carbamothioyl-1H-pyrazolo[3,4-d]pyrimidin-1-yl)-3,4-dihydroxytetrahydrofuran-2-yl]methyl Sulfamate Compound I-60

The titled compound was prepared as described in Example 35 Step 5 substituting [(3aR,4R,6R,6aR)-6-(4-amino-3-carbamothioyl-1H-pyrazolo[3,4-d]pyrimidin-1-yl)-2,2-dimethyltetrahydrofuro[3,4-d][1,3]dioxol-4-yl] methyl sulfamate for {(3aR,4R,6R,6aR)-6-[4-amino-3-(phenylsulfanyl)-1H-pyrazolo[3,4-d]pyrimidin-1-yl]-2,2-dimethyltetrahydrofuro[3,4-d][1,3]dioxol-4-yl}methyl sulfamate. LCMS (FA): m/z 406 (M+H); $^1$H NMR (400 MHz, $d_6$-DMSO) δ 8.25 (s, 1H), 6.26 (d, J=3.3 Hz, 1H), 4.61 (br t, J=4.3 Hz, 1H), 4.43 (br t, J=5.3 Hz, 1H), 4.26 (br d, J=8.3 Hz, 1H), 4.04-4.19 (m, 2H).

199

Example 39: sodium 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-thiolate Intermediate 85 and 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-thiol Intermediate 86

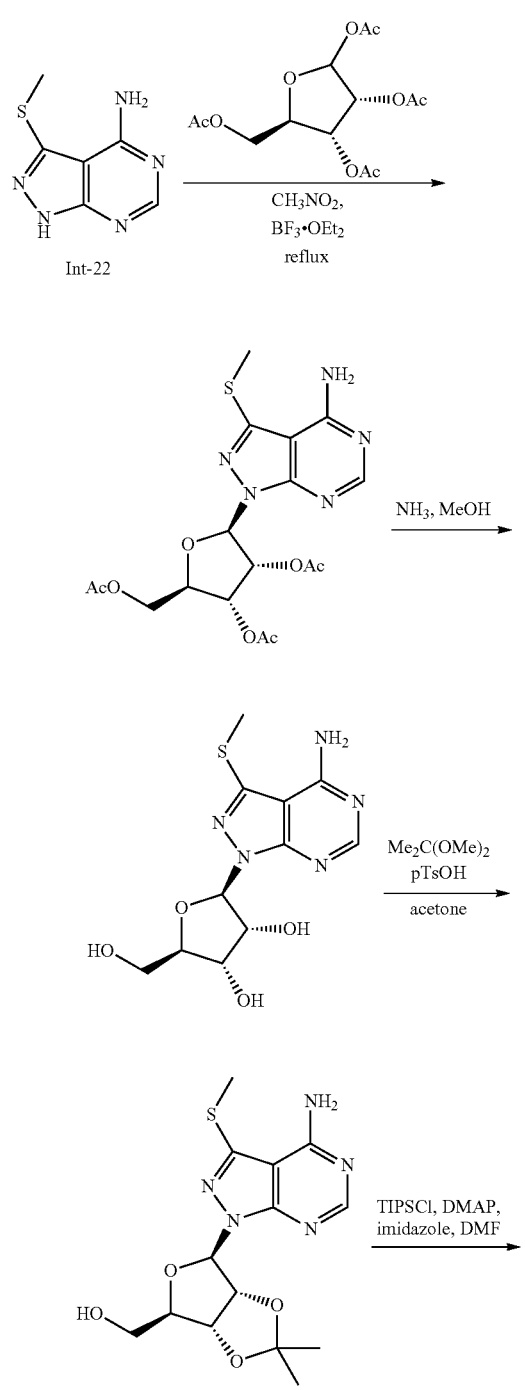

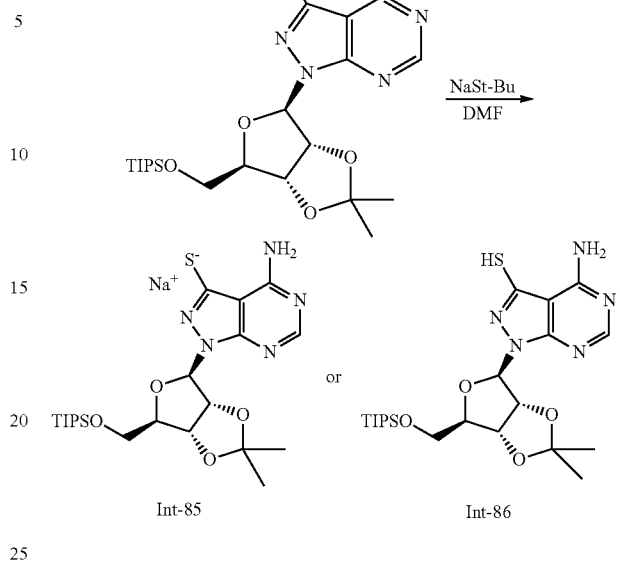

Step 1: (2R,3R,4R,5R)-2-(acetoxymethyl)-5-[4-amino-3-(methylsulfanyl)-1H-pyrazolo[3,4-d]pyrimidin-1-yl]tetrahydrofuran-3,4-diyl Diacetate 1,2,3,5-Tetra-O-acetyl-β-D-ribofuranose (1.32 g, 4.16 mmol), Intermediate 22 (580 mg, 3.20 mmol) and nitromethane (10.4 mL) were combined in a 250 mL flask fitted with a stirbar and reflux condenser. The mixture was warmed to reflux (at 105° C.) in an oil bath. Boron trifluoride etherate (0.710 mL, 5.60 mmol) was then added dropwise to the heated mixture by syringe. The reaction mixture became homogeneous and refluxed vigorously after completion of $BF_3$ addition. The reaction mixture was allowed to stir at reflux for 1 h under argon atmosphere. The mixture turned dark brown and was cooled to rt, concentrated under vacuum, quenched with saturated aqueous sodium bicarbonate solution (50 mL) and then diluted with EtOAc. The mixture was extracted with EtOAc and the organic layers were combined, washed with brine, dried over $Na_2SO_4$, filtered and concentrated. The resulting crude material was purified by column chromatography to give (2R,3R,4R,5R)-2-(acetoxymethyl)-5-[4-amino-3-(methylsulfanyl)-1H-pyrazolo[3,4-d]pyrimidin-1-yl]tetrahydrofuran-3,4-diyl diacetate (1.10 g, 75%) as light brown solid. LCMS (AA): m/z 440 (M+H); $^1$H NMR (400 MHz, $CDCl_3$) δ 8.31-8.37 (m, 1H), 6.52 (d, J=3.3 Hz, 1H), 6.08 (br s, 2H), 5.91-6.02 (m, 1H), 5.77-5.91 (m, 1H), 4.38-4.49 (m, 2H), 4.19-4.29 (m, 1H), 2.71 (s, 3H), 2.08-2.16 (m, 9H).

Step 2: (2R,3R,4S,5R)-2-[4-amino-3-(methylsulfanyl)-1H-pyrazolo[3,4-d]pyrimidin-1-yl]-5-(hydroxymethyl)tetrahydrofuran-3,4-diol (2R,3R,4R,5R)-2-(Acetoxymethyl)-5-[4-amino-3-(methylsulfanyl)-1H-pyrazolo[3,4-d]pyrimidin-1-yl]tetrahydrofuran-3,4-diyl diacetate (18.0 g, 41.0 mmol) was dissolved in methanol (300 mL) to which a solution of ammonia in methanol (7.0 M, 165 mL) was subsequently added. The resulting mixture was stirred at rt under nitrogen overnight and then concentrated under vacuum to give (2R,3R,4S,5R)-2-[4-amino-3-(methylsulfanyl)-1H-pyrazolo[3,4-d]pyrimidin-1-yl]-5-(hydroxymethyl)tetrahydrofuran-3,4-diol (12.0 g, 100%) as an orange solid. LCMS (FA): m/z 314 (M+H); $^1$H NMR (400 MHz, d$_6$-DMSO) δ 8.20 (s, 1H), 6.07 (d, J=4.4 Hz, 1H), 5.38 (d, J=5.8 Hz, 1H), 5.11 (d, J=5.7 Hz, 1H), 4.80 (t, J=5.8 Hz, 1H), 4.58 (q, J=5.0 Hz, 1H), 4.24 (q, J=5.0 Hz, 1H), 3.87-3.96 (m, 1H), 3.55-3.63 (m, 1H), 3.37-3.51 (m, 1H), 2.61 (s, 3H).

Step 3: {(3aR,4R,6R,6aR)-6-[4-amino-3-(methylsulfanyl)-1H-pyrazolo[3,4-d]pyrimidin-1-yl]-2,2-dimethyltetrahydrofuro[3,4-d][1,3]dioxol-4-yl}methanol (2R,3R,4S,5R)-2-[4-Amino-3-(methylsulfanyl)-1H-pyrazolo[3,4-d]pyrimidin-1-yl]-5-(hydroxymethyl)tetrahydrofuran-3,4-diol (14.0 g, 44.7 mmol) was suspended in acetone (450 mL) and 2,2-dimethoxypropane (110 mL). To this mixture was added p-toluenesulfonic acid monohydrate (17.0 g, 89.4 mmol). The resulting mixture was allowed to stir at rt overnight. Filtration provided a solid which was washed with water three times and dried under vacuum to give {(3aR,4R,6R,6aR)-6-[4-amino-3-(methylsulfanyl)-1H-pyrazolo[3,4-d]pyrimidin-1-yl]-2,2-dimethyltetrahydrofuro[3,4-d][1,3]dioxol-4-yl}methanol (16.0 g, 100%) as a yellow solid. LCMS (FA): m/z 354 (M+H); $^1$H NMR (400 MHz, d$_6$-DMSO) δ 8.36 (s, 1H), 7.49 (d, J=8.0 Hz, 2H), 7.12 (d, J=7.9 Hz, 2H), 6.30 (d, J=1.5 Hz, 1H), 5.29 (dd, J=1.5, 6.0 Hz, 1H), 4.96 (dd, J=1.9, 6.0 Hz, 1H), 4.17 (br t, J=5.9 Hz, 1H), 3.56 (dd, J=7.5, 11.17 Hz, 1H), 3.43 (dd, J=6.1, 11.2 Hz, 1H), 2.66 (s, 3H), 1.53 (s, 3H), 1.35 (s, 3H).

Step 4: 1-[(3aR,4R,6R,6aR)-2,2-dimethyl-6-{[(triisopropylsilyl)oxy]methyl}tetrahydrofuro[3,4-d][1,3]dioxol-4-yl]-3-(methylsulfanyl)-1H-pyrazolo[3,4-d]pyrimidin-4-amine To a stirred solution of {(3aR,4R,6R,6aR)-6-[4-amino-3-(methylsulfanyl)-1H-pyrazolo[3,4-d]pyrimidin-1-yl]-2,2-dimethyltetrahydrofuro[3,4-d][1,3]dioxol-4-yl}methanol (3.0 g, 8.0 mmol) in DMF (37 mL) at rt under an atmosphere of nitrogen gas was added 1H-imidazole (2.00 g, 30.0 mmol), DMAP (207 mg, 1.70 mmol) and triisopropylsilyl chloride (5.40 mL, 25.5 mmol). The mixture was allowed to stirred at rt overnight and then treated with cold, saturated NH$_4$Cl solution (at 0° C.). The resulting mixture was extracted with EtOAc. The organic extracts were combined, washed with water and brine, dried over sodium sulfate, filtered and concentrated under reduced pressure. The crude material was purified by column chromatography to give 1-[(3aR,4R,6R,6aR)-2,2-dimethyl-6-{[(triisopropylsilyl)oxy]methyl}tetrahydrofuro[3,4-d][1,3]dioxol-4-yl]-3-(methylsulfanyl)-1H-pyrazolo[3,4-d]pyrimidin-4-amine (3.3 g, 80%) as a white solid. LCMS (AA): m/z 510 (M+H); $^1$H NMR (400 MHz, CDCl$_3$) δ 8.33 (s, 1H), 5.46 (dd, J=1.9, 6.0 Hz, 1H), 5.06 (dd, J=1.9, 6.1 Hz, 1H), 4.38 (ddd, J=1.9, 5.7, 7.8 Hz, 1H), 3.68-3.92 (m, 2H), 2.71 (s, 3H), 1.64 (s, 3H), 1.43 (s, 3H), 1.02-1.07 (m, 18H).

Step 5: sodium 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-thiolate Intermediate 85

A solution of 1-[(3aR,4R,6R,6aR)-2,2-dimethyl-6-{[(triisopropylsilyl)oxy]methyl}tetrahydrofuro[3,4-d][1,3]dioxol-4-yl]-3-(methylsulfanyl)-1H-pyrazolo[3,4-d]pyrimidin-4-amine (1.5 g, 2.9 mmol) in DMF (45 mL) was treated with sodium tert-butylsulfide (3.33 g, 30.0 mmol). The reaction mixture was heated at 165° C. overnight to provide a DMF solution of sodium 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidine-3-thiolate (Intermediate 85) which was used without purification in subsequent steps. LCMS (FA): m/z 496 (M-Na).

Alternative Step 5: 4-amino-1-[(3aR,4R,6R,6aR)-2,2-dimethyl-6-{[(triisopropylsilyl) oxy]methyl}tetrahydrofuro[3,4-d][1,3]dioxol-4-yl]-1H-pyrazolo[3,4-d]pyrimidine-3-thiol Intermediate 86

Into a microwave vial (10-20 mL) was added 1-[(3aR,4R,6R,6aR)-2,2-dimethyl-6-{[(triisopropylsilyl)oxy]methyl}tetrahydrofuro[3,4-d][1,3]dioxol-4-yl]-3-(methylsulfanyl)-1H-pyrazolo[3,4-d]pyrimidin-4-amine (1.00 g, 1.96 mmol), DMF (10 mL) and sodium tert-butylsulfide (2.00 g, 20.0 mmol). The reaction mixture was allowed to heat at 165° C. overnight. Upon completion, the reaction was allowed to cool to rt, quenched with sat. NH$_4$Cl solution and extracted into ethyl acetate (2×). The combined extracts were washed with water and brine, dried over sodium sulfate, filtered and concentrated under reduced pressure to afford a brown solid (640 mg, 66%). LCMS (FA): m/z=496 (M+H).

Example 40: [(2R,3S,4R,5R)-5-(4-amino-3-{[(1-hydroxycyclohexyl)methyl]sulfanyl}-1H-pyrazolo[3,4-d]pyrimidin-1-yl)-3,4-dihydroxytetrahydrofuran-2-yl]methyl Sulfamate Compound I-86 and [(2R,3S,4R,5R)-5-{4-amino-3-[(cyclohex-1-en-1-ylmethyl)sulfanyl]-1H-pyrazolo[3,4-d]pyrimidin-1-yl}-3,4-dihydroxytetrahydrofuran-2-yl]methyl Sulfamate Compound I-91

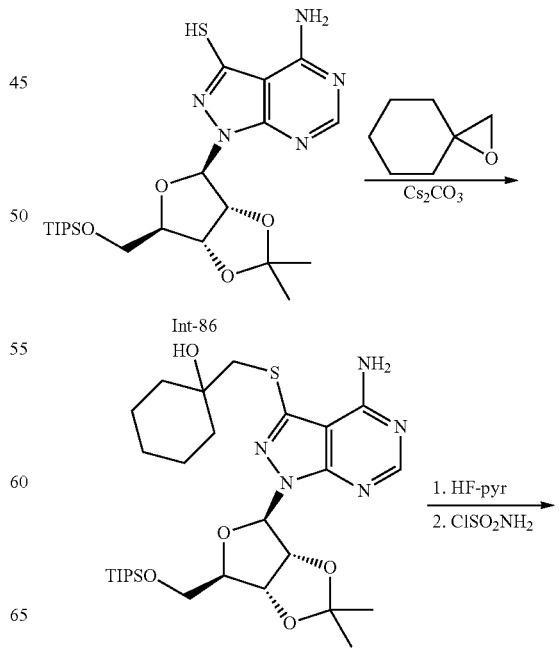

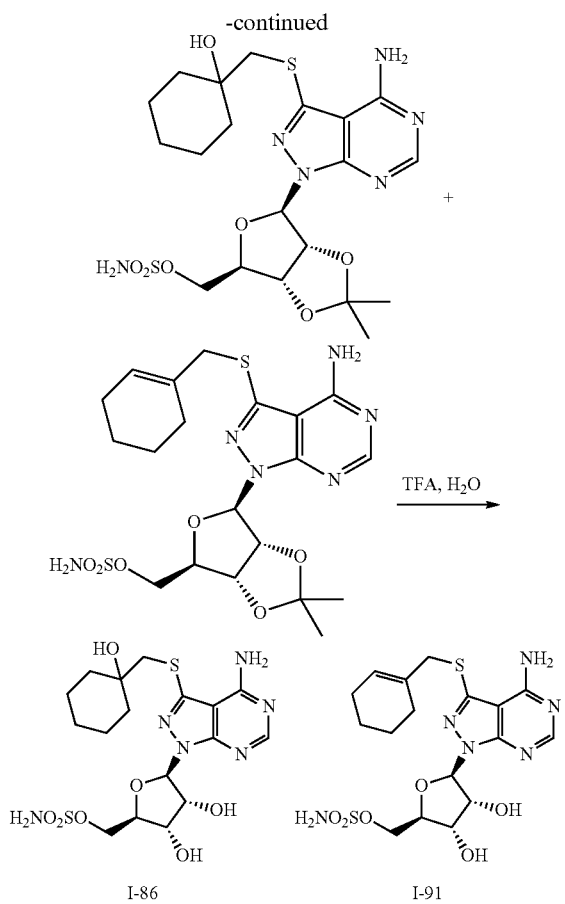

Step 1: 1-[({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl})sulfanyl)methyl]cyclohexanol Intermediate 86 (150 mg, 0.30 mmol) was dissolved in DMF (2.34 mL) and cesium carbonate (197 mg, 0.605 mmol) was added. A solution of 1-oxaspiro[2,5]octane (57.2 mg, 0.484 mmol) in DMF (0.70 mL) was added and the resulting mixture was heated at 40° C. for 1 h, 50° C. for 1 h, and then stirred at rt overnight. Water and EtOAc were added and the aqueous phase was extracted into EtOAc (2×). The organics were combined and washed with water and brine, dried over sodium sulfate, filtered, and concentrated under reduced pressure. The crude material was purified by silica gel chromatography to afford 1-[({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)methyl]cyclohexanol (80 mg, 40%). LCMS (FA): m/z 608 (M+H).

Steps 2 and 3: [(3aR,4R,6R,6aR)-6-(4-amino-3-{[(1-hydroxycyclohexyl)methyl]sulfanyl}-1H-pyrazolo[3,4-d]pyrimidin-1-yl)-2,2-dimethyltetrahydrofuro[3,4-d][1,3]dioxol-4-yl]methyl Sulfamate and [(3aR,4R,6R,6aR)-6-{4-amino-3-[(cyclohex-1-en-1-ylmethyl)sulfanyl]-1H-pyrazolo[3,4-d]pyrimidin-1-yl}-2,2-dimethyltetrahydrofuro[3,4-d][1,3]dioxol-4-yl]methyl Sulfamate A mixture of the titled compounds was prepared following the procedure described in Example 5 Step 7, substituting 1-[({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl})sulfanyl)methyl]cyclohexanol for Intermediate 20; followed by the procedure described in Example 1 Step 7. LCMS (FA): m/z 531 (M+H) and LCMS (FA): m/z 513 (M+H).

Step 4: [(2R,3S,4R,5R)-5-(4-amino-3-{[(1-hydroxycyclohexyl)methyl]sulfanyl}-1H-pyrazolo[3,4-d]pyrimidin-1-yl)-3,4-dihydroxytetrahydrofuran-2-yl]methyl Sulfamate Compound I-86 and [(2R,3S,4R,5R)-5-{4-amino-3-[(cyclohex-1-en-1-ylmethyl)sulfanyl]-1H-pyrazolo[3,4-d]pyrimidin-1-yl}-3,4-dihydroxytetrahydrofuran-2-yl]methyl Sulfamate Compound I-91

The mixture of [(3aR,4R,6R,6aR)-6-(4-amino-3-{[(1-hydroxycyclohexyl)methyl]sulfanyl}-1H-pyrazolo[3,4-d]pyrimidin-1-yl)-2,2-dimethyltetrahydrofuro[3,4-d][1,3]dioxol-4-yl]methyl sulfamate and [(3aR,4R,6R,6aR)-6-{4-amino-3-[(cyclohex-1-en-1-ylmethyl)sulfanyl]-1H-pyrazolo[3,4-d]pyrimidin-1-yl}-2,2-dimethyltetrahydrofuro[3,4-d][1,3]dioxol-4-yl]methyl sulfamate was treated as described in Example 35 Step 5. The crude material was purified by preparative reverse phase HPLC to afford [(2R,3S,4R,5R)-5-(4-amino-3-{[(1-hydroxycyclohexyl)methyl]sulfanyl})-1H-pyrazolo[3,4-d]pyrimidin-1-yl)-3,4-dihydroxytetrahydrofuran-2-yl]methyl sulfamate Compound I-86 (5 mg, 7%). LCMS (FA): m/z 491 (M+H); $^1$H NMR (400 MHz, d$_6$-DMSO) δ 8.24 (s, 1H), 7.51 (s, 2H), 6.12 (d, J=3.3 Hz, 1H), 4.43-4.52 (m, 1H), 4.34 (t, J=5.4 Hz, 1H), 4.25 (dd, J=10.4, 3.3 Hz, 1H), 4.08-4.17 (m, 1H), 4.02 (dd, J=10.4, 7.3 Hz, 1H), 3.29 (s, 2H), 1.25-1.60 (m, 10H) and [(2R,3S,4R,5R)-5-{4-amino-3-[(cyclohex-1-en-1-ylmethyl)sulfanyl]-1H-pyrazolo[3,4-d]pyrimidin-1-yl}-3,4-dihydroxytetrahydrofuran-2-yl]methyl sulfamate Compound I-91 (6 mg, 9%). LCMS (FA): m/z 473 (M+H); $^1$H NMR (400 MHz, d$_6$-DMSO) δ 8.21 (s, 1H), 7.52 (s, 2H), 6.13 (d, J=3.0 Hz, 1H), 5.61 (d, J=5.3 Hz, 1H), 5.54 (br s, 1H), 5.38 (d, J=6.4 Hz, 1H), 4.41-4.49 (m, 1H), 4.32-4.40 (m, 1H), 4.26 (dd, J=10.4, 3.2 Hz, 1H), 4.08-4.18 (m, 1H), 3.97-4.06 (m, 1H), 3.70 (s, 2H), 2.08 (br d, J=3.3 Hz, 2H), 1.88 (br s, 2H), 1.50-1.63 (m, 2H), 1.41-1.49 (m, 2H).

Example 41

The following compounds were prepared following the procedures in Example 40 using Intermediate 85 or Intermediate 86 with the reagents and conditions described in the table below.

| Compound number | Halide | Alkylation Conditions | Final deprotection conditions | LCMS data | $^1$H NMR Data |
|---|---|---|---|---|---|
| I-28 | 2,2-dimethyloxirane | Cs$_2$CO$_3$, DMF, 100° C. 1 h | Example 35 Step 5 | LCMS (FA): m/z 451 (M + H) | $^1$H NMR (400 MHz, d$_6$-DMSO) δ 8.20 (s, 1H), 7.52 (s, 2H), 6.11 (d, J = 3.3 Hz, 1H), 5.60 (d, J = 5.3 Hz, 1H), |

| Compound number | Halide | Alkylation Conditions | Final deprotection conditions | LCMS data | ¹H NMR Data |
|---|---|---|---|---|---|
| | | | | | 5.39 (d, J = 6.3 Hz, 1H), 4.86 (s, 1H), 4.40-4.52 (m, 1H), 4.29-4.38 (m, 1H), 4.24 (dd, J = 10.3, 3.5 Hz, 1H), 4.08-4.15 (m, 1H), 3.98-4.05 (m, 1H), 3.26 (s, 2H), 1.22 (d, J = 4.0 Hz, 6H). |
| I-67 | 1-(chloromethyl)naphthalene | $Cs_2CO_3$, DMF, rt ON | Example 35 Step 5 | LCMS (FA): m/z 519 (M + H) | ¹H NMR (400 MHz, $d_6$-DMSO) δ 8.19 (s, 1H), 7.97 (br d, J = 7.8 Hz, 1H), 7.88 (br d, J = 8.2 Hz, 1H), 7.51-7.64 (m, 4H), 7.38-7.48 (m, 1H), 6.17 (d, J = 3.0 Hz, 1H), 4.90 (d, J = 5.3 Hz, 2H), 4.51-4.60 (m, 1H), 4.41 (br t, J = 5.1 Hz, 1H), 4.30 (br d, J = 7.5 Hz, 1H), 4.06-4.19 (m, 2H). |
| I-73 | 2-(bromomethyl)-5-chlorofuran | $Cs_2CO_3$, DMF, rt ON | Example 35 Step 5 | LCMS (FA): m/z 493 (M + H) | ¹H NMR (400 MHz, $d_6$-DMSO) δ 8.21 (s, 1H), 7.54 (s, 2H), 6.34 (d, J = 5.4 Hz, 2H), 6.14 (d, J = 3.1 Hz, 1H), 5.63 (d, J = 5.3 Hz, 1H), 5.39 (d, J = 6.3 Hz, 1H), 4.43-4.55 (m, 1H), 4.31-4.43 (m, 3H), 4.26 (dd, J = 10.4, 3.1 Hz, 1H), 4.10-4.18 (m, 1H), 4.05 (br d, J = 10.4 Hz, 1H). |
| I-70 | (1-bromoethyl)benzene | $Cs_2CO_3$, DMF, rt ON | Example 35 Step 5 | LCMS (FA): m/z 483 (M + H) | ¹H NMR (400 MHz, $CD_3OD$) δ 8.16 (s, 1H), 7.15-7.38 (m, 5H), 6.28 (t, J = 3.0 Hz, 1H), 4.71-4.85 (m, 1H), 4.51-4.62 (m, 2H), 4.38 (ddd, J = 10.1, 6.8, 3.1 Hz, 1H), 4.16-4.30 (m, 2H), 1.77 (dd, J = 10.5, 7.0 Hz, 3H). |
| I-43 | (3-bromoprop-1-yn-1-yl)trimethylsilane | $Cs_2CO_3$, DMF, rt ON | Example 35 Step 5 | LCMS (FA): m/z 417 (M + H) | ¹H NMR (400 MHz, $CD_3OD$) δ 8.24 (s, 1H), 6.31 (d, J = 3.3 Hz, 1H), 6.23 (t, J = 6.4 Hz, 1H), 5.03 (dd, J = 6.4, 2.1 Hz, 2H), 4.70 (dd, J = 5.1, 3.1 Hz, 1H), 4.60 (t, J = 5.3 Hz, 1H), 4.37 (dd, J = 9.9, 2.9 Hz, 1H), 4.18-4.31 (m, 2H). |
| I-45 | 3-(bromomethyl)pyridine | $Cs_2CO_3$, DMF, rt ON | Example 35 Step 5 | LCMS (FA): m/z 470 (M + H) | ¹H NMR (400 MHz, $d_6$-DMSO) δ 8.56 (s, 1H), 8.44 (br d, J = 4.4 Hz, 1H), 8.20 (s, 1H), 7.79 (br d, J = 7.8 Hz, 1H), 7.58 (s, 2H), 7.34 (dd, J = 7.7, 4.8 Hz, 1H), 6.13 (d, J = 3.1 Hz, 1H), 5.60 (br s, 1H), 5.38 (br d, J = 4.4 Hz, 1H), 4.46 (br s, 1H), 4.41 (d, J = 1.4 Hz, 2H), 4.33 (br d, J = 4.4 Hz, 1H), 4.25 (dd, J = 10.4, 3.1 Hz, 1H), 4.09-4.15 (m, 1H), 4.00-4.06 (m, 1H). |
| I-83 | 1,1,1-trifluoro-2-iodoethane | $Cs_2CO_3$, DMF, rt ON | Example 35 Step 5 | LCMS (FA): m/z 461 (M + H) | ¹H NMR (400 MHz, $d_6$-DMSO) δ 8.24 (s, 1H), 7.51 (s, 2H), 6.15 (d, J = 2.9 Hz, 1H), 5.62 (d, J = 5.3 Hz, 1H), 5.39 (d, J = 6.4 Hz, 1H), 4.41-4.53 (m, 1H), 4.36 (q, J = 5.9 Hz, 1H), 4.25 (dd, J = 10.5, 3.3 Hz, 1H), 4.06-4.19 (m, 3H), 4.02 (dd, J = 10.5, 7.3 Hz, 1H). |
| I-59 | 2-(bromomethyl)pyridine | $Cs_2CO_3$, DMF, rt ON | Example 35 Step 5 | LCMS (FA): m/z 470 (M + H) | ¹H NMR (400 MHz, $d_6$-DMSO) δ 8.51 (br d, J = 4.1 Hz, 1H), 8.20 (s, 1H), 7.74 (td, J = 7.7, 1.8 Hz, 1H), 7.55 (s, 2H), 7.43 (d, J = 7.8 Hz, 1H), 7.27-7.33 (m, 1H), 6.12 (d, J = 3.0 Hz, 1H), 5.60 (d, J = 5.3 Hz, 1H), 5.36 (d, J = 6.3 Hz, 1H), 4.48 (s, 2H), |

-continued

| Compound number | Halide | Alkylation Conditions | Final deprotection conditions | LCMS data | $^1$H NMR Data |
|---|---|---|---|---|---|
| | | | | | 4.43-4.46 (m, 1H), 4.33 (q, J = 6.0 Hz, 1H), 4.25 (dd, J = 10.3, 3.1 Hz, 1H), 4.07-4.18 (m, 1H), 3.99-4.05 (m, 1H). |
| I-39 | 1-(bromomethyl)-2-methylbenzene | $Cs_2CO_3$, DMF, rt ON | Example 35 Step 5 | LCMS (FA): m/z 483 (M + H) | $^1$H NMR (400 MHz, $d_6$-DMSO) δ 8.20 (s, 1H), 7.53 (s, 2H), 7.28 (d, J = 7.3 Hz, 1H), 7.16-7.24 (m, 2H), 7.13 (br d, J = 7.3 Hz, 1H), 6.15 (d, J = 3.1 Hz, 1H), 5.62 (d, J = 5.3 Hz, 1H), 5.38 (d, J = 6.3 Hz, 1H), 4.46-4.56 (m, 1H), 4.41 (s, 2H), 4.38 (br d, J = 5.4 Hz, 1H), 4.27 (dd, J = 10.2, 3.0 Hz, 1H), 4.11-4.17 (m, 1H), 4.04-4.11 (m, 1H), 2.39 (s, 3H). |
| I-88 | (2-bromoethyl)benzene | $Cs_2CO_3$, DMF, rt ON | Example 35 Step 5 | LCMS (FA): m/z 483 (M + H) | $^1$H NMR (400 MHz, $d_6$-DMSO) δ 8.22 (s, 1H), 7.51 (br s, 2H), 7.25-7.35 (m, 4H), 7.22 (br d, J = 6.8 Hz, 1H), 6.15 (d, J = 3.1 Hz, 1H), 5.64 (d, J = 5.3 Hz, 1H), 5.40 (br d, J = 6.4 Hz, 1H), 4.48-4.59 (m, 1H), 4.38 (q, J = 5.7 Hz, 1H), 4.27 (dd, J = 10.3, 3.1 Hz, 1H), 4.14 (td, J = 6.5, 3.3 Hz, 1H), 4.03-4.09 (m, 1H), 3.38-3.46 (m, 2H), 3.02 (t, J = 7.4 Hz, 2H). |
| I-46 | 2-(2-bromoethoxy)tetrahydro-2H-pyran | $Cs_2CO_3$, DMF, rt ON | Example 35 Step 5 | LCMS (FA): m/z 423 (M + H) | $^1$H NMR (400 MHz, $d_6$-DMSO) δ 8.22 (s, 1H), 7.51 (br s, 2H), 6.13 (d, J = 3.1 Hz, 1H), 5.61 (d, J = 5.3 Hz, 1H), 5.38 (br d, J = 6.0 Hz, 1H), 4.94-5.18 (m, 1H), 4.44-4.52 (m, 1H), 4.31-4.39 (m, 1H), 4.25 (dd, J = 10.4, 3.3 Hz, 1H), 4.09-4.17 (m, 1H), 3.99-4.07 (m, 1H), 3.63-3.72 (m, 2H), 3.16-3.25 (m, 2H). |
| I-77 | 1-bromo-2-methylpropane | $Cs_2CO_3$, DMF, rt ON | Example 35 Step 5 | LCMS (FA): m/z 435 (M + H) | $^1$H NMR (400 MHz, $d_6$-DMSO) δ 8.22 (s, 1H), 7.51 (s, 2H), 6.13 (d, J = 3.0 Hz, 1H), 4.43-4.54 (m, 1H), 4.36 (t, J = 5.3 Hz, 1H), 4.25 (dd, J = 10.4, 3.3 Hz, 1H), 4.12 (td, J = 6.6, 3.4 Hz, 1H), 3.99-4.06 (m, 1H), 3.06 (d, J = 6.8 Hz, 2H), 1.95 (dt, J = 13.4, 6.6 Hz, 1H), 1.02 (dd, J = 6.7, 2.3 Hz, 6H). |
| I-90 | 2-bromoacetonitrile | $Cs_2CO_3$, DMF, rt ON | Example 35 Step 5 | LCMS (FA): m/z 418 (M + H) | $^1$H NMR (400 MHz, $d_6$-DMSO) δ 8.26 (s, 1H), 7.50 (s, 2H), 6.17 (d, J = 2.5 Hz, 1H), 4.47-4.53 (m, 1H), 4.43 (t, J = 5.5 Hz, 1H), 4.24-4.32 (m, 3H), 4.12-4.18 (m, 1H), 4.03-4.11 (m, 1H). |
| I-80 | 2-bromo-N,N-dimethylethan-1-amine | $Cs_2CO_3$, DMF rt ON | Example 35 Step 5 | LCMS (FA): m/z 450 (M + H) | $^1$H NMR (400 MHz, $d_6$-DMSO) δ 8.20 (s, 1H), 6.13 (d, J = 3.3 Hz, 1H), 4.48 (dd, J = 4.8, 3.4 Hz, 1H), 4.35 (t, J = 5.4 Hz, 1H), 4.24 (dd, J = 10.2, 3.2 Hz, 1H), 4.12 (td, J = 6.4, 3.5 Hz, 1H), 4.00-4.07 (m, 1H), 3.24 (br t, J = 6.9 Hz, 2H), 2.53-2.65 (m, 2H), 2.18 (s, 6H). |

-continued

| Compound number | Halide | Alkylation Conditions | Final deprotection conditions | LCMS data | $^1$H NMR Data |
|---|---|---|---|---|---|
| I-35 | 1-bromo-2-methoxyethane | Cs$_2$CO$_3$, DMF, rt, ON | Example 35 Step 5 | LCMS (FA): m/z 437 (M + H) | $^1$H NMR (400 MHz, d$_6$-DMSO) δ 8.22 (s, 1H), 7.51 (s, 2H), 6.13 (d, J = 3.3 Hz, 1H), 5.61 (d, J = 5.3 Hz, 1H), 5.38 (d, J = 6.4 Hz, 1H), 4.45-4.55 (m, 1H), 4.35 (q, J = 5.9 Hz, 1H), 4.25 (dd, J = 10.4, 3.3 Hz, 1H), 4.07-4.17 (m, 1H), 3.99-4.07 (m, 1H), 3.57-3.69 (m, 2H), 3.30-3.32 (m, 2H), 3.28 (s, 3H). |
| I-51 | Ethyl bromide | Cs$_2$CO$_3$, DMF, rt, ON | Example 3 Step 7 | LCMS (FA): m/z 407 (M + H) | $^1$H NMR (400 MHz, d$_6$-DMSO) δ 8.22 (s, 1H), 7.51 (s, 2H), 6.14 (d, J = 3.1 Hz, 1H), 4.40-4.57 (m, 1H), 4.37 (t, J = 5.3 Hz, 1H), 4.25 (dd, J = 10.4, 3.3 Hz, 1H), 4.13 (td, J = 6.5, 3.5 Hz, 1H), 4.00-4.07 (m, 1H), 3.14 (q, J = 7.3 Hz, 2H), 1.34 (t, J = 7.3 Hz, 3H). |
| I-85 | NaCO$_2$CF$_2$Cl | DMF, 80° C. 2 h | Example 3 Step 7 | LCMS (FA): m/z 429 (M + H) | $^1$H NMR (400 MHz, d$_6$-DMSO) δ 8.29 (s, 1H), 7.33-7.71 (m, 3H), 6.20 (d, J = 3.1 Hz, 1H), 5.66 (d, J = 5.3 Hz, 1H), 5.44 (d, J = 6.3 Hz, 1H), 4.46-4.58 (m, 1H), 4.39 (q, J = 5.9 Hz, 1H), 4.26 (dd, J = 10.5, 3.3 Hz, 1H), 4.09-4.20 (m, 1H), 4.04 (dd, J = 10.4, 7.4 Hz, 1H). |
| I-72 | tert-butyl 3-bromoazetidine-1-carboxylate | NaOH, dioxane, 80° C. | Example 35 Step 5 | LCMS(AA) m/z 434 (M + H) | $^1$H NMR (400 MHz, CD$_3$OD) δ 8.23 (s, 1H), 6.14-6.41 (m, 1H), 4.64-4.78 (m, 1H), 4.56-4.64 (m, 2H), 4.41-4.50 (m, 2H), 4.32-4.38 (m, 1H), 4.27 (br d, J = 7.0 Hz, 2H), 3.99-4.11 (m, 2H) |
| I-50 | (bromomethyl)cyclopropane | NaOH, dioxane, 80° C. | Example 1 Step 8 | LCMS(FA) m/z 433 (M + H) | $^1$H NMR (400 MHz, CD$_3$OD) δ ppm 8.19 (s, 1H), 6.28 (d, J = 3.0 Hz, 1H), 4.64-4.68 (m, 1H), 4.58 (t, J = 5.1 Hz, 1H), 4.35 (dd, J = 9.5, 2.4 Hz, 1H), 4.18-4.29 (m, 2H), 3.12 (d, J = 7.2 Hz, 2H), 1.12-1.24 (m, 1H), 0.54-0.61 (m, 2H), 0.24-0.31 (m, 2H) |
| I-56 | bromocyclobutane | NaOH, dioxane, 80° C. | Example 1 Step 8 | LCMS(FA) m/z 433 (M + H) | $^1$H NMR (400 MHz, CD$_3$OD) δ ppm 8.19 (s, 1H), 6.29 (d, J = 2.9 Hz, 1H), 4.63-4.67 (m, 1H), 4.58-4.62 (m, 1H), 4.37 (dd, J = 10.0, 3.1 Hz, 1H), 4.14-4.30 (m, 3H), 2.43-2.56 (m, 2H), 2.12-2.24 (m, 2H), 1.96-2.07 (m, 2H) |
| I-62 | bromocyclopentane | NaOH, water/dioxane, rt | Example 1 Step 8 | LCMS(FA) m/z 447 (M + H) | $^1$H NMR (400 MHz, CD$_3$OD) δ ppm 8.19 (s, 1H), 6.29 (d, J = 2.5 Hz, 1H), 4.63-4.68 (m, 1H), 4.57-4.63 (m, 1H), 4.34-4.39 (m, 1H), 4.18-4.30 (m, 2H), 3.88-3.97 (m, 1H), 2.17 (br dd, J = 11.0, 6.8 Hz, 2H), 1.63-1.85 (m, 6H) |

Example 42: [(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl] methyl Sulfamate and [(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl Sulfamate Compounds I-55a and I-55b

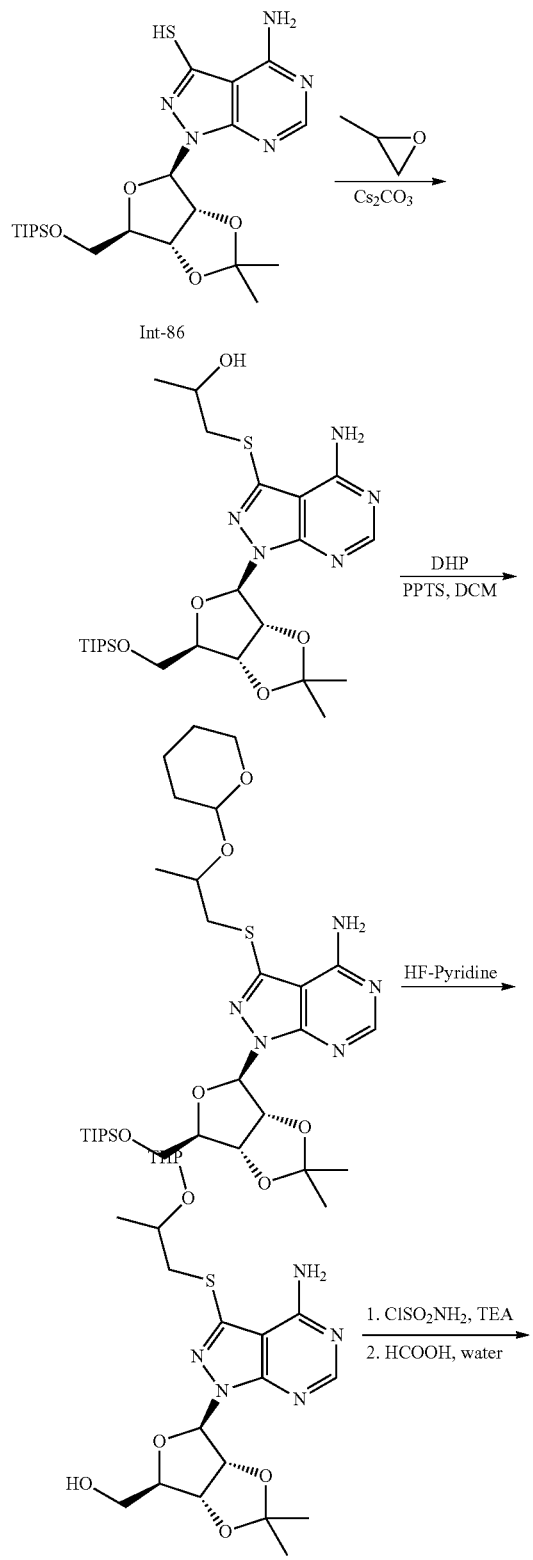

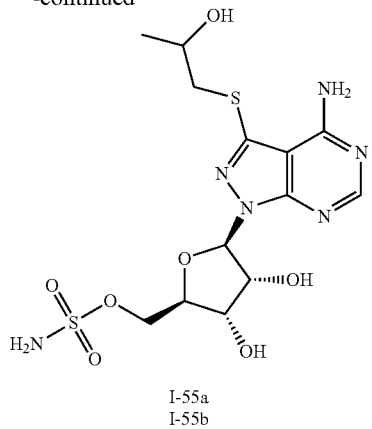

I-55a
I-55b

Step 1: (2R)-1-({4-amino-1-[(3aR,4R,6R,6aR)-2,2-dimethyl-6-{[(triisopropylsilyl) oxy]methyl}tetrahydrofuro[3,4-d][1,3]dioxol-4-yl]-1H-pyrazolo[3,4-d]pyrimidin-3-yl}sulfanyl)propan-2-ol and (2S)-1-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)propan-2-ol The mixture of titled compounds was prepared as described in Example 40 Step 1 utilizing propylene oxide instead of 1-oxaspiro[2,5]octane. LCMS (FA): m/z 554 (M+H)

Step 2: 1-[(3aR,4S,6R,6aR)-2,2-dimethyl-4-{[(triisopropylsilyl)oxy]methyl}hexahydrofuro[3,4-b]furan-6-yl]-3-({(2R)-2-[(2R)-tetrahydro-2H-pyran-2-yloxy]propyl}sulfanyl)-1H-pyrazolo[3,4-d]pyrimidin-4-amine and 1-[(3aR,4S,6R,6aR)-2,2-dimethyl-4-{[(triisopropylsilyl)oxy]methyl}hexahydrofuro[3,4-b]furan-6-yl]-3-({(2S)-2-[(2R)-tetrahydro-2H-pyran-2-yloxy]propyl}sulfanyl)-1H-pyrazolo[3,4-d]pyrimidin-4-amine and 1-[(3aR,4S,6R,6aR)-2,2-dimethyl-4-{[(triisopropylsilyl)oxy]methyl}hexahydrofuro[3,4-b]furan-6-yl]-3-({(2R)-2-[(2S)-tetrahydro-2H-pyran-2-yloxy]propyl}sulfanyl)-1H-pyrazolo[3,4-d]pyrimidin-4-amine and 1-[(3aR,4S,6R,6aR)-2,2-dimethyl-4-{[(triisopropylsilyl)oxy]methyl}hexahydrofuro[3,4-b]furan-6-yl]-3-({(2S)-2-[(2S)-tetrahydro-2H-pyran-2-yloxy]propyl}sulfanyl)-1H-pyrazolo[3,4-d]pyrimidin-4-amine A mixture of (2R)-1-({4-Amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl)}sulfanyl)propan-2-ol and (2S)-1-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)propan-2-ol (197 mg, 0.356 mmol) was dissolved in DCM (5 mL) and dihydropyran (0.324 mL, 3.56 mmol) was added. To this solution was added pyridinium p-toluenesulfonate (44.7 mg, 0.178 mmol) and the mixture was allowed to stir at rt overnight. To this reaction mixture was added further dihydropyran (0.324 mL, 3.56 mmol) and pyridinium p-toluenesulfonate (44.7 mg, 0.178 mmol) and the reaction mixture was stirred for 2 days. The reaction mixture was treated with water and extracted with EtOAc (3×). The organic solutions were combined, washed with brine, dried over sodium sulfate, filtered and concentrated to dryness. The crude material was purified by column chromatography to give the titled compounds (137 mg, 64%). LCMS (FA): m/z 554 (M+H).

Steps 3-5: [(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate or [(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl] methyl Sulfamate Compound I-55a; and [(2R,3S, 4R,5R)-5-(4-amino-3-{[(2R)-2-hydroxypropyl] sulfanyl}-1H-pyrazolo[3,4-d]pyrimidin-1-yl)-3,4-dihydroxytetrahydrofuran-2-yl]methyl sulfamate or [(2R,3S,4R,5R)-5-(4-amino-3-{[(2S)-2-hydroxypropyl]sulfanyl}-1H-pyrazolo[3,4-d]pyrimidin-1-yl)-3, 4-dihydroxytetrahydrofuran-2-yl]methyl Sulfamate Compound I-55b The titled compounds were prepared as described in Example 40 Steps 2-4 to afford a mixture of diastereomers which were further separated by preparative reverse phase HPLC. Absolute configuration of the products is unknown.

Peak 1 Compound I-55a: $^1$H NMR (400 MHz d$_6$-DMSO) δ 8.21 (s, 1H), 6.09-6.18 (m, 1H), 4.44-4.51 (m, 1H), 4.35 (t, J=5.4 Hz, 1H), 4.25 (dd, J=10.4, 3.2 Hz, 1H), 4.11 (br dd, J=5.6, 3.3 Hz, 1H), 4.03 (td, J=6.9, 3.7 Hz, 1H), 3.90 (br dd, J=11.1, 5.2 Hz, 1H), 3.10-3.23 (m, 2H), 1.18 (d, J=6.1 Hz, 3H); LCMS (FA): m/z 437 (M+H).

Peak 2 Compound I-55b: $^1$H NMR (400 MHz, d$_6$-DMSO) δ 8.21 (s, 1H), 6.12 (d, J=3.1 Hz, 1H), 4.42-4.53 (m, 1H), 4.34 (t, J=5.3 Hz, 1H), 4.25 (dd, J=10.4, 3.2 Hz, 1H), 4.12 (td, J=6.4, 3.4 Hz, 1H), 3.98-4.07 (m, 1H), 3.89 (dt, J=11.3, 5.6 Hz, 1H), 3.11-3.23 (m, 3H), 1.18 (d, J=6.1 Hz, 3H); LCMS (FA): m/z 437 (M+H).

Example 43: [(2R,3S,4R,5R)-5-(4-amino-3-{[(1R, 2R)-2-hydroxycyclopentyl]sulfanyl}-1H-pyrazolo[3, 4-d]pyrimidin-1-yl)-3,4-dihydroxytetrahydrofuran-2-yl]methyl Sulfamate and [(2R,3S,4R,5R)-5-(4-amino-3-{[(1S,2S)-2-hydroxycyclopentyl]sulfanyl}-1H-pyrazolo[3,4-d]pyrimidin-1-yl)-3,4-dihydroxytetrahydrofuran-2-yl]methyl Sulfamate Compound I-54

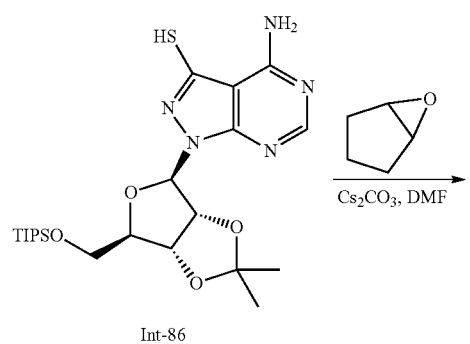

Int-86

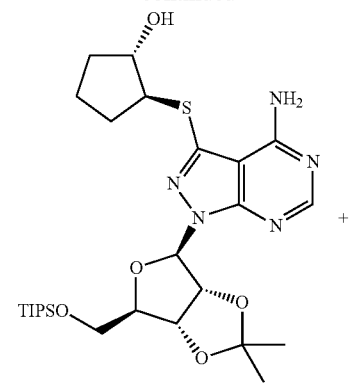

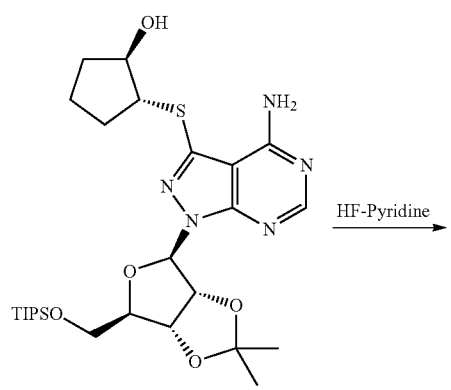

HF-Pyridine

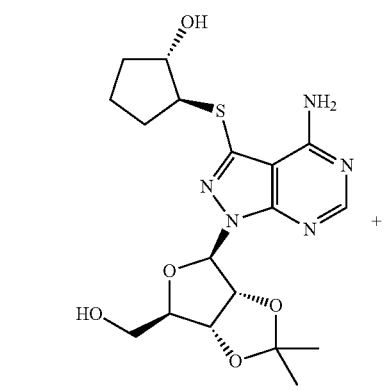

1. TBSCl, imidazole, DMAP
2. HCl, EtOH

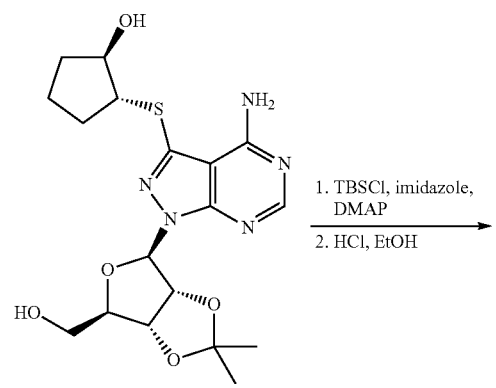

-continued

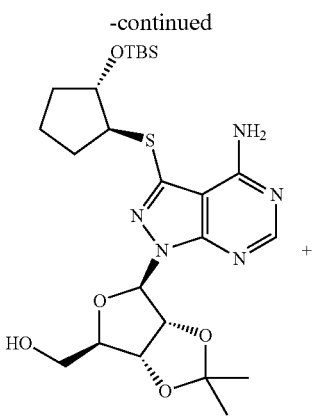

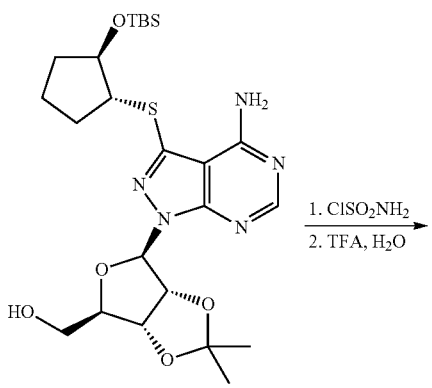

1. ClSO₂NH₂
2. TFA, H₂O

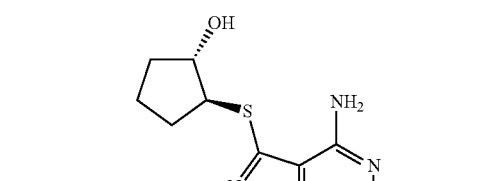

+

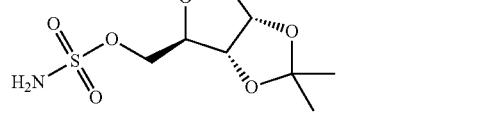

I-54

Step 1: (1S,2S)-2-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)cyclopentanol and (1R,2R)-2-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-11H-pyrazolo[3,4-d]pyrimidin-3-yl}sulfanyl)cyclopentanol The mixture of titled compounds were prepared as described in Example 40 Step 1 utilizing cyclopentene oxide instead of 1-oxaspiro[2,5]octane. LCMS (FA): m/z 581 (M+H).

Step 2: (1S,2S)-2-({4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}sulfanyl)cyclopentanol and (1R,2R)-2-({4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}sulfanyl)cyclopentanol To a solution of (1S,2S)-2-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)cyclopentanol and (1R,2R)-2-({4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-yl}sulfanyl)cyclopentanol (84.0 mg, 0.140 mmol) in methanol (1.0 mL) was added pyridine hydrofluoride (100 uL, 1.00 mmol). The mixture was allowed to stir at rt overnight. The reaction mixture was diluted with water and EtOAc and the aqueous phase was extracted into EtOAc (2×). The organic phases were combined and washed with water and brine, dried over sodium sulfate, filtered, and concentrated under reduced pressure. The crude material was used directly in the next reaction. LCMS (FA): m/z 424 (M+H).

Step 3: 3-{[(1S,2S)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine and 3-{[(1R,2R)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine To a solution of (1S,2S)-2-({4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}sulfanyl)cyclopentanol and (1R,2R)-2-({4-amino-1-[(3aR,4R,6R,6aR)-6-(hydroxymethyl)-2,2-dimethyltetrahydrofuro[3,4-d][1,3]dioxol-4-yl]-1H-pyrazolo[3,4-d]pyrimidin-3-yl}sulfanyl)cyclopentanol (60.0 mg, 0.100 mmol) in DMF (1.0 mL) was added DMAP (3.46 mg, 0.028 mmol), tert-butyldimethylsilyl chloride (100 mg, 0.708 mmol), and 1H-imidazole (48.2 mg, 0.708 mmol). The reaction mixture was allowed to stir at rt for 2 days. Water and EtOAc were then added and the aqueous phase was extracted into EtOAc (2×). The organics were combined and washed with water and brine, dried over sodium sulfate, filtered, and concentrated under reduced pressure. The crude residue was purified by column chromatography to give 3-{[(1S,2S)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine and 3-{[(1R,2R)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine (50 mg, 50%). LCMS (FA): m/z 653 (M+H).

Step 4: [(3aR,4R,6R,6aR)-6-(4-amino-3-{[(1S,2S)-2-{[tert-butyl(dimethyl)silyl]oxy}cyclopentyl]sulfanyl}-1H-pyrazolo[3,4-d]pyrimidin-1-yl)-2,2-dimethyltetrahydrofuro[3,4-d][1,3]dioxol-4-yl]methanol and [(3aR,4R,6R,6aR)-6-(4-amino-3-{[(1R,2R)-2-{[tert-butyl(dimethyl)silyl]oxy}cyclopentyl]sulfanyl}-H-pyrazolo[3,4-d]pyrimidin-1-yl)-2,2-dimethyltetrahydrofuro[3,4-d][1,3]dioxol-4-yl]methanol The titled compounds were prepared as described in Example 65 Step 5 substituting 3-{[(1S,2S)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine and 3-{[(1R,2R)-2-{[tert-butyl(dimethyl)silyl]oxy}cyclopentyl]sulfanyl}-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-4-amine for Intermediate 100. LCMS (FA): m/z 538 (M+H).

Step 5: [(2R,3S,4R,5R)-5-(4-amino-3-{[(1R,2R)-2-hydroxycyclopentyl]sulfanyl}-1H-pyrazolo[3,4-d]pyrimidin-1-yl)-3,4-dihydroxytetrahydrofuran-2-yl]methyl Sulfamate and [(2R,3S,4R,5R)-5-(4-amino-3-{[(1S,2S)-2-hydroxycyclopentyl]sulfanyl}-1H-pyrazolo[3,4-d]pyrimidin-1-yl)-3,4-dihydroxytetrahydrofuran-2-yl]methyl Sulfamate Compound I-54

The titled compound was prepared as described in Example 1, Step 7, followed by Example 35, Step 5 to afford [(2R,3S,4R,5R)-5-(4-amino-3-{[(1R,2R)-2-hydroxycyclopentyl]sulfanyl)}-1H-pyrazolo[3,4-d]pyrimidin-1-yl)-3,4-dihydroxytetrahydrofuran-2-yl]methyl sulfamate and [(2R,3S,4R,5R)-5-(4-amino-3-{[(1S,2S)-2-hydroxycyclopentyl]sulfanyl)}-1H-pyrazolo[3,4-d]pyrimidin-1-yl)-3,4-dihydroxytetrahydrofuran-2-yl]methyl sulfamate. LCMS (FA): m/z 463 (M+H); $^1$H NMR (400 MHz, d$_6$-DMSO) δ 8.23 (s, 1H), 7.51 (s, 2H), 6.15 (d, J=2.9 Hz, 1H), 5.62 (dd, J=5.1, 3.1 Hz, 1H), 5.41 (dd, J=6.3, 2.7 Hz, 1H), 5.33 (dd, J=10.7, 5.5 Hz, 1H), 4.48 (dq, J=8.4, 5.1 Hz, 1H), 4.37 (q, J=5.6 Hz, 1H), 4.26 (dt, J=10.4, 3.6 Hz, 1H), 4.10-4.19 (m, 1H), 3.97-4.07 (m, 1H), 2.92-3.06 (m, 1H), 1.92-2.08 (m, 2H), 1.61 (br s, 2H), 1.15-1.47 (m, 4H).

Example 44: [(2R,3S,4R,5R)-5-(4-amino-3-{[(1R,2R)-2-hydroxycyclohexyl]sulfanyl}-1H-pyrazolo[3,4-d]pyrimidin-1-yl)-3,4-dihydroxytetrahydrofuran-2-yl]methyl Sulfamate and [(2R,3S,4R,5R)-5-(4-amino-3-{[(1S,2S)-2-hydroxycyclohexyl]sulfanyl}-1H-pyrazolo[3,4-d]pyrimidin-1-yl)-3,4-dihydroxytetrahydrofuran-2-yl]methyl Sulfamate Compound I-47

The titled compounds were prepared as described in Example 43 utilizing cyclohexene oxide in place of cyclopentene oxide. LCMS (FA): m/z 477 (M+H); $^1$H NMR (400 MHz, d$_6$-DMSO) δ 8.23 (s, 1H), 7.51 (s, 2H), 6.15 (d, J=2.9 Hz, 1H), 5.62 (dd, J=5.1, 3.1 Hz, 1H), 5.41 (dd, J=6.3, 2.7 Hz, 1H), 5.33 (dd, J=10.7, 5.5 Hz, 1H), 4.48 (dq, J=8.4, 5.1 Hz, 1H), 4.37 (q, J=5.6 Hz, 1H), 4.26 (dt, J=10.4, 3.6 Hz, 1H), 4.10-4.19 (m, 1H), 3.97-4.07 (m, 1H), 2.92-3.06 (m, 1H), 1.92-2.08 (m, 2H), 1.61 (br s, 2H), 1.15-1.47 (m, 4H).

Example 45: {(2R,3S,4R,5R)-5-[4-amino-3-(cyclopropylsulfanyl)-1H-pyrazolo[3,4-d]pyrimidin-1-yl]-3,4-dihydroxytetrahydrofuran-2-yl}methyl Sulfamate Compound I-65

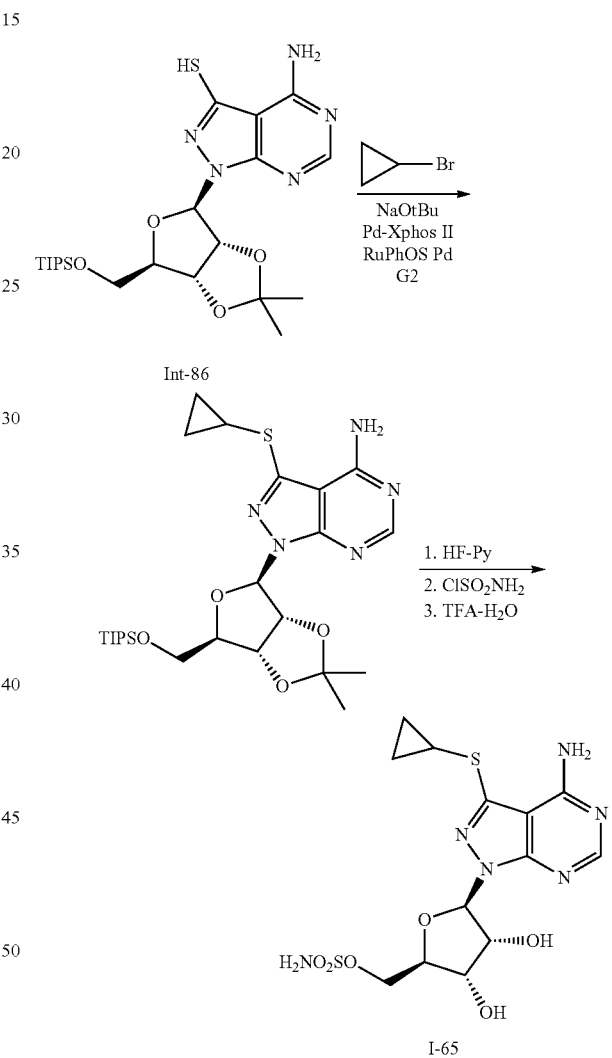

Step 1: 3-(cyclopropylsulfanyl)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine A microwave vial was charged with Intermediate 86 (1.10 g, 2.22 mmol), sodium t-butoxide (0.640 g, 6.66 mmol), bromocyclopropane (0.978 mL, 12.2 mmol), chloro(2-dicyclohexylphosphino-2',4',6'-tri-i-propyl-1,1'-biphenyl) [2-(2-aminoethyl)phenyl]palladium(II) methyl-t-butylether adduct (Pd-Xphos II, 328 mg, 0.444 mmol), chloro(2- dicyclohexylphosphino-2',6'-diisopropoxy-1,1'-biphenyl)[2-(2'-amino-1,1'-biphenyl)]palladium(II) (RuPhos Pd G2, 10.0 mg, 0.014 mmol), and DMF (15.7 mL). The mixture was degassed three times, back filled with argon gas and then heated at 120° C. overnight. Water was added, the mixture was extracted with EtOAc and the organic phases were combined, washed with brine, dried over $Na_2SO_4$, filtered and concentrated. The resulting crude material was purified by column chromatography to give 3-(cyclopropylsulfanyl)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine (282 mg, 24%). LCMS (FA): m/z 536 (M+H).

Steps 2-4: {(2R,3S,4R,5R)-5-[4-amino-3-(cyclopropylsulfanyl)-1H-pyrazolo[3,4-d]pyrimidin-1-yl]-3,4-dihydroxytetrahydrofuran-2-yl}methyl Sulfamate Compound I-65

The titled compound was prepared following the procedures described in Example 5 Step 7, Example 1 Step 7 and Example 35 Step 5 sequentially substituting 3-(cyclopropylsulfanyl)-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-4-amine for Intermediate 20 in Example 5 Step 7. LCMS (FA): m/z 419 (M+H); $^1$H NMR (400 MHz, $d_6$-DMSO) δ 8.23 (s, 1H), 7.53 (s, 2H), 6.16 (d, J=2.5 Hz, 1H), 5.65 (d, J=4.9 Hz, 1H), 5.40 (br d, J=6.3 Hz, 1H), 4.36-4.58 (m, 2H), 4.24-4.30 (m, 1H), 4.10 (br dd, J=18.3, 9.2 Hz, 2H), 1.01 (br d, J=7.0 Hz, 2H), 0.62-0.78 (m, 2H).

Example 46

The following compounds were prepared as described following the procedures in Example 45 using Intermediate 85 or Intermediate 86 with the reagents and conditions described in the table below.

Example 47: {(2R,3S,4R,5R)-5-[4-amino-3-(cyanomethyl)-1H-pyrazolo[3,4-d]pyrimidin-1-yl]-3,4-dihydroxytetrahydrofuran-2-yl}methyl Sulfamate Compound I-29

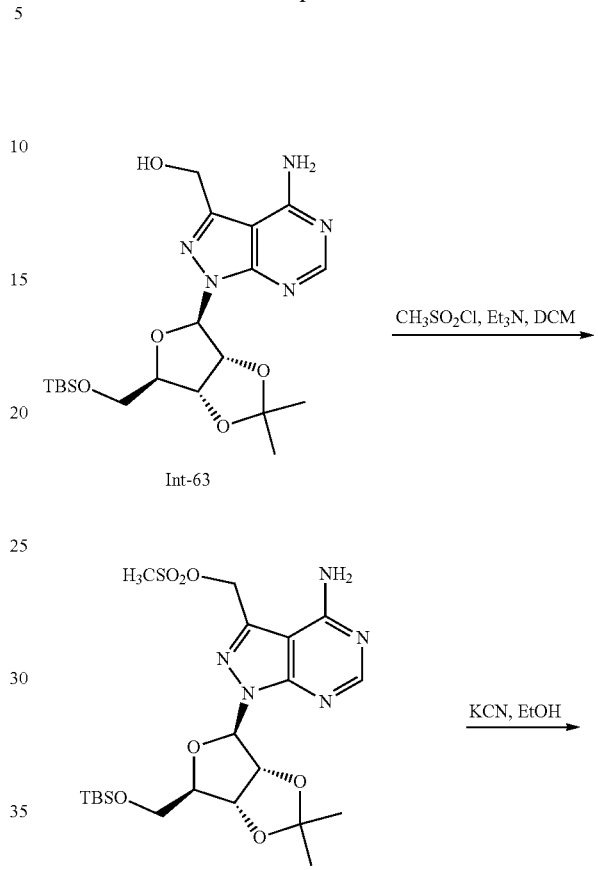

| Compound number | Halide | Coupling Conditions: modifications to Step 1 | Final deprotection conditions | LCMS data | $^1$H NMR Data |
|---|---|---|---|---|---|
| I-36 | 4-iodo-1-(tetrahydro-2H-pyran-2-yl)-1H-pyrazole | Intermediate 86, Xphos precatalyst, 120° C., 3 d $Cs_2CO_3$, DMF | Example 35 Step 5 | LCMS (FA): m/z 445 (M + H) | $^1$H NMR (400 MHz, $d_6$-DMSO) δ 13.21 (br s, 1H), 8.22 (s, 1H), 8.10 (s, 1H), 7.68 (s, 1H), 7.54 (s, 2H), 6.10 (d, J = 3.1 Hz, 1H), 5.61 (d, J = 5.3 Hz, 1H), 5.37 (d, J = 6.4 Hz, 1H), 4.39-4.46 (m, 1H), 4.23-4.30 (m, 1H), 4.20 (dd, J = 10.5, 3.3 Hz, 1H), 4.06-4.13 (m, 1H), 3.96 (dd, J = 10.5, 7.6 Hz, 1H). |
| I-61 | 4-iodo-1-methyl-1H-pyrazole | Intermediate 86, Xphos precatalyst, 120° C., ON $Cs_2CO_3$, DMF | Example 35 Step 5 | LCMS (FA): m/z 459 (M + H) | $^1$H NMR (400 MHz, $d_6$-DMSO) δ 8.24 (s, 1H), 8.00 (s, 1H), 7.65 (s, 1H), 7.55 (s, 2H), 6.11 (d, J = 3.1 Hz, 1H), 4.38-4.46 (m, 1H), 4.24-4.31 (m, 1H), 4.20 (dd, J = 10.5, 3.3 Hz, 1H), 4.06-4.14 (m, 1H), 3.94 (dd, J = 10.4, 7.5 Hz, 1H), 3.84 (s, 3H). |
| I-66 | 4-bromopyridine | Intermediate 85, Xphos precatalyst, 120° C., ON $Cs_2CO_3$, DMF | Example 1 Step 8 | LCMS(AA): m/z 456 (M + H) | 1H NMR (400 MHz, $CD_3OD$) δ 8.31-8.42 (m, 2H), 8.28 (s, 1H), 7.20 (d, J = 6.3 Hz, 2H), 6.39 (d, J = 3.0 Hz, 1H), 4.76 (dd, J = 4.8, 3.3 Hz, 1H), 4.57 (t, J = 5.3 Hz, 1H), 4.25-4.40 (m, 2H), 4.16-4.25 (m, 1H). |

-continued

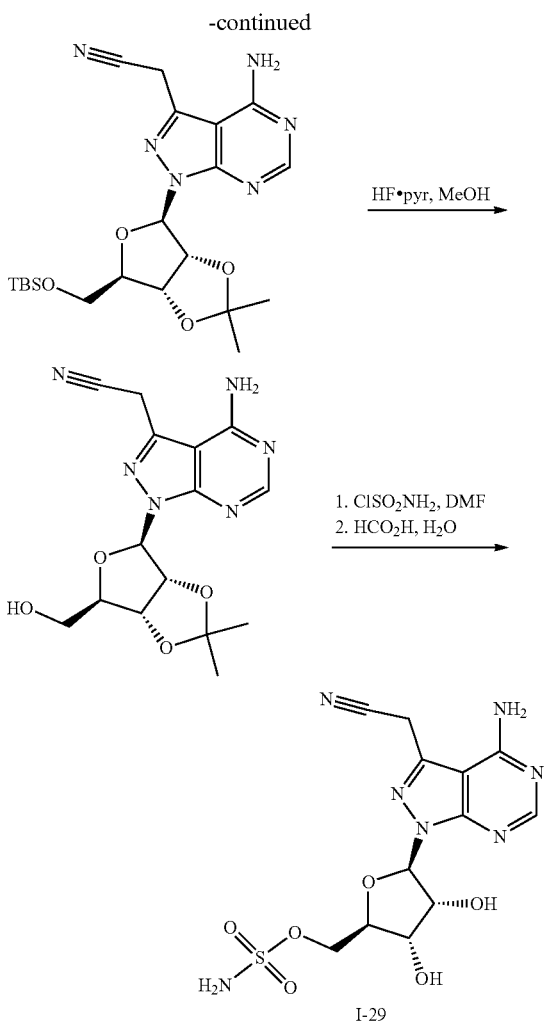

Step 1: [{4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}methyl Methanesulfonate To a solution of Intermediate 63 (0.199 g, 0.441 mmol) in methylene chloride (7 mL) and triethylamine (0.18 mL, 1.3 mmol) was added methanesulfonyl chloride (0.068 mL, 0.88 mmol) at 0° C. The mixture was stirred for 1 h in an ice-water bath. The still-cooled reaction solution was diluted with methylene chloride (50 mL) and water (50 mL). The phases separated and the aqueous phase was extracted with methylene chloride (25 mL). The extracts were combined, washed with brine, dried over sodium sulfate, filtered and concentrated under reduced pressure. The crude residue was purified by silica gel chromatography (24 g, 80/20 to 30/70 hexanes/ethyl acetate gradient) to afford the product as a white solid (202 mg, 86%). LCMS (AA): m/z 530 (M+H); $^1$H NMR (400 MHz, CDCl$_3$) δ 8.41 (s, 1H), 6.54 (d, J=2.1 Hz, 1H), 5.92 (s, 2H), 5.50 (s, 2H), 5.46 (dd, J=6.1, 2.2 Hz, 1H), 5.00 (dd, J=6.2, 2.2 Hz, 1H), 4.32 (ddd, J=7.5, 5.4, 2.3 Hz, 1H), 3.69 (dd, J=10.5, 7.4 Hz, 1H), 3.61 (dd, J=10.5, 5.5 Hz, 1H), 3.09 (s, 3H), 1.62 (s, 4H), 1.41 (s, 4H), 0.88 (s, 9H), 0.00 (s, 6H).

Step 2: {4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}acetonitrile To a solution of {4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}methyl methanesulfonate (0.201 g, 0.379 mmol) in absolute ethanol (5.0 mL) was added a solution of potassium cyanide (0.074 g, 1.14 mmol) in water (1.0 mL) and the mixture was stirred at rt overnight. The reaction mixture was diluted with acetonitrile (30 mL) and then ethanol (100 mL). Celite was added (2.5 g) and the mixture was concentrated under reduced pressure to dryness. The crude material was purified by silica gel chromatography (12 g, 60/40 hexanes/ethyl acetate to ethyl acetate gradient) to afford the product (80 mg, 46%). LCMS (AA): m/z 461 (M+H); $^1$H NMR (400 MHz, CDCl$_3$) δ 8.35 (s, 1H), 6.51 (d, J=2.2 Hz, 1H), 6.15 (s, 2H), 5.42 (dd, J=6.2, 2.2 Hz, 1H), 4.97 (dd, J=6.2, 2.3 Hz, 1H), 4.33-4.28 (m, 1H), 4.06 (s, 2H), 3.71 (dd, J=10.6, 7.1 Hz, 1H), 3.63 (dd, J=10.6, 5.6 Hz, 1H), 1.60 (s, 3H), 1.40 (s, 3H), 0.86 (d, J=2.8 Hz, 9H), 0.00 (d, J=3.0 Hz, 6H).

Step 3: {4-amino-1-[(3aR,4R,6R,6aR)-6-(hydroxymethyl)-2,2-dimethyltetrahydrofuro[3, 4-d][1, 3]dioxol-4-yl]-1H-pyrazolo[3,4-d]pyrimidin-3-yl}acetonitrile A solution of {4-amino-1-[(3aR,4R,6R,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidin-3-yl}acetonitrile (0.080 g, 0.17 mmol) in MeOH (7.0 mL) was transferred to a polypropylene conical vial fitted with a stirbar. A solution of hydrogen fluoride in pyridine (6.4 M, 0.17 mL, 1.1 mmol) was added and the reaction mixture stirred at rt overnight. The mixture was diluted with MeOH (25 mL) and gently stirred with 2 g of MP-carbonate for 70 minutes. The mixture was filtered through a cotton plug into a 50 mL syringe fitted with a 0.2 um frit. The MP beads were washed with MeOH (10 and 5 mL) and the filtrate was concentrated under reduced pressure and twice coevaporated from toluene. The crude product was dissolved in MeOH, adsorbed onto 1 g celite and eluted through a silica gel column (12 g, 40/60 hexanes/ethyl acetate to ethyl acetate gradient) to afford purified product (46 mg, 76%). LCMS (AA): m/z 347 (M+H); $^1$H NMR (400 MHz, d$_6$-DMSO) δ 8.24 (s, 1H), 6.28 (d, J=2.2 Hz, 1H), 5.30 (dd, J=6.2, 2.1 Hz, 1H), 4.93 (m, 2H), 4.58-4.44 (m, 2H), 4.14 (m, 1H), 3.63-3.51 (m, 1H), 3.41 (dt, J=11.6, 5.9 Hz, 1H), 1.53 (s, 3H), 1.34 (s, 3H).

Steps 4 and 5: {(2R,3S,4R,5R)-5-[4-amino-3-(cyanomethyl)-1H-pyrazolo[3,4-d]pyrimidin-1-yl]-3,4-dihydroxytetrahydrofuran-2-yl}methyl Sulfamate Compound I-29

The titled compound was prepared following the procedures described in Example 1 Steps 7 and 8 substituting {4-amino-1-[(3aR,4R,6R,6aR)-6-(hydroxymethyl)-2,2-dimethyltetrahydrofuro[3, 4-d][1,3]dioxol-4-yl]-1H-pyrazolo[3,4-d]pyrimidin-3-yl}acetonitrile for Intermediate 7. LCMS (AA): m/z 386 (M+H); $^1$H NMR (400 MHz, d$_6$-DMSO with D$_2$O) δ 8.18 (s, 1H), 6.10 (d, J=3.4 Hz, 1H), 4.47 (dd, J=5.0, 3.5 Hz, 1H), 4.40 (m, 2H), 4.35-4.31 (m, 1H), 4.21 (dd, J=10.5, 3.1 Hz, 1H), 4.12-4.06 (m, 1H), 4.01 (dd, J=10.4, 7.4 Hz, 1H).

Example 48: {(2R,3S,5R)-5-[4-amino-3-(ethylsulfanyl)-1H-pyrazolo[3,4-d]pyrimidin-1-yl]-3-hydroxytetrahydrofuran-2-yl}methyl Sulfamate Compound I-172

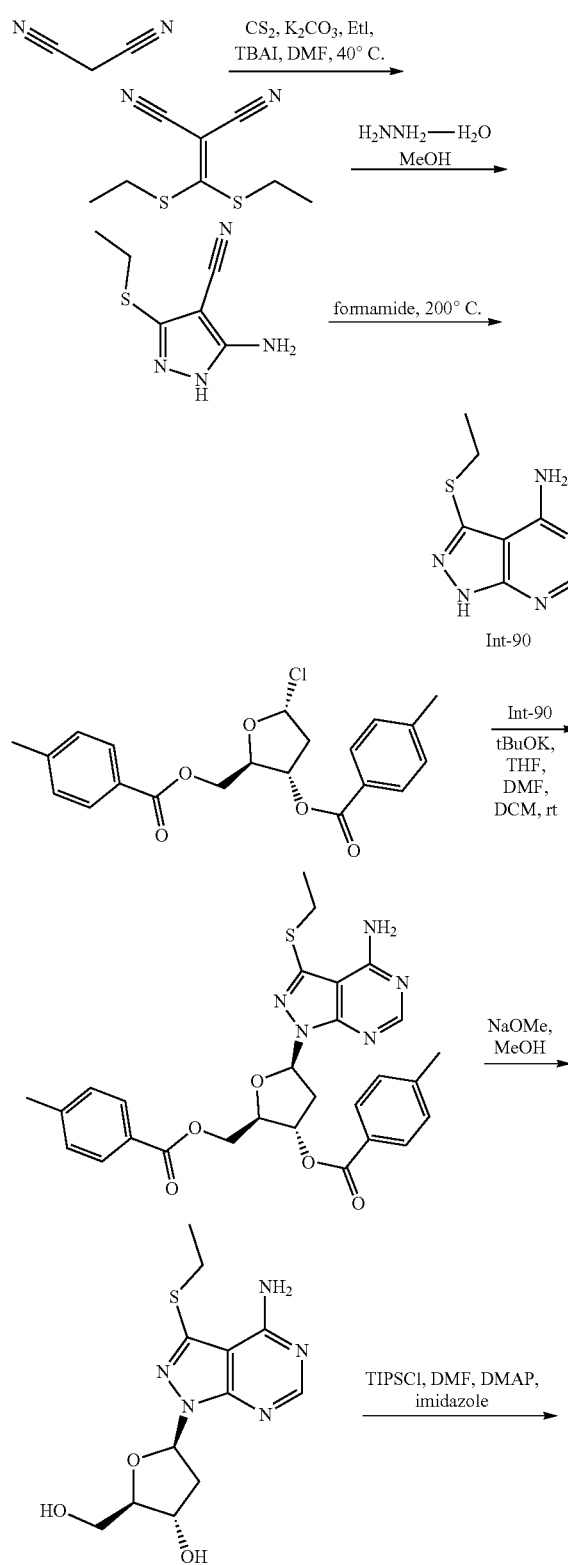

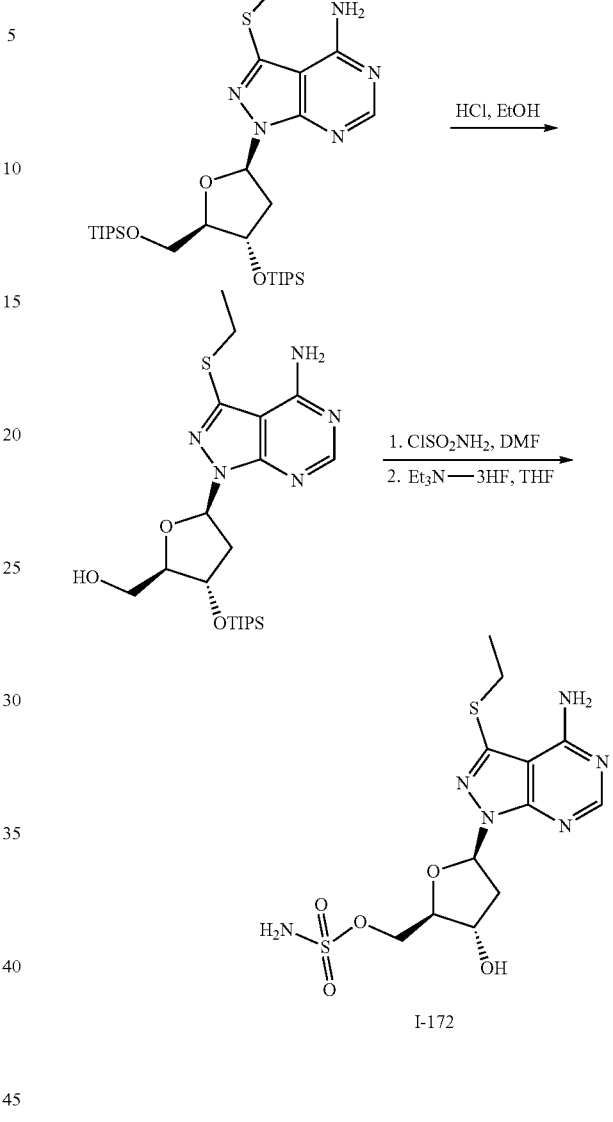

Step 1: 2-(bis(ethylthio)methylene)malononitrile

To a solution of malononitrile (100 g, 1.51 mol) in DMF (1 L) was added solid potassium carbonate (209 g, 1.51 mol). The mixture was allowed to stir at 25° C. for 15 min, then carbon disulfide (115 g, 1.51 mol) was added dropwise. After being allowed to stir for 15 min, tetra-n-butylammonium iodide (55.9 g, 151 mmol) was added to the reaction mixture. The reaction mixture was allowed to cool in an ice-water bath and ethyl iodide (354 g, 2.27 mol) was added dropwise over one hour. Upon completion of addition, the reaction mixture was warmed to 50° C. for 16 h. Following the heating interval, the reaction mixture was cooled to rt, poured into a separatory funnel, diluted with water (1 L) and extracted with EtOAc (3×500 mL). The combined extracts were twice washed with brine, dried over sodium sulfate, filtered and concentrated under reduced pressure. The resulting crude product was purified by silica gel chromatography to afford the product (120 g, 40%) as a yellow oil. $^1$H NMR (400 MHz, CDCl$_3$) δ 3.29 (q, J=7.4 Hz, 4H), 1.43 (t, J=7.4 Hz, 6H).

Step 2: 5-amino-3-(ethylsulfanyl)-1H-pyrazole-4-carbonitrile 2-(Bis(ethylthio)methylene)malononitrile (120 g, 0.605 mol) was dissolved in MeOH (1 L). The solution was allowed to stir at rt. To the stirred solution was added hydrazine hydrate (35.3 mL, 726 mmol) dropwise over 1 h. Upon completion of addition, the reaction mixture was allowed to stir at 50° C. for 4 h before cooling to rt, at which time the reaction was complete. Solvent was removed under reduced pressure to afford the product (100 g, 98%) as a yellow solid which was used as obtained. $^1$H NMR (400 MHz, d$_6$-DMSO) δ 6.36 (s, 2H), 2.95 (q, J=7.3 Hz, 2H), 1.24 (t, J=7.3 Hz, 3H).

Step 3: 3-(ethylsulfanyl)-1H-pyrazolo[3,4-d]pyrimidin-4-amine Intermediate 90

5-Amino-3-(ethylsulfanyl)-1H-pyrazole-4-carbonitrile (100 g, 595 mmol) was dissolved in formamide (500 mL). The resulting solution was allowed to stir at 200° C. for 2 h. After cooling to rt, the reaction mixture was poured into water (700 mL), stirred 30 min and filtered. The solids isolated were suspended in 1:1 hexanes:EtOAc (300 mL) and stirred 30 min. The washed solids were isolated by suction filtration and dried in vacuo to afford the desired product (100 g, 86%) as a white solid. $^1$H NMR (400 MHz, d$_6$-DMSO) δ 8.16 (s, 1H), 3.04 (q, J=7.3 Hz, 2H), 1.27 (t, J=7.3 Hz, 3H).

Step 4: (2R,3S,5R)-5-[4-amino-3-(ethylsulfanyl)-1H-pyrazolo[3,4-d]pyrimidin-1-yl]-2-{[(4-methylbenzoyl)oxy]methyl}tetrahydrofuran-3-yl-4-methylbenzoate Intermediate 90 (55.23 g, 282.9 mmol) was dissolved in a 1:1 mixture of DMF and MeCN (1.8 L). Solid potassium tert-butoxide (31.74 g, 282.9 mmol) was added, and the resulting mixture was allowed to stir at rt for 15 min. THF (1.8 L) was added, followed by (2R,3S,5R)-5-chloro-2-{[(4-methylbenzoyl)oxy]methyl}tetrahydrofuran-3-yl-4-methylbenzoate (100 g, 257 mmol). The resulting mixture was stirred at rt for 2 h, and then concentrated under reduced pressure. The residue was partitioned between water (1 L) and DCM (500 mL). The phases were separated and the aqueous phase was extracted with additional DCM (500 mL×2). The extracts were combined, washed with brine, dried over sodium sulfate, filtered and concentrated under reduced pressure. The crude residue was purified by silica gel chromatography to afford (2R,3S,5R)-5-[4-amino-3-(ethylsulfanyl)-1H-pyrazolo[3,4-d]pyrimidin-1-yl]-2-{[(4-methylbenzoyl)oxy]methyl}tetrahydrofuran-3-yl-4-methylbenzoate (180 g, 44%) as a white solid. LCMS (FA): m/z=548 (M+H); $^1$H NMR (400 MHz, CDCl$_3$) δ 8.33-8.42 (m, 1H), 7.99 (d, J=8.2 Hz, 4H), 7.20-7.36 (m, 4H), 6.91 (t, J=6.6 Hz, 1H), 5.95 (s, 2H), 5.81-5.92 (m, 1H), 4.61-4.70 (m, 2H), 4.49-4.60 (m, 1H), 3.42-3.58 (m, 1H), 3.15 (qd, J=7.3, 1.1 Hz, 2H), 2.68 (ddd, J=14.1, 6.5, 3.0 Hz, 1H), 2.46 (s, 3H), 2.42 (s, 3H), 1.40 (t, J=7.3 Hz, 3H).

Step 5: (2R,3S,5R)-5-[4-amino-3-(ethylsulfanyl)-1H-pyrazolo[3,4-d]pyrimidin-1-yl]-2-(hydroxymethyl)tetrahydrofuran-3-ol The titled compound was prepared following the procedure outlined in Example 3 Step 4 substituting (2R,3S,5R)-5-[4-amino-3-(ethylsulfanyl)-1H-pyrazolo[3,4-d]pyrimidin-1-yl]-2-{[(4-methylbenzoyl)oxy]methyl}tetrahydrofuran-3-yl-4-methylbenzoate for Intermediate 10. LCMS (FA): m/z=311 (M+H); $^1$H NMR (400 MHz, CD$_3$OD) δ 8.19 (s, 1H), 6.67 (t, J=6.4 Hz, 1H), 4.61-4.71 (m, 1H), 4.03 (q, J=4.2 Hz, 1H), 3.74-3.87 (m, 1H), 3.63-3.71 (m, 1H), 3.18 (q, J=7.3 Hz, 2H), 2.86-3.01 (m, 1H), 2.41 (ddd, J=13.5, 6.9, 4.3 Hz, 1H), 1.42 (t, J=7.3 Hz, 3H).

Step 6: 3-(Ethylsulfanyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine The titled compound was prepared following the procedure outlined in Example 95 Step 8 substituting (2R,3S,5R)-5-[4-amino-3-(ethylsulfanyl)-1H-pyrazolo[3,4-d]pyrimidin-1-yl]-2-(hydroxymethyl)tetrahydrofuran-3-ol for Intermediate 120. LCMS (FA): m/z=391 (M+H); $^1$H NMR (400 MHz, CDCl$_3$) δ 8.36 (s, 1H), 6.77 (t, J=6.8 Hz, 1H), 5.81 (br s, 2H), 4.80-4.93 (m, 1H), 4.08-4.18 (m, 1H), 3.80-3.87 (m, 1H), 3.71-3.77 (m, 1H), 3.21 (s, 1H), 3.11-3.25 (m, 2H), 2.36 (ddd, J=13.2, 6.3, 2.4 Hz, 1H), 1.42 (t, J=7.3 Hz, 3H), 0.98-1.19 (m, 42H).

Step 7: {(2R,3S,5R)-5-[4-Amino-3-(ethylsulfanyl)-1H-pyrazolo[3,4-d]pyrimidin-1-yl]-3-[(triisopropylsilyl)oxy]tetrahydrofuran-2-yl}methanol The titled compound was prepared following the procedure outlined in Example 95 Step 9 substituting 3-(ethylsulfanyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine for Intermediate 121. $^1$H NMR (400 MHz, CDCl$_3$) δ 8.35 (s, 1H), 6.72 (dd, J=8.3, 6.3 Hz, 1H), 5.90 (br s, 2H), 5.29-5.44 (m, 1H), 4.83 (br d, J=5.0 Hz, 1H), 4.21 (s, 1H), 3.96 (br d, J=12.9 Hz, 1H), 3.63-3.72 (m, 1H), 3.08-3.24 (m, 2H), 2.97 (ddd, J=13.3, 8.2, 5.3 Hz, 1H), 2.35-2.48 (m, 1H), 1.42 (t, J=7.3 Hz, 3H), 1.04-1.21 (m, 21H).

Step 8: {(2R,3S,5R)-5-[4-amino-3-(ethylsulfanyl)-1H-pyrazolo[3,4-d]pyrimidin-1-yl]-3-[(triisopropylsilyl)oxy]tetrahydrofuran-2-yl}methyl Sulfamate The titled compound was prepared following the procedure described in Example 1 Step 7, substituting {(2R,3S,5R)-5-[4-amino-3-(ethylsulfanyl)-1H-pyrazolo[3,4-d]pyrimidin-1-yl]-3-[(triisopropylsilyl)oxy]tetrahydrofuran-2-yl}methanol for Intermediate 7. $^1$H NMR (400 MHz, CDCl$_3$) δ 8.16 (s, 1H), 7.16 (s, 1H), 6.63 (t, J=6.3 Hz, 1H), 6.18 (br s, 2H), 5.25-5.74 (m, 1H), 4.66-4.80 (m, 1H), 4.29-4.39 (m, 1H), 4.29-4.39 (m, 1H), 4.19-4.28 (m, 1H), 4.09-4.15 (m, 1H), 2.79-2.89 (m, 2H), 2.19-2.34 (m, 1H), 1.30 (t, J=7.3 Hz, 3H), 0.88-1.10 (m, 21H).

Step 9: {(2R,3S,5R)-5-[4-amino-3-(ethylsulfanyl)-1H-pyrazolo[3,4-d]pyrimidin-1-yl]-3-hydroxytetrahydrofuran-2-yl}methyl Sulfamate I-172

The titled compound was prepared following the procedure outlined in Example 65 Step 7 substituting {(2R,3S,5R)-5-[4-amino-3-(ethylsulfanyl)-1H-pyrazolo[3,4-d]pyrimidin-1-yl]-3-[(triisopropylsilyl)oxy]tetrahydrofuran-2-yl}methyl sulfamate for {(2R,3R,4S,5R)-5-[4-amino-3-(isopropylsulfanyl)-1H-pyrazolo[3,4-d]pyrimidin-1-yl]-4-fluoro-3-[(triisopropylsilyl)oxy]tetrahydrofuran-2-yl}methyl sulfamate. LCMS (AA): m/z=391 (M+H); $^1$H NMR (400 MHz, CD$_3$OD) δ 8.21 (s, 1H), 6.70 (br t, J=6.0 Hz, 1H), 4.75 (br s, 1H), 4.28-4.43 (m, 1H), 4.18 (br d, J=4.8 Hz, 2H), 3.22 (q, J=7.3 Hz, 2H), 2.90-3.09 (m, 1H), 2.32-2.55 (m, 1H), 1.43 (t, J=7.3 Hz, 3H).

Example 49: {(2R,3S,5R)-5-[4-amino-3-(isopropylsulfanyl)-1H-pyrazolo[3,4-d]pyrimidin-1-yl]-3-hydroxytetrahydrofuran-2-yl}methyl Sulfamate Compound I-181

The titled compound was prepared as described in Example 48 substituting Intermediate 99 for Intermediate 90 in Step 4. LCMS (FA): m/z 405 (M+H); $^1$H NMR (400 MHz CD$_3$OD) δ 8.22 (s, 1H), 6.71 (dd, J=6.7, 5.3 Hz, 1H), 4.67-4.82 (m, 1H), 4.29-4.38 (m, 1H), 4.12-4.24 (m, 2H), 3.74 (spt, J=6.7 Hz, 1H), 3.00 (dt, J=13.5, 5.8 Hz, 1H), 2.41-2.50 (m, 1H), 1.43 (t, J=6.6 Hz, 6H).

Example 50: {(2R,3S,5R)-5-[4-amino-3-(methylsulfanyl)-1H-pyrazolo[3,4-d]pyrimidin-1-yl]-3-hydroxytetrahydrofuran-2-yl}methyl Sulfamate Compound I-200

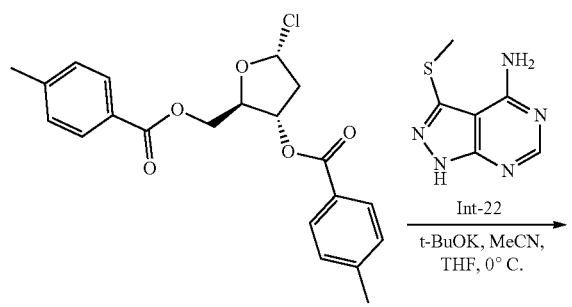

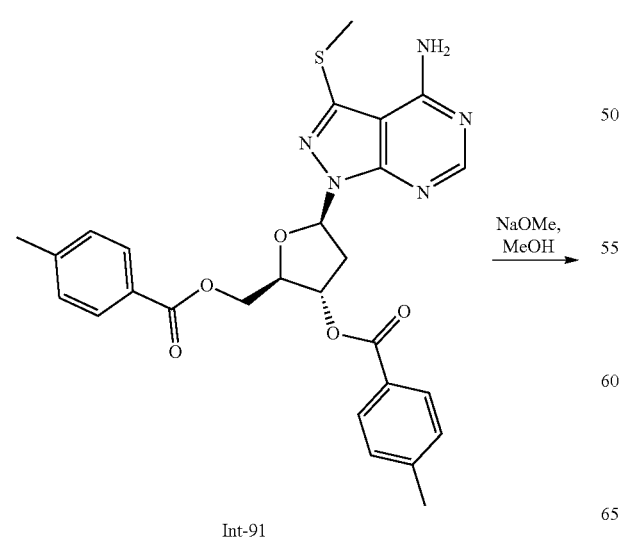

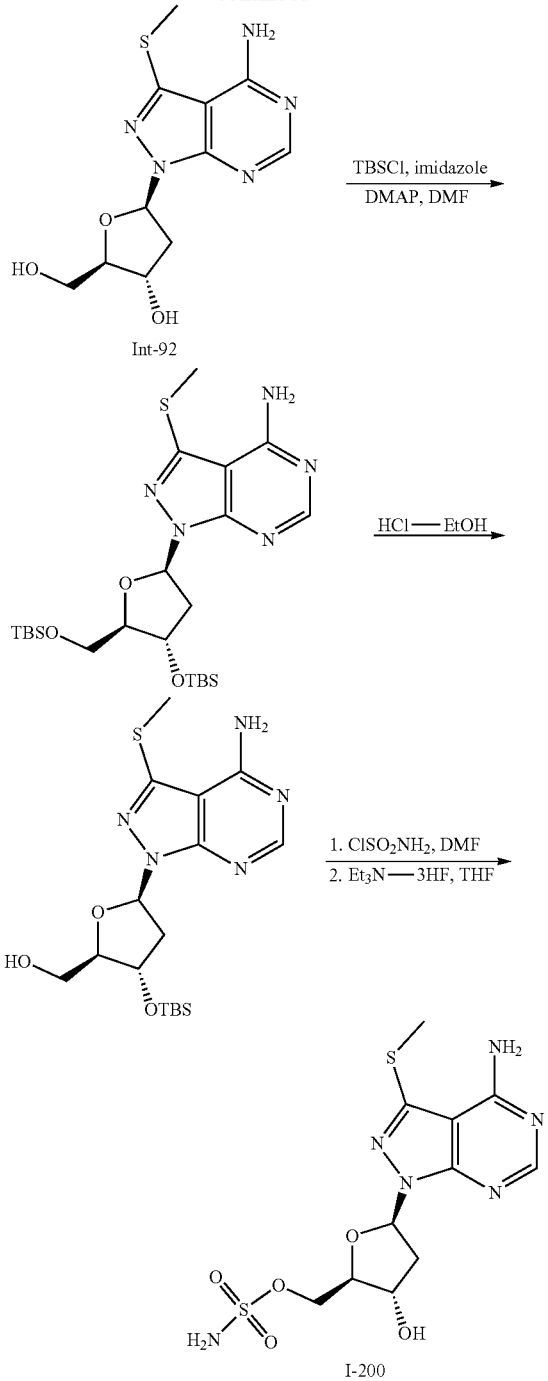

Step 1: (2R,3S,5R)-5-[4-amino-3-(methylsulfanyl)-1H-pyrazolo[3,4-d]pyrimidin-1-yl]-2-{[(4-methylbenzoyl)oxy]methyl}tetrahydrofuran-3-yl 4-methylbenzoate Intermediate 91

The titled compound was prepared following the procedure detailed in Example 48 Step 4, substituting Intermediate 22 for Intermediate 90. LCMS (FA): m/z=534 (M+H); $^1$H NMR (400 MHz, CDCl$_3$) δ 8.36 (s, 1H), 7.96-8.01 (m, 4H), 7.29 (br d, J=8.0 Hz, 2H), 7.24 (d, J=7.9 Hz, 2H), 6.89 (t, J=6.5 Hz, 1H), 5.88-5.94 (m, 1H), 5.86 (s, 1H), 4.62-4.70

(m, 1H), 4.53-4.60 (m, 1H), 3.43-3.52 (m, 1H), 2.68-2.71 (m, J=3.3, 6.5 Hz, 1H), 2.67 (s, 3H), 2.46 (s, 3H), 2.42 (s, 3H).

Step 2: (2R,3S,5R)-5-[4-amino-3-(methylsulfanyl)-1H-pyrazolo[3,4-d]pyrimidin-1-yl]-2-(hydroxymethyl)tetrahydrofuran-3-ol Intermediate 92

The titled compound was prepared following the procedure outlined in Example 3 Step 4 substituting Intermediate 91 for Intermediate 10. LCMS (FA): m/z=298 (M+H); $^1$H NMR (400 MHz, CD$_3$OD) δ 8.19 (s, 1H), 6.66 (t, J=6.4 Hz, 1H), 4.63-4.68 (m, 1H), 4.00-4.05 (m, 1H), 3.75-3.82 (m, 1H), 3.67 (dd, J=5.3, 11.9 Hz, 1H), 2.94 (td, J=6.1, 13.5 Hz, 1H), 2.69 (s, 3H), 2.40 (ddd, J=4.1, 6.9, 13.5 Hz, 1H).

Step 3: 1-[(2R,4S,5R)-4-{[tert-butyl(dimethyl)silyl]oxy}-5-({[tert-butyl(dimethyl)silyl]oxy}methyl)tetrahydrofuran-2-yl]-3-(methylsulfanyl)-1H-pyrazolo[3,4-d]pyrimidin-4-amine The titled compound was prepared following the procedure outlined in Example 65 Step 4 substituting Intermediate 92 for (2R,3R,4S,5R)-5-[4-amino-3-(isopropylsulfanyl)-1H-pyrazolo[3,4-d]pyrimidin-1-yl]-4-fluoro-2-(hydroxymethyl)tetrahydrofuran-3-ol. LCMS (FA): m/z=527 (M+H); $^1$H NMR (400 MHz, CDCl$_3$) δ 8.21 (s, 1H), 6.57 (t, J=6.5 Hz, 1H), 5.78 (br s, 2H), 4.58 (td, J=3.1, 5.7 Hz, 1H), 3.86 (ddd, J=2.9, 4.8, 7.2 Hz, 1H), 3.57-3.63 (m, 1H), 3.50-3.56 (m, 1H), 2.90-2.98 (m, 1H), 2.54 (s, 3H), 2.15 (ddd, J=3.6, 6.5, 13.1 Hz, 1H), 0.80 (s, 9H), 0.75 (s, 9H), 0.00 (s, 6H), −0.11 (s, 3H), −0.13 (s, 3H).

Step 4: [(2R,3S,5R)-5-[4-amino-3-(methylsulfanyl)-1H-pyrazolo[3,4-d]pyrimidin-1-yl]-3-{[tert-butyl(dimethyl)silyl]oxy}tetrahydrofuran-2-yl]methanol The titled compound was prepared following the procedure outlined in Example 65 Step 5 substituting 1-[(2R,4S,5R)-4-{[tert-butyl(dimethyl)silyl]oxy}-5-({[tert-butyl(dimethyl)silyl]oxy}methyl)tetrahydrofuran-2-yl]-3-(methylsulfanyl)-1H-pyrazolo[3,4-d]pyrimidin-4-amine for 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-(isopropylsulfanyl)-1H-pyrazolo[3,4-d]pyrimidin-4-amine. LCMS (FA): m/z=412 (M+H); $^1$H NMR (400 MHz, CDCl$_3$) δ 8.20 (s, 1H), 6.58 (t, J=7.0 Hz, 1H), 5.92 (br s, 2H), 5.19 (s, 1H), 4.59-4.65 (m, 1H), 4.00 (d, J=2.0 Hz, 1H), 3.81 (dd, J=1.9, 12.7 Hz, 1H), 3.61 (br d, J=12.1 Hz, 1H), 2.78 (ddd, J=5.6, 7.6, 13.3 Hz, 1H), 2.57 (s, 3H), 2.23 (ddd, J=2.3, 6.3, 13.3 Hz, 1H), 0.81 (s, 9H), 0.00 (s, 6H).

Step 5: [(2R,3S,5R)-5-[4-amino-3-(methylsulfanyl)-1H-pyrazolo[3,4-d]pyrimidin-1-yl]-3-{[tert-butyl(dimethyl)silyl]oxy}tetrahydrofuran-2-yl]methyl Sulfamate The titled compound was prepared following the procedure described in Example 1 Step 7 substituting [(2R,3S,5R)-5-[4-amino-3-(methylsulfanyl)-1H-pyrazolo[3,4-d]pyrimidin-1-yl]-3-{[tert-butyl(dimethyl)silyl]oxy}tetrahydrofuran-2-yl]methanol for Intermediate 7. LCMS (AA): m/z=491 (M+H); $^1$H NMR (400 MHz, CDCl$_3$) δ 8.19 (s, 1H), 6.59 (t, J=6.3 Hz, 1H), 5.63 (br s, 2H), 5.06 (br s, 2H), 4.59-4.63 (m, 1H), 4.27-4.32 (m, 1H), 4.18-4.24 (m, 1H), 4.00-4.04 (m, 1H), 2.77 (td, J=6.3, 13.0 Hz, 1H), 2.59 (s, 3H), 2.19 (ddd, J=4.3, 6.3, 13.1 Hz, 1H), 0.80 (s, 9H), 0.00 (s, 6H).

Step 6: {(2R,3S,5R)-5-[4-amino-3-(methylsulfanyl)-1H-pyrazolo[3,4-d]pyrimidin-1-yl]-3-hydroxytetrahydrofuran-2-yl}methyl Sulfamate I-200

The titled compound was prepared following the procedure outlined in Example 65 Step 7 substituting [(2R,3S,5R)-5-[4-amino-3-(methylsulfanyl)-1H-pyrazolo[3,4-d]pyrimidin-1-yl]-3-{[tert-butyl(dimethyl)silyl]oxy}tetrahydrofuran-2-yl]methyl sulfamate for Intermediate 101. LCMS (AA): m/z=377 (M+H); $^1$H NMR (400 MHz, d$_6$-DMSO) δ 8.20 (s, 1H), 7.50 (br s, 2H), 6.57 (dd, J=5.1, 6.9 Hz, 1H), 5.51 (br s, 1H), 4.54 (br s, 1H), 4.19-4.25 (m, 1H), 3.99-4.05 (m, 2H), 2.79 (td, J=5.9, 13.0 Hz, 1H), 2.63 (s, 3H), 2.30-2.39 (m, 1H).

Example 51: {(2R,3S,5R)-5-[4-amino-3-(trifluoromethyl)-1H-pyrazolo[3,4-d]pyrimidin-1-yl]-3-hydroxytetrahydrofuran-2-yl}methyl Sulfamate Compound I-171

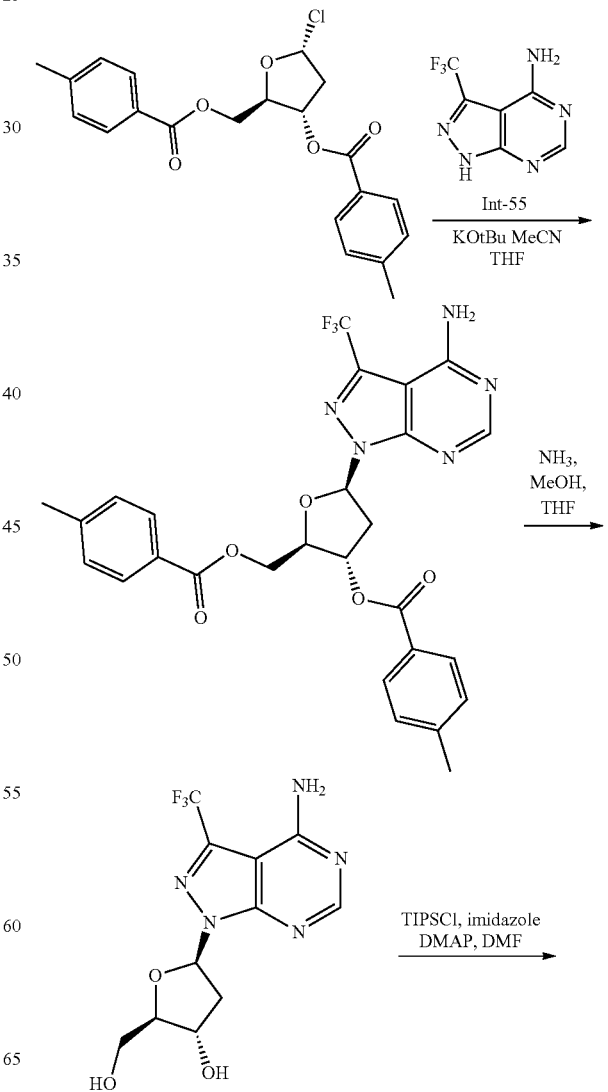

-continued

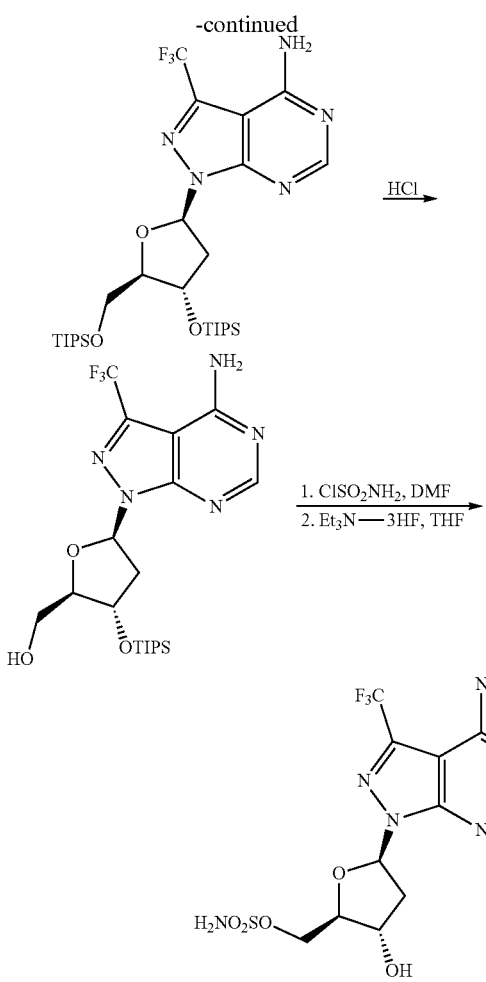

I-171

Steps 1-2: (2R,3S,5R)-5-[4-amino-3-(trifluoromethyl)-1H-pyrazolo[3,4-d]pyrimidin-1-yl]-(hydroxymethyl)tetrahydrofuran-3-ol The titled compound was prepared as described in Example 50 Step 1 substituting Intermediate 55 for Intermediate 22 followed by Example 5 Step 3. The hydrolysis of the tolyl esters required 3 days at room temperature.

Steps 3-4: {(2S,3S,5R)-5-[4-amino-3-(trifluoromethyl)-1H-pyrazolo[3,4-d]pyrimidin-1-yl]-3-[(triisopropylsilyl)oxy]tetrahydrofuran-2-yl}methanol The titled compound was prepared as described in Example 53 Steps 3 and 4 substituting (2R,3S,5R)-5-[4-amino-3-(trifluoromethyl)-1H-pyrazolo[3,4-d]pyrimidin-1-yl]-2-(hydroxymethyl)tetrahydrofuran-3-ol for Intermediate 93.

Steps 5-6: {(2R,3S,5R)-5-[4-amino-3-(trifluoromethyl)-1H-pyrazolo[3,4-d]pyrimidin-1-yl]-3-hydroxytetrahydrofuran-2-yl}methyl Sulfamate I-171

The titled compound was prepared as described in Example 1 Step 7 and Example 65 Step 7 substituting {(2S,3S,5R)-5-[4-amino-3-(trifluoromethyl)-1H-pyrazolo [3,4-d]pyrimidin-1-yl]-3-[(triisopropylsilyl)oxy]tetrahydrofuran-2-yl}methanol for Intermediate 7 (155 mg, 84%). LCMS (FA): m/z 399 (M+H); $^1$H NMR (400 MHz, d$_6$-DMSO) δ 8.37 (s, 1H), 7.51 (s, 2H), 6.69 (dd, J=6.9, 5.0 Hz, 1H), 5.60 (d, J=4.9 Hz, 1H), 4.51-4.58 (m, 1H), 4.21 (dd, J=10.2, 4.1 Hz, 1H), 4.02-4.09 (m, 1H), 3.93-4.01 (m, 1H), 2.77-2.85 (m, 1H), 2.37-2.48 (m, 1H).

Example 52 [(2R,3S,5R)-5-(4-amino-3-methoxy-1H-pyrazolo[3,4-d]pyrimidin-1-yl)-3-hydroxytetrahydrofuran-2-yl]methyl Sulfamate Compound I-190

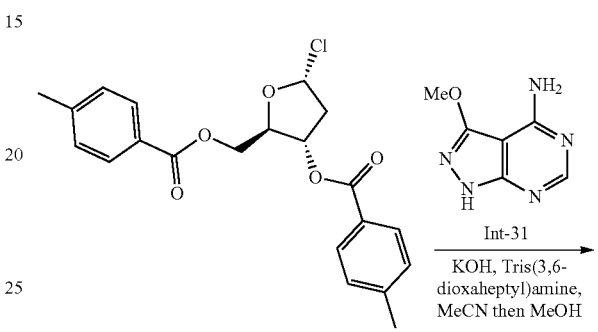

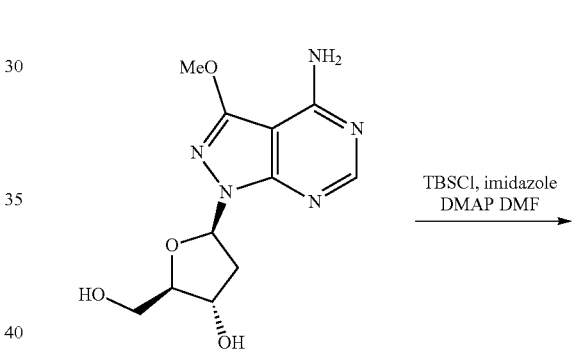

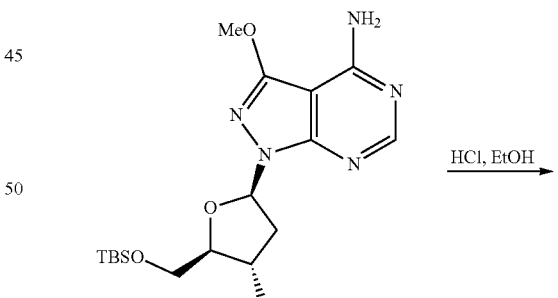

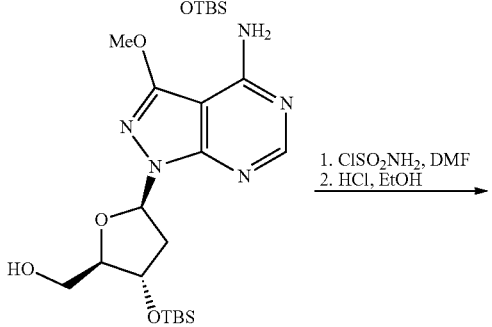

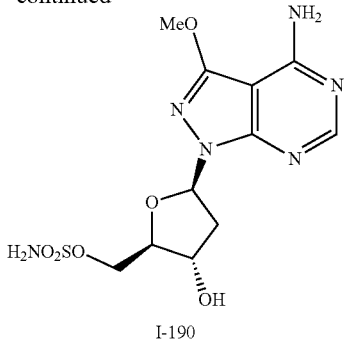

I-190

Step 1: (2R,3S,5R)-5-(4-amino-3-methoxy-1H-pyrazolo[3,4-d]pyrimidin-1-yl)-2-(hydroxymethyl)tetrahydrofuran-3-ol Intermediate 31 (354 mg, 2.14 mmol), and acetonitrile (26.5 mL) were combined in a round bottom flask. Tris(3,6-dioxaheptyl)amine (68.6 mL, 0.21 mmol) and crushed potassium hydroxide (481 mg, 8.57 mmol) were added. The reaction mixture was allowed to stir at rt for 10 min. A suspension of (2R,3S,5R)-5-chloro-2-{[(4-methylbenzoyl)oxy]methyl}tetrahydrofuran-3-yl 4-methylbenzoate (1.00 g, 2.57 mmol) in THF (9.8 mL) was added and the reaction mixture was allowed to stir at rt for 90 min. After this time LCMS showed that the glycosylation reaction was complete. Methanol (50 mL) was added and the mixture was allowed to stir for 1 h. The solvents were partially evaporated and further methanol was added. The mixture was allowed to stir for a further 30 min., after which time LCMS showed complete conversion to the desired product. The reaction mixture was adsorbed onto celite and the crude compound was purified by column chromatography (0% to 20% EtOH/DCM elution) to give (2R,3S,5R)-5-(4-amino-3-methoxy-1H-pyrazolo[3,4-d]pyrimidin-1-yl)-2-(hydroxymethyl)tetrahydrofuran-3-ol (191 mg, 32%) as a pale yellow solid. LCMS (FA): m/z 282 (M+H); $^1$H NMR (400 MHz, CD$_3$OD) δ 8.15 (s, 1H), 6.61 (t, J=6.5 Hz, 1H), 4.62 (dt, J=6.3, 3.4 Hz, 1H), 4.08 (s, 3H), 3.97-4.02 (m, 1H), 3.75-3.82 (m, 1H), 3.65-3.72 (m, 1H), 2.90 (dt, J=13.5, 6.2 Hz, 1H), 2.35 (ddd, J=13.6, 6.8, 4.0 Hz, 1H).

Step 2: 1-[(2R,4S,5R)-4-{[tert-butyl(dimethyl)silyl]oxy}-5-({[tert-butyl(dimethyl)silyl]oxy}methyl)tetrahydrofuran-2-yl]-3-methoxy-1H-pyrazolo[3,4-d]pyrimidin-4-amine The titled compound was prepared following the procedure outlined in Example 65 Step 4 substituting (2R,3S,5R)-5-(4-amino-3-methoxy-1H-pyrazolo[3,4-d]pyrimidin-1-yl)-2-(hydroxymethyl)tetrahydrofuran-3-ol for (2R,3R,4S,5R)-5-[4-amino-3-(isopropylsulfanyl)-1H-pyrazolo[3,4-d]pyrimidin-1-yl]-4-fluoro-2-(hydroxymethyl)tetrahydrofuran-3-ol. LCMS (FA): m/z=510 (M+H); $^1$H NMR (400 MHz, CDCl$_3$) δ 8.18 (s, 1H), 6.53 (t, J=6.6 Hz, 1H), 5.62 (br s, 2H), 4.55 (dt, J=5.5, 2.8 Hz, 1H), 3.93 (s, 3H), 3.83 (ddd, J=7.2, 4.9, 2.6 Hz, 1H), 3.52-3.63 (m, 2H), 2.81-2.91 (m, 1H), 2.10 (ddd, J=13.1, 6.4, 3.2 Hz, 1H), 0.81 (s, 9H), 0.76 (s, 9H), 0.00 (s, 6H), −0.10 (d, J=7.0 Hz, 6H).

Step 3: [(2R,3S,5R)-5-(4-amino-3-methoxy-1H-pyrazolo[3,4-d]pyrimidin-1-yl)-3-{[tert-butyl(dimethyl)silyl]oxy}tetrahydrofuran-2-yl]methanol The titled compound was prepared following the procedure outlined in Example 65 Step 5 substituting 1-[(2R,4S,5R)-4-{[tert-butyl(dimethyl)silyl]oxy}-5-({[tert-butyl(dimethyl)silyl]oxy}methyl)tetrahydrofuran-2-yl]-3-methoxy-1H-pyrazolo[3,4-d]pyrimidin-4-amine for 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-(isopropylsulfanyl)-1H-pyrazolo[3,4-d]pyrimidin-4-amine. LCMS (FA): m/z=396 (M+H); $^1$H NMR (400 MHz, CDCl$_3$) δ 8.18 (s, 1H), 6.54 (t, J=7.0 Hz, 1H), 5.71 (br s, 2H), 4.58-4.63 (m, 1H), 3.98 (br d, J=1.8 Hz, 1H), 3.95 (s, 3H), 3.80 (dd, J=12.5, 1.9 Hz, 1H), 3.60 (m, J=11.2 Hz, 1H), 2.74 (ddd, J=13.3, 7.4, 5.6 Hz, 1H), 2.21 (ddd, J=13.3, 6.5, 2.1 Hz, 1H), 0.81 (s, 9H), 0.00 (s, 6H)

Step 4: [(2R,3S,5R)-5-(4-amino-3-methoxy-1H-pyrazolo[3,4-d]pyrimidin-1-yl)-3-hydroxytetrahydrofuran-2-yl]methyl Sulfamate I-190

[(2R,3S,5R)-5-(4-amino-3-methoxy-1H-pyrazolo[3,4-d]pyrimidin-1-yl)-3-{[tert-butyl(dimethyl)silyl]oxy}tetrahydrofuran-2-yl]methanol (84.0 mg, 0.21 mmol) was dissolved in DMF (2.0 mL) and the solution was cooled to 0° C. Chlorosulfonamide (49.1 mg, 0.42 mmol) was added and the reaction was allowed to warm slowly to rt and allowed to stir overnight. Water was added and the reaction mixture was extracted with EtOAc. The organic solutions were combined, washed with water (2×) and brine, dried over Na$_2$SO$_4$, filtered and concentrated. EtOH (8.0 mL) was added followed by 1.0 M HCl (0.63 mL, 0.64 mmol) and the reaction was allowed to stir at rt overnight. The precipitated solid was filtered off, washed with ether and dried under vacuum. Pyridine (0.103 mL, 1.27 mmol) was added to the filtrate and the solvents were evaporated. The residue was combined with the solid and the crude material was purified by preparative reverse phase HPLC to give [(2R,3S,5R)-5-(4-amino-3-methoxy-1H-pyrazolo[3,4-d]pyrimidin-1-yl)-3-hydroxytetrahydrofuran-2-yl]methyl sulfamate (1-190) (7.6 mg, 11%) as a white solid. LCMS (FA): m/z=361 (M+H); $^1$H NMR (400 MHz, CD$_3$OD) δ 8.16 (s, 1H), 6.64 (dd, J=6.8, 5.5 Hz, 1H), 4.69-4.74 (m, 1H), 4.31-4.37 (m, 1H), 4.19-4.26 (m, 1H), 4.12-4.17 (m, 1H), 4.11 (s, 3H), 2.95 (dt, J=13.4, 5.9 Hz, 1H), 2.38 (ddd, J=13.6, 7.0, 4.6 Hz, 1H).

Example 53: [(2R,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl Sulfamate Compound I-161

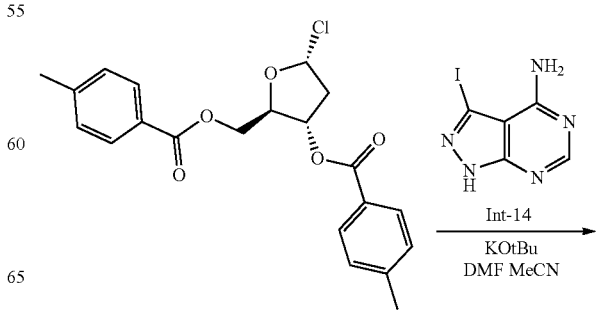

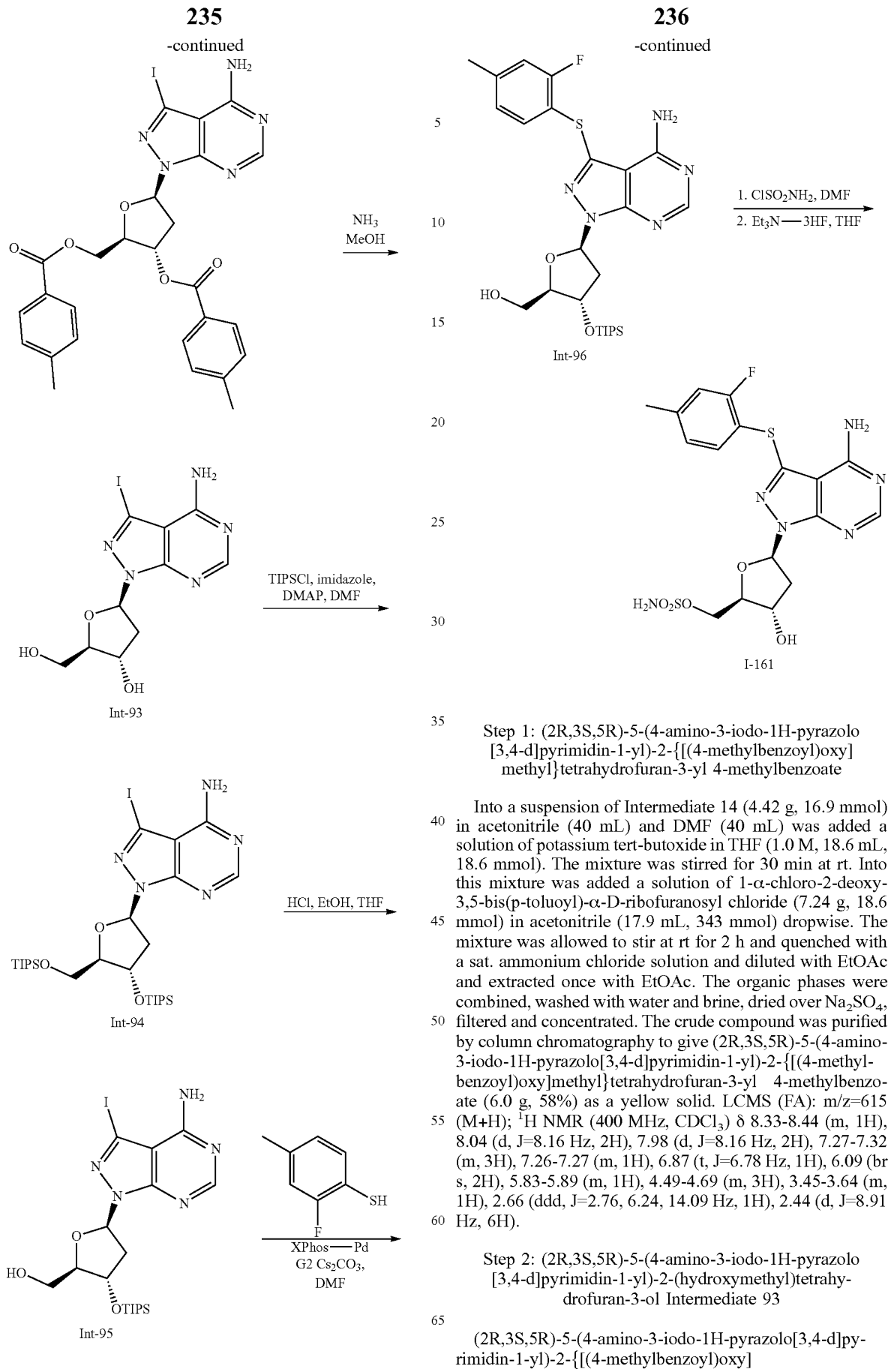

Step 1: (2R,3S,5R)-5-(4-amino-3-iodo-1H-pyrazolo[3,4-d]pyrimidin-1-yl)-2-{[(4-methylbenzoyl)oxy]methyl}tetrahydrofuran-3-yl 4-methylbenzoate Into a suspension of Intermediate 14 (4.42 g, 16.9 mmol) in acetonitrile (40 mL) and DMF (40 mL) was added a solution of potassium tert-butoxide in THF (1.0 M, 18.6 mL, 18.6 mmol). The mixture was stirred for 30 min at rt. Into this mixture was added a solution of 1-α-chloro-2-deoxy-3,5-bis(p-toluoyl)-α-D-ribofuranosyl chloride (7.24 g, 18.6 mmol) in acetonitrile (17.9 mL, 343 mmol) dropwise. The mixture was allowed to stir at rt for 2 h and quenched with a sat. ammonium chloride solution and diluted with EtOAc and extracted once with EtOAc. The organic phases were combined, washed with water and brine, dried over $Na_2SO_4$, filtered and concentrated. The crude compound was purified by column chromatography to give (2R,3S,5R)-5-(4-amino-3-iodo-1H-pyrazolo[3,4-d]pyrimidin-1-yl)-2-{[(4-methylbenzoyl)oxy]methyl}tetrahydrofuran-3-yl 4-methylbenzoate (6.0 g, 58%) as a yellow solid. LCMS (FA): m/z=615 (M+H); $^1$H NMR (400 MHz, $CDCl_3$) δ 8.33-8.44 (m, 1H), 8.04 (d, J=8.16 Hz, 2H), 7.98 (d, J=8.16 Hz, 2H), 7.27-7.32 (m, 3H), 7.26-7.27 (m, 1H), 6.87 (t, J=6.78 Hz, 1H), 6.09 (br s, 2H), 5.83-5.89 (m, 1H), 4.49-4.69 (m, 3H), 3.45-3.64 (m, 1H), 2.66 (ddd, J=2.76, 6.24, 14.09 Hz, 1H), 2.44 (d, J=8.91 Hz, 6H).

Step 2: (2R,3S,5R)-5-(4-amino-3-iodo-1H-pyrazolo[3,4-d]pyrimidin-1-yl)-2-(hydroxymethyl)tetrahydrofuran-3-ol Intermediate 93

(2R,3S,5R)-5-(4-amino-3-iodo-1H-pyrazolo[3,4-d]pyrimidin-1-yl)-2-{[(4-methylbenzoyl)oxy]

methyl}tetrahydrofuran-3-yl 4-methylbenzoate (3.80 g, 6.19 mmol) was dissolved in a solution of ammonia in MeOH (7.0 M, 81.5 mL, 0.570 mol). The reaction vessel was sealed and heated at 65° C. overnight. The mixture was cooled to rt and then concentrated under reduced pressure to give (2R,3S,5R)-5-(4-amino-3-iodo-1H-pyrazolo[3,4-d]pyrimidin-1-yl)-2-(hydroxymethyl)tetrahydrofuran-3-ol (1.87 g, 80%) as white solid. LCMS (FA): m/z=378 (M+H); $^1$H NMR (400 MHz, d$_6$-DMSO) δ 8.23 (s, 1H), 6.50 (t, J=6.40 Hz, 1H), 5.27 (d, J=4.52 Hz, 1H), 4.76 (t, J=5.77 Hz, 1H), 4.37-4.48 (m, 1H), 3.76-3.86 (m, 1H), 3.51 (td, J=5.62, 11.36 Hz, 1H), 3.31-3.42 (m, 2H), 2.70-2.84 (m, 1H), 2.19-2.29 (m, 1H)

Step 3: 3-iodo-1-[(2R,4S,5R)-4-[(triisopropylsilyl) oxy]-5-{[(triisopropylsilyl)oxy] methyl}tetrahydrofuran-2-yl]-1H-pyrazolo[3,4-d] pyrimidin-4-amine Intermediate 94

To a stirred solution under an atmosphere of nitrogen of Intermediate 93 (7.00 g, 18.6 mmol) in DMF (90 mL) at rt was added 1H-imidazole (7.58 g, 111.4 mmol), DMAP (453.5 mg, 3.71 mmol) and triisopropylsilyl chloride (23.59 mL, 111.4 mmol). The mixture was allowed to stir at rt overnight. The reaction mixture was quenched by the addition of a cooled saturated ammonium chloride solution (at 0° C.), and the mixture was extracted with EtOAc. The organic phases were combined, washed with water and brine, dried over sodium sulfate, filtered and concentrated to give 3-iodo-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine (12.8 g, 100%) as a white solid. LCMS (FA): m/z=691 (M+H); $^1$H NMR (400 MHz, CDCl$_3$) δ 8.37 (s, 1H), 6.73 (t, J=6.84 Hz, 1H), 5.91 (br s, 2H), 4.74-4.91 (m, 1H), 4.11 (br t, J=5.21 Hz, 1H), 3.64-3.89 (m, 2H), 3.10-3.30 (m, 1H), 2.23-2.43 (m, 1H), 0.92-1.28 (m, 36H)

Step 4: {(2R,3S,5R)-5-(4-amino-3-iodo-1H-pyrazolo[3,4-d]pyrimidin-1-yl)-3-[(triisopropylsilyl)oxy] tetrahydrofuran-2-yl}methanol Intermediate 95

Intermediate 94 (2.89 g, 4.19 mmol) was dissolved in ethanol (31 mL). The reaction mixture was cooled to 0° C. and a solution of hydrochloric acid in EtOH (2.5 M, 5.03 mL, 12.6 mmol) diluted in EtOH (7.34 mL, 126 mmol) was added dropwise. The reaction mixture was stirred at rt overnight. A solution of ammonia in MeOH (7.0 M, 1.80 mL, 12.6 mmol) was added and all solvent was removed in vacuo. The resulting crude material was purified by column chromatography to give {(2R,3S,5R)-5-(4-amino-3-iodo-1H-pyrazolo[3,4-d]pyrimidin-1-yl)-3-[(triisopropylsilyl) oxy]tetrahydrofuran-2-yl}methanol (1.33 g, 60%) as a white solid. LCMS (FA): m/z=534 (M+H); $^1$H NMR (400 MHz, CDCl$_3$) δ 8.26 (s, 1H), 6.59 (dd, J=6.02, 8.66 Hz, 1H), 6.07 (br d, J=8.78 Hz, 2H), 4.71 (d, J=5.14 Hz, 1H), 4.12 (s, 1H), 3.85 (dd, J=1.82, 12.74 Hz, 1H), 3.67 (dd, J=1.95, 12.74 Hz, 1H), 2.87 (ddd, J=5.21, 8.44, 13.33 Hz, 1H), 2.31 (dd, J=5.52, 12.55 Hz, 1H), 0.98-1.03 (m, 18H)

Step 5: {(2R,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methanol Intermediate 96

Intermediate 95 (2.50 g, 4.69 mmol), cesium carbonate (3.05 g, 9.37 mmol) and XPhos Pd G2 (200 mg, 0.3 mmol) were added to a microwave vial and suspended in DMF (32 mL). 2-Fluoro-4-methylbenzenethiol (0.117 g, 8.20 mmol) was added, the reaction mixture was degassed, the vial was capped and the reaction mixture was subjected to microwave irradiation at 100° C. for 3 h. The mixture was diluted with ethyl acetate (30 mL), filtered and concentrated. The resulting crude compound was purified by column chromatography to give {(2R,3S,5R)-5-{4-amino-3-[(2-fluoro-4-methylphenyl)sulfanyl]-1H-pyrazolo[3,4-d]pyrimidin-1-yl}}-3-[(triisopropylsilyl)oxy]tetrahydrofuran-2-yl}methanol (547 mg, 100%) as a white solid. LCMS (FA): m/z=548 (M+H); $^1$H NMR (400 MHz, CDCl$_3$) δ 8.32 (s, 1H), 7.19-7.22 (m, 1H), 6.94-6.99 (m, 2H), 6.70-6.74 (m, 1H), 4.81 (br d, J=5.14 Hz, 1H), 4.20 (s, 1H), 3.92 (d, J=11.04 Hz, 1H), 3.74 (br d, J=13.43 Hz, 1H), 2.86-2.96 (m, 1H), 2.40-2.46 (m, 1H), 2.36 (s, 3H), 1.09-1.12 (m, 18H)

Step 6: {(2R,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl Sulfamate Intermediate 96 (2.56 g, 4.67 mmol) was dissolved in DMF (36 mL). Chlorosulfonamide (1.08 g, 9.35 mmol) was added and the mixture was stirred at rt for 1 h. Saturated sodium bicarbonate solution was added and the two phase mixture was extracted with ethyl acetate. The extracts were combined, washed with water and brine, dried over sodium sulfate, filtered and concentrated under reduced pressure. The crude material was purified by column chromatography to give {(2R,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl sulfamate (2.93 g, 77%) as a sticky oil. LCMS (FA): m/z=627 (M+H); $^1$H NMR (400 MHz, CDCl$_3$) δ 8.28-8.40 (m, 1H), 7.36 (t, J=7.97 Hz, 1H), 6.93-7.01 (m, 2H), 6.78 (t, J=6.40 Hz, 1H), 6.36 (br s, 2H), 5.08 (br s, 2H), 4.78 (td, J=3.28, 6.12 Hz, 1H), 4.43 (dd, J=2.70, 11.61 Hz, 1H), 4.20-4.34 (m, 2H), 4.15 (q, J=7.15 Hz, 4H), 2.92 (td, J=6.31, 12.99 Hz, 1H), 2.38-2.45 (m, 1H), 2.37 (s, 4H), 1.10-1.14 (m, 18H)).

Step 7: [(2R,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl Sulfamate Into a solution of {(2R,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl sulfamate (2.00 g, 3.19 mmol) in THF (26 mL) was added triethylamine trishydrofluoride (3.1 mL, 19.14 mmol) dropwise at 0° C. The mixture was stirred at rt for 2 days and then treated with a solution of ammonia in MeOH (7.0 M, 3.2 mL, 22.33 mmol). The mixture was then concentrated under reduced pressure and dried in vacuo. The resulting material was purified by column chromatography to give [(2R,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl sulfamate (900 mg, 60%) as a white solid. LCMS (FA): m/z=471 (M+H); $^1$H NMR (400 MHz, CD$_3$OD) δ 8.23 (s, 1H), 7.29 (t, J=7.84 Hz, 1H), 6.97-7.11 (m, 2H), 6.69 (dd, J=4.71, 6.96 Hz, 1H), 4.51-4.70 (m, 1H), 4.11-4.30 (m, 2H), 4.01-4.09 (m, 1H), 3.33 (td, J=1.58, 3.23 Hz, 5H), 2.91 (ddd, J=4.77, 6.43, 13.52 Hz, 1H), 2.39-2.51 (m, 1H), 2.36 (s, 3H).

Example 54: [(2R,3S,5R)-5-(4-amino-3-iodo-1H-pyrazolo[3,4-d]pyrimidin-1-yl)-3-hydroxytetrahydrofuran-2-yl]methyl Sulfamate Compound I-192

Intermediate 95 was used in place of Intermediate 96 in Example 53 Step 6 and Step 7 to provide the titled compound. LCMS (FA): m/z 457 (M+H); $^1$H NMR (400 MHz, $d_6$-DMSO) δ 8.35 (s, 1H), 6.56 (t, J=5.9 Hz, 1H), 4.49 (q, J=5.4 Hz, 1H), 4.20 (dd, J=10.1, 4.1 Hz, 1H), 3.92-4.08 (m, 2H), 2.67-2.81 (m, 1H), 2.20-2.45 (m, 1H).

Example 55

The following compounds were prepared as described following the procedures in Example 53 using Intermediate 93 and the reagents and conditions described in the table below.

| Compound number | Thiol | Pd Coupling Conditions | Temperature of Sulfamoylation Reaction (Step 6) | LCMS data | $^1$H NMR Data |
|---|---|---|---|---|---|
| I-182 | 2-fluorobenzenethiol | Xphos Pd G2 MW 100° C. 3 h Cs$_2$CO$_3$ DMF | rt | LCMS(FA): m/z 457 (M + H) | $^1$H NMR (400 MHz, CD$_3$OD) δ 8.25 (s, 1H), 7.28-7.43 (m, 2H), 7.11-7.27 (m, 2H), 6.71 (dd, J = 7.0, 4.8 Hz, 1H), 4.60-4.70 (m, 1H), 4.12-4.27 (m, 2H), 4.02-4.10 (m, 1H), 2.87-3.00 (m, 1H), 2.38-2.52 (m, 1H). |
| I-179 | 3-chlorobenzenethiol | Xphos Pd G2 MW 150° C. 1.5 h Cs$_2$CO$_3$ DMF | rt | LCMS(FA): m/z 473 (M + H) | $^1$H NMR (400 MHz, $d_6$-DMSO) δ 8.27 (s, 1H), 7.44 (s, 1H), 7.29-7.39 (m, 2H), 7.18 (d, J = 6.7 Hz, 1H), 6.64 (dd, J = 6.7, 5.1 Hz, 1H), 4.51 (q, J = 5.6 Hz, 1H), 4.21 (dd, J = 10.3, 3.9 Hz, 1H), 3.91-4.10 (m, 2H), 2.73-2.92 (m, 1H), 2.33-2.48 (m, 1H). |
| I-177 | 2-methylpropane-2-thiol | Xphos Pd G2 MW 150° C. 1.5 h Cs$_2$CO$_3$ DMF | rt | LCMS(FA): m/z 419 (M + H) | $^1$H NMR (400 MHz, $d_6$-DMSO) δ 8.25 (s, 1H), 7.50 (s, 2H), 6.63 (dd, J = 7.0, 4.8 Hz, 1H), 5.57 (d, J = 4.8 Hz, 1H), 4.55 (br t, J = 5.0 Hz, 1H), 4.23 (dd, J = 10.2, 4.3 Hz, 1H), 3.92-4.07 (m, 2H), 2.79 (dt, J = 12.7, 5.7 Hz, 1H), 2.33-2.47 (m, 1H), 1.37 (s, 9H). |
| I-194 | pyridine-2-thiol | Xphos Pd G2 MW 150° C. 1.5 h Cs$_2$CO$_3$ DMF | rt | LCMS (FA): m/z 440 (M + H) | $^1$H NMR (400 MHz, $d_6$-DMSO) δ 8.41 (dd, J = 4.8, 0.9 Hz, 1H), 8.29 (s, 1H), 7.70 (td, J = 7.8, 1.9 Hz, 1H), 7.51 (s, 2H), 7.20-7.28 (m, 1H), 7.12 (d, J = 8.0 Hz, 1H), 6.66 (dd, J = 6.8, 5.1 Hz, 1H), 5.56 (br s, 1H), 4.52 (br d, J = 4.1 Hz, 1H), 4.19 (dd, J = 10.2, 4.1 Hz, 1H), 3.90-4.08 (m, 2H), 2.78-2.92 (m, 1H), 2.35-2.43 (m, 1H). |
| I-198 | 3-(trifluoromethoxy)benzenethiol | Xphos Pd G2, Cs$_2$CO$_3$ DMF MW 140° C. 1 h | rt* | LCMS(FA): m/z 523 (M + H) | N/A |
| I-184 | 4-isopropoxybenzenethiol | Xphos Pd G2, Cs$_2$CO$_3$ DMF MW 140° C. 1 h | rt* | LCMS (FA): m/z 497 (M + H) | N/A |
| I-185 | 1-methyl-5-sulfanyl-1,3-dihydro-2H-indol-2-one | Xphos Pd G2, Cs$_2$CO$_3$ DMF MW 140° C. 1 h | rt* | LCMS (FA): m/z 508 (M + H) | N/A |
| I-201 | 2,3-dihydro-1,4-benzodioxine-6-thiol | Xphos Pd G2, Cs$_2$CO$_3$ DMF MW 140° C. 1 h | rt* | LCMS(FA): m/z 497 (M + H) | N/A |

-continued

| Compound number | Thiol | Pd Coupling Conditions | Temperature of Sulfamoylation Reaction (Step 6) | LCMS data | $^1$H NMR Data |
|---|---|---|---|---|---|
| I-197 | 4-(trifluoromethoxy)benzenethiol | Xphos Pd G2, Cs$_2$CO$_3$ DMF MW 140° C. 1 h | rt* | LCMS(FA): m/z 523 (M + H) | N/A |
| I-163 | 4-tert-butylbenzenethiol | Xphos Pd G2, Cs$_2$CO$_3$ DMF MW 140° C. 1 h | rt* | LCMS(FA): m/z 495 (M + H) | N/A |

*An equivalent of TEA was added to this reaction mixture.

Example 56

The following compounds were prepared as described in Example 53 starting with Intermediate 94 with the reagents and conditions described in the table below.

| Compound number | Thiol | Pd Coupling Conditions: | LCMS data | $^1$H NMR Data |
|---|---|---|---|---|
| I-187 | 4-fluorobenzenethiol | XphosPd G2, 150° C. 1 h | LCMS (FA): m/z 457 (M + H) | $^1$H NMR (400 MHz, d$_6$-DMSO) δ 8.25 (s, 1H), 7.54 (br s, 2H), 7.43-7.49 (m, 2H), 7.06-7.30 (m, 2H), 6.62 (dd, J = 7.0, 4.8 Hz, 1H), 5.55 (br d, J = 4.1 Hz, 1H), 4.50 (br s, 1H), 4.20 (dd, J = 10.3, 4.1 Hz, 1H), 3.89-4.07 (m, 2H), 2.74-2.91 (m, 1H), 2.32-2.44 (m, 1H). |
| I-206 | 3-fluorobenzenethiol | Xphos Pd G2, 140° C. 1 h | LCMS (FA): m/z 457 (M + H) | $^1$H NMR (400 MHz, CD$_3$OD) δ 8.25 (br s, 1H), 7.35 (br d, J = 5.1 Hz, 1H), 7.13 (br s, 2H), 7.00 (br s, 1H), 6.76 (br s, 1H), 4.72 (br s, 1H), 4.10-4.39 (m, 3H), 3.33 (br s, 1H), 3.03 (br s, 1H), 2.50 (br d, J = 4.8 Hz, 1H). |
| I-174 | thiazole-2-thiol | CuI, TBAB (cat), 140° C. 30 min | LCMS (FA): m/z 446 (M + H) | $^1$H NMR (400 MHz, CD$_3$OD) δ 8.28 (s, 1H), 7.78 (d, J = 3.4 Hz, 1H), 7.62 (d, J = 3.5 Hz, 1H), 6.77 (dd, J = 7.0, 4.8 Hz, 1H), 4.73-4.78 (m, 1H), 4.26-4.33 (m, 1H), 4.14-4.22 (m, 2H), 3.03 (ddd, J = 13.6, 6.4, 4.9 Hz, 1H), 2.50 (ddd, J = 13.6, 7.1, 5.4 Hz, 1H). |
| I-167 | 1,2-dicyclopropyldisulfane | Zn, NiBr$_2$, Bipyridine, 110° C., 12 h | LCMS (FA): m/z 403 (M + H) | $^1$H NMR (400 MHz, d$_6$-DMSO) δ 8.23 (s, 1H), 8.14 (s, 1H), 7.50 (s, 2H), 6.60 (dd, J = 6.9, 4.8 Hz, 1H), 4.59 (br d, J = 3.5 Hz, 1H), 4.20-4.29 (m, 1H), 3.96-4.09 (m, 2H), 2.74-2.88 (m, 1H), 2.31-2.49 (m, 2H), 0.97-1.08 (m, 2H), 0.62-0.77 (m, 2H). |
| I-199 | 3-methoxybenzenethiol | Xphos Pd G2, Cs$_2$CO$_3$ DMF MW 150° C. 1 h | LCMS (FA): m/z 469 (M + H) | $^1$H NMR (400 MHz, d$_6$-DMSO) δ 8.26 (s, 1H), 7.52 (s, 2H), 7.22-7.29 (m, 1H), 6.93-6.98 (m, 1H), 6.77-6.88 (m, 2H), 6.62-6.67 (m, 1H), 5.56 (d, J = 4.8 Hz, 1H), 4.49-4.58 (m, 1H), 4.22 (dd, J = 10.2, 4.2 Hz, 1H), 4.02-4.07 (m, 1H), 3.93-4.00 (m, 1H), 3.72 (s, 3H), 2.80-2.89 (m, 1H), 2.36-2.45 (m, 1H). |

Example 57

The following compounds were prepared as described in Example 53 starting with Intermediate 95 and the reagents and conditions described in the table below.

| Compound number | Halide | Pd Coupling Conditions | Temp of Sulfamoylation Reaction (Step 6) | LCMS data | $^1$H NMR Data |
| --- | --- | --- | --- | --- | --- |
| I-207 | 3,4-dimethoxybenzenethiol | Xphos Pd G2 MW 140° C. 1 h Cs$_2$CO$_3$ DMF | 0° C. | LCMS (FA): m/z 499 (M + H) | $^1$H NMR (400 MHz, CD$_3$OD) δ 8.22 (s, 1H), 7.11 (d, J = 2.2 Hz, 1H), 7.05-7.09 (m, 1H), 6.98 (d, J = 8.5 Hz, 1H), 6.71 (dd, J = 6.9, 5.0 Hz, 1H), 4.65-4.70 (m, 1H), 4.22-4.28 (m, 1H), 4.15-4.20 (m, 1H), 4.06-4.13 (m, 1H), 3.83 (s, 3H), 3.81 (s, 3H), 2.92-2.99 (m, 1H), 2.40-2.49 (m, 1H). |
| I-186 | 2,3-dihydrobenzofuran-5-thiol | Xphos Pd G2 MW 140° C. 1 h Cs$_2$CO$_3$ DMF | 0° C. | LCMS (FA): m/z 481 (M + H) | $^1$H NMR (400 MHz, CD$_3$OD) δ 8.21 (s, 1H), 7.37 (s, 1H), 7.31 (d, J = 8.3 Hz, 1H), 6.75 (d, J = 8.3 Hz, 1H), 6.68 (dd, J = 7.0, 4.6 Hz, 1H), 4.63-4.70 (m, 1H), 4.56 (t, J = 8.7 Hz, 2H), 4.21-4.28 (m, 1H), 4.13-4.20 (m, 1H), 4.04-4.12 (m, 1H), 3.16-3.26 (m, 2H), 2.89-2.97 (m, 1H), 2.38-2.48 (m, 1H). |
| I-15 | benzo[d][1,3]dioxole-5-thiol | Xphos Pd G2 MW 140° C. 1 h Cs$_2$CO$_3$ DMF | 0° C. | LCMS (FA): m/z 483 (M + H) | $^1$H NMR (400 MHz, CD$_3$OD) δ 8.22 (s, 1H), 7.02 (dd, J = 8.0, 1.8 Hz, 1H), 6.95 (d, J = 1.8 Hz, 1H), 6.83 (d, J = 8.2 Hz, 1H), 6.71 (dd, J = 6.8, 5.0 Hz, 1H), 5.98 (s, 2H), 4.66-4.73 (m, 1H), 4.23-4.31 (m, 1H), 4.15-4.21 (m, 1H), 4.07-4.14 (m, 1H), 2.92-3.01 (m, 1H), 2.41-2.50 (m, 1H). |
| I-191 | 2-fluoro-5-methylbenzenethiol | Xphos Pd G2 MW 100° C. 3 h Cs$_2$CO$_3$ DMF | 0° C. | LCMS (FA): m/z 471 (M + H) | $^1$H NMR (400 MHz, CD$_3$OD) δ 8.24 (s, 1H), 7.05-7.23 (m, 3H), 6.70 (t, J = 5.7 Hz, 1H), 4.61-4.69 (m, 1H), 4.20-4.27 (m, 1H), 4.14-4.20 (m, 1H), 4.02-4.12 (m, 1H), 2.88-2.98 (m, 1H), 2.40-2.51 (m, 1H), 2.27 (s, 3H). |
| I-196 | 3,4-dimethylbenzenethiol | Xphos Pd G2 MW 140° C. 1 h Cs$_2$CO$_3$ DMF | 0° C. | LCMS (FA): m/z 467 (M + H) | $^1$H NMR (400 MHz, CD$_3$OD) δ 8.22 (s, 1H), 7.21 (s, 1H), 7.08-7.16 (m, 2H), 6.72 (dd, J = 6.8, 5.0 Hz, 1H), 4.66-4.73 (m, 1H), 4.24-4.31 (m, 1H), 4.16-4.22 (m, 1H), 4.07-4.15 (m, 1H), 2.94-3.03 (m, 1H), 2.41-2.50 (m, 1H), 2.24 (s, 6H). |
| I-183 | quinoline-2-thiol | CuI, TBAB(cat.), MW 170° C. 40 min NaOtBu, DMF | rt | LCMS (FA): m/z 490 (M + H) | $^1$H NMR (400 MHz, d$_6$-DMSO) δ 8.31 (s, 1H), 8.26 (br d, J = 8.8 Hz, 1H), 7.94 (br d, J = 8.0 Hz, 1H), 7.73-7.83 (m, 2H), 7.57 (br t, J = 7.2 Hz, 1H), 7.16 (br d, J = 8.7 Hz, 1H), 6.70 (br t, J = 5.6 Hz, 1H), 4.54 (br d, J = 4.6 Hz, 1H), 4.21 (br dd, J = 9.9, 3.5 Hz, 1H), 3.95-4.11 (m, 2H), 3.33 (br s, 1H), 2.81-2.94 (m, 1H), 2.43 (dt, J = 12.9, 6.5 Hz, 1H). |
| I-170 | 1H-indole-3-thiol | Xphos Pd G2, MW 150° C. 1 h Cs$_2$CO$_3$ DMF | rt | LCMS (FA): m/z 478 (M + H) | $^1$H NMR (400 MHz, d$_6$-DMSO) δ 8.17 (s, 1H), 7.91 (s, 1H), 7.62 (d, J = 7.5 Hz, 1H), 7.42 (d, J = 7.8 Hz, 1H), 6.99-7.19 (m, 2H), 6.53 (br d, J = 4.8 Hz, 1H), 4.41-4.54 (m, 1H), 4.22 (dd, J = 10.4, 4.4 Hz, 1H), 3.95-4.02 (m, 1H), 2.66-2.78 (m, 1H), 2.48-2.52 (m, 1H), 2.25-2.41 (m, 1H). |

| Compound number | Halide | Pd Coupling Conditions | Temp of Sulfamoylation Reaction (Step 6) | LCMS data | ¹H NMR Data |
|---|---|---|---|---|---|
| I-208 | 4-methylthiazole-2-thiol | CuI, TBAB(cat.) MW 140° C. 1 h NaOtBu, DMF | rt | LCMS (FA): m/z 460 (M + H) | ¹H NMR (400 MHz, d₆-DMSO) δ 8.29 (s, 1H), 7.51 (s, 2H), 7.25 (s, 1H), 6.66 (br t, J = 5.8 Hz, 1H), 5.58 (d, J = 4.8 Hz, 1H), 4.50-4.62 (m, 1H), 4.20 (br dd, J = 10.1, 4.0 Hz, 1H), 3.79-4.11 (m, 2H), 2.75-3.02 (m, 1H), 2.51 (br s, 3H), 2.41 (dt, J = 13.0, 6.4 Hz, 1H). |
| I-166 | naphthalene-2-thiol | Xphos Pd G2, MW 140° C. 1 h Cs₂CO₃ DMF | rt | LCMS (FA): m/z 489 (M + H) | ¹H NMR (400 MHz, CD₃OD) δ 8.24 (s, 1H), 7.91 (s, 1H), 7.78-7.88 (m, 3H), 7.45-7.55 (m, 2H), 7.42 (dd, J = 8.7, 1.9 Hz, 1H), 6.75 (dd, J = 6.9, 4.9 Hz, 1H), 4.67-4.75 (m, 1H), 4.26-4.37 (m, 1H), 4.09-4.25 (m, 2H), 2.97-3.10 (m, 1H), 2.48 (ddd, J = 13.4, 7.1, 5.3 Hz, 1H). |
| I-193 | 4-methylbenzenethiol | Xphos Pd G2, MW 140° C. 1 h Cs₂CO₃ DMF | rt | LCMS (FA): m/z 453 (M + H) | ¹H NMR (400 MHz, CD₃OD) δ 8.14-8.25 (m, 1H), 7.30 (d, J = 8.3 Hz, 2H), 7.19 (d, J = 8.2 Hz, 2H), 6.72 (dd, J = 7.0, 5.0 Hz, 1H), 4.62-4.72 (m, 1H), 4.23-4.33 (m, 1H), 4.09-4.21 (m, 2H), 2.91-3.04 (m, 1H), 2.41-2.50 (m, 1H). |
| I-205 | 3-methylbenzenethiol | Xphos Pd G2, MW 150° C. 1 h Cs₂CO₃ DMF | rt | LCMS (FA): m/z 453 (M + H) | ¹H NMR (400 MHz, CD₃OD) δ 8.24 (s, 1H), 7.20-7.33 (m, 2H), 7.13 (dd, J = 15.2, 7.7 Hz, 2H), 6.74 (dd, J = 7.0, 5.0 Hz, 1H), 4.63-4.77 (m, 1H), 4.23-4.39 (m, 1H), 4.11-4.22 (m, 2H), 2.95-3.07 (m, 1H), 2.47 (ddd, J = 13.5, 7.1, 5.3 Hz, 1H). |
| I-176 | 2-methylbenzenethiol | Xphos Pd G2, MW 150° C. 1 h Cs₂CO₃ DMF | rt | LCMS (FA): m/z 453 (M + H) | ¹H NMR (400 MHz, CD₃OD) δ 8.24 (s, 1H), 7.29-7.35 (m, 1H), 7.13-7.27 (m, 3H), 6.70 (dd, J = 7.0, 4.7 Hz, 1H), 4.56-4.61 (m, 1H), 4.12-4.20 (m, 2H), 3.98-4.06 (m, 1H), 2.90 (ddd, J = 13.5, 6.4, 4.6 Hz, 1H), 2.50 (s, 3H), 2.45 (dd, J = 7.2, 5.6 Hz, 1H). |
| I-189 | 5-chloropyridine-2-thiol | Xphos Pd G2, MW 150° C. 1 h Cs₂CO₃ DMF | rt | LCMS (FA): m/z 474 (M + H) | ¹H NMR (400 MHz, CD₃OD) δ 8.41 (d, J = 2.4 Hz, 1H), 8.28 (s, 1H), 7.74 (dd, J = 8.5, 2.5 Hz, 1H), 7.21 (d, J = 8.5 Hz, 1H), 6.78 (dd, J = 6.9, 5.0 Hz, 1H), 4.70-4.78 (m, 1H), 4.26-4.35 (m, 1H), 4.13-4.23 (m, 2H), 3.02-3.11 (m, 1H), 2.45-2.55 (m, 1H). |

Example 58: [(2R,3S,5R)-5-{4-amino-3-[(6-fluoro-2,3-dihydro-1H-inden-5-yl)sulfanyl]-1H-pyrazolo[3,4-d]pyrimidin-1-yl}-3-hydroxytetrahydrofuran-2-yl] methyl Sulfamate Compound I-203

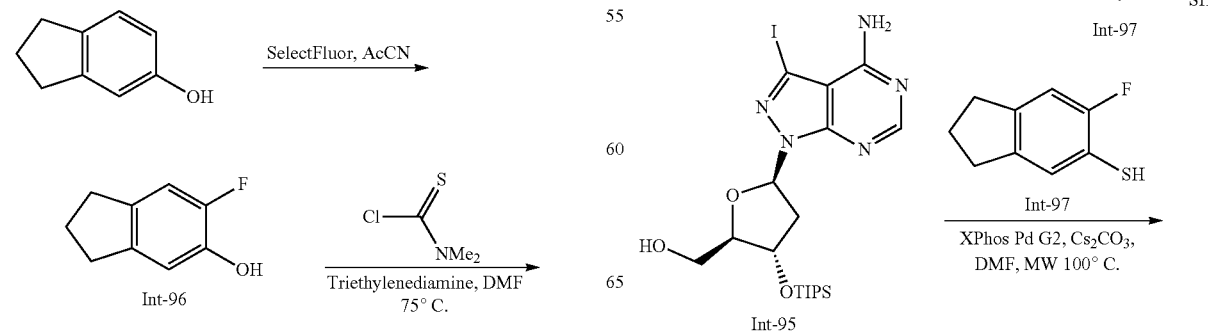

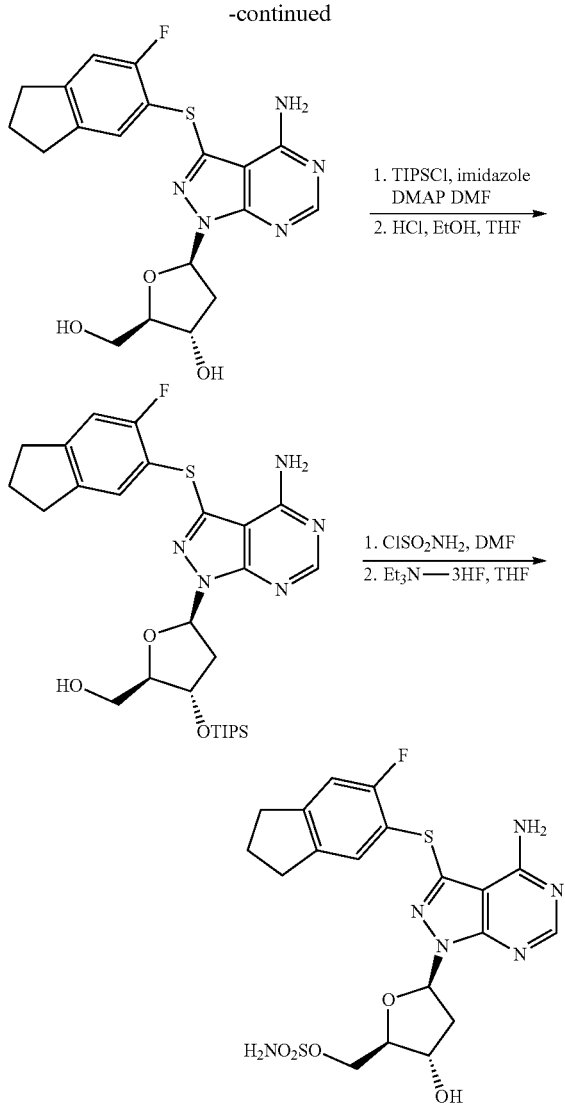

Step 1: 6-fluoroindan-5-ol Intermediate 96

Into a solution of indan-5-ol (6.71 g, 50.0 mmol) in acetonitrile (500 mL) was added 1-chloromethyl-4-fluoro-1,4-diazoniabicyclo[2.2.2]octane bis(tetrafluoroborate) (17.7 g, 50.0 mmol). The mixture was allowed to stir at rt for 4.5 h. The mixture was concentrated under reduced pressure. DCM was added and the organic phase was washed with water and brine, dried over sodium sulfate, filtered and concentrated under reduced pressure. The crude compound was purified by column chromatography (SiO$_2$, 220 g, 30/70 DCM/hexanes to DCM gradient) to give the pure product (0.471 g, 6%). $^1$H NMR (400 MHz, CDCl$_3$) δ 6.94 (d, J=10.5 Hz, 1H), 6.88 (d, J=8.3 Hz, 1H), 2.79-2.97 (m, 4H), 2.04-2.17 (m, 2H).

Step 2: O-(6-fluoro-2,3-dihydro-1H-inden-5-yl) dimethylcarbamothioate

Into a solution of Intermediate 96 (0.469 g, 3.08 mmol) in DMF (4.8 mL) was added triethylenediamine (0.691 g, 6.16 mmol) and N,N-dimethylthiocarbamoyl chloride (0.574 g, 4.64 mmol). The mixture was allowed to stir at 75° C. for 4 h. To the mixture was added water and allowed to stir at rt for 2 days. The solids were isolated by suction filtration to give the product (0.684 g, 93%). LCMS (FA): m/z 240 (M+H). $^1$H NMR (400 MHz, d$_6$-DMSO) δ 7.16 (d, J=10.3 Hz, 1H), 7.03 (d, J=7.4 Hz, 1H), 3.37 (s, 3H), 3.31 (s, 3H), 2.78-2.93 (m, 4H), 2.06 (t, J=7.4 Hz, 2H).

Step 3: S-(6-fluoro-2,3-dihydro-1H-inden-5-yl) dimethylcarbamothioate

Into a microwave vial was added O-(6-fluoro-2,3-dihydro-1H-inden-5-yl) dimethylcarbamothioate (0.677 g, 2.83 mmol), potassium carbonate (7.82 mg, 0.06 mmol) and Dowtherm (2.21 mL). The mixture was subjected to microwave irradiation at 250° C. for 4 h. The mixture was purified by column chromatography (SiO$_2$, 40 g, hexanes to 20/80 hexanes/ethyl acetate gradient) to give the pure product (0.346 g, 51%). LCMS (FA): m/z 240 (M+H). $^1$H NMR (400 MHz, CD$_3$OD) δ 7.27 (d, J=6.7 Hz, 1H), 7.05 (d, J=8.9 Hz, 1H), 2.81-3.23 (m, 10H), 2.07-2.19 (m, 2H).

Step 4: (2R,3S,5R)-5-{4-amino-3-[(6-fluoro-2,3-dihydro-1H-inden-5-yl)sulfanyl]-1H-pyrazolo[3,4-d]pyrimidin-1-yl}-2-(hydroxymethyl)tetrahydrofuran-3-ol Intermediate 97

To a solution of S-(6-fluoro-2,3-dihydro-1H-inden-5-yl) dimethylcarbamothioate (0.346 g, 1.44 mmol) in methanol (7.84 mL) was added 25% sodium methoxide in methanol (0.51 mL, 2.23 mmol). The mixture was allowed to stir at reflux for 3 h. The solution was concentrated to dryness, ether was added and the organic phase was washed with 1N HCl solution and water, dried over sodium sulfate, filtered and concentrated to afford 6-fluoroindane-5-thiol which was used as obtained.

To a microwave vial was added Intermediate 95 (0.491 g, 0.921 mmol), cesium carbonate (0.600 g, 1.84 mmol), XPhos Pd G2 (0.072 g, 0.092 mmol), 6-fluoroindane-5-thiol (0.220 g, 1.31 mmol) and DMF (6.35 mL). The mixture was degassed and was subjected to microwave irradiation at 170° C. for 3 h. The mixture was then allowed to cool to rt, diluted with water and extracted twice with ethyl acetate. The extracts were combined, washed with brine, dried over sodium sulfate, filtered and concentrated under reduced pressure. The crude compound was purified by column chromatography (SiO$_2$, 40 g, methylene chloride to 10/90 methanol/methylene chloride gradient) to give the pure product as a white solid (0.202 g, 48% over the 2 steps). LCMS (FA): m/z 418 (M+H); $^1$H NMR (400 MHz, CD$_3$OD) δ 8.20 (s, 1H), 7.19 (d, J=6.9 Hz, 1H), 7.02 (d, J=9.5 Hz, 1H), 6.66 (t, J=6.2 Hz, 1H), 4.55-4.63 (m, 1H), 3.97-4.05 (m, 1H), 3.68 (dd, J=11.9, 4.3 Hz, 1H), 3.53 (dd, J=12.0, 5.7 Hz, 1H), 2.86-2.96 (m, 3H), 2.77-2.85 (m, 2H), 2.36-2.46 (m, 1H), 2.02-2.13 (m, 2H).

Step 5: 3-[(6-fluoro-2,3-dihydro-1H-inden-5-yl)sulfanyl]-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine The titled compound was prepared following the procedure outlined in Example 95 Step 8 substituting (2R,3S,5R)-5-{4-amino-3-[(6-fluoro-2,3-dihydro-1H-inden-5-yl)sulfanyl]-1H-pyrazolo[3,4-d]pyrimidin-1-yl}-2-(hydroxymethyl)tetrahydrofuran-3-ol for Intermediate 120 (71%). LCMS (FA): m/z=730 (M+H); $^1$H NMR (400 MHz, CDCl$_3$) δ 8.35 (s, 1H), 7.07 (d, J=7.0 Hz, 1H), 6.96 (d, J=9.4

Hz, 1H), 6.78 (t, J=6.8 Hz, 1H), 6.20 (br s, 2H), 4.84-4.88 (m, 1H), 4.11-4.17 (m, 1H), 3.86 (dd, J=10.5, 7.8 Hz, 1H), 3.72 (dd, J=10.5, 4.9 Hz, 1H), 3.20-3.30 (m, 1H), 2.88 (t, J=7.5 Hz, 2H), 2.78 (t, J=7.5 Hz, 2H), 2.33-2.43 (m, 1H), 2.05-2.11 (m, 2H), 1.01-1.17 (m, 42H).

Step 6: {(2R,3S,5R)-5-{4-amino-3-[(6-fluoro-2,3-dihydro-1H-inden-5-yl)sulfanyl]-1H-pyrazolo[3,4-d]pyrimidin-1-yl}-3-[(triisopropylsilyl)oxy]tetrahydrofuran-2-yl}methanol The titled compound was prepared following the procedure outlined in Example 95 Step 9 substituting 3-[(6-fluoro-2,3-dihydro-1H-inden-5-yl)sulfanyl]-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine for Intermediate 121 (83%). LCMS (FA): m/z=574 (M+H); $^1$H NMR (400 MHz, CDCl$_3$) δ 8.26 (s, 1H), 7.16 (d, J=7.0 Hz, 1H), 6.90 (d, J=9.3 Hz, 1H), 6.63 (dd, J=8.7, 5.9 Hz, 1H), 6.14-6.42 (m, 2H), 4.74 (d, J=4.9 Hz, 1H), 4.13-4.18 (m, 1H), 3.88 (dd, J=12.8, 1.7 Hz, 1H), 3.63-3.76 (m, 1H), 2.73-2.95 (m, 5H), 2.34 (dd, J=13.0, 5.9 Hz, 1H), 1.97-2.04 (m, 2H), 0.98-1.12 (m, 21H).

Step 7: {(2R,3S,5R)-5-{4-amino-3-[(6-fluoro-2,3-dihydro-1H-inden-5-yl)sulfanyl]-1H-pyrazolo[3,4-d]pyrimidin-1-yl}-3-[(triisopropylsilyl)oxy]tetrahydrofuran-2-yl}methyl sulfamate The titled compound was prepared following the procedure described in Example 1 Step 7, substituting {(2R,3S,5R)-5-{4-amino-3-[(6-fluoro-2,3-dihydro-1H-inden-5-yl)sulfanyl]-1H-pyrazolo[3,4-d]pyrimidin-1-yl}-3-[(triisopropylsilyl)oxy]tetrahydrofuran-2-yl}methanol for Intermediate 7 (85%). LCMS (FA): m/z=653 (M+H); $^1$H NMR (400 MHz, CDCl$_3$) δ 8.31 (s, 1H), 7.26-7.28 (m, 1H), 6.98 (d, J=9.3 Hz, 1H), 6.77 (t, J=6.5 Hz, 1H), 6.29 (br s, 2H), 5.40 (br s, 2H), 4.78 (dt, J=6.0, 3.2 Hz, 1H), 4.44 (dd, J=11.8, 2.8 Hz, 1H), 4.27-4.33 (m, 1H), 4.21-4.26 (m, 1H), 2.81-2.94 (m, 5H), 2.34-2.43 (m, 1H), 2.08-2.14 (m, 2H), 1.03-1.17 (m, 21H).

Step 8: [(2R,3S,5R)-5-{4-amino-3-[(6-fluoro-2,3-dihydro-1H-inden-5-yl)sulfanyl]-1H-pyrazolo[3,4-d]pyrimidin-1-yl}-3-hydroxytetrahydrofuran-2-yl] methyl Sulfamate The titled compound was prepared following the procedure outlined in Example 53 Step 7 substituting {(2R,3S,5R)-5-{4-amino-3-[(6-fluoro-2,3-dihydro-1H-inden-5-yl)sulfanyl]-1H-pyrazolo[3,4-d]pyrimidin-1-yl}-3-[(triisopropylsilyl)oxy]tetrahydrofuran-2-yl}methyl sulfamate for {(2R,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl sulfamate (78%). LCMS (FA): m/z=497 (M+H); $^1$H NMR (400 MHz, CD$_3$OD) δ 8.23 (s, 1H), 7.23 (d, J=6.9 Hz, 1H), 7.07 (d, J=9.4 Hz, 1H), 6.69 (dd, J=6.9, 4.6 Hz, 1H), 4.61-4.67 (m, 1H), 4.13-4.24 (m, 2H), 4.04 (dd, J=10.0, 6.4 Hz, 1H), 2.80-2.98 (m, 5H), 2.40-2.47 (m, 1H), 2.03-2.15 (m, 2H).

Example 59

The following compounds were prepared as described in Example 58 starting with Step 2 utilizing the phenol listed below in place of 6-fluoroindan-5-ol (Intermediate 96).

| Compound number | Phenol used in place of Intermediate 96 | Carbamothioate prepared (LCMS data) | Transition-metal Catalyzed Coupling Conditions | Temp of Sulfamoylation Reaction | LCMS data for product | $^1$H NMR data for product |
|---|---|---|---|---|---|---|
| I-178 | 2-fluoro-4-methoxyphenol | S-(2-fluoro-4-methoxyphenyl) dimethylcarbamothioate (LCMS (FA): m/z 230 (M + H)) | Xphos Pd G2 MW 100° C. 3 h Cs$_2$CO$_3$ DMF | 0° C. | LCMS (FA): m/z 487 (M + H) | $^1$H NMR (400 MHz, CD$_3$OD) δ 8.21 (s, 1H), 7.46-7.52 (m, 1H), 6.80-6.87 (m, 2H), 6.66 (dd, J = 7.0, 4.5 Hz, 1H), 4.58-4.63 (m, 1H), 4.11-4.21 (m, 2H), 4.02 (dd, J = 10.0, 6.4 Hz, 1H), 3.83 (s, 3H), 2.82-2.90 (m, 1H), 2.37-2.46 (m, 1H). |
| I-168 | 2,3-dihydrobenzofuran-6-ol | S-(2,3-dihydro-1-benzofuran-6-yl) dimethylcarbamothioate (LCMS (FA): m/z 224 (M + H)) | Xphos Pd G2 MW 140° C. 1 h Cs$_2$CO$_3$ DMF | 0° C. | LCMS (FA): m/z 481 (M + H) | $^1$H NMR (400 MHz, CD$_3$OD) δ 8.23 (s, 1H), 7.19 (d, J = 7.8 Hz, 1H), 6.87 (dd, J = 7.7, 1.6 Hz, 1H), 6.71-6.76 (m, 2H), 4.68-4.74 (m, 1H), 4.56 (t, J = 8.7 Hz, 2H), 4.25-4.32 (m, 1H), 4.16-4.22 (m, 1H), 4.09-4.16 (m, 1H), 3.18 (t, J = 8.7 Hz, 2H), 2.97-3.04 (m, 1H), 2.42-2.52 (m, 1H). |
| I-173 | 2-fluoro-5-methoxyphenol | S-(2-fluoro-5-methoxyphenyl) dimethylcarbamothioate (LCMS | Xphos Pd G2 MW 100° C. 3 h Cs$_2$CO$_3$ DMF | 0° C. | LCMS (FA): m/z 487 (M + H) | $^1$H NMR (400 MHz, CD$_3$OD) δ 8.25 (s, 1H), 7.09-7.16 (m, 1H), 6.86-6.92 (m, 1H), 6.81 (dd, J = 5.8, |

-continued

| Compound number | Phenol used in place of Intermediate 96 | Carbamo-thioate prepared (LCMS data) | Transition-metal Catalyzed Coupling Conditions | Temp of Sulfamo-ylation Reaction | LCMS data for product | $^1$H NMR data for product |
|---|---|---|---|---|---|---|
| | | (FA): m/z 230 (M + H) | | | | 3.1 Hz, 1H), 6.72 (dd, J = 6.8, 5.0 Hz, 1H), 4.63-4.71 (m, 1H), 4.22-4.28 (m, 1H), 4.15-4.21 (m, 1H), 4.04-4.12 (m, 1H), 3.71 (s, 3H), 2.90-3.00 (m, 1H), 2.41-2.50 (m, 1H). |

Example 60: {(2R,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl Sulfamate Compound I-160

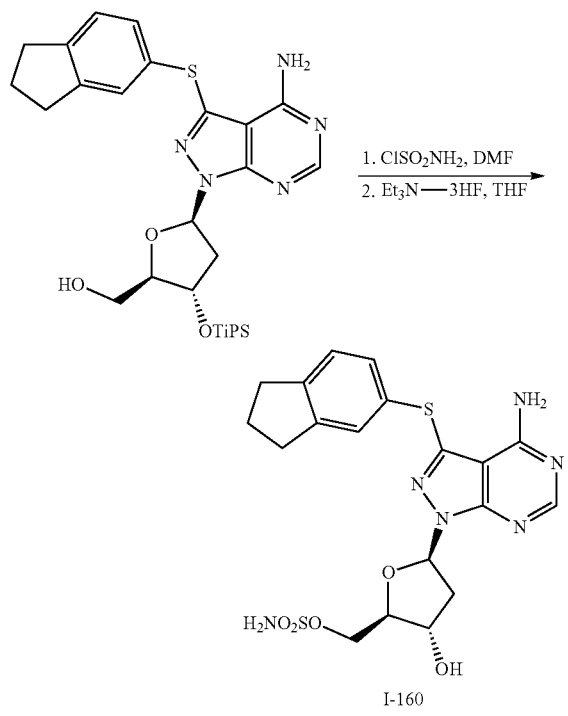

Step 1: {(2R,3S,5R)-5-[4-amino-3-(2,3-dihydro-1H-inden-5-ylsulfanyl)-1H-pyrazolo[3,4-d]pyrimidin-1-yl]-3-[(triisopropylsilyl)oxy]tetrahydrofuran-2-yl}methanol To a microwave vial was added Intermediate 95 (2.50 g, 4.69 mmol), indane-5-thiol (1.00 g, 6.66 mmol), cesium carbonate (3.05 g, 9.37 mmol), XPhos Pd G2 (369 mg, 0.47 mmol) and DMF (32 mL). The vial was capped, evacuated and backfilled with argon from a balloon. The reaction mixture was subjected to microwave irradiation at 140° C. for 1 h. The mixture was partitioned between water and ethyl acetate. The phases were separated and the aqueous phase was extracted twice with ethyl acetate. The extracts were combined, washed with water and brine and then dried over sodium sulfate, filtered and concentrated under reduced pressure. The crude compound was purified by column chromatography (120 g, methylene chloride to 50/50 methylene chloride/ethyl acetate gradient) to give the pure product as a white solid (1.8 g, 69%). LCMS (FA): m/z 556 (M+H); $^1$H NMR (400 MHz, CDCl3) δ 8.31 (s, 1H), 7.12-7.21 (m, 3H), 6.71 (dd, J=5.90, 8.78 Hz, 1H), 6.17 (s, 2H), 4.80 (d, J=5.02 Hz, 1H), 4.20-4.25 (m, 1H), 3.95 (dd, J=1.76, 12.67 Hz, 1H), 3.77 (d, J=12.17 Hz, 1H), 2.98-3.06 (m, 1H), 2.81-2.89 (m, 4H), 2.38-2.45 (m, 1H), 2.03-2.09 (m, 2H), 1.02-1.15 (m, 21H).

Step 2: {(2R,3S,5R)-5-[4-amino-3-(2,3-dihydro-1H-inden-5-ylsulfanyl)-1H-pyrazolo[3,4-d]pyrimidin-1-yl]-3-[(triisopropylsilyl)oxy]tetrahydrofuran-2-yl}methyl Sulfamate {(2R,3S,5R)-5-[4-amino-3-(2,3-dihydro-1H-inden-5-ylsulfanyl)-1H-pyrazolo[3,4-d]pyrimidin-1-yl]-3-[(triisopropylsilyl)oxy]tetrahydrofuran-2-yl}methanol (1.81 g, 3.25 mmol) was dissolved in DMF (26.8 mL) and cooled at 0° C. Chlorosulfonamide (0.75 g, 6.50 mmol) was added at 0° C. and the mixture was stirred at the same temperature for 30 min. The mixture was poured into saturated aqueous sodium bicarbonate solution and extracted twice with ethyl acetate. The extracts were combined, washed with water and brine and then dried over sodium sulfate, filtered and concentrated under reduced pressure. The crude compound was purified by column chromatography (80 g, 10/90 to 30/70 (1/4/5 EtOH/EA/Hex)/hexanes gradient) to give the pure product as a white solid (1.66 g, 80%). LCMS (FA): m/z 635 (M+H); $^1$H NMR (400 MHz, CD$_3$OD) δ 8.20 (s, 1H), 7.24 (s, 1H), 7.12-7.19 (m, 2H), 6.70 (dd, J=5.46, 6.46 Hz, 1H), 4.86-4.90 (m, 1H), 4.24-4.31 (m, 1H), 4.17-4.23 (m, 1H), Step 3: {(2R,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl Sulfamate Into a solution of {(2R,3S,5R)-5-[4-amino-3-(2,3-dihydro-1H-inden-5-ylsulfanyl)-1H-pyrazolo[3,4-d]pyrimidin-1-yl]-3-[(triisopropylsilyl)oxy]tetrahydrofuran-2-yl}methyl sulfamate (1.63 g, 2.57 mmol) in THF (34 mL) was added triethylamine trishydrofluoride (3.34 mL, 20.5 mmol) at 0° C. The mixture was allowed to stir at rt for 3 days. The mixture was concentrated under reduced pressure and purified by HPLC (75/25 to 50/50 water/acetonitrile gradient, with 0.1% formic acid) to give the pure titled compound as a white solid (0.92 g, 75%). LCMS (FA): m/z 479 (M+H); $^1$H NMR (400 MHz, CD$_3$OD) δ 8.22 (s, 1H), 7.27 (s, 1H), 7.16-7.23 (m, 2H), 6.71 (t, J=5.88 Hz, 1H), 4.66-4.73 (m, 1H), 4.24-4.30 (m, 1H), 4.16-4.22 (m, 1H), 4.08-4.15 (m, 1H), 2.93-3.02 (m, 1H), 2.84-2.93 (m, 4H), 2.41-2.50 (m, 1H), 2.03-2.11 (m, 2H).

Example 61: [(2R,3S,5R)-5-{4-amino-3-[(cyclopropylmethyl)sulfanyl]-1H-pyrazolo[3,4-d]pyrimidin-1-yl}-3-hydroxytetrahydrofuran-2-yl]methyl Sulfamate Compound I-202

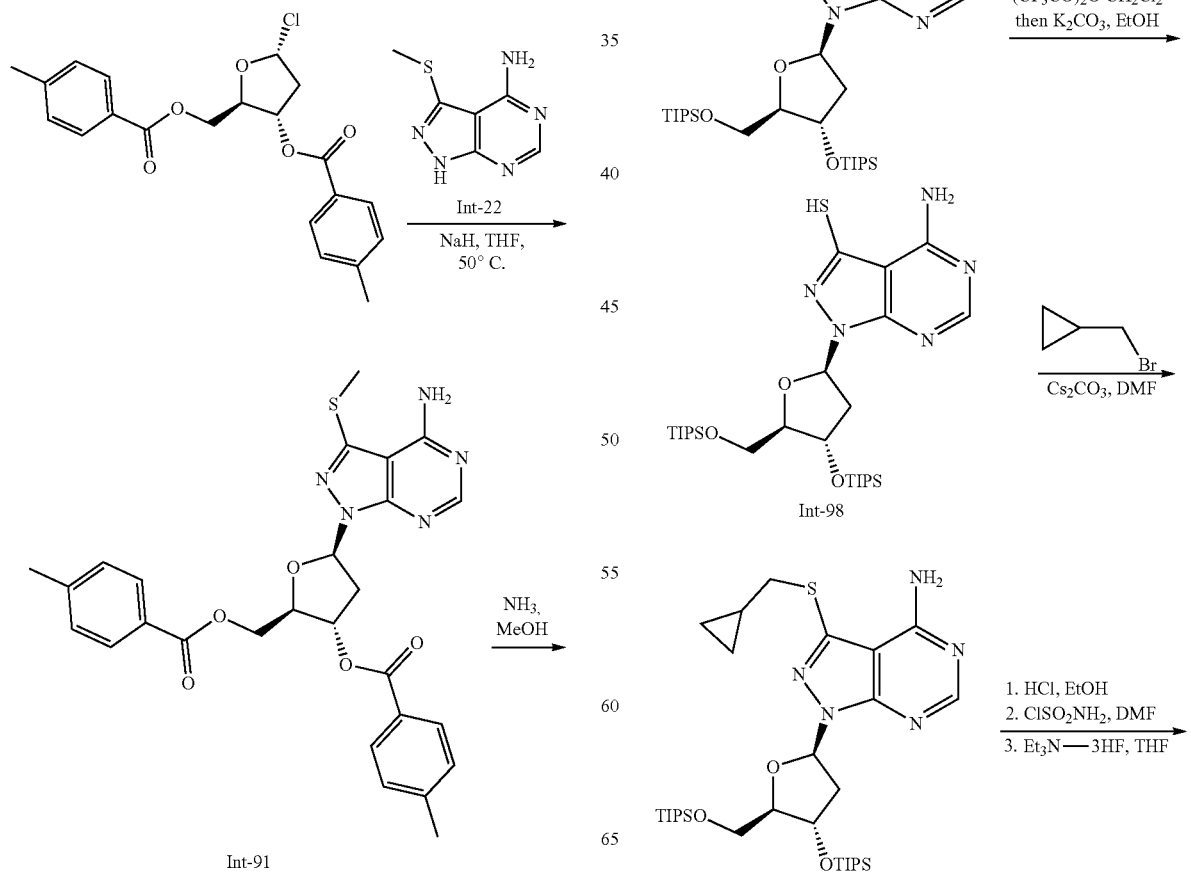

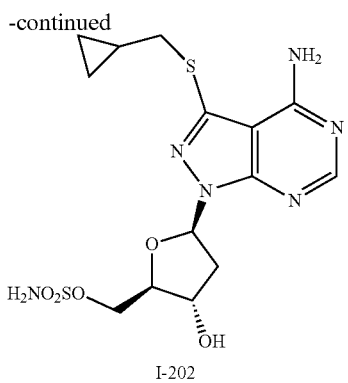

I-202

Step 1: (2R,3S,5R)-5-[4-amino-3-(methylsulfanyl)-1H-pyrazolo[3,4-d]pyrimidin-1-yl]-2-{[(4-methylbenzoyl)oxy]methyl}tetrahydrofuran-3-yl 4-methylbenzoate Intermediate 91

To a stirred suspension of NaH (60:40, NaH:mineral oil, 240 mg, 6.1 mmol) in acetonitrile at 0° C. (37 mL) was added 3-(methylsulfanyl)-1H-pyrazolo[3,4-d]pyrimidin-4-amine (1.00 g, 5.52 mmol). The suspension was stirred for 45 minutes. 1-α-Chloro-2-deoxy-3,5-bis(p-toluoyl)-α-D-ribofuranosyl chloride (2.36 g, 6.07 mmol) in THF (60 mL) was added and the suspension was heated at reflux (50° C.) for 1 h under an atmosphere of argon. The reaction mixture was allowed to cool to rt and then in an ice bath, water was added and the resulting mixture was extracted with DCM. The extracts were combined, washed with water and brine, dried over sodium sulfate, filtered and concentrated under reduced pressure. The crude material was purified by column chromatography to give Intermediate 91 (1.78 g, 59%) as a yellow oil. LCMS: (FA) ES+=535 (M+H); $^1$H NMR (400 MHz, CDCl$_3$) δ 8.30-8.43 (m, 1H), 7.95-8.02 (m, 4H), 7.28-7.32 (m, 2H), 7.24 (d, J=8.03 Hz, 2H), 6.90 (t, J=6.53 Hz, 1H), 5.88-5.93 (m, 1H), 5.74 (s, 2H), 4.53-4.78 (m, 3H), 3.39-3.58 (m, 1H), 2.67 (s, 3H), 2.46 (s, 3H), 2.42 (s, 3H).

Step 2: (2R,3S,5R)-5-[4-amino-3-(methylsulfanyl)-1H-pyrazolo[3,4-d]pyrimidin-1-yl]-2-(hydroxymethyl)tetrahydrofuran-3-ol To a solution of Intermediate 91 (11.6 g, 21.7 mmol) in THF (85 mL) was added a solution of ammonia in methanol (7.0 M, 601 mL). The resulting white suspension was stirred at rt for 5 days. The reaction solvents were removed under reduced pressure and the resulting white solid was triturated with ether and isolated by filtration to give Intermediate 92 (6.01 g, 93%). LCMS: (FA) ES+=298 (M+1); $^1$H NMR (400 MHz, CD$_3$OD) δ 8.17-8.22 (m, 1H), 6.66 (t, J=6.40 Hz, 1H), 4.62-4.69 (m, 1H), 4.03 (br d, J=4.52 Hz, 1H), 3.78 (dd, J=4.14, 11.92 Hz, 1H), 3.64-3.71 (m, 1H), 2.94 (td, J=6.12, 13.49 Hz, 1H), 2.68 (s, 3H), 2.35-2.45 (m, 1H).

Step 3: 3-(Methylsulfanyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine The title compound was prepared following the procedure outlined in Example 95 Step 8, substituting Intermediate 92 for Intermediate 120. LCMS (FA): m/z=610 (M+H); $^1$H NMR (400 MHz, CDCl$_3$) δ 8.26-8.46 (m, 1H), 6.75 (t, J=6.84 Hz, 1H), 5.88 (s, 2H), 4.83-4.91 (m, 1H), 4.11 (ddd, J=1.88, 5.11, 7.43 Hz, 1H), 3.69-3.90 (m, 2H), 3.20 (ddd, J=5.27, 7.37, 13.08 Hz, 1H), 2.67 (s, 3H), 2.35 (ddd, J=2.57, 6.34, 13.18 Hz, 1H), 1.03-1.22 (m, 42H).

Step 4: 3-(Methylsulfinyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine To a solution of 3-(methylsulfanyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine (0.200 g, 0.328 mmol) in methylene chloride (4 mL) at 0° C. was added a solution of m-chloroperbenzoic acid (0.90 g, 5.19 mmol) in methylene chloride (4.9 mL). The resulting mixture was stirred at 0° C. for 1 hour. Saturated aqueous sodium bicarbonate solution was added and the mixture was extracted twice with methylene chloride. The combined organic extracts were washed with water and brine, dried over sodium sulfate, filtered and concentrated. The crude material was purified by silica gel chromatography to afford 3-(methylsulfinyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine (171 mg, 83%) as a white solid. LCMS (FA): m/z=627 (M+H).

Step 5: 4-amino-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidine-3-thiol Intermediate 98

To a solution of 3-(methylsulfinyl)-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine (3.15 g, 5.03 mmol) in methylene chloride (32 mL) was added trifluoroacetic anhydride (32.4 mL, 229 mmol). The resulting mixture was stirred at rt overnight and concentrated under reduced pressure. The solid was dissolved in ethanol (32 mL) and potassium carbonate (2.78 g, 20.1 mmol) was added at rt. The resulting mixture was stirred for 15 minutes. Saturated aqueous ammonium chloride solution was added and the mixture was extracted twice with ethyl acetate. The combined extracts were washed with water and brine, then dried over sodium sulfate, filtered and concentrated under reduced pressure to afford 4-amino-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidine-3-thiol (3.00 g, 100%) as brown solid. LCMS (FA): m/z=597 (M+H).

Step 6: 3-[(Cyclopropylmethyl)sulfanyl]-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine In a round-bottom flask, a solution of Intermediate 98 (340 mg, 0.57 mmol) in DMF (5 mL) was added cyclopropylmethyl bromide (0.166 mL, 1.71 mmol) followed by cesium carbonate (371 mg, 1.14 mmol) and the resulting mixture was stirred under argon at rt for 2 h. Water and EtOAc were added and the aqueous phase was extracted twice with EtOAc. The organic phases were combined and washed with water and brine, dried over sodium sulfate, filtered, and concentrated under reduced pressure. The resulting crude material was purified by silica gel chromatography to afford 3-[(cyclopropylmethyl)sulfanyl]-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine as white solid. LCMS (FA): m/z=651; $^1$H NMR (400 MHz, CDCl3) δ 8.35 (s, 1H), 6.76 (t, J=6.84 Hz, 1H), 5.80 (br d, J=2.13 Hz, 2H), 4.81-4.90 (m, 1H), 4.10-4.20 (m, 1H), 3.79-3.89 (m, 1H), 3.74 (dd, J=4.89, 10.4z, 1H), 3.15-3.25 (m, 1H), 3.08 (dd, J=2.89, 7.28 Hz, 2H), 2.37 (br dd, J=2.82, 6.21 Hz, 1H), 1.27-1.31 (m, 1H), 1.04-1.19 (m, 42H), 0.59-0.66 (m, 2H), 0.29 (d, J=5.77 Hz, 2H).

Step 7: {(2R,3S,5R)-5-{4-amino-3-[(cyclopropylmethyl)sulfanyl]-1H-pyrazolo[3,4-d]pyrimidin-1-yl}-3-[(triisopropylsilyl)oxy]tetrahydrofuran-2-yl}methanol The titled compound was prepared following the procedure outlined in Example 95 Step 9 substituting 3-[(cyclopropylmethyl)sulfanyl]-1-[(2R,4S,5R)-4-[(triisopropylsilyl)oxy]-5-{[(triisopropylsilyl)oxy]methyl}tetrahydrofuran-2-yl]-1H-pyrazolo[3,4-d]pyrimidin-4-amine for Intermediate 121. LCMS (FA): m/z=494 (M+H).

Step 8: {(2R,3S,5R)-5-{4-amino-3-[(cyclopropylmethyl)sulfanyl]-1H-pyrazolo[3,4-d]pyrimidin-1-yl}-3-[(triisopropylsilyl)oxy]tetrahydrofuran-2-yl}methyl Sulfamate The titled compound was prepared following the procedure described in Example 1 Step 7, substituting {(2R,3S,5R)-5-{4-amino-3-[(cyclopropylmethyl)sulfanyl]-1H-pyrazolo[3,4-d]pyrimidin-1-yl}-3-[(triisopropylsilyl)oxy]tetrahydrofuran-2-yl}methanol for Intermediate 7. LCMS (FA): m/z=574 (M+H).

Step 9: [(2R,3S,5R)-5-{4-amino-3-[(cyclopropylmethyl)sulfanyl]-1H-pyrazolo[3,4-d]pyrimidin-1-yl}-3-hydroxytetrahydrofuran-2-yl]methyl Sulfamate
I-202

The titled compound was prepared following the procedure outlined in Example 65 Step 7 substituting {(2R,3S,5R)-5-{4-amino-3-[(cyclopropylmethyl)sulfanyl]-1H-pyrazolo[3,4-d]pyrimidin-1-yl}-3-[(triisopropylsilyl)oxy]tetrahydrofuran-2-yl}methyl sulfamate for {(2R,3R,4S,5R)-5-[4-amino-3-(isopropylsulfanyl)-1H-pyrazolo[3,4-d]pyrimidin-1-yl]-4-fluoro-3-[(triisopropylsilyl)oxy]tetrahydrofuran-2-yl}methyl sulfamate. LCMS (AA): m/z=417; $^1$H NMR (400 MHz, d$_6$-DMSO) δ 8.21 (s, 1H), 8.11-8.18 (m, 1H), 7.50 (s, 2H), 6.57 (br t, J=5.9 Hz, 1H), 5.52 (br s, 1H), 4.46-4.60 (m, 1H), 4.21 (br dd, J=9.0, 3.1 Hz, 1H), 3.92-4.06 (m, 2H), 3.10 (d, J=7.2 Hz, 2H), 2.73-2.86 (m, 1H), 2.36 (br d, J=6.4 Hz, 1H), 1.11-1.23 (m, 1H), 0.50-0.60 (m, 2H), 0.28 (br d, J=1.9 Hz, 2H).

Example 62

The following compounds were prepared as described following the procedures in Example 61 using Intermediate 98 with the reagents and conditions described in the table below.

| Compound Number | Halide | Alkylation Conditions | LCMS data | $^1$H NMR Data |
|---|---|---|---|---|
| I-180 | 2-bromo-N,N-dimethylacetamide | Cs$_2$CO$_3$, DMF, rt, ON | LCMS (FA): m/z 448 (M + H) | $^1$H NMR (400 MHz, d$_6$-DMSO) δ 8.21 (br s, 1H), 6.57 (br s, 1H), 4.53 (br s, 1H), 4.10-4.29 (m, 3H), 4.02 (br s, 2H), 3.03 (br s, 3H), 2.86 (br s, 3H), 2.70-2.81 (m, 1H), 2.29-2.41 (m, 1H) |
| I-159 | 2-bromoacetamide | Cs$_2$CO$_3$, DMF, rt, ON | LCMS (FA): m/z 420 (M + H) | $^1$H NMR (400 MHz, d$_6$-DMSO) δ 8.20 (s, 1H), 7.61 (br s, 1H), 7.19 (br s, 1H), 6.55 (br t, J = 5.6 Hz, 1H), 4.53 (br d, J = 3.3 Hz, 1H), 4.21 (br d, J = 6.7 Hz, 1H), 3.97-4.06 (m, 2H), 3.80 (s, 2H), 2.74-2.86 (m, 1H), 2.34 (dt, J = 12.6, 6.2 Hz, 1H). |
| I-188 | 2-bromoacetonitrile | Cs$_2$CO$_3$, DMF, rt, ON | LCMS (FA): m/z 402 (M + H) | $^1$H NMR (400 MHz, d$_6$-DMSO) δ 8.30 (s, 1H), 6.66 (dd, J = 7.0, 4.8 Hz, 1H), 5.58 (br d, J = 4.0 Hz, 1H), 4.64 (br s, 1H), 4.26-4.40 (m, 3H), 4.03-4.18 (m, 2H), 2.77-2.95 (m, 1H), 2.32-2.50 (m, 1H). |
| I-169 | sodium 2-chloro-2,2-difluoroacetate | K$_2$CO$_3$, DMF/Water 80° C., 2-3 h | LCMS (FA): m/z 413 (M + H) | $^1$H NMR (400 MHz, d$_6$-DMSO) δ 8.28 (s, 1H), 7.34-7.64 (m, 3H), 6.64 (dd, J = 7.0, 4.8 Hz, 1H), 5.56 (br s, 1H), 4.57 (br d, J = 4.8 Hz, 1H), 4.21 (dd, J = 10.1, 4.0 Hz, 1H), 3.92-4.09 (m, 2H), 2.75-2.89 (m, 1H), 2.35-2.44 (m, 1H). |
| I-164 | bromocyclobutane | NaOH, DMSO, 80° C., ON | LCMS (FA): m/z 417 (M + H) | $^1$H NMR (400 MHz, CD$_3$OD) δ 8.21 (s, 1H), 8.08-8.19 (m, 1H), 6.70 (dd, J = 7.0, 5.1 Hz, 1H), 4.73-4.82 (m, 1H), 4.31-4.37 (m, 1H), 4.15-4.23 (m, 3H), 2.95-3.02 (m, 1H), 2.42-2.56 (m, 3H), 2.14-2.24 (m, 2H), 1.98-2.08 (m, 2H). |
| I-165 | 1,1-difluoro-2-iodoethane | DMF, DIPEA, rt (aDR-3) | LCMS(FA) m/z 427 (M + H) | $^1$H NMR (400 MHz, CD$_3$OD) δ 8.21 (s, 1H), 6.68 (dd, J = 7.0, 5.1 Hz, 1H), 5.99-6.37 (m, 1H), 4.70-4.75 (m, 1H), 4.26-4.32 (m, 1H), 4.13-4.19 |

-continued

| Compound Number | Halide | Alkylation Conditions | LCMS data | ¹H NMR Data |
|---|---|---|---|---|
| I-204 | 3-(bromomethyl)benzo[b]thiophene* | Cs₂CO₃, DMF, ON | LCMS (FA): m/z 509 (M + H) | (m, 2H), 3.61 (tdd, J = 15.5, 15.5, 11.3, 4.1 Hz, 2H), 2.93-3.01 (m, 1H), 2.40-2.47 (m, 1H).<br>¹H NMR (400 MHz CD₃OD) δ 8.17 (s, 1H), 7.57-7.87 (m, 2H), 7.29 (ddd, J = 7.3, 5.4, 1.4 Hz, 2H), 7.18 (s, 1H), 6.68 (dd, J = 6.8, 5.3 Hz, 1H), 4.57-4.81 (m, 3H), 4.26-4.38 (m, 1H), 4.12-4.21 (m, 2H), 2.89 (dt, J = 13.2, 5.9 Hz, 1H), 2.37 (ddd, J = 13.5, 7.0, 5.0 Hz, 1H). |

*Prepared as described below.

Example 63: 3-(bromomethyl)benzo[b]thiophene

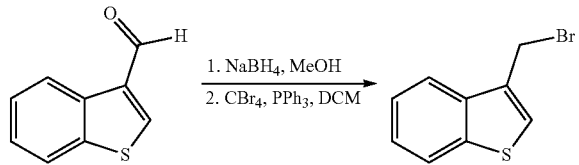 [SMILES: O=Cc1csc2ccccc12 ; BrCc1csc2ccccc12]

To a solution of 1-benzothiophene-5-carbaldehyde (800 mg, 5 mmol) in MeOH (10 mL) was added sodium tetrahydroborate (0.28 g, 7.4 mmol) at 0° C. The reaction mixture was allowed to stir at 0° C. for 1 h, at which point a saturated aqueous solution of NH₄Cl (50 mL) and water (50 mL) was added. The mixture was extracted with DCM (3×). The organic solutions were combined, dried over MgSO₄, filtered, and concentrated to dryness. The crude solid was then dissolved in DCM (100 mL) under argon and triphenyl phosphine (2.30 g, 8.78 mmol) and carbon tetrabromide (2.0 g, 5.9 mmol) were added. After stirring for 1 h, diethyl ether was added and the resulting mixture was filtered and washed with diethyl ether (2×). The filtrate was concentrated to dryness and the crude residue was purified by column chromatography to afford 5-(bromomethyl)-1-benzothiophene (760 mg, 70%) as a white solid. ¹H NMR (400 MHz, CDCl₃) δ 7.80-7.92 (m, 2H), 7.51 (d, J=5.4 Hz, 1H), 7.41 (dd, J=8.3, 1.8 Hz, 1H), 7.35 (d, J=5.4 Hz, 1H), 4.68 (s, 2H).

Example 64: [(2R,3S,5R)-5-{4-amino-3-[(2-hydroxyethyl)sulfanyl]-1H-pyrazolo[3,4-d]pyrimidin-1-yl}-3-hydroxytetrahydrofuran-2-yl]methyl Sulfamate Compound I-162

Steps 1-3: 2-((4-amino-1-((2R,4S,5R)-4-((triisopropylsilyl)oxy)-5-(((triisopropylsilyl)oxy)methyl)tetrahydrofuran-2-yl)-1H-pyrazolo[3,4-d]pyrimidin-3-yl)thio)ethyl Benzoate The titled compound was prepared as described above in Example 61 substituting 2-bromoethyl benzoate for cyclopropylmethyl bromide in Step 6. The product of step 6 was deprotected and sulfamoylated as described in Steps 7 and 8 to give 2-((4-amino-1-((2R,4S,5R)-4-((triisopropylsilyl)oxy)-5-(((triisopropylsilyl)oxy)methyl)tetrahydrofuran-2-yl)-1H-pyrazolo[3,4-d]pyrimidin-3-yl)thio)ethyl benzoate.

Step 4: {(2R,3S,5R)-5-{4-amino-3-[(2-hydroxyethyl)sulfanyl]-1H-pyrazolo[3,4-d]pyrimidin-1-yl}-3-[(triisopropylsilyl)oxy]tetrahydrofuran-2-yl}methyl Sulfamate 2-[(4-Amino-1-{(2R,4S,5R)-5-[(sulfamoyloxy)methyl]-4-[(triisopropylsilyl)oxy]tetrahydrofuran-2-yl}-1H-pyrazolo[3,4-d]pyrimidin-3-yl)sulfanyl]ethyl benzoate (210 mg, 0.3 mmol) was dissolved in a solution of ammonia in MeOH (7.0 M, 5 mL) and the reaction mixture was allowed to stir at rt overnight. An additional 3 mL of the 7 M ammonia in methanol solution was added and the resulting reaction mixture was allowed to stir for 2 days. The reaction mixture was then concentrated to dryness to yield {(2R,3S,5R)-5-{4-amino-3-[(2-hydroxyethyl)sulfanyl]-1H-pyrazolo[3,4-d]pyrimidin-1-yl}-3-[(triisopropylsilyl)oxy]tetrahydrofuran-2-yl}methyl sulfamate which was used without further purification in the next step.

Step 5: [(2R,3S,5R)-5-{4-amino-3-[(2-hydroxyethyl)sulfanyl]-1H-pyrazolo[3,4-d]pyrimidin-1-yl}-3-hydroxytetrahydrofuran-2-yl]methyl Sulfamate I-162

Final deprotection was achieved as described in Example 61 Step 9 to give the titled compound. LCMS (FA): m/z 407 (M+H); ¹H NMR (400 MHz, d₆-DMSO) δ 8.21 (s, 1H), 8.14 (s, 1H), 7.52 (s, 2H), 6.57 (dd, J=6.9, 5.0 Hz, 1H), 5.53 (br s, 1H), 5.08 (br s, 1H), 4.53 (br d, J=4.4 Hz, 1H), 4.21 (dd, J=9.7, 3.9 Hz, 1H), 3.94-4.04 (m, 2H), 3.68 (t, J=6.2 Hz, 2H), 3.13-3.32 (m, 2H), 2.78 (dt, J=13.0, 5.9 Hz, 1H), 2.35 (ddd, J=13.1, 7.3, 5.4 Hz, 1H).

Example 65: {(2R,3R,4S,5R)-5-[4-amino-3-(isopropylsulfanyl)-1H-pyrazolo[3,4-d]pyrimidin-1-yl]-4-fluoro-3-hydroxytetrahydrofuran-2-yl}methyl Sulfamate Compound I-139

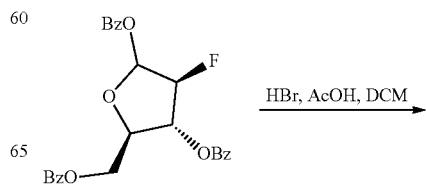

-continued

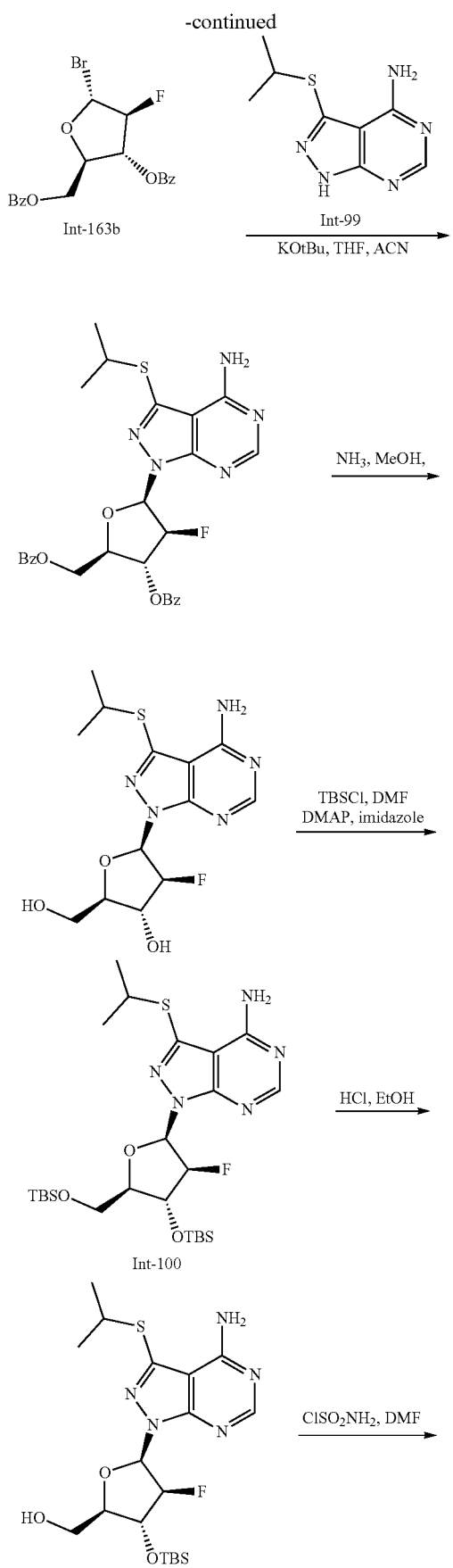

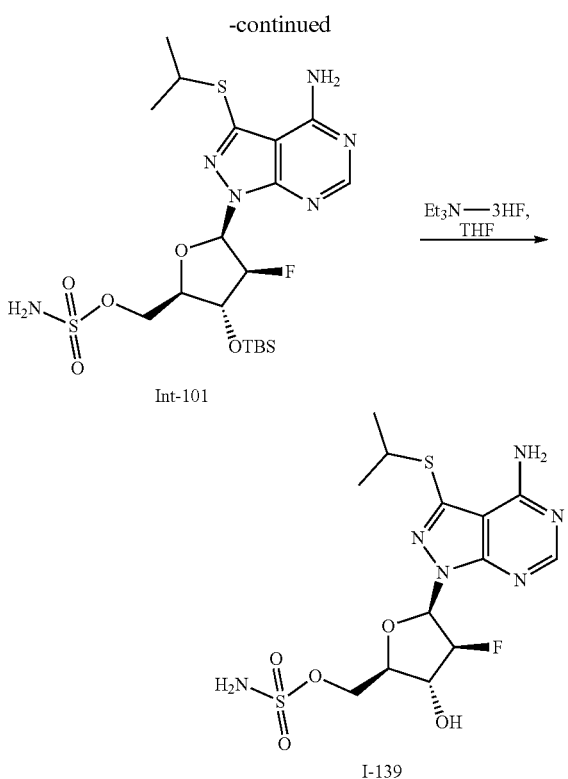

Step 1: (3S,4R,5R)-5-[(benzoyloxy)methyl]-3-fluorotetrahydrofuran-2,4-diyl Dibenzoate To a solution of 1,3,5-tri-O-benzoyl-2-deoxy-2-fluoro-α-D-arabinofuranose (25.0 g, 53.8 mmol) in DCM (200 mL) was added hydrobromic acid (43.6 mL, 30% solution in acetic acid). The reaction mixture was allowed to stir overnight at rt. Excess acid was quenched by the addition of saturated aqueous sodium bicarbonate solution at 0° C. (ca. 400 mL, until pH 7). The mixture was diluted with DCM and the phases were shaken and separated. The aqueous phase was extracted with additional DCM (2×350 mL). The extracts were combined, washed with 20% aqueous sodium thiosulfate/saturated aqueous sodium bicarbonate (1:1 to remove orange color), water and brine, and then dried over sodium sulfate. The extracts were filtered and concentrated under reduced pressure. The product was isolated as a pale yellow oil (23.84 g, quant.) and was transferred to a tared 500 mL round bottom flask, azeotropically dried in toluene and dried in vacuo. The material was used with no further purification. $^1$H NMR (400 MHz, CDCl$_3$) δ 8.12 (dd, J=17.8, 7.6 Hz, 4H), 7.56-7.73 (m, 2H), 7.42-7.55 (m, 4H), 7.15-7.32 (m, 1H), 6.66 (d, J=12.2 Hz, 1H), 5.52-5.73 (m, 2H), 4.69-4.93 (m, 2H).

Step 2: [(2R,3R,4S,5R)-5-[4-amino-3-(isopropylsulfanyl)-1H-pyrazolo[3,4-d]pyrimidin-1-yl]-3-(benzoyloxy)-4-fluorotetrahydrofuran-2-yl]methyl Benzoate Int-163b 3-(Isopropylsulfanyl)-1H-pyrazolo[3,4-d]pyrimidin-4-amine (Intermediate 99) was prepared following the procedures detailed in Example 48 Steps 1-3, substituting isopropyl iodide for ethyl iodide.

To a suspension of Intermediate 99 (10.2 g, 49.0 mmol) in acetonitrile (100 mL) and DMF (100 mL) at rt was added potassium tert-butoxide (1.0 M in THF, 53.9 mL, 53.9 mmol) over 30 min from a dropping funnel. Following completion of base addition, the reaction mixture was allowed to stir at rt for an additional 30 min. Into the stirred base mixture was added a solution of [(2R,3R,4S,5R)-3-(benzoyloxy)-5-bromo-4-fluorotetrahydrofuran-2-yl]methyl benzoate (22.8 g, 53.9 mmol) in acetonitrile (50 mL) dropwise over 20 min. Following addition, the reaction mixture was allowed to stir at rt for 3 h. Excess base was quenched by the addition of saturated aqueous ammonium chloride solution (150 mL). The reaction mixture was then concentrated under reduced pressure to remove water-miscible solvents. The resulting crude mixture was extracted with EtOAc (700+300 mL). The combined extracts were washed with water (500 mL) and brine, dried over sodium sulfate, filtered and concentrated under reduced pressure. The crude product was purified by silica gel chromatography. LCMS (FA): m/z 552; $^1$H NMR (400 MHz, CDCl$_3$) δ 8.37 (s, 1H), 8.07-8.14 (m, 2H), 7.96-8.04 (m, 2H), 7.60-7.68 (m, 1H), 7.46-7.56 (m, 3H), 7.33-7.41 (m, 2H), 6.87 (d, J=6.3 Hz, 1H), 6.55 (dt, J=16.2, 6.9 Hz, 1H), 6.03 (br s, 2H), 5.60-5.81 (m, 1H), 4.90-4.97 (m, 1H), 4.82-4.89 (m, 1H), 4.60 (td, J=7.1, 4.6 Hz, 1H), 3.86 (spt, J=6.8 Hz, 1H), 1.51 (dd, J=12.5, 6.7 Hz, 6H).

Step 3: (2R,3R,4S,5R)-5-[4-amino-3-(isopropylsulfanyl)-1H-pyrazolo[3,4-d]pyrimidin-1-yl]-4-fluoro-2-(hydroxymethyl)tetrahydrofuran-3-ol The title compound was prepared following the procedure detailed in Example 5 Step 3, substituting [(2R,3R,4S,5R)-5-[4-amino-3-(isopropylsulfanyl)-1H-pyrazolo[3,4-d]pyrimidin-1-yl]-3-(benzoyloxy)-4-fluorotetrahydrofuran-2-yl]methyl benzoate for Intermediate 15. LCMS (FA): m/z 344. $^1$H NMR (400 MHz, CD$_3$OD) δ 8.22 (s, 1H), 6.66 (d, J=6.3 Hz, 1H), 5.22-5.47 (m, 1H), 4.93 (dt, J=18.3, 7.4 Hz, 1H), 3.96-4.07 (m, 1H), 3.92 (d, J=4.6 Hz, 2H), 3.58-3.79 (m, 1H), 1.43 (t, J=7.2 Hz, 6H).

Step 4: 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-(isopropylsulfanyl)-1H-pyrazolo[3,4-d]pyrimidin-4-amine Intermediate 100

To a 1 L flask containing (2R,3R,4S,5R)-5-[4-amino-3-(isopropylsulfanyl)-1H-pyrazolo[3,4-d]pyrimidin-1-yl]-4-fluoro-2-(hydroxymethyl)tetrahydrofuran-3-ol (9.98 g, 29.1 mmol) was added DMF (150 mL). As the reaction mixture was being stirred at rt, 1H-Imidazole (7.91 g, 116 mmol) and DMAP (1.8 g, 14 mmol) were added, followed by TBS-chloride (17.5 g, 116 mmol). The mixture was stirred under nitrogen at rt overnight. The reaction mixture was poured into a separatory funnel containing EtOAc (800 mL) and water (900 mL). The phases were shaken and separated. The aqueous phase was extracted with additional EtOAc (500 mL). The extracts were combined, washed with water (1 L) and brine, dried over sodium sulfate, filtered and concentrated under reduced pressure. The crude residue was purified by silica gel chromatography to afford product (10.48 g, 63%). $^1$H NMR (400 MHz, CDCl3) δ 8.20 (s, 1H), 6.57 (dd, J=6.4, 1.8 Hz, 1H), 5.80 (br s, 2H), 4.96-5.20 (m, 1H), 4.77-4.91 (m, 1H), 3.75-3.93 (m, 3H), 3.52 (spt, J=6.7 Hz, 1H), 1.30 (dd, J=8.8, 6.8 Hz, 6H), 0.78 (d, J=16.7 Hz, 18H), 0.00 (s, 6H), −0.11 (d, J=4.5 Hz, 6H).

Step 5: [(2R,3R,4S,5R)-5-[4-amino-3-(isopropylsulfanyl)-1H-pyrazolo[3,4-d]pyrimidin-1-yl]-3-{[tert-butyl(dimethyl)silyl]oxy}-4-fluorotetrahydrofuran-2-yl]methanol To a 2 L round-bottom flask containing 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-(isopropylsulfanyl)-1H-pyrazolo[3,4-d]pyrimidin-4-amine (Intermediate 100, 10.48 g, 18.32 mmol) was added EtOH (160 mL). The reaction solution was allowed to cool in a dry ice/acetone bath. A pre-cooled 1% HCl in EtOH solution (500 mL, prepared by adding 5 mL conc. aqueous HCl to 495 mL EtOH) was added. The reaction mixture was allowed to stir at −20° C. overnight. Upon completion, the reaction mixture was cooled in a dry ice/acetone bath and remaining acid was neutralized by the addition of saturated aqueous sodium bicarbonate solution (300 mL). After warming to rt, the mixture was diluted with water (200 mL) and concentrated under reduced pressure to remove most of the ethanol. The resulting white suspension was diluted with additional water and extracted with EtOAc (700+500 mL). The combined extracts were washed with water and brine, dried over sodium sulfate, filtered and concentrated under reduced pressure. The crude residue was purified by silica gel chromatography to afford the desired product (7.90 g, 94%). LCMS (FA): m/z 458; $^1$H NMR (400 MHz, CDCl$_3$) δ 8.20 (s, 1H), 6.52 (dd, J=6.3, 2.5 Hz, 1H), 5.89 (br s, 2H), 4.93-5.22 (m, 2H), 4.47 (br s, 1H), 3.88-3.95 (m, 2H), 3.68 (br d, J=12.17 Hz, 1H), 3.53 (spt, J=6.7 Hz, 1H), 1.27 (dd, J=11.9, 6.8 Hz, 6H), 0.75-0.79 (m, 9H), −0.01 (d, J=7.7 Hz, 6H).

Step 6: [(2R,3R,4S,5R)-5-[4-amino-3-(isopropylsulfanyl)-1H-pyrazolo[3,4-d]pyrimidin-1-yl]-3-{[tert-butyl(dimethyl)silyl]oxy}-4-fluorotetrahydrofuran-2-yl]methyl Sulfamate Intermediate 101

The titled compound was prepared following the procedure described in Example 1 Step 7, substituting [(2R,3R,4S,5R)-5-[4-amino-3-(isopropylsulfanyl)-1H-pyrazolo[3,4-d]pyrimidin-1-yl]-3-{[tert-butyl(dimethyl)silyl]oxy}-4-fluorotetrahydrofuran-2-yl]methanol for Intermediate 7. LCMS (FA): m/z 537; $^1$H NMR (400 MHz, CDCl$_3$) δ 8.13 (s, 1H), 6.54 (t, J=5.7 Hz, 1H), 5.89 (br s, 2H), 5.31 (br s, 2H), 4.91-5.15 (m, 1H), 4.82 (dt, J=17.8, 6.4 Hz, 1H), 4.43 (d, J=4.0 Hz, 2H), 3.92-4.07 (m, 1H), 3.55 (spt, J=6.7 Hz, 1H), 1.27 (dd, J=10.6, 6.7 Hz, 6H), 0.77 (s, 9H), −0.01 (d, J=5.4 Hz, 6H).

Step 7: {(2R,3R,4S,5R)-5-[4-amino-3-(isopropylsulfanyl)-1H-pyrazolo[3,4-d]pyrimidin-1-yl]-4-fluoro-3-hydroxytetrahydrofuran-2-yl}methyl Sulfamate I-139

To a round bottom flask containing a solution of [(2R,3R,4S,5R)-5-[4-amino-3-(isopropylsulfanyl)-1H-pyrazolo[3,4-d]pyrimidin-1-yl]-3-{[tert-butyl(dimethyl)silyl]oxy}-4-fluorotetrahydrofuran-2-yl]methyl sulfamate (Intermediate 101, 8.55 g, 15.9 mmol) in THF (250 mL) was added triethylamine trishydrofluoride (10.4 mL, 63.7 mmol). The reaction mixture was allowed to stir at rt overnight. Upon completion, the reaction mixture was concentrated and purified by silica gel chromatography to afford the desired product (5.32 g, 79%). LCMS (FA): m/z 423; $^1$H NMR (400 MHz, d$_6$-DMSO) δ 8.21 (s, 1H), 6.62 (d, J=6.7 Hz, 1H), 5.29-5.58 (m, 1H), 4.77 (br d, J=18.3 Hz, 1H), 4.29-4.43 (m, 1H), 4.25 (dd, J=10.5, 8.5 Hz, 1H), 3.92-4.12 (m, 2H), 3.66 (quin, J=6.7 Hz, 1H), 1.35 (dd, J=12.0, 6.7 Hz, 6H).

Example 66: {(2R,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl Sulfamate Compound I-115

The titled compound was prepared as described in Example 65 with the following modification: the conditions for the glycosylation described in step 2 were changed to those described in Example 78 Step 2 with Intermediate 22 used in place of Intermediate 14 and NaH used instead of potassium t-butoxide. LCMS (FA): m/z=395 (M+H); $^1$H NMR (400 MHz, CD$_3$OD) δ 8.21 (s, 1H), 6.64 (d, J=6.5 Hz, 1H), 5.37 (dt, J=53.3, 7.2 Hz, 1H), 5.01 (dt, J=17.7, 7.5 Hz, 1H), 4.40-4.57 (m, 2H), 4.18 (td, J=7.4, 3.6 Hz, 1H), 2.74 (s, 3H).

Example 67: [(2R,3R,4S,5R)-5-(4-amino-3-methoxy-1H-pyrazolo[3,4-d]pyrimidin-1-yl)-4-fluoro-3-hydroxytetrahydrofuran-2-yl]methyl Sulfamate Compound I-105

Step 1: [(2R,3R,4S,5R)-5-(4-amino-3-methoxy-1H-pyrazolo[3,4-d]pyrimidin-1-yl)-3-(benzoyloxy)-4-fluorotetrahydrofuran-2-yl]methyl Benzoate Intermediate 31 (0.180 g, 1.09 mmol) was azeotropically dried in toluene and further dried in vacuo prior to use. The dried powder was suspended in DMF (2.5 mL) and the mixture was cooled in an ice-water bath. Once cooled, sodium hydride (60% in mineral oil, 0.050 g, 1.2 mmol) was added. The mixture slowly turned homogeneous over several minutes. [(2R,3R,4S,5R)-3-(Benzoyloxy)-5-bromo-4-fluorotetrahydrofuran-2-yl]methyl benzoate (0.42 g, 0.99 mmol) was transferred to a 50 mL conical flask and azeotropically dried in acetonitrile, and then further dried in vacuo before dissolution in DMF (2.5 mL). The bromofuranose solution was added dropwise by syringe to the cooled base/sodium hydride mixture over several minutes. The resulting mixture was stirred at 0° C. for 15 min and then warmed to rt and stirred 4 h. The reaction mixture was diluted with half-saturated aqueous ammonium chloride (50 mL) and extracted with ethyl acetate (2×). The extracts were combined, washed with water and brine and then dried over sodium sulfate, filtered and concentrated under reduced pressure. The crude residue was purified by silica gel chromatography to yield the product as a mixture of diastereomers. LCMS (FA): m/z=508 (M+H); $^1$H NMR (major diastereomer, 400 MHz, CDCl$_3$) δ 8.33 (s, 1H), 8.07-8.12 (m, 2H), 7.92-8.01 (m, 2H), 7.61-7.66 (m, 1H), 7.46-7.53 (m, 3H), 7.30-7.37 (m, 2H), 6.80 (d, J=6.5 Hz, 1H), 6.52 (dt, J=16.3, 6.9 Hz, 1H), 5.80 (br d, J=3.3 Hz, 2H), 5.56-5.77 (m, 1H), 4.88-4.97 (m, 2H), 4.53-4.59 (m, 1H), 4.18 (s, 3H).

Steps 2-6: [(2R,3R,4S,5R)-5-(4-amino-3-methoxy-1H-pyrazolo[3,4-d]pyrimidin-1-yl)-4-fluoro-3-hydroxytetrahydrofuran-2-yl]methyl Sulfamate I-105

The titled compound was completed by taking [(2R,3R,4S,5R)-5-(4-amino-3-methoxy-1H-pyrazolo[3,4-d]pyrimidin-1-yl)-3-(benzoyloxy)-4-fluorotetrahydrofuran-2-yl] methyl benzoate through steps 3-7 of Example 65. LCMS (FA): m/z=379 (M+H); $^1$H NMR (400 MHz, CD$_3$OD) δ 8.17 (s, 1H), 6.57 (d, J=6.5 Hz, 1H), 5.32 (ddd, J=53.5, 7.5, 6.5 Hz, 1H), 5.01 (dt, J=17.8, 8.0 Hz, 1H), 4.54 (dd, J=10.5, 7.3 Hz, 1H), 4.48 (dd, J=10.5, 3.3 Hz, 1H), 4.10-4.17 (m, 4H).

Example 68: [(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-hydroxytetrahydrofuran-2-yl]methyl Sulfamate and [(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-hydroxytetrahydrofuran-2-yl]methyl Sulfamate Compound I-101

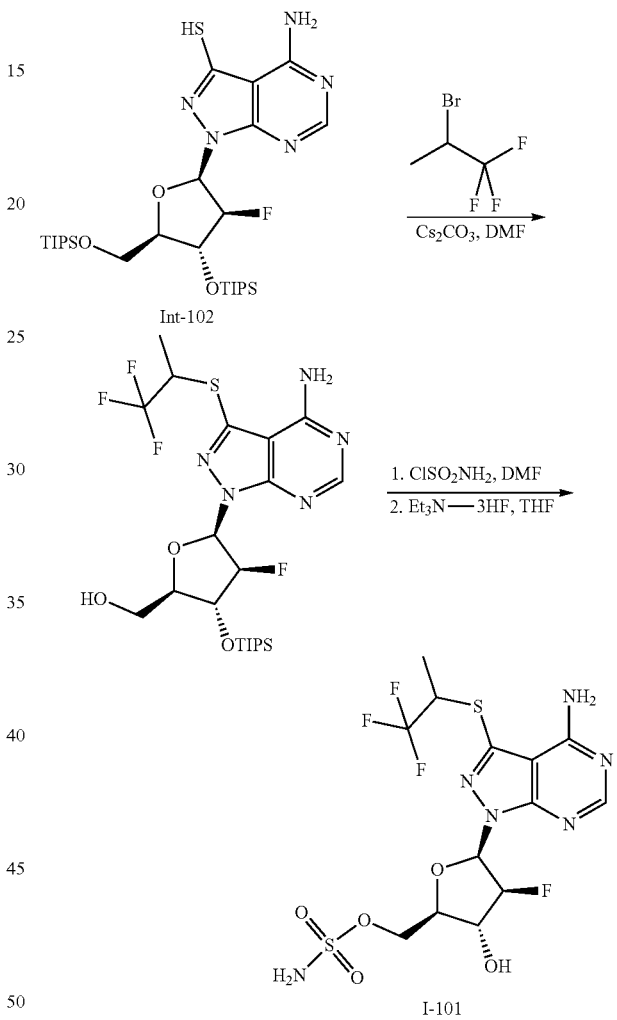

Step 1: {(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol and {(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol 4-Amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidine-3-thiol (Intermediate 102, 700 mg, 1.14 mmol) and 2-bromo-1,1,1-trifluoropropane (605 mg, 3.42 mmol) were dissolved in DMF (10.0 mL) in a vial. Cesium carbonate (1.11 g, 3.42 mmol) was added and the vial was sealed. The reaction mixture was allowed to stir at 90° C. for 7 h, then allowed to cool to rt and water was added. The reaction mixture was extracted with EtOAc. The organic solutions were combined, washed with water (2×) and brine, dried over $Na_2SO_4$, filtered and concentrated. The crude compound was purified by column chromatography to give {(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol and {(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol (169 mg, 27%) as a pale yellow solid. LCMS (FA): m/z 554 (M+H).

Steps 2 and 3: [(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-hydroxytetrahydrofuran-2-yl]methyl Sulfamate and [(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-hydroxytetrahydrofuran-2-yl]methyl Sulfamate I-101

The title compounds were prepared as described in Example 65 Steps 6 and 7 using {(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol and {(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-[(triisopropylsilyl)oxy]tetrahydrofuran-2-yl}methanol as the starting material. LCMS (FA): m/z 477 (M+H); $^1$H NMR (400 MHz, $CD_3OD$) δ 8.26 (s, 1H), 6.74-6.78 (m, 1H), 5.62-5.80 (m, 2H), 4.16-4.31 (m, 2H), 3.93-4.07 (m, 2H), 1.58-1.64 (m, 3H).

Example 69

The following compounds were prepared as described following the procedures in Example 68 using Intermediate 102 (4-amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidine-3-thiol) with the reagents and conditions described in the table below.

| Compound number | Halide | Alkylation Conditions | LCMS data | $^1$H NMR Data |
|---|---|---|---|---|
| I-154 | 1-bromo-2-methoxyethane | $Cs_2CO_3$, DMF, rt | LCMS (FA): m/z 439 (M + H) | $^1$H NMR (400 MHz, $d_6$-DMSO) δ 8.21 (s, 1H), 7.57 (s, 2H), 6.60 (d, J = 6.5 Hz, 1H), 6.11 (d, J = 5.8 Hz, 1H), 5.35-5.54 (m, 1H), 4.70-4.81 (m, 1H), 4.35 (dd, J = 10.8, 2.3 Hz, 1H), 4.24 (dd, J = 10.4, 8.7 Hz, 1H), 4.00-4.06 (m, 1H), 3.60-3.67 (m, 2H), 3.35-3.41 (m, 2H), 3.28 (s, 3H). |
| I-140 | 1-(bromomethyl)-2-methylcyclopropane | $Cs_2CO_3$, DMF, rt | LCMS (FA): m/z 449 (M + H) | $^1$H NMR (400 MHz, $d_6$-DMSO) δ 8.22 (s, 1H), 7.55 (s, 2H), 6.61 (dd, J = 6.7, 1.3 Hz, 1H), 6.08-6.13 (m, 1H), 5.35-5.55 (m, 1H), 4.33-4.39 (m, 1H), 4.23-4.31 (m, 1H), 3.99-4.07 (m, 1H), 3.02-3.16 (m, 2H), 0.94 (dd, J = 6.0, 2.3 Hz, 3H), 0.83-0.90 (m, 1H), 0.62-0.71 (m, 1H), 0.39-0.49 (m, 1H), 0.26-0.34 (m, 1H). |
| I-157 | (1-bromoethyl)cyclopropane | $Cs_2CO_3$, DMF, rt | LCMS (FA): m/z 449 (M + H) | $^1$H NMR (400 MHz, $d_6$-DMSO) δ 8.22 (br s, 1H), 7.55 (br s, 2H), 6.56-6.71 (m, 1H), 6.11 (d, J = 5.1 Hz, 1H), 5.33-5.59 (m, 1H), 4.76 (dd, J = 12.8, 5.1 Hz, 1H), 4.17-4.43 (m, 2H), 3.98-4.11 (m, 1H), 2.82-3.02 (m, 1H), 1.29-1.51 (m, 3H), 0.90-1.11 (m, 1H), 0.38-0.62 (m, 2H), 0.15-0.37 (m, 2H). |
| I-131 | 2-(bromomethyl)-1,1-difluorocyclopropane | $Cs_2CO_3$, DMF, rt | LCMS (FA): m/z 471 (M + H) | $^1$H NMR (400 MHz, $d_6$-DMSO) δ 8.23 (s, 1H), 7.56 (s, 2H), 6.63 (d, J = 6.7 Hz, 1H), 6.12 (dd, J = 9.0, 5.7 Hz, 1H), 5.36-5.56 (m, 1H), 4.72-4.82 (m, 1H), 4.32-4.40 (m, 1H), 4.21-4.29 (m, 1H), 4.01-4.09 (m, 1H), 3.34-3.45 (m, 1H), 3.13-3.30 (m, 1H), 2.04-2.18 (m, 1H), 1.64-1.74 (m, 1H), 1.34-1.43 (m, 1H) |
| I-135 | (bromomethyl)cyclopropane | $Cs_2CO_3$, DMF, rt | LCMS (FA): m/z 435 (M + H) | $^1$H NMR (400 MHz, $d_6$-DMSO) δ 8.21 (s, 1H), 7.55 (s, 2H), 6.61 (d, J = 6.5 Hz, 1H), 6.11 (d, J = 5.8 Hz, 1H), 5.34-5.54 (m, 1H), 4.74-4.84 (m, 1H), 4.32-4.40 (m, 1H), 4.27 (dd, J = 10.5, 8.4 Hz, 1H), 3.99-4.07 (m, 1H), 3.05-3.18 (m, 2H), 1.13-1.23 (m, 1H), 0.51-0.59 (m, 2H), 0.25-0.33 (m, 2H). |
| I-107 | 2-chloro-6-methoxypyridine | DIPEA, DMF, rt | LCMS (FA): m/z 488 (M + H) | $^1$H NMR (400 MHz, $CD_3OD$) δ 8.28 (s, 1H), 7.52-7.58 (m, 1H), 6.75-6.81 (m, 2H), 6.57 (d, J = 8.0 Hz, 1H), |

-continued

| Compound number | Halide | Alkylation Conditions | LCMS data | ¹H NMR Data |
|---|---|---|---|---|
| | | | | 5.30-5.51 (m, 1H), 4.92-5.02 (m, 1H), 4.41-4.53 (m, 2H), 4.21 (d, J = 3.3 Hz, 1H), 3.61 (s, 3H). |
| I-111 | 2-chloro-5-nitropyridine | $Cs_2CO_3$, DMF, rt | LCMS (FA): m/z 503 (M + H) | ¹H NMR (400 MHz, $d_6$-DMSO) δ 9.21 (d, J = 2.6 Hz, 1H), 8.45 (dd, J = 8.9, 2.8 Hz, 1H), 8.33 (s, 1H), 7.26 (d, J = 9.0 Hz, 1H), 6.77 (d, J = 6.4 Hz, 1H), 5.40-5.61 (m, 1H), 4.72-4.84 (m, 1H), 4.30 (dd, J = 10.6, 2.3 Hz, 1H), 4.19 (dd, J = 10.6, 8.6 Hz, 1H), 4.04-4.10 (m, 1H). |
| I-98 | sodium 2-chloro-2,2-difluoroacetate | $K_2CO_3$, DMF, $H_2O$, 80° C. | LCMS (FA): m/z 431 (M + H) | ¹H NMR (400 MHz, $CD_3OD$) δ 8.28 (s, 1H), 7.29 (dd, J = 112.3, 56.0 Hz, 1H), 6.75 (d, J = 6.3 Hz, 1H), 5.31-5.51 (m, 1H), 5.01 (dt, J = 17.7, 7.5 Hz, 1H), 4.43-4.56 (m, 2H), 4.21 (td, J = 7.6, 3.1 Hz, 1H). |
| I-149 | 2-chloro-propane-nitrile | DIPEA, DMF, 60° C. | LCMS (FA): m/z 434 (M + H) | ¹H NMR (400 MHz, $CD_3OD$) δ 8.27 (s, 0.5H), 8.26 (s, 0.5H), 6.74 (t, J = 6.5 Hz, 1H), 5.30-5.50 (m, 1H), 4.98-5.16 (m, 1H), 4.44-4.61 (m, 3H), 4.16-4.24 (m, 1H), 1.70-1.79 (m, 3H). |
| I-124 | 4-(bromometh-yl)pyridine hydrobromide | $Cs_2CO_3$, DMF, 60° C. | LCMS (AA): m/z 472 (M + H) | ¹H NMR (400 MHz, $CD_3OD$) δ 8.40-8.44 (m, 2H), 8.19 (s, 1H), 7.43 (d, J = 6.0 Hz, 2H), 6.65 (d, J = 5.8 Hz, 1H), 5.24-5.45 (m, 1H), 4.77-4.84 (m, 1H), 4.35-4.52 (m, 4H), 4.09-4.18 (m, 1H). |
| I-121 | 3-(bromometh-yl)pyridine hydrobromide | $Cs_2CO_3$, DMF, 60° C. | LCMS (FA): m/z 472 (M + H) | ¹H NMR (400 MHz, $d_6$-DMSO) δ 8.57 (s, 1H), 8.39-8.51 (m, 1H), 8.20 (s, 1H), 7.68-7.89 (m, 1H), 7.60 (s, 2H), 7.32 (s, 2H), 6.63 (d, J = 5.1 Hz, 1H), 5.99-6.19 (m, 1H), 5.33-5.57 (m, 1H), 4.67-4.84 (m, 1H), 4.18-4.50 (m, 4H), 4.04 (br s, 1H). |
| I-119 | 2-(chlorometh-yl)pyridine hydrochloride | $Cs_2CO_3$, DMF, 60° C. | LCMS (FA): m/z 472 (M + H) | ¹H NMR (400 MHz, $d_6$-DMSO) δ 8.52 (d, J = 4.3 Hz, 1H), 8.20 (s, 1H), 7.74 (td, J = 7.7, 1.7 Hz, 1H), 7.58 (br s, 1H), 7.43 (d, J = 7.8 Hz, 1H), 7.29 (dd, J = 7.0, 5.1 Hz, 1H), 6.60 (d, J = 6.7 Hz, 1H), 5.94-6.18 (m, 1H), 5.33-5.55 (m, 1H), 4.77 (dt, J = 18.1, 7.8 Hz, 1H), 4.45-4.57 (m, 2H), 4.31-4.38 (m, 1H), 4.21-4.30 (m, 1H), 4.03 (td, J = 8.0, 2.3 Hz, 1H). |
| I-120 | 3-bromopentane | $Cs_2CO_3$, DMF, rt | LCMS (FA): m/z 451 (M + H) | ¹H NMR (400 MHz, $d_6$-DMSO) δ 8.20-8.27 (m, 1H), 7.57 (s, 2H), 6.62 (d, J = 6.7 Hz, 1H), 6.13 (d, J = 5.8 Hz, 1H), 5.28-5.57 (m, 1H), 4.68-4.89 (m, 1H), 4.18-4.42 (m, 2H), 4.04 (td, J = 8.2, 2.2 Hz, 1H), 3.37-3.50 (m, 1H), 1.63-1.80 (m, 4H), 1.01 (td, J = 7.3, 0.9 Hz, 6H). |
| I-142 | trifluoro(iodo)methane | NaH, DMF, rt | LCMS(FA): m/z 449 (M + H) | ¹H NMR (400 MHz, $d_6$-DMSO) δ ppm 8.32 (s, 1H), 7.57 (s, 2H), 6.75 (d, J = 6.4 Hz, 1H), 6.19 (d, J = 5.6 Hz, 1H), 5.38-5.65 (m, 1H), 4.70-4.87 (m, 1H), 4.32-4.44 (m, 1H), 4.20-4.31 (m, 1H), 4.01-4.14 (m, 1H) |
| I-144 | 2-chloropropyl benzoate**** | DIPEA, DMF, 80° C. | LCMS(FA): m/z 439 (M + H) | ¹H NMR (400 MHz, $CD_3OD$) δ 8.22 (s, 1H), 6.68 (d, J = 6.4 Hz, 1H), 5.28-5.46 (m, 1H), 4.97 (dtd, J = 17.7, 7.5, 7.5, 2.5 Hz, 1H), 4.44-4.53 (m, 2H), 4.19 (td, J = 7.4, 3.8 Hz, 1H), 3.62-3.82 (m, 3H), 1.40-1.46 (m, 3H). |
| I-148 | (bromometh-yl)cyclobutane | $Cs_2CO_3$, DMF, rt | LCMS (FA): m/z 450 (M + H) | ¹H NMR (400 MHz, $d_6$-DMSO) δ 8.21 (s, 1H), 7.56 (s, 2H), 6.60 (d, J = 6.7 Hz, 1H), 6.12 (d, J = 5.8 Hz, 1H), 5.34-5.55 (m, 1H), 4.71-4.84 (m, 1H), 4.34-4.40 (m, 1H), 4.27 (dd, J = 10.5, 8.5 Hz, 1H), 4.04 (td, J = 8.1, 2.4 Hz, 1H), 3.17-3.28 (m, 2H), 2.58-2.70 (m, 1H), 2.01-2.11 (m, 2H), 1.68-1.89 (m, 4H). |

-continued

| Compound number | Halide | Alkylation Conditions | LCMS data | ¹H NMR Data |
|---|---|---|---|---|
| I-128 | 4-(chloromethyl)pyridazine*** | DIPEA, DMF, rt | LCMS (FA): m/z = 473 (M + H) | ¹H NMR (400 MHz, d₆-DMSO) δ 9.24 (dd, J = 2.3, 1.1 Hz, 1H), 9.11 (dd, J = 5.3, 1.3 Hz, 1H), 8.21 (s, 1H), 7.53-7.64 (m, 3H), 6.61 (d, J = 6.4 Hz, 1H), 6.07 (d, J = 5.8 Hz, 1H), 5.30-5.58 (m, 1H), 4.62-4.78 (m, 1H), 4.37-4.52 (m, 2H), 4.31-4.35 (m, 1H), 4.21 (dd, J = 10.6, 8.1 Hz, 1H), 4.02 (td, J = 7.8, 2.3 Hz, 1H). |
| I-97 | 3-(bromomethyl)-1,1-difluorocyclobutane | Cs₂CO₃, DMF, rt | LCMS (FA) m/z 485 (M + H) | ¹H NMR (400 MHz, d₆-DMSO) δ 8.22 (s, 1H), 7.56 (s, 2H), 6.61 (d, J = 6.5 Hz, 1H), 6.12 (d, J = 5.6 Hz, 1H), 5.32-5.59 (m, 1H), 4.75 (br dd, J = 18.4, 5.8 Hz, 1H), 4.32-4.41 (m, 1H), 4.25 (dd, J = 10.6, 8.3 Hz, 1H), 4.04 (td, J = 8.0, 2.4 Hz, 1H), 3.24-3.44 (m, 2H), 2.63-2.80 (m, 2H), 2.32-2.45 (m, 2H). |
| I-127 | 3-(chloromethyl)pyridazine** | DIPEA, DMF, rt | LCMS (FA): m/z = 473 (M + H) | ¹H NMR (400 MHz, CD₃OD) δ 9.07 (dd, J = 5.0, 1.6 Hz, 1H), 8.20 (s, 1H), 7.82 (dd, J = 8.5, 1.5 Hz, 1H), 7.66 (dd, J = 8.5, 4.9 Hz, 1H), 6.63 (d, J = 6.4 Hz, 1H), 5.17-5.45 (m, 1H), 4.61-4.82 (m, 2H), 4.33-4.46 (m, 2H), 4.13 (td, J = 7.1, 3.8 Hz, 1H). |
| I-145 | 4-(chloromethyl)-1-methyl-1H-pyrazole* | Cs₂CO₃, DMF, rt | LCMS (FA): m/z 475 (M + H) | ¹H NMR (400 MHz, d₆-DMSO) δ 8.21 (s, 1H), 7.52-7.67 (m, 3H), 7.40 (s, 1H), 6.63 (br d, J = 6.4 Hz, 1H), 6.11 (br d, J = 5.6 Hz, 1H), 5.35-5.59 (m, 1H), 4.82 (br dd, J = 17.9, 6.5 Hz, 1H), 4.19-4.44 (m, 4H), 4.05 (br t, J = 6.8 Hz, 1H), 3.76 (s, 3H). |
| I-104 | 2-bromo-N,N-diethylethan-1-amine | Cs₂CO₃, DMF, 60° C. | LCMS(AA): m/z 480 (M + H) | ¹H NMR (400 MHz, CD₃OD) δ 8.24 (s, 1H), 6.69 (dd, J = 6.4, 2.1 Hz, 1H), 5.29-5.47 (m, 1H), 4.96 (dt, J = 17.9, 7.2 Hz, 1H), 4.46 (d, J = 5.0 Hz, 2H), 4.17 (dt, J = 7.4, 5.0 Hz, 1H), 3.49-3.58 (m, 1H), 3.34-3.41 (m, 1H), 3.21-3.27 (m, 2H), 2.99 (q, J = 7.2 Hz, 4H), 1.20 (t, J = 7.2 Hz, 6H). |
| I-112 | 2-(chloromethyl)-1-methyl-1H-imidazole | Cs₂CO₃, DMF, rt | LCMS (FA): m/z 475 (M + H) | ¹H NMR (400 MHz, d₆-DMSO) δ 8.22 (s, 1H), 7.62 (s, 2H), 7.12 (d, J = 1.0 Hz, 1H), 6.81 (d, J = 1.0 Hz, 1H), 6.63 (d, J = 6.7 Hz, 1H), 6.08 (d, J = 5.8 Hz, 1H), 5.31-5.58 (m, 1H), 4.78-4.95 (m, 1H), 4.49 (s, 2H), 4.31-4.39 (m, 2H), 3.99-4.12 (m, 1H), 3.61 (s, 3H). |
| I-123 | 3-iodotetrahydrofuran | NaOH, H₂O, THF, 80° C. | LCMS(FA): m/z 451 (M + H) | ¹H NMR (400 MHz, CD₃OD) δ 8.22 (d, J = 2.0 Hz, 1H), 6.67 (dd, J = 6.3, 3.8 Hz, 1H), 5.28-5.47 (m, 1H), 4.94-5.04 (m, 1H), 4.46 (dd, J = 5.3, 2.0 Hz, 2H), 4.13-4.34 (m, 3H), 3.95-4.04 (m, 1H), 3.84-3.93 (m, 2H), 2.43-2.56 (m, 1H), 1.98-2.15 (m, 1H). |
| I-147 | bromocyclobutane | NaOH, dioxane, rt | LCMS (FA) m/z 435 (M + H) | ¹H NMR (400 MHz, CD₃OD) δ 8.22 (s, 1H), 6.66 (d, J = 6.5 Hz, 1H), 5.26-5.51 (m, 1H), 5.00 (dt, J = 17.6, 7.6 Hz, 1H), 4.42-4.58 (m, 2H), 4.14-4.28 (m, 2H), 2.42-2.61 (m, 2H), 2.13-2.31 (m, 2H), 1.96-2.09 (m, 2H). |

*Prepared as described below in Example 70.
**Prepared as described below in Example 71.
***Prepared as described below in Example 72.
****Prepared as described below in Example 73.

Example 70: 4-(chloromethyl)-1-methyl-1H-pyrazole

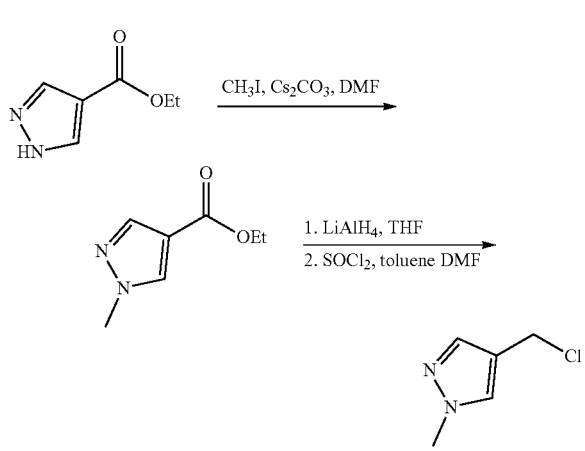

Step 1: ethyl 1-methyl-1H-pyrazole-4-carboxylate

Into a solution of ethyl 1H-pyrazole-4-carboxylate (1.00 g, 7.14 mmol) in DMF (25 mL) was added cesium carbonate (5.81 g, 17.8 mmol) and methyl iodide (0.53 mL, 8.56 mmol) and the reaction mixture was stirred at rt overnight. After complete conversion, the reaction mixture was diluted with EtOAc and water and then extracted with EtOAc (2×). The combined extracts were washed with water and brine, dried over sodium sulfate, filtered and concentrated under reduced pressure to give the product as colorless oil (1.16 g, quant.) LCMS (FA) m/z 155 (M+H).

Step 2: (1-methyl-1H-pyrazol-4-yl)methanol

A solution of ethyl 1-methyl-1H-pyrazole-4-carboxylate (1.16 g, 7.52 mmol) in THF (13.3 mL) was added into a solution of lithium aluminumhydride (1.0 M in THF, 15.05 mL, 15.05 mmol) in THF (53 mL) dropwise at 0° C. The resulting mixture was allowed to heat at 60° C. for 1 h. After 1 h, the reaction was allowed to cool to rt. Sodium sulfate decahydrate (4.0 g) was added portion wise and the resulting mixture was stirred for 1 h at rt. EtOAc (150 mL) was added and the resulting mixture was stirred overnight. The mixture was filtered through a pad of celite and the residual solid was washed with EtOAc several times. The filtrate was concentrated in vacuo to afford the title compound as colorless oil (790 mg, 93%). $^1$H NMR (400 MHz, CDCl$_3$) δ 7.49 (s, 1H), 7.39 (s, 1H), 4.59 (s, 2H), 3.90 (s, 3H).

Step 3: 4-(chloromethyl)-1-methyl-1H-pyrazole

Into a solution of (1-methyl-1H-pyrazol-4-yl)methanol (790 mg, 7.04 mmol) in DCM (2.6 mL) was added a solution of thionyl chloride (1.28 mL, 17.6 mmol) in toluene (3.50 mL) drop wise. The reaction mixture was then stirred at rt for 1 h. Upon completion, the reaction mixture was concentrated to afford the titled compound as an off white solid (790 mg, 86%). $^1$H NMR (400 MHz, CDCl$_3$) δ 7.78 (s, 1H), 7.63 (s, 1H), 4.56 (s, 2H), 4.17 (s, 3H).

Example 71: 3-(chloromethyl)pyridazine

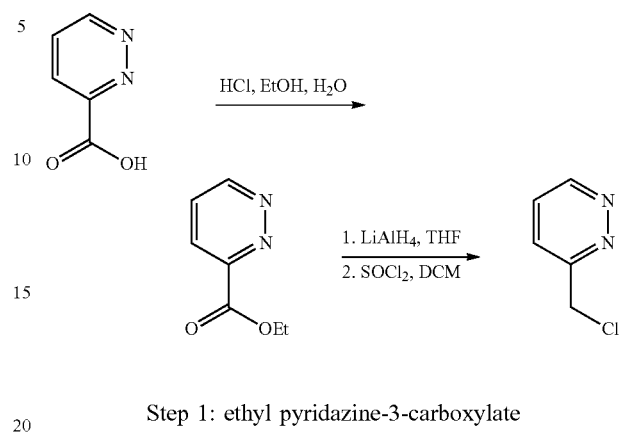

Step 1: ethyl pyridazine-3-carboxylate

A mixture of pyridazine-3-carboxylic acid (1.00 g, 8.06 mmol), ethanol (18.5 mL) and conc. HCl (0.370 mL, 12.1 mmol) was refluxed overnight. The reaction mixture was concentrated and diluted with EtOAc. Saturated NaHCO$_3$ solution was added and the mixture was extracted with EtOAc (2×). The combined extracts were washed with brine, dried over sodium sulfate, filtered and concentrated under reduced pressure. The crude product was purified by silica gel chromatography to afford the product as a tan solid (671 mg, 55%). LCMS (FA): m/z 153 (M+H).

Step 2: pyridazin-3-ylmethanol

To a solution of ethyl pyridazine-3-carboxylate (0.641 g, 4.21 mmol) in THF (20 mL) at 0° C. was added a solution of lithium aluminum hydride in tetrahydrofuran (1.0 M, 4.21 mL, 4.21 mmol) dropwise. The resulting suspension was stirred for 30 min. Solid Na$_2$SO$_4$.10 H$_2$O was added and the mixture was diluted with EtOAc and stirred for 1 h. The mixture was filtered through a pad of celite and the residual solid was washed with EtOAc several times. The filtrate was concentrated under reduced pressure. The crude product was purified by silica gel chromatography to afford the product as brown solid (120 mg, 26%). LCMS (AA): m/z 111 (M+H).

Step 3: 3-(chloromethyl)pyridazine

To a solution of pyridazin-3-ylmethanol (0.120 g, 1.09 mmol) in DCM (4.0 mL) was added a solution of thionyl chloride (0.20 mL, 2.7 mmol) in DCM (5.5 mL) dropwise at 0° C. The reaction mixture was stirred for 2 h. The solvent was removed under reduced pressure to afford the crude compound (181 mg) which was used without further purification. LCMS (AA): m/z 129 (M+H).

Example 72: 4-(chloromethyl)pyridazine

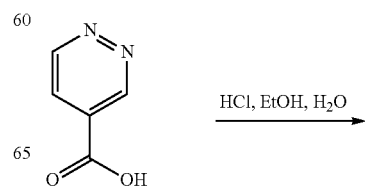

275
-continued

The titled compound was prepared following the procedures detailed in Example 71 substituting pyridazine-4-carboxylic acid for pyridazine-3-carboxylic acid. LCMS (AA): m/z 129 (M+H).

Example 73: 2-chloropropyl Benzoate

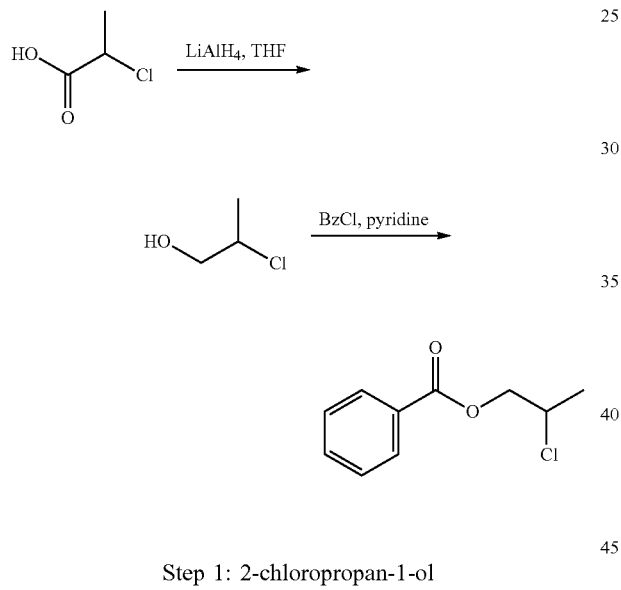

Step 1: 2-chloropropan-1-ol

The titled compound was prepared following the procedures detailed in Example 71 substituting 2-chloropropanoic acid for ethyl pyridazine-3-carboxylate in step 2.

Step 2: 2-chloropropyl Benzoate

To a solution of 2-chloropropan-1-ol (0.654 g, 6.92 mmol) in pyridine (2.5 mL, 31 mmol) was added benzoyl chloride (0.80 mL, 6.9 mmol) at 0° C. The resulting white suspension was stirred at rt for 2 h. Brine was added and the mixture was extracted with DCM (2×). The combined extracts were washed with 1 N HCl, saturated NaHCO₃ solution and brine, dried over sodium sulfate, filtered and concentrated under reduced pressure. The crude product was purified by silica gel chromatography to afford the product as a colorless oil (906 mg, 66%). $^1$H NMR (400 MHz, CDCl$_3$) δ 8.00-8.18 (m, 2H), 7.55-7.67 (m, 1H), 7.41-7.53 (m, 2H), 4.29-4.48 (m, 3H), 1.63 (d, J=6.7 Hz, 3H).

276

Example 74: [(2R,3R,4S,5R)-5-{4-amino-3-[(2-hydroxyethyl)sulfanyl]-1H-pyrazolo[3,4-d]pyrimidin-1-yl}-4-fluoro-3-hydroxytetrahydrofuran-2-yl] methyl Sulfamate I-151

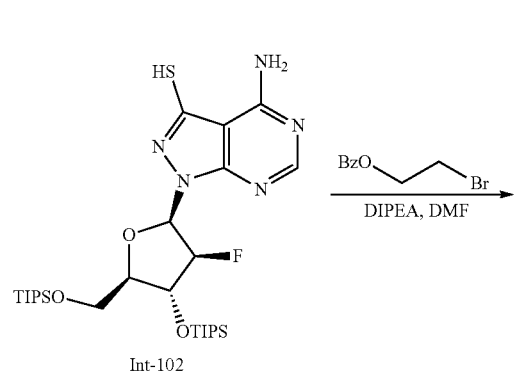

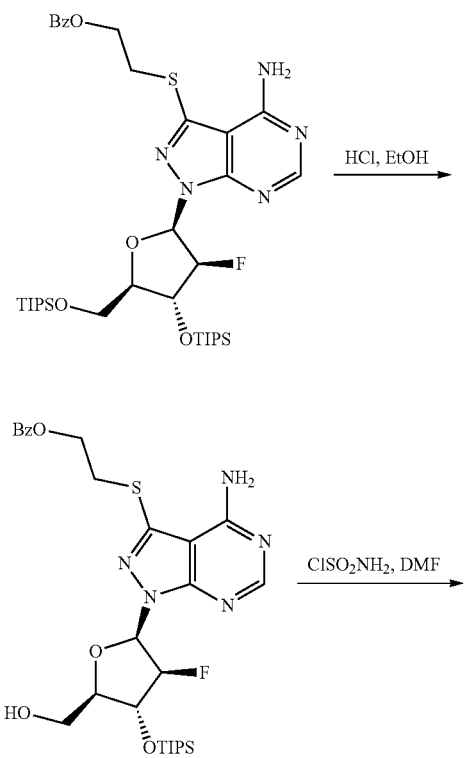

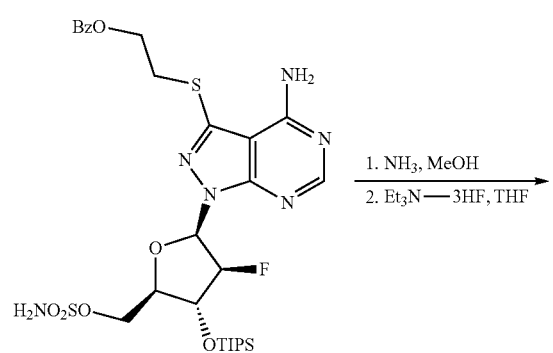

-continued

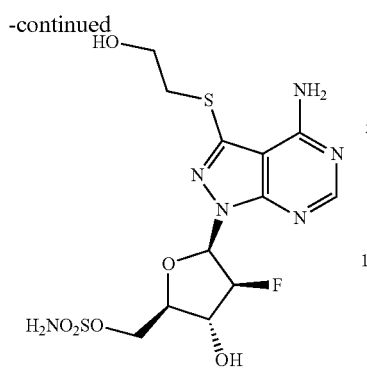

Step 1: 2-({4-amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-3-yl}sulfanyl)ethyl Benzoate The title compound was prepared as described in Example 68 Step 1 substituting 2-bromoethyl benzoate for 2-bromo-1,1,1-trifluoropropane and DIPEA for cesium carbonate. The reaction was run at rt.

Steps 2-3: 2-[(4-amino-1-{(2R,3S,4R,5R)-3-fluoro-5-[(sulfamoyloxy)methyl]-4-[(triisopropylsilyl)oxy]tetrahydrofuran-2-yl}-1H-pyrazolo[3,4-d]pyrimidin-3-yl)sulfanyl]ethyl Benzoate The title compound was prepared as described in Example 65 Steps 5 and 6 substituting 2-({4-amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-3-yl}sulfanyl)ethyl benzoate for Intermediate 100.

Step 4: {(2R,3R,4S,5R)-5-{4-amino-3-[(2-hydroxyethyl)sulfanyl]-1H-pyrazolo[3,4-d]pyrimidin-1-yl}-4-fluoro-3-[(triisopropylsilyl)oxy]tetrahydrofuran-2-yl}methyl Sulfamate The title compound was prepared as described in Example 5 Step 3 substituting 2-[(4-amino-1-{(2R,3S,4R,5R)-3-fluoro-5-[(sulfamoyloxy)methyl]-4-[(triisopropylsilyl)oxy]tetrahydrofuran-2-yl}-1H-pyrazolo[3,4-d]pyrimidin-3-yl)sulfanyl]ethyl benzoate for Intermediate 15.

Step 5: [(2R,3R,4S,5R)-5-{4-amino-3-[(2-hydroxyethyl)sulfanyl]-1H-pyrazolo[3,4-d]pyrimidin-1-yl}-4-fluoro-3-hydroxytetrahydrofuran-2-yl]methyl Sulfamate I-151

The title compound was prepared as described in Example 65 Step 7 substituting {(2R,3R,4S,5R)-5-{4-amino-3-[(2-hydroxyethyl)sulfanyl]-1H-pyrazolo[3,4-d]pyrimidin-1-yl}-4-fluoro-3-[(triisopropylsilyl)oxy]tetrahydrofuran-2-yl}methyl sulfamate for Intermediate 101. LCMS (FA): m/z 425 (M+H); $^1$H NMR (400 MHz, $d_6$-DMSO) δ 8.21 (s, 1H), 7.55 (s, 2H), 6.60 (d, J=6.7 Hz, 1H), 6.10 (d, J=5.8 Hz, 1H), 5.31-5.58 (m, 1H), 5.09 (br t, J=5.0 Hz, 1H), 4.69-4.87 (m, 1H), 4.30-4.45 (m, 1H), 4.21-4.30 (m, 1H), 3.98-4.09 (m, 1H), 3.69 (q, J=5.8 Hz, 2H), 3.11-3.29 (m, 3H).

Example 75: {(2R,3R,4S,5R)-5-[4-amino-3-(pyridin-4-ylsulfanyl)-1H-pyrazolo[3,4-d]pyrimidin-1-yl]-4-fluoro-3-hydroxytetrahydrofuran-2-yl}methyl Sulfamate Compound I-150

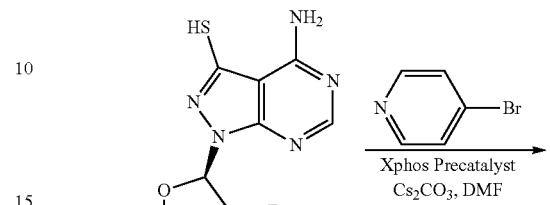

Int-102

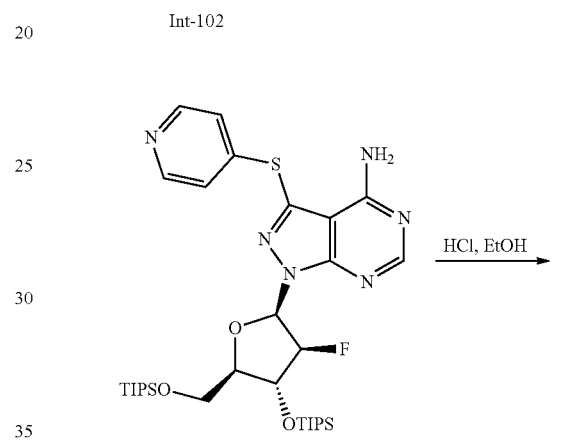

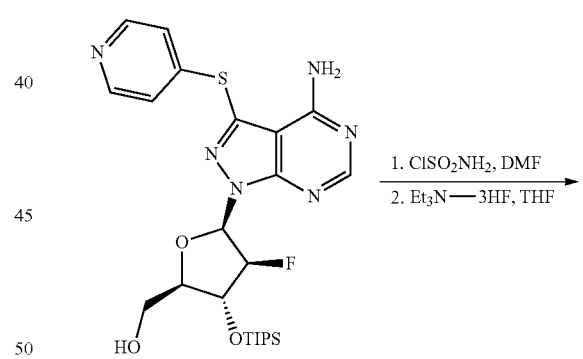

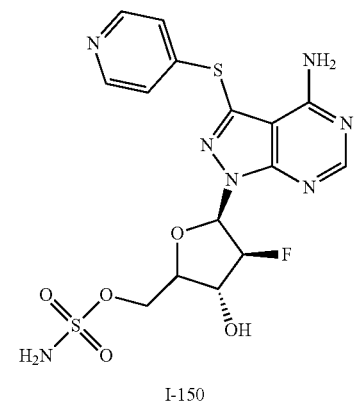

I-150

Step 1: 1-[(2R,3S,4R,5R)-3-fluoro-4-[(triisopropyl-silyl)oxy]-5-{[(triisopropylsilyl)oxy]methyl}tetrahydrofuran-2-yl]-3-(pyridin-4-ylsulfanyl)-1H-pyrazolo[3,4-d]pyrimidin-4-amine To a microwave vial was added Intermediate 102 (0.24 g, 0.39 mmol), 4-bromopyridine hydrochloride (0.151 g, 0.776 mmol), cesium carbonate (0.379 g, 1.16 mmol), XPhos precatalyst (0.057 g, 0.077 mmol) and DMF (3 mL). The vial was capped, evacuated and backfilled with argon from a balloon. The reaction mixture was allowed to stir at 120° C. overnight. The mixture was partitioned between water and ethyl acetate. The phases were separated and the aqueous phase was extracted twice with ethyl acetate. The extracts were combined, washed with water and brine, dried over sodium sulfate, filtered and concentrated under reduced pressure. The crude compound was purified by silica gel chromatography to afford the pure product as a white solid (0.117 g, 44%). LCMS (FA): m/z 691 (M+H); $^1$H NMR (400 MHz, CDCl$_3$) δ 8.35-8.49 (m, 3H), 7.03 (d, J=6.1 Hz, 2H), 6.79-6.90 (m, 1H), 5.20-5.40 (m, 1H), 5.07-5.18 (m, 1H), 4.00-4.12 (m, 2H), 0.99-1.13 (m, 42H).

Steps 2-4: {(2R,3R,4S,5R)-5-[4-amino-3-(pyridin-4-ylsulfanyl)-1H-pyrazolo[3,4-d]pyrimidin-1-yl]-4-fluoro-3-hydroxytetrahydrofuran-2-yl}methyl Sulfamate I-150

The title compound was prepared sequentially following procedures described in Example 65 step 5, Example 1 Step 7 and Example 65 Step 7, from {(2R,3R,4S,5R)-5-[4-amino-3-(pyridin-4-ylsulfanyl)-1H-pyrazolo[3,4-d]pyrimidin-1-yl]-4-fluoro-3-[(triisopropylsilyl)oxy]tetrahydrofuran-2-yl}methyl sulfamate (33 mg, 69%). LCMS (FA): m/z 458 (M+H); $^1$H NMR (400 MHz, d$_6$-DMSO) δ 8.43 (d, J=5.6 Hz, 2H), 8.31 (s, 1H), 7.56 (br s, 2H), 7.10 (d, J=5.9 Hz, 2H), 6.77 (d, J=6.5 Hz, 1H), 6.17 (d, J=5.6 Hz, 1H), 5.42-5.64 (m, 1H), 4.69-4.82 (m, 1H), 4.29-4.38 (m, 1H), 4.18-4.27 (m, 1H), 4.02-4.13 (m, 1H).

Example 76

The following compounds were prepared according to the procedures described in Example 75 from Intermediate 102 with the reagents and conditions described in the table below.

Example 77: [(2R,3R,4S,5R)-5-{4-amino-3-[(1-methyl-1H-imidazol-5-yl)sulfanyl]-1H-pyrazolo[3,4-d]pyrimidin-1-yl}-4-fluoro-3-hydroxytetrahydrofuran-2-yl]methyl Sulfamate Compound I-134

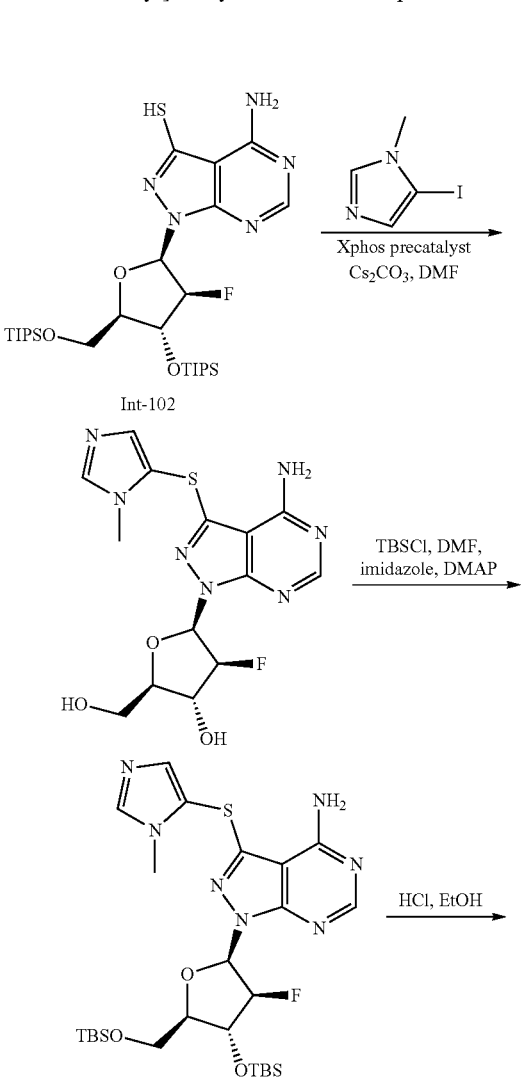

Int-102

| Compound number | Halide | Pd Coupling Conditions | LCMS data | $^1$H NMR Data |
|---|---|---|---|---|
| I-137 | 4-iodo-1-methyl-1H-imidazole | Xphos precatalyst, Cs$_2$CO$_3$, DMF MW 115° C., ON | LCMS (AA): m/z 461 (M + H) | $^1$H NMR (400 MHz, d$_6$-DMSO) δ 8.21 (s, 1H), 7.77 (s, 1H), 7.61 (s, 1H), 6.60 (d, J = 6.5 Hz, 1H), 6.11 (d, J = 5.8 Hz, 1H), 5.34-5.54 (m, 1H), 4.71-4.82 (m, 1H), 4.27-4.34 (m, 1H), 4.18-4.26 (m, 1H), 3.98-4.07 (m, 1H), 3.64 (s, 3H). |
| I-153 | 3-iodo-benzonitrile | CuI, NaOtBu, DMF, TBAB, MW 190° C., 1 h, | LCMS (FA): m/z 482 (M + H) | $^1$H NMR (400 MHz, d$_6$-DMSO) δ 8.29 (s, 1H), 7.71-7.93 (m, 2H), 7.48-7.65 (m, 4H), 6.67-6.79 (m, 1H), 6.08-6.21 (m, 1H), 5.39-5.62 (m, 1H), 4.64-4.80 (m, 1H), 4.25-4.39 (m, 1H), 4.13-4.25 (m, 1H), 4.01-4.12 (m, 1H). |

-continued

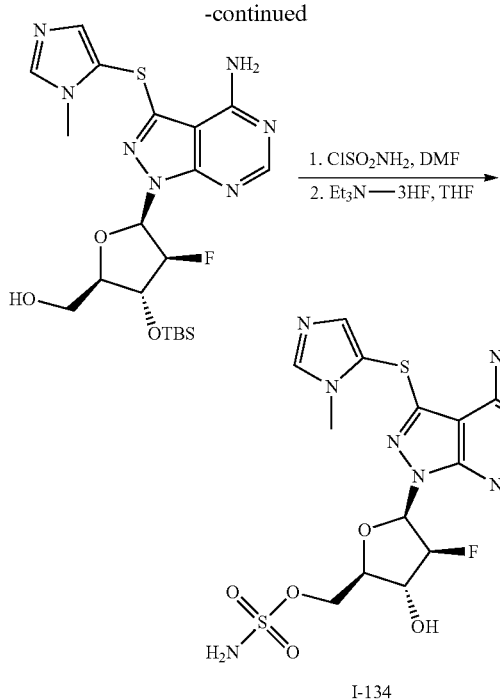

I-134

Steps 1-5: [(2R,3R,4S,5R)-5-{4-amino-3-[(1-methyl-1H-imidazol-5-yl)sulfanyl]-1H-pyrazolo[3,4-d]pyrimidin-1-yl}-3-{[tert-butyl(dimethyl)silyl]oxy}-4-fluorotetrahydrofuran-2-yl]methyl Sulfamate I-134

The title compound was prepared as described in Example 75 with the following alterations. Intermediate 102 and 5-iodo-1-methyl-1H-imidazole were coupled as described Example 75 Step 1 to provide (2R,3R,4S,5R)-5-{4-amino-3-[(1-methyl-1H-imidazol-5-yl)sulfanyl]-1H-pyrazolo[3,4-d]pyrimidin-1-yl}-4-fluoro-2-(hydroxymethyl)tetrahydrofuran-3-ol. This diol was then taken through the steps described in Example 65 Steps 4-7. LCMS (FA): m/z 461 (M+H); $^1$H NMR (400 MHz, d$_6$-DMSO) δ 8.23 (s, 1H), 7.92 (s, 1H), 7.52 (br s, 2H), 7.43 (d, J=0.9 Hz, 1H), 6.56 (d, J=6.5 Hz, 1H), 6.09 (d, J=5.4 Hz, 1H), 5.29-5.50 (m, 1H), 4.36-4.49 (m, 1H), 4.16 (dd, J=10.5, 1.8 Hz, 1H), 3.93-4.01 (m, 1H), 3.84-3.92 (m, 1H), 3.65 (s, 3H).

Example 78: [(2R,3R,4S,5R)-5-{4-amino-3-[(3-methylphenyl)sulfanyl]-1H-pyrazolo[3,4-d]pyrimidin-1-yl}-4-fluoro-3-hydroxytetrahydrofuran-2-yl]methyl Sulfamate Compound I-141

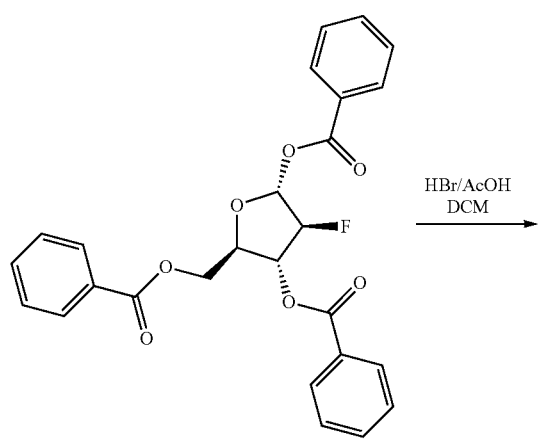

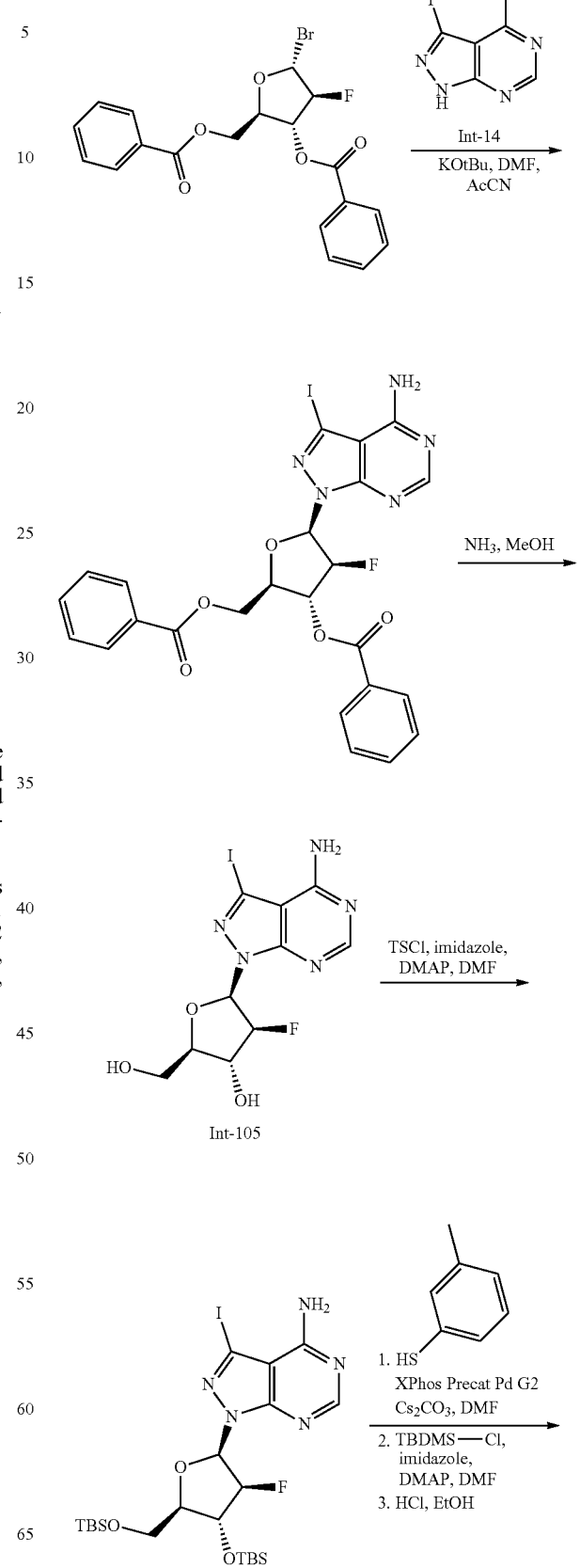

-continued

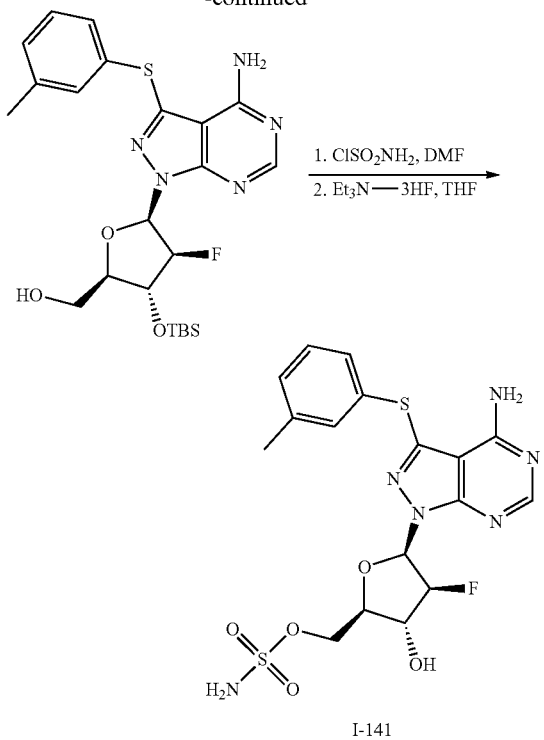

I-141

Step 1: [(2R,3R,4S,5R)-3-(benzoyloxy)-5-bromo-4-fluorotetrahydrofuran-2-yl]methyl Benzoate (2R,3S,4R,5R)-5-[(Benzoyloxy)methyl]-3-fluorotetrahydrofuran-2,4-diyl dibenzoate (25 g, 53.8 mmol) was dissolved in methylene chloride (200 mL). To this solution was added a solution of HBr in acetic acid (30%, 44 mL). The resulting mixture was stirred at rt overnight. Excess acid was quenched by the careful addition of saturated aqueous NaHCO₃ solution at 0° C. The mixture was then diluted with ethyl acetate and the phases separated. The aqueous phase was twice extracted into ethyl acetate. The extracts were combined, washed with 20% aqueous sodium thiosulfate, water and brine then dried over sodium sulfate, filtered and concentrated under reduced pressure to give [(2R,3R,4S,5R)-3-(benzoyloxy)-5-bromo-4-fluorotetrahydrofuran-2-yl] methyl benzoate (22.6 g, 99%). ¹H NMR (400 MHz, CDCl₃) δ 8.03-8.19 (m, 4H), 7.56-7.68 (m, 2H), 7.43-7.55 (m, 4H), 6.66 (d, J=12.2 Hz, 1H), 5.46-5.74 (m, 2H), 4.67-4.94 (m, 3H).

Step 2: [(2R,3R,4S,5R)-5-(4-amino-3-iodo-1H-pyrazolo[3,4-d]pyrimidin-1-yl)-3-(benzoyloxy)-4-fluorotetrahydrofuran-2-yl]methyl Benzoate To a suspension of Intermediate 14 (Int-14, 12.6 g, 48.3 mmol) in acetonitrile (100 mL) and DMF (100 mL) was added a solution potassium tert-butoxide in THF (1.0 M, 53.2 mL, 53.2 mmol). The resulting mixture was stirred at rt for 30 minutes. To this mixture was added a solution of [(2R,3R,4S,5R)-3-(benzoyloxy)-5-bromo-4-fluorotetrahydrofuran-2-yl]methyl benzoate (22.5 g, 53.2 mmol) in acetonitrile (50 mL) dropwise and the resulting mixture was stirred at rt for 2 hours. Excess base was quenched by the addition of saturated aqueous ammonium chloride solution.

The reaction mixture was then diluted with ethyl acetate and twice extracted with additional ethyl acetate. The extracts were combined, washed with water and brine then dried over sodium sulfate and filtered. After concentration under reduced pressure, the crude product was purified by silica gel chromatography to give [(2R,3R,4S,5R)-5-(4-amino-3-iodo-1H-pyrazolo[3,4-d]pyrimidin-1-yl)-3-(benzoyloxy)-4-fluorotetrahydrofuran-2-yl]methyl benzoate as a white solid (18.7 g, 64%). LCMS (FA): m/z 604 (M+H). ¹H NMR (400 MHz, CDCl₃) δ 8.37 (s, 1H), 8.10 (d, J=7.7 Hz, 2H), 8.00-8.06 (m, 3H), 7.59-7.68 (m, 1H), 7.47-7.54 (m, 3H), 7.34-7.40 (m, 2H), 6.85 (d, J=6.3 Hz, 1H), 6.44-6.56 (m, 1H), 5.59-5.82 (m, 1H), 4.90-4.98 (m, 1H), 4.78-4.87 (m, 1H), 4.54-4.64 (m, 1H).

Step 3: (2R,3R,4S,5R)-5-(4-amino-3-iodo-1H-pyrazolo[3,4-d]pyrimidin-1-yl)-4-fluoro-2-(hydroxymethyl)tetrahydrofuran-3-ol Intermediate 105

[(2R,3R,4S,5R)-5-(4-amino-3-iodo-1H-pyrazolo[3,4-d]pyrimidin-1-yl)-3-(benzoyloxy)-4-fluorotetrahydrofuran-2-yl]methyl benzoate (18.0 g, 29.8 mmol) was dissolved in a solution of ammonia in methanol (7.0 M, 850 mL). After stirring at rt overnight, the mixture was concentrated under reduced pressure. Ether was added to the resulting solid which was subsequently isolated by suction filtration (8.7 g, 74%). LCMS (FA): m/z 396 (M+H); ¹H NMR (400 MHz, CD₃OD) δ 8.23 (s, 1H), 6.63 (dd, J=6.4, 1.8 Hz, 1H), 5.22-5.45 (m, 1H), 4.81-4.88 (m, 1H), 3.95-4.04 (m, 1H), 3.85-3.93 (m, 2H).

Step 4: 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-iodo-H-pyrazolo[3,4-d]pyrimidin-4-amine The titled compound was prepared from Intermediate 105 following the procedure outlined in Example 5 Step 3. LCMS (FA): m/z 624 (M+H).

Steps 5-6: 1-[(2R,3S,4R,5R)-4-{[tert-butyl(dimethyl)silyl]oxy}-5-({[tert-butyl(dimethyl) silyl]oxy}methyl)-3-fluorotetrahydrofuran-2-yl]-3-[(3-methylphenyl)sulfanyl]-1H-pyrazolo[3,4-d]pyrimidin-4-amine 1-[(2R,3S,4R,5R)-4-{[Tert-butyl(dimethyl)silyl]oxy}-5-({[tert-butyl(dimethyl)silyl]oxy}methyl)-3-fluorotetrahydrofuran-2-yl]-3-iodo-1H-pyrazolo[3,4-d]pyrimidin-4-amine (1.02 g, 1.64 mmol) and 3-methylbenzenethiol (389 mL, 3.27 mmol) were dissolved in DMF (12 mL). The reaction mixture was degassed with argon and then cesium carbonate (1.06 g, 3.27 mmol) and XPhos Pd G2 (240 mg, 0.31 mmol) were added. The reaction mixture was degassed again and was allowed to stir under an atmosphere of argon at 120° C. for 7 h. The reaction mixture was allowed to cool to rt and water was added. The reaction mixture was extracted with EtOAc. The organic solution was washed with water (2×) and brine, dried over Na₂SO₄, filtered and concentrated. The resulting crude diol was reprotected as described in Example 65 Step 4 to give 1-[(2R,3S,4R,5R)-4-{[tert-butyl(dimethyl)silyl]oxy}-5-({[tert-butyl(dimethyl) silyl]oxy}methyl)-3-fluorotetrahydrofuran-2-yl]-3-[(3-methylphenyl)sulfanyl]-1H-pyrazolo[3,4-d]pyrimidin-4-amine (270 mg, 27%) as a brown solid. LCMS (FA): m/z 620 (M+H).

Steps 7-9: [(2R,3R,4S,5R)-5-{4-amino-3-[(3-methylphenyl)sulfanyl]-1H-pyrazolo[3,4-d]pyrimidin-1-yl}-4-fluoro-3-hydroxytetrahydrofuran-2-yl]methyl Sulfamate I-141

The titled compound was prepared from 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-[(3-methylphenyl)sulfanyl]-1H-pyrazolo[3,4-d]pyrimidin-4-amine following the procedures described in Example 65 Steps 5-7. LCMS (FA): m/z 471 (M+H); $^1$H NMR (400 MHz, CD$_3$OD) δ 8.24 (s, 1H), 7.10-7.30 (m, 4H), 6.71 (br d, J=6.3 Hz, 1H), 5.28-5.49 (m, 1H), 4.79-4.87 (m, 1H), 4.31-4.43 (m, 2H), 4.13-4.25 (m, 1H), 2.32 (s, 3H).

Example 79

The following compounds were prepared as described in the procedures in Example 78 using intermediate Intermediate 105 with the reagents and conditions described in the table below.

| Compound Number | Coupling Partner | Coupling Conditions | LC/MS Data | $^1$H NMR Data |
|---|---|---|---|---|
| I-143 | 5-(trifluoromethyl)pyridine-2-thiol | CuI, MW 190° C. 1 h NaOtBu, DMF, TBAB | LCMS (FA): m/z 526 (M + H) | (400 MHz, d$_6$-DMSO) δ 8.81 (s, 1H), 8.32 (s, 1H), 8.08 (dd, J = 8.6, 2.1 Hz, 1H), 7.54 (s, 2H), 7.24 (d, J = 8.5 Hz, 1H), 6.76 (d, J = 6.4 Hz, 1H), 6.14 (d, J = 5.8 Hz, 1H), 5.40-5.61 (m, 1H), 4.72-4.84 (m, 1H), 4.28-4.36 (m, 1H), 4.17-4.26 (m, 1H), 4.06-4.13 (m, 1H). |
| I-130 | 2-mercaptoisonicotinonitrile | CuI, MW 190° C. 1 h NaOtBu, DMF, TBAB | LCMS (FA): m/z 483 (M + H) | (400 MHz, d$_6$-DMSO) δ 8.61 (d, J = 4.9 Hz, 1H), 8.31 (s, 1H), 7.64-7.71 (m, 2H), 7.53 (s, 2H), 6.74 (d, J = 6.4 Hz, 1H), 6.13 (d, J = 5.8 Hz, 1H), 5.40-5.60 (m, 1H), 4.71-4.83 (m, 1H), 4.27-4.36 (m, 1H), 4.17-4.27 (m, 1H), 4.03-4.10 (m, 1H) |
| I-146 | 5-chloropyridine-2-thiol | XphosPd G2, MW 150° C. 1 h Cs$_2$CO$_3$ DMF | LCMS (FA): m/z 492 (M + H) | (400 MHz, d$_6$-DMSO) δ 8.50 (br s, 1H), 8.30 (s, 1H), 7.84 (d, J = 8.7 Hz, 1H), 7.55 (s, 2H), 7.12 (d, J = 8.5 Hz, 1H), 6.74 (d, J = 6.3 Hz, 1H), 6.14 (d, J = 5.5 Hz, 1H), 5.39-5.61 (m, 1H), 4.72-4.86 (m, 1H), 4.33 (d, J = 10.2 Hz, 1H), 4.16-4.26 (m, 1H), 4.02-4.12 (m, 1H). |
| I-126 | 4-fluorobenzenethiol | XphosPd G2, MW 150° C. 1 h Cs$_2$CO$_3$ DMF | LCMS (FA): m/z 475 (M + H) | $^1$H NMR (400 MHz, d$_6$-DMSO) δ 8.26 (s, 1H), 7.46-7.61 (m, 4H), 7.20-7.32 (m, 2H), 6.61-6.75 (m, 1H), 6.04-6.19 (m, 1H), 5.35-5.60 (m, 1H), 4.57-4.79 (m, 1H), 4.28 (d, J = 8.0 Hz, 1H), 4.10-4.21 (m, 1H), 3.97-4.10 (m, 1H). |
| I-116 | 3-fluorobenzenethiol | XphosPd G2, MW 150° C. 1 h Cs$_2$CO$_3$ DMF | LCMS (FA): m/z 475 (M + H) | (400 MHz, d$_6$-DMSO) δ 8.22 (s, 1H), 7.51 (br s, 2H), 7.29-7.40 (m, 1H), 6.99-7.19 (m, 3H), 6.66 (d, J = 6.3 Hz, 1H), 6.09 (d, J = 5.4 Hz, 1H), 5.31-5.56 (m, 1H), 4.60-4.76 (m, 1H), 4.27 (d, J = 9.8 Hz, 1H), 4.10-4.20 (m, 1H), 3.96-4.06 (m, 1H). |
| I-109 | 2-fluorobenzenethiol | XphosPd G2, MW 150° C. 1 h Cs$_2$CO$_3$ DMF | LCMS (FA): m/z 475 (M + H) | (400 MHz, d$_6$-DMSO) δ 8.27 (s, 1H), 7.55 (s, 2H), 7.20-7.46 (m, 4H), 6.63 (d, J = 6.5 Hz, 1H), 6.07 (d, J = 5.6 Hz, 1H), 5.31-5.55 (m, 1H), 4.48-4.61 (m, 1H), 4.14-4.23 (m, 1H), 3.95-4.05 (m, 2H). |
| I-122 | cyclohexanethiol | XphosPd G2, MW 150° C. 1 h Cs$_2$CO$_3$ DMF | LCMS (FA): m/z 463 (M + H) | (400 MHz, d$_6$-DMSO) δ 8.22 (s, 1H), 7.56 (br s, 2H), 6.62 (d, J = 6.7 Hz, 1H), 6.13 (d, J = 2.0 Hz, 1H), 5.33-5.56 (m, 1H), 4.72-4.82 (m, 1H), 4.37 (dd, J = 10.5, 2.4 Hz, 1H), 4.26 (dd, J = 10.7, 8.7 Hz, 1H), 4.01-4.09 (m, 1H), 3.46-3.56 (m, 1H), 1.97-2.11 (m, 2H), 1.69-1.78 (m, 2H), 1.53-1.61 (m, 1H), 1.24-1.51 (m, 7H). |
| I-152 | 5-methylpyridine-2-thiol | XphosPd G2, MW 150° C. 1 h Cs$_2$CO$_3$ DMF | LCMS (FA): m/z 472 (M + H) | (400 MHz, d$_6$-DMSO) δ 8.26-8.31 (m, 2H), 7.52-7.59 (m, 3H), 7.03 (d, J = 8.2 Hz, 1H), 6.72 (d, J = 6.5 Hz, 1H), 6.13 (d, J = 5.8 Hz, 1H), 5.39-5.60 (m, 1H), 4.71-4.84 (m, 1H), 4.32 (dd, J = 10.7, 2.3 Hz, 1H), 4.21 (dd, J = 10.6, 8.7 Hz, 1H), 4.02-4.09 (m, 1H), 2.24 (s, 3H). |
| I-138 | pyridine-3-thiol# | XphosPd G2, MW 150° C. 1 h Cs$_2$CO$_3$ DMF | LCMS (AA): m/z 458 (M + H) | (400 MHz, d$_6$-DMSO) δ 8.62 (d, J = 2.0 Hz, 1H), 8.51 (dd, J = 4.8, 1.4 Hz, 1H), 8.27 (s, 1H), 7.73-7.79 (m, 1H), 7.58 (s, 2H), 7.41 (dd, J = 7.9, 4.6 Hz, 1H), 6.68 (d, J = 6.5 Hz, 1H), 6.12 (d, J = 5.8 Hz, 1H), 5.37-5.57 (m, 1H), 4.59-4.69 (m, 1H), 4.26 (dd, J = 10.5, 1.9 Hz, 1H), 4.08-4.16 (m, 1H), 3.98-4.07 (m, 1H). |

| Compound Number | Coupling Partner | Coupling Conditions | LC/MS Data | ¹H NMR Data |
|---|---|---|---|---|
| I-117 | 4-(trifluoro-methyl)pyridine-2-thiol | CuI, MW 190° C. 1 h NaOtBu, DMF, TBAB | LCMS (FA): m/z 526 (M + H) | (400 MHz, $d_6$-DMSO) δ 8.65 (d, J = 5.1 Hz, 1H), 8.31 (s, 1H), 7.58 (d, J = 5.0 Hz, 1H), 7.49-7.56 (m, 3H), 6.75 (d, J = 6.4 Hz, 1H), 6.11 (d, J = 5.8 Hz, 1H), 5.39-5.62 (m, 1H), 4.67-4.87 (m, 1H), 4.29-4.38 (m, 1H), 4.17-4.27 (m, 1H), 4.02-4.12 (m, 1H). |
| I-118 | 2-methyl-propane-2-thiol | XphosPd G2, MW 150° C. 1 h $Cs_2CO_3$ DMF | LCMS (FA): m/z 437 (M + H) | ¹H NMR (400 MHz, $d_6$-DMSO) δ 8.25 (s, 1H), 7.56 (s, 2H), 6.69 (d, J = 6.7 Hz, 1H), 6.16 (d, J = 5.8 Hz, 1H), 5.37-5.59 (m, 1H), 4.73-4.83 (m, 1H), 4.37 (dd, J = 10.6, 2.3 Hz, 1H), 4.25 (dd, J = 10.5, 8.8 Hz, 1H), 4.03-4.09 (m, 1H), 1.38 (s, 9 H). |
| I-125 | 1-methyl-1H-imidazole-2-thiol | XphosPd G2, MW 150° C. 1 h $Cs_2CO_3$ DMF | LCMS (AA): m/z 461 (M + H) | ¹H NMR (400 MHz, $d_6$-DMSO) δ 8.23 (s, 1H), 7.58 (s, 2H), 7.45 (d, J = 1.1 Hz, 1H), 7.09 (d, J = 1.3 Hz, 1H), 6.63 (d, J = 6.5 Hz, 1H), 6.14 (d, J = 5.8 Hz, 1H), 5.33-5.56 (m, 1H), 4.64-4.75 (m, 1H), 4.31 (dd, J = 10.6, 2.2 Hz, 1H), 4.18 (dd, J = 10.6, 8.7 Hz, 1H), 4.00-4.08 (m, 1H), 3.72 (s, 3H). |
| I-133 | 4-chloro-benzene-thiol | XphosPd G2, MW 150° C. 1 h $Cs_2CO_3$ DMF | LCMS (FA): m/z 491 (M + H) | ¹H NMR (400 MHz, $d_6$-DMSO) δ 8.27 (s, 1H), 7.58 (s, 2H), 7.31-7.46 (m, 4H), 6.69 (d, J = 6.5 Hz, 1H), 6.13 (d, J = 5.8 Hz, 1H), 5.36-5.58 (m, 1H), 4.65-4.79 (m, 1H), 4.31 (dd, J = 10.7, 2.4 Hz, 1H), 4.20 (dd, J = 10.6, 8.7 Hz, 1H), 4.01-4.10 (m, 1H). |
| I-114 | 4-methyl-pyridine-2-thiol | XphosPd G2, MW 150° C. 1 h $Cs_2CO_3$ DMF | LCMS (FA): m/z 472 (M + H) | ¹H NMR (400 MHz, $d_6$-DMSO) δ 8.30 (s, 1H), 7.51-7.62 (m, 3H), 7.10 (d, J = 7.5 Hz, 1H), 6.77 (d, J = 7.9 Hz, 1H), 6.73 (d, J = 6.4 Hz, 1H), 6.14 (d, J = 5.8 Hz, 1H), 5.37-5.61 (m, 1H), 4.70-4.84 (m, 1H), 4.28-4.38 (m, 1H), 4.16-4.27 (m, 1H), 4.02-4.11 (m, 1H), 2.42 (s, 3H). |
| I-102 | 6-methyl-pyridine-2-thiol | XphosPd G2, MW 150° C. 1 h $Cs_2CO_3$ DMF | LCMS (FA): m/z 472 (M + H); | ¹H NMR (400 MHz, $d_6$-DMSO) δ 8.30 (s, 1H), 7.51-7.62 (m, 3H), 7.10 (d, J = 7.5 Hz, 1H), 6.77 (d, J = 7.9 Hz, 1H), 6.73 (d, J = 6.4 Hz, 1H), 6.14 (d, J = 5.8 Hz, 1H), 5.37-5.61 (m, 1H), 4.70-4.84 (m, 1H), 4.28-4.38 (m, 1H), 4.16-4.27 (m, 1H), 4.02-4.11 (m, 1H), 2.42 (s, 3H). |
| I-132 | 4-(trifluoro-methyl)benzene-thiol | XphosPd G2, MW 150° C. 1 h $Cs_2CO_3$ DMF | LCMS (FA): m/z 525 (M + H) | ¹H NMR (400 MHz, $d_6$-DMSO) δ 8.30 (s, 1H), 7.71 (d, J = 8.4 Hz, 2H), 7.59 (s, 2H), 7.43 (d, J = 8.3 Hz, 2H), 6.75 (d, J = 6.4 Hz, 1H), 6.17 (d, J = 5.6 Hz, 1H), 5.42-5.63 (m, 1H), 4.70-4.85 (m, 1H), 4.29-4.38 (m, 1H), 4.18-4.28 (m, 1H), 4.03-4.12 (m, 1H). |
| I-158 | 3-(trifluoro-methyl)benzene-thiol | XphosPd G2, MW 150° C. 1 h $Cs_2CO_3$ DMF | LCMS (FA): m/z 525 (M + H) | ¹H NMR (400 MHz, $d_6$-DMSO) δ 8.28 (s, 1H), 7.73 (s, 1H), 7.50-7.66 (m, 3H), 6.73 (d, J = 6.5 Hz, 1H), 5.40-5.61 (m, 1H), 4.67-4.79 (m, 1H), 4.30-4.36 (m, 1H), 4.16-4.25 (m, 1H), 4.02-4.12 (m, 1H). |
| I-100 | 2-methyl-furan-3-thiol | XphosPd G2, MW 150° C. 1 h $Cs_2CO_3$ DMF | LCMS (FA): m/z 461 (M + H) | ¹H NMR (400 MHz, $d_6$-DMSO) δ 8.23 (s, 1H), 7.61-7.66 (m, 1H), 7.56 (s, 2H), 6.54-6.61 (m, 2H), 6.10 (d, J = 4.6 Hz, 1H), 5.30-5.52 (m, 1H), 4.51-4.64 (m, 1H), 4.16-4.27 (m, 1H), 3.93-4.12 (m, 2H), 2.38 (s, 3H). |
| I-110 | 2,5-dimethyl-furan-3-thiol | XphosPd G2, MW 150° C. 1 h $Cs_2CO_3$ DMF | LCMS (FA): m/z 475 (M + H) | ¹H NMR (400 MHz, $d_6$-DMSO) δ 8.22 (s, 1H), 7.57 (s, 2H), 6.57 (d, J = 6.5 Hz, 1H), 6.14 (s, 1H), 6.11 (d, J = 5.8 Hz, 1H), 5.31-5.51 (m, 1H), 4.54-4.67 (m, 1H), 4.20-4.33 (m, 1H), 4.05-4.13 (m, 1H), 3.96-4.04 (m, 1H), 2.33 (s, 3H), 2.23 (s, 3H). |
| I-103 | cyclo-pentane-thiol | XphosPd G2, 100° C. ON $Cs_2CO_3$ DMF | LCMS (FA): m/z 449 (M + H) | ¹H NMR (400 MHz, $d_6$-DMSO) δ 8.21 (s, 1H), 7.56 (s, 2H), 6.61 (d, J = 6.7 Hz, 1H), 6.11 (d, J = 5.8 Hz, 1H), 5.35-5.55 (m, 1H), 4.74-4.85 (m, 1H), 4.36 (dd, J = 10.6, 2.6 Hz, 1H), 4.27 (dd, J = 10.5, 8.5 Hz, 1H), 4.03-4.07 (m, 1H), 3.83-3.90 (m, 1H), 2.04-2.18 (m, 2H), 1.57-1.77 (m, 6H). |

-continued

| Compound Number | Coupling Partner | Coupling Conditions | LC/MS Data | $^1$H NMR Data |
|---|---|---|---|---|
| I-113 | pyridine-2-thiol | XphosPd G2, MW 150° C. 1 h $Cs_2CO_3$ DMF | LCMS (FA): m/z 458 (M + H) | $^1$H NMR (400 MHz, $CD_3OD$) δ 8.40-8.47 (m, 1H), 8.28 (s, 1H), 7.68-7.75 (m, 1H), 7.22-7.28 (m, 1H), 7.17 (d, J = 8.2 Hz, 1H), 6.79 (d, J = 6.1 Hz, 1H), 5.33-5.52 (m, 1H), 4.92-4.99 (m, 1H), 4.38-4.51 (m, 2H), 4.16-4.25 (m, 1H). |
| I-136 | butane-2-thiol | XphosPd G2, 100° C. ON $Cs_2CO_3$ DMF | LCMS (FA): m/z 437 (M + H) | $^1$H NMR (400 MHz, $d_6$-DMSO) δ 8.23 (s, 1H), 7.58 (s, 2H), 6.63 (d, J = 6.5 Hz, 1H), 6.14 (d, J = 5.6 Hz, 1H), 5.35-5.58 (m, 1H), 4.77 (br dd, J = 18.1, 6.9 Hz, 1H), 4.21-4.43 (m, 2H), 4.04 (br t, J = 7.2 Hz, 1H), 3.45-3.58 (m, 1H), 1.58-1.82 (m, 2H), 1.36 (dd, J = 14.2, 6.8 Hz, 3H), 1.01 (t, J = 7.3 Hz, 3H). |
| I-129 | 3-methyl-butane-2-thiol | XphosPd G2, 100° C. ON $Cs_2CO_3$ DMF | LCMS (FA): m/z 451 (M + H) | $^1$H NMR (400 MHz, $d_6$-DMSO) δ 8.21 (d, J = 1.0 Hz, 1H), 7.57 (d, J = 1.3 Hz, 2H), 6.61 (dd, J = 6.7, 1.4 Hz, 1H), 6.14 (dd, J = 5.8, 1.5 Hz, 1H), 5.30-5.57 (m, 1H), 4.76 (br dd, J = 18.1, 5.8 Hz, 1H), 4.32-4.42 (m, 1H), 4.20-4.29 (m, 1H), 3.99-4.08 (m, 1H), 3.62 (dt, J = 6.8, 4.2 Hz, 1H), 2.01 (s, 1H), 1.32 (dd, J = 16.7, 6.9 Hz, 3H), 0.90-1.08 (m, 6H). |
| I-156 | [1,2,4]tri-azolo[4,3-a]pyridine-3-thiol | CuI, TBAB, 190° C. 1 h MW NaOtBu | LCMS (FA): m/z 498 (M + H) | $^1$H NMR (400 MHz, $d_6$-DMSO) δ 8.54 (d, J = 6.9 Hz, 1H), 8.24 (s, 1H), 7.93 (d, J = 9.3 Hz, 1H), 7.56 (dd, J = 8.3, 6.8 Hz, 1H), 7.19 (t, J = 6.8 Hz, 1H), 6.57 (d, J = 6.5 Hz, 1H), 5.25-5.48 (m, 1H), 4.32-4.46 (m, 1H), 4.18 (br d, J = 8.9 Hz, 1H), 3.85-4.02 (m, 2H). |
| I-155 | Phenyl-methane-thiol | XPhos Pd G2, dioxane, 100° C.* | LCMS (FA): m/z 471 (M + H) | $^1$H NMR (400 MHz, $CD_3OD$) δ 8.18 (s, 1 H), 7.16-7.37 (m, 5 H), 6.66 (d, J = 6.4 Hz, 1 H), 5.33 (dt, J = 53.3, 7.0 Hz, 1 H), 4.92-5.01 (m, 1 H), 4.33-4.53 (m, 4 H), 4.18 (td, J = 7.3, 3.8 Hz, 1 H). |
| I-108 | cyclo-propyl-boronic acid** | $Pd(OAc)_2$, $Cy_3P$, $K_3PO_4$, dioxane, water, 100° C. ON | LCMS (FA): m/z 389 (M + H) | $^1$H NMR (400 MHz, $CD_3OD$) δ 8.18 (s, 1H), 6.60 (d, J = 6.4 Hz, 1H), 5.22-5.43 (m, 1H), 4.95 (dt, J = 17.7, 7.4 Hz, 1H), 4.41-4.53 (m, 2H), 4.15 (td, J = 7.5, 3.6 Hz, 1H), 2.26-2.34 (m, 1H), 1.00-1.12 (m, 4H). |

Pyridine-3-thiol was prepared by treating S-(pyridin-3-yl) dimethylcarbamothioate with NaOMe in MeOH at reflux for 2 hours.
*Final deprotection was performed using TFA/water(Example 35 Step 5) instead of HF/Et$_3$N.
**See Example 34, Step 1 for coupling procedure Example 80: [(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl Sulfamate and [(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl Sulfamate Compounds I-136a and I-136b The titled compounds were separated by SFC-HPLC (Chiralpak IA 250×10 mm 5 micron column, from Chiral Technologies Inc., flow rate=10 mL/min, CO$_2$/0.3% diethyl amine in 2-propanol (80/20)). Peak 1: I-136b: LCMS (FA): m/z 437 (M+H); $^1$H NMR (400 MHz, d$_6$-DMSO) δ 8.22 (s, 1H), 7.57 (s, 2H), 6.63 (d, J=6.5 Hz, 1H), 6.13 (d, J=5.6 Hz, 1H), 5.33-5.59 (m, 1H), 4.69-4.84 (m, 1H), 4.21-4.42 (m, 2H), 4.04 (br t, J=7.3 Hz, 1H), 3.53 (q, J=6.6 Hz, 1H), 1.55-1.81 (m, 2H), 1.32-1.42 (m, 3H), 1.01 (t, J=7.3 Hz, 3H). Peak 2: I-136a: LCMS (FA): m/z 437 (M+H); $^1$H NMR (400 MHz, d$_6$-DMSO) δ 8.22 (s, 1H), 6.63 (d, J=6.7 Hz, 1H), 5.32-5.58 (m, 1H), 4.71-4.85 (m, 1H), 4.32-4.42 (m, 1H), 4.22-4.31 (m, 1H), 4.05 (s, 1H), 3.52 (br d, J=6.7 Hz, 1H), 1.59-1.83 (m, 3H), 1.34 (d, J=6.8 Hz, 3H), 1.01 (t, J=7.3 Hz, 3H).

Example 81: [(2R,3R,4S,5R)-5-{4-amino-3-[(3-chlorophenyl)sulfanyl]-1H-pyrazolo[3,4-d]pyrimidin-1-yl}-4-fluoro-3-hydroxytetrahydrofuran-2-yl]methyl Sulfamate Compound I-106

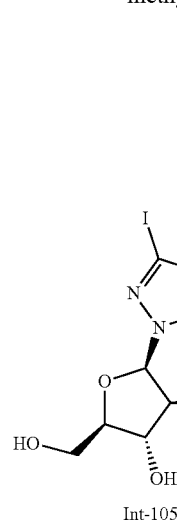

Int-105

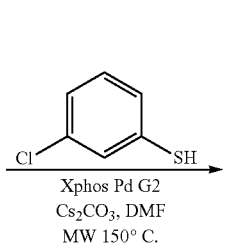

Xphos Pd G2
Cs$_2$CO$_3$, DMF
MW 150° C.

-continued

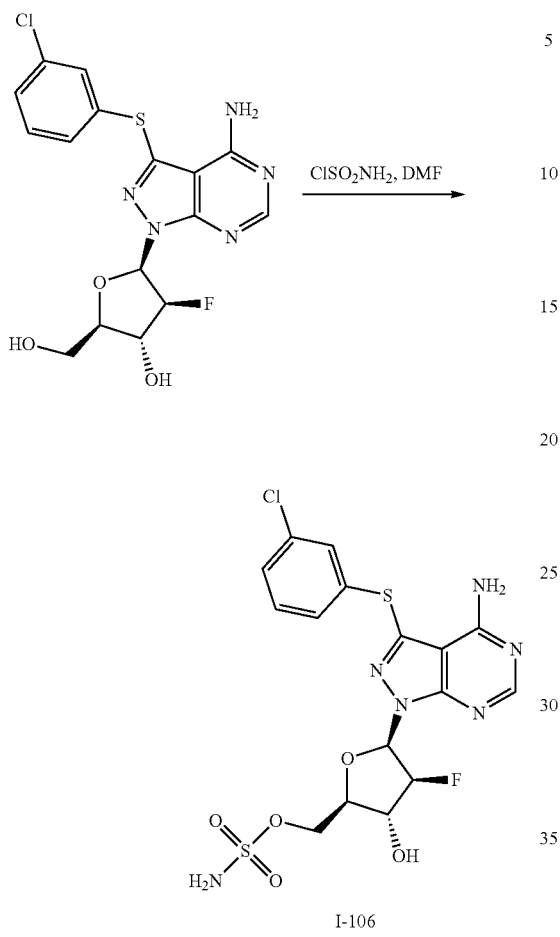

I-106

Step 1: (2R,3R,4S,5R)-5-(4-amino-3-((3-chlorophenyl)thio)-1H-pyrazolo[3,4-d]pyrimidin-1-yl)-4-fluoro-2-(hydroxymethyl)tetrahydrofuran-3-ol The title compound was prepared from Intermediate 105 as described in Example 78 Step 5 substituting 3-chlorobenzenethiol for 3-methylbenzenethiol. In this example heating was applied through microwave irradiation at 150° C. for 1 h.

Step 2: [(2R,3R,4S,5R)-5-{4-amino-3-[(3-chlorophenyl)sulfanyl]-1H-pyrazolo[3,4-d]pyrimidin-1-yl}-4-fluoro-3-hydroxytetrahydrofuran-2-yl]methyl Sulfamate The title compound was prepared following the procedure described in Example 1 step 7, substituting (2R,3R,4S,5R)-5-{4-amino-3-[(3-chlorophenyl)sulfanyl]-1H-pyrazolo[3,4-d]pyrimidin-1-yl}-4-fluoro-2-(hydroxymethyl)tetrahydrofuran-3-ol for Intermediate 7 (62 mg, 58%). LCMS (FA): m/z 491 (M+H); $^1$H NMR (400 MHz, CD$_3$OD) δ 8.26 (s, 1H), 7.42 (s, 1H), 7.25-7.37 (m, 3H), 6.75 (d, J=6.4 Hz, 1H), 5.30-5.51 (m, 1H), 4.81-4.88 (m, 1H), 4.35-4.47 (m, 2H), 4.14-4.24 (m, 1H).

Example 82: {(2R,3R,4S,5R)-5-[4-amino-3-(difluoromethoxy)-1H-pyrazolo[3,4-d]pyrimidin-1-yl]-4-fluoro-3-hydroxytetrahydrofuran-2-yl}methyl Sulfamate Compound I-99

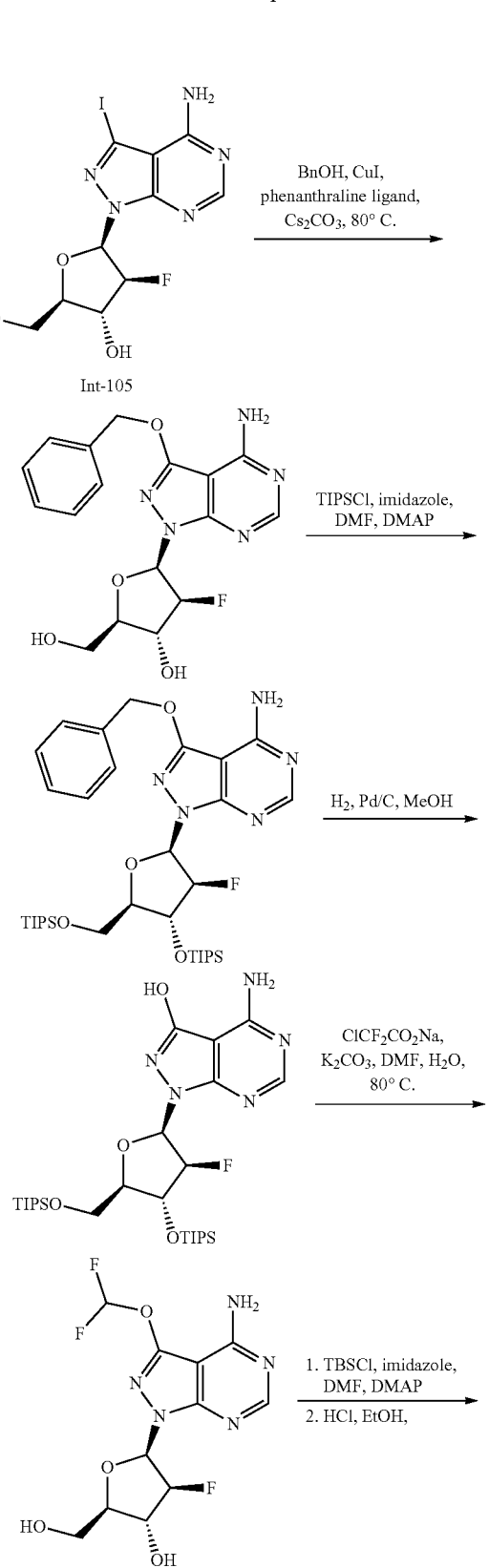

-continued

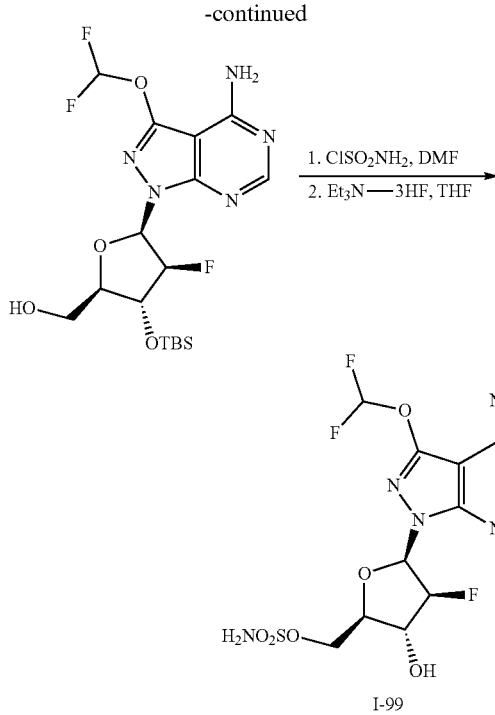

Step 1: (2R,3R,4S,5R)-5-[4-amino-3-(benzyloxy)-1H-pyrazolo[3,4-d]pyrimidin-1-yl]-4-fluoro-2-(hydroxymethyl)tetrahydrofuran-3-ol Intermediate 105 (1.00 g, 2.53 mmol), copper(I) iodide (49 mg, 0.26 mmol), 3,4,7,8-tetramethyl-1,10-phenanthroline (120 mg, 0.506 mmol) and cesium carbonate (1.66 g, 5.10 mmol) were combined in a round bottomed flask equipped with a stir bar. Benzyl alcohol (10.0 mL, 96.6 mmol) was then added and the reaction mixture was sonicated under an atmosphere of argon. The resulting mixture was allowed to heat at 80° C. for 24 h. Upon completion, the reaction mixture was diluted with MeOH and filtered through a pad of silica gel which was washed with MeOH several times. The filtrate was evaporated under reduced pressure. The crude product was purified by silica gel chromatography to afford (2R,3R,4S,5R)-5-[4-amino-3-(benzyloxy)-1H-pyrazolo[3,4-d]pyrimidin-1-yl]-4-fluoro-2-(hydroxymethyl)tetrahydrofuran-3-ol as a white solid (430 mg, 45%). LCMS (FA): m/z 376 (M+H).

Step 2: 3-(benzyloxy)-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-4-amine Into a stirred solution of (2R,3R,4S,5R)-5-[4-amino-3-(benzyloxy)-1H-pyrazolo[3,4-d]pyrimidin-1-yl]-4-fluoro-2-(hydroxymethyl)tetrahydrofuran-3-ol (172 mg, 0.458 mmol) in DMF (4.3 mL) at rt under an atmosphere of $N_2$ was added 1H-Imidazole (187 mg, 2.75 mmol), DMAP (11 mg, 0.092 mmol) and triisopropylsilyl chloride (0.582 mL, 2.75 mmol). The mixture was stirred at rt overnight but reaction was not complete. Additional TIPSCl (0.190 mL, 0.898 mmol) and 1H-imidazole (62.0 mg, 0.912 mmol) were added and the mixture was stirred at rt for 2 days. Upon completion, excess silylating reagent was quenched by the addition of saturated $NH_4Cl$ solution at 0° C., and the mixture was extracted with ethyl acetate twice. The combined extracts were washed with saturated sodium bicarbonate solution and brine, dried over sodium sulfate, filtered and concentrated under reduced pressure. The crude product was purified by silica gel chromatography to afford 3-(benzyloxy)-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-4-amine as a white solid (187 mg, 58%). LCMS (FA): m/z 689 (M+H).

Step 3: 4-amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-3-ol 3-(Benzyloxy)-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-4-amine (0.215 g, 0.313 mmol) was dissolved in MeOH (9 mL). The reaction flask was fitted with a 3-way valve. Air was removed under reduced pressure and the flask was backfilled with argon. Pd (10% on carbon, 51 mg, 0.048 mmol) was added. The flask was evacuated and backfilled with hydrogen from a balloon, and the reaction mixture was allowed to stir at rt under an atmosphere of hydrogen for 5 h. After complete reaction, the reaction mixture was diluted with MeOH and filtered through a pad of celite which was washed several times with MeOH. The filtrate was evaporated under reduced pressure. The crude product was purified by silica gel chromatography to afford 4-amino-1-[(2R,3S,4R,5R)-3-fluoro-4-[(triisopropylsilyl)oxy]-5-{[(triisopropylsilyl) oxy]methyl}tetrahydrofuran-2-yl]-1H-pyrazolo[3,4-d]pyrimidin-3-ol as a white solid (125 mg, 67%). LCMS (FA): m/z 598 (M+H).

Step 4: (2R,3R,4S,5R)-5-[4-amino-3-(difluoromethoxy)-1H-pyrazolo[3,4-d]pyrimidin-1-yl]-4-fluoro-2-(hydroxymethyl)tetrahydrofuran-3-ol The title compound was prepared following the procedures detailed in Example 15 Step 6 substituting 4-amino-1-[(2R,3S,4R,5R)-3-fluoro-4-[(triisopropylsilyl)oxy]-5-{[(triisopropylsilyl)oxy]methyl}tetrahydrofuran-2-yl]-1H-pyrazolo[3,4-d]pyrimidin-3-ol for 4-amino-1-[(3aR,4R,6R,6aR)-2,2-dimethyl-6-{[(triisopropylsilyl)oxy]methyl}tetrahydrofuro[3,4-d][1,3]dioxol-4-yl]-1H-pyrazolo[3,4-d]pyrimidin-3-ol. LCMS (FA): m/z 336 (M+H).

Steps 5-8: {(2R,3R,4S,5R)-5-[4-amino-3-(difluoromethoxy)-1H-pyrazolo[3,4-d]pyrimidin-1-yl]-4-fluoro-3-hydroxytetrahydrofuran-2-yl}methyl Sulfamate The title compound was prepared following the procedures detailed in Example 65 Steps 4-7 substituting (2R,3R,4S,5R)-5-[4-amino-3-(difluoromethoxy)-1H-pyrazolo[3,4-d]pyrimidin-1-yl]-4-fluoro-2-(hydroxymethyl)tetrahydrofuran-3-ol for (2R,3R,4S,5R)-5-[4-amino-3-(isopropylsulfanyl)-1H-pyrazolo[3,4-d]pyrimidin-1-yl]-4-fluoro-2-(hydroxymethyl)tetrahydrofuran-3-ol. LCMS (FA): m/z 415 (M+H); $^1$H NMR (400 MHz, $CD_3OD$) δ 8.24 (s, 1H), 7.22-7.67 (m, 1H), 6.64 (d, J=6.5 Hz, 1H), 5.23-5.52 (m, 1H), 4.99 (dt, J=17.5, 7.7 Hz, 1H), 4.39-4.51 (m, 2H), 4.06-4.17 (m, 1H).

Example 83: {(2R,3R,5S)-5-[4-amino-3-(methylsulfanyl)-1H-pyrazolo[3,4-d]pyrimidin-1-yl]-3-hydroxytetrahydrofuran-2-yl}methyl Sulfamate Compound I-219
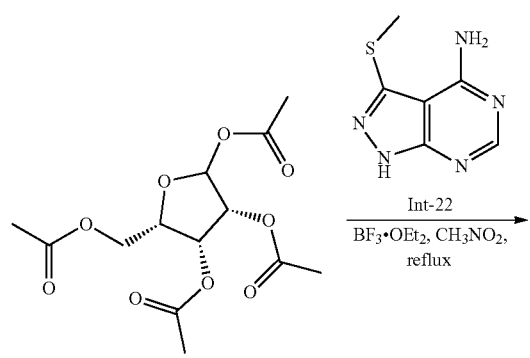
Int-22
BF$_3$·OEt$_2$, CH$_3$NO$_2$,
reflux
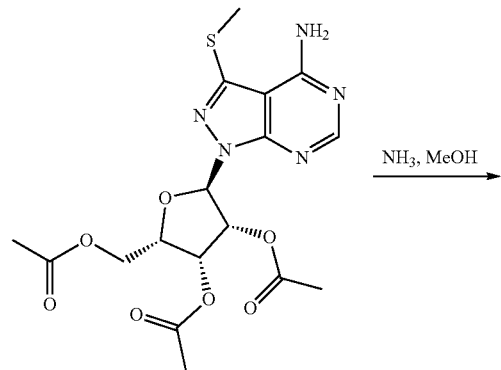
NH$_3$, MeOH
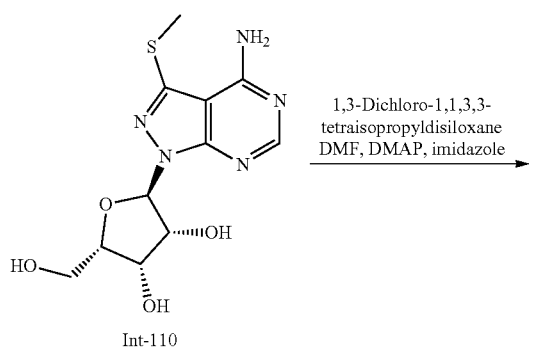
Int-110
1,3-Dichloro-1,1,3,3-tetraisopropyldisiloxane
DMF, DMAP, imidazole
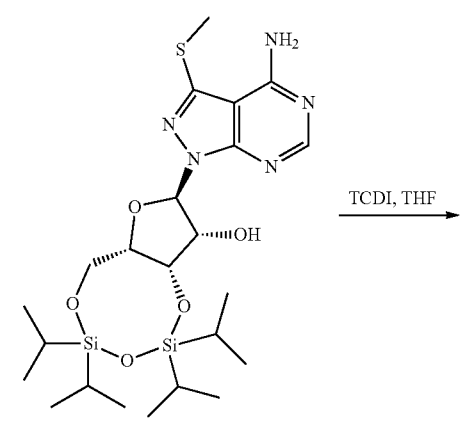
TCDI, THF
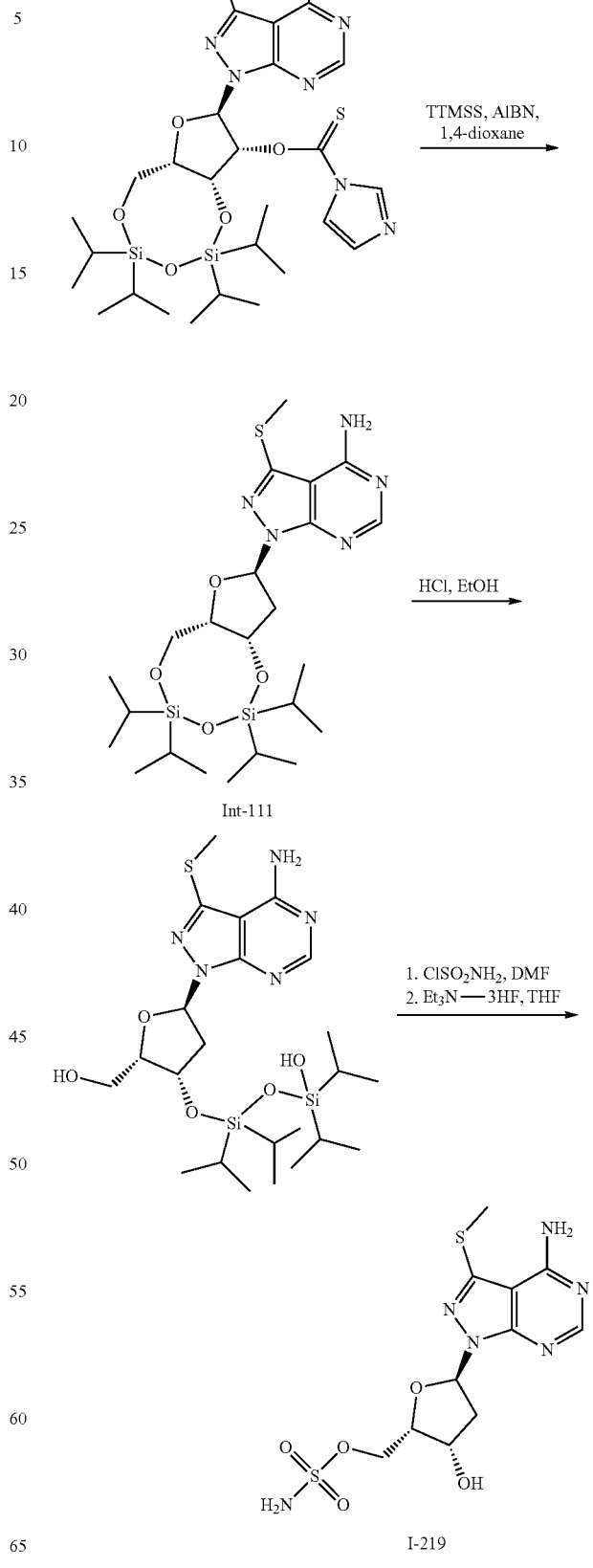
TTMSS, AIBN,
1,4-dioxane
HCl, EtOH
Int-111
1. ClSO$_2$NH$_2$, DMF
2. Et$_3$N—3HF, THF
I-219

Step 1: (2R,3S,4S,5S)-2-(acetoxymethyl)-5-[4-amino-3-(methylsulfanyl)-1H-pyrazolo[3,4-d]pyrimidin-1-yl]tetrahydrofuran-3,4-diyl Diacetate The title compound was prepared following procedures described in Example 5 Step 2, substituting Intermediate 22 for Intermediate 14 and 1,2,3,5-tetra-O-acetyl-L-lyxofuranose (prepared from L-lyxose as detailed in *Carbohydrate Res.* 1979, 69, 135-142) for 1,2,3,5-tetra-O-acetyl-β-D-ribofuranose. LCMS (FA): m/z 440 (M+H); $^1$H NMR (400 MHz, CDCl$_3$) δ 8.37 (s, 1H), 6.55 (d, J=5.1 Hz, 1H), 6.26 (t, J=5.0 Hz, 1H), 5.93 (t, J=4.6 Hz, 1H), 5.75 (s, 2H), 4.86 (dt, J=7.0, 4.8 Hz, 1H), 4.31-4.41 (m, 1H), 4.20-4.31 (m, 1H), 2.72 (s, 3H), 2.19 (s, 3H), 2.08 (s, 3H), 2.07 (s, 3H).

Step 2: (2R,3R,4S,5S)-2-[4-amino-3-(methylsulfanyl)-1H-pyrazolo[3,4-d]pyrimidin-1-yl]-5-(hydroxymethyl)tetrahydrofuran-3,4-diol Intermediate 110

The title compound was prepared following the procedure described in Example 5 Step 3, substituting (2R,3S,4S,5S)-2-(acetoxymethyl)-5-[4-amino-3-(methylsulfanyl)-1H-pyrazolo[3,4-d]pyrimidin-1-yl]tetrahydrofuran-3,4-diyl diacetate for Intermediate 15. LCMS (FA): m/z 314 (M+H). $^1$H NMR (400 MHz, d$_6$-DMSO) δ 8.20 (s, 1H), 6.07 (d, J=6.5 Hz, 1H), 5.37 (d, J=7.3 Hz, 1H), 5.07 (d, J=4.4 Hz, 1H), 4.99 (td, J=6.9, 4.5 Hz, 1H), 4.61 (t, J=5.7 Hz, 1H), 4.16-4.30 (m, 2H), 3.59-3.71 (m, 1H), 3.44-3.57 (m, 1H), 2.62 (s, 3H).

Step 3: (6aR,8S,9S,9aR)-8-[4-amino-3-(methylsulfanyl)-1H-pyrazolo[3,4-d]pyrimidin-1-yl]-2,2,4,4-tetraisopropyltetrahydro-6H-furo[3,2-f][1,3,5,2,4]trioxadisilocin-9-ol To a solution of (2R,3R,4S,5S)-2-[4-amino-3-(methylsulfanyl)-1H-pyrazolo[3,4-d]pyrimidin-1-yl]-5-(hydroxymethyl)tetrahydrofuran-3,4-diol (Intermediate 110, 1.67 g, 4.40 mmol) in DMF (35 mL) was added 1H-imidazole (1.20 g, 17.7 mmol) and DMAP (110 mg, 0.88 mmol). While the reaction mixture was allowed to stir at rt, a solution of 1,3-dichloro-1,1,3,3-tetraisopropyldisiloxane (1.39 mL, 4.42 mmol) in DMF (8.5 mL) was added by syringe. Stirring at rt was continued overnight. Upon complete reaction, the reaction mixture was transferred to separatory funnel and diluted with brine. The mixture was extracted twice with EtOAc. The combined extracts were washed with water and brine, dried over sodium sulfate, filtered and concentrated under reduced pressure to afford crude product which was purified by silica gel chromatography (1.45 g, 59%). LCMS (FA): m/z 557 (M+H). $^1$H NMR (400 MHz, CDCl$_3$) δ 8.28-8.45 (m, 1H), 6.26 (d, J=6.3 Hz, 1H), 5.80 (s, 2H), 5.39 (ddd, J=11.2, 6.3, 4.8 Hz, 1H), 4.64 (dd, J=4.6, 2.6 Hz, 1H), 4.56 (ddd, J=10.2, 4.7, 2.4 Hz, 1H), 3.92-4.03 (m, 1H), 3.81-3.90 (m, 1H), 2.81 (d, J=11.3 Hz, 1H), 2.70 (s, 3H), 1.04-1.23 (m, 28H).

Step 4: O-{(6aR,8S,9S,9aS)-8-[4-amino-3-(methylsulfanyl)-1H-pyrazolo[3,4-d]pyrimidin-1-yl]-2,2,4,4-tetraisopropyltetrahydro-6H-furo[3,2-f][1,3,5,2,4]trioxadisilocin-9-yl}-1H-imidazole-1-carbothioate To solution of (6aS,8R,9R,9aS)-8-[4-amino-3-(methylsulfanyl)-1H-pyrazolo[3,4-d]pyrimidin-1-yl]-2,2,4,4-tetraisopropyltetrahydro-6H-furo[3,2-f][1,3,5,2,4]trioxadisilocin-9-ol (4.0 g, 7.2 mmol) in THF (72 mL) was added 1,1'-thiocarbonyldiimidazole (3.56 g, 18.0 mmol) and the reaction mixture was allowed to stir under reflux for 5 h. Midway through the heating period, an additional sample of 1,1'-thiocarbonyldiimidazole (3.56 g, 18.0 mmol) was added. Upon completion of chemical reaction, the reaction flask was removed from the heating bath and the contents allowed to cool to rt and concentrated under reduced pressure. The crude residue was purified by silica gel chromatography to afford the product (3.51 g, 76%). LCMS (FA): m/z 667 (M+H); $^1$H NMR (400 MHz, CDCl$_3$) δ 8.35 (s, 1H), 8.31 (s, 1H), 7.58 (s, 1H), 7.00 (d, J=0.9 Hz, 1H), 6.94 (dd, J=7.2, 4.0 Hz, 1H), 6.75 (d, J=7.0 Hz, 1H), 5.76 (s, 2H), 5.04 (dd, J=3.9, 2.3 Hz, 1H), 4.68 (ddd, J=10.1, 4.8, 2.1 Hz, 1H), 3.95-4.04 (m, 1H), 3.88 (dd, J=10.4, 4.9 Hz, 1H), 2.69 (s, 3H), 0.84-1.18 (m, 28H).

Step 5: 3-(methylsulfanyl)-1-[(6aR,8S,9aR)-2,2,4,4-tetraisopropyltetrahydro-6H-furo[3,2-f][1,3,5,2,4]trioxadisilocin-8-yl]-1H-pyrazolo[3,4-d]pyrimidin-4-amine Intermediate 111

O-{(6aS,8R,9R,9aR)-8-[4-Amino-3-(methylsulfanyl)-1H-pyrazolo[3,4-d]pyrimidin-1-yl]-2,2,4,4-tetraisopropyltetrahydro-6H-furo[3,2-f][1,3,5,2,4]trioxadisilocin-9-yl}1H-imidazole-1-carbothioate (9.53 g, 14.3 mmol) was azeotropically dried from toluene prior to use. The resulting oil was further dried in vacuo. This evacuated flask was purged with dry nitrogen and 1,4-dioxane (200 mL) was added followed by 2,2'-azo-bis-isobutyronitrile (705 mg, 4.3 mmol) and tris(trimethylsilyl)silane (7.1 mL, 23 mmol). The reaction flask was fitted with a reflux condenser and the resulting yellow solution was allowed to stir at a vigorous reflux (oil bath at 130° C.) for 4 h. The yellow solution was allowed to cool to rt and concentrated under reduced pressure. The crude mixture was purified by silica gel chromatography to afford the product (5.55 g, 72%). LCMS (FA): m/z 540 (M+H); $^1$H NMR (400 MHz, CDCl$_3$) δ 8.11 (s, 1H), 6.56 (t, J=7.1 Hz, 1H), 5.65 (br s, 2H), 4.53 (dd, J=4.1, 2.7 Hz, 1H), 4.18 (ddd, J=9.8, 5.0, 2.6 Hz, 1H), 3.61-3.73 (m, 2H), 3.05 (ddd, J=13.6, 7.8, 4.5 Hz, 1H), 2.44 (s, 3H), 2.14-2.29 (m, 1H), 0.75-0.95 (m, 28H).

Step 6: 3-{[(2S,3S,5R)-5-[4-amino-3-(methylsulfanyl)-1H-pyrazolo[3,4-d]pyrimidin-1-yl]-2-(hydroxymethyl)tetrahydrofuran-3-yl]oxy}-1,1,3,3-tetraisopropyldisiloxan-1-ol To an ice-water-cooled solution of Intermediate 111 (1.79 g, 3.32 mmol) in ethanol (35 mL) was added aqueous hydrochloric acid (1.0 M, 10 mL). The reaction mixture was cooled in an ice-water bath and stirring was allowed to continue for another 8 h. Reaction was not complete and the reaction flask was stored at −20° C. overnight. The reaction mixture was allowed to continue stirring in 10 h 0° C./−20° C. overnight intervals until reaction was complete. Excess acid was neutralized by the addition of saturated aqueous sodium bicarbonate solution (added at 0° C.). The reaction mixture was allowed to warm to rt and was subsequently extracted twice with EtOAc. The combined extracts were washed with brine, dried over sodium sulfate, filtered and concentrated under reduced pressure. Residual moisture was removed by a reduced-pressure coevaporation from toluene, followed by an interval under full vacuum. The crude product was sufficiently pure to use without further manipulation. LCMS (FA): m/z=559 (M+H); $^1$H NMR (400 MHz, CDCl$_3$) δ 8.36 (s, 1H), 6.72-6.80 (m, 1H), 5.79 (br s, 2H), 5.27 (q, J=5.0 Hz, 1H), 4.39 (q, J=5.2 Hz, 1H), 3.90 (br d, J=5.1 Hz, 2H), 3.07-3.20 (m, 1H), 2.67 (s, 3H), 2.41-2.59 (m, 2H), 0.93-1.17 (m, 28H).

Step 7: {(2S,3S,5R)-5-[4-amino-3-(methylsulfanyl)-1H-pyrazolo[3,4-d]pyrimidin-1-yl]-3-[(3-hydroxy-1,1,3,3-tetraisopropyldisiloxanyl)oxy]tetrahydrofuran-2-yl}methyl Sulfamate The title compound was prepared following the procedure described in Example 1, Step 7, substituting 3-{[(2S,3S,5R)-5-[4-amino-3-(methylsulfanyl)-1H-pyrazolo[3,4-d]pyrimidin-1-yl]-2-(hydroxymethyl)tetrahydrofuran-3-yl]oxy}-1,1,3,3-tetraisopropyldisiloxan-1-ol for Intermediate 7. LCMS (FA): m/z 637 (M+H); $^1$H NMR (400 MHz, CDCl$_3$) δ 8.33 (s, 1H), 6.79 (dd, J=6.9, 5.4 Hz, 1H), 5.79 (br s, 2H), 5.04-5.27 (m, 3H), 4.63 (dt, J=7.5, 3.9 Hz, 1H), 4.40-4.58 (m, 2H), 3.13 (dt, J=13.7, 5.5 Hz, 2H), 2.67 (s, 3H), 2.58 (ddd, J=13.7, 7.0, 3.5 Hz, 1H), 0.90-1.21 (m, 28H).

by the dropwise addition of ammonium hydroxide (until pH=5.5). The resulting mixture was concentrated under reduced pressure to dryness. The crude product was purified by silica gel chromatography and triturated from a small amount of water to afford pure product (0.47 g, 53%). LCMS (AA): m/z 377; $^1$H NMR (400 MHz, d$_6$-DMSO) δ 8.21 (s, 1H), 7.49 (s, 2H), 6.62 (t, J=6.5 Hz, 1H), 5.37 (br d, J=4.9 Hz, 1H), 4.65 (br s, 1H), 4.36 (br dd, J=7.5, 3.7 Hz, 1H), 4.27 (dd, J=10.7, 2.7 Hz, 1H), 4.10 (dd, J=10.7, 8.3 Hz, 1H), 2.91-3.06 (m, 1H), 2.61 (s, 3H), 2.36 (br dd, J=12.7, 7.2 Hz, 1H).

Example 84

The following compounds were prepared as described in the procedures in Example 83 using the reagents and conditions described in the table below.

| Compound number | Pyrazolopyrimidine used in glycosylation | Modification to Deoxygenation conditons | LCMS data | $^1$H NMR Data |
| --- | --- | --- | --- | --- |
| I-213 | Intermediate 90 | Bu$_3$SnH, xylenes, 140° C. | LCMS(FA): m/z 391 (M + H) | $^1$H NMR (400 MHz, CD$_3$OD) δ 8.20 (s, 1H), 6.73 (dd, J = 7.0, 5.9 Hz, 1H), 4.74-4.78 (m, 1H), 4.52 (dt, J = 7.5, 3.8 Hz, 1H), 4.37-4.43 (m, 1H), 4.23-4.30 (m, 1H), 3.10-3.20 (m, 3H), 2.46 (ddd, J = 14.1, 7.2, 2.1 Hz, 1H), 1.39 (t, J = 7.3 Hz, 3H). |
| I-220 | Intermediate 99 | Bu$_3$SnH, xylenes, 140° C. | LCMS (FA): m/z 405 (M + H) | $^1$H NMR (400 MHz, d$_6$-DMSO) δ 8.23 (s, 1H), 7.49 (s, 2H), 6.65 (t, J = 6.5 Hz, 1H), 4.63-4.70 (m, 1H), 4.31-4.39 (m, 1H), 4.27 (dd, J = 10.9, 3.0 Hz, 1H), 4.10 (dd, J = 10.8, 8.2 Hz, 1H), 3.54-3.65 (m, 1H), 2.94-3.03 (m, 1H), 2.31-2.48 (m, 1H), 1.34 (d, J = 1.1 Hz, 3H), 1.32 (d, J = 1.1 Hz, 3H). |
| I-225 | Intermediate 31 | Bu$_3$SnH, xylenes, 140° C. | LCMS (FA): m/z 361 (M + H) | $^1$H NMR (400 MHz, d$_6$-DMSO) δ 8.15 (s, 1H), 7.49 (br s, 2H), 6.56 (t, J = 6.7 Hz, 1H), 5.34 (d, J = 5.1 Hz, 1H), 4.57-4.65 (m, 1H), 4.29-4.35 (m, 1H), 4.25 (dd, J = 10.7, 3.0 Hz, 1H), 4.08 (dd, J = 10.7, 8.1 Hz, 1H), 3.98 (s, 3H), 2.90-2.96 (m, 1H), 2.27 -2.36 (m, 1H). |
| I-226 | 1H-pyrazolo[3,4-d]pyrimidin-4-amine | TTMSS, AIBN, 1,4-dioxane, reflux | LCMS (FA): m/z 331 (M + H) | $^1$H NMR (400 MHz, CD$_3$OD) δ 8.21 (s, 1H), 8.12 (s, 1H), 6.77 (t, J = 6.5 Hz, 1H), 4.72-4.78 (m, 1H), 4.50-4.55 (m, 1H), 4.40 (dd, J = 10.8, 3.8 Hz, 1H), 4.27 (dd, J = 10.8, 7.3 Hz, 1H), 3.12-3.19 (m, 1H), 2.43-2.51 (m, 1H). |

Step 8: {(2S,3S,5R)-5-[4-amino-3-(methylsulfanyl)-1H-pyrazolo[3,4-d]pyrimidin-1-yl]-3-hydroxytetrahydrofuran-2-yl}methyl Sulfamate I-219

To a solution of {(2S,3S,5R)-5-[4-amino-3-(methylsulfanyl)-1H-pyrazolo[3,4-d]pyrimidin-1-yl]-3-[(3-hydroxy-1,1,3,3-tetraisopropyldisilyanyl)oxy]tetrahydrofuran-2-yl}methyl sulfamate (1.50 g, 2.36 mmol) in THF (40 mL) was added triethylamine trishydrofluoride (2.68 mL, 16.5 mmol). The reaction mixture was allowed to stir at rt over the weekend. Excess hydrofluoride reagent was neutralized Example 85: {(2S,3S,5R)-5-[4-amino-3-(trifluoromethyl)-1H-pyrazolo[3,4-d]pyrimidin-1-yl]-3-hydroxytetrahydrofuran-2-yl}methyl Sulfamate Compound I-209

The title compound was prepared as described above in Example 83 substituting Intermediate 55 for Intermediate 22 in Step 1 and utilizing tributyl tin hydride in place of TTMSS in Step 5. LCMS (FA): m/z 399 (M+H); $^1$H NMR (400 MHz, d$_6$-DMSO) δ 8.37 (s, 1H), 7.50 (br s, 2H), 6.76 (t, J=6.6 Hz, 1H), 5.34-5.52 (m, 1H), 4.62-4.71 (m, 1H), 4.36-4.45 (m, 1H), 4.28 (dd, J=10.8, 2.5 Hz, 1H), 4.12 (dd, J=10.7, 8.3 Hz, 1H), 2.93-3.03 (m, 1H), 2.32-2.48 (m, 1H).

Example 86: {(2R,3S,5R)-5-[4-amino-3-(difluoromethoxy)-1H-pyrazolo[3,4-d]pyrimidin-1-yl]-3-hydroxytetrahydrofuran-2-yl}methyl Sulfamate Compound I-195

The title compound was prepared as described in Example 83 substituting Intermediate 35 for Intermediate 110 in Step 3 and substituting tributyl tin hydride and toluene for TTMSS, AIBN and dioxane in Step 5. LCMS (FA): m/z 397 (M+H); $^1$H NMR (400 MHz, CD$_3$OD) δ 8.23 (s, 1H), 7.21-7.69 (m, 1H), 6.68 (dd, J=7.0, 5.0 Hz, 1H), 4.69-4.77 (m, 1H), 4.25-4.31 (m, 1H), 4.12-4.23 (m, 2H), 2.92 (dt, J=13.6, 5.8 Hz, 1H), 2.42 (ddd, J=13.6, 7.1, 5.1 Hz, 1H).

Example 87: {(2S,3S,4R,5R)-5-[4-amino-3-(methylsulfanyl)-1H-pyrazolo[3,4-d]pyrimidin-1-yl]-3,4-dihydroxytetrahydrofuran-2-yl}methyl Sulfamate Compound I-94

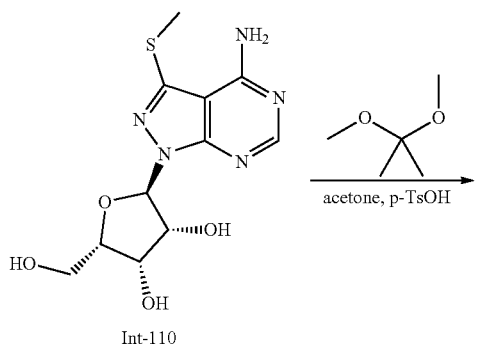

Int-110

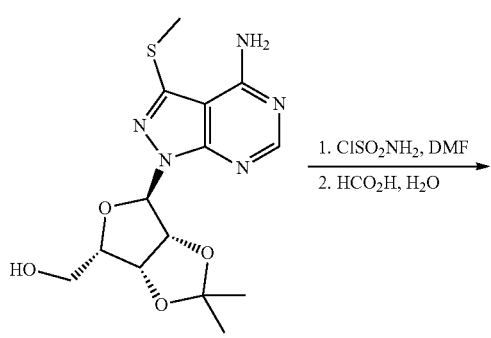

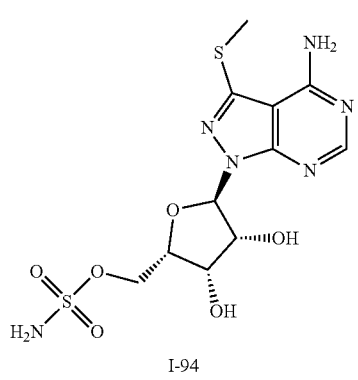

I-94

Step 1: {(3aR,4S,6R,6aR)-6-[4-amino-3-(methylsulfanyl)-1H-pyrazolo[3,4-d]pyrimidin-1-yl]-2,2-dimethyltetrahydrofuro[3,4-d][1,3]dioxol-4-yl}methanol Intermediate 110 was treated as described in Example 1 Step 6.

Step 2: {(3aR,4S,6R,6aR)-6-[4-amino-3-(methylsulfanyl)-1H-pyrazolo[3,4-]pyrimidin-1-yl]-2,2-dimethyltetrahydrofuro[3,4-d][1,3]dioxol-4-yl}methyl Sulfamate {(3aR,4S,6R,6aR)-6-[4-Amino-3-(methylsulfanyl)-1H-pyrazolo[3,4-d]pyrimidin-1-yl]-2,2-dimethyltetrahydrofuro[3,4-d][1,3]dioxol-4-yl}methanol was treated as described in Example 1 Step 7.

Step 3: {(2S,3S,4R,5R)-5-[4-amino-3-(methylsulfanyl)-1H-pyrazolo[3,4-d]pyrimidin-1-yl]-3,4-dihydroxytetrahydrofuran-2-yl}methyl Sulfamate I-94

{(3aR,4S,6R,6aR)-6-[4-Amino-3-(methylsulfanyl)-1H-pyrazolo[3,4-]pyrimidin-1-yl]-2,2-dimethyltetrahydrofuro[3,4-d][1,3]dioxol-4-yl}methyl sulfamate was treated as described in Example 1 Step 8. LCMS (FA): m/z 393 (M+H); $^1$H NMR (400 MHz, DMSO-d$_6$) δ 8.21 (s, 1H), 7.50 (s, 2H), 6.12 (d, J=6.53 Hz, 1H), 5.52 (d, J=6.9 Hz, 1H), 5.44-5.38 (m, 1H), 4.95-5.06 (m, 1H), 4.45-4.54 (m, 1H), 4.34-4.23 (m, 2H), 4.14 (dd, J=8.1, 10.7 Hz, 1H), 2.62 (s, 3H).

Example 87a: {(2S,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl Sulfamate I-95

The title compound was prepared as described in Example 87 substituting {(3aR,4R,6R,6aR)-6-[4-amino-3 (isopropylsulfanyl)-1H-pyrazolo[3,4-d]pyrimidin-1-yl]-2,2-dimethyltetrahydrofuro[3,4-d][1,3]dioxol-4-yl}methanol for Intermediate 110 in Step 1. LCMS (FA): m/z 421 (M+H); $^1$H NMR (400 MHz, DMSO-d$_6$) δ 8.17-8.30 (m, 1H), 7.52 (br s, 2H), 6.15 (d, J=6.4 Hz, 1H), 5.56 (d, J=6.8 Hz, 1H), 5.45 (d, J=4.6 Hz, 1H), 4.99 (d, J=4.6 Hz, 1H), 4.43-4.59 (m, 1H), 4.32 (d, J=3.6 Hz, 1H), 4.23-4.30 (m, 1H), 4.15 (dd, J=10.6, 8.2 Hz, 1H), 3.53-3.73 (m, 1H), 1.34 (dd, J=6.7, 3.1 Hz, 6H).

Example 88: [(2S,3S,5R)-5-(4-amino-3-methyl-1H-pyrazolo[3,4-d]pyrimidin-1-yl)-3-hydroxytetrahydrofuran-2-yl]methyl Sulfamate Compound I-218

The title compound was prepared as described in Example 83 substituting Intermediate 9 for Intermediate 22 in Step 1. LCMS (FA) m/z 345 (M+H); $^1$H NMR (400 MHz, CD$_3$OD) δ 8.18 (s, 1H), 6.73 (t, J=6.6 Hz, 1H), 4.71-4.79 (m, 1H), 4.53 (td, J=3.8, 7.4 Hz, 1H), 4.38-4.45 (m, 1H), 4.22-4.33 (m, 1H), 3.13 (td, J=5.9, 14.0 Hz, 1H), 2.61 (s, 3H), 2.44 (ddd, J=1.95, 7.1, 14.0 Hz, 1H).

303
Example 89: {(2S,3S,5R)-5-[4-amino-3-(2-naphth-ylsulfanyl)-1H-pyrazolo[3,4-d]pyrimidin-1-yl]-3-hydroxytetrahydrofuran-2-yl}methyl Sulfamate
Compound I-210
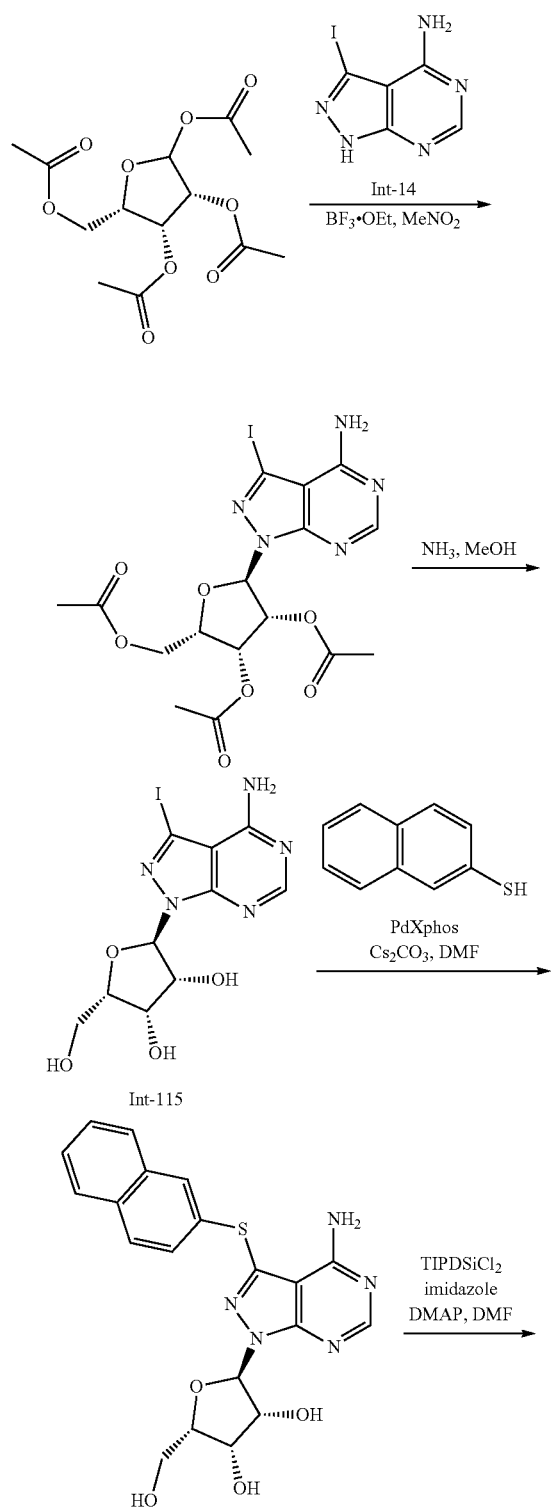
304
-continued
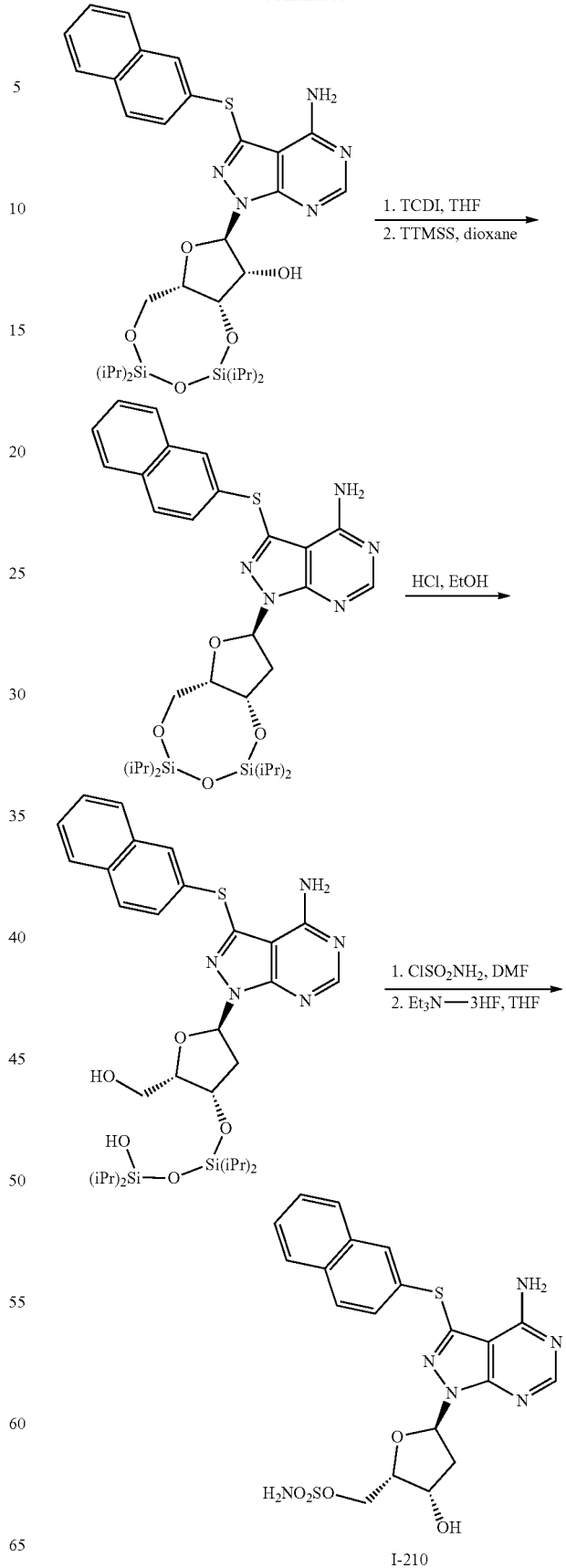

Step 1: (2S,3R,4R,5R)-2-(acetoxymethyl)-5-(4-amino-3-iodo-1H-pyrazolo[3,4-d]pyrimidin-1-yl)tetrahydrofuran-3,4-diyl Diacetate 4-Amino-3-iodo-1H-pyrazolo[3,4-d]pyrimidine (Intermediate 14, 18.38 g, 70.42 mmol) and 1,2,3,5-tetra-O-acetyl-L-lyxofuranose (prepared from L-lyxose as detailed in *Carbohydrate Res.* 1979, 69, 135-142) (29.14 g, 91.54 mmol) were dissolved in nitromethane (640 mL) under an atmosphere of argon. The reaction was cooled to 0° C. and boron trifluoride etherate (13.39 mL, 105.6 mmol) was added dropwise. The reaction mixture was allowed to warm slowly to rt and was stirred overnight. Saturated $NaHCO_3$ solution was added and the reaction mixture was extracted with EtOAc (2×). The organic solutions were combined, washed with water and brine, dried over $Na_2SO_4$, filtered and concentrated. The crude compound was purified by column chromatography to give (2S,3R,4R,5R)-2-(acetoxymethyl)-5-(4-amino-3-iodo-1H-pyrazolo[3,4-d]pyrimidin-1-yl)tetrahydrofuran-3,4-diyl diacetate (13.03 g, 35.6%) as a pale yellow oil. LCMS (FA): m/z 520 (M+H).

Step 2: (2R,3R,4S,5S)-2-(4-amino-3-iodo-1H-pyrazolo[3,4-d]pyrimidin-1-yl)-5-(hydroxymethyl)tetrahydrofuran-3,4-diol Intermediate 115

The title compound was prepared following the procedure described in Example 5 Step 3, substituting (2S,3R,4R,5R)-2-(acetoxymethyl)-5-(4-amino-3-iodo-1H-pyrazolo[3,4-d]pyrimidin-1-yl)tetrahydrofuran-3,4-diyl diacetate for Intermediate 15. LCMS (FA): m/z 394 (M+H).

Step 3: (2R,3R,4S,5S)-2-[4-amino-3-(2-naphthylsulfanyl)-1H-pyrazolo[3,4-d]pyrimidin-1-yl]-5-(hydroxymethyl)tetrahydrofuran-3,4-diol (2R,3R,4S,5S)-2-(4-Amino-3-iodo-1H-pyrazolo[3,4-d]pyrimidin-1-yl)-5-(hydroxymethyl)tetrahydrofuran-3,4-diol (Intermediate 115, 1.80 g, 4.58 mmol) and 2-naphthalenethiol (1.47 g, 9.16 mmol) were dissolved in DMF (20.5 mL). Cesium carbonate (2.98 g, 9.16 mmol) was added and the mixture was degassed with argon. XPhos Pd G2 (180 mg, 0.23 mmol) was added and the mixture was degassed again and then allowed to stir at 110° C. for 8 h. The mixture was adsorbed onto celite and the crude compound was purified by column chromatography to give (2R,3R,4S,5S)-2-[4-amino-3-(2-naphthylsulfanyl)-1H-pyrazolo[3,4-d]pyrimidin-1-yl]-5-(hydroxymethyl)tetrahydrofuran-3,4-diol (861 mg, 44%) as an orange solid. LCMS (FA): m/z=426 (M+H).

Steps 4-9: {(2S,3S,5R)-5-[4-amino-3-(2-naphthylsulfanyl)-1H-pyrazolo[3,4-d]pyrimidin-1-yl]-3-hydroxytetrahydrofuran-2-yl}methyl Sulfamate I-210

The title compound was prepared from (2R,3R,4S,5S)-2-[4-amino-3-(2-naphthylsulfanyl)-1H-pyrazolo[3,4-d]pyrimidin-1-yl]-5-(hydroxymethyl)tetrahydrofuran-3,4-diol following the procedures described in Example 83, steps 3-8. LCMS (FA): m/z=489 (M+H); $^1$H NMR (400 MHz, $CD_3OD$) δ 8.26 (s, 1H), 7.81-7.87 (m, 3H), 7.76-7.80 (m, 1H), 7.46-7.54 (m, 2H), 7.35-7.40 (m, 1H), 6.85 (dd, J=7.0, 5.9 Hz, 1H), 4.74-4.79 (m, 1H), 4.58 (dt, J=7.4, 3.7 Hz, 1H), 4.40-4.46 (m, 1H), 4.28-4.35 (m, 1H), 3.21 (dt, J=14.2, 5.8 Hz, 1H), 2.54 (ddd, J=14.1, 7.2, 1.9 Hz, 1H).

Example 90

The following compounds were prepared as described in the procedures in Example 89 using intermediate Intermediate 115 with the reagents and conditions described in the table below.

| Compound number | Sulfide | Step 1: Pd-catalyzed coupling Conditions | LCMS data | $^1$H NMR Data |
|---|---|---|---|---|
| I-215 | 2-fluoro-benzene-thiol | XPhos Pd G2, $Cs_2CO_3$, DMF, 105° C. 3 h MWI | LCMS (FA): m/z 457 (M + H) | $^1$H NMR (400 MHz, $d_6$-DMSO) δ 8.28 (s, 1H), 7.50 (br s, 2H), 7.28-7.40 (m, 2H), 7.08-7.20 (m, 2H), 6.68 (t, J = 6.5 Hz, 1H), 5.39 (d, J = 5.1 Hz, 1H), 4.57-4.64 (m, 1H), 4.30-4.36 (m, 1H), 4.26 (dd, J = 10.9, 2.9 Hz, 1H), 4.09 (dd, J = 10.8, 8.2 Hz, 1H), 2.96 (dt, J = 14.0, 5.8 Hz, 1H), 2.36-2.45 (m, 1H). |
| I-214 | 4-methyl benzene-thiol | XPhos Pd G2, $Cs_2CO_3$, DMF, 110° C. 2 h MWI | LCMS (FA): m/z 453 (M + H) | $^1$H NMR (400 MHz, $d_6$-DMSO) δ 8.24 (s, 1H), 7.49 (s, 2H), 7.19-7.23 (m, 2H), 7.14-7.18 (m, 2H), 6.67 (t, J = 6.5 Hz, 1H), 5.39 (d, J = 5.1 Hz, 1H), 4.61-4.66 (m, 1H), 4.35-4.40 (m, 1H), 4.27 (dd, J = 10.9, 2.9 Hz, 1H), 4.10 (dd, J = 10.9, 8.1 Hz, 1H), 3.01 (dt, J = 13.9, 5.9 Hz, 1H), 2.37-2.45 (m, 1H), 2.25 (s, 3H). |
| I-224 | 3-chloro-benzene-thiol | XPhos Pd G2, 140° C. 1 h $Cs_2CO_3$ DMF | LCMS (FA): m/z 473 (M + H) | $^1$H NMR (400 MHz, $d_6$-DMSO) δ 8.26 (s, 1H), 7.27-7.39 (m, 3H), 7.16 (d, J = 7.5 Hz, 1H), 6.71 (t, J = 6.5 Hz, 1H), 4.60-4.67 (m, 1H), 4.33-4.42 (m, 1H), 4.28 (dd, J = 10.8, 2.8 Hz, 1H), 4.10 (dd, J = 10.7, 8.2 Hz, 1H), 2.96-3.06 (m, 1H), 2.39-2.49 (m, 1H). |

-continued

| Compound number | Sulfide | Step 1: Pd-catalyzed coupling Conditions | LCMS data | $^1$H NMR Data |
|---|---|---|---|---|
| I-223 | 4-fluoro-benzene-thiol | XPhos Pd G2, 140° C. 1 h Cs$_2$CO$_3$ DMF | LCMS (FA): m/z 457 (M + H) | $^1$H NMR (400 MHz, CD$_3$OD) δ 8.23 (s, 1H), 7.35-7.46 (m, 2H), 7.04-7.15 (m, 2H), 6.78 (t, J = 6.2 Hz, 1H), 4.70-4.76 (m, 1H), 4.47-4.58 (m, 1H), 4.41 (dd, J = 10.8, 3.4 Hz, 1H), 4.27 (dd, J = 10.8, 7.5 Hz, 1H), 3.08-3.19 (m, 1H), 2.43-2.54 (m, 1H). |
| I-222 | 5-chloro-pyridine-2-thiol | XPhos Pd G2, 140° C. 1 h Cs$_2$CO$_3$ DMF | LCMS (FA): m/z 474 (M + H) | $^1$H NMR (400 MHz, d$_6$-DMSO) δ 8.48 (d, J = 2.3 Hz, 1H), 8.29 (s, 1H), 7.83 (dd, J = 8.6, 2.5 Hz, 1H), 7.50 (br s, 2H), 7.17 (d, J = 8.6 Hz, 1H), 6.73 (t, J = 6.5 Hz, 1H), 4.60-4.68 (m, 1H), 4.34-4.45 (m, 1H), 4.28 (dd, J = 10.8, 2.7 Hz, 1H), 4.11 (dd, J = 10.8, 8.3 Hz, 1H), 2.95-3.06 (m, 1H), 2.34-2.47 (m, 1H). |
| I-216 | 2,3-dihydro-1H-indene-5-thiol | XPhos Pd G2, 140° C. 1 h Cs$_2$CO$_3$ DMF | LCMS (FA): m/z 479 (M + H) | $^1$H NMR (400 MHz, CD$_3$OD) δ 8.23 (s, 1H), 7.08-7.27 (m, 3H), 6.80 (t, J = 6.4 Hz, 1H), 4.73-4.79 (m, 1H), 4.50-4.58 (m, 1H), 4.42 (dd, J = 10.8, 3.8 Hz, 1H), 4.29 (dd, J = 10.8, 7.3 Hz, 1H), 3.12-3.23 (m, 1H), 2.80-2.94 (m, 4H), 2.45-2.56 (m, 1H), 2.00-2.12 (m, 2H). |

Example 91: [(2S,3S,5R)-5-(4-amino-3-ethyl-1H-pyrazolo[3,4-d]pyrimidin-1-yl)-3-hydroxytetrahydrofuran-2-yl]methylsulfamate Compound I-212

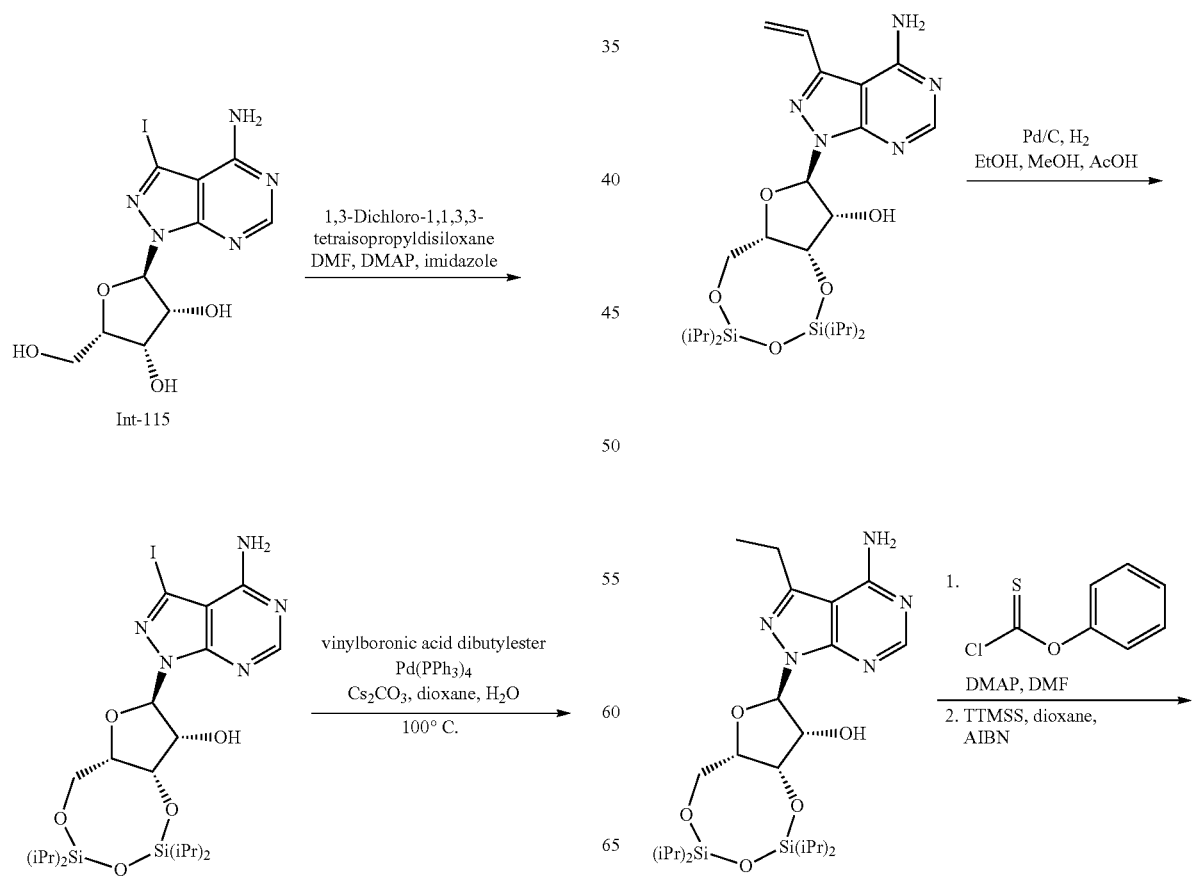

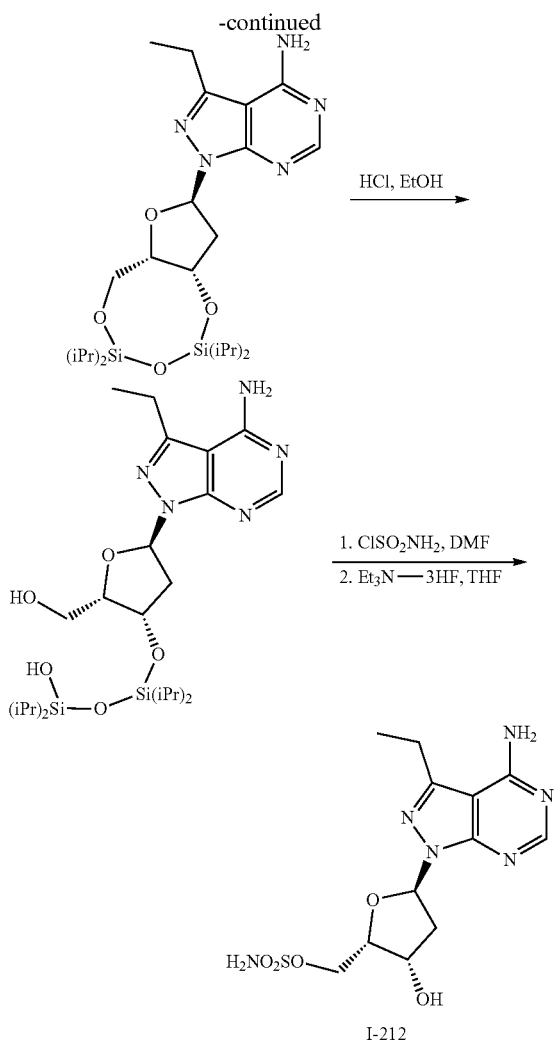

I-212

Step 1: (6aS,8R,9R,9aS)-8-(4-amino-3-iodo-1H-pyrazolo[3,4-d]pyrimidin-1-yl)-2,2,4,4-tetraisopropyltetrahydro-6H-furo[3,2-f][1,3,5,2,4]trioxadisilocin-9-ol The title compound was prepared as described in Example 83 Step 3 substituting Intermediate 115 for Intermediate 110 (57%). LCMS (FA): m/z 636 (M+H); $^1$H NMR (400 MHz, CDCl$_3$) δ 8.28 (s, 1H), 6.24 (d, J=6.4 Hz, 1H), 5.34 (br s, 1H), 4.60-4.64 (m, 1H), 4.54-4.60 (m, 1H), 3.91-4.00 (m, 1H), 3.84 (dd, J=10.3, 4.6 Hz, 1H), 3.04-3.17 (m, 1H), 0.93-1.16 (m, 28H).

Step 2: (6aS,8R,9R,9aS)-8-(4-amino-3-vinyl-1H-pyrazolo[3,4-d]pyrimidin-1-yl)-2,2,4,4-tetraisopropyltetrahydro-6H-furo[3,2-f][1,3,5,2,4]trioxadisilocin-9-ol To a microwave vial was added (6aS,8R,9R,9aS)-8-(4-amino-3-iodo-1Hpyrazolo[3,4-d]pyrimidin-1-yl)-2,2,4,4-tetraisopropyltetrahydro-6H-furo[3,2-f][1,3,5,2,4]trioxadisilocin-9-ol (0.915 g, 1.44 mmol), cesium carbonate (1.41 g, 4.32 mmol), vinylboronic acid dibutyl ester (0.476 mL, 2.16 mmol), tetrakis(triphenylphosphine)palladium(0) (0.083 g, 0.072 mmol), 1,4-dioxane (10.0 mL) and water (3.5 mL). The vial was capped, evacuated and backfilled with argon from a balloon. The reaction mixture was allowed to stir at 100° C. overnight. The mixture was partitioned between water and ethyl acetate. The phases were separated and the aqueous phase was extracted twice with ethyl acetate. The extracts were combined, washed with water and brine, dried over sodium sulfate, filtered and concentrated under reduced pressure. The crude compound was purified by silica gel chromatography to give (6aS,8R,9R,9aS)-8-(4-amino-3-vinyl-1H-pyrazolo[3,4-d]pyrimidin-1-yl)-2,2,4,4-tetraisopropyltetrahydro-6H-furo[3,2-f][1,3,5,2,4]trioxadisilocin-9-ol as a white solid (0.533 g, 69%). LCMS (FA): m/z 536 (M+H); $^1$H NMR (400 MHz, CDCl$_3$) δ 8.35 (s, 1H), 6.89-7.02 (m, 1H), 6.31 (d, J=6.4 Hz, 1H), 5.96-6.03 (m, 1H), 5.65-5.73 (m, 1H), 5.35-5.43 (m, 1H), 4.62-4.68 (m, 1H), 4.54-4.62 (m, 1H), 3.98 (t, J=10.2 Hz, 1H), 3.82-3.89 (m, 1H), 2.88-2.98 (m, 1H), 1.05-1.19 (m, 28H).

Step 3: (6aS,8R,9R,9aS)-8-(4-amino-3-ethyl-1H-pyrazolo[3,4-d]pyrimidin-1-yl)-2,2,4,4-tetraisopropyltetrahydro-6H-furo[3,2-f][1,3,5,2,4]trioxadisilocin-9-ol To a solution of (6aS,8R,9R,9aS)-8-(4-amino-3-vinyl-1H-pyrazolo[3,4-d]pyrimidin-1-yl)-2,2,4,4-tetraisopropyltetrahydro-6H-furo[3,2-f][1,3,5,2,4]trioxadisilocin-9-ol (0.51 g, 0.95 mmol) in ethanol (13.6 mL), methanol (15 mL) and acetic acid (0.054 mL) was added Pd/C (0.051 g, 10 wt. %). The mixture was allowed to stir under an atmosphere of hydrogen for 5 days. The mixture was diluted with ethanol and filtered through Celite. The filtrate was concentrated under reduced pressure and then dried in vacuo at 40° C. to afford the product (0.29 g, 57%). LCMS (FA): m/z 538 (M+H).

Step 4: O-[(6aS,8R,9R,9aR)-8-(4-amino-3-ethyl-1H-pyrazolo[3,4-d]pyrimidin-1-yl)-2,2,4,4-tetraisopropyltetrahydro-6H-furo[3,2-f][1,3,5,2,4]trioxadisilocin-9-yl] O-phenyl carbonothioate To a solution of (6aS,8R,9R,9aS)-8-(4-amino-3-ethyl-1H-pyrazolo[3,4-d]pyrimidin-1-yl)-2,2,4,4-tetraisopropyltetrahydro-6H-furo[3,2-f][1,3,5,2,4]trioxadisilocin-9-ol (0.50 g, 0.93 mmol) in DMF (10.0 mL) was added DMAP (0.227 mg, 1.86 mmol) and phenyl chlorothionocarbonate (0.154 mL, 1.11 mmol). The reaction mixture was allowed to stir at rt overnight. The mixture was partitioned between 0.1 N HCl solution and ethyl acetate. The phases were separated and the organic phase was washed with water and brine, dried over sodium sulfate, filtered and concentrated under reduced pressure. The crude compound was purified by silica gel chromatography to give O-[(6aS,8R,9R,9aR)-8-(4-amino-3-ethyl-1H-pyrazolo[3,4-d]pyrimidin-1-yl)-2,2,4,4-tetraisopropyltetrahydro-6H-furo[3,2-f][1,3,5,2,4]trioxadisilocin-9-yl] O-phenyl carbonothioate as a white solid (0.277 g, 44%). $^1$H NMR (400 MHz, CDCl$_3$) δ 8.22 (s, 1H), 7.17-7.25 (m, 2H), 7.08-7.12 (m, 1H), 6.82-6.89 (m, 2H), 6.65-6.72 (m, 1H), 6.54-6.60 (m, 1H), 5.49 (br s, 2H), 4.83-4.90 (m, 1H), 4.48-4.57 (m, 1H), 3.85 (t, J=10.2 Hz, 1H), 3.68-3.76 (m, 1H), 2.81 (q, J=7.5 Hz, 2H), 1.26 (t, J=7.5 Hz, 3H), 0.88-1.05 (m, 28H).

Step 5: 3-ethyl-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine To a solution of O-[(6aS,8R,9R,9aR)-8-(4-amino-3-ethyl-1H-pyrazolo[3,4-d]pyrimidin-1-yl)-2,2,4,4-tetraisopropyltetrahydro-6H-furo[3,2-f][1,3,5,2,4]trioxadisilocin-9-yl]O-phenyl carbonothioate (0.260 g, 0.386 mmol) in 1,4-dioxane (6.0 mL) was added AIBN (0.019 mg, 0.116 mmol) and tris(trimethylsilyl)silane (0.19 mL, 0.62 mmol). The reaction mixture was allowed to stir at 110° C. for 2 hours. The solution was concentrated to dryness and purified by silica gel chromatography to give 3-ethyl-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine as a white solid (0.15 g, 75%). LCMS (FA): m/z 522 (M+H); $^1$H NMR (400 MHz, CDCl$_3$) δ 8.20 (s, 1H), 6.66 (t, J=7.2 Hz, 1H), 5.48 (br s, 2H), 4.60-4.65 (m, 1H), 4.24-4.32 (m, 1H), 3.70-3.83 (m, 2H), 3.10-3.21 (m, 1H), 2.81 (q, J=7.6 Hz, 2H), 2.25-2.34 (m, 1H), 1.26 (t, J=7.5 Hz, 3H), 0.89-1.03 (m, 28H).

Steps 6-8: [(2S,3S,5R)-5-(4-amino-3-ethyl-1H-pyrazolo[3,4-d]pyrimidin-1-yl)-3-hydroxytetrahydrofuran-2-yl]methylsulfamate Compound I-212

The title compound was prepared as described in Example 83 Step 6 substituting 3-ethyl-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine for Intermediate 111 and then carrying the resulting compound through the procedures described in Example 1 Step 7 and Example 83 Step 8. LCMS (FA): m/z 359 (M+H); $^1$H NMR (400 MHz, d$_6$-DMSO) δ 8.17 (s, 1H), 7.48 (s, 2H), 6.61 (t, J=6.7 Hz, 1H), 5.35 (d, J=5.3 Hz, 1H), 4.59-4.67 (m, 1H), 4.30-4.37 (m, 1H), 4.26 (dd, J=10.8, 3.0 Hz, 1H), 4.09 (dd, J=10.7, 8.2 Hz, 1H), 2.93-3.04 (m, 3H), 2.29-2.38 (m, 1H), 1.22 (t, J=7.5 Hz, 3H).

Example 92: {(2S,3S,5R)-5-[4-amino-3-(difluoromethyl)-1H-pyrazolo[3,4-d]pyrimidin-1-yl]-3-hydroxytetrahydrofuran-2-yl}methyl Sulfamate Compound I-217

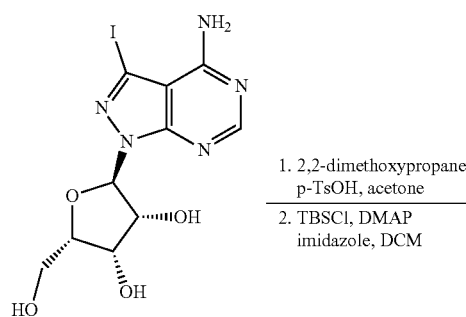
Int-115

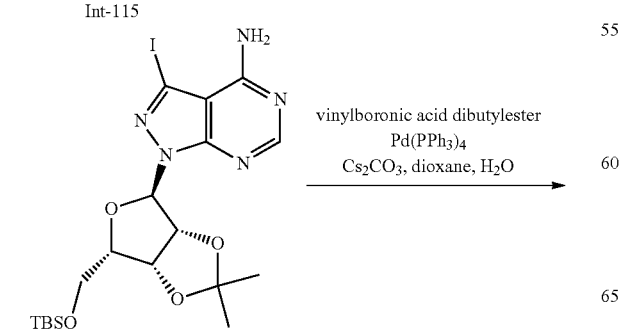

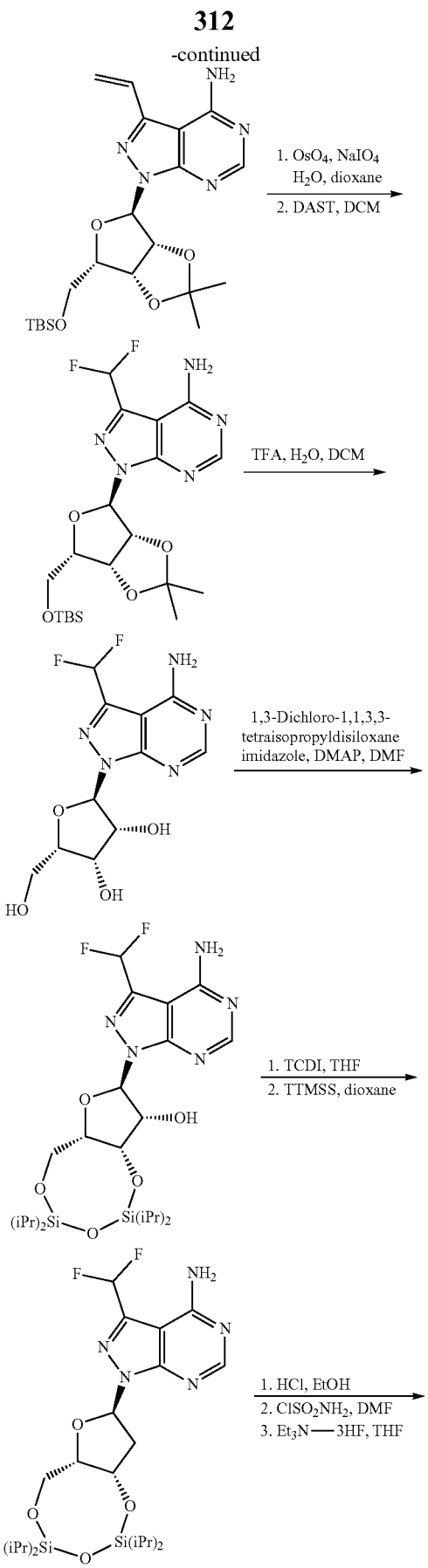

-continued

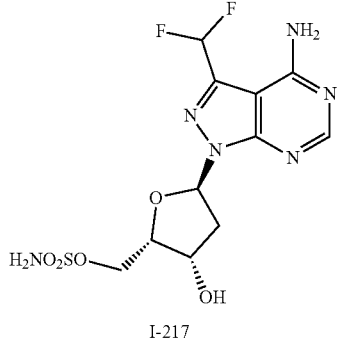

I-217

Step 1: [(3aR,4S,6R,6aR)-6-(4-amino-3-iodo-1H-pyrazolo[3,4-d]pyrimidin-1-yl)-2,2-dimethyltetrahydrofuro[3,4-d][1,3]dioxol-4-yl]methanol The title compound was prepared as described in Example 1 Step 6 substituting Intermediate 115 for Intermediate 6.

Step 2: 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-iodo-1H-pyrazolo[3,4-d]pyrimidin-4-amine The title compound was prepared as described in Example 5 Step 5 substituting [(3aR,4S,6R,6aR)-6-(4-amino-3-iodo-1H-pyrazolo[3,4-d]pyrimidin-1-yl)-2,2-dimethyltetrahydrofuro[3,4-d][1,3]dioxol-4-yl]methanol for Intermediate 17.

Step 3: 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-vinyl-1H-pyrazolo[3,4-d]pyrimidin-4-amine The title compound was prepared as described in Example 91 step 2 substituting 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-iodo-1H-pyrazolo[3,4-d]pyrimidin-4-amine for (6aS,8R,9R,9aS)-8-[4-amino-3-iodo-1H-pyrazolo[3,4-d]pyrimidin-1-yl]-2,2,4,4-tetraisopropyltetrahydro-6H-furo[3,2-f][1,3,5,2,4]trioxadisilocin-9-ol.

Step 4: 4-amino-1-[(3aR,4R,6S,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carbaldehyde To a solution of 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-vinyl-1H-pyrazolo[3,4-d]pyrimidin-4-amine (0.252 g, 0.563 mmol) in 1,4-dioxane (3.1 mL) and water (1.2 mL) was added 4% osmium tetroxide in water solution (0.06 mL, 0.017 mmol). The reaction mixture was allowed to stir at rt for 1 h. To the mixture was added sodium metaperiodate (0.361 g, 1.69 mmol) and the mixture was allowed to stir at rt for an additional 2 h. The mixture was partitioned between water and ethyl acetate. The phases were separated and the aqueous phase was extracted twice with ethyl acetate. The extracts were combined, washed with saturated sodium bisulfite solution, water and brine and then dried over sodium sulfate, filtered and concentrated under reduced pressure. The crude compound was purified by silica gel chromatography to give 4-amino-1-[(3aR,4R,6S,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carbaldehyde as a white solid (0.177 g, 70%). LCMS (FA): m/z 450 (M+H); $^1$H NMR (400 MHz, CDCl$_3$) δ 9.95 (s, 1H), 8.36 (s, 1H), 6.51-6.53 (m, 1H), 5.36 (d, J=5.9 Hz, 1H), 5.07-5.13 (m, 1H), 4.37-4.43 (m, 1H), 3.92-3.99 (m, 1H), 3.75-3.83 (m, 1H), 1.52 (s, 3H), 1.36 (s, 3H), 0.83 (s, 9H), 0.02 (s, 3H), 0.00 (s, 3H).

Step 5: 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine To a solution of 4-amino-1-[(3aR,4R,6S,6aR)-6-({[tert-butyl(dimethyl)silyl]oxy}methyl)-2,2-dimethyltetrahydrofuro[3,4-d][1,3]dioxol-4-yl]-1H-pyrazolo[3,4-d]pyrimidine-3-carbaldehyde (0.170 g, 0.378 mmol) in methylene chloride (2 mL) at 0° C. was added diethylaminosulfur trifluoride (0.125 mL, 0.948 mmol) dropwise. Upon completion of addition, the mixture was warmed to rt and stirred for 90 min. Excess fluorinating agent was quenched with saturated sodium bicarbonate solution and then diluted with ethyl acetate. The mixture was twice extracted into ethyl acetate. The extracts were combined, washed with brine, then dried over sodium sulfate, filtered and concentrated under reduced pressure. The crude compound was purified by silica gel chromatography to give 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine as a white solid (0.078 g, 44%). LCMS (FA): m/z 472 (M+H); $^1$H NMR (400 MHz, CDCl$_3$) δ 8.36 (s, 1H), 6.62-6.94 (m, 1H), 6.45 (s, 1H), 5.28 (d, J=5.9 Hz, 1H), 5.01-5.07 (m, 1H), 4.25-4.37 (m, 1H), 3.88-3.94 (m, 1H), 3.72-3.78 (m, 1H), 1.48 (s, 3H), 1.32 (s, 3H), 0.81 (s, 9H), 0.00 (s, 3H), −0.02 (s, 3H).

Step 6: (2R,3R,4S,5S)-2-[4-amino-3-(difluoromethyl)-1H-pyrazolo[3,4-d]pyrimidin-1-yl]-5-(hydroxymethyl)tetrahydrofuran-3,4-diol To a solution of 1-[(3aR,4R,6S,6aR)-6-({[tert-butyl(dimethyl)silyl]oxy}methyl)-2,2-dimethyltetrahydrofuro[3,4-d][1,3]dioxol-4-yl]-3-(difluoromethyl)-1H-pyrazolo[3,4-d]pyrimidin-4-amine (0.078 g, 0.16 mmol) in methylene chloride (2 mL) was added water (0.031 mL) and trifluoroacetic acid (0.31 mL, 4.14 mmol). The mixture was allowed to stir at rt for 3 h and was then concentrated to dryness. The crude product was purified by silica gel chromatography to give (2R,3R,4S,5S)-2-[4-amino-3-(difluoromethyl)-1H-pyrazolo[3,4-d]pyrimidin-1-yl]-5-(hydroxymethyl)tetrahydrofuran-3,4-diol as a white solid (0.035 g, 67%). LCMS (FA): m/z 318 (M+H); $^1$H NMR (400 MHz, CD$_3$OD) δ 8.33 (s, 1H), 6.94-7.27 (m, 1H), 6.37 (d, J=5.9 Hz, 1H), 5.10-5.17 (m, 1H), 4.45-4.51 (m, 2H), 3.76-3.87 (m, 2H).

Steps 7-12: {(2S,3S,5R)-5-[4-amino-3-(difluoromethyl)-1H-pyrazolo[3,4-d]pyrimidin-1-yl]-3-hydroxytetrahydrofuran-2-yl}methyl Sulfamate I-217

The title compound was prepared as described in Example 83 Steps 3-8 using (2R,3R,4S,5S)-2-[4-amino-3-(difluoromethyl)-1H-pyrazolo[3,4-d]pyrimidin-1-yl]-5-(hydroxymethyl)tetrahydrofuran-3,4-diol. LCMS (FA): m/z 381 (M+H); $^1$H NMR (400 MHz, CD$_3$OD) δ 8.33 (s, 1H), 6.92-7.23 (m, 1H), 6.84 (t, J=6.5 Hz, 1H), 4.75-4.80 (m, 1H), 4.52-4.58 (m, 1H), 4.42 (dd, J=10.8, 3.9 Hz, 1H), 4.29 (dd, J=10.8, 7.3 Hz, 1H), 3.13-3.21 (m, 1H), 2.49-2.57 (m, 1H).

Example 93: [(2S,3S,5R)-5-{4-amino-3-[(2,2-difluoroethyl)sulfanyl]-1H-pyrazolo[3,4-d]pyrimidin-1-yl}-3-hydroxytetrahydrofuran-2-yl]methyl Sulfamate Compound I-227

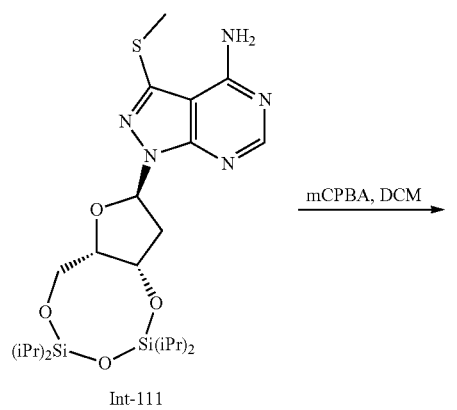

Int-111

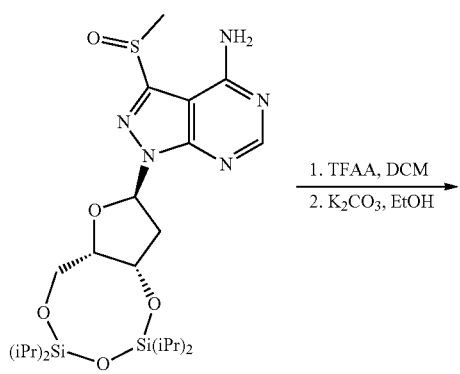

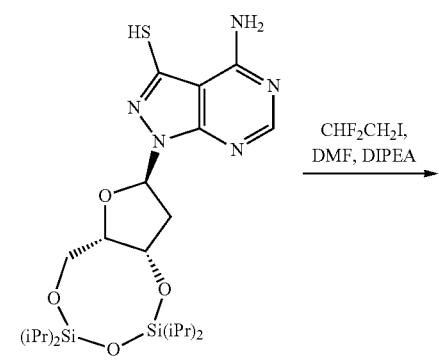

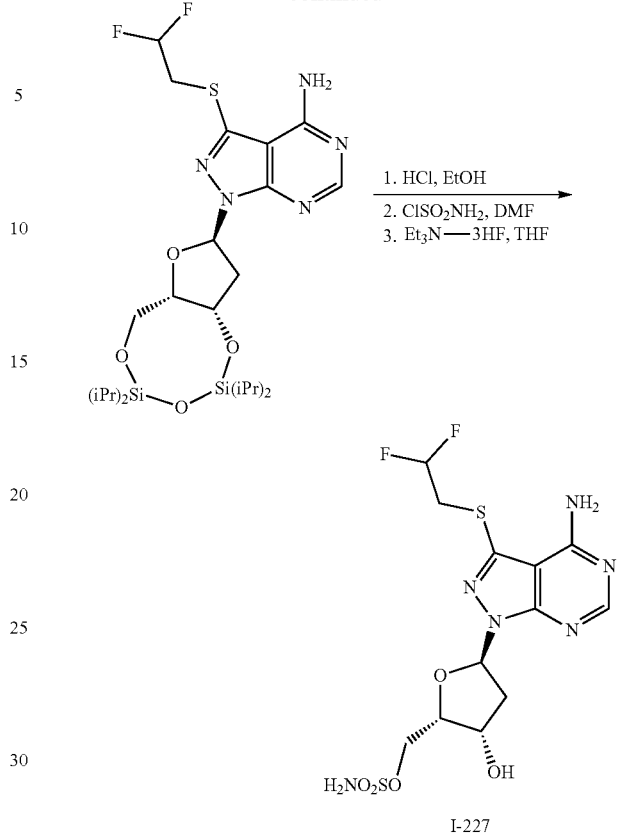

I-227

Step 1: 3-[(R)-methylsulfinyl]-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine and 3-[(S)-methylsulfinyl]-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine Into a solution of Intermediate 111 (0.590 g, 1.09 mmol) in DCM (12.4 mL) was added a solution of 77% mCPBA/water (0.269 g, 1.20 mmol) in DCM (16.5 mL) at 0° C. and the reaction mixture was allowed to stir for 1 h at the same temperature. The reaction mixture was quenched with saturated NaHCO₃ solution and extracted into DCM 2×. The organic phases were combined, washed with water and brine then dried over sodium sulfate, filtered and concentrated under reduced pressure. The crude product was purified by silica gel to afford the product as a mixture of diasteromers (515 mg, 85%). This his compound was isolated as a mixture of two stereoisomers. LCMS (FA): m/z 557 (M+H); $^1$H NMR (400 MHz, CDCl₃) δ 8.42 (s, 1H), 8.24 (br s, 1H), 6.85 (dt, J=16.5, 7.1 Hz, 1H), 5.91 (br s, 1H), 4.76 (br s, 1H), 4.39 (dddd, J=19.9, 9.8, 4.9, 2.6 Hz, 1H), 3.81-3.98 (m, 2H), 3.13-3.26 (m, 1H), 2.99 (s, 1.5H), 2.99 (s, 1.5H), 2.50 (ddd, J=13.6, 6.6, 4.3 Hz, 1H), 0.99-1.17 (m, 28H).

Step 2: 4-amino-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidine-3-thiol A solution of 3-(methylsulfinyl)-1-[(6aR,8S,9aR)-2,2,4,4-tetraisopropyltetrahydro-6H-furo[3,2-f][1,3,5,2,4]trioxadisilocin-8-yl]-1H-pyrazolo[3,4-d]pyrimidin-4-amine (0.515 g, 0.926 mmol), DCM (11.8 mL) and trifluoroacetic anhydride (5.97 mL, 42.2 mmol) was allowed to stir at rt overnight under an atmosphere of argon. After complete consumption of starting material, the reaction mixture was diluted with dry DCM (30 mL) and concentrated under reduced pressure at 30° C. then dried under vacuum. The crude compound was placed into an ice bath and ethanol (6 mL) was added followed by potassium carbonate (0.512 g, 3.71 mmol). The reaction was allowed to warm at rt and to stir for 15 min under an argon atmosphere. The reaction mixture was diluted with ethyl acetate (50 mL) and filtered to remove excess $K_2CO_3$. A saturated solution of $NH_4Cl$ (50 mL) was added and the mixture was extracted with ethyl acetate twice. The extracts were combined, washed with brine then dried over sodium sulfate, filtered and concentrated under reduced pressure to afford the product as a yellow solid (522 mg, quant.). LCMS (FA): m/z 526 (M+H).

Step 3: 3-[(2,2-difluoroethyl)sulfanyl]-1-[(6aS,8R, 9aS)-2,2,4,4-tetraisopropyltetrahydro-6H-furo[3,2-f] [1,3,5,2,4]trioxadisilocin-8-yl]-1H-pyrazolo[3,4-d] pyrimidin-4-amine 4-Amino-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidine-3-thiol (0.209 g, 0.397 mmol) was dissolved in DMF (1.00 mL) and DIPEA (0.208 mL, 1.19 mmol) was added, followed by the 2-iodo-1,1-difluoroethane (0.114 g, 0.596 mmol). The reaction mixture was allowed to stir at rt overnight. Upon completion, the product was extracted into ethyl acetate (2×50 mL). The organic phases were combined, washed with water and brine then dried over sodium sulfate, filtered and concentrated under reduced pressure. The crude product was purified by silica gel chromatography to afford 3-[(2,2-difluoroethyl)sulfanyl]-1-[(6aS,8R,9aS)-2,2,4,4-tetraisopropyltetrahydro-6H-furo[3,2-f][1,3,5,2,4]trioxadisilocin-8-yl]-1H-pyrazolo[3,4-d]pyrimidin-4-amine as a white solid (117 mg, 50%). $^1$H NMR (400 MHz, CDCl$_3$) δ 8.37 (s, 1H), 6.79 (t, J=7.2 Hz, 1H), 5.89-6.27 (m, 1H), 4.76-4.79 (m, 1H), 4.39 (ddd, J=9.8, 4.8, 2.5 Hz, 1H), 3.84-3.96 (m, 2H), 3.42-3.55 (m, 2H), 3.19-3.28 (m, 1H), 2.47 (dd, J=13.6, 6.6 Hz, 1H), 1.02-1.16 (m, 28H).

Steps 4-6: [(2S,3S,5R)-5-{4-amino-3-[(2,2-difluoroethyl)sulfanyl]-1H-pyrazolo[3,4-d]pyrimidin-1-yl}-3-hydroxytetrahydrofuran-2-yl]methyl Sulfamate I-227

The title compound was prepared as described in Example 83 Steps 6-8 substituting 3-[(2,2-difluoroethyl)sulfanyl]-1-[(6aS,8R,9aS)-2,2,4,4-tetraisopropyltetrahydro-6H-furo[3, 2-f][1,3,5,2,4]trioxadisilocin-8-yl]-1H-pyrazolo[3,4-d]pyrimidin-4-amine for Intermediate 111 LCMS (FA): m/z 427 (M+H); $^1$H NMR (400 MHz, CD$_3$OD) δ 8.21 (s, 1H), 6.74 (t, J=6.4 Hz, 1H), 5.96-6.34 (m, 1H), 4.74-4.78 (m, 1H), 4.51 (dt, J=7.4, 3.8 Hz, 1H), 4.35-4.43 (m, 1H), 4.22-4.30 (m, 1H), 3.46-3.62 (m, 2H), 3.13 (dt, J=14.1, 5.8 Hz, 1H), 2.47 (ddd, J=14.0, 7.2, 2.2 Hz, 1H).

Example 94: {(2S,3S,5R)-5-[4-amino-3-(benzylsulfanyl)-1H-pyrazolo[3,4-d]pyrimidin-1-yl]-3-hydroxytetrahydrofuran-2-yl}methyl Sulfamate Compound I-221

The title compound was prepared as described above in Example 93 using benzyl bromide instead of 2-iodo-1,1-difluoroethane in Step 3. LCMS (FA): m/z 453 (M+H); $^1$H NMR (400 MHz, CD$_3$OD) δ 8.16 (s, 1H), 7.15-7.29 (m, 5H), 6.71 (t, J=6.4 Hz, 1H), 4.71 (br s, 1H), 4.36-4.47 (m, 2H), 4.22-4.35 (m, 3H), 3.07 (dt, J=14.1, 5.7 Hz, 1H), 2.43 (ddd, J=14.1, 7.3, 1.8 Hz, 1H).

Example 95: [(2S,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl Sulfamate Compound I-211

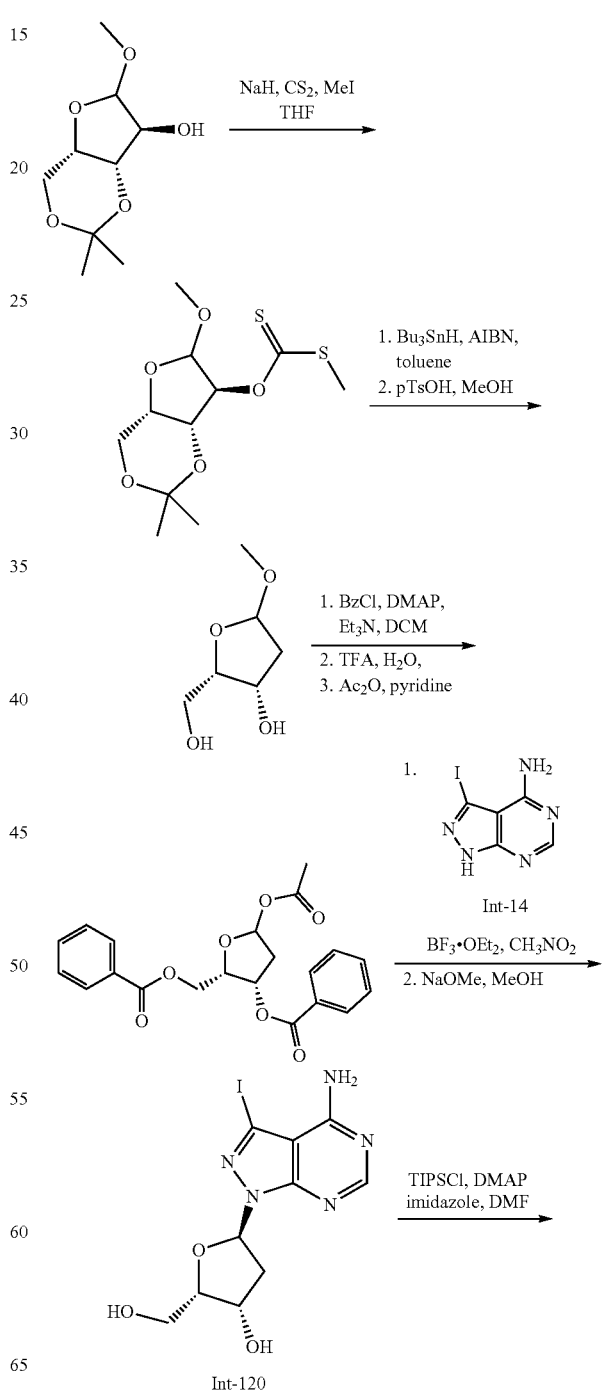

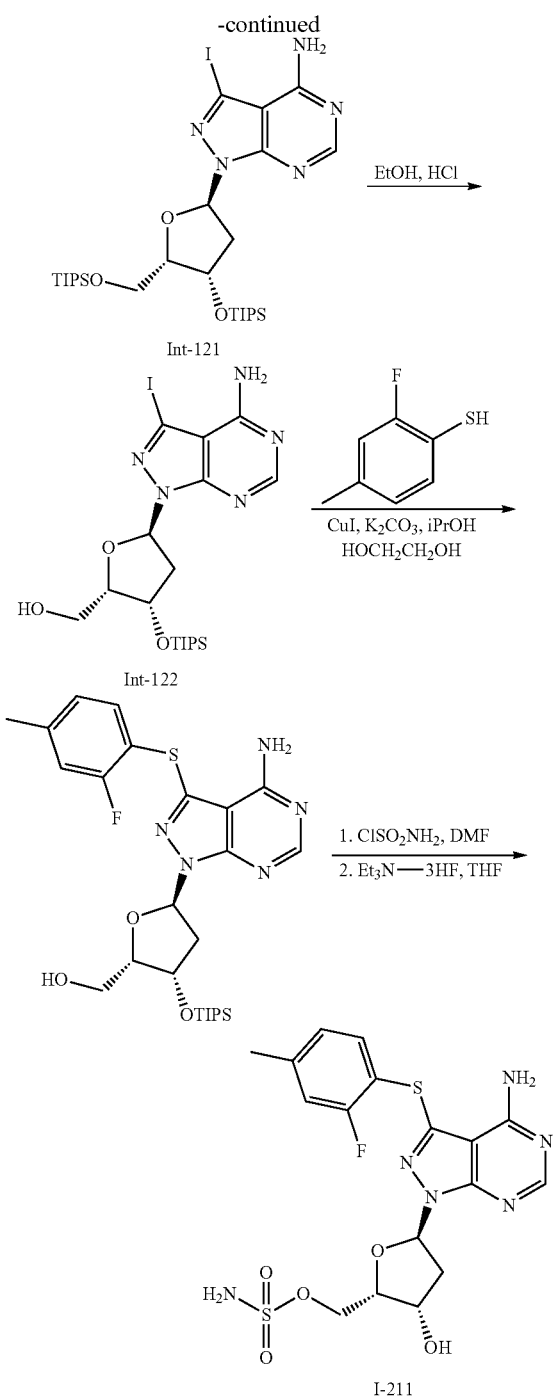

was stirred for another 0.5 h. Methyl iodide (229.4 g, 1.6 mol) was subsequently added dropwise and the reaction mixture was allowed to stir an additional 15 min at rt. Excess base was quenched by the careful dropwise addition acetic acid (30 mL). The resulting mixture was diluted with ether and solids were removed by suction filtration. The filtrate was concentrated under reduced pressure and the crude oily residue was purified by silica gel chromatography to afford the desired product as a mixture of diastereomers (210 g, 97.1% yield). $^1$H NMR (400 MHz, CDCl$_3$) δ 5.79 (s, 1H), 5.72 (dd, J=4.5, 2.0 Hz, 1H), 5.37 (d, J=4.5 Hz, 1H), 5.10 (s, 1H), 4.55 (dd, J=4.0, 2.0 Hz, 1H), 4.41 (d, J=4.4 Hz, 1H), 4.27-4.34 (m, 1H), 4.05-4.21 (m, 2H), 3.96-4.04 (m, 1H), 3.84-3.95 (m, 2H), 3.46 (s, 3H), 3.41 (s, 3H), 2.61 (d, J=2.3 Hz, 6H), 1.37-1.47 (m, 12H).

Step 2: (2S,3S)-2-(hydroxymethyl)-5-methoxytetrahydrofuran-3-ol

A solution of O-[(4aS,7S,7aR)-6-methoxy-2,2-dimethyltetrahydro-4H-furo[3,2-d][1,3]dioxin-7-yl] S-methyl carbonodithioate (200 g, 679 mmol) and AIBN (33.45 g, 203.8 mmol) in toluene (2400 mL) was stirred at reflux under nitrogen. To this heated solution was added tributyltin hydride (337.4 g, 1.15 mol). Upon completion of addition, heating was continued for 4 h. The reaction mixture was allowed to cool to rt and MeOH (1200 mL) was added followed by p-toluenesulfonic acid monohydrate (129 g, 679 mmol). The mixture was allowed to stir at rt for 1 h. Ammonium hydroxide (1000 mL) was added and the mixture was stirred at rt for 1 h. The aqueous layer was separated and washed with petroleum ether (2×1000 mL) to remove tin byproducts. The washed aqueous phase was concentrated under reduced pressure to afford an oily solid mixture. The mixture was suspended in EtOAc (1000 mL) and the solids removed under suction filtration. The solids were washed with additional EtOAc. The filtrate was concentrated under reduced pressure to afford a crude residue which was further purified by silica gel chromatography to afford the product as a colorless oil (172 g. 55% yield) which was slightly impure and a mixture of diastereomers.

Step 3: [(2S,3S)-3-(benzoyloxy)-5-methoxytetrahydrofuran-2-yl]methyl Benzoate

To a solution of (2S,3S)-2-(hydroxymethyl)-5-methoxytetrahydrofuran-3-ol (100 g, 0.67 mol) in DCM (2000 mL) was added DMAP (16.5 g, 0.13 mol) and triethylamine (341.5 g, 3.37 mol). The reaction mixture was allowed to cool in an ice-water bath and then benzoyl chloride (237.2 g, 1.69 mol) was added dropwise. Upon completion of addition, the reaction mixture was allowed to warm to rt and to stir 1 h. The reaction mixture was washed with water (1000 mL×2) then brine (1000 mL×2), dried over sodium sulfate, filtered and concentrated under reduced pressure. The crude product was purified by silica gel chromatography to afford the desired product as two separable diastereomers (90 g, 39%) and (90 g, 39%) which were individually characterized, but mixed for use in the following step.

Diastereomer 1 (less polar): $^1$H NMR (400 MHz, CDCl$_3$) δ 7.88-7.94 (m, 4H), 7.41-7.50 (m, 2H), 7.29-7.36 (m, 4H), 5.66 (ddd, J=6.8, 4.0, 3.3 Hz, 1H), 5.17 (dd, J=5.5, 2.6 Hz, 1H), 4.50-4.55 (m, 2H), 4.44-4.50 (m, 1H), 3.32 (s, 3H), 2.34-2.42 (m, 1H), 2.23-2.31 (m, 1H).

Diastereomer 2 (more polar): $^1$H NMR (400 MHz, CDCl$_3$) δ 7.86-7.95 (m, 4H), 7.39-7.49 (m, 2H), 7.30 (td, Step 1: O-[(4aS,7S,7aR)-6-methoxy-2,2-dimethyltetrahydro-4H-furo[3,2-d][1,3]dioxin-7-yl] S-methyl Carbonodithioate To a solution of (4aS,7S,7aS)-6-methoxy-2,2-dimethyltetrahydro-4H-furo[3,2-d][1,3]dioxin-7-ol (prepared from L-xylose as described in *Bioorg. Med. Chem.*, 2002, 10, 215-226, 150.0 g, 734.5 mmol) in THF (3 L) was added sodium hydride (60% in oil, 52.88 g, 1.3 mol) in 3 portions at rt. After addition of the base, the resulting mixture was allowed to stir at rt for 0.5 h. Carbon disulfide (190.2 g, 2.5 mol) was then added dropwise at rt and the resulting mixture J=7.5, 5.8 Hz, 4H), 5.66 (ddd, J=7.0, 4.9, 2.0 Hz, 1H), 5.01-5.08 (m, 1H), 4.46-4.60 (m, 3H), 3.34 (s, 3H), 2.42 (ddd, J=14.6, 7.1, 5.5 Hz, 1H), 2.18 (d, J=14.6 Hz, 1H).

Step 4: [(2S,3S)-3-(benzoyloxy)-5-hydroxytetrahydrofuran-2-yl]methyl Benzoate To a cooled (0° C.) solution of [(2S,3S)-3-(benzoyloxy)-5-methoxytetrahydrofuran-2-yl]methyl benzoate (mixed diastereomers, 150 g, 0.42 mol) in water (150 mL) was added TFA (600 mL). The reaction mixture was allowed to stir at rt for 2 h, then diluted with water (200 mL) and neutralized with saturated aqueous sodium bicarbonate solution. The mixture was extracted with EtOAc, washed with water and brine, dried over sodium sulfate, filtered and concentrated under reduced pressure to afford the crude titled product (140 g, 97%) as brown oil, which was used as obtained.

Step 5: (2S,3S)-5-acetoxy-2-[(benzoyloxy)methyl]tetrahydrofuran-3-yl Benzoate To a solution of [(2S,3S)-3-(benzoyloxy)-5-hydroxytetrahydrofuran-2-yl]methyl benzoate (175 g, 0.511 mol) in pyridine (1750 mL, 22.49 mol) was added acetic anhydride (875 mL, 9.71 mol). The reaction mixture was allowed to stir at rt for 2 h before being concentrated under reduced pressure. The residue was dissolved in DCM (1000 mL) and neutralized with saturated sodium bicarbonate solution. The phases were separated and the aqueous layer was extracted with DCM (500 mL×3). The combined extracts were washed with water and brine then dried over sodium sulfate, filtered and concentrated under reduced pressure to afford the product as a crude oil. The desired product was purified by silica gel chromatography and recovered as a pale yellow oil (89 g, 45%). $^1$H NMR (400 MHz, CDCl$_3$) δ 7.92 (d, J=8.3 Hz, 4H), 7.43-7.54 (m, 2H), 7.29-7.41 (m, 4H), 6.46 (dd, J=5.5, 2.8 Hz, 1H), 5.76 (dt, J=6.3, 4.4 Hz, 1H), 4.49-4.66 (m, 3H), 2.42-2.57 (m, 2H), 2.01 (s, 3H).

Step 6: (2S,3S,5R)-5-(4-amino-3-iodo-1H-pyrazolo[3,4-d]pyrimidin-1-yl)-2-[(benzoyloxy)methyl]tetrahydrofuran-3-yl Benzoate A mixture of Intermediate 14 (54 g, 207 mmol) and (2S,3S)-5-acetoxy-2-[(benzoyloxy)methyl]tetrahydrofuran-3-yl benzoate (87.5 g, 227 mmol) was azeotropically dried by coevaporation from acetonitrile (400 mL) 3 times. The mixture was suspended in dry nitromethane (1500 mL) and cooled in an ice-water bath. To this suspension was added boron trifluoride etherate (39.9 mL, 314 mmol) dropwise. This mixture was allowed to warm to rt and stirred for 16 h. The mixture was diluted with EtOAc (250 mL) and saturated aqueous sodium bicarbonate solution (250 mL) was added. The phases were separated and the aqueous layer was extracted with EtOAc (250 mL×3). The combined extracts were washed with water and brine, dried over sodium sulfate, filtered and concentrated under reduced pressure. After purification by silica gel chromatography, the desired product was isolated as a pale yellow solid (54 g, 45.2% yield). LCMS (FA): m/z 586 (M+H); $^1$H NMR (400 MHz, CDCl$_3$) δ 8.37 (s, 1H), 8.04-8.09 (m, 2H), 7.96-8.02 (m, 2H), 7.57-7.63 (m, 1H), 7.50-7.56 (m, 1H), 7.43-7.50 (m, 2H), 7.36-7.43 (m, 2H), 6.90 (dd, J=7.2, 5.4 Hz, 1H), 6.38 (br s, 2H), 6.14 (ddd, J=6.1, 4.0, 2.6 Hz, 1H), 4.90-5.00 (m, 1H), 4.55-4.75 (m, 2H), 3.45 (dt, J=14.5, 5.9 Hz, 1H), 2.69-2.84 (m, 1H).

Step 7: (2S,3S,5R)-5-(4-amino-3-iodo-1H-pyrazolo[3,4-d]pyrimidin-1-yl)-2-(hydroxymethyl)tetrahydrofuran-3-ol Intermediate 120

The title compound was prepared following the procedure outlined in Example 3 Step 4, substituting ((2S,3S,5R)-5-(4-amino-3-iodo-1H-pyrazolo[3,4-d]pyrimidin-1-yl)-2-[(benzoyloxy)methyl]tetrahydrofuran-3-yl benzoate for Intermediate 10 to afford Intermediate 120 as a yellow solid (84%). LCMS (FA): m/z 378 (M+H); $^1$H NMR (400 MHz, d$_6$-DMSO) δ 8.24 (s, 1H), 6.57 (t, J=6.7 Hz, 1H), 5.03 (d, J=5.0 Hz, 1H), 4.43-4.59 (m, 2H), 4.02-4.19 (m, 1H), 3.57-3.69 (m, 1H), 3.43-3.57 (m, 1H), 2.93 (dt, J=14.1, 5.8 Hz, 1H), 2.32 (ddd, J=13.7, 7.1, 1.3 Hz, 1H).

Step 8: 3-iodo-1-[(2R,4S,5S)-4-[(triisopropylsilyl)oxy]-5-{[(triisopropylsilyl)oxy]methyl}tetrahydrofuran-2-yl]-1H-pyrazolo[3,4-d]pyrimidin-4-amine Intermediate 121

To a solution of Intermediate 120 (44 g, 117 mmol), DMAP (2.85 g, 23.33 mmol) and 1H-imidazole (79.42 g, 1.17 mol) in DMF (440 mL) was added triisopropylsilyl chloride (180. g, 933 mmol). The reaction mixture was stirred at 40° C. for 48 h. After cooling to rt, the reaction mixture was diluted with saturated aqueous sodium bicarbonate solution (1000 mL) and extracted with EtOAc (1000 mL×3). The extracts were combined and washed with brine, dried over sodium sulfate, filtered and concentrated under reduced pressure. The crude mixture was purified by silica gel chromatography to afford the product (42.8 g, 70% yield) as white solid. LCMS (FA): m/z 690 (M+H); $^1$H NMR (400 MHz, CDCl$_3$) δ 8.34 (s, 1H), 6.70 (t, J=5.6 Hz, 1H), 5.99 (br s, 2H), 5.01 (dd, J=4.0, 9.2 Hz, 1H), 4.35 (dd, J=5.2, 9.6 Hz, 1H), 4.02 (dd, J=5.6, 10.8 Hz, 1H), 3.89-3.90 (m, 1H), 3.00-3.05 (m, 1H), 2.50-2.55 (m, 1H), 1.03-1.15 (m, 42H).

Step 9: {(2S,3S,5R)-5-(4-amino-3-iodo-1H-pyrazolo[3,4-d]pyrimidin-1-yl)-3-[(triisopropylsilyl)oxy]tetrahydrofuran-2-yl}methanol Intermediate 122

To an ice water-cooled mixture of Intermediate 121 (42.75 g, 61.97 mmol) in EtOH (640 mL) was added a solution of HCl in EtOH (1.0 M, 186 mL). The reaction mixture was allowed to stir at rt for 16 h. Excess acid was quenched by the addition of triethylamine and the reaction mixture was concentrated under reduced pressure. The crude material was purified by silica gel chromatography to afford the product, contaminated with an impurity. The impurity was removed by trituration with MTBE (150 mL) to afford pure product (14.75 g, 45%) as white solid. LCMS (FA): m/z 534 (M+H); $^1$H NMR (400 MHz, CDCl$_3$) δ 8.34 (s, 1H), 6.73 (dd, J=3.6, 7.2 Hz, 1H), 6.11 (br s, 2H), 5.20-5.25 (m, 1H), 4.35-4.38 (m, 1H), 3.93 (dd, J=5.6, 12.8 Hz, 1H), 3.85 (dd, J=3.2, 8.8 Hz, 1H), 3.00-3.06 (m, 1H), 2.49-2.55 (m, 1H), 1.10-1.13 (m, 21H).

Step 10: {(2S,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methanol To a solution of Intermediate 122 (8.0 g, 15 mmol) in 2-propanol (160 mL) was added copper(I) iodide (430 mg, 2.3 mmol), potassium carbonate (4.2 g, 30 mmol) and ethane-1,2-diol (1.9 g, 30 mmol), followed by 2-fluoro-4-methylbenzenethiol (6.4 g, 45 mmol). The resulting mixture was degassed under nitrogen flow, warmed and allowed to stir at reflux for 4 h. The reaction mixture was allowed to cool to rt and was filtered to remove solids. The filtrate was diluted with EtOAc (200 mL). The resulting mixture washed with water (200 mL×3), dried over sodium sulfate, filtered and concentrated under reduced pressure. The crude residue was purified by silica gel chromatography to provide the desired product (5.74 g, 70%) as a light yellow solid. LCMS (FA): m/z 548 (M+H); $^1$H NMR (400 MHz, CDCl$_3$) δ 8.32 (s, 1H), 7.19 (dd, J=8.0, 8.0 Hz, 1H), 6.88 (dd, J=10.0, 17.6 Hz, 1H), 6.75-6.78 (m, 1H), 6.16 (br s, 1H), 5.20-5.25 (m, 1H), 4.32-4.35 (m, 1H), 3.91 (dd, J=4.8, 12.4 Hz, 1H), 3.84-3.89 (m, 1H), 2.98-3.10 (m, 1H), 2.49-2.54 (m, 1H), 2.32 (s, 3H), 1.09-1.25 (m, 21H).

Step 11: {(2S,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl Sulfamate The titled compound was prepared following the procedure described in Example 1 Step 7, substituting {(2R,3R,5S)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methanol for Intermediate 7. LCMS (AA): m/z 627 (M+H); $^1$H NMR (400 MHz, d$_6$-DMSO) δ 8.26 (s, 1H), 7.53 (s, 2H), 7.12-7.30 (m, 2H), 7.02 (br d, J=7.9 Hz, 1H), 6.61 (br d, J=2.1 Hz, 1H), 4.99 (br d, J=4.4 Hz, 1H), 4.35 (br s, 1H), 4.23 (br s, 1H), 4.12 (br d, J=8.2 Hz, 1H), 2.86 (br d, J=4.8 Hz, 1H), 2.37-2.47 (m, 1H), 2.32 (s, 3H), 1.06 (br s, 21H).

Step 12: [(2S,3S,5R)-5-{4-amino-3-[(2-fluoro-4-methylphenyl)sulfanyl]-1H-pyrazolo[3,4-d]pyrimidin-1-yl}-3-hydroxytetrahydrofuran-2-yl]methyl Sulfamate I-211

The titled compound was prepared following the procedure detailed in Example 65 Step 7, substituting {(2S,3S,5R)-5-{4-amino-3-[(2-fluoro-4-methylphenyl)sulfanyl]-1H-pyrazolo[3,4-d]pyrimidin-1-yl}-3-[(triisopropylsilyl)oxy]tetrahydrofuran-2-yl}methyl sulfamate for Intermediate 101. This reaction mixture was stirred for 7 days. LCMS (AA): m/z 471 (M+H); $^1$H NMR (400 MHz, d$_6$-DMSO) δ 8.27 (s, 1H), 7.50 (s, 2H), 7.08-7.20 (m, 2H), 7.01 (br d, J=7.7 Hz, 1H), 6.66 (br t, J=6.3 Hz, 1H), 5.38 (br d, J=4.5 Hz, 1H), 4.60 (br s, 1H), 4.32 (br s, 1H), 4.26 (br d, J=10.8 Hz, 1H), 4.11 (br d, J=8.4 Hz, 1H), 2.87-3.03 (m, 1H), 2.39 (br dd, J=13.5, 7.1 Hz, 1H), 2.30 (s, 3H).

Example 96: {(2S,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl Sulfamate I-96

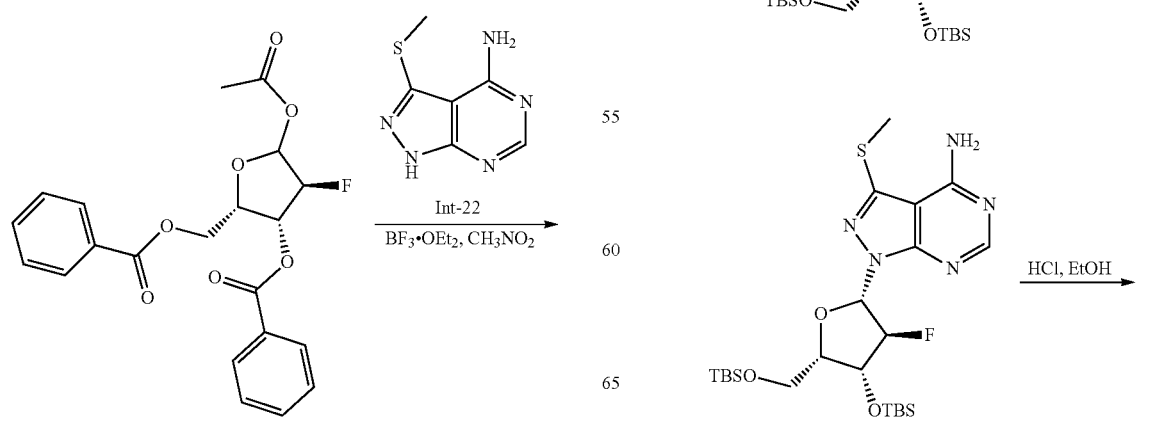

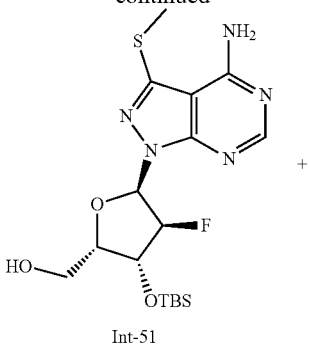

Int-51

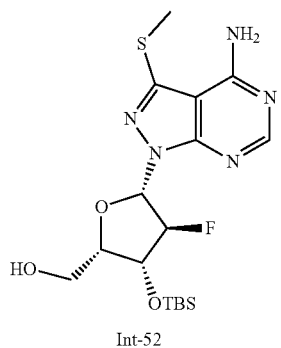

Int-52

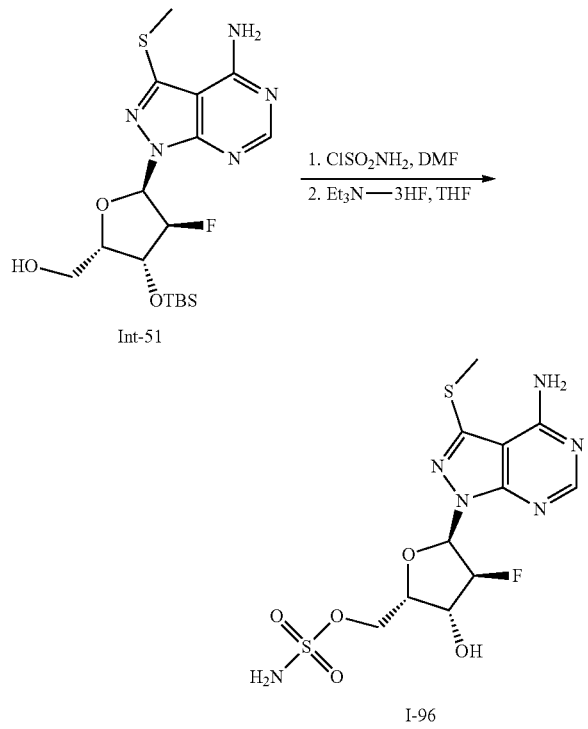

Step 1: [(2S,3R,4S,5R)-5-[4-amino-3-(methylsulfanyl)-1H-pyrazolo[3,4-d]pyrimidin-1-yl]-3-(benzoyloxy)-4-fluorotetrahydrofuran-2-yl]methyl benzoate and [(2S,3R,4S,5S)-5-[4-amino-3-(methylsulfanyl)-1H-pyrazolo[3,4-d]pyrimidin-1-yl]-3-(benzoyloxy)-4-fluorotetrahydrofuran-2-yl]methyl benzoate The title compounds were prepared as an inseparable mixture of anomers from [(2S,3R,4S)-5-acetoxy-3-(benzoyloxy)-4-fluorotetrahydrofuran-2-yl]methyl benzoate (prepared as described *Nucleosides, Nucleotides & Nucleic Acids* 2003, 22(5-8), 1147-1149 and references cited therein) and Intermediate 22 following the procedure described in Example 39 Step 1, LCMS (FA): m/z=524 (M+H) (2 peaks by LCMS).

Steps 2-3: 1-[(2R,3S,4R,5S)-4-{[tert-butyl(dimethyl)silyl]oxy}-5-({[tert-butyl(dimethyl)silyl]oxy}methyl)-3-fluorotetrahydrofuran-2-yl]-3-(methylsulfanyl)-1H-pyrazolo[3,4-d]pyrimidin-4-amine and 1-[(2S,3S,4R,5S)-4-{[tert-butyl(dimethyl)silyl]oxy}-5-({[tert-butyl(dimethyl)silyl]oxy}methyl)-3-fluorotetrahydrofuran-2-yl]-3-(methylsulfanyl)-1H-pyrazolo[3,4-d]pyrimidin-4-amine The title compounds were prepared as an inseparable mixture of anomers following the procedure detailed in Example 5 Step 3 followed immediately by the procedure detailed in Example 65 Step 4. The material was used as obtained in the following step Step 4: [(2S,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methanol and [(2R,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methanol The title compounds were prepared as described in Example 65 Step 5 substituting the mixture of anomers prepared in step 2 (1-[(2R,3S,4R,5S)-4-{[tert-butyl(dimethyl)silyl]oxy}-5-({[tert-butyl(dimethyl)silyl]oxy}methyl)-3-fluorotetrahydrofuran-2-yl]-3-(methyl sulfanyl)-1H-pyrazolo[3,4-d]pyrimidin-4-amine and 1-[(2S,3S,4R,5S)-4-{[tert-butyl(dimethyl)silyl]oxy}-5-({[tert-butyl(dimethyl)silyl]oxy}methyl)-3-fluorotetrahydrofuran-2-yl]-3-(methylsulfanyl)-1H-pyrazolo[3,4-d]pyrimidin-4-amine) for 1-[(2R,3S,4R,5R)-4-{[tert-butyl(dimethyl)silyl]oxy}-5-({[tert-butyl(dimethyl)silyl]oxy}methyl)-3-fluorotetrahydrofuran-2-yl]-3-(isopropylsulfanyl)-1H-pyrazolo[3,4-d]pyrimidin-4-amine. At this point, the anomers were separated by silica gel chromatography, with the desired □-anomer Intermediate 51, eluting later than the undesired □-anomer Intermediate 52.

[(2S,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methanol (Intermediate 51): $^1$H NMR (400 MHz, CDCl$_3$) δ 8.15 (s, 1H), 6.52 (d, J=6.3 Hz, 1H), 5.69 (br s, 2H), 5.06-5.32 (m, 2H), 4.42-4.47 (m, 1H), 3.66-3.72 (m, 1H), 3.56-3.64 (m, 1H), 2.51 (s, 3H), 0.78 (s, 9H), 0.00 (s, 6H);

[(2R,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methanol (Intermediate 52): $^1$H NMR (400 MHz, CDCl$_3$) δ 8.16 (s, 1H), 6.29 (dd, J=14.7, 6.0 Hz, 1H), 5.55-5.78 (m, 3H), 4.57-4.71 (m, 1H), 4.08-4.16 (m, 1H), 3.73 (br d, J=3.0 Hz, 2H), 2.55 (s, 3H), 0.79 (s, 9H), 0.01 (d, J=4.3 Hz, 6H).

Step 5: [(2S,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methyl Sulfamate The title compound was prepared following the procedure detailed in Example 1 Step 7 substituting [(2S,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methanol for Intermediate 7. $^1$H NMR (400 MHz, CDCl$_3$) δ 8.13 (s, 1H), 6.52 (dd, J=5.6, 4.3 Hz, 1H), 5.82 (br s, 2H), 4.98-5.18 (m, 3H), 4.75 (td, J=6.3, 3.6 Hz, 1H), 4.22-4.32 (m, 2H), 2.52 (s, 3H), 0.78 (s, 9H), 0.00 (s, 6H).

Step 6: {(2S,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl Sulfamate I-96

The title compound was prepared following the procedure detailed in Example 65 Step 7 substituting [(2S,3R,4S,5R)-5-[4-amino-3-(methylsulfanyl)-1H-pyrazolo[3,4-d]pyrimidin-1-yl]-3-{[tert-butyl(dimethyl)silyl]oxy}-4-fluorotetrahydrofuran-2-yl]methyl sulfamate for Intermediate 101. LCMS (AA): m z=395 (M+H); $^1$H NMR (400 MHz, CD$_3$OD) δ 8.18-8.26 (m, 1H), 6.66 (dd, J=5.9, 3.6 Hz, 1H), 5.39 (t, J=5.9 Hz, 1H), 5.24-5.28 (m, 1H), 5.18 (ddd, J=18.2, 7.1, 5.7 Hz, 1H), 4.38-4.45 (m, 1H), 4.26-4.33 (m, 1H), 2.69 (s, 3H).

Example 97: ATG7 Enzyme Assay

The total volume of the ATG7 enzymatic assay is 50 μL and contains 50 mM HEPES Hemisodium (pH 7.5), 0.05% BSA, 0.01% Tween-20, 25 mM NaCl, 5 mM MgCl$_2$, 10 μM ATP, 250 μM GSH, 5 nM ATG3-GST, 5 nM Flag-Gabarap, 100 μM TCEP and 0.15 nM recombinant human His-ATG7 enzyme. The enzymatic reaction mixture, with and without inhibitor, was incubated at 24° C. for 105 min in a 384-well plate before termination with 25 μM of Stop/Detection buffer (0.1M HEPES Hemisodium pH 7.5, 0.05% Tween20, 20 mM EDTA, 410 mM KF, 0.53 nM Europium-Cryptate labeled monoclonal anti-Flag M2 Antibody (CisBio International) and 8.125 μg/ml PHYCOLINK goat anti-GST allophycocyanin (XL-APC) antibody (Prozyme)). After incubation for 2 hours at 24° C., quantification of FRET is performed on the Pherostar™ (BMG Labtech). Percentage inhibition values at a single concentration or enzyme inhibition (IC$_{50}$) values are determined from those curves. One skilled in the art will appreciate that the values generated either as percentage inhibition at a single concentration or IC$_{50}$ values are subject to experimental variation.

Example 98: Cell Viability Assay

293HEK cells were plated in 6 well plates in fresh complete MEM media to a final seeding density of 2.5×10$^5$ cells/well and incubated 37° C. for 96 hours. Serial dilutions of each compound were prepared in DMSO and then diluted 1:100 in MEM media. Media was removed from the cells and replaced with media containing compound. Plates were gently mixed and incubated for 8 hours at 37° C. in a 5% CO$_2$ incubator. Plates were then removed from the incubator and 1 mL of media from each well was retained. Each well was rinsed 1 mL of PBS, aspirated and treated with 300 uL of Trypsin-EDTA. Plates were incubated at 37° C. for 2 min and then each well was treated with 800 uL of the saved media to inactivate the Trypsin-EDTA. Cell suspensions were spun 5K for 5 minutes in a microcentrifuge. Samples were treated with 60 uL cold NP40 lysis buffer (50 mM HEPES, pH 7.5, 150 mM NaCl, 1% NP40, 1% Glycerol, 1 mM EDTA, 10 mM Iodoacetamide, 10 mM NEM, 1 mM Na Orthovanadate, 1/5000 Benzonase [Novagen, D00080732] and Complete Mini EDTA-free Protease Inhibitor Cocktail [Roche, 11 836 170 001]) and resuspended, vortexed and incubated on ice for 15 min; this process was repeated 2 times. Samples were then spun at 4° C. for 15 minutes at 14K. Supernatant was transferred to fresh 1.5 mL Eppendorf tubes on ice. Protein concentration was determined using the Bio-Rad DC Protein Assay kit (#500-0112) or similar according to the manufacturer's instructions. Samples were analyzed using SDS-PAGE and western blotting. Cell lystate samples were prepared using NuPAGE (4x) LDS sample buffer. It is important not to heat or add reducing agent to the samples. 15 ug total protein per sample was loaded onto Invitogen 1.5 mm 4-12% NuPAGE Bis/Tris gels. Gels were run using ice cold 1x NuPAGE MES SDS running buffer.

SDS-PAGE gels were transferred to Immobilon PVDF (Millipore, IPFL00010) and blocked at room temperature for 1 hour with 5% nonfat dry milk in 1xTBST. Primary antibody (anti-ATG7 Rabbit monoclonal, Epitomics 2054-1) was diluted 1:2500 in 5% nonfat dry milk in 1xTBST and blots were incubated overnight at 4° C. with rocking. The membranes were washed in TBS and then incubated in secondary antibody (Alexa Fluor 680 goat anti-rabbit IgG (H+L) conjugating antibody; Molecular Probes #A-21109) diluted 1:2500 in 5% nonfat dry milk in TBST for 2 hours at room temperature in the dark. Membranes were then washed 6x in TBS and dried in the dark for 15 minutes. Quantification was performed using a Licor instrument. IC50s were calculated using the ratio of ATG7 thioester intensity divided by total ATG7 intensity (thioester plus uncharged ATG7) normalized to the beta-actin loading control.

As detailed above, chemical entities of the disclosure inhibit ATG7. In certain embodiments, chemical entities of the disclosure inhibit ATG7 with the percent inhibition at the concentrations shown in the table below. In certain embodiments, chemical entities of the disclosure inhibit ATG7 with the IC$_{50}$ values shown in the table below.

| Compound number | IC50 (nM) | Percent Inhibition | Concentration (μM) |
| --- | --- | --- | --- |
| I-1 | C | 51 | 0.123 |
| I-2 | D | 42 | 0.123 |
| I-3 | D | 24 | 0.069 |
| I-4 | D | 32 | 0.069 |
| I-5 | D | 23 | 0.069 |
| I-6 | D | 31 | 0.069 |
| I-7 | E | 7 | 0.069 |
| I-8 | D | 32 | 0.069 |
| I-9 | C | 52 | 0.069 |
| I-10 | C | 48 | 0.069 |
| I-11 | E | 9 | 0.069 |
| I-12 | D | 20 | 0.123 |
| I-13 | B | 80 | 0.123 |
| I-14 | D | 17 | 0.069 |
| I-15 | E | 16 | 0.069 |
| I-16 | D | 22 | 0.069 |
| I-17 | E | 10 | 0.069 |
| I-18 | C | 62 | 0.123 |
| I-19 | D | 32 | 0.123 |
| I-20 | D | 45 | 0.123 |
| I-21 | D | 22 | 0.123 |
| I-22 | E | 5 | 0.123 |
| I-23b | D | 22 | 0.123 |
| I-23a | E | 19 | 0.123 |
| I-24 | E | 11 | 0.123 |
| I-25 | C | 64 | 0.123 |
| I-26 | C | 53 | 0.123 |
| I-27 | B | 78 | 0.123 |
| I-28 | C | 71 | 0.123 |
| I-29 | E | 26 | 0.123 |
| I-30 | E | 15 | 0.123 |
| I-31 | B | 85 | 0.123 |
| I-32 | B | 73 | 0.123 |
| I-33 | B | 82 | 0.123 |

| Compound number | IC50 (nM) | Percent Inhibition | Concentration (μM) |
|---|---|---|---|
| I-34 | C | 70 | 0.123 |
| I-35 | B | 72 | 0.123 |
| I-36 | A | 88 | 0.111 |
| I-37 | E | 7 | 0.069 |
| I-38 | B | 84 | 0.123 |
| I-39 | B | 75 | 0.123 |
| I-40 | A | 85 | 0.123 |
| I-41 | B | 85 | 0.111 |
| I-42 | A | 79 | 0.111 |
| I-43 | B | 75 | 0.123 |
| I-44 | B | 84 | 0.123 |
| I-45 | B | 73 | 0.123 |
| I-46 | A | 88 | 0.123 |
| I-47 | D | 48 | 0.123 |
| I-48 | D | 16 | 0.069 |
| I-49 | E | 7 | 0.069 |
| I-50 | A | 88 | 0.111 |
| I-51 | B | 85 | 0.123 |
| I-52 | B | 83 | 0.123 |
| I-53 | B | 82 | 0.123 |
| I-54 | B | 75 | 0.123 |
| I-55b | C | 68 | 0.123 |
| I-55a | C | 71 | 0.123 |
| I-56 | A | 84 | 0.111 |
| I-57 | E | 13 | 0.123 |
| I-58 | A | 87 | 0.123 |
| I-59 | B | 75 | 0.123 |
| I-60 | C | 59 | 0.123 |
| I-61 | B | 83 | 0.123 |
| I-62 | A | 89 | 0.123 |
| I-63 | B | 83 | 0.111 |
| I-64 | B | 84 | 0.123 |
| I-65 | A | 89 | 0.123 |
| I-66 | B | 68 | 0.123 |
| I-67 | C | 64 | 0.123 |
| I-68 | E | 10 | 0.123 |
| I-69 | A | 86 | 0.111 |
| I-70 | C | 70 | 0.123 |
| I-71 | D | 38 | 0.123 |
| I-72 | C | 65 | 0.123 |
| I-73 | B | 83 | 0.123 |
| I-74 | C | 61 | 0.123 |
| I-75 | D | 41 | 0.123 |
| I-76 | D | 31 | 0.123 |
| I-77 | B | 85 | 0.123 |
| I-78 | B | 80 | 0.123 |
| I-79 | A | 85 | 0.123 |
| I-80 | D | 51 | 0.123 |
| I-81 | C | 69 | 0.123 |
| I-82 | B | 80 | 0.111 |
| I-83 | B | 82 | 0.123 |
| I-84 | C | 62 | 0.123 |
| I-85 | B | 77 | 0.123 |
| I-86 | C | 64 | 0.123 |
| I-87 | C | 58 | 0.123 |
| I-88 | B | 78 | 0.123 |
| I-89 | A | 86 | 0.111 |
| I-90 | B | 84 | 0.123 |
| I-91 | B | 76 | 0.123 |
| I-92 | D | 50 | 0.123 |
| I-93 | D | 47 | 0.123 |
| I-94 | D | 28 | 0.111 |
| I-95 | D | 47 | 0.123 |
| I-96 | D | 44 | 0.111 |
| I-97 | B | 66 | 0.111 |
| I-98 | B | 77 | 0.111 |
| I-99 | B | 70 | 0.111 |
| I-100 | D | 50 | 0.111 |
| I-101 | E | 13 | 0.111 |
| I-102 | C | 68 | 0.111 |
| I-103 | A | 84 | 0.111 |
| I-104 | D | 38 | 0.111 |
| I-105 | D | 42 | 0.123 |
| I-106 | B | 78 | 0.123 |
| I-107 | C | 61 | 0.111 |
| I-108 | E | 19 | 0.111 |
| I-109 | B | 82 | 0.111 |
| I-110 | C | 56 | 0.111 |
| I-111 | B | 73 | 0.111 |
| I-112 | D | 44 | 0.111 |
| I-113 | A | 89 | 0.111 |
| I-114 | A | 90 | 0.111 |
| I-115 | B | 73 | 0.123 |
| I-116 | B | 75 | 0.111 |
| I-117 | B | 83 | 0.111 |
| I-118 | A | 86 | 0.111 |
| I-119 | C | 65 | 0.111 |
| I-120 | D | 46 | 0.111 |
| I-121 | C | 65 | 0.111 |
| I-122 | B | 80 | 0.111 |
| I-123 | B | 78 | 0.111 |
| I-124 | C | 52 | 0.111 |
| I-125 | D | 37 | 0.111 |
| I-126 | B | 71 | 0.111 |
| I-127 | C | 61 | 0.111 |
| I-128 | C | 52 | 0.111 |
| I-129 | D | 48 | 0.111 |
| I-130 | B | 77 | 0.111 |
| I-131 | B | 76 | 0.111 |
| I-132 | C | 60 | 0.111 |
| I-133 | B | 67 | 0.111 |
| I-134 | D | 37 | 0.111 |
| I-135 | B | 82 | 0.111 |
| I-136 | B | 69 | 0.111 |
| I-136b | C | 61 | 0.111 |
| I-136a | C | 63 | 0.111 |
| I-137 | B | 80 | 0.111 |
| I-138 | C | 64 | 0.111 |
| I-139 | B | 84 | 0.111 |
| I-140 | B | 75 | 0.111 |
| I-141 | B | 76 | 0.123 |
| I-142 | C | 57 | 0.111 |
| I-143 | C | 68 | 0.111 |
| I-144 | B | 74 | 0.111 |
| I-145 | B | 74 | 0.111 |
| I-146 | B | 86 | 0.111 |
| I-147 | A | 89 | 0.111 |
| I-148 | A | 83 | 0.111 |
| I-149 | B | 82 | 0.111 |
| I-150 | D | 46 | 0.111 |
| I-151 | B | 76 | 0.111 |
| I-152 | A | 88 | 0.111 |
| I-153 | C | 58 | 0.111 |
| I-154 | C | 64 | 0.111 |
| I-155 | B | 75 | 0.123 |
| I-156 | D | 30 | 0.111 |
| I-157 | B | 71 | 0.111 |
| I-158 | C | 56 | 0.111 |
| I-159 | D | 29 | 0.111 |
| I-160 | C | 62 | 0.111 |
| I-161 | C | 59 | 0.111 |
| I-162 | D | 50 | 0.111 |
| I-163 | C | 58 | 0.111 |
| I-164 | C | 70 | 0.111 |
| I-165 | C | 62 | 0.111 |
| I-166 | D | 50 | 0.111 |
| I-167 | C | 68 | 0.111 |
| I-168 | B | 77 | 0.111 |
| I-169 | C | 57 | 0.111 |
| I-170 | D | 50 | 0.111 |
| I-171 | D | 48 | 0.111 |
| I-172 | C | 68 | 0.111 |
| I-173 | B | 81 | 0.111 |
| I-174 | B | 73 | 0.111 |
| I-175 | C | 66 | 0.111 |
| I-176 | D | 26 | 0.111 |
| I-177 | B | 70 | 0.111 |
| I-178 | B | 74 | 0.111 |
| I-179 | D | 50 | 0.111 |
| I-180 | D | 29 | 0.111 |
| I-181 | B | 81 | 0.123 |
| I-182 | C | 66 | 0.111 |
| I-183 | D | 28 | 0.111 |
| I-184 | C | 64 | 0.111 |

-continued

| Compound number | IC50 (nM) | Percent Inhibition | Concentration (μM) |
|---|---|---|---|
| I-185 | C | 56 | 0.111 |
| I-186 | B | 74 | 0.111 |
| I-187 | C | 56 | 0.111 |
| I-188 | D | 37 | 0.111 |
| I-189 | C | 60 | 0.111 |
| I-190 | D | 35 | 0.123 |
| I-191 | C | 63 | 0.111 |
| I-192 | C | 61 | 0.111 |
| I-193 | D | 46 | 0.111 |
| I-194 | B | 79 | 0.111 |
| I-195 | C | 53 | 0.111 |
| I-196 | C | 65 | 0.111 |
| I-197 | D | 45 | 0.111 |
| I-198 | D | 42 | 0.111 |
| I-199 | B | 74 | 0.111 |
| I-200 | B | 70 | 0.111 |
| I-201 | B | 68 | 0.111 |
| I-202 | C | 62 | 0.111 |
| I-203 | C | 58 | 0.111 |
| I-204 | D | 50 | 0.111 |
| I-205 | C | 55 | 0.111 |
| I-206 | D | 44 | 0.111 |
| I-207 | C | 65 | 0.111 |
| I-208 | D | 44 | 0.111 |
| I-209 | D | 42 | 0.111 |
| I-210 | D | 35 | 0.111 |
| I-211 | C | 64 | 0.111 |
| I-212 | E | 7 | 0.111 |
| I-213 | D | 46 | 0.111 |
| I-214 | D | 43 | 0.111 |
| I-215 | D | 45 | 0.111 |
| I-216 | D | 41 | 0.111 |
| I-217 | D | 34 | 0.111 |
| I-218 | E | 8 | 0.111 |
| I-219 | D | 48 | 0.111 |
| I-220 | C | 65 | 0.111 |
| I-221 | D | 26 | 0.111 |
| I-222 | C | 59 | 0.111 |
| I-223 | D | 35 | 0.111 |
| I-224 | D | 39 | 0.111 |
| I-225 | E | 10 | 0.111 |
| I-226 | E | 5 | 0.111 |
| I-227 | D | 48 | 0.111 |

$IC_{50}$: A) less than 20 nM;
B) 20 nM-50 nM;
C) 50-100 nM;
D) 100 nM-500 nM;
E) greater than 500 nM

What is claimed is:

1. A chemical entity which is a compound or a pharmaceutically acceptable salt of formula (I):

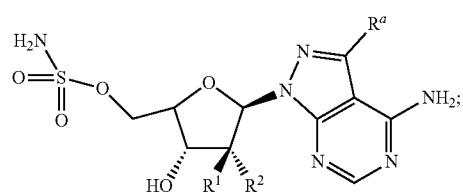

(I)

wherein:
$R^1$ is H and $R^2$ is H; or $R^1$ is H and $R^2$ is —OH; or $R^1$ is F and $R^2$ is H;
$R^a$ is H, I, —CN, —$CO_2CH_3$, —$C(O)CH_3$, —C(S)$NH_2$, —$C(O)NH_2$, —$S(O)CH_3$, $C_{1-3}$ fluoroaliphatic, —O—$C_{1-3}$ fluoroaliphatic, —S—$C_{1-3}$ fluoroaliphatic, -$T_1$-$R^b$, $R^{bb}$, —O-$T_1$-$R^b$, —O—$R^{dd}$, —S-$T_1$-$R^c$, or —S—$R^{ee}$;

$T_1$ is absent or $C_1$-$C_3$ alkylene optionally substituted with 1 or 2 independent occurrences of —$CH_3$,
$R^b$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each $R^b$ is substituted with 0-5 $R^d$;
$R^c$ is 3-7 membered cycloaliphatic; 4-10-membered heterocyclyl having 1-4 heteroatoms independently selected from nitrogen, oxygen, and sulfur; 6-10-membered aryl; or 5-10-membered heteroaryl having 1-5 heteroatoms independently selected from nitrogen, oxygen, and sulfur; wherein each $R^c$ is substituted with 0-5 $R^f$;
each occurrence of $R^d$ is independently halo, —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —$SO_2CH_3$, —S(O)$CH_3$, or —O—$CH_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^d$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;
each occurrence of $R^f$ is independently halo, —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —$SO_2CH_3$, —S(O)$CH_3$, or —O—$CH_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;
$R^{bb}$ is $C_{1-3}$ aliphatic substituted with 0-5 $R^{bx}$;
$R^{dd}$ is $C_{1-3}$ aliphatic substituted with 0-5 $R^{dx}$;
$R^{ee}$ is $C_{1-3}$ aliphatic substituted with 0-5 $R^{fx}$;
each occurrence of $R^{bx}$ is independently —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —$SO_2CH_3$, —S(O)$CH_3$, or —O—$CH_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{bx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^8$;
each occurrence of $R^{dx}$ is independently —Cl, —OH, —CN, —$NO_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —SO$_2$CH$_3$, —S(O)CH$_3$, or —O—CH$_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{dx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^8$;

each occurrence of $R^{fx}$ is independently —OH, —CN, —NO$_2$, $C_{1-4}$ aliphatic, —O—$C_{1-3}$ aliphatic, $C_{1-3}$ fluoroaliphatic, —O—$C_{1-3}$ fluoroaliphatic, —S—$C_{1-3}$ aliphatic, —S—$C_{1-3}$ fluoroaliphatic, —N($R^e$)$_2$, —C(O)—N($R^e$)$_2$, —SO$_2$CH$_3$, —S(O)CH$_3$, or —O—CH$_2$-phenyl wherein the phenyl ring is optionally substituted with 1 or 2 independent occurrences of halo, —CN, $C_{1-3}$ aliphatic, or —O—$C_{1-3}$ aliphatic; or two occurrences of $R^{fx}$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$;

$R^g$ is $C_{1-3}$ aliphatic; and $R^e$ is hydrogen or $C_{1-3}$ aliphatic.

2. The chemical entity of claim 1, wherein $R^1$ is H and $R^2$ is H.

3. The chemical entity of claim 1, wherein $R^a$ is I, $C_{1-3}$ fluoroaliphatic, —O—$C_{1-3}$ fluoroaliphatic, —S—$C_{1-3}$ fluoroaliphatic, -T$_1$-$R^b$, $R^{bb}$, —O-T$_1$-$R^b$, —O—$R^{dd}$, —S-T$_1$-$R^c$, or —S—$R^{ee}$.

4. The chemical entity of claim 1 wherein $R^a$ is —O—$C_{1-3}$ fluoroaliphatic, or —O—$R^{dd}$.

5. The chemical entity of claim 1 wherein:

$R^a$ is —S—$C_{1-3}$ fluoroaliphatic, —S-T$_1$-$R^c$, or —S—$R^{ee}$;

each occurrence of $R^f$ is independently halo, —OH, —CN, $C_{1-4}$ aliphatic, —O—$C_{1-3}$ aliphatic, —O—$C_{1-3}$ fluoroaliphatic, —N($R^e$)$_2$, or —C(O)—N($R^e$)$_2$; or two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$; and each occurrence of $R^{fx}$ is independently —OH, —CN, $C_{1-4}$ aliphatic, —O—$C_{1-3}$ aliphatic, $C_{1-3}$ fluoroaliphatic, —N($R^e$)$_2$, or —C(O)—N($R^e$)$_2$, or 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$.

6. The chemical entity of claim 1 which is a compound or a pharmaceutically acceptable salt of formulas (III-a)-(III-d):

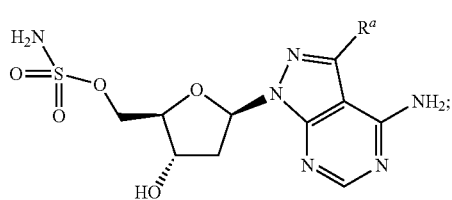
(III-a)

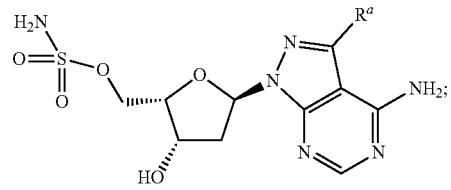
(III-aa)

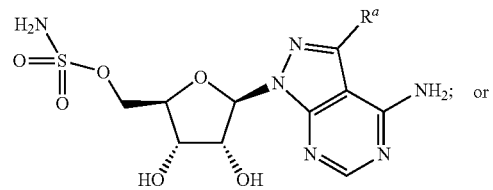
(III-b)

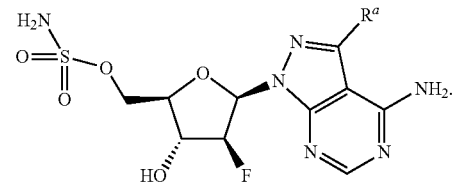
(III-c)

7. The chemical entity of claim 6, wherein $R^a$ is I, —CN, $C_{1-3}$ fluoroaliphatic, —O—$C_{1-3}$ fluoroaliphatic, —S—$C_{1-3}$ fluoroaliphatic, -T$_1$-$R^b$, $R^{bb}$, —O-T$_1$-$R^b$, —O—$R^{dd}$, —S-T$_1$-$R^c$, or —S—$R^{ee}$.

8. The chemical entity of claim 7, wherein $R^a$ is I, —CN, $C_{1-3}$ fluoroaliphatic, —O—$C_{1-3}$ fluoroaliphatic, $R^{bb}$, or O—$R^{dd}$.

9. The chemical entity of claim 7, wherein:

$R^a$ is —S—$C_{1-3}$ fluoroaliphatic or —S—$R^{ee}$;

$R^{ee}$ is $C_{1-3}$ aliphatic substituted with 0-2 $R^{fx}$; and each occurrence of $R^{fx}$ is independently —OH, —CN, $C_{1-4}$ aliphatic, —O—$C_{1-3}$ aliphatic, $C_{1-3}$ fluoroaliphatic, —N($R^e$)$_2$, or —C(O)—N($R^e$)$_2$.

10. The chemical entity of claim 7, wherein $R^a$ is -T$_1$-$R^b$, —O-T$_1$-$R^b$, or —S-T$_1$-$R^c$.

11. The chemical entity of claim 10, wherein:

$R^a$ is -T$_1$-$R^b$, —O-T$_1$-$R^b$;

T$_1$ is absent, —CH$_2$— or —CH$_2$CH$_2$—; and $R^b$ is substituted with 0-2 $R^d$.

12. The chemical entity of claim 10, wherein:

$R^a$ is —S-T$_1$-$R^c$; and

T$_1$ is absent, —CH$_2$— or —CH$_2$CH$_2$—.

13. The chemical entity of claim 12, wherein:

$R^c$ is 3-7 membered cycloaliphatic or 4-10-membered heterocyclyl having 1-4 heteroatoms independently selected from nitrogen, oxygen, and sulfur;

$R^c$ is substituted with 0-2 $R^f$;

each occurrence of $R^f$ is independently $R^{fa}$; and $R^{fa}$ is halo, —OH, —CN, or $C_{1-4}$ aliphatic.

14. The chemical entity of claim 12, wherein:

$R^c$ is a 6-10-membered aryl; or 5-10-membered heteroaryl having 1-5 heteroatoms, $R^c$ is substituted with 0-2 $R^f$; and $R^e$ is —H, —CH$_3$, or —CH$_2$CH$_3$.

15. The chemical entity of claim 14, wherein:

two occurrences of $R^f$ are taken together to form a 5 or 6 membered cycloaliphatic or heterocyclic ring, having 1-2 heteroatoms independently selected from nitrogen, oxygen, and sulfur, which is further optionally substituted with one occurrence of =O and optionally substituted with one occurrence of $R^g$; and
$R^g$ is methyl.

16. The chemical entity of claim 14, wherein:
each occurrence of $R^f$ is independently $R^{fb}$; and
$R^{fb}$ is halo, —OH, —CN, $C_{1-4}$ aliphatic, —O—$C_{1-3}$ aliphatic, —O—$C_{1-3}$ fluoroaliphatic, —N($R^e$)$_2$, or —C(O)—N($R^e$)$_2$.

17. The chemical entity of claim 14, wherein $R^c$ is phenyl, pyridyl, furanyl or pyrazolyl optionally substituted by one occurrence of —CH$_3$, —OCH$_3$, or —F, and optionally substituted by one occurrence of —CH$_3$, —OCH$_3$, —F, —Cl, —CF$_3$, or —OCF$_3$.

18. The chemical entity of claim 1, wherein the chemical entity is selected from the group consisting of:

[(2R,3S,4R,5R)-5-(4-amino-3-methoxy-1H-pyrazolo[3,4-d]pyrimidin-1-yl)-3,4-dihydroxytetrahydrofuran-2-yl]methyl sulfamate;

[(2R,3S,4R,5R)-5-(4-amino-3-methyl-1H-pyrazolo[3,4-d]pyrimidin-1-yl)-3,4-dihydroxytetrahydrofuran-2-yl]methyl sulfamate;

[(2R,3S,4R,5R)-5-(4-amino-3-isopropyl-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(benzyloxy)methyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-ethoxy-1H-pyrazolo[3,4-d]pyrimidin-1-yl)-3,4-dihydroxytetrahydrofuran-2-yl]methyl sulfamate;

[(2R,3S,4R,5R)-5-(4-amino-3-ethyl-1H-pyrazolo[3,4-d]pyrimidin-1-yl)-3,4-dihydroxytetrahydrofuran-2-yl]methyl sulfamate;

[(2R,3S,4R,5R)-5-(4-amino-3-isopropoxy-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(hydroxymethyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-ethynyl-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(trifluoromethyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(3-methoxyprop-1-yn-1-yl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(2-phenylethyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-cyano-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(prop-1-yn-1-yl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(aminomethyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-carbamoyl-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(3-aminoprop-1-yn-1-yl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-vinyl-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(methoxymethyl)-1H-pyrazolo[3,4-d]pyrimidin-1-yl]-3,4-dihydroxytetrahydrofuran-2-yl}methyl sulfamate methyl 4-amino-1-{(2R,3R,4S,5R)-3,4-dihydroxy-5-[(sulfamoyloxy)methyl]tetrahydrofuran-2-yl}-1H-pyrazolo[3,4-d]pyrimidine-3-carboxylate;

[(2R,3S,4R,5R)-5-(3-acetyl-4-amino-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(1R)-1-methoxyethyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(1S)-1-methoxyethyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(1R)-1-hydroxyethyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(1S)-1-hydroxyethyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(2-hydroxypropan-2-yl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(difluoromethyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-cyclopropyl-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(difluoromethoxy)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(2-hydroxy-2-methylpropyl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(cyanomethyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(1,3-thiazol-2-yl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(3-methylbenzyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-{[4-(trifluoromethoxy)benzyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[4-(trifluoromethyl)benzyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(2,4-dichlorophenyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(2-methoxyethyl) sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(1H-pyrazol-4-ylsulfanyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-phenoxy-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(4-methoxybenzyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(2-methylbenzyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(3-chlorophenyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(4-methylbenzyl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(methylsulfanyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(prop-2-yn-1-ylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(3-fluorobenzyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(pyridin-3-ylmethyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(2-hydroxyethyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-{[(1R,2R)-2-hydroxycyclohexyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(1S,2S)-2-hydroxycyclohexyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-1H-pyrazolo[3,4-d]pyrimidin-1-yl)-3,4-dihydroxytetrahydrofuran-2-yl]methyl sulfamate;

[(2R,3S,4R,5R)-5-(4-amino-3-phenyl-1H-pyrazolo[3,4-d]pyrimidin-1-yl)-3,4-dihydroxytetrahydrofuran-2-yl] methyl sulfamate;

[(2R,3S,4R,5R)-5-{4-amino-3-[(cyclopropylmethyl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(ethylsulfanyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(benzylsulfanyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(tert-butylsulfanyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-{[(1R,2R)-2-hydroxycyclopentyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(1S,2S)-2-hydroxycyclopentyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2R)-2-hydroxypropyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2S)-2-hydroxypropyl]sulfanyl}-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(cyclobutylsulfanyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(1,3-oxazol-2-yl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(pyridin-2-ylmethyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-carbamothioyl-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(1-methyl-1H-pyrazol-4-yl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(cyclopentylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(4-fluorobenzyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(4-chlorophenyl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(cyclopropylsulfanyl)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(pyridin-4-ylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(1-naphthylmethyl) sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(1H-pyrazol-5-yl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(3-methylphenyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-{[(1R)-1-phenylethyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(1S)-1-phenylethyl]sulfanyl}-1H-pyrazolo[3,4-d]pyrimidin-1-yl)-3,4-dihydroxytetrahydrofuran-2-yl]methyl sulfamate;

{(2R,3S,4R,5R)-5-[3-(allyloxy)-4-amino-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(azetidin-3-ylsulfanyl)-1H-pyrazolo[3,4-d]pyrimidin-1-yl]-3,4-dihydroxytetrahydrofuran-2-yl}methyl sulfamate;

[(2R,3S,4R,5R)-5-(4-amino-3-{[(5-chloro-2-furyl)methyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(2-methylphenyl) sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(2-chloroethoxy)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(benzyloxy)-1H-pyrazolo[3,4-d]pyrimidin-1-yl]-3,4-dihydroxytetrahydrofuran-2-yl}methyl sulfamate;

{(2R,3S,4R,5R)-5-[4-amino-3-(isobutylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(2-chlorophenyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-iodo-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[2-(dimethylamino)ethyl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(2-methyl-3-furyl) sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(phenylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(2,2,2-trifluoroethyl)sulfanyl]-1H-pyrazolo[3,4-d]pyrimidin-1-yl}-3,4-dihydroxytetrahydrofuran-2-yl]methyl sulfamate;

{(2R,3S,4R,5R)-5-[4-amino-3-(1-naphthylsulfanyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(difluoromethyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-{[(1-hydroxycyclohexyl)methyl]sulfanyl}-1H-pyrazolo[3,4-d]pyrimidin-1-yl)-3,4-dihydroxytetrahydrofuran-2-yl]methyl sulfamate;

{(2R,3S,4R,5R)-5-[4-amino-3-(methylsulfinyl)-1H-pyrazolo[3,4-d]pyrimidin-1-yl]-3,4-dihydroxytetrahydrofuran-2-yl}methyl sulfamate;

[(2R,3S,4R,5R)-5-{4-amino-3-[(2-phenylethyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(4-methylphenyl) sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(cyanomethyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-{4-amino-3-[(cyclohex-1-en-1-ylmethyl)sulfanyl]-1H-pyrazolo[3,4-d]pyrimidin-1-yl}-3,4-dihydroxytetrahydrofuran-2-yl]methyl sulfamate;

[(2R,3S,4R,5R)-5-(4-amino-3-{[(2S,3R)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2R,3R)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2R,3S)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-(4-amino-3-{[(2S,3S)-2-methyltetrahydrofuran-3-yl]sulfanyl}-1H-pyrazolo[3,4-d]pyrimidin-1-yl)-3,4-dihydroxytetrahydrofuran-2-yl]methyl sulfamate;

[(2R,3S,4R,5R)-5-{4-amino-3-[(methylsulfanyl)methyl]-1H-pyrazolo[3,4-d]pyrimidin-1-yl}-3,4-dihydroxytetrahydrofuran-2-yl]methyl sulfamate;

{(2S,3S,4R,5R)-5-[4-amino-3-(methylsulfanyl)-1H-pyrazolo[3,4-d]pyrimidin-1-yl]-3,4-dihydroxytetrahydrofuran-2-yl}methyl sulfamate;

{(2S,3S,4R,5R)-5-[4-amino-3-(isopropylsulfanyl)-1H-pyrazolo[3,4-d]pyrimidin-1-yl]-3,4-dihydroxytetrahydrofuran-2-yl}methyl sulfamate;

{(2S,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-(4-amino-3-{[(3,3-difluorocyclobutyl)methyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(difluoromethyl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(difluoromethoxy)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(2-methyl-3-furyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[(2R)-1,1,1-trifluoropropan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(2S)-1,1,1-trifluoropropan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(6-methylpyridin-2-yl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(cyclopentylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-(4-amino-3-{[2-(diethylamino)ethyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-methoxy-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(3-chlorophenyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(6-methoxypyridin-2-yl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-cyclopropyl-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(2-fluorophenyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2,5-dimethyl-3-furyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(5-nitropyridin-2-yl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[(1-methyl-1H-imidazol-2-yl)methyl]sulfanyl}-1H-pyrazolo[3,4-d]pyrimidin-1-yl)-4-fluoro-3-hydroxytetrahydrofuran-2-yl]methyl sulfamate;

{(2R,3R,4S,5R)-5-[4-amino-3-(pyridin-2-ylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(4-methylpyridin-2-yl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(methylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(3-fluorophenyl) sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[4-(trifluoromethyl)pyridin-2-yl]sulfanyl}-1H-pyrazolo[3,4-d]pyrimidin-1-yl)-4-fluoro-3-hydroxytetrahydrofuran-2-yl]methyl sulfamate;

{(2R,3R,4S,5R)-5-[4-amino-3-(tert-butylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(pyridin-2-ylmethyl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(pentan-3-ylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(pyridin-3-ylmethyl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(cyclohexylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(3R)-tetrahydrofuran-3-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(3S)-tetrahydrofuran-3-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(pyridin-4-ylmethyl) sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(1-methyl-1H-imidazol-2-yl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(4-fluorophenyl) sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(pyridazin-3-ylmethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(pyridazin-4-ylmethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[(2R)-3-methylbutan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(2S)-3-methylbutan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(4-cyanopyridin-2-yl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-({[(1R)-2,2-difluorocyclopropyl]methyl}sulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-({[(1S)-2,2-difluorocyclopropyl]methyl}sulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-(4-amino-3-{[4-(trifluoromethyl)phenyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(4-chlorophenyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(1-methyl-1H-imidazol-5-yl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(cyclopropylmethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2R)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2S)-butan-2-ylsulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(1-methyl-1H-imidazol-4-yl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(pyridin-3-ylsulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-(isopropylsulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-({[(1R,2R)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-({[(1S,2R)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-({[(1R,2S)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-({[(1S,2S)-2-methylcyclopropyl]methyl}sulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(3-methylphenyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(trifluoromethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[5-(trifluoromethyl)pyridin-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(2R)-1-hydroxypropan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(2S)-1-hydroxypropan-2-yl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{R 1-methyl-1H-pyrazol-4-yl)methyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-{4-amino-3-[(5-chloropyridin-2-yl)sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(cyclobutylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(cyclobutylmethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-(4-amino-3-{[(1R)-1-cyanoethyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(1S)-1-cyanoethyl]sulfanyl}-1H-pyrazolo[3,4-d]pyrimidin-1-yl)-4-fluoro-3-hydroxytetrahydrofuran-2-yl]methyl sulfamate;

{(2R,3R,4S,5R)-5-[4-amino-3-(pyridin-4-ylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-{4-amino-3-[(2-hydroxyethyl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(5-methylpyridin-2-yl)sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(3-cyanophenyl) sulfanyl]-1H-pyrazolo[3,4-d]pyrimidin-1-yl}-4-fluoro-3-hydroxytetrahydrofuran-2-yl]methyl sulfamate;

[(2R,3R,4S,5R)-5-{4-amino-3-[(2-methoxyethyl) sulfanyl]-1H-pyrazolo[3,4-d]pyrimidin-1-yl}-4-fluoro-3-hydroxytetrahydrofuran-2-yl]methyl sulfamate;

{(2R,3R,4S,5R)-5-[4-amino-3-(benzylsulfanyl)-1H-pyrazolo[3,4-d]pyrimidin-1-yl]-4-fluoro-3-hydroxytetrahydrofuran-2-yl}methyl sulfamate;

{(2R,3R,4S,5R)-5-[4-amino-3-([1,2,4]triazolo[4,3-a]pyridin-3-ylsulfanyl)-1H-pyrazolo[3,4-d]pyrimidin-1-yl]-4-fluoro-3-hydroxytetrahydrofuran-2-yl}methyl sulfamate;

[(2R,3R,4S,5R)-5-(4-amino-3-{[(1R)-1-cyclopropylethyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[(1S)-1-cyclopropylethyl]sulfanyl}-1H-pyrazolo[3,4-d]pyrimidin-1-yl)-4-fluoro-3-hydroxytetrahydrofuran-2-yl]methyl sulfamate;

[(2R,3R,4S,5R)-5-(4-amino-3-{[3-(trifluoromethyl)phenyl]sulfanyl}-1H-pyrazolo[3,4-d]pyrimidin-1-yl)-4-fluoro-3-hydroxytetrahydrofuran-2-yl]methyl sulfamate;

[(2R,3S,5R)-5-{4-amino-3-[(2-amino-2-oxoethyl) sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2-fluoro-4-methylphenyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(2-hydroxyethyl)sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(4-tert-butylphenyl)sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(cyclobutylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2,2-difluoroethyl)sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(2-naphthylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(cyclopropylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(2,3-dihydro-1-benzofuran-6-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(difluoromethyl) sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(1H-indol-3-ylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(trifluoromethyl)-1H-pyrazolo[3,4-d]pyrimidin-1-yl]-3-hydroxytetrahydrofuran-2-yl}methyl sulfamate;

{(2R,3S,5R)-5-[4-amino-3-(ethylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2-fluoro-5-methoxyphenyl) sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(1,3-thiazol-2-ylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(1,3-benzodioxol-5-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2-methylphenyl)sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(tert-butylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2-fluoro-4-methoxyphenyl)sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(3-chlorophenyl)sulfanyl]-1H-pyrazolo[3,4-d]pyrimidin-1-yl}-3-hydroxytetrahydrofuran-2-yl]methyl sulfamate;

[(2R,3S,5R)-5-(4-amino-3-{[2-(dimethylamino)-2-oxoethyl]sulfanyl}-1H-pyrazolo[3,4-d]pyrimidin-1-yl)-3-hydroxytetrahydrofuran-2-yl]methyl sulfamate;

{(2R,3S,5R)-5-[4-amino-3-(isopropylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(2-fluorophenyl) sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(quinolin-2-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(4-isopropoxyphenyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(1-methyl-2-oxo-2,3-dihydro-1H-indol-5-yl)sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(2,3-dihydro-1-benzofuran-5-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(4-fluorophenyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(cyanomethyl)sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(5-chloropyridin-2-yl) sulfanyl]-1H-pyrazolo[3,4-d]pyrimidin-1-yl}-3-hydroxytetrahydrofuran-2-yl]methyl sulfamate;

[(2R,3S,5R)-5-(4-amino-3-methoxy-1H-pyrazolo[3,4-d]pyrimidin-1-yl)-3-hydroxytetrahydrofuran-2-yl]methyl sulfamate;

[(2R,3S,5R)-5-{4-amino-3-[(2-fluoro-5-methylphenyl)sulfanyl]-1H-pyrazolo[3,4-d]pyrimidin-1-yl}-3-hydroxytetrahydrofuran-2-yl]methyl sulfamate;

[(2R,3S,5R)-5-(4-amino-3-iodo-1H-pyrazolo[3,4-d]pyrimidin-1-yl)-3-hydroxytetrahydrofuran-2-yl]methyl sulfamate;

[(2R,3S,5R)-5-{4-amino-3-[(4-methylphenyl)sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(pyridin-2-ylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(difluoromethoxy)-1H-pyrazolo[3,4-d]pyrimidin-1-yl]-3-hydroxytetrahydrofuran-2-yl}methyl sulfamate;

[(2R,3S,5R)-5-{4-amino-3-[(3,4-dimethylphenyl) sulfanyl]-1H-pyrazolo[3,4-d]pyrimidin-1-yl}-3-hydroxytetrahydrofuran-2-yl]methyl sulfamate;

[(2R,3S,5R)-5-(4-amino-3-{[4-(trifluoromethoxy)phenyl]sulfanyl}-1H-pyrazolo[3,4-d]pyrimidin-1-yl)-3-hydroxytetrahydrofuran-2-yl]methyl sulfamate;

[(2R,3S,5R)-5-(4-amino-3-{[3-(trifluoromethoxy)phenyl]sulfanyl}-1H-pyrazolo[3,4-d]pyrimidin-1-yl)-3-hydroxytetrahydrofuran-2-yl]methyl sulfamate;

[(2R,3S,5R)-5-{4-amino-3-[(3-methoxyphenyl) sulfanyl]-1H-pyrazolo[3,4-d]pyrimidin-1-yl}-3-hydroxytetrahydrofuran-2-yl]methyl sulfamate;

{(2R,3S,5R)-5-[4-amino-3-(methylsulfanyl)-1H-pyrazolo[3,4-d]pyrimidin-1-yl]-3-hydroxytetrahydrofuran-2-yl}methyl sulfamate;

{(2R,3S,5R)-5-[4-amino-3-(2,3-dihydro-1,4-benzodioxin-6-ylsulfanyl)-1H-pyrazolo[3,4-d]pyrimidin-1-yl]-3-hydroxytetrahydrofuran-2-yl}methyl sulfamate;

[(2R,3S,5R)-5-{4-amino-3-[(cyclopropylmethyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(6-fluoro-2,3-dihydro-1H-inden-5-yl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(1-benzothiophen-2-ylmethyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(3-methylphenyl)sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(3-fluorophenyl) sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(3,4-dimethoxyphenyl)sulfanyl]-1H-pyrazolo[3,4-d]pyrimidin-1-yl}-3-hydroxytetrahydrofuran-2-yl]methyl sulfamate;

[(2R,3S,5R)-5-{4-amino-3-[(4-methyl-1,3-thiazol-2-yl) sulfanyl]-1H-pyrazolo[3,4-d]pyrimidin-1-yl}-3-hydroxytetrahydrofuran-2-yl]methyl sulfamate;

{(2S,3S,5R)-5-[4-amino-3-(trifluoromethyl)-1H-pyrazolo[3,4-d]pyrimidin-1-yl]-3-hydroxytetrahydrofuran-2-yl}methyl sulfamate;

{(2S,3S,5R)-5-[4-amino-3-(2-naphthylsulfanyl)-1H-pyrazolo[3,4-d]pyrimidin-1-yl]-3-hydroxytetrahydrofuran-2-yl}methyl sulfamate;

[(2S,3S,5R)-5-{4-amino-3-[(2-fluoro-4-methylphenyl) sulfanyl]-1H-pyrazolo[3,4-d]pyrimidin-1-yl}-3-hydroxytetrahydrofuran-2-yl]methyl sulfamate;

[(2S,3S,5R)-5-(4-amino-3-ethyl-1H-pyrazolo[3,4-d]pyrimidin-1-yl)-3-hydroxytetrahydrofuran-2-yl]methyl sulfamate;

{(2S,3S,5R)-5-[4-amino-3-(ethylsulfanyl)-1H-pyrazolo[3,4-d]pyrimidin-1-yl]-3-hydroxytetrahydrofuran-2-yl}methyl sulfamate;

[(2S,3S,5R)-5-{4-amino-3-[(4-methylphenyl) sulfanyl]-1H-pyrazolo[3,4-d]pyrimidin-1-yl}-3-hydroxytetrahydrofuran-2-yl]methyl sulfamate;

[(2S,3S,5R)-5-{4-amino-3-[(2-fluorophenyl)sulfanyl]-1H-pyrazolo[3,4-d]pyrimidin-1-yl}-3-hydroxytetrahydrofuran-2-yl]methyl sulfamate;

{(2S,3S,5R)-5-[4-amino-3-(2,3-dihydro-1H-inden-5-ylsulfanyl)-1H-pyrazolo[3,4-d]pyrimidin-1-yl]-3-hydroxytetrahydrofuran-2-yl}methyl sulfamate;

{(2S,3S,5R)-5-[4-amino-3-(difluoromethyl)-1H-pyrazolo[3,4-d]pyrimidin-1-yl]-3-hydroxytetrahydrofuran-2-yl}methyl sulfamate;

[(2S,3S,5R)-5-(4-amino-3-methyl-1H-pyrazolo[3,4-d]pyrimidin-1-yl)-3-hydroxytetrahydrofuran-2-yl]methyl sulfamate;

{(2S,3S,5R)-5-[4-amino-3-(methylsulfanyl)-1H-pyrazolo[3,4-d]pyrimidin-1-yl]-3-hydroxytetrahydrofuran-2-yl}methyl sulfamate;

{(2S,3S,5R)-5-[4-amino-3-(isopropylsulfanyl)-1H-pyrazolo[3,4-d]pyrimidin-1-yl]-3-hydroxytetrahydrofuran-2-yl}methyl sulfamate;

{(2S,3S,5R)-5-[4-amino-3-(benzylsulfanyl)-1H-pyrazolo[3,4-d]pyrimidin-1-yl]-3-hydroxytetrahydrofuran-2-yl}methyl sulfamate;

[(2S,3S,5R)-5-{4-amino-3-[(5-chloropyridin-2-yl) sulfanyl]-1H-pyrazolo[3,4-d]pyrimidin-1-yl}-3-hydroxytetrahydrofuran-2-yl]methyl sulfamate;

[(2S,3S,5R)-5-{4-amino-3-[(4-fluorophenyl) sulfanyl]-1H-pyrazolo[3,4-d]pyrimidin-1-yl}-3-hydroxytetrahydrofuran-2-yl]methyl sulfamate;

[(2S,3S,5R)-5-{4-amino-3-[(3-chlorophenyl) sulfanyl]-1H-pyrazolo[3,4-d]pyrimidin-1-yl}-3-hydroxytetrahydrofuran-2-yl]methyl sulfamate;

[(2S,3S,5R)-5-(4-amino-3-methoxy-1H-pyrazolo[3,4-d]pyrimidin-1-yl)-3-hydroxytetrahydrofuran-2-yl]methyl sulfamate;

[(2S,3S,5R)-5-(4-amino-1H-pyrazolo[3,4-d]pyrimidin-1-yl)-3-hydroxytetrahydrofuran-2-yl]methyl sulfamate; and

[(2S,3S,5R)-5-{4-amino-3-[(2,2-difluoroethyl) sulfanyl]-1H-pyrazolo[3,4-d]pyrimidin-1-yl}-3-hydroxytetrahydrofuran-2-yl]methyl sulfamate, or a pharmaceutically acceptable salt thereof.

19. A pharmaceutical composition comprising a chemical entity of claim 1, and a pharmaceutically acceptable carrier.

\* \* \* \* \*